US011165028B2

(12) United States Patent
Tsai et al.

(10) Patent No.: US 11,165,028 B2
(45) **Date of Patent: *Nov. 2, 2021**

(54) ORGANIC ELECTROLUMINESCENT MATERIALS AND DEVICES

(71) Applicant: Universal Display Corporation, Ewing, NJ (US)

(72) Inventors: Jui-Yi Tsai, Newtown, PA (US); Alexey Borisovich Dyatkin, Ambler, PA (US); Zhiqiang Ji, Chalfont, PA (US); Walter Yeager, Yardley, PA (US); Pierre-Luc T. Boudreault, Pennington, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,219

(22) Filed: Feb. 22, 2019

(65) Prior Publication Data

US 2019/0280219 A1 Sep. 12, 2019

Related U.S. Application Data

(63) Continuation-in-part of application No. 16/235,390, filed on Dec. 28, 2018.

(Continued)

(51) Int. Cl.

*H01L 51/00* (2006.01)
*C07F 15/00* (2006.01)

(Continued)

(52) U.S. Cl.

CPC ........ *H01L 51/0085* (2013.01); *C07D 405/04* (2013.01); *C07F 15/0033* (2013.01);

(Continued)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Saito et al. "Arching a bay area of triphenyleno[1,12-bcd]thiophene with group 14 functionalities: Synthesis of the first triphenylene derivatives having thiophene and metallafluorene moieties" Journal of Organometallic Chemistry 2010, 695, 1035-1041. (Year: 2010).*

(Continued)

*Primary Examiner* — Robert S Loewe
(74) *Attorney, Agent, or Firm* — Duane Morris LLP

(57) ABSTRACT

A compound comprising a first ligand selected from Formula I,

, (Continued)

and Formula II,

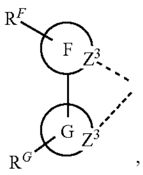

is disclosed. In these structures, $Y^1$ to $Y^{12}$ and $Z^3$ and $Z^4$ are independently CR or N; where each R, R', R", $R^F$, and $R^G$ is hydrogen or a substituent, where at least one dashed arc represents Rs joined into a 5-membered or 6-membered carbocyclic or heterocyclic ring; where the first ligand is complexed to a metal M; where ring G is a fused ring structure comprising five or more fused heterocyclic or carbocyclic rings, of which at least one ring is of Formula III

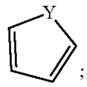

;

where the fused heterocyclic or carbocyclic rings of Ring G are 5- or 6-membered; where Y is selected from BR', NR', PR', O, S, Se, C═O, S═O, $SO_2$, CR'R", SiR'R", and GeR'R". Organic light emitting devices and consumer products containing the compounds are also disclosed.

20 Claims, 2 Drawing Sheets

Related U.S. Application Data

(60) Provisional application No. 62/643,472, filed on Mar. 15, 2018, provisional application No. 62/641,644, filed on Mar. 12, 2018, provisional application No. 62/673,178, filed on May 18, 2018.

(51) Int. Cl.

| | |
|---|---|
| ***C09K 11/02*** | (2006.01) |
| ***C09K 11/06*** | (2006.01) |
| ***H05B 33/14*** | (2006.01) |
| ***C07D 405/04*** | (2006.01) |
| *H01L 51/50* | (2006.01) |

(52) U.S. Cl.

CPC .............. *C09K 11/02* (2013.01); *C09K 11/06* (2013.01); *H01L 51/00* (2013.01); *H05B 33/14* (2013.01); *C09K 2211/1007* (2013.01); *C09K 2211/1029* (2013.01); *C09K 2211/1088* (2013.01); *C09K 2211/185* (2013.01); *H01L 51/5012* (2013.01); *H01L 51/5016* (2013.01); *H01L 2251/5384* (2013.01)

(56) References Cited

U.S. PATENT DOCUMENTS 5,247,190 A 9/1993 Friend et al.
5,703,436 A 12/1997 Forrest et al.
5,707,745 A 1/1998 Forrest et al.
5,834,893 A 11/1998 Bulovic et al.
5,844,363 A 12/1998 Gu et al.
6,013,982 A 1/2000 Thompson et al.
6,087,196 A 7/2000 Sturm et al.
6,091,195 A 7/2000 Forrest et al.
6,097,147 A 8/2000 Baldo et al.
6,294,398 B1 9/2001 Kim et al.
6,303,238 B1 10/2001 Thompson et al.
6,337,102 B1 1/2002 Forrest et al.
6,468,819 B1 10/2002 Kim et al.
6,528,187 B1 3/2003 Okada
6,687,266 B1 2/2004 Ma et al.
6,835,469 B2 12/2004 Kwong et al.
6,921,915 B2 7/2005 Takiguchi et al.
7,087,321 B2 8/2006 Kwong et al.
7,090,928 B2 8/2006 Thompson et al.
7,154,114 B2 12/2006 Brooks et al.
7,250,226 B2 7/2007 Tokito et al.
7,279,704 B2 10/2007 Walters et al.
7,332,232 B2 2/2008 Ma et al.
7,338,722 B2 3/2008 Thompson et al.
7,393,599 B2 7/2008 Thompson et al.
7,396,598 B2 7/2008 Takeuchi et al.
7,431,968 B1 10/2008 Shtein et al.
7,445,855 B2 11/2008 Mackenzie et al.
7,534,505 B2 5/2009 Lin et al.
8,692,241 B1 * 4/2014 Zeng ...................... C09K 11/06 257/40
8,946,697 B1 * 2/2015 Ma ...................... H01L 51/5024 257/40
2002/0034656 A1 3/2002 Thompson et al.
2002/0134984 A1 9/2002 Igarashi
2002/0158242 A1 10/2002 Son et al.
2003/0138657 A1 7/2003 Li et al.
2003/0152802 A1 8/2003 Tsuboyama et al.
2003/0162053 A1 8/2003 Marks et al.
2003/0175553 A1 9/2003 Thompson et al.
2003/0230980 A1 12/2003 Forrest et al.
2004/0036077 A1 2/2004 Ise
2004/0137267 A1 7/2004 Igarashi et al.
2004/0137268 A1 7/2004 Igarashi et al.
2004/0174116 A1 9/2004 Lu et al.
2005/0025993 A1 2/2005 Thompson et al.
2005/0112407 A1 5/2005 Ogasawara et al.
2005/0238919 A1 10/2005 Ogasawara
2005/0244673 A1 11/2005 Satoh et al.
2005/0260441 A1 11/2005 Thompson et al.
2005/0260449 A1 11/2005 Walters et al.
2006/0008670 A1 1/2006 Lin et al.
2006/0202194 A1 9/2006 Jeong et al.
2006/0240279 A1 10/2006 Adamovich et al.
2006/0251923 A1 11/2006 Lin et al.
2006/0263635 A1 11/2006 Ise
2006/0280965 A1 12/2006 Kwong et al.
2007/0190359 A1 8/2007 Knowles et al.
2007/0278938 A1 12/2007 Yabunouchi et al.
2008/0015355 A1 1/2008 Schafer et al.
2008/0018221 A1 1/2008 Egen et al.
2008/0106190 A1 5/2008 Yabunouchi et al.
2008/0124572 A1 5/2008 Mizuki et al.
2008/0220265 A1 9/2008 Xia et al.
2008/0297033 A1 12/2008 Knowles et al.
2009/0008605 A1 1/2009 Kawamura et al.
2009/0009065 A1 1/2009 Nishimura et al.
2009/0017330 A1 1/2009 Iwakuma et al.
2009/0030202 A1 1/2009 Iwakuma et al.
2009/0039776 A1 2/2009 Yamada et al.
2009/0045730 A1 2/2009 Nishimura et al.
2009/0045731 A1 2/2009 Nishimura et al.
2009/0101870 A1 4/2009 Prakash et al.
2009/0108737 A1 4/2009 Kwong et al.
2009/0115316 A1 5/2009 Zheng et al.
2009/0165846 A1 7/2009 Johannes et al.
2009/0167162 A1 7/2009 Lin et al.
2009/0179554 A1 7/2009 Kuma et al.
2012/0061654 A1 * 3/2012 Rayabarapu ........... H05B 33/14 257/40
2012/0205645 A1 * 8/2012 Fuchs ................... H01L 51/009 257/40
2012/0292601 A1 * 11/2012 Kottas .................. C07D 235/18 257/40

(56) References Cited

U.S. PATENT DOCUMENTS

2012/0302753 A1* 11/2012 Li ....................... H01L 51/0087 546/4
2013/0026452 A1* 1/2013 Kottas ..................... H01L 51/50 257/40
2013/0119354 A1* 5/2013 Ma ......................... C09K 11/06 257/40
2014/0131676 A1* 5/2014 Beers .................. H01L 51/0085 257/40
2014/0131687 A1* 5/2014 Lin ......................... H01L 51/50 257/40
2014/0231755 A1* 8/2014 Xia ..................... H01L 51/0085 257/40
2015/0008419 A1* 1/2015 Li ....................... H01L 51/5016 257/40
2015/0137096 A1* 5/2015 Xia ..................... H01L 51/0085 257/40
2015/0162552 A1* 6/2015 Li ....................... C07F 15/0086 546/4
2015/0236276 A1* 8/2015 Boudreault ......... H01L 51/0085 257/40
2015/0315222 A1* 11/2015 Boudreault ........ C07D 491/048 257/40
2015/0357576 A1 12/2015 Kawamura et al.
2015/0364702 A1* 12/2015 Abe .................... C07F 15/0033 257/40
2016/0049597 A1 2/2016 Ma et al.
2016/0049599 A1 2/2016 Ma et al.
2016/0141522 A1* 5/2016 Ma ...................... H01L 51/0072 257/40
2016/0260907 A1 9/2016 Low et al.
2016/0329508 A1* 11/2016 Saito ................... H01L 51/5016
2016/0351835 A1* 12/2016 Yen ..................... C07F 15/0033
2017/0373259 A1 12/2017 Su et al.
2018/0097185 A1* 4/2018 Su ....................... H01L 51/0068
2018/0254417 A1 9/2018 Ma et al.
2018/0337351 A1* 11/2018 Feldman ................ C09K 11/06
2019/0051844 A1 2/2019 Ji et al.
2019/0074455 A1* 3/2019 Chen ................... H01L 51/0087

FOREIGN PATENT DOCUMENTS

EP 2034538 3/2009
EP 2594573 5/2013
EP 2982729 2/2016
JP 200511610 1/2005
JP 2007123392 5/2007
JP 2007254297 10/2007
JP 2008074939 4/2008
JP 2012-74444 4/2012
WO 01/39234 5/2001
WO 02/02714 1/2002
WO 02015654 2/2002
WO 03040257 5/2003
WO 03060956 7/2003
WO 2004093207 10/2004
WO 04107822 12/2004
WO 2005014551 2/2005
WO 2005019373 3/2005
WO 2005030900 4/2005
WO 2005089025 9/2005
WO 2005123873 12/2005
WO 2006009024 1/2006
WO 2006056418 6/2006
WO 2006072002 7/2006
WO 2006082742 8/2006
WO 2006098120 9/2006
WO 2006100298 9/2006
WO 2006103874 10/2006
WO 2006114966 11/2006
WO 2006132173 12/2006
WO 2007002683 1/2007
WO 2007004380 1/2007
WO 2007063754 6/2007
WO 2007063796 6/2007
WO 2008056746 5/2008
WO 2008101842 8/2008
WO 2008132085 11/2008
WO 2009000673 12/2008
WO 2009003898 1/2009
WO 2009008311 1/2009
WO 2009018009 2/2009
WO 2009021126 2/2009
WO 2009050290 4/2009
WO 2009062578 5/2009
WO 2009063833 5/2009
WO 2009066778 5/2009
WO 2009066779 5/2009
WO 2009086028 7/2009
WO 2009100991 8/2009
WO WO-2014097865 * 6/2014 ............ H01L 51/50
WO 2016080786 5/2016

OTHER PUBLICATIONS

Saito et al. "Synthesis and structures of heterasumanenes having differenct heteroatom functionalities" Tetrahedron Letters, 2010, 51, 672-675. (Year: 2010).*
Machine translation of WO-2014097865, translation generated May 2020, 90 pages. (Year: 2020).*
Sato, et al. (Coronene-transition metal complex: View from quantum chemistry and statistical mechanics), In AIP Conference Proceedings, vol. 1504, No. 1, pp. 887-890. American Institute of Physics, 2012. (Year: 2012).*
Winkler et al. "Gas phase pyrolysis of heterocyclic compounds, part 4: flow of pyrolysis and annulation reactions of some oxygen heterocycles: furan, benzo[b]furan and dibenzofuran. A product oriented study.", Journal of Analytical and Applied Pyrolysis, vol. 57, Issue 1, Jan. 2001, pp. 133-144.
Velusamy et al., "Synthesis, structure and electroluminescent properties of cyclometalated iridium complexes possessing sterically hindered ligands", Dalton Transactions, 2007, 28, pp. 3025-3034.
Zeng, Qun et al., "Spin-orbit coupling effect on Au—C60 interaction: A density functional theory study," Chemical Physics 395 (2012) pp. 82-86.
Extended European Search Report dated Jul. 10, 2019 for corresponding European Application No. 19161973.3.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 1, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato)beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1)162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSLYKE, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application is a continuation-in-part of U.S. Utility application Ser. No. 16/235,390, filed Dec. 28, 2018, which is a non-provisional of U.S. Provisional Application No. 62/643,472, filed Mar. 15, 2018, and this application claims priority under 35 U.S.C. § 119(e) to U.S. Provisional Application No. 62/641,644, filed Mar. 12, 2018, and U.S. Provisional Application No. 62/673,178, filed May 18, 2018, the entire contents of which are incorporated herein by reference.

FIELD

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted $Ir(ppy)_3$, which has the following structure:

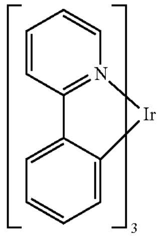

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative) Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to one aspect of the present disclosure, a compound comprising a first ligand $L_A$ having the structure of Formula I

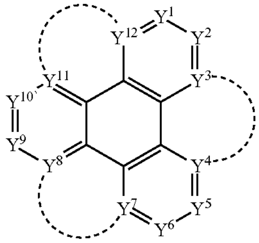

, is provided. In the structure of Formula I:

each of $Y^1$ to $Y^{12}$ are independently CR or N;

each R can be same or different, and any two adjacent Rs are optionally joined or fused into a ring;

at least one pair selected from the group consisting of $Y^3$ and $Y^4$, $Y^7$ and $Y^8$, and $Y^{11}$ and $Y^{12}$ are CR where the Rs are joined or fused into a 5-membered or 6-membered carbocyclic or heterocyclic ring;

each R is independently hydrogen or one of the general substituents defined above;

$L_A$ is complexed to a metal M, which has an atomic mass higher than 40;

M is optionally coordinated to other ligands; and the ligand $L_A$ is optionally linked with other ligands to comprise a bidentate, tridentate, tetradentate, pentadentate, or hexadentate ligand.

According to another aspect of the present disclosure, a compound comprising a first ligand $L_X$ of Formula II,

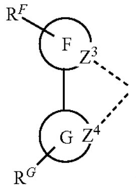

, is provided. In the compound of Formula II,

F is a 5-membered or 6-membered carbocyclic or heterocyclic ring;

$R^F$ and $R^G$ independently represent mono to the maximum possible number of substitutions, or no substitution;

$Z^3$ and $Z^4$ are each independently C or N and coordinated to a metal M to form a 5-membered chelate ring;

G is a fused ring structure comprising five or more fused heterocyclic or carbocyclic rings, of which at least one ring is of Formula III,

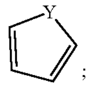

;

the fused heterocyclic or carbocyclic rings comprised by Ring G are 5-membered or 6-membered; of which if two or more 5-membered rings are present, at least two of the 5-membered rings are fused to one another;

Y is selected from the group consisting of BR', NR', PR', O, S, Se, C═O, S═O, $SO_2$, CR'R", SiR'R", and GeR'R";

each R', R", $R^F$, and $R^G$ is independently hydrogen or one of the general substituents defined above;

metal M is optionally coordinated to other ligands; and the ligand $L_X$ is optionally linked with other ligands to comprise a tridentate, tetradentate, pentadentate, or hexadentate ligand.

An OLED comprising one or more of the compound of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
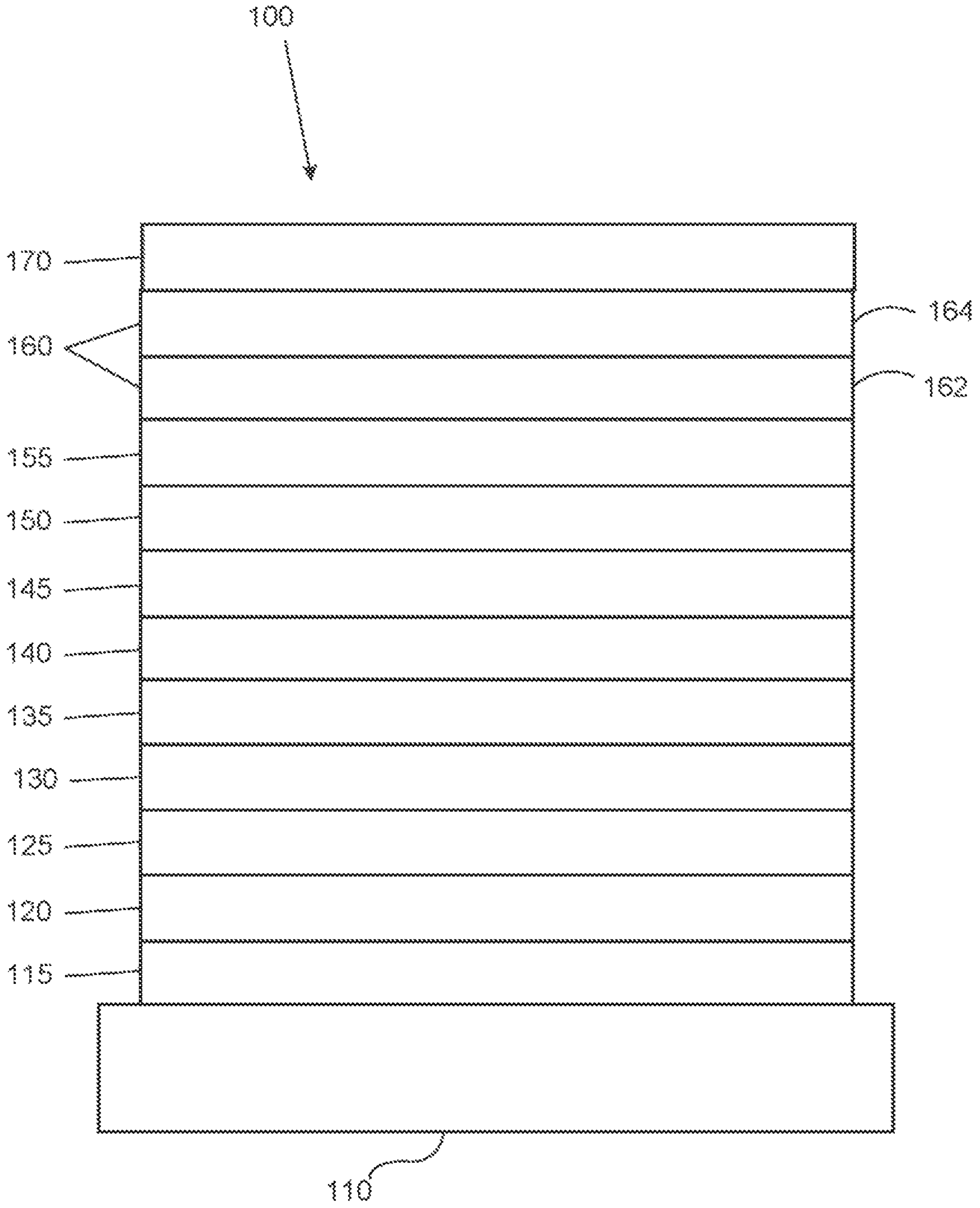
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
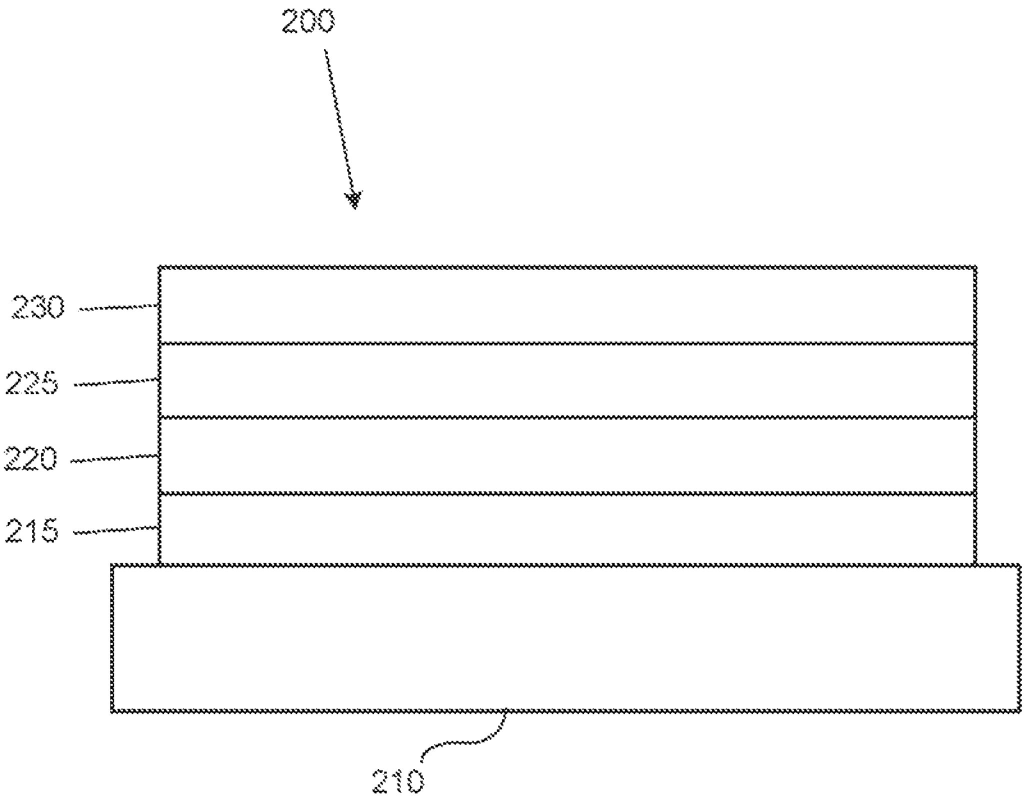
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —$OR_s$ radical.

The terms "sulfanyl" or "thio-ether" are used interchangeably and refer to a —$SR_s$ radical.

The term "sulfinyl" refers to a —S(O)—R, radical.

The term "sulfonyl" refers to a —$SO_2$—R, radical.

The term "phosphino" refers to a —$P(R_s)_3$ radical, wherein each R can be same or different.

The term "silyl" refers to a —$Si(R_s)_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution) Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups.

Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C-H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to an aspect of the present disclosure, a compound comprising a first ligand $L_A$ having the structure of Formula I

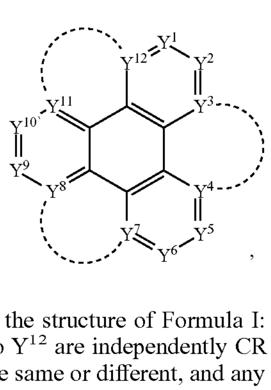

, is disclosed. In the structure of Formula I:

each of $Y^1$ to $Y^{12}$ are independently CR or N;

each R can be same or different, and any two adjacent Rs are optionally joined or fused into a ring; at least one pair selected from the group consisting of $Y^3$ and $Y^4$, $Y^7$ and $Y^8$, and $Y^{11}$ and $Y^{12}$ are CR where the Rs are joined or fused into a 5-membered or 6-membered carbocyclic or heterocyclic ring;

each R is independently hydrogen or one of the general substituents defined above;

$L_A$ is complexed to a metal M, which has an atomic mass higher than 40;

M is optionally coordinated to other ligands; and the ligand $L_A$ is optionally linked with other ligands to comprise a bidentate, tridentate, tetradentate, pentadentate, or hexadentate ligand.

In Formula I, the dashed lines represent optional structures where adjacent Rs are joined or fused into a 5-membered or 6-membered carbocyclic or heterocyclic ring.

In some embodiments, each R is independently hydrogen or one of the preferred general substituents or one of the more preferred general substituents defined above.

In some embodiments, the first ligand $L_A$ is a bidentate ligand.

In some embodiments, one R comprises a 5-membered or 6-membered carbocyclic or heterocyclic ring, which is coordinated to M. In some embodiments, one R comprises a 5-membered or 6-membered aryl or heteroaryl ring. In some embodiments, $Y^1$ is $CR^{Y1}$, where $R^{Y1}$ is aryl or heteroaryl and $R^{Y1}$ is coordinated to M. In some embodiments, $Y^2$ is $N^{Y2}$ or $CR^{Y2}$ and $N^{Y2}$ or $R^{Y2}$ is coordinated to M.

In some embodiments, one R comprises a substituted or unsubstituted ring selected from the group consisting of pyridine, pyrimidine, imidazole, pyrazole, and N-heterocyclic carbene, wherein the substituted or unsubstituted ring is coordinated to M by a dative bond. In some embodiments, one R comprises a benzene ring, which is coordinated to M by a sigma bond.

In some embodiments, $Y^1$ to $Y^{12}$ are each C. In some embodiments, at least one of $Y^1$ to $Y^{12}$ is N.

In some embodiments, exactly one pair selected from the group consisting of $Y^3$ and $Y^4$, $Y^7$ and $Y^8$, and $Y^{11}$ and $Y^{12}$ are CR where the Rs are joined or fused into a 5-membered or 6-membered carbocyclic or heterocyclic ring. In some embodiments, exactly one pair selected from the group consisting of $Y^3$ and $Y^4$, $Y^7$ and $Y^8$, and $Y^{11}$ and $Y^{12}$ are CR where the Rs are joined or fused into a 5-membered or 6-membered aryl or heteroaryl ring.

In some embodiments, at least one pair selected from the group consisting of $Y^3$ and $Y^4$, $Y^7$ and $Y^8$, and $Y^{11}$ and $Y^{12}$ are CR where the Rs are fused to form ring selected from the group consisting of a furan ring, a thiophene ring, a pyrrole ring, a silole ring, a benzene ring, and a pyridine ring. In some embodiments, exactly one pair selected from the group consisting of $Y^3$ and $Y^4$, $Y^7$ and $Y^8$, and $Y^{11}$ and $Y^{12}$ are CR where the Rs are fused to form ring selected from the group consisting of a furan ring, a thiophene ring, a pyrrole ring, a silole ring, a benzene ring, and a pyridine ring.

In some embodiments, is selected from the group consisting of Os, Ir, Pd, Pt, Cu, and Au. In some embodiments, M is Pt or Ir. In some embodiments, M is Pt(II) or Ir(III).

In some embodiments, the compound is homoleptic. In some embodiments, the compound is heteroleptic.

In some embodiments, $L_A$ comprises a formula selected from the group consisting of:

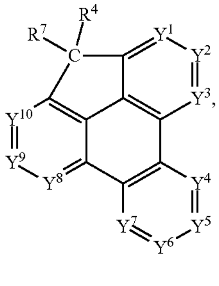

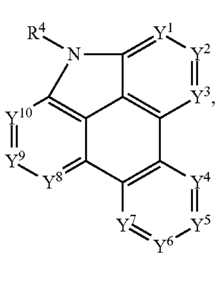

-continued

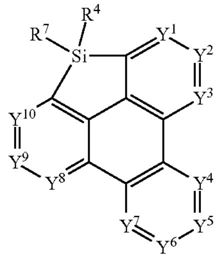
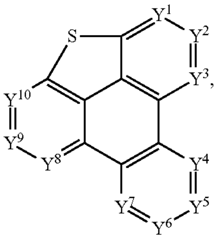
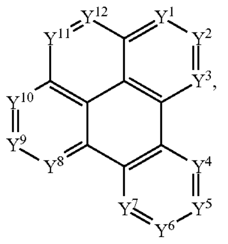
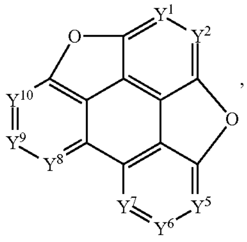
,
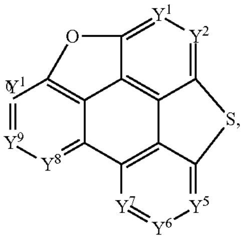
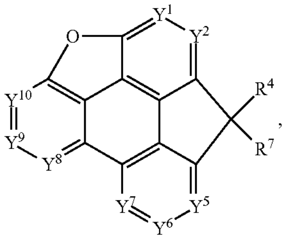
,
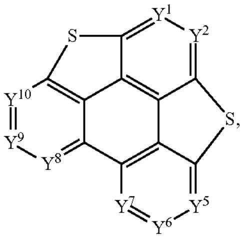
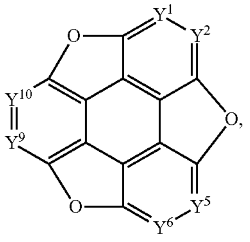
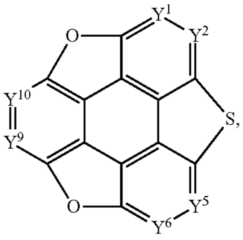
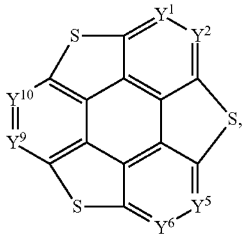
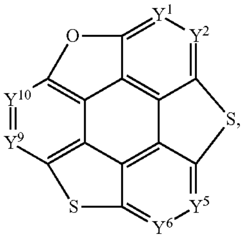

wherein $R^4$ and $R^7$ are independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof.

In some embodiments, $L_A$ is selected from the group consisting of:

$L_{A1\text{-}1}$

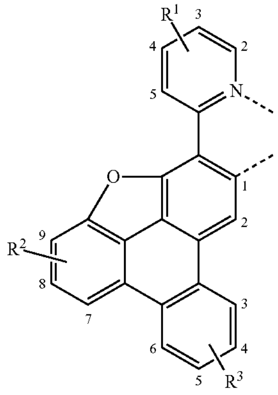
, $L_{A2\text{-}1}$

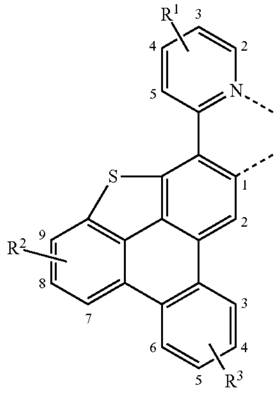
, $L_{A3\text{-}1}$

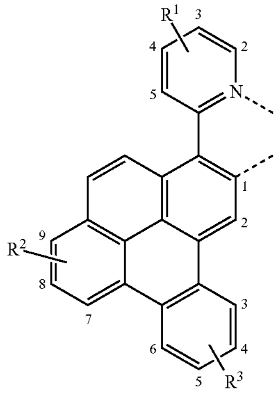
, $L_{A4\text{-}1}$

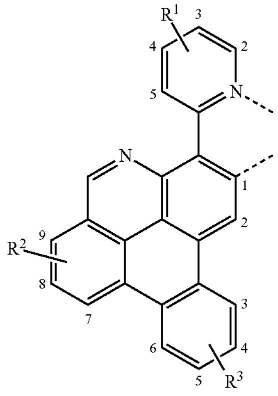
,

L$_{A5-1}$
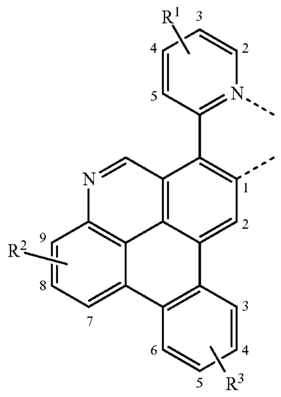
,
L$_{A6-1}$
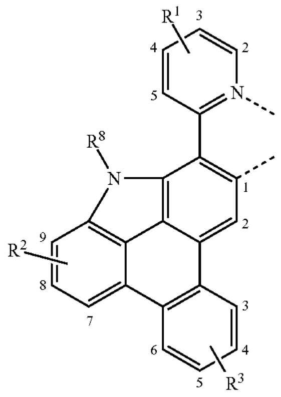
,
L$_{A7-1}$
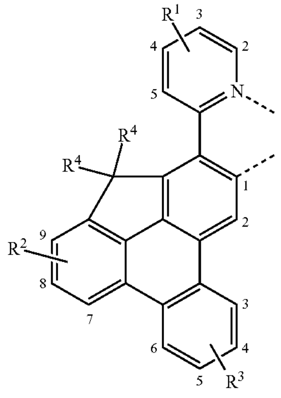
,
L$_{A1-2}$
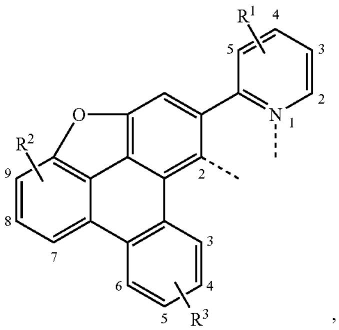
,
L$_{A2-2}$
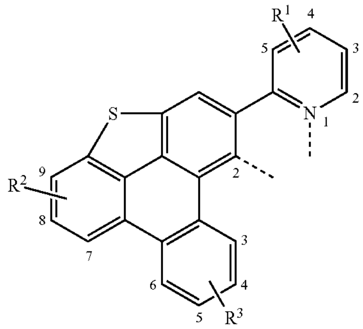
,
L$_{A-3-2}$
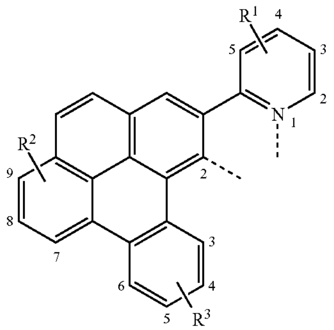
,
L$_{A4-2}$
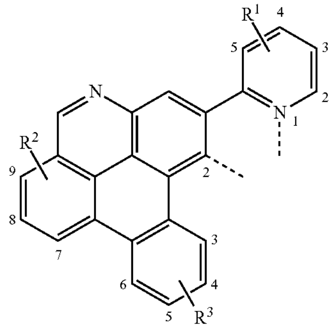
,
L$_{A5-2}$
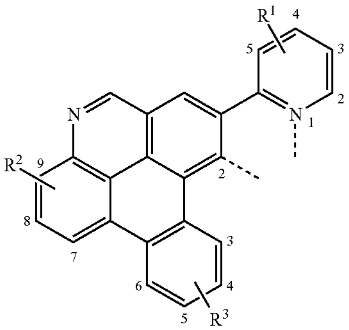
, -continued
$L_{A6-2}$
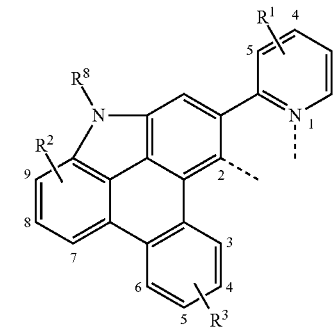
,
$L_{A7-2}$
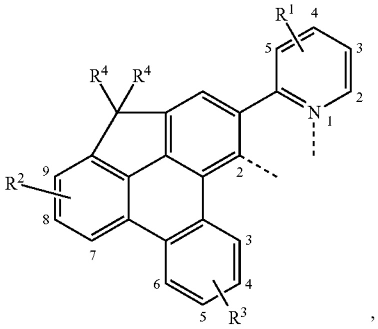
,
$L_{A1-3}$
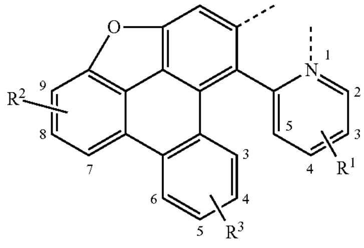
,
$L_{A2-3}$
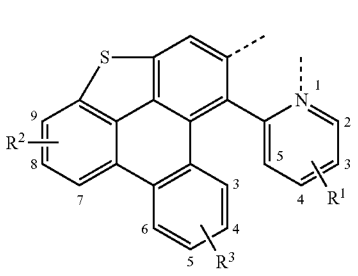
,
$L_{A3-3}$
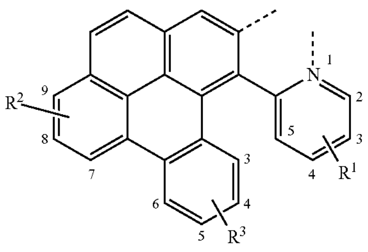
,
-continued
$L_{A4-3}$
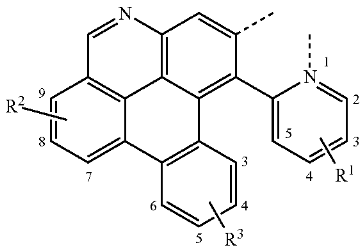
,
$L_{A5-3}$
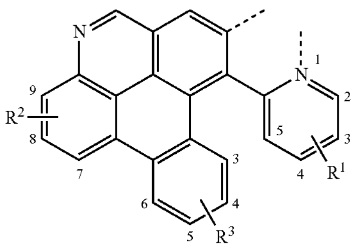
,
$L_{A6-3}$
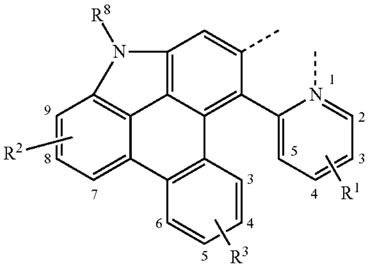
,
$L_{A7-3}$
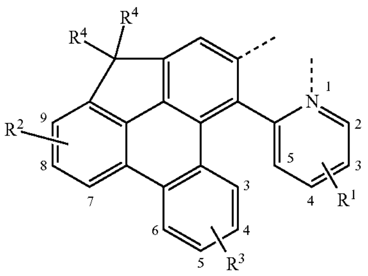
,
$L_{A1-4}$
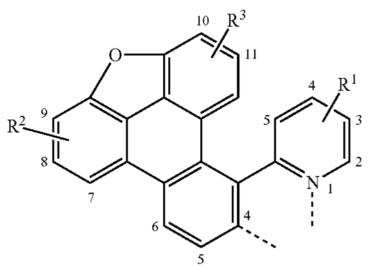
,
$L_{A2-4}$
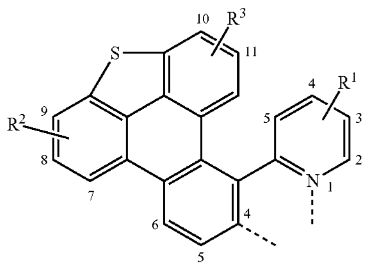
, -continued
$L_{A3-4}$
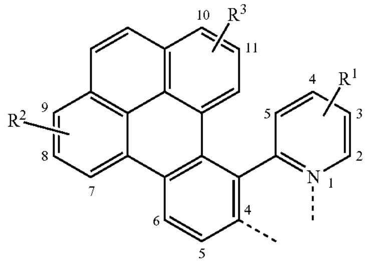
,
$L_{A4-4}$
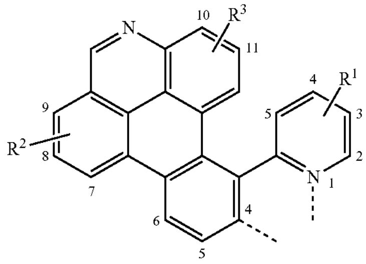
,
$L_{A5-4}$
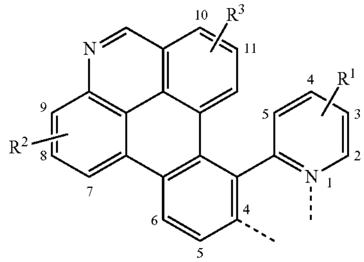
,
$L_{A6-4}$
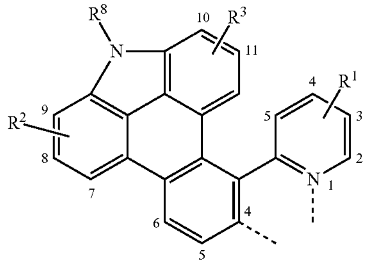
,
$L_{A7-4}$
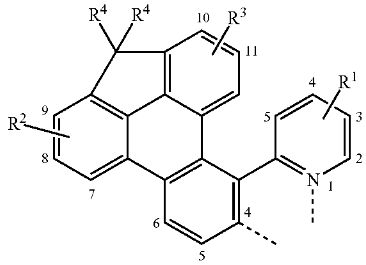
,
-continued
$L_{A1-5}$
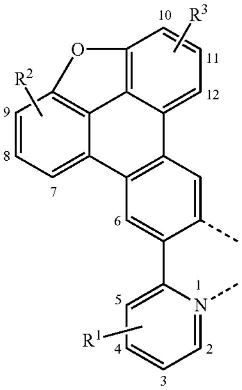
,
$L_{A2-5}$
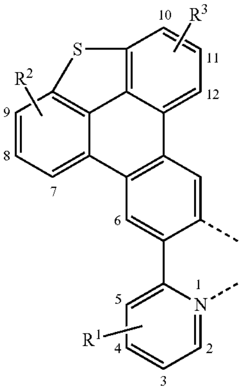
,
$L_{A3-5}$
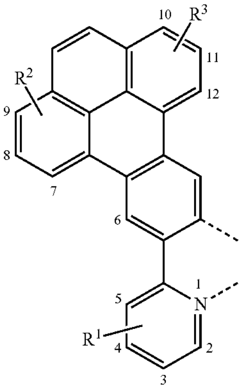
,
$L_{A4-5}$
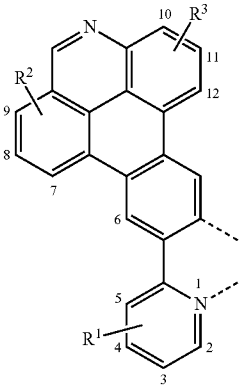
, $L_{A5-5}$
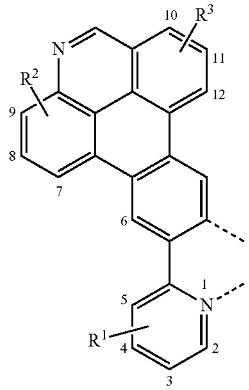
,
$L_{A6-5}$
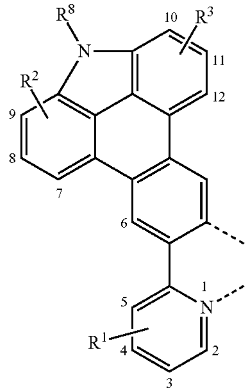
,
$L_{A7-5}$
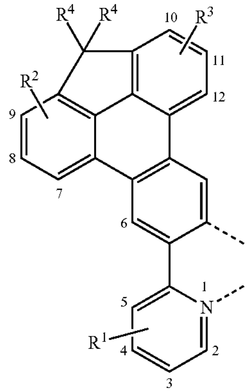
,
$L_{A1-6}$
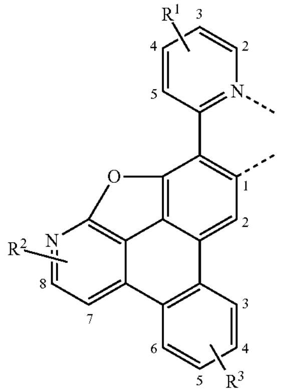
,
$L_{A1-7}$
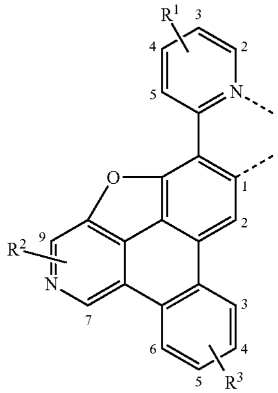
,
$L_{A1-8}$
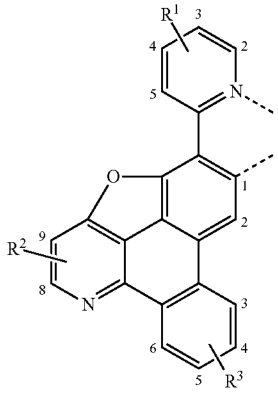
,
$L_{A1-9}$
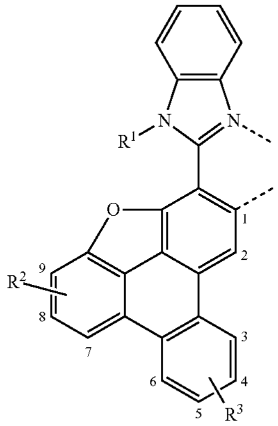
, -continued
$L_{A2-9}$
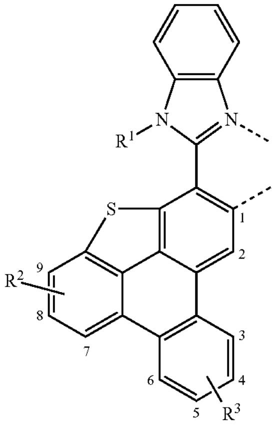
,
$L_{A3-9}$
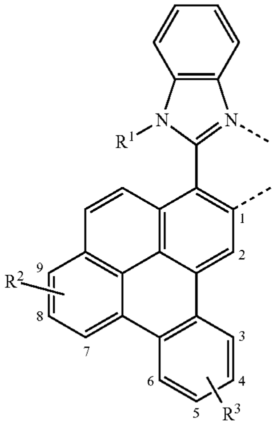
,
$L_{A4-9}$
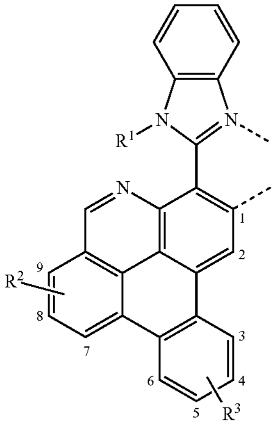
,
-continued
$L_{A5-9}$
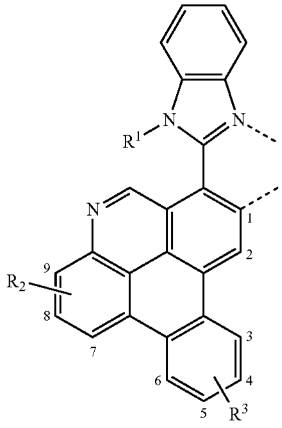
,
$L_{A6-9}$
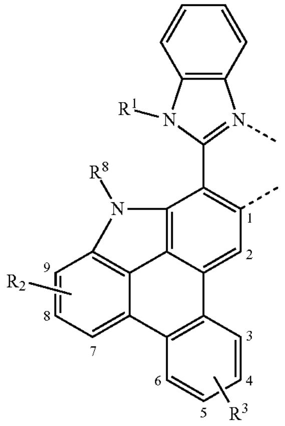
,
$L_{A1-10}$
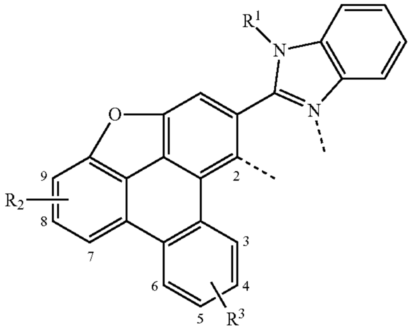
,
$L_{A2-10}$
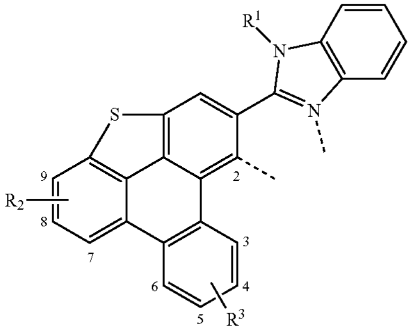
, -continued
$L_{A3-10}$
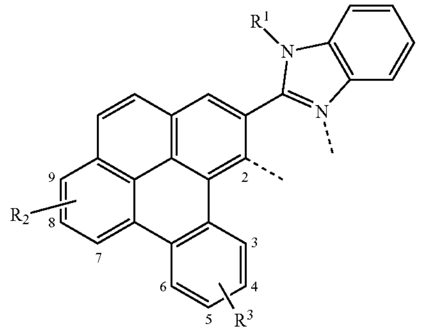
,
$L_{A4-10}$
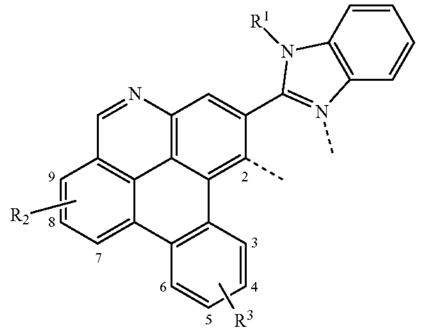
,
$L_{A5-10}$
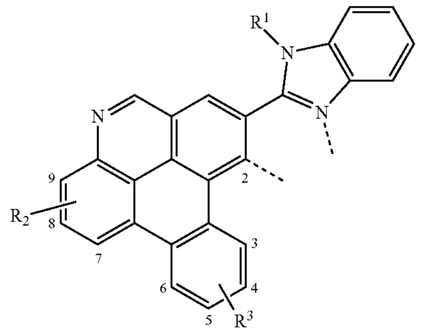
,
$L_{A6-10}$
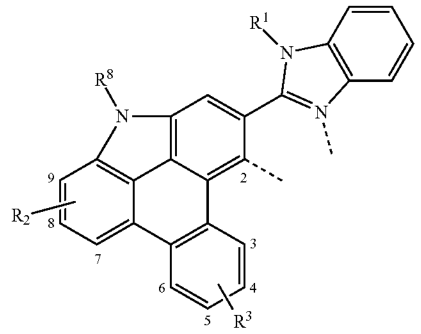
,
$L_{A1-11}$
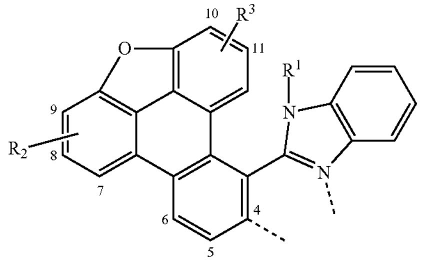
,
-continued
$L_{A2-11}$
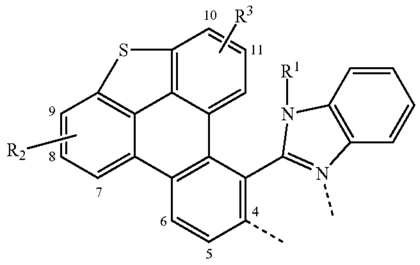
,
$L_{A3-11}$
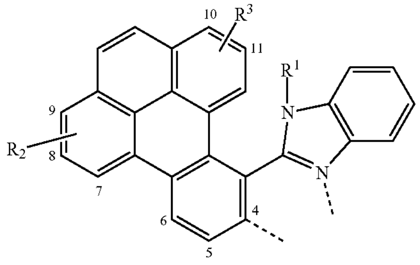
,
$L_{A4-11}$
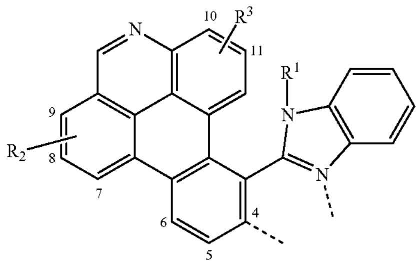
,
$L_{A5-11}$
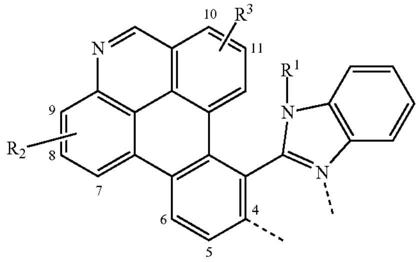
,
$L_{A6-11}$
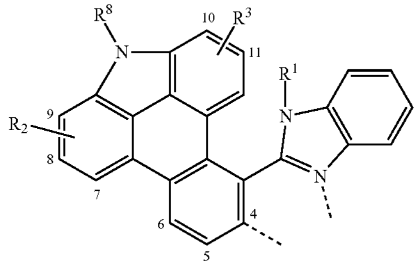
, -continued
L$_{A1-12}$
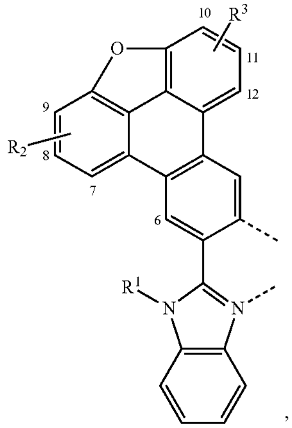
,
L$_{A2-12}$
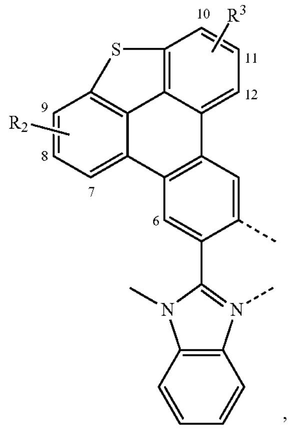
,
L$_{A3-12}$
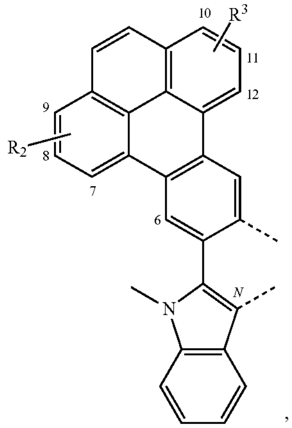
,
-continued
L$_{A4-12}$
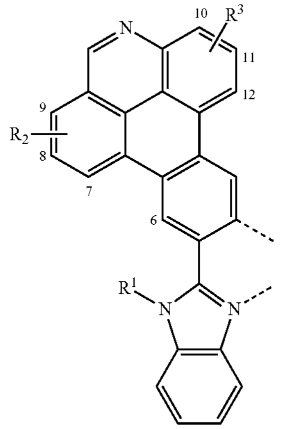
,
L$_{A5-12}$
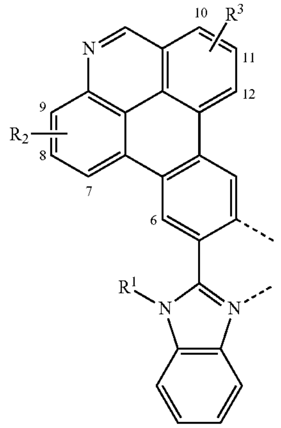
,
L$_{A6-12}$
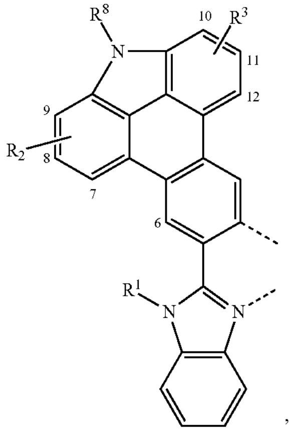
, -continued
L$_{A1\text{-}13}$
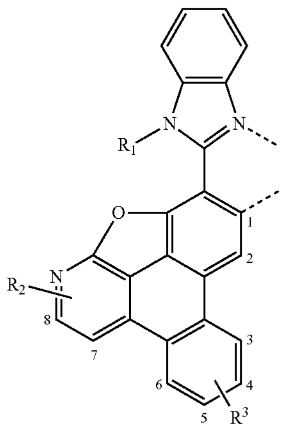
,
L$_{A1\text{-}14}$
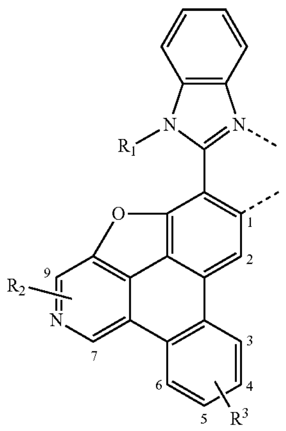
,
L$_{A1\text{-}15}$
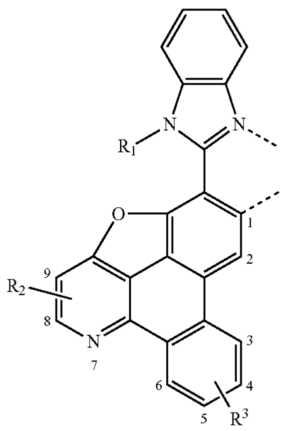
,
-continued
L$_{A1\text{-}16}$
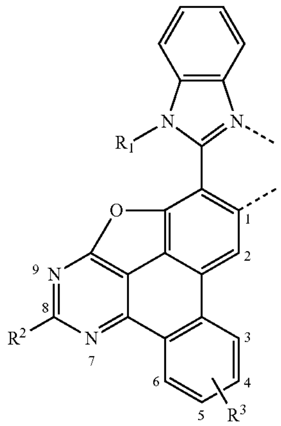
,
L$_{A1\text{-}17}$
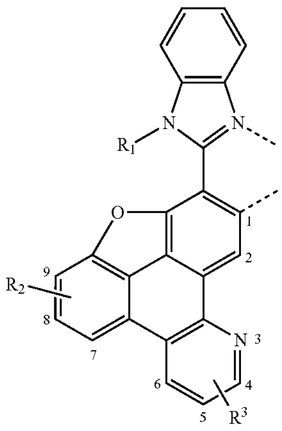
,
L$_{A1\text{-}18}$
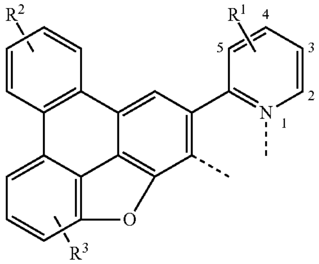
,
L$_{A1\text{-}19}$
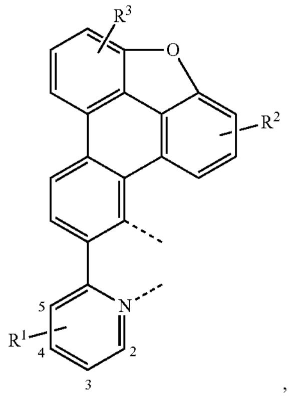
, -continued

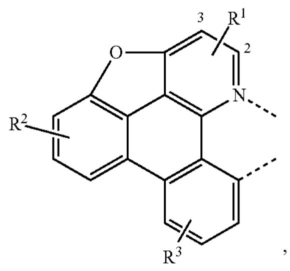

$L_{A1-20}$

, and

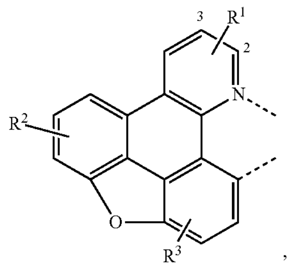

$L_{A1-21}$

, wherein

| $L_{A\,i}$ where i is | Ligand subtype | $R^1$ | $R^2$ | $R^3$ | $R^4$ | $R^8$ |
|---|---|---|---|---|---|---|
| 1. | $L_{A\,1-1}$ | 3-Me | H | H | — | — |
| 2. | $L_{A\,1-1}$ | 3-Me | 8-Me | H | — | — |
| 3. | $L_{A\,1-1}$ | 4-Me | H | H | — | — |
| 4. | $L_{A\,1-1}$ | 3,4-Me | H | H | — | — |
| 5. | $L_{A\,1-1}$ | 4-iPr | H | H | — | — |
| 6. | $L_{A\,1-1}$ | 4-$CH_2CMe_3$ | H | H | — | — |
| 7. | $L_{A\,1-1}$ | 4-Me | H | 5-Me | — | — |
| 8. | $L_{A\,2-1}$ | 3-Me | H | H | — | — |
| 9. | $L_{A\,2-1}$ | 3-Me | 9-Me | H | — | — |
| 10. | $L_{A\,2-1}$ | 4-Me | H | H | — | — |
| 11. | $L_{A\,3-1}$ | 3-Me | H | H | — | — |
| 12. | $L_{A\,3-1}$ | 4-Me | H | H | — | — |
| 13. | $L_{A\,3-1}$ | 3,4-Me | H | H | — | — |
| 14. | $L_{A\,3-1}$ | 4-iPr | H | H | — | — |
| 15. | $L_{A\,3-1}$ | 4-$CH_2CMe_3$ | H | H | — | — |
| 16. | $L_{A\,3-1}$ | 4-Me | 5-Me | H | — | — |
| 17. | $L_{A\,4-1}$ | 4-Me | H | H | — | — |
| 18. | $L_{A\,4-1}$ | 3,4-Me | H | H | — | — |
| 19. | $L_{A\,4-1}$ | 4-Me | 9-Me | H | — | — |
| 20. | $L_{A\,4-1}$ | 3,4-Me | 8-Me | H | — | — |
| 21. | $L_{A\,4-1}$ | 4-Me | H | 5-Me | — | — |
| 22. | $L_{A\,4-1}$ | 3,4-Me | H | 5-Me | — | — |
| 23. | $L_{A\,4-1}$ | 4-Me | 9-Me | 5-Me | — | — |
| 24. | $L_{A\,4-1}$ | 3,4-Me | 8-Me | 5-Me | — | — |
| 25. | $L_{A\,5-1}$ | 4-Me | H | H | — | — |
| 26. | $L_{A\,5-1}$ | 3,4-Me | H | H | — | — |
| 27. | $L_{A\,6-1}$ | 4-Me | H | H | — | Ph |
| 28. | $L_{A\,6-1}$ | 3,4-Me | H | H | — | Ph |
| 29. | $L_{A\,7-1}$ | 3,4-Me | 5-Me | H | Me | — |
| 30. | $L_{A\,1-2}$ | 3-Me | H | H | — | — |
| 31. | $L_{A\,1-2}$ | 4-Me | H | H | — | — |
| 32. | $L_{A\,1-2}$ | 3,4-Me | H | H | — | — |
| 33. | $L_{A\,1-2}$ | 4-iPr | H | H | — | — |
| 34. | $L_{A\,1-2}$ | 4-$CH_2CMe_3$ | H | H | — | — |
| 35. | $L_{A\,1-2}$ | 4-Me | 5-Me | H | — | — |
| 36. | $L_{A\,2-2}$ | 4-Me | H | H | — | — |
| 37. | $L_{A\,3-2}$ | 4-Me | H | H | — | — |
| 38. | $L_{A\,4-2}$ | 4-Me | H | H | — | — |
| 39. | $L_{A\,5-2}$ | 4-Me | H | H | — | — |
| 40. | $L_{A\,6-2}$ | 4-Me | H | H | — | Ph |
| 41. | $L_{A\,7-2}$ | 4-Me | H | H | Me | — |
| 42. | $L_{A\,1-3}$ | 3-Me | H | H | — | — |
| 43. | $L_{A\,2-3}$ | 3-Me | H | H | — | — |
| 44. | $L_{A\,3-3}$ | 3-Me | H | H | — | — |

-continued

| $L_{A\,i}$ where i is | Ligand subtype | $R^1$ | $R^2$ | $R^3$ | $R^4$ | $R^8$ |
|---|---|---|---|---|---|---|
| 45. | $L_{A\,4-3}$ | 3-Me | H | H | — | — |
| 46. | $L_{A\,5-3}$ | 3-Me | H | H | — | — |
| 47. | $L_{A\,6-3}$ | 3-Me | H | H | — | Ph |
| 48. | $L_{A\,7-3}$ | 3-Me | H | H | Me | — |
| 49. | $L_{A\,1-4}$ | 3-Me | H | H | — | — |
| 50. | $L_{A\,2-4}$ | 3-Me | H | H | — | — |
| 51. | $L_{A\,3-4}$ | 3-Me | H | H | — | — |
| 52. | $L_{A\,4-4}$ | 3-Me | H | H | — | — |
| 53. | $L_{A\,5-4}$ | 3-Me | H | H | — | — |
| 54. | $L_{A\,6-4}$ | 3-Me | H | H | — | Ph |
| 55. | $L_{A\,7-4}$ | 3-Me | H | H | Me | — |
| 56. | $L_{A\,1-5}$ | 3-Me | 9-Me | H | — | — |
| 57. | $L_{A\,1-5}$ | 4-Me | 9-Me | H | — | — |
| 58. | $L_{A\,1-5}$ | 3-Me | H | 10-Me | — | — |
| 59. | $L_{A\,1-5}$ | 4-Me | H | 10-Me | — | — |
| 60. | $L_{A\,1-5}$ | 3,4-Me | H | H | — | — |
| 61. | $L_{A\,2-5}$ | 3,4-Me | H | H | — | — |
| 62. | $L_{A\,3-5}$ | 3,4-Me | H | H | — | — |
| 63. | $L_{A\,3-5}$ | 3,4-Me | 9-Me | H | — | — |
| 64. | $L_{A\,3-5}$ | 3,4-Me | 8-Me | H | — | — |
| 65. | $L_{A\,3-5}$ | 3,4-Me | H | 10-Me | — | — |
| 66. | $L_{A\,4-5}$ | 3,4-Me | H | H | — | — |
| 67. | $L_{A\,5-5}$ | 3,4-Me | H | H | — | — |
| 68. | $L_{A\,6-5}$ | 3,4-Me | H | H | — | Ph |
| 69. | $L_{A\,7-5}$ | 3,4-Me | H | H | Me | — |
| 70. | $L_{A\,1-6}$ | 3-Me | 8-Me | H | — | — |
| 71. | $L_{A\,1-6}$ | 4-Me | 8-Me | H | — | — |
| 72. | $L_{A\,1-6}$ | 3,4-Me | 8-Me | H | — | — |
| 73. | $L_{A\,1-6}$ | 3-$CH_2CMe_3$ | 8-Me | H | — | — |
| 74. | $L_{A\,1-6}$ | 4-$CH_2CMe_3$ | 8-Me | H | — | — |
| 75. | $L_{A\,1-6}$ | 4-Me | H | 5-Me | — | — |
| 76. | $L_{A\,1-6}$ | 4-Me | 8-Me | 5-Me | — | — |
| 77. | $L_{A\,1-6}$ | 4-Me | 8-Me | 5-Ph | — | — |
| 78. | $L_{A\,1-7}$ | 3-Me | H | H | — | — |
| 79. | $L_{A\,1-7}$ | 4-Me | H | H | — | — |
| 80. | $L_{A\,1-7}$ | 3,4-Me | H | H | — | — |
| 81. | $L_{A\,1-7}$ | 3-$CH_2CMe_3$ | H | H | — | — |
| 82. | $L_{A\,1-7}$ | 4-$CH_2CMe_3$ | H | H | — | — |
| 83. | $L_{A\,1-7}$ | 4-Me | 7,9-Me | H | — | — |
| 84. | $L_{A\,1-8}$ | 3-Me | H | H | — | — |
| 85. | $L_{A\,1-8}$ | 4-Me | H | 5-Me | — | — |
| 86. | $L_{A\,1-8}$ | 3,4-Me | H | H | — | — |
| 87. | $L_{A\,1-8}$ | 3-$CH_2CMe_3$ | H | H | — | — |
| 88. | $L_{A\,1-8}$ | 4-$CH_2CMe_3$ | H | H | — | — |
| 89. | $L_{A\,1-8}$ | Me | 8-Me | 5-Me | — | — |
| 90. | $L_{A\,1-8}$ | Me | 8-Me | H | — | — |
| 91. | $L_{A\,1-9}$ | Me | H | H | — | — |
| 92. | $L_{A\,2-9}$ | Me | H | H | — | — |
| 93. | $L_{A\,3-9}$ | Me | H | H | — | — |
| 94. | $L_{A\,4-9}$ | Me | H | H | — | — |
| 95. | $L_{A\,5-9}$ | Me | H | H | — | — |
| 96. | $L_{A\,6-9}$ | Me | H | H | — | Ph |
| 97. | $L_{A\,1-10}$ | Me | H | H | — | — |
| 98. | $L_{A\,2-10}$ | Me | H | H | — | — |
| 99. | $L_{A\,3-10}$ | Me | H | H | — | — |
| 100. | $L_{A\,4-10}$ | Me | H | H | — | — |
| 101. | $L_{A\,5-10}$ | Me | H | H | — | — |
| 102. | $L_{A\,6-10}$ | Me | H | H | — | Ph |
| 103. | $L_{A\,1-11}$ | Me | H | H | — | — |
| 104. | $L_{A\,2-11}$ | Me | H | H | — | — |
| 105. | $L_{A\,3-11}$ | Me | H | H | — | — |
| 106. | $L_{A\,4-11}$ | Me | H | H | — | — |
| 107. | $L_{A\,6-11}$ | Me | H | H | — | Ph |
| 108. | $L_{A\,1-12}$ | Me | H | H | — | — |
| 109. | $L_{A\,2-12}$ | Me | H | H | — | — |
| 110. | $L_{A\,3-12}$ | Me | H | H | — | — |
| 111. | $L_{A\,4-12}$ | Me | H | H | — | — |
| 112. | $L_{A\,5-12}$ | Me | H | H | — | — |
| 113. | $L_{A\,6-12}$ | Me | H | H | — | Ph |
| 114. | $L_{A\,1-13}$ | Me | 8-Me | H | — | — |
| 115. | $L_{A\,1-14}$ | Me | 7,9-Me | H | — | — |
| 116. | $L_{A\,1-15}$ | Me | 8-Me | H | — | — |
| 117. | $L_{A\,1-16}$ | Me | 8-Me | H | — | — |
| 118. | $L_{A\,1-17}$ | Me | H | 4-Me | — | — |
| 119. | $L_{A\,1-18}$ | 4-Me | H | H | — | — |
| 120. | $L_{A\,1-19}$ | 4-Me | H | H | — | — |

-continued

| $L_{A\ i}$ where i is | Ligand subtype | $R^1$ | $R^2$ | $R^3$ | $R^4$ | $R^8$ |
|---|---|---|---|---|---|---|
| 121. | $L_{A\ 1\text{-}20}$ | 3-Me | H | H | — | — |
| 122. | $L_{A\ 1\text{-}21}$ | 3-Me | H | H | — | — |

For clarity, in the above table, ligand $L_{A1}$ is based on ligand $L_{A1\text{-}1}$,

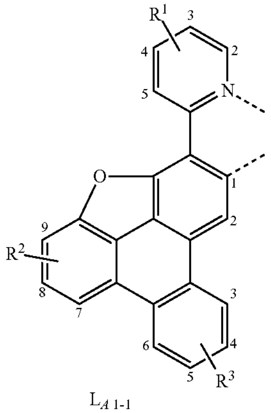

$L_{A\ 1\text{-}1}$ and the atom labeled 3 on the $R^1$ ring is methyl, while all other atoms or $R^1$, $R^2$, and $R^3$ are H. Similarly, $L_{A2}$ is based on ligand $L_{A1\text{-}1}$,

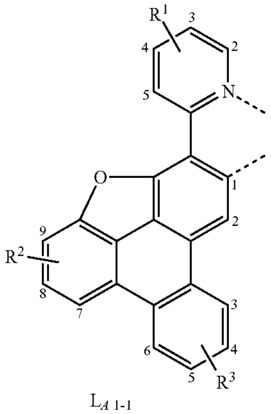

$L_{A\ 1\text{-}1}$ the atom labeled 3 on the $R^1$ ring is methyl, the atom labeled 8 on the $R^2$ ring is methyl, while all other atoms or $R^1$, $R^2$, and $R^3$ are H.

In some embodiments, the compound has a formula of $M(L_A)_x(L_B)_y(L_C)_z$ where each one of $L_B$ and $L_C$ is a bidentate ligand; where x is 1, 2, or 3; y is 0, 1, or 2; z is 0, 1, or 2; and x+y+z is the oxidation state of the metal M. In some such embodiments, the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; and $L_A$, $L_B$, and $L_C$ are different from each other.

In some embodiments, the compound has a formula of $Pt(L_A)(L_B)$, and $L_A$ and $L_B$ can be same or different. In some such embodiments, $L_A$ and $L_B$ are connected to form a tetradentate ligand. In some such embodiments, $L_A$ and $L_B$ are connected at two places to form a macrocyclic tetradentate ligand.

In some embodiments where the compound has a structure of $M(L_A)_x(L_B)_y(L_C)_z$, ligands $L_B$ and $L_C$ are each independently selected from the group consisting of:

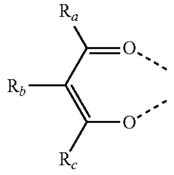

,

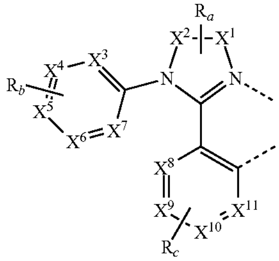

,

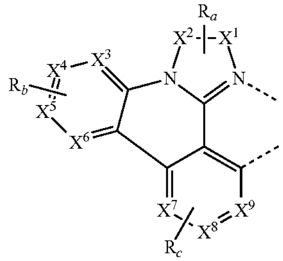

,

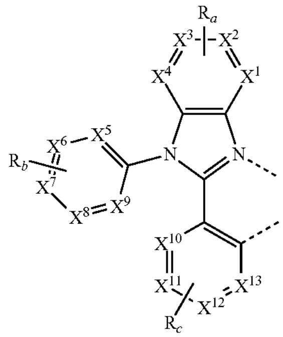

,

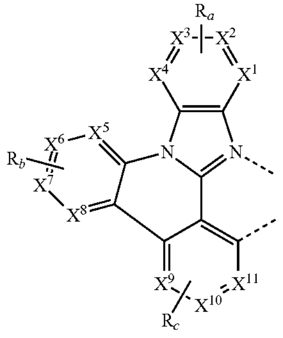

,

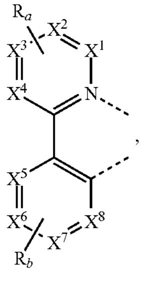

,

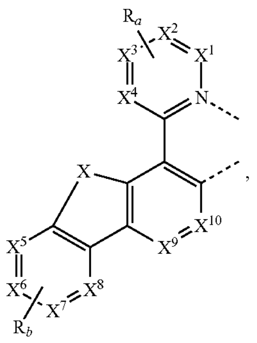

,

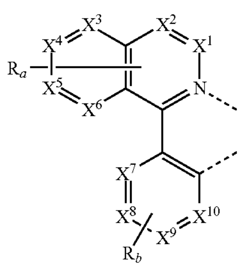

,

-continued

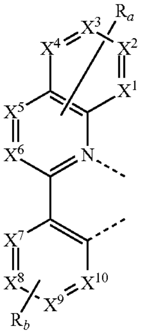

,

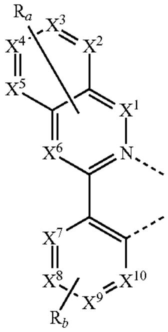

,

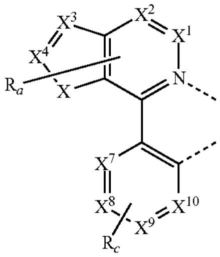

,

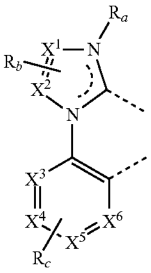

,

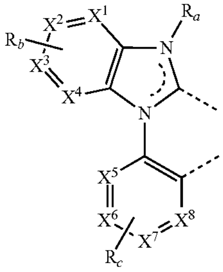

,

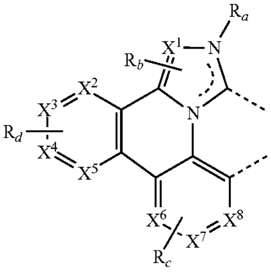

,

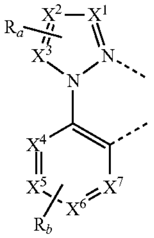

,

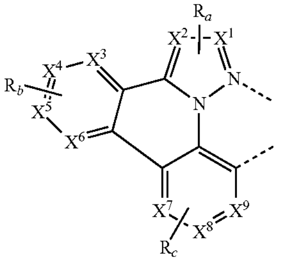

,

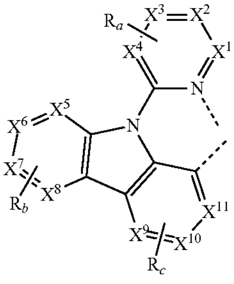

,

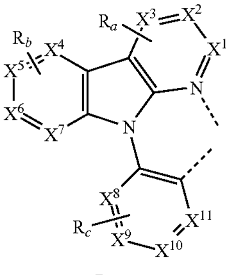

, and

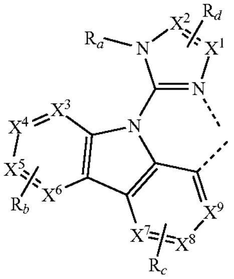

, where:

each $X^1$ to $X^{13}$ are independently selected from the group consisting of carbon and nitrogen;

X is selected from the group consisting of BR', NR', PR', O, S, Se, C═O, S═O, $SO_2$, CR'R", SiR'R", and GeR'R";

R' and R" are optionally fused or joined to form a ring;

each $R_a$, $R_b$, $R_c$, and $R_d$ may represent from mono substitution to the possible maximum number of substitution, or no substitution;

R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any two adjacent substitutents of $R_a$, $R_b$, $R_c$, and $R_d$ are optionally fused or joined to form a ring or form a multidentate ligand.

In some embodiments where the compound has a structure of $M(L_A)_x(L_B)_y(L_C)_z$, ligands $L_B$ and $L_C$ are each independently selected from the group consisting of:

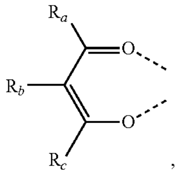

,

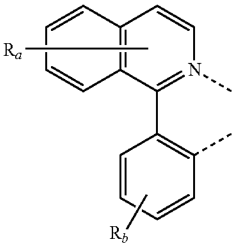

,

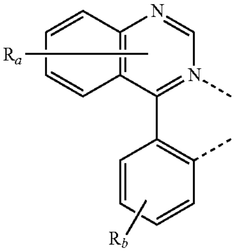

,

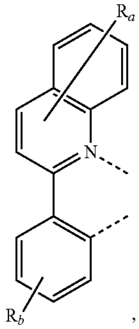

,

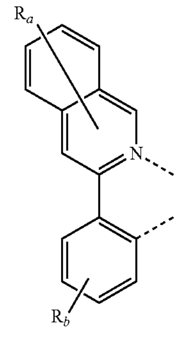

,

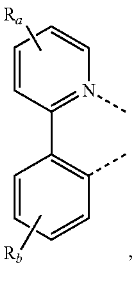

,

-continued
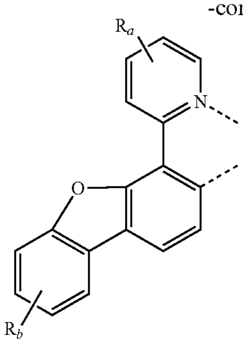
,
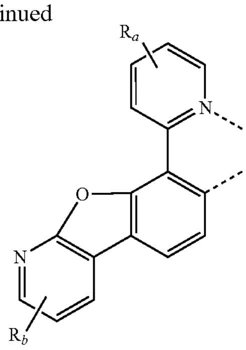
,
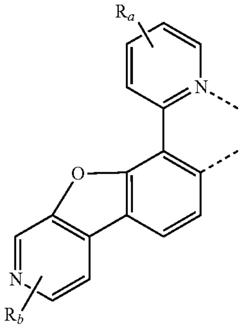
,
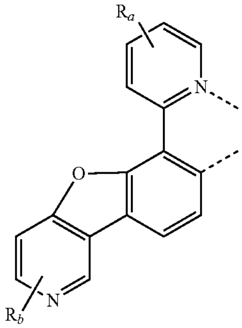
,
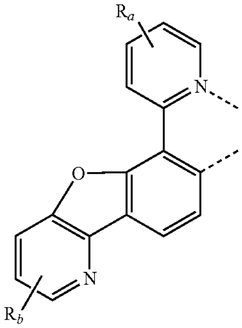
,
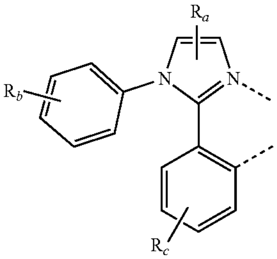
,
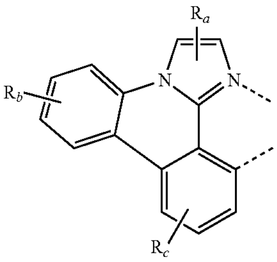
,
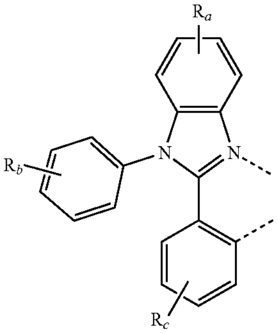
,
-continued
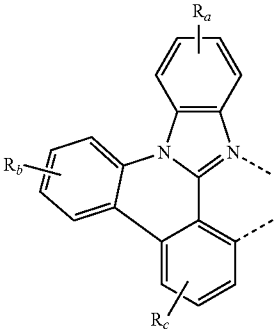
,
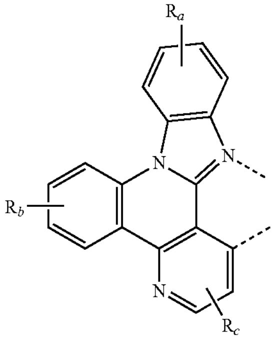
,
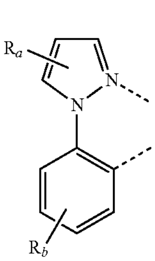
,
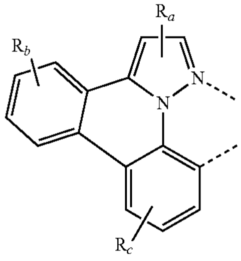
,
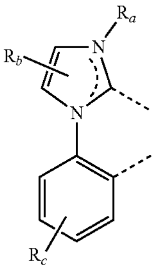
,
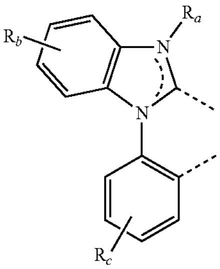
,
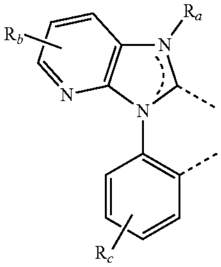
,
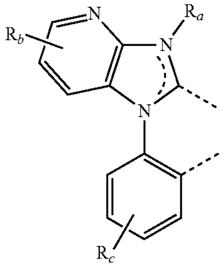
, -continued

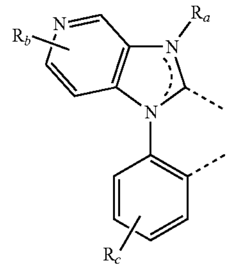
,
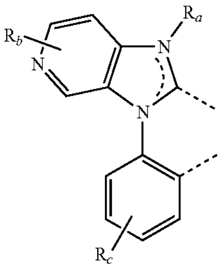
,
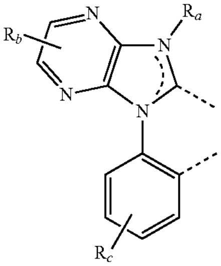
,
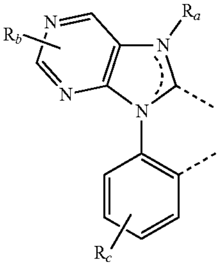
,
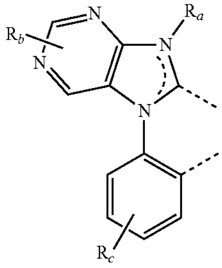
, and
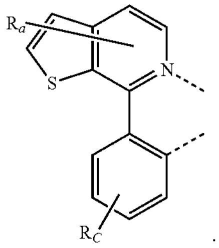
.

In some embodiments, the compound is Compound Ax having the formula $Ir(L_{Ai})_3$, Compound By having the formula $Ir(L_{Ai})(L_{Bk})_2$, or Compound Cz having the formula $Ir(L_{Ai})_2(L_{Cj})$. In such embodiments, x=i, y=468i+k−468, and z=1260j+j−1260; where i is an integer from 1 to 122, k is an integer from 1 to 468, and j is an integer from 1 to 1260. In such embodiments, $L_{Bk}$ has the following structures:

$L_{B1}$

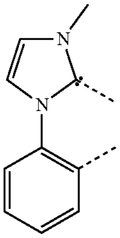
, $L_{B2}$

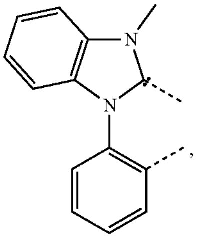
,

-continued $L_{B3}$

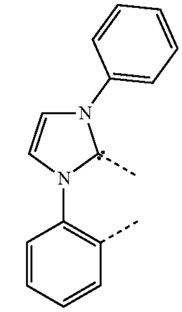
, $L_{B4}$

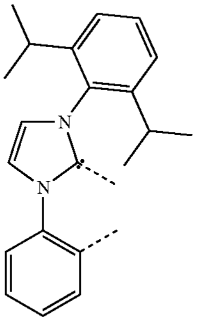
, $L_{B5}$

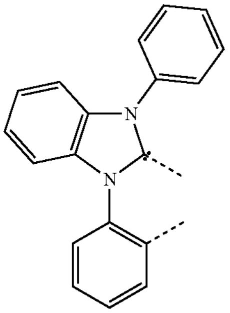
, $L_{B6}$

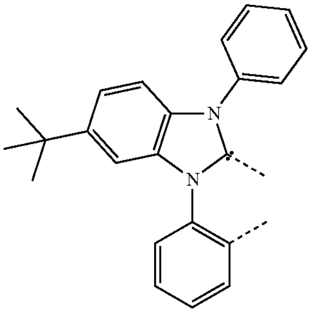
, $L_{B7}$

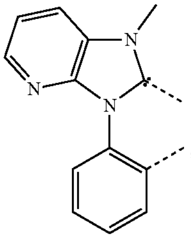
,

-continued
$L_{B8}$
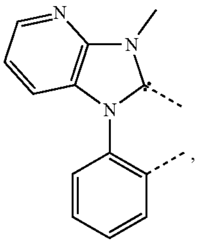
$L_{B9}$
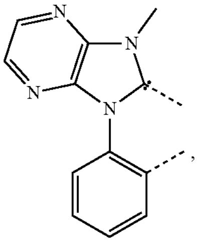
$L_{B10}$
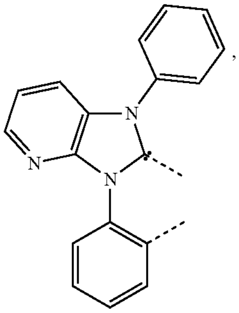
$L_{B11}$
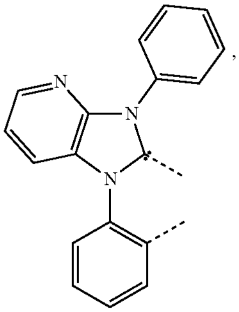
$L_{B12}$
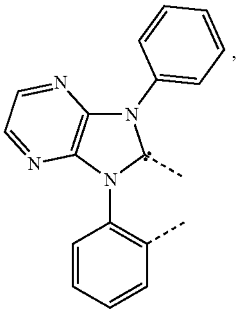
-continued
$L_{B13}$
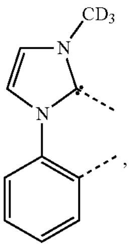
$L_{B14}$
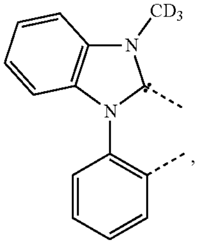
$L_{B15}$
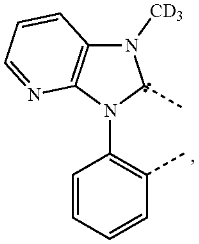
$L_{B16}$
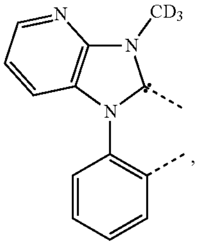
$L_{B17}$
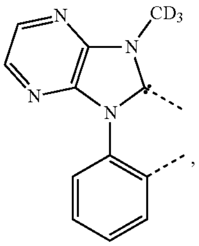
$L_{B18}$
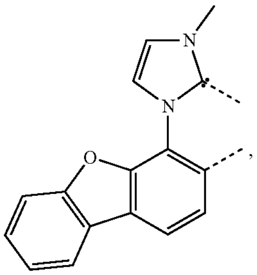

-continued
$L_{B19}$
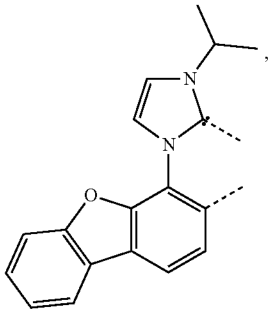
$L_{B20}$
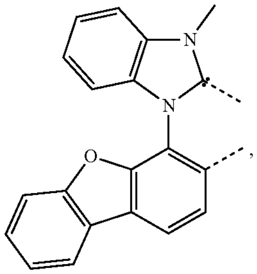
$L_{B21}$
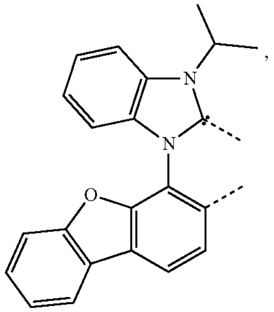
$L_{B22}$
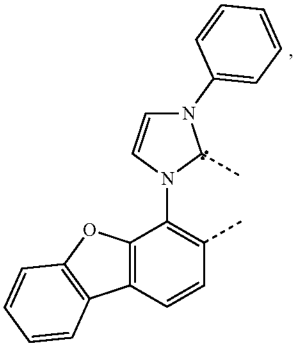
$L_{B23}$
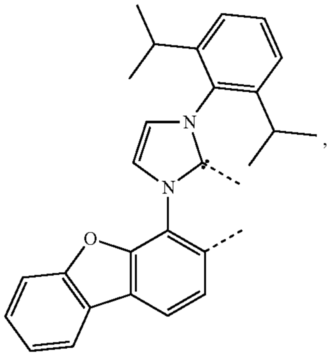
-continued
$L_{B24}$
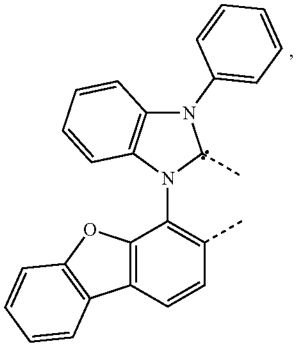
$L_{B25}$
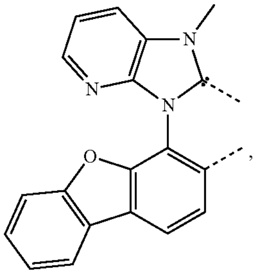
$L_{B26}$
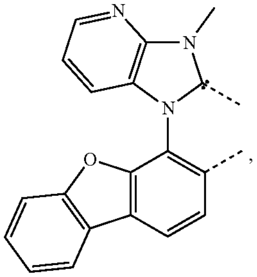
$L_{B27}$
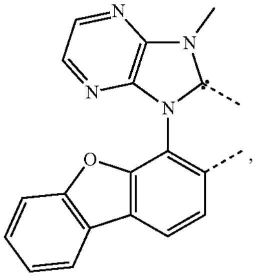
$L_{B28}$
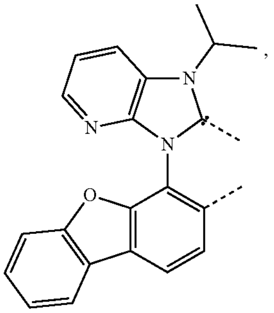

-continued
$L_{B29}$
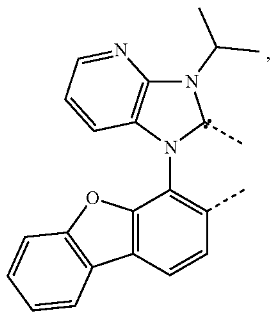
$L_{B30}$
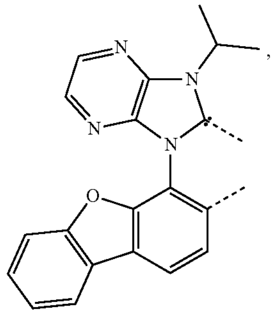
$L_{B31}$
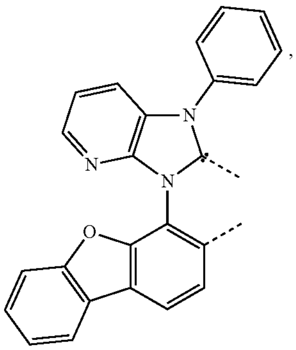
$L_{B32}$
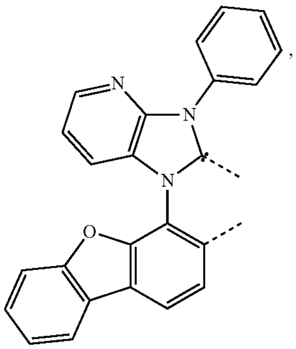
-continued
$L_{B33}$
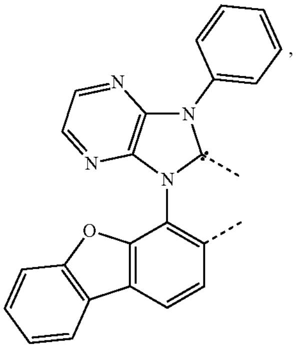
$L_{B34}$
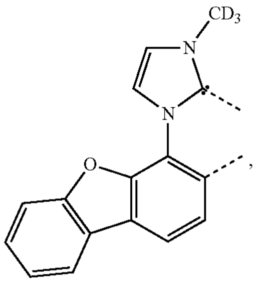
$L_{B35}$
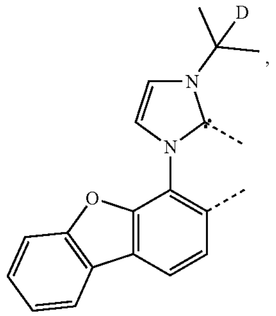
$L_{B36}$
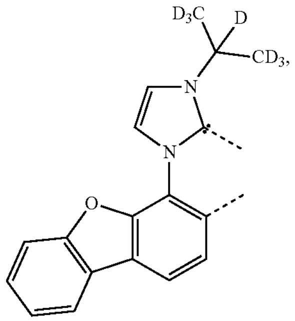
$L_{B37}$
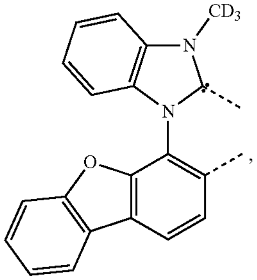

-continued
$L_{B38}$
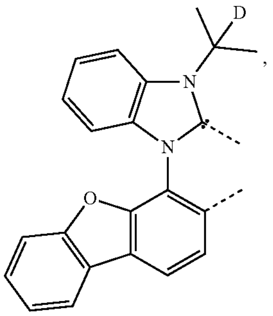
$L_{B39}$
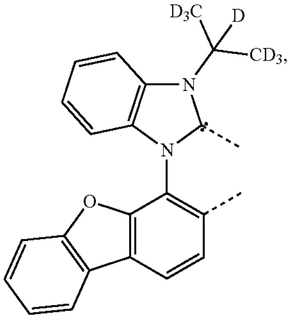
$L_{B40}$
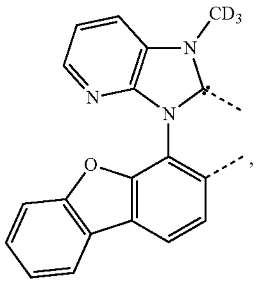
$L_{B41}$
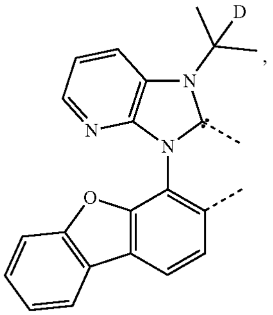
$L_{B42}$
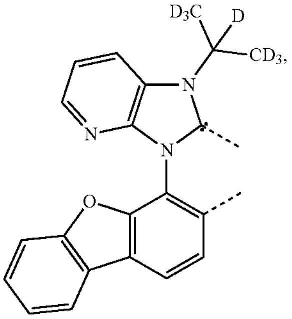
-continued
$L_{B43}$
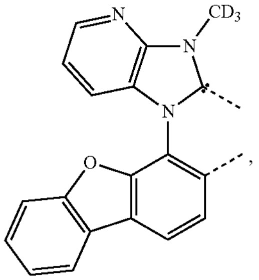
$L_{B44}$
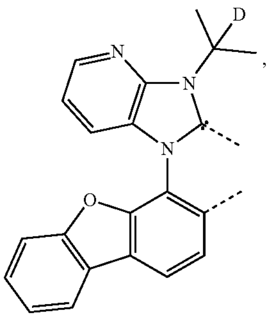
$L_{B45}$
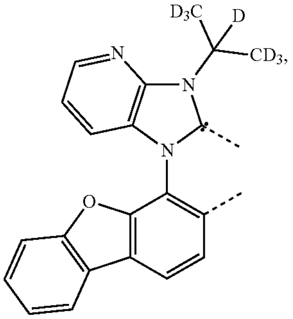
$L_{B46}$
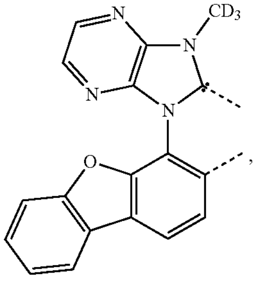
$L_{B47}$
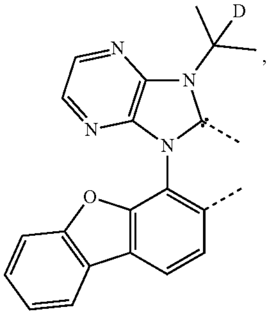

-continued
$L_{B48}$
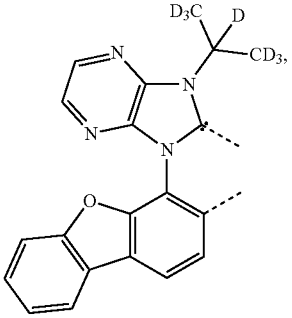
$L_{B49}$
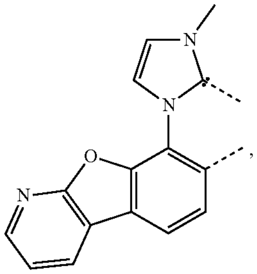
,
$L_{B50}$
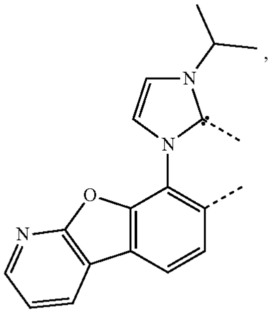
,
$L_{B51}$
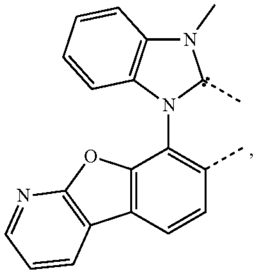
,
$L_{B52}$
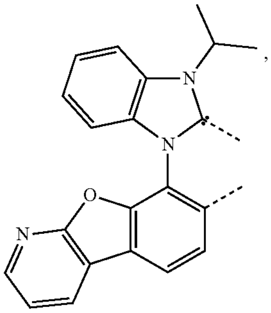
,
-continued
$L_{B53}$
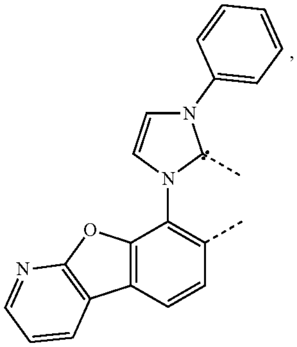
,
$L_{B54}$
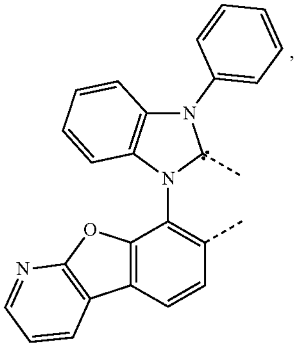
,
$L_{B55}$
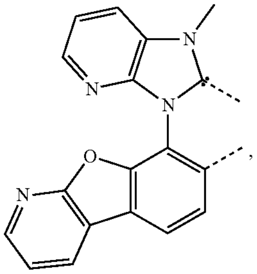
,
$L_{B56}$
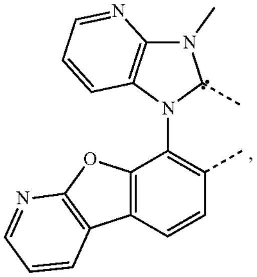
,
$L_{B57}$
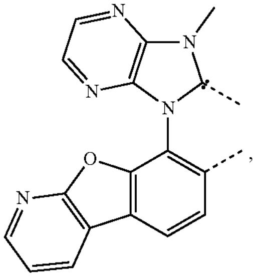
, -continued
L$_{B58}$
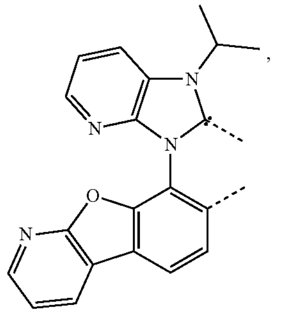
L$_{B59}$
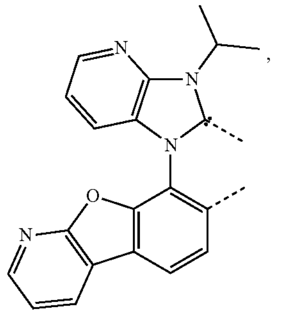
L$_{B60}$
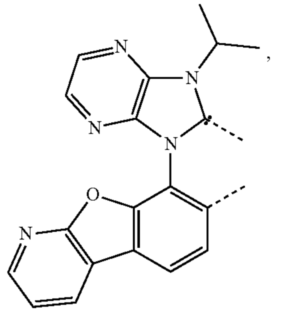
L$_{B61}$
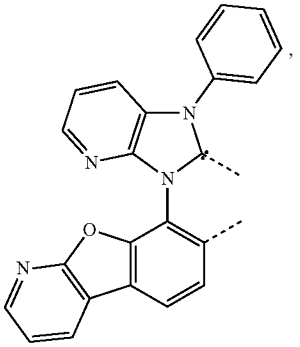
-continued
L$_{B62}$
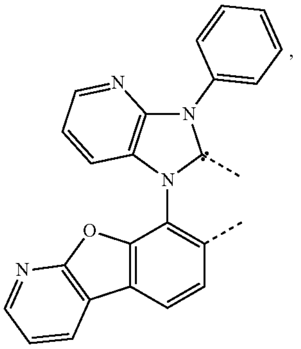
L$_{B63}$
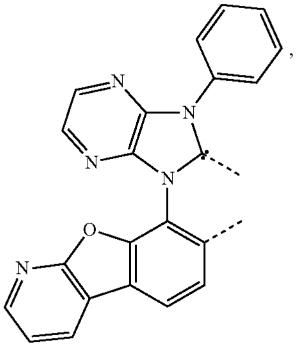
L$_{B64}$
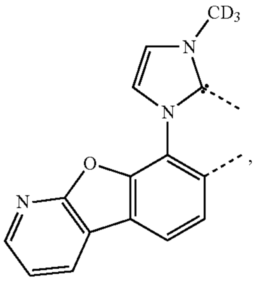
L$_{B65}$
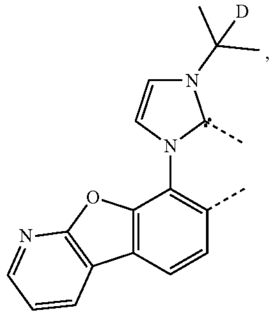
L$_{B66}$
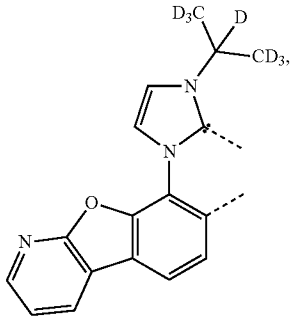

-continued
$L_{B67}$
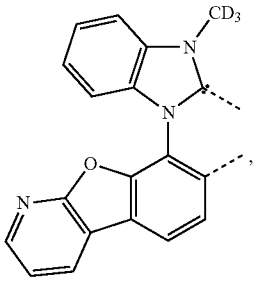
$L_{B68}$
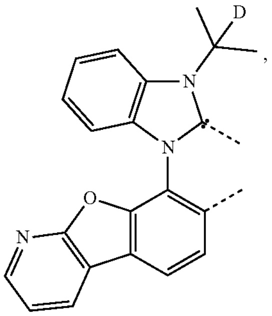
$L_{B69}$
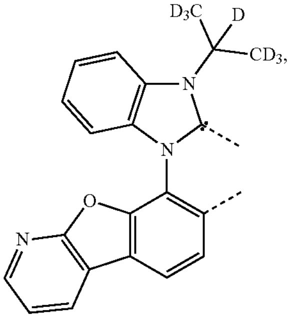
$L_{B70}$
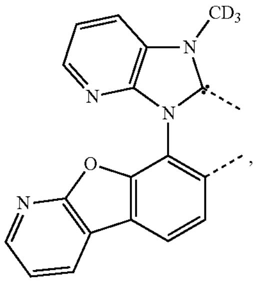
$L_{B71}$
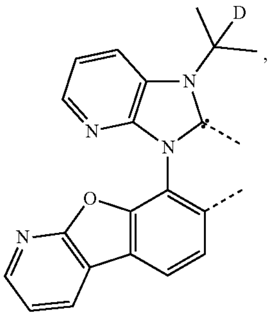
-continued
$L_{B72}$
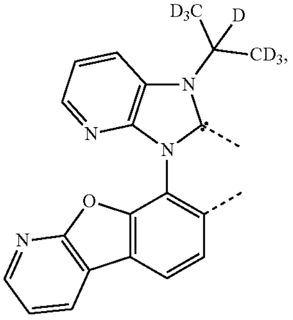
$L_{B73}$
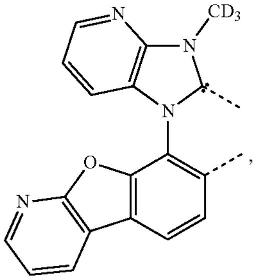
$L_{B74}$
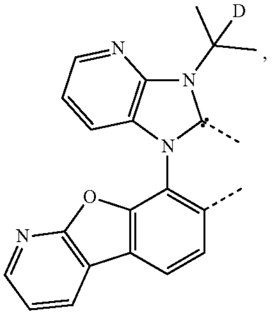
$L_{B75}$
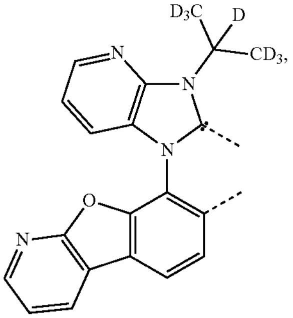
$L_{B76}$
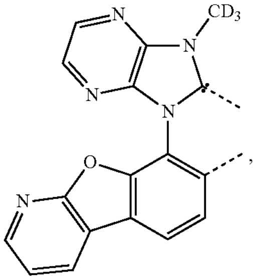

-continued
$L_{B77}$
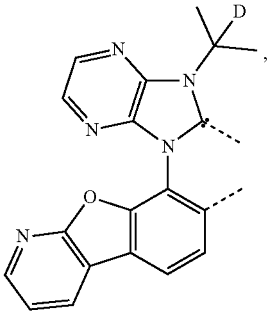
$L_{B78}$
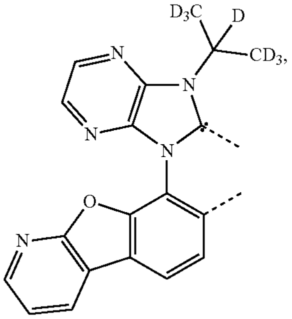
$L_{B79}$
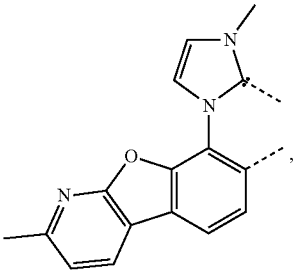
$L_{B80}$
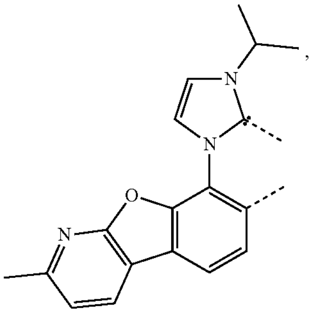
$L_{B81}$
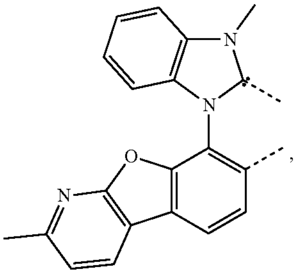
-continued
$L_{B82}$
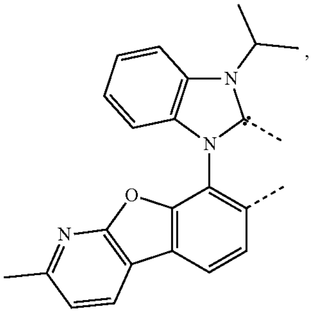
$L_{B83}$
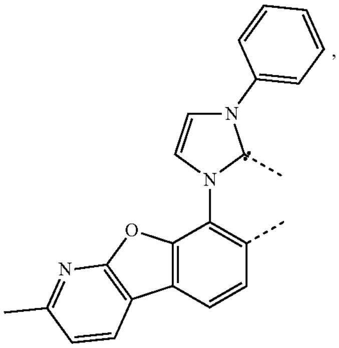
$L_{B84}$
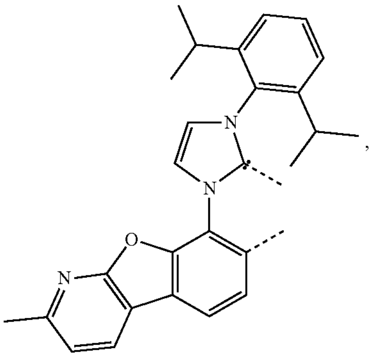
$L_{B85}$
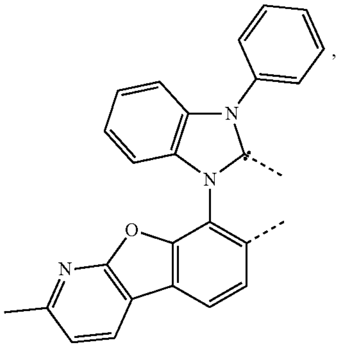

$L_{B86}$
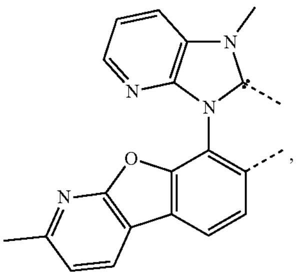
$L_{B87}$
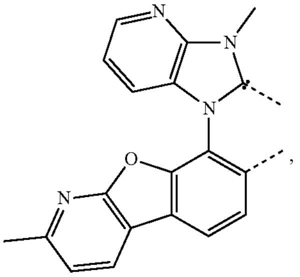
$L_{B88}$
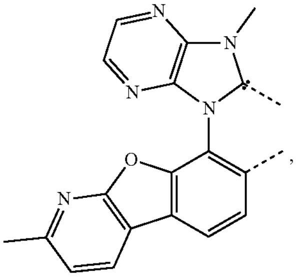
$L_{B89}$
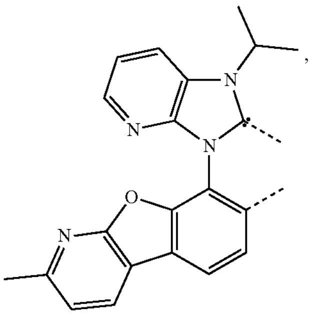
$L_{B90}$
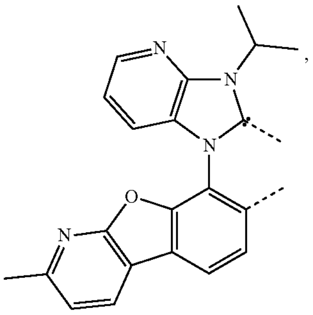
$L_{B91}$
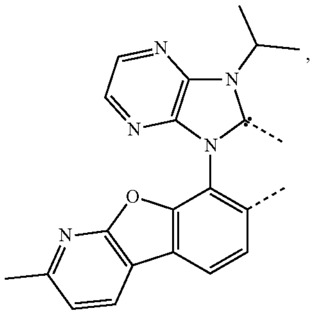
$L_{B92}$
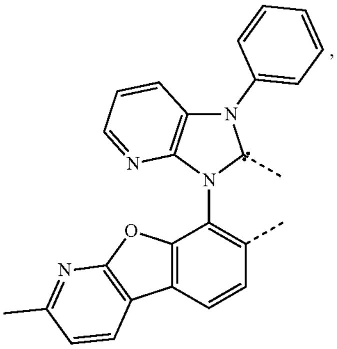
$L_{B93}$
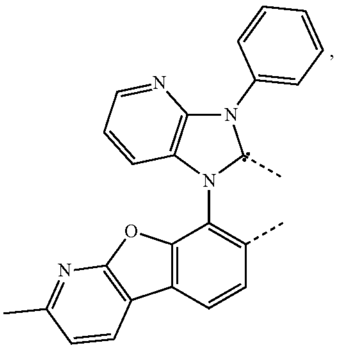
$L_{B94}$
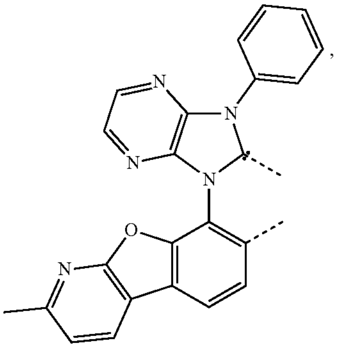

-continued
$L_{B95}$
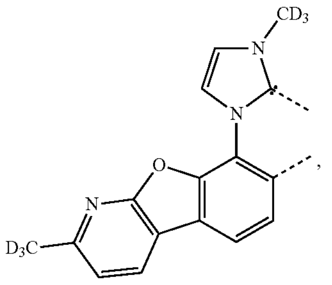
$L_{B96}$
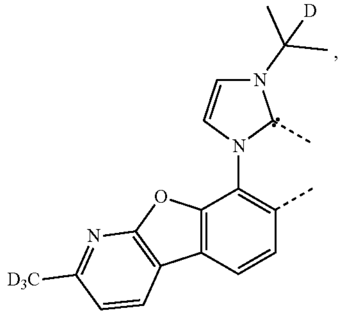
$L_{B97}$
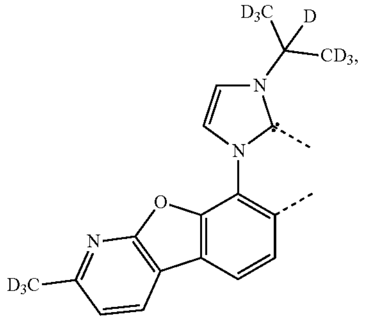
$L_{B98}$
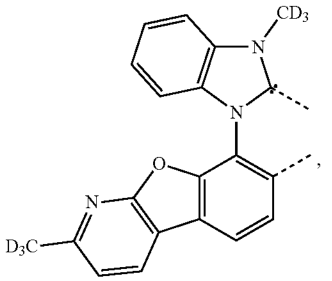
$L_{B99}$
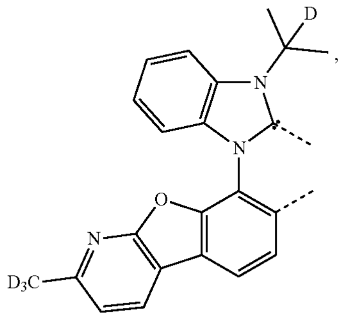
-continued
$L_{B100}$
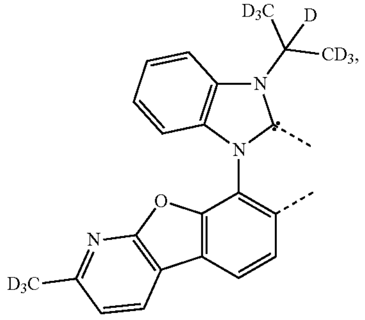
$L_{B101}$
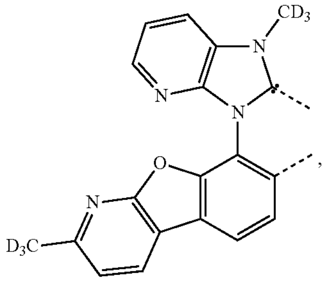
$L_{B102}$
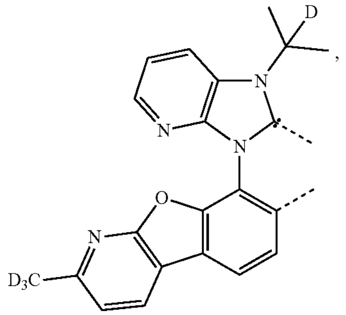
$L_{B103}$
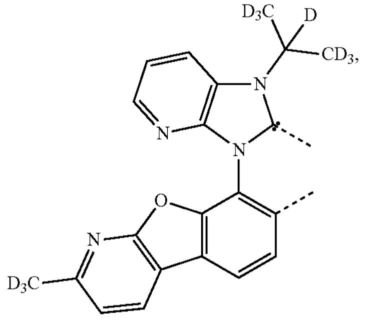
$L_{B104}$
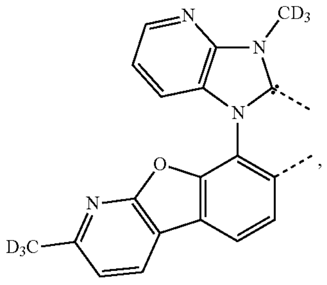

-continued
$L_{B105}$
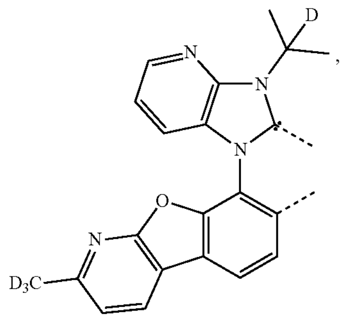
$L_{B106}$
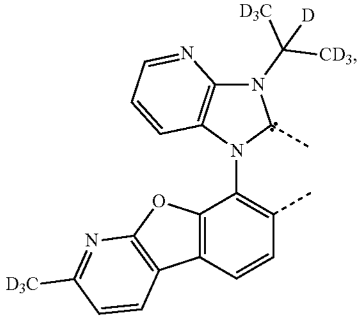
$L_{B107}$
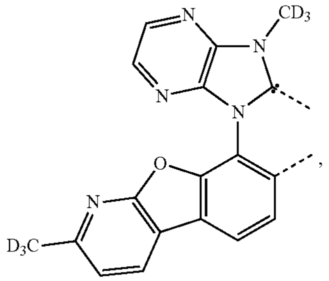
$L_{B108}$
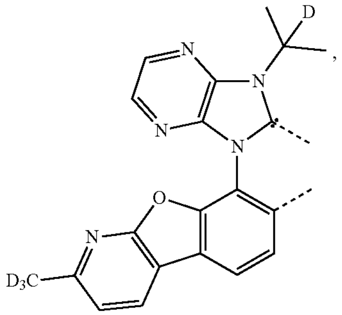
$L_{B109}$
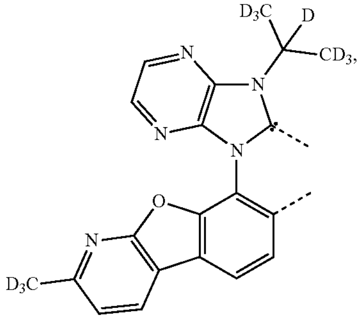
-continued
$L_{B110}$
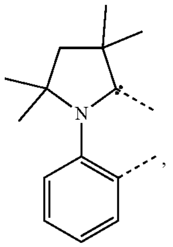
$L_{B111}$
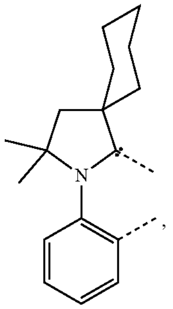
$L_{B112}$
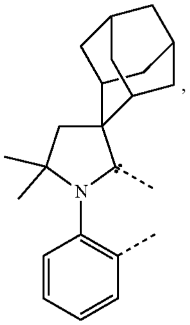
$L_{B113}$
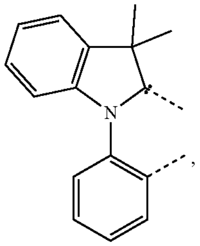
$L_{B114}$
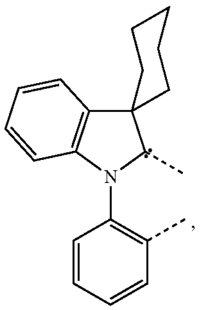

-continued
$L_{B115}$
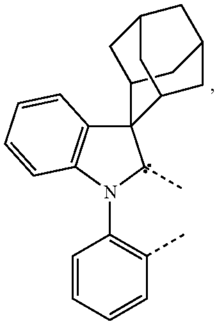
$L_{B116}$
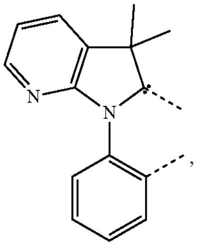
$L_{B117}$
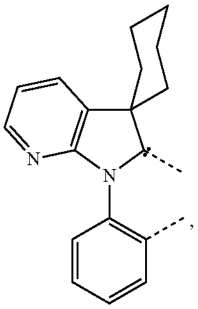
$L_{B118}$
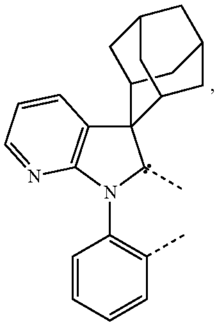
$L_{B119}$
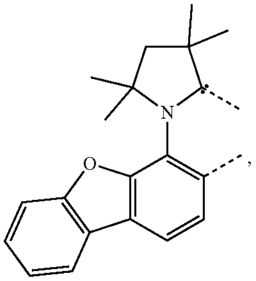
-continued
$L_{B120}$
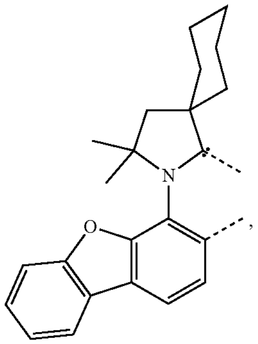
$L_{B121}$
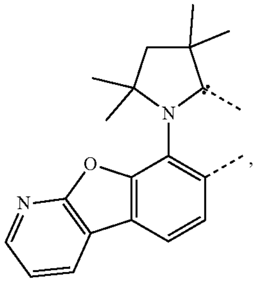
$L_{B122}$
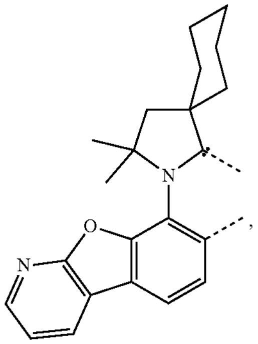
$L_{B123}$
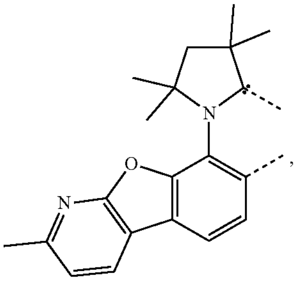
$L_{B124}$
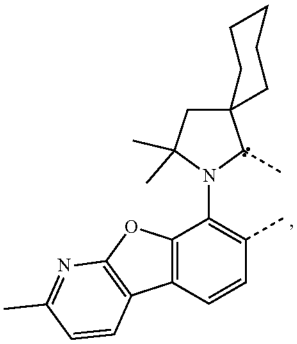

-continued
$L_{B125}$
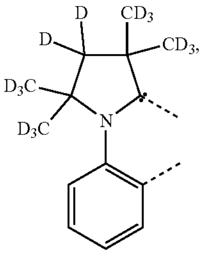
$L_{B126}$
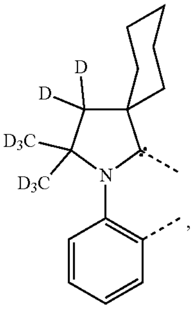
$L_{B127}$
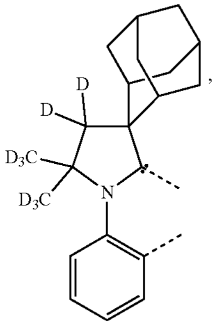
$L_{B128}$
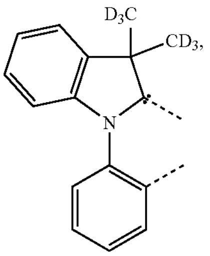
$L_{B129}$
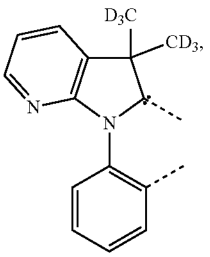
-continued
$L_{B130}$
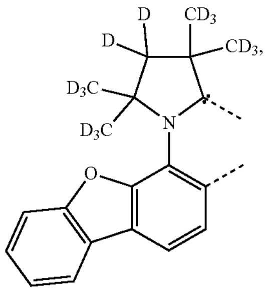
$L_{B131}$
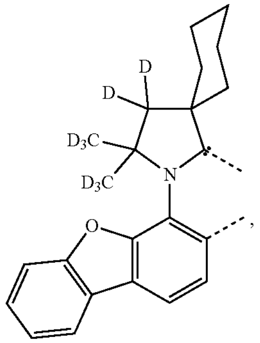
$L_{B132}$
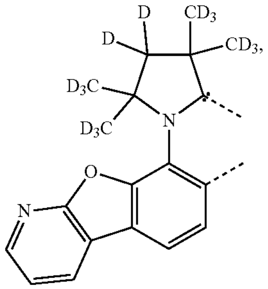
$L_{B133}$
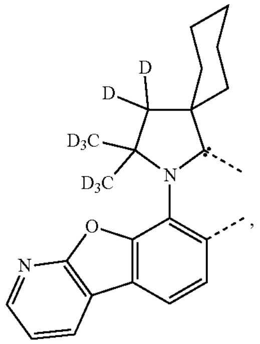
$L_{B134}$
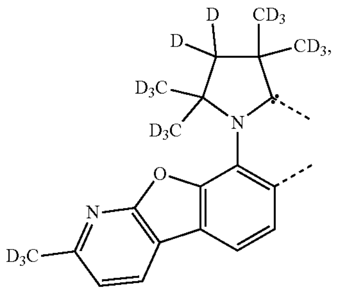

-continued
$L_{B135}$
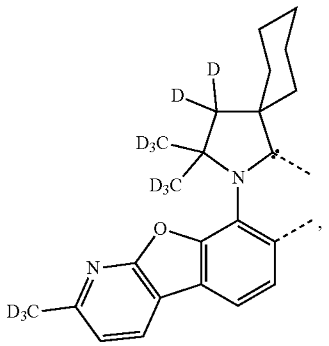
$L_{B136}$
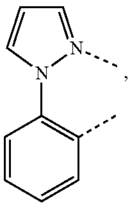
$L_{B137}$
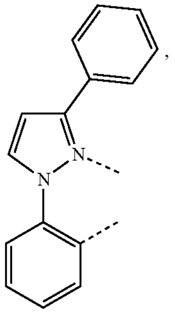
$L_{B138}$
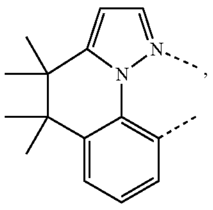
$L_{B139}$
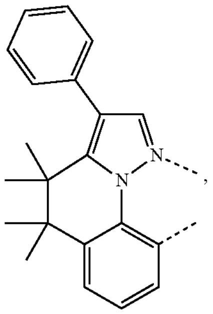
-continued
$L_{B140}$
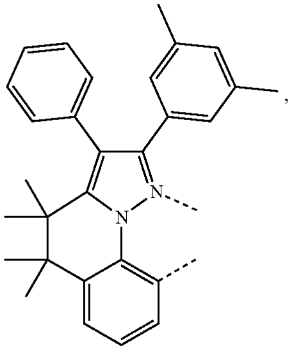
$L_{B141}$
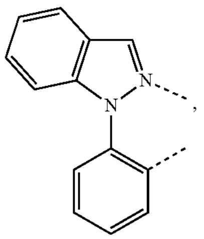
$L_{B142}$
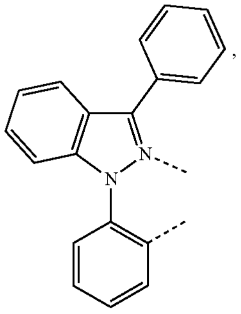
$L_{B143}$
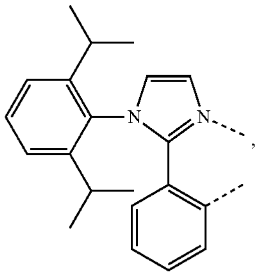
$L_{B144}$
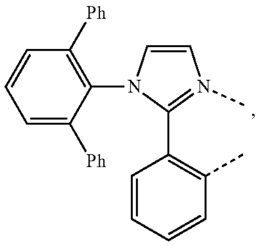

-continued
$L_{B145}$
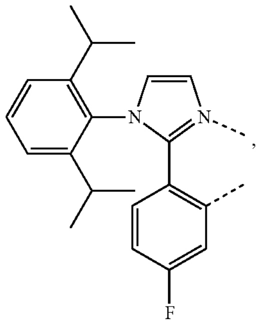
$L_{B146}$
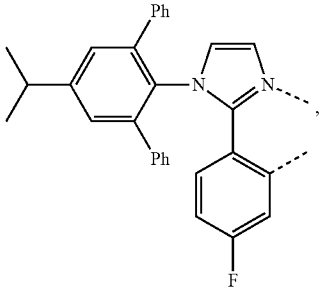
$L_{B147}$
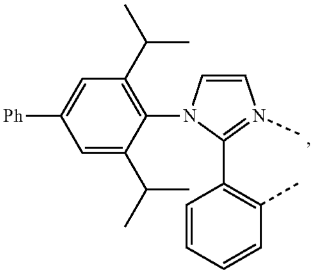
$L_{B148}$
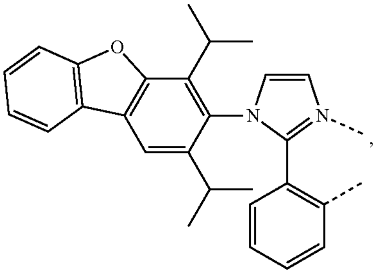
$L_{B149}$
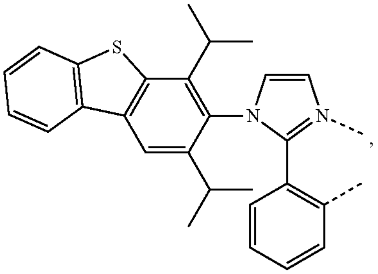
-continued
$L_{B150}$
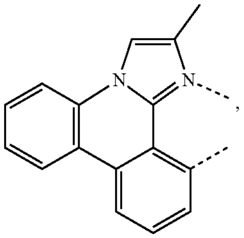
$L_{B151}$
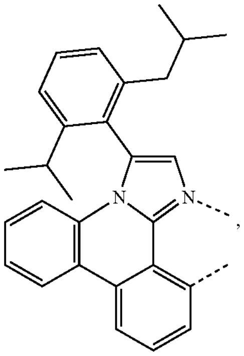
$L_{B152}$
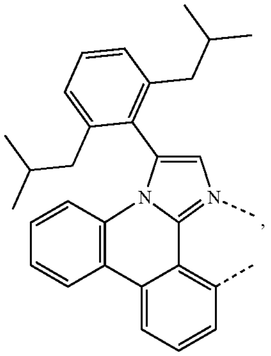
$L_{B153}$
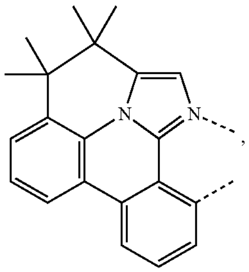
$L_{B154}$
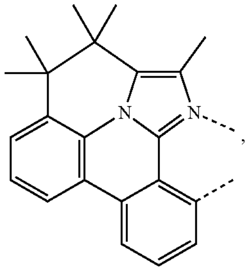

-continued
$L_{B155}$
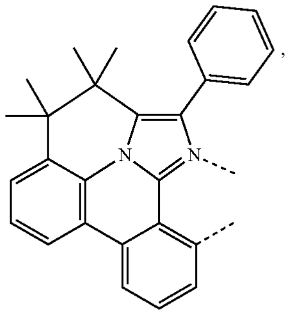
$L_{B156}$
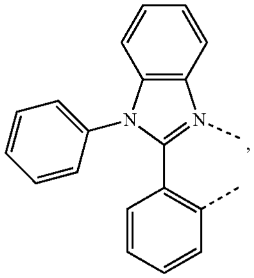
$L_{B157}$
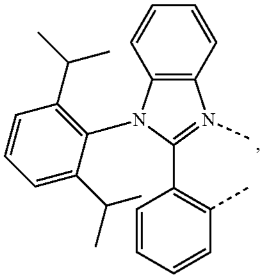
$L_{B158}$
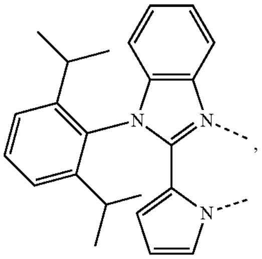
$L_{B159}$
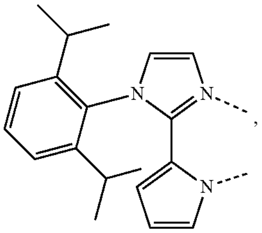
$L_{B160}$
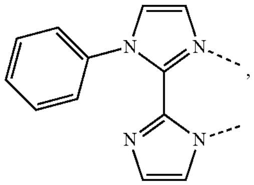
-continued
$L_{B161}$
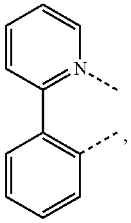
$L_{B162}$
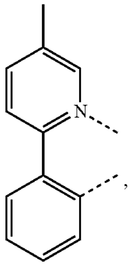
$L_{B163}$
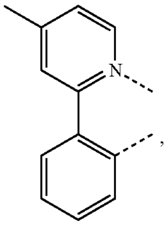
$L_{B164}$
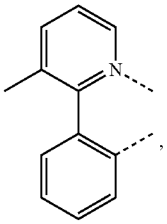
$L_{B165}$
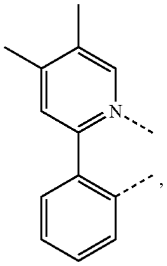
$L_{B166}$
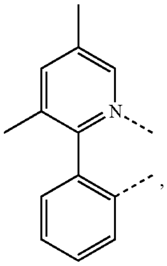

-continued
$L_{B167}$
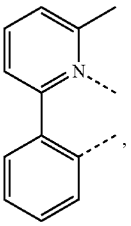
$L_{B168}$
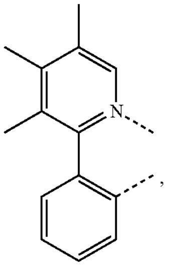
$L_{B169}$
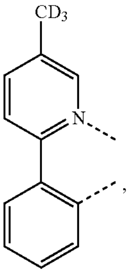
$L_{B170}$
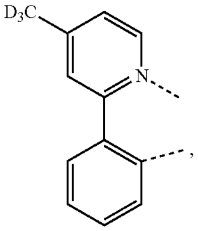
$L_{B171}$
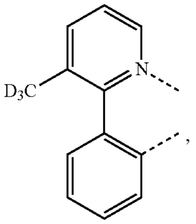
$L_{B172}$
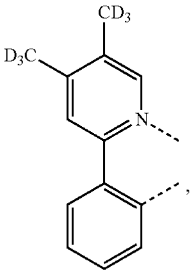
-continued
$L_{B173}$
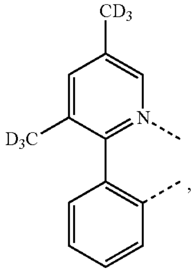
$L_{B174}$
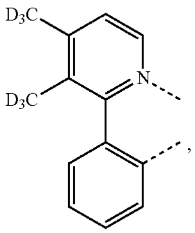
$L_{B175}$
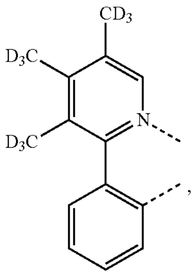
$L_{B176}$
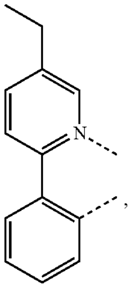
$L_{B177}$
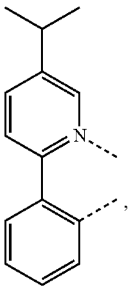

-continued
$L_{B178}$
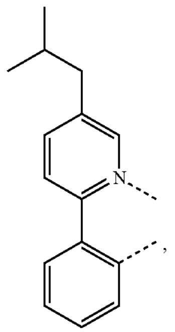
$L_{B179}$
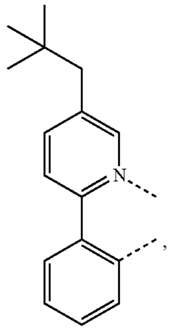
$L_{B180}$
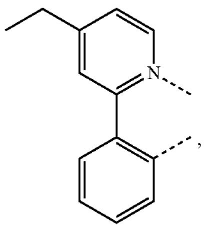
$L_{B181}$
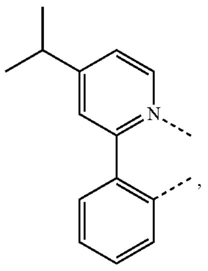
$L_{B182}$
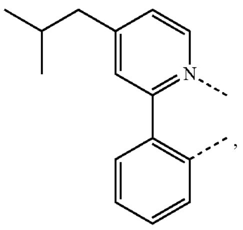
-continued
$L_{B183}$
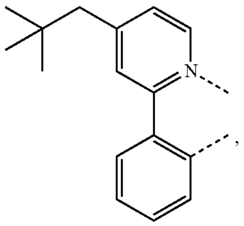
$L_{B184}$
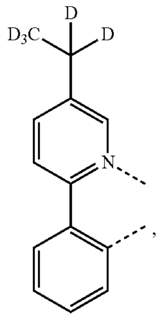
$L_{B185}$
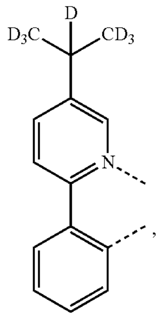
$L_{B186}$
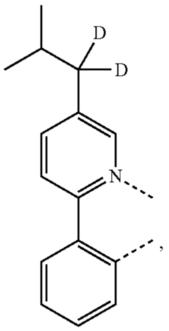
$L_{B187}$
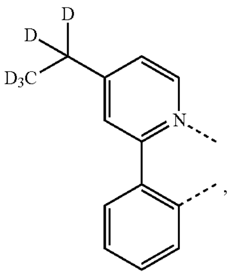

-continued
$L_{B188}$
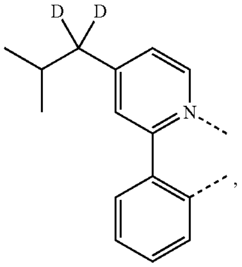
$L_{B189}$
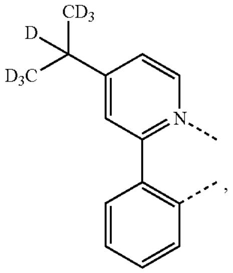
$L_{B190}$
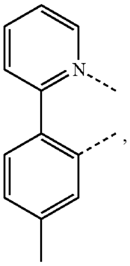
$L_{B191}$
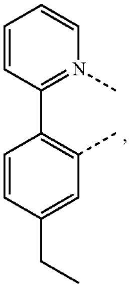
$L_{B192}$
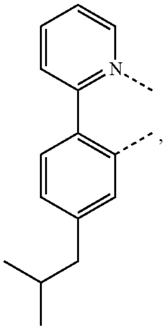
-continued
$L_{B193}$
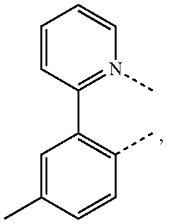
$L_{B194}$
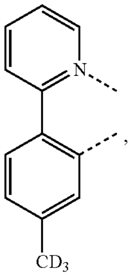
$L_{B195}$
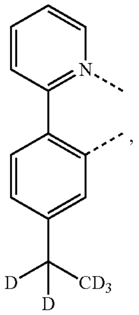
$L_{B196}$
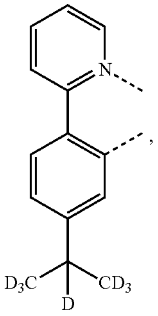
$L_{B197}$
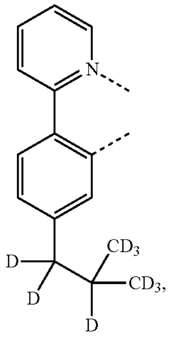

-continued
$L_{B198}$
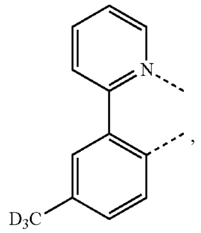
$L_{B199}$
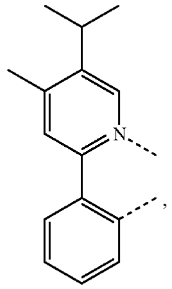
$L_{B200}$
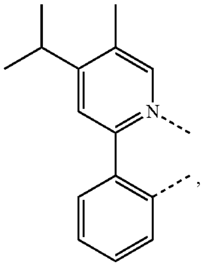
$L_{B201}$
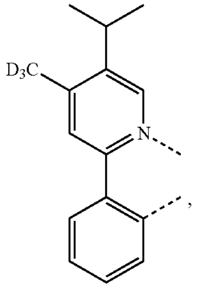
$L_{B202}$
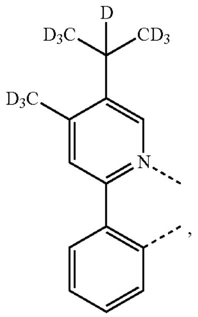
-continued
$L_{B203}$
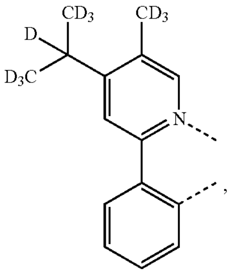
$L_{B204}$
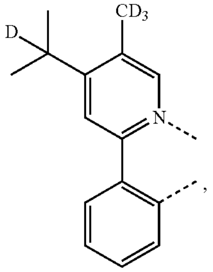
$L_{B205}$
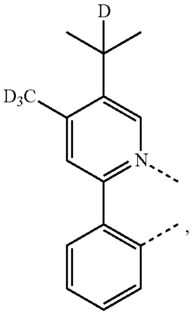
$L_{B206}$
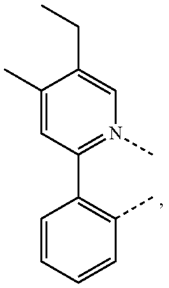
$L_{B207}$
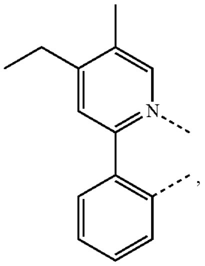

-continued
$L_{B208}$
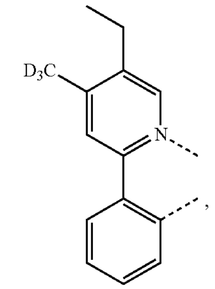
$L_{B209}$
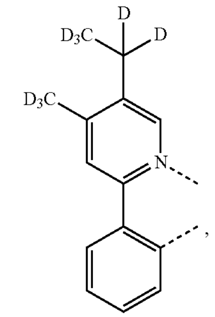
$L_{B210}$
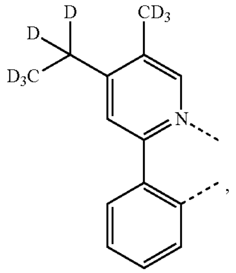
$L_{B211}$
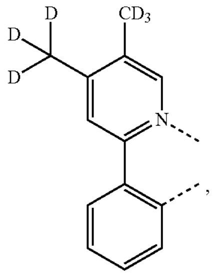
$L_{B212}$
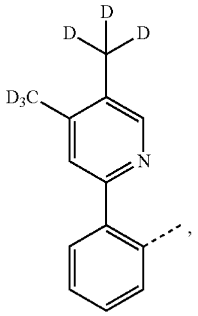
-continued
$L_{B213}$
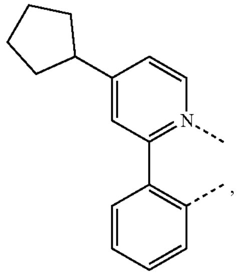
$L_{B214}$
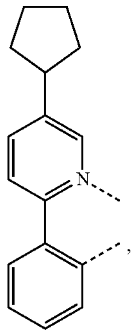
$L_{B215}$
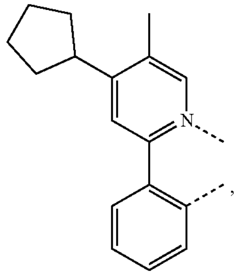
$L_{B216}$
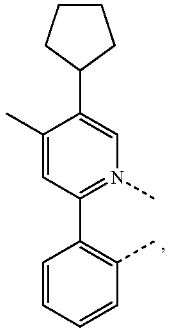
$L_{B217}$
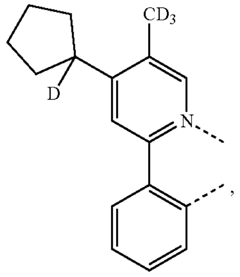

-continued
$L_{B218}$
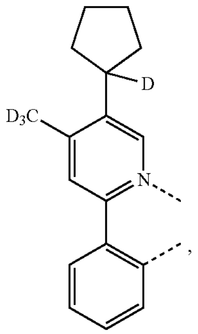
$L_{B219}$
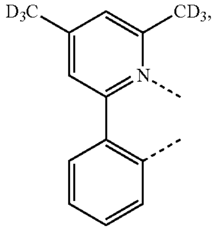
$L_{B220}$
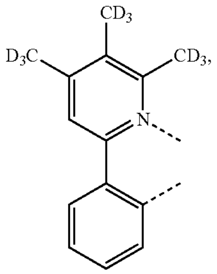
$L_{B221}$
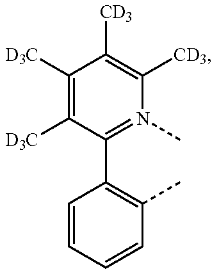
$L_{B222}$
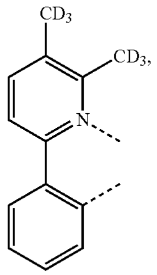
-continued
$L_{B223}$
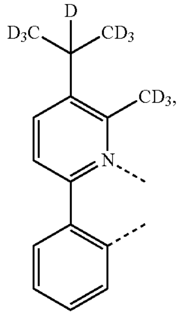
$L_{B224}$
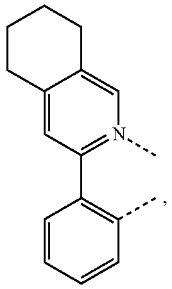
$L_{B225}$
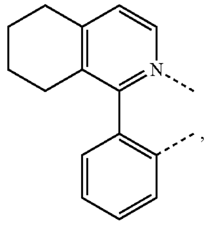
$L_{B226}$
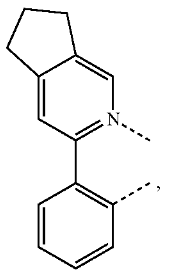
$L_{B227}$
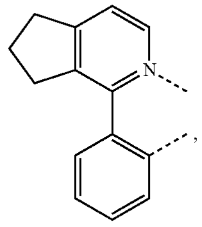

-continued
L$_{B228}$
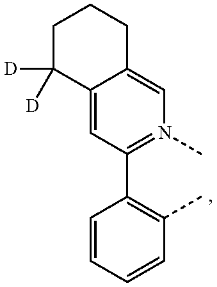
L$_{B229}$
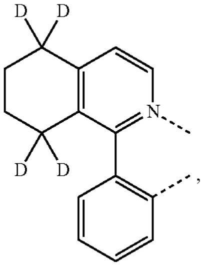
L$_{B230}$
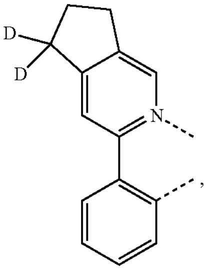
L$_{B231}$
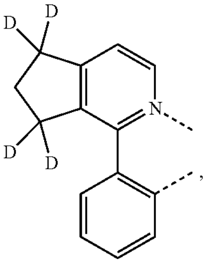
L$_{B232}$
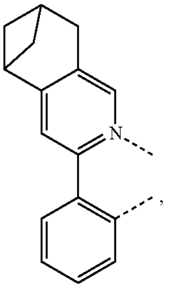
-continued
L$_{B233}$
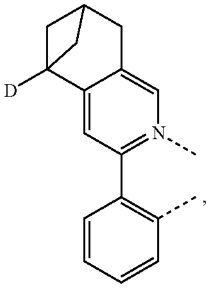
L$_{B234}$
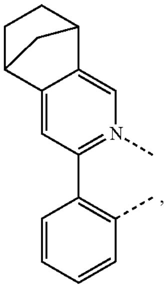
L$_{B235}$
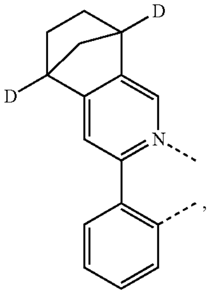
L$_{B236}$
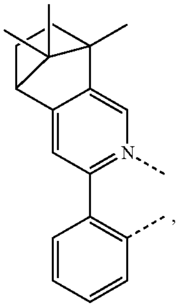
L$_{B237}$
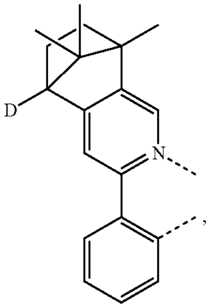

-continued
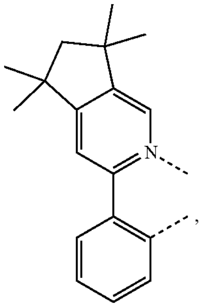
$L_{B238}$
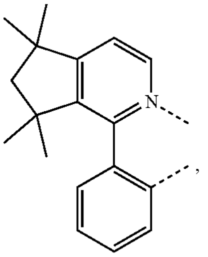
$L_{B239}$
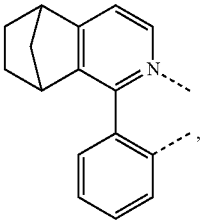
$L_{B240}$
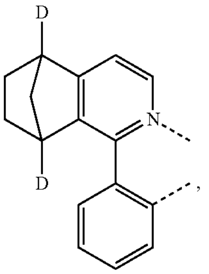
$L_{B241}$
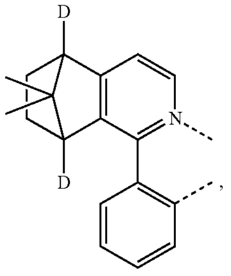
$L_{B242}$
-continued
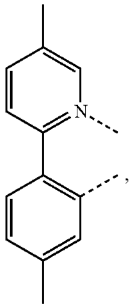
$L_{B243}$
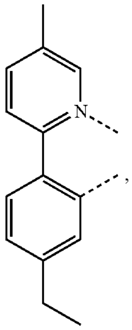
$L_{B244}$
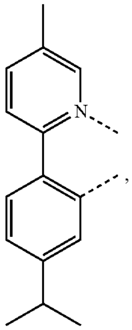
$L_{B245}$
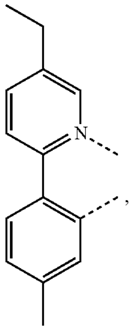
$L_{B246}$ -continued
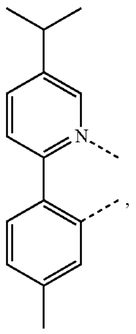
$L_{B247}$
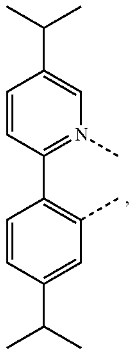
$L_{B248}$
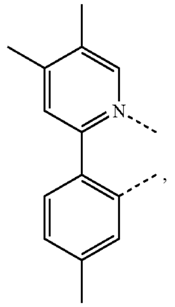
$L_{B249}$
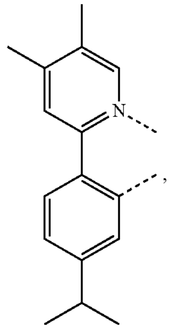
$L_{B250}$
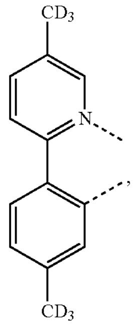
$L_{B251}$
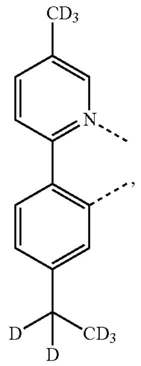
$L_{B252}$
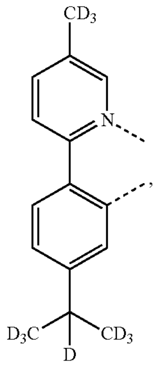
$L_{B253}$
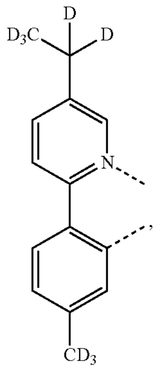
$L_{B254}$ L$_{B255}$
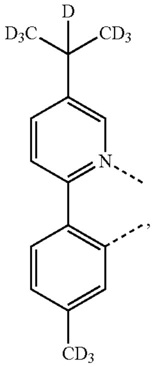
L$_{B256}$
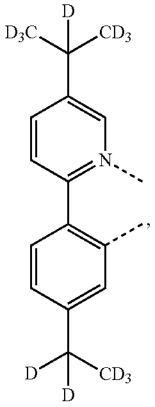
L$_{B257}$
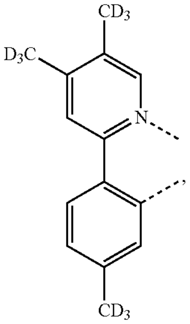
L$_{B258}$
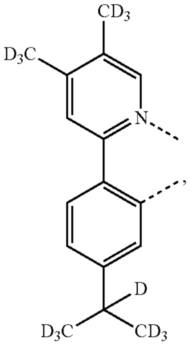
L$_{B259}$
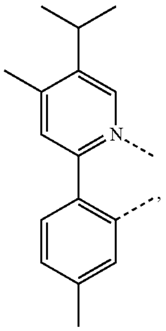
L$_{B260}$
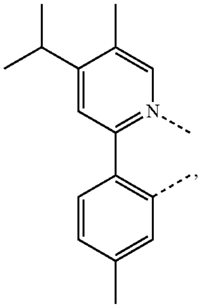
L$_{B261}$
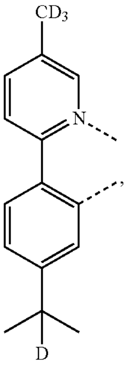
L$_{B262}$
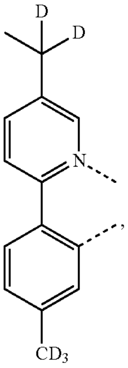

-continued
$L_{B263}$
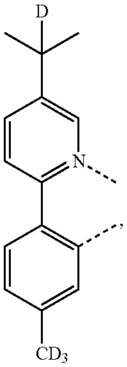
$L_{B264}$
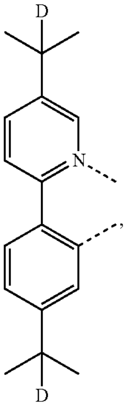
$L_{B265}$
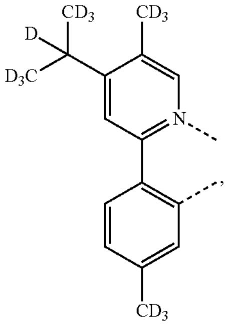
$L_{B266}$
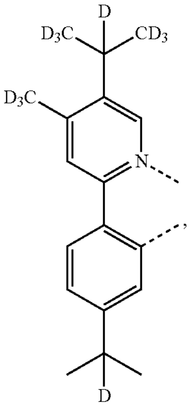
-continued
$L_{B267}$
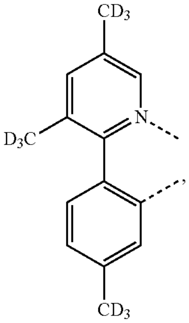
$L_{B268}$
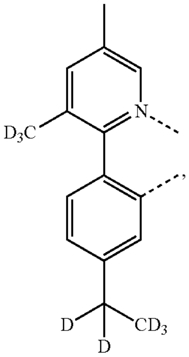
$L_{B269}$
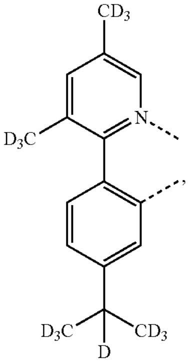
$L_{B270}$
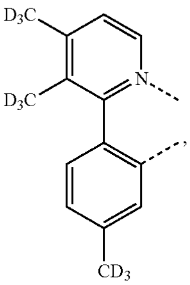

-continued
$L_{B271}$
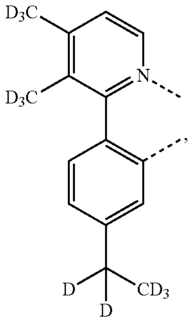
$L_{B272}$
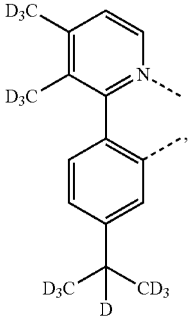
$L_{B273}$
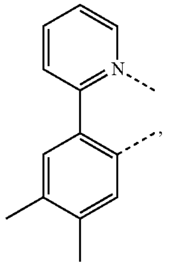
$L_{B274}$
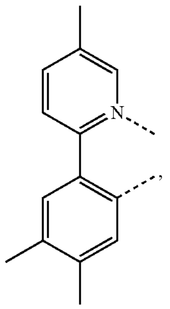
$L_{B275}$
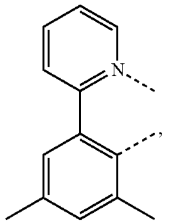
-continued
$L_{B276}$
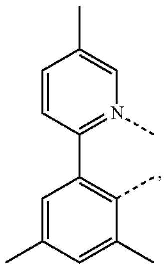
$L_{B277}$
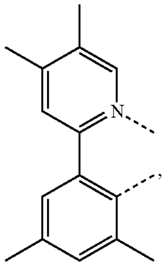
$L_{B278}$
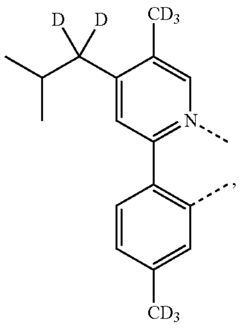
$L_{B279}$
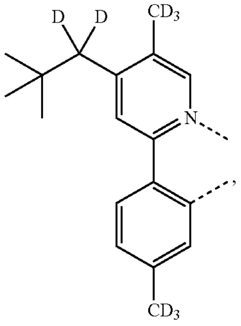
$L_{B280}$
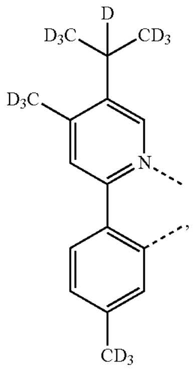

-continued
$L_{B281}$
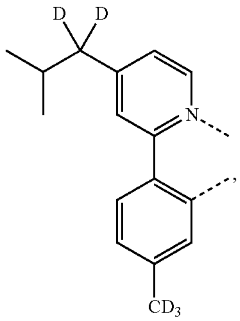
$L_{B282}$
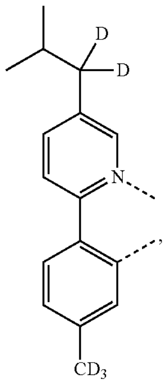
$L_{B283}$
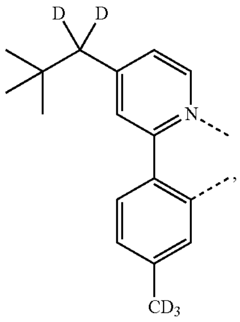
$L_{B284}$
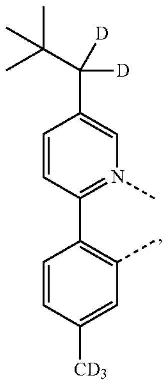
-continued
$L_{B285}$
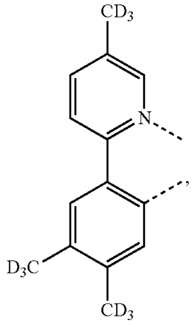
$L_{B286}$
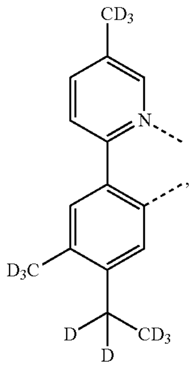
$L_{B287}$
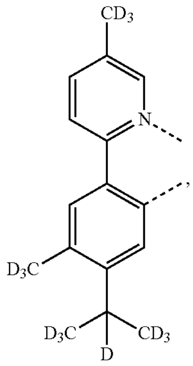
$L_{B288}$
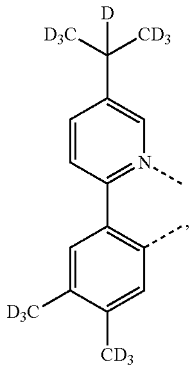

-continued
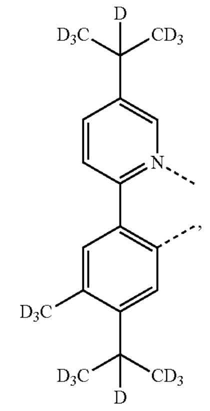
$L_{B289}$
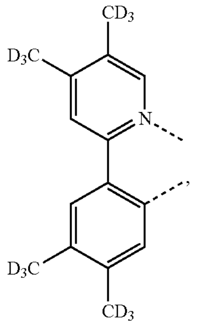
$L_{B290}$
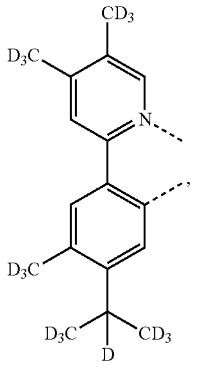
$L_{B291}$
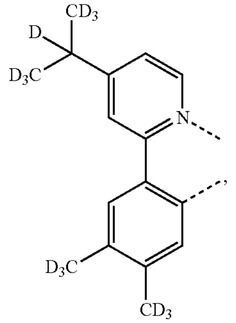
$L_{B292}$
-continued
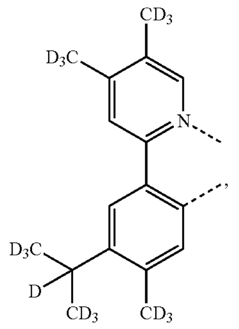
$L_{B293}$
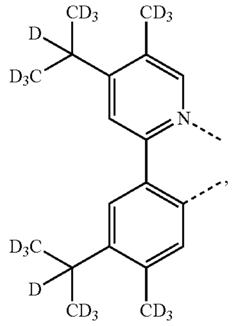
$L_{B294}$
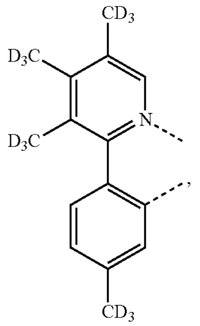
$L_{B295}$
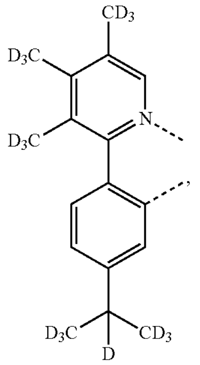
$L_{B296}$ -continued
$L_{B297}$
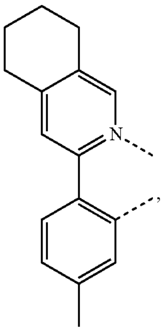
$L_{B298}$
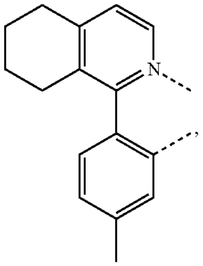
$L_{B299}$
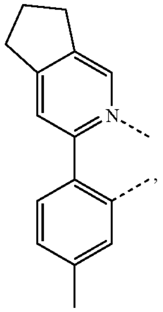
$L_{B300}$
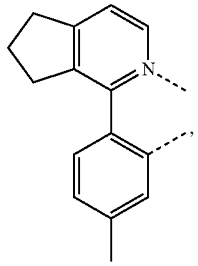
$L_{B301}$
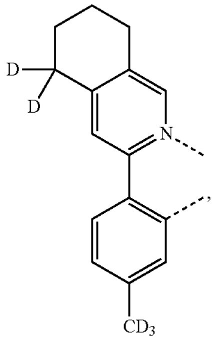
-continued
$L_{B302}$
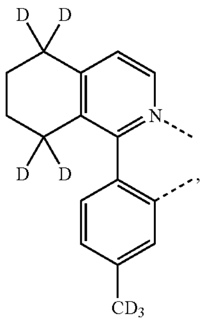
$L_{B303}$
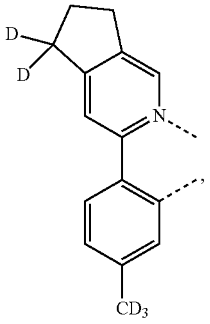
$L_{B304}$
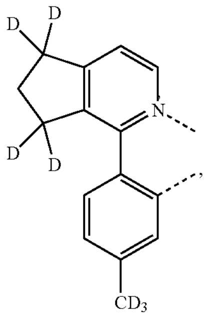
$L_{B305}$
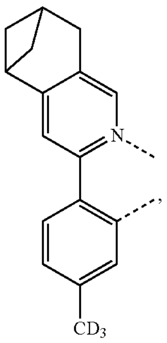

-continued
L$_{B306}$
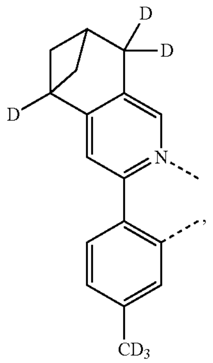
L$_{B307}$
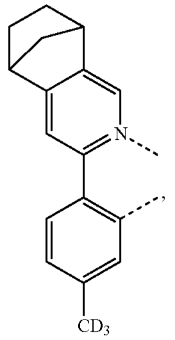
L$_{B308}$
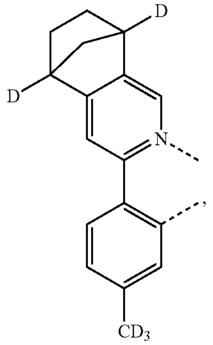
L$_{B309}$
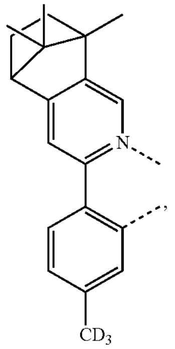
-continued
L$_{B310}$
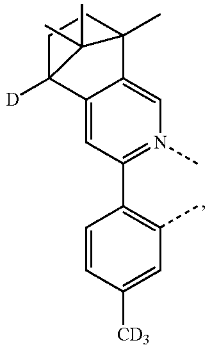
L$_{B311}$
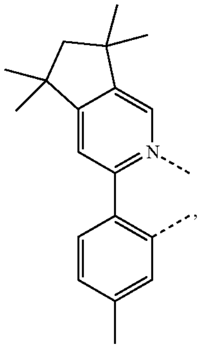
L$_{B312}$
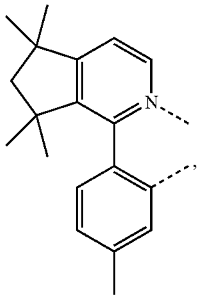
L$_{B312}$
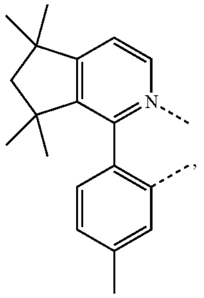
L$_{B313}$
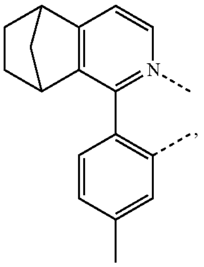

$L_{B314}$
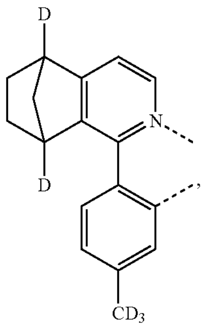
$L_{B315}$
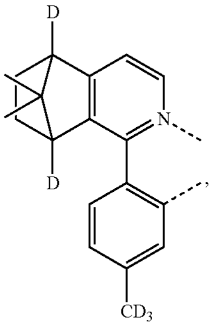
$L_{B316}$
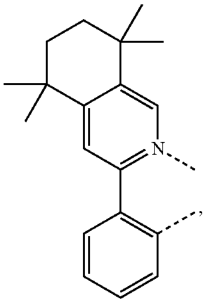
$L_{B317}$
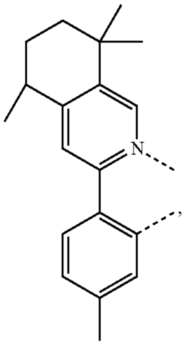
$L_{B318}$
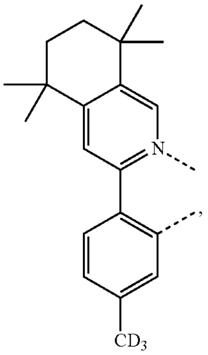
$L_{B319}$
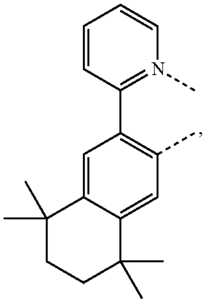
$L_{B320}$
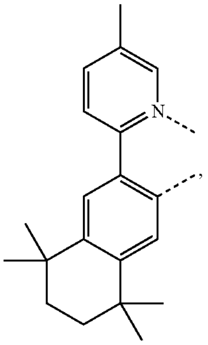
$L_{B321}$
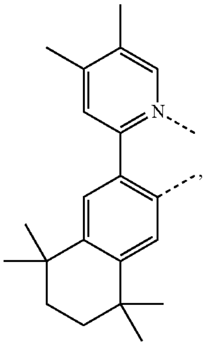

-continued
$L_{B322}$
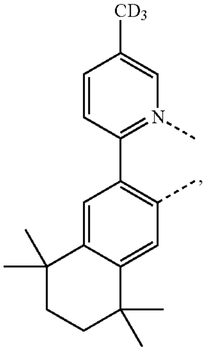
$L_{B323}$
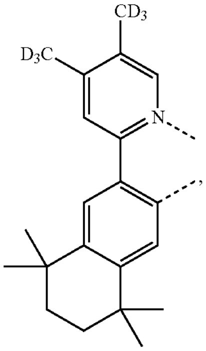
$L_{B324}$
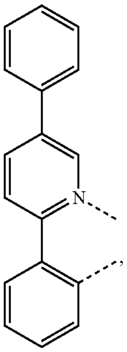
$L_{B325}$
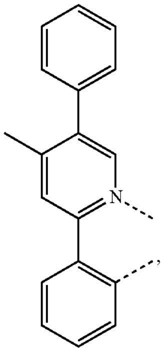
-continued
$L_{B326}$
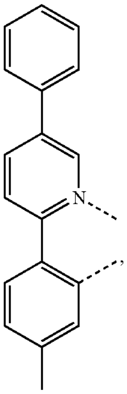
$L_{B327}$
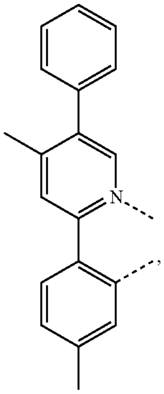
$L_{B328}$
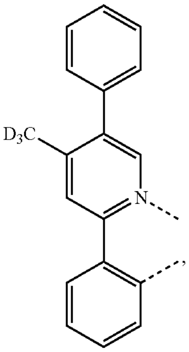
$L_{B329}$
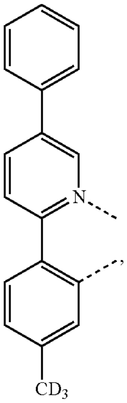

-continued
$L_{B330}$
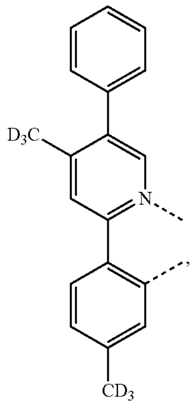
$L_{B331}$
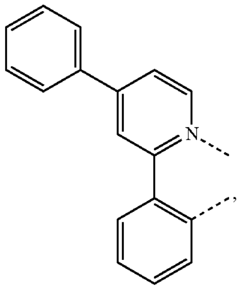
$L_{B332}$
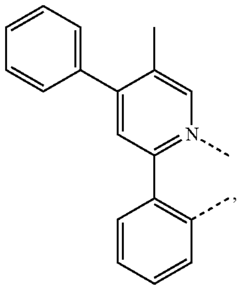
$L_{B333}$
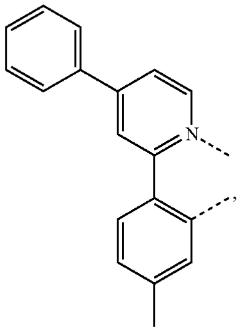
-continued
$L_{B334}$
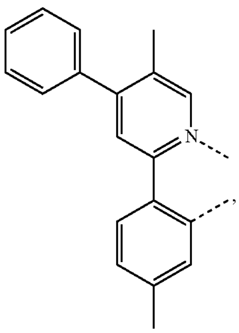
$L_{B335}$
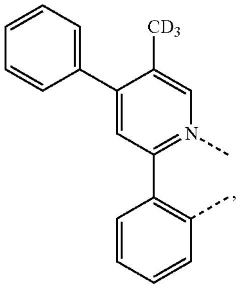
$L_{B336}$
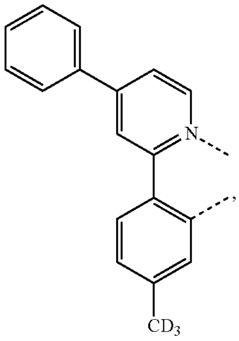
$L_{B337}$
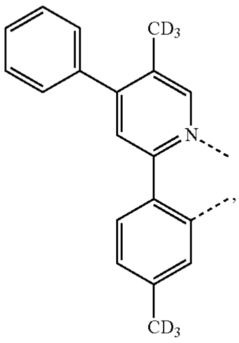

-continued
L$_{B338}$
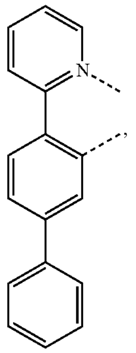
L$_{B339}$
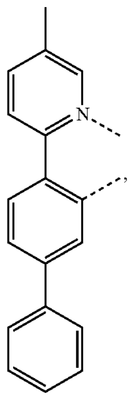
L$_{B340}$
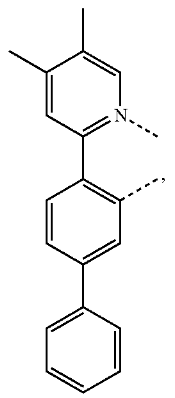
L$_{B341}$
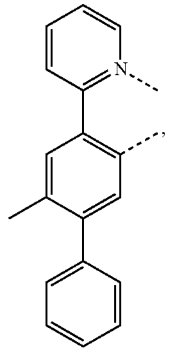
-continued
L$_{B342}$
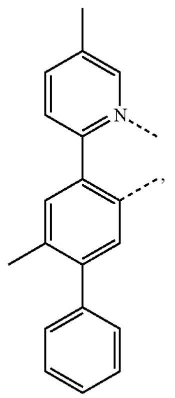
L$_{B343}$
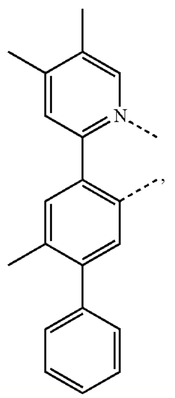
L$_{B344}$
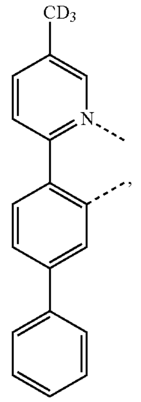
L$_{B345}$
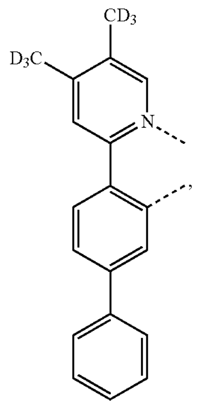

$L_{B346}$
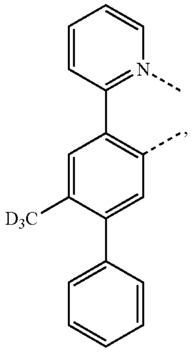
$L_{B347}$
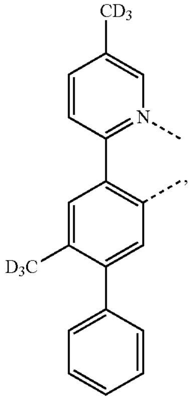
$L_{B348}$
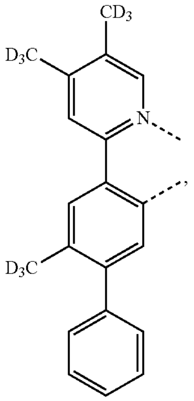
$L_{B349}$
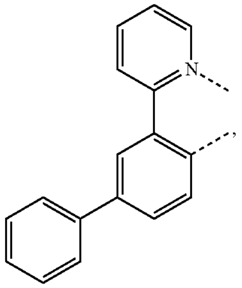
$L_{B350}$
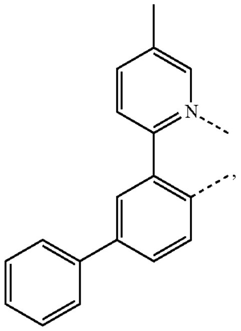
$L_{B351}$
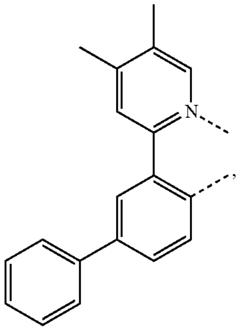
$L_{B352}$
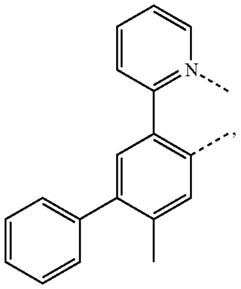
$L_{B353}$
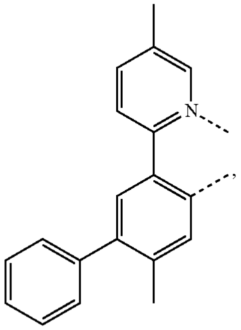
$L_{B354}$
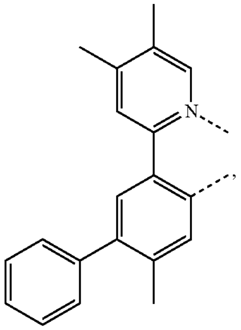

-continued
$L_{B355}$
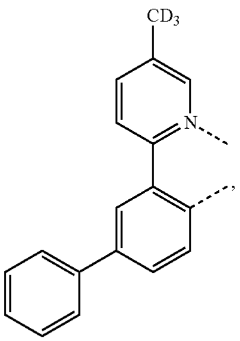
$L_{B356}$
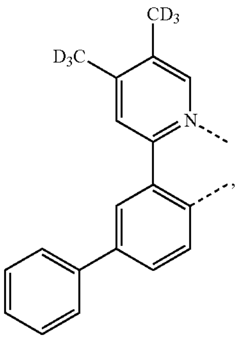
$L_{B357}$
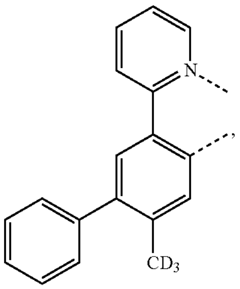
$L_{B358}$
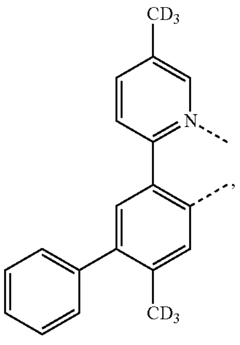
-continued
$L_{B359}$
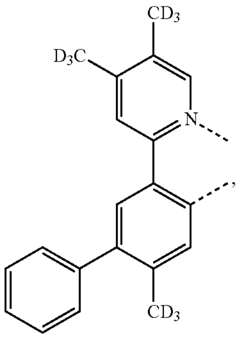
$L_{B360}$
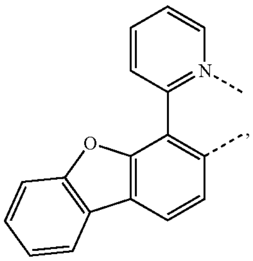
$L_{B361}$
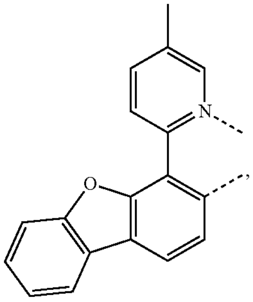
$L_{B362}$
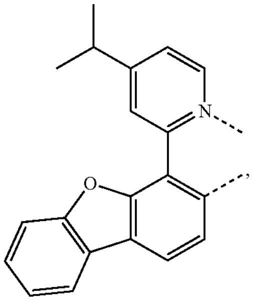
$L_{B363}$
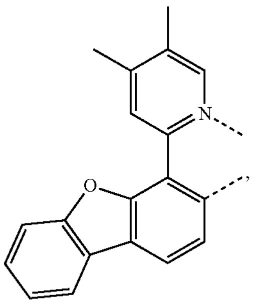

-continued
$L_{B364}$
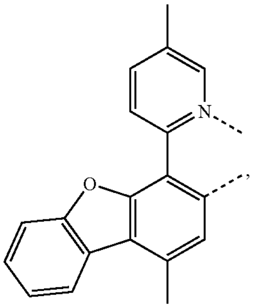
$L_{B365}$
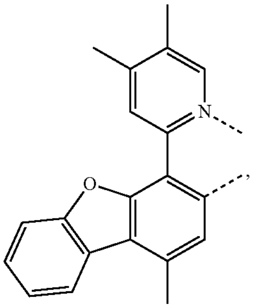
$L_{B366}$
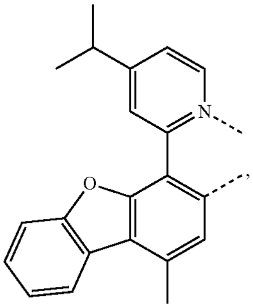
$L_{B367}$
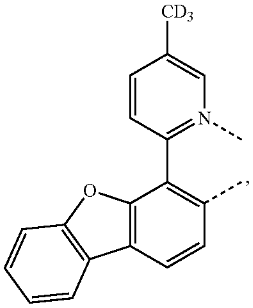
$L_{B368}$
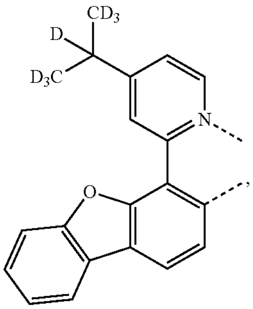
-continued
$L_{B369}$
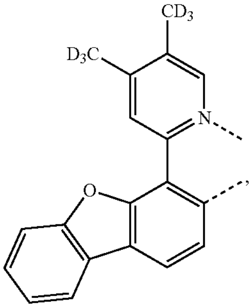
$L_{B370}$
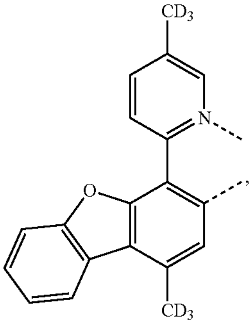
$L_{B371}$
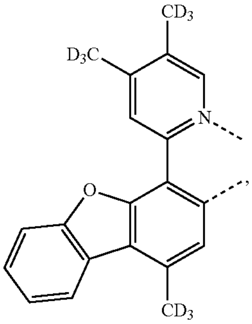
$L_{B372}$
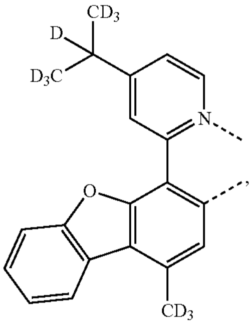
$L_{B373}$
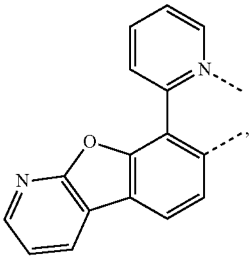

-continued
$L_{B374}$
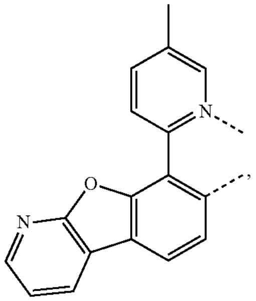
$L_{B375}$
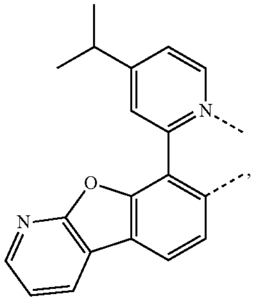
$L_{B376}$
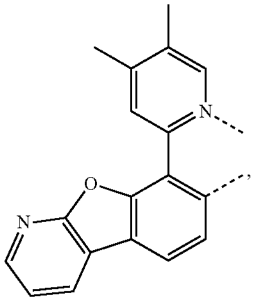
$L_{B377}$
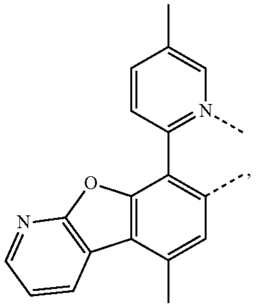
$L_{B378}$
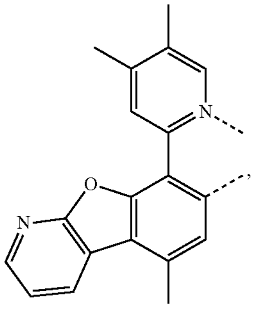
-continued
$L_{B379}$
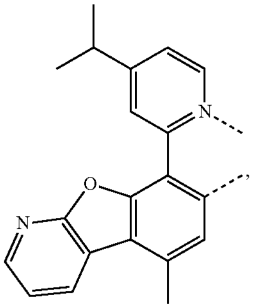
$L_{B380}$
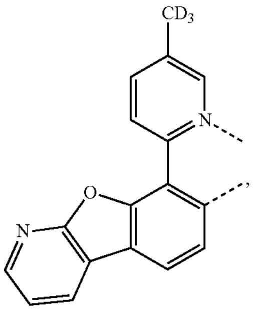
$L_{B381}$
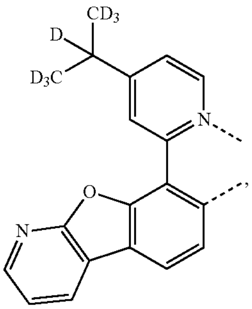
$L_{B382}$
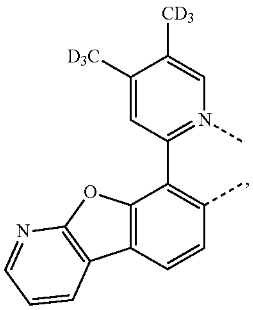
$L_{B383}$
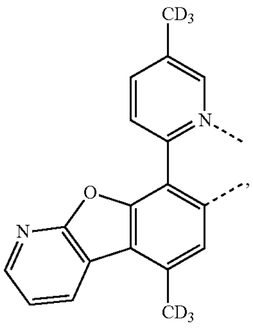

-continued
$L_{B384}$
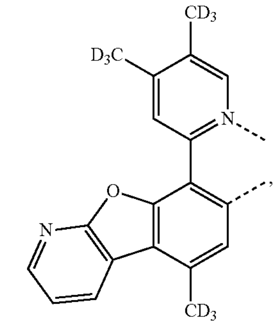
$L_{B385}$
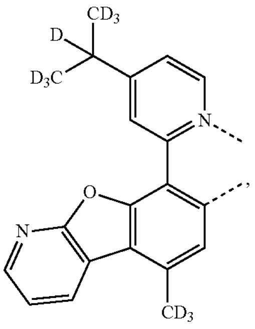
$L_{B386}$
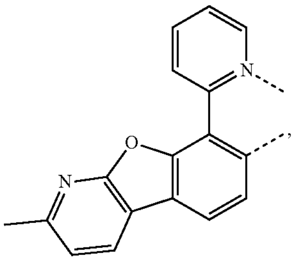
$L_{B387}$
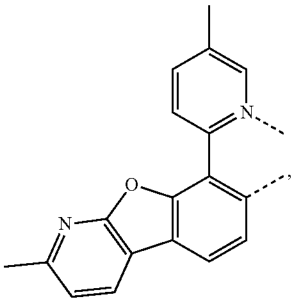
$L_{B388}$
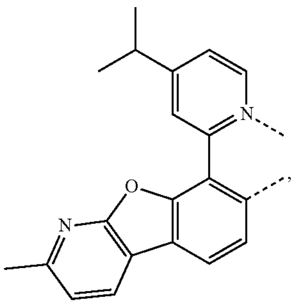
-continued
$L_{B389}$
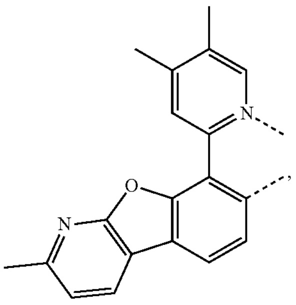
$L_{B390}$
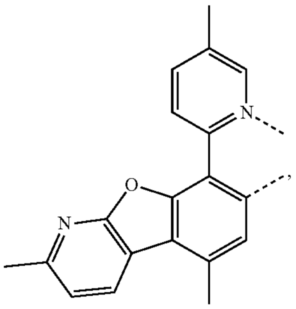
$L_{B391}$
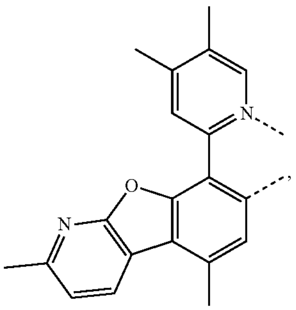
$L_{B392}$
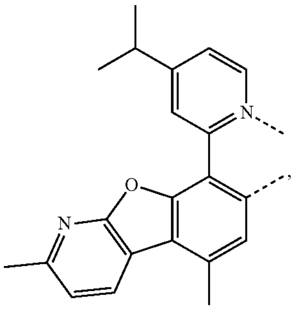
$L_{B393}$
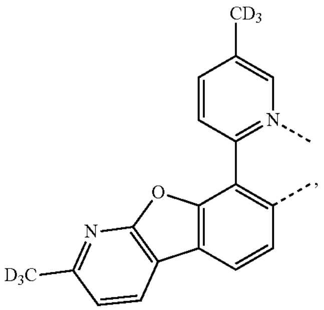

-continued
$L_{B394}$
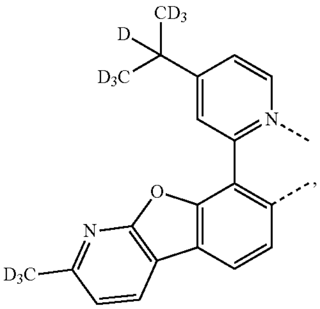
$L_{B395}$
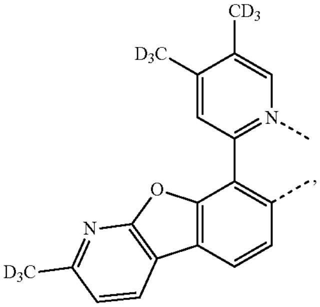
$L_{B396}$
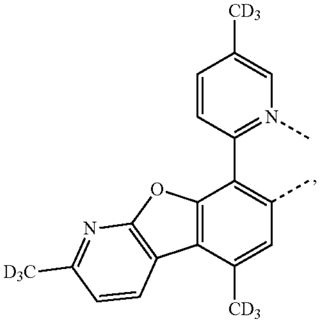
$L_{B397}$
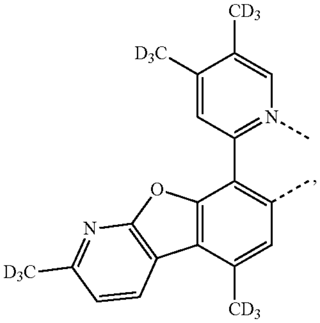
$L_{B398}$
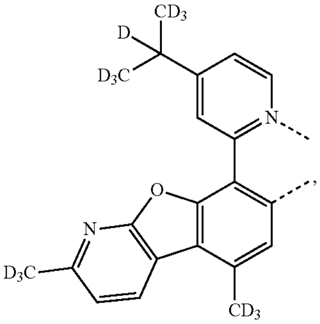
-continued
$L_{B399}$
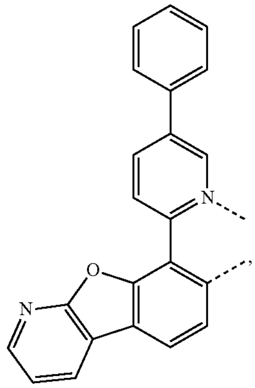
$L_{B400}$
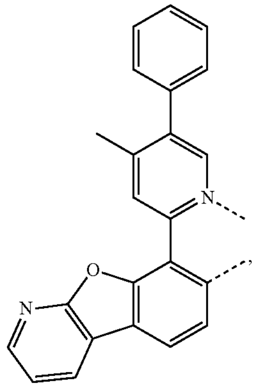
$L_{B401}$
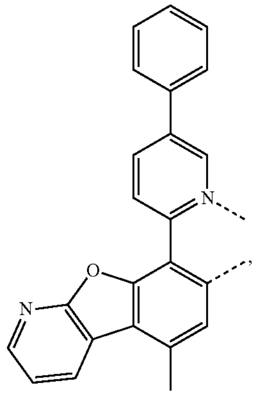
$L_{B402}$
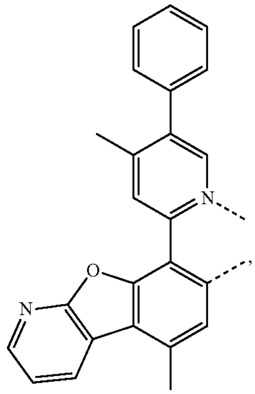

-continued
$L_{B403}$
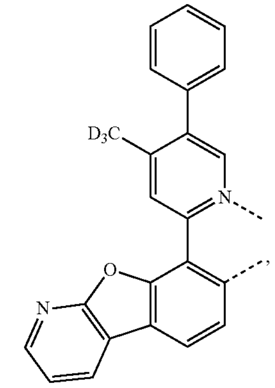
$L_{B404}$
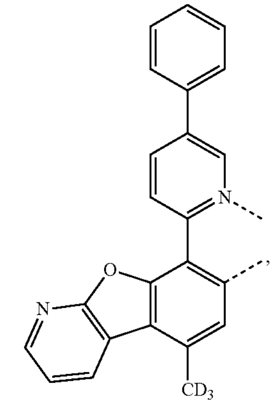
$L_{B405}$
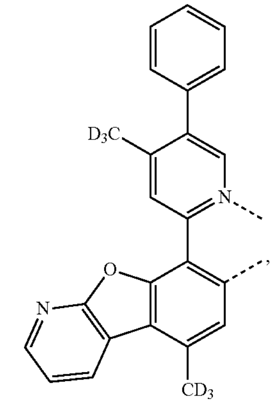
$L_{B406}$
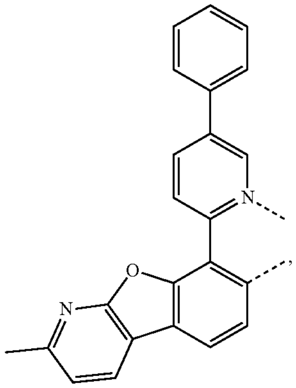
-continued
$L_{B407}$
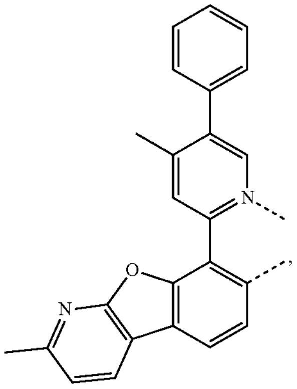
$L_{B408}$
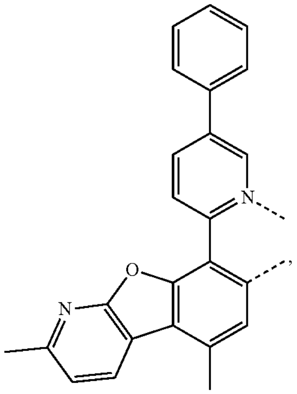
$L_{B409}$
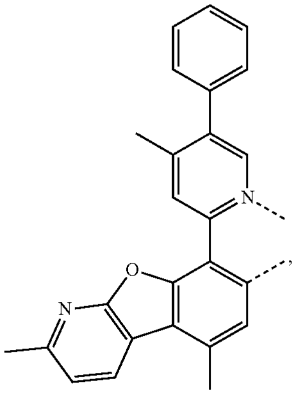
$L_{B410}$
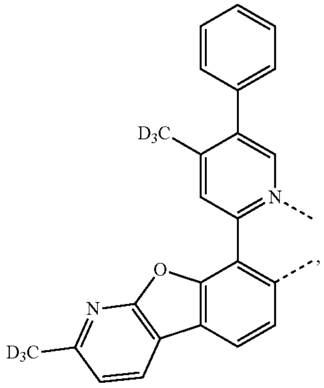

$L_{B411}$
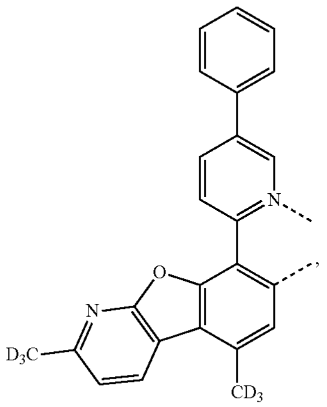
$L_{B412}$
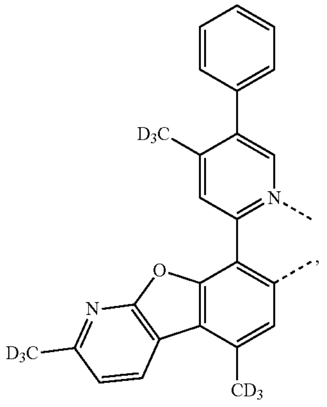
$L_{B413}$
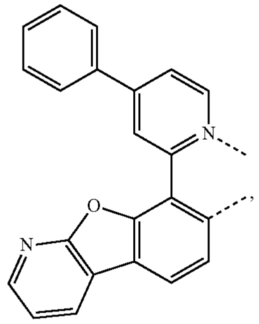
$L_{B414}$
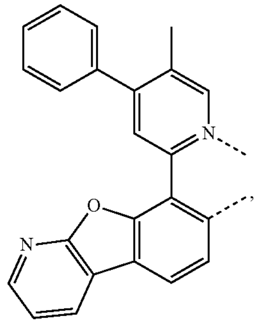
$L_{B415}$
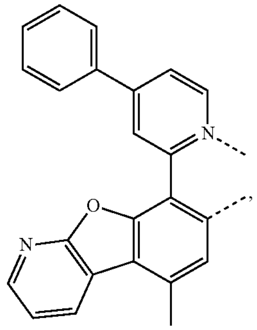
$L_{B416}$
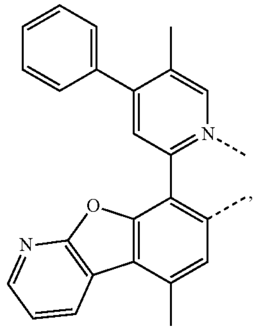
$L_{B417}$
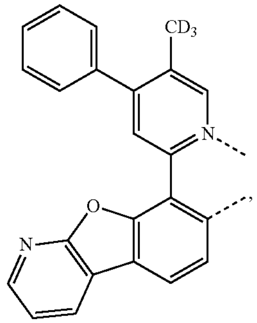
$L_{B418}$
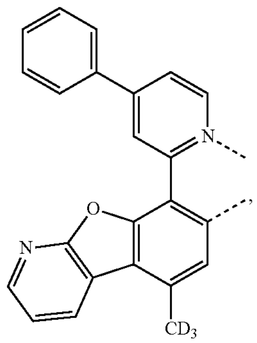

-continued
$L_{B419}$
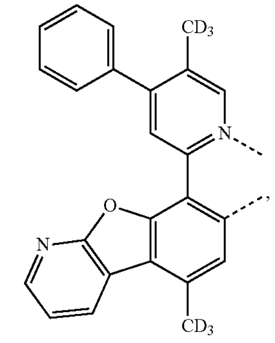
$L_{B420}$
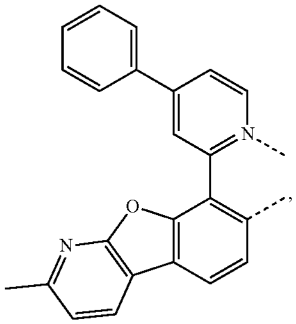
$L_{B421}$
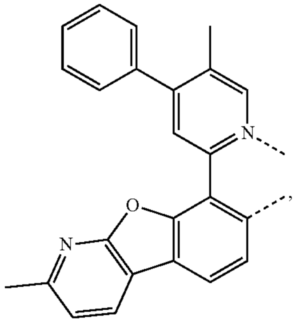
$L_{B422}$
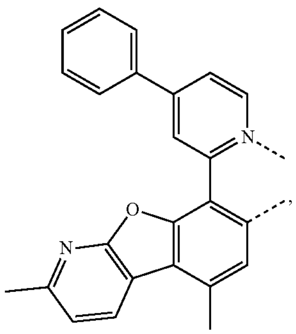
-continued
$L_{B423}$
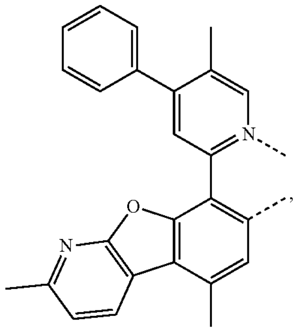
$L_{B424}$
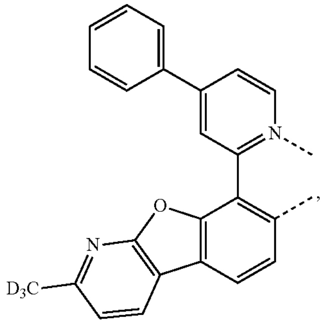
$L_{B425}$
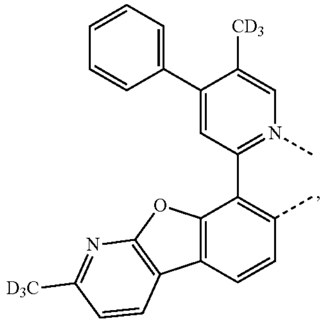
$L_{B426}$
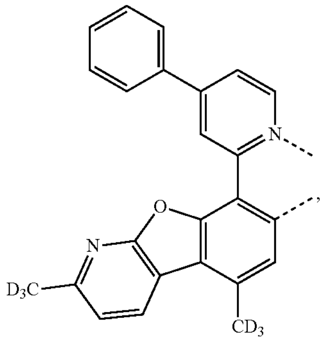

-continued
$L_{B427}$
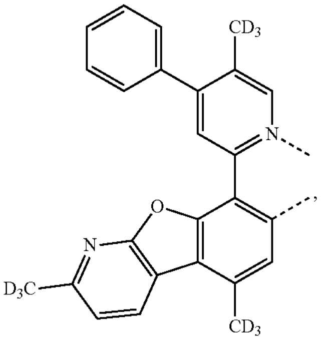
$L_{B428}$
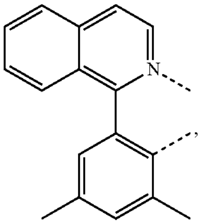
$L_{B429}$
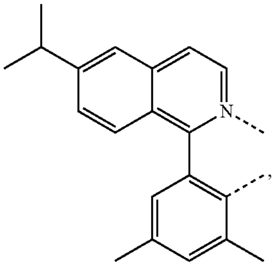
$L_{B430}$
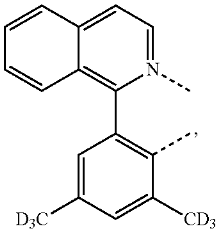
$L_{B431}$
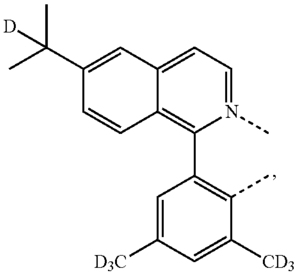
-continued
$L_{B432}$
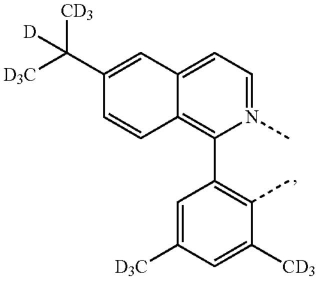
$L_{B433}$
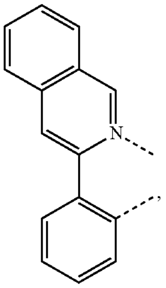
$L_{B434}$
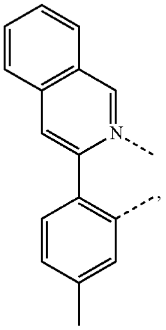
$L_{B435}$
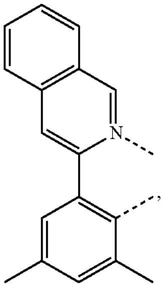
$L_{B436}$
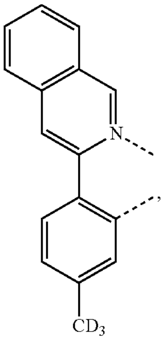

L$_{B437}$
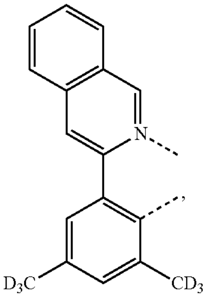
L$_{B438}$
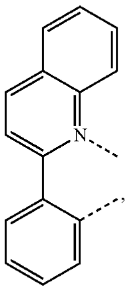
L$_{B439}$
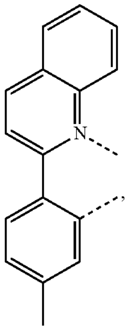
L$_{B440}$
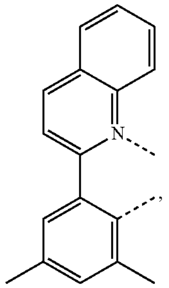
L$_{B441}$
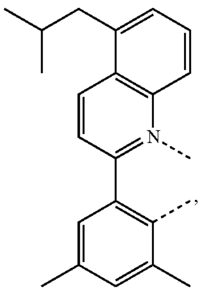
L$_{B442}$
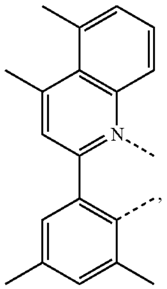
L$_{B443}$
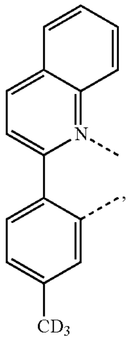
L$_{B444}$
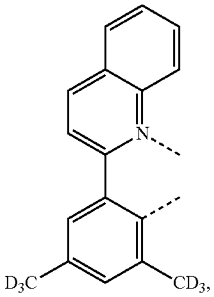
L$_{B445}$
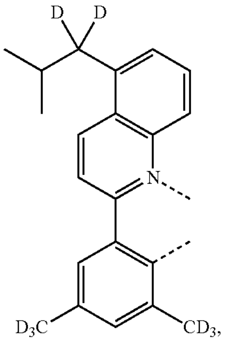
L$_{B446}$
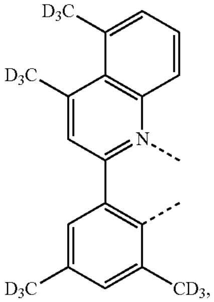

-continued
$L_{B447}$
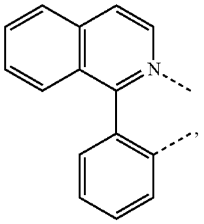
$L_{B448}$
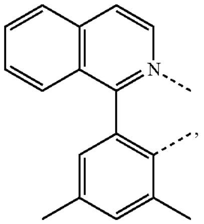
$L_{B449}$
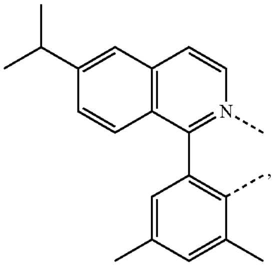
$L_{B450}$
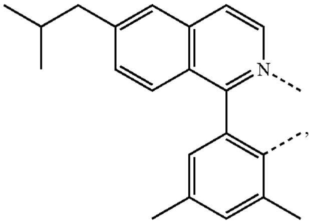
$L_{B451}$
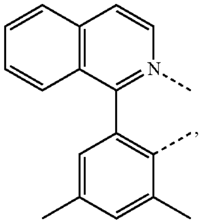
$L_{B452}$
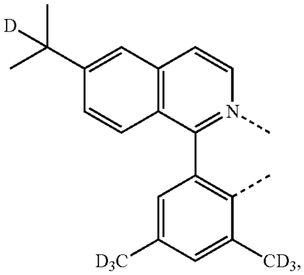
-continued
$L_{B453}$
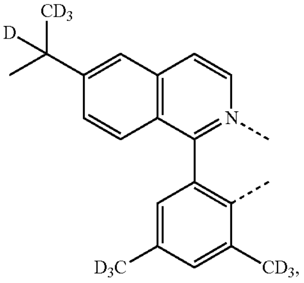
$L_{B454}$
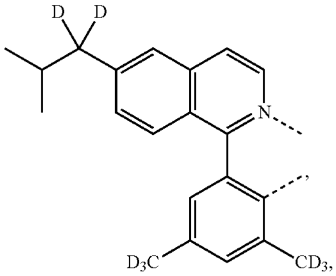
$L_{B455}$
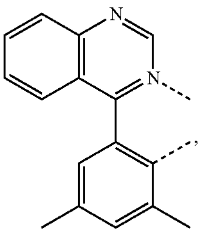
$L_{B456}$
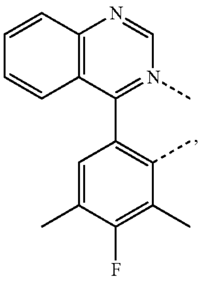
$L_{B457}$
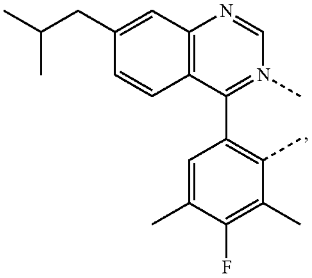

-continued
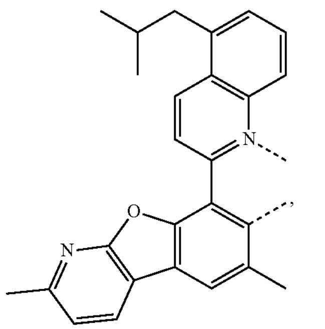
$L_{B458}$
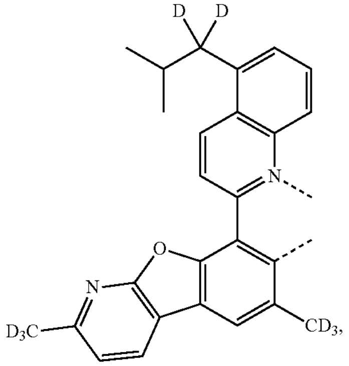
$L_{B459}$
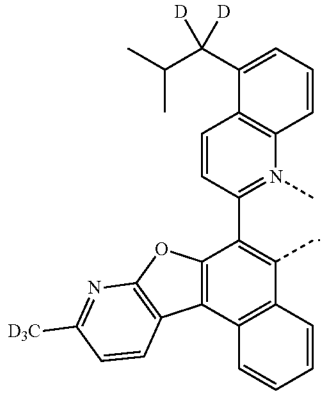
$L_{B460}$
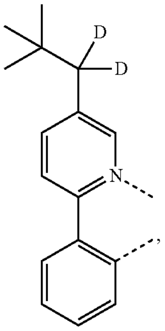
$L_{B461}$
-continued
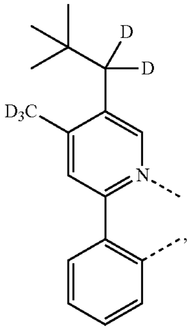
$L_{B462}$
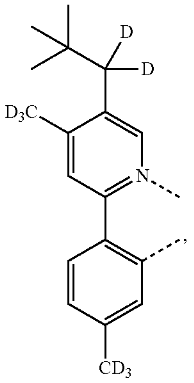
$L_{B463}$
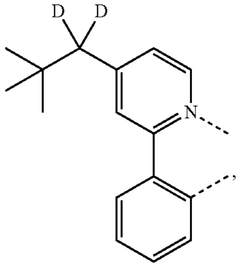
$L_{B464}$
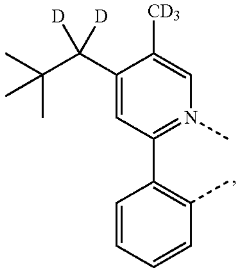
$L_{B465}$
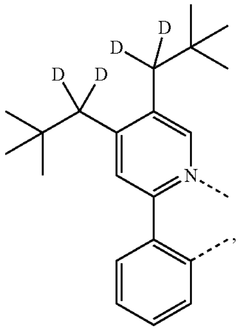
$L_{B466}$ -continued
$L_{B467}$
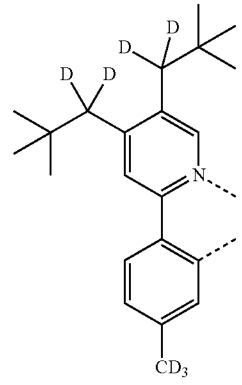
and
$L_{B468}$
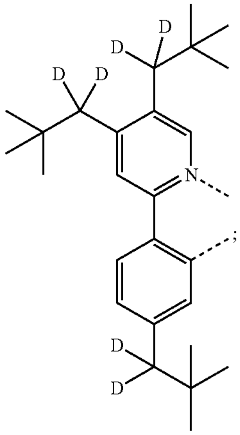
;
$L_{B457}$
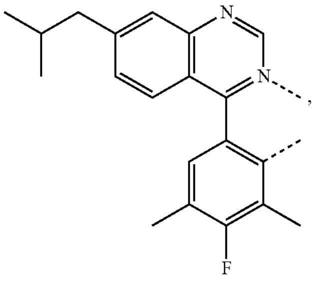
$L_{B458}$
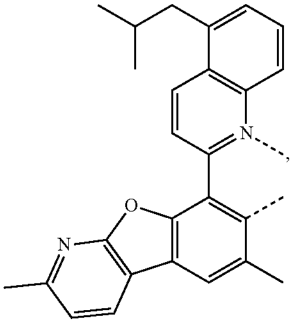
-continued
$L_{B459}$
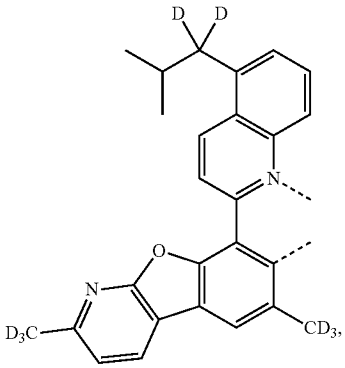
$L_{B460}$
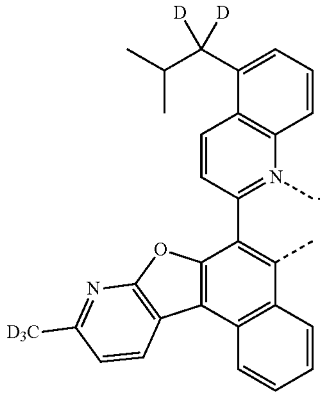
$L_{B461}$
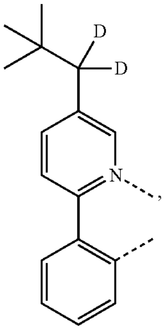
$L_{B462}$
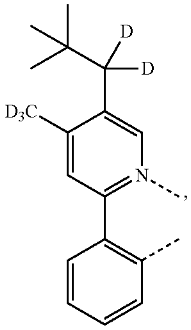

-continued $L_{B463}$

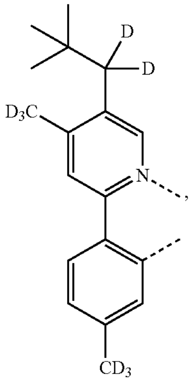

$L_{B464}$

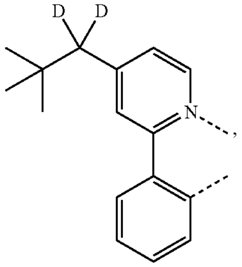

$L_{B465}$

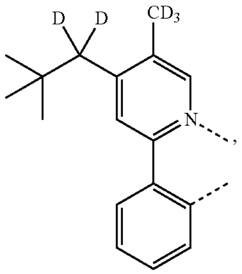

$L_{B466}$

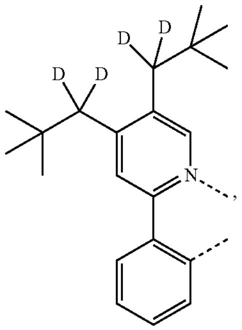

-continued $L_{B467}$

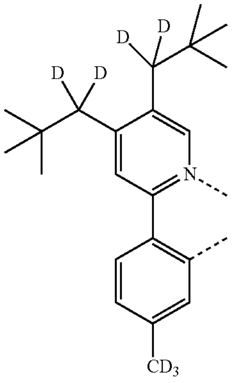

and $L_{B468}$

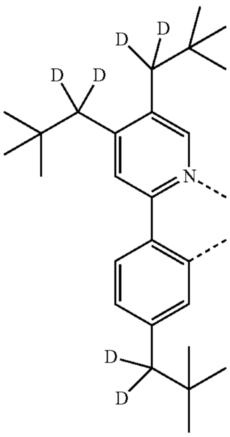

;

and where $L_{C1}$ through $L_{C1260}$ are based on a structure of Formula X,

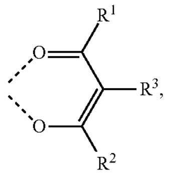

in which $R^1$, $R^2$, and $R^3$ are defined as:

| Ligand | $R^1$ | $R^2$ | $R^3$ |
|---|---|---|---|
| $L_{C1}$ | $R^{D1}$ | $R^{D1}$ | H |
| $L_{C2}$ | $R^{D2}$ | $R^{D2}$ | H |
| $L_{C3}$ | $R^{D3}$ | $R^{D3}$ | H |
| $L_{C4}$ | $R^{D4}$ | $R^{D4}$ | H |
| $L_{C5}$ | $R^{D5}$ | $R^{D5}$ | H |
| $L_{C6}$ | $R^{D6}$ | $R^{D6}$ | H |
| $L_{C7}$ | $R^{D7}$ | $R^{D7}$ | H |
| $L_{C8}$ | $R^{D8}$ | $R^{D8}$ | H |
| $L_{C9}$ | $R^{D9}$ | $R^{D9}$ | H |
| $L_{C10}$ | $R^{D10}$ | $R^{D10}$ | H |
| $L_{C11}$ | $R^{D11}$ | $R^{D11}$ | H |
| $L_{C12}$ | $R^{D12}$ | $R^{D12}$ | H |
| $L_{C13}$ | $R^{D13}$ | $R^{D13}$ | H |
| $L_{C14}$ | $R^{D14}$ | $R^{D14}$ | H |
| $L_{C15}$ | $R^{D15}$ | $R^{D15}$ | H |
| $L_{C16}$ | $R^{D16}$ | $R^{D16}$ | H |
| $L_{C17}$ | $R^{D17}$ | $R^{D17}$ | H |

-continued

| Ligand | $R^1$ | $R^2$ | $R^3$ |
|---|---|---|---|
| $L_{C18}$ | $R^{D18}$ | $R^{D18}$ | H |
| $L_{C19}$ | $R^{D19}$ | $R^{D19}$ | H |
| $L_{C20}$ | $R^{D20}$ | $R^{D20}$ | H |
| $L_{C21}$ | $R^{D21}$ | $R^{D21}$ | H |
| $L_{C22}$ | $R^{D22}$ | $R^{D22}$ | H |
| $L_{C23}$ | $R^{D23}$ | $R^{D23}$ | H |
| $L_{C24}$ | $R^{D24}$ | $R^{D24}$ | H |
| $L_{C25}$ | $R^{D25}$ | $R^{D25}$ | H |
| $L_{C26}$ | $R^{D26}$ | $R^{D26}$ | H |
| $L_{C27}$ | $R^{D27}$ | $R^{D27}$ | H |
| $L_{C28}$ | $R^{D28}$ | $R^{D28}$ | H |
| $L_{C29}$ | $R^{D29}$ | $R^{D29}$ | H |
| $L_{C30}$ | $R^{D30}$ | $R^{D30}$ | H |
| $L_{C31}$ | $R^{D31}$ | $R^{D31}$ | H |
| $L_{C32}$ | $R^{D32}$ | $R^{D32}$ | H |
| $L_{C33}$ | $R^{D33}$ | $R^{D33}$ | H |
| $L_{C34}$ | $R^{D34}$ | $R^{D34}$ | H |
| $L_{C35}$ | $R^{D35}$ | $R^{D35}$ | H |
| $L_{C36}$ | $R^{D40}$ | $R^{D40}$ | H |
| $L_{C37}$ | $R^{D41}$ | $R^{D41}$ | H |
| $L_{C38}$ | $R^{D42}$ | $R^{D42}$ | H |
| $L_{C39}$ | $R^{D64}$ | $R^{D64}$ | H |
| $L_{C40}$ | $R^{D66}$ | $R^{D66}$ | H |
| $L_{C41}$ | $R^{D68}$ | $R^{D68}$ | H |
| $L_{C42}$ | $R^{D76}$ | $R^{D76}$ | H |
| $L_{C43}$ | $R^{D1}$ | $R^{D2}$ | H |
| $L_{C44}$ | $R^{D1}$ | $R^{D3}$ | H |
| $L_{C45}$ | $R^{D1}$ | $R^{D4}$ | H |
| $L_{C46}$ | $R^{D1}$ | $R^{D5}$ | H |
| $L_{C47}$ | $R^{D1}$ | $R^{D6}$ | H |
| $L_{C48}$ | $R^{D1}$ | $R^{D7}$ | H |
| $L_{C49}$ | $R^{D1}$ | $R^{D8}$ | H |
| $L_{C50}$ | $R^{D1}$ | $R^{D9}$ | H |
| $L_{C51}$ | $R^{D1}$ | $R^{D10}$ | H |
| $L_{C52}$ | $R^{D1}$ | $R^{D11}$ | H |
| $L_{C53}$ | $R^{D1}$ | $R^{D12}$ | H |
| $L_{C54}$ | $R^{D1}$ | $R^{D13}$ | H |
| $L_{C55}$ | $R^{D1}$ | $R^{D14}$ | H |
| $L_{C56}$ | $R^{D1}$ | $R^{D15}$ | H |
| $L_{C57}$ | $R^{D1}$ | $R^{D16}$ | H |
| $L_{C58}$ | $R^{D1}$ | $R^{D17}$ | H |
| $L_{C59}$ | $R^{D1}$ | $R^{D18}$ | H |
| $L_{C60}$ | $R^{D1}$ | $R^{D19}$ | H |
| $L_{C61}$ | $R^{D1}$ | $R^{D20}$ | H |
| $L_{C62}$ | $R^{D1}$ | $R^{D21}$ | H |
| $L_{C63}$ | $R^{D1}$ | $R^{D22}$ | H |
| $L_{C64}$ | $R^{D1}$ | $R^{D23}$ | H |
| $L_{C65}$ | $R^{D1}$ | $R^{D24}$ | H |
| $L_{C66}$ | $R^{D1}$ | $R^{D25}$ | H |
| $L_{C67}$ | $R^{D1}$ | $R^{D26}$ | H |
| $L_{C68}$ | $R^{D1}$ | $R^{D27}$ | H |
| $L_{C69}$ | $R^{D1}$ | $R^{D28}$ | H |
| $L_{C70}$ | $R^{D1}$ | $R^{D29}$ | H |
| $L_{C71}$ | $R^{D1}$ | $R^{D30}$ | H |
| $L_{C72}$ | $R^{D1}$ | $R^{D31}$ | H |
| $L_{C73}$ | $R^{D1}$ | $R^{D32}$ | H |
| $L_{C74}$ | $R^{D1}$ | $R^{D33}$ | H |
| $L_{C75}$ | $R^{D1}$ | $R^{D34}$ | H |
| $L_{C76}$ | $R^{D1}$ | $R^{D35}$ | H |
| $L_{C77}$ | $R^{D1}$ | $R^{D40}$ | H |
| $L_{C78}$ | $R^{D1}$ | $R^{D41}$ | H |
| $L_{C79}$ | $R^{D1}$ | $R^{D42}$ | H |
| $L_{C80}$ | $R^{D1}$ | $R^{D64}$ | H |
| $L_{C81}$ | $R^{D1}$ | $R^{D66}$ | H |
| $L_{C82}$ | $R^{D1}$ | $R^{D68}$ | H |
| $L_{C83}$ | $R^{D1}$ | $R^{D76}$ | H |
| $L_{C84}$ | $R^{D2}$ | $R^{D1}$ | H |
| $L_{C85}$ | $R^{D2}$ | $R^{D3}$ | H |
| $L_{C86}$ | $R^{D2}$ | $R^{D4}$ | H |
| $L_{C87}$ | $R^{D2}$ | $R^{D5}$ | H |
| $L_{C88}$ | $R^{D2}$ | $R^{D6}$ | H |
| $L_{C89}$ | $R^{D2}$ | $R^{D7}$ | H |
| $L_{C90}$ | $R^{D2}$ | $R^{D8}$ | H |
| $L_{C91}$ | $R^{D2}$ | $R^{D9}$ | H |
| $L_{C92}$ | $R^{D2}$ | $R^{D10}$ | H |
| $L_{C93}$ | $R^{D2}$ | $R^{D11}$ | H |
| $L_{C94}$ | $R^{D2}$ | $R^{D12}$ | H |

-continued

| Ligand | $R^1$ | $R^2$ | $R^3$ |
|---|---|---|---|
| $L_{C95}$ | $R^{D2}$ | $R^{D13}$ | H |
| $L_{C96}$ | $R^{D2}$ | $R^{D14}$ | H |
| $L_{C97}$ | $R^{D2}$ | $R^{D15}$ | H |
| $L_{C98}$ | $R^{D2}$ | $R^{D16}$ | H |
| $L_{C99}$ | $R^{D2}$ | $R^{D17}$ | H |
| $L_{C100}$ | $R^{D2}$ | $R^{D18}$ | H |
| $L_{C101}$ | $R^{D2}$ | $R^{D19}$ | H |
| $L_{C102}$ | $R^{D2}$ | $R^{D20}$ | H |
| $L_{C103}$ | $R^{D2}$ | $R^{D21}$ | H |
| $L_{C104}$ | $R^{D2}$ | $R^{D22}$ | H |
| $L_{C105}$ | $R^{D2}$ | $R^{D23}$ | H |
| $L_{C106}$ | $R^{D2}$ | $R^{D24}$ | H |
| $L_{C107}$ | $R^{D2}$ | $R^{D25}$ | H |
| $L_{C108}$ | $R^{D2}$ | $R^{D26}$ | H |
| $L_{C109}$ | $R^{D2}$ | $R^{D27}$ | H |
| $L_{C110}$ | $R^{D2}$ | $R^{D28}$ | H |
| $L_{C111}$ | $R^{D2}$ | $R^{D29}$ | H |
| $L_{C112}$ | $R^{D2}$ | $R^{D30}$ | H |
| $L_{C113}$ | $R^{D2}$ | $R^{D31}$ | H |
| $L_{C114}$ | $R^{D2}$ | $R^{D32}$ | H |
| $L_{C115}$ | $R^{D2}$ | $R^{D33}$ | H |
| $L_{C116}$ | $R^{D2}$ | $R^{D34}$ | H |
| $L_{C117}$ | $R^{D2}$ | $R^{D35}$ | H |
| $L_{C118}$ | $R^{D2}$ | $R^{D40}$ | H |
| $L_{C119}$ | $R^{D2}$ | $R^{D41}$ | H |
| $L_{C120}$ | $R^{D2}$ | $R^{D42}$ | H |
| $L_{C121}$ | $R^{D2}$ | $R^{D64}$ | H |
| $L_{C122}$ | $R^{D2}$ | $R^{D66}$ | H |
| $L_{C123}$ | $R^{D2}$ | $R^{D68}$ | H |
| $L_{C124}$ | $R^{D2}$ | $R^{D76}$ | H |
| $L_{C125}$ | $R^{D3}$ | $R^{D4}$ | H |
| $L_{C126}$ | $R^{D3}$ | $R^{D5}$ | H |
| $L_{C127}$ | $R^{D3}$ | $R^{D6}$ | H |
| $L_{C128}$ | $R^{D3}$ | $R^{D7}$ | H |
| $L_{C129}$ | $R^{D3}$ | $R^{D8}$ | H |
| $L_{C130}$ | $R^{D3}$ | $R^{D9}$ | H |
| $L_{C131}$ | $R^{D3}$ | $R^{D10}$ | H |
| $L_{C132}$ | $R^{D3}$ | $R^{D11}$ | H |
| $L_{C133}$ | $R^{D3}$ | $R^{D12}$ | H |
| $L_{C134}$ | $R^{D3}$ | $R^{D13}$ | H |
| $L_{C135}$ | $R^{D3}$ | $R^{D14}$ | H |
| $L_{C136}$ | $R^{D3}$ | $R^{D15}$ | H |
| $L_{C137}$ | $R^{D3}$ | $R^{D16}$ | H |
| $L_{C138}$ | $R^{D3}$ | $R^{D17}$ | H |
| $L_{C139}$ | $R^{D3}$ | $R^{D18}$ | H |
| $L_{C140}$ | $R^{D3}$ | $R^{D19}$ | H |
| $L_{C141}$ | $R^{D3}$ | $R^{D20}$ | H |
| $L_{C142}$ | $R^{D3}$ | $R^{D21}$ | H |
| $L_{C143}$ | $R^{D3}$ | $R^{D22}$ | H |
| $L_{C144}$ | $R^{D3}$ | $R^{D23}$ | H |
| $L_{C145}$ | $R^{D3}$ | $R^{D24}$ | H |
| $L_{C146}$ | $R^{D3}$ | $R^{D25}$ | H |
| $L_{C147}$ | $R^{D3}$ | $R^{D26}$ | H |
| $L_{C148}$ | $R^{D3}$ | $R^{D27}$ | H |
| $L_{C149}$ | $R^{D3}$ | $R^{D28}$ | H |
| $L_{C150}$ | $R^{D3}$ | $R^{D29}$ | H |
| $L_{C151}$ | $R^{D3}$ | $R^{D30}$ | H |
| $L_{C152}$ | $R^{D3}$ | $R^{D31}$ | H |
| $L_{C153}$ | $R^{D3}$ | $R^{D32}$ | H |
| $L_{C154}$ | $R^{D3}$ | $R^{D33}$ | H |
| $L_{C155}$ | $R^{D3}$ | $R^{D34}$ | H |
| $L_{C156}$ | $R^{D3}$ | $R^{D35}$ | H |
| $L_{C157}$ | $R^{D3}$ | $R^{D40}$ | H |
| $L_{C158}$ | $R^{D3}$ | $R^{D41}$ | H |
| $L_{C159}$ | $R^{D3}$ | $R^{D42}$ | H |
| $L_{C160}$ | $R^{D3}$ | $R^{D64}$ | H |
| $L_{C161}$ | $R^{D3}$ | $R^{D66}$ | H |
| $L_{C162}$ | $R^{D3}$ | $R^{D68}$ | H |
| $L_{C163}$ | $R^{D3}$ | $R^{D76}$ | H |
| $L_{C164}$ | $R^{D4}$ | $R^{D5}$ | H |
| $L_{C165}$ | $R^{D4}$ | $R^{D6}$ | H |
| $L_{C166}$ | $R^{D4}$ | $R^{D7}$ | H |
| $L_{C167}$ | $R^{D4}$ | $R^{D8}$ | H |
| $L_{C168}$ | $R^{D4}$ | $R^{D9}$ | H |
| $L_{C169}$ | $R^{D4}$ | $R^{D10}$ | H |
| $L_{C170}$ | $R^{D4}$ | $R^{D11}$ | H |
| $L_{C171}$ | $R^{D4}$ | $R^{D12}$ | H |

-continued

| Ligand | $R^1$ | $R^2$ | $R^3$ |
|---|---|---|---|
| $L_{C172}$ | $R^{D4}$ | $R^{D13}$ | H |
| $L_{C173}$ | $R^{D4}$ | $R^{D14}$ | H |
| $L_{C174}$ | $R^{D4}$ | $R^{D15}$ | H |
| $L_{C175}$ | $R^{D4}$ | $R^{D16}$ | H |
| $L_{C176}$ | $R^{D4}$ | $R^{D17}$ | H |
| $L_{C177}$ | $R^{D4}$ | $R^{D18}$ | H |
| $L_{C178}$ | $R^{D4}$ | $R^{D19}$ | H |
| $L_{C179}$ | $R^{D4}$ | $R^{D20}$ | H |
| $L_{C180}$ | $R^{D4}$ | $R^{D21}$ | H |
| $L_{C181}$ | $R^{D4}$ | $R^{D22}$ | H |
| $L_{C182}$ | $R^{D4}$ | $R^{D23}$ | H |
| $L_{C183}$ | $R^{D4}$ | $R^{D24}$ | H |
| $L_{C184}$ | $R^{D4}$ | $R^{D25}$ | H |
| $L_{C185}$ | $R^{D4}$ | $R^{D26}$ | H |
| $L_{C186}$ | $R^{D4}$ | $R^{D27}$ | H |
| $L_{C187}$ | $R^{D4}$ | $R^{D28}$ | H |
| $L_{C188}$ | $R^{D4}$ | $R^{D29}$ | H |
| $L_{C189}$ | $R^{D4}$ | $R^{D30}$ | H |
| $L_{C190}$ | $R^{D4}$ | $R^{D31}$ | H |
| $L_{C191}$ | $R^{D4}$ | $R^{D32}$ | H |
| $L_{C192}$ | $R^{D4}$ | $R^{D33}$ | H |
| $L_{C193}$ | $R^{D4}$ | $R^{D34}$ | H |
| $L_{C194}$ | $R^{D4}$ | $R^{D35}$ | H |
| $L_{C195}$ | $R^{D4}$ | $R^{D40}$ | H |
| $L_{C196}$ | $R^{D4}$ | $R^{D41}$ | H |
| $L_{C197}$ | $R^{D4}$ | $R^{D42}$ | H |
| $L_{C198}$ | $R^{D4}$ | $R^{D64}$ | H |
| $L_{C199}$ | $R^{D4}$ | $R^{D66}$ | H |
| $L_{C200}$ | $R^{D4}$ | $R^{D68}$ | H |
| $L_{C201}$ | $R^{D4}$ | $R^{D76}$ | H |
| $L_{C202}$ | $R^{D4}$ | $R^{D1}$ | H |
| $L_{C203}$ | $R^{D7}$ | $R^{D5}$ | H |
| $L_{C204}$ | $R^{D7}$ | $R^{D6}$ | H |
| $L_{C205}$ | $R^{D7}$ | $R^{D8}$ | H |
| $L_{C206}$ | $R^{D7}$ | $R^{D9}$ | H |
| $L_{C207}$ | $R^{D7}$ | $R^{D10}$ | H |
| $L_{C208}$ | $R^{D7}$ | $R^{D11}$ | H |
| $L_{C209}$ | $R^{D7}$ | $R^{D12}$ | H |
| $L_{C210}$ | $R^{D7}$ | $R^{D13}$ | H |
| $L_{C211}$ | $R^{D7}$ | $R^{D14}$ | H |
| $L_{C212}$ | $R^{D7}$ | $R^{D15}$ | H |
| $L_{C213}$ | $R^{D7}$ | $R^{D16}$ | H |
| $L_{C214}$ | $R^{D7}$ | $R^{D17}$ | H |
| $L_{C215}$ | $R^{D7}$ | $R^{D18}$ | H |
| $L_{C216}$ | $R^{D7}$ | $R^{D19}$ | H |
| $L_{C217}$ | $R^{D7}$ | $R^{D20}$ | H |
| $L_{C218}$ | $R^{D7}$ | $R^{D21}$ | H |
| $L_{C219}$ | $R^{D7}$ | $R^{D22}$ | H |
| $L_{C220}$ | $R^{D7}$ | $R^{D23}$ | H |
| $L_{C221}$ | $R^{D7}$ | $R^{D24}$ | H |
| $L_{C222}$ | $R^{D7}$ | $R^{D25}$ | H |
| $L_{C223}$ | $R^{D7}$ | $R^{D26}$ | H |
| $L_{C224}$ | $R^{D7}$ | $R^{D27}$ | H |
| $L_{C225}$ | $R^{D7}$ | $R^{D28}$ | H |
| $L_{C226}$ | $R^{D7}$ | $R^{D29}$ | H |
| $L_{C227}$ | $R^{D7}$ | $R^{D30}$ | H |
| $L_{C228}$ | $R^{D7}$ | $R^{D31}$ | H |
| $L_{C229}$ | $R^{D7}$ | $R^{D32}$ | H |
| $L_{C230}$ | $R^{D7}$ | $R^{D33}$ | H |
| $L_{C231}$ | $R^{D7}$ | $R^{D34}$ | H |
| $L_{C232}$ | $R^{D7}$ | $R^{D35}$ | H |
| $L_{C233}$ | $R^{D7}$ | $R^{D40}$ | H |
| $L_{C234}$ | $R^{D7}$ | $R^{D41}$ | H |
| $L_{C235}$ | $R^{D7}$ | $R^{D42}$ | H |
| $L_{C236}$ | $R^{D7}$ | $R^{D64}$ | H |
| $L_{C237}$ | $R^{D7}$ | $R^{D66}$ | H |
| $L_{C238}$ | $R^{D7}$ | $R^{D68}$ | H |
| $L_{C239}$ | $R^{D7}$ | $R^{D76}$ | H |
| $L_{C240}$ | $R^{D8}$ | $R^{D5}$ | H |
| $L_{C241}$ | $R^{D8}$ | $R^{D6}$ | H |
| $L_{C242}$ | $R^{D8}$ | $R^{D9}$ | H |
| $L_{C243}$ | $R^{D8}$ | $R^{D10}$ | H |
| $L_{C244}$ | $R^{D8}$ | $R^{D11}$ | H |
| $L_{C245}$ | $R^{D8}$ | $R^{D12}$ | H |
| $L_{C246}$ | $R^{D8}$ | $R^{D13}$ | H |
| $L_{C247}$ | $R^{D8}$ | $R^{D14}$ | H |
| $L_{C248}$ | $R^{D8}$ | $R^{D15}$ | H |

-continued

| Ligand | $R^1$ | $R^2$ | $R^3$ |
|---|---|---|---|
| $L_{C249}$ | $R^{D8}$ | $R^{D16}$ | H |
| $L_{C250}$ | $R^{D8}$ | $R^{D17}$ | H |
| $L_{C251}$ | $R^{D8}$ | $R^{D18}$ | H |
| $L_{C252}$ | $R^{D8}$ | $R^{D19}$ | H |
| $L_{C253}$ | $R^{D8}$ | $R^{D20}$ | H |
| $L_{C254}$ | $R^{D8}$ | $R^{D21}$ | H |
| $L_{C255}$ | $R^{D8}$ | $R^{D22}$ | H |
| $L_{C256}$ | $R^{D8}$ | $R^{D23}$ | H |
| $L_{C257}$ | $R^{D8}$ | $R^{D24}$ | H |
| $L_{C258}$ | $R^{D8}$ | $R^{D25}$ | H |
| $L_{C259}$ | $R^{D8}$ | $R^{D26}$ | H |
| $L_{C260}$ | $R^{D8}$ | $R^{D27}$ | H |
| $L_{C261}$ | $R^{D8}$ | $R^{D28}$ | H |
| $L_{C262}$ | $R^{D8}$ | $R^{D29}$ | H |
| $L_{C263}$ | $R^{D8}$ | $R^{D30}$ | H |
| $L_{C264}$ | $R^{D8}$ | $R^{D31}$ | H |
| $L_{C265}$ | $R^{D8}$ | $R^{D32}$ | H |
| $L_{C266}$ | $R^{D8}$ | $R^{D33}$ | H |
| $L_{C267}$ | $R^{D8}$ | $R^{D34}$ | H |
| $L_{C268}$ | $R^{D8}$ | $R^{D35}$ | H |
| $L_{C269}$ | $R^{D8}$ | $R^{D40}$ | H |
| $L_{C270}$ | $R^{D8}$ | $R^{D41}$ | H |
| $L_{C271}$ | $R^{D8}$ | $R^{D42}$ | H |
| $L_{C272}$ | $R^{D8}$ | $R^{D64}$ | H |
| $L_{C273}$ | $R^{D8}$ | $R^{D66}$ | H |
| $L_{C274}$ | $R^{D8}$ | $R^{D68}$ | H |
| $L_{C275}$ | $R^{D8}$ | $R^{D76}$ | H |
| $L_{C276}$ | $R^{D11}$ | $R^{D5}$ | H |
| $L_{C277}$ | $R^{D11}$ | $R^{D6}$ | H |
| $L_{C278}$ | $R^{D11}$ | $R^{D9}$ | H |
| $L_{C279}$ | $R^{D11}$ | $R^{D10}$ | H |
| $L_{C280}$ | $R^{D11}$ | $R^{D12}$ | H |
| $L_{C281}$ | $R^{D11}$ | $R^{D13}$ | H |
| $L_{C282}$ | $R^{D11}$ | $R^{D14}$ | H |
| $L_{C283}$ | $R^{D11}$ | $R^{D15}$ | H |
| $L_{C284}$ | $R^{D11}$ | $R^{D16}$ | H |
| $L_{C285}$ | $R^{D11}$ | $R^{D17}$ | H |
| $L_{C286}$ | $R^{D11}$ | $R^{D18}$ | H |
| $L_{C287}$ | $R^{D11}$ | $R^{D19}$ | H |
| $L_{C288}$ | $R^{D11}$ | $R^{D20}$ | H |
| $L_{C289}$ | $R^{D11}$ | $R^{D21}$ | H |
| $L_{C290}$ | $R^{D11}$ | $R^{D22}$ | H |
| $L_{C291}$ | $R^{D11}$ | $R^{D23}$ | H |
| $L_{C292}$ | $R^{D11}$ | $R^{D24}$ | H |
| $L_{C293}$ | $R^{D11}$ | $R^{D25}$ | H |
| $L_{C294}$ | $R^{D11}$ | $R^{D26}$ | H |
| $L_{C295}$ | $R^{D11}$ | $R^{D27}$ | H |
| $L_{C296}$ | $R^{D11}$ | $R^{D28}$ | H |
| $L_{C297}$ | $R^{D11}$ | $R^{D29}$ | H |
| $L_{C298}$ | $R^{D11}$ | $R^{D30}$ | H |
| $L_{C299}$ | $R^{D11}$ | $R^{D31}$ | H |
| $L_{C300}$ | $R^{D11}$ | $R^{D32}$ | H |
| $L_{C301}$ | $R^{D11}$ | $R^{D33}$ | H |
| $L_{C302}$ | $R^{D11}$ | $R^{D34}$ | H |
| $L_{C303}$ | $R^{D11}$ | $R^{D35}$ | H |
| $L_{C304}$ | $R^{D11}$ | $R^{D40}$ | H |
| $L_{C305}$ | $R^{D11}$ | $R^{D41}$ | H |
| $L_{C306}$ | $R^{D11}$ | $R^{D42}$ | H |
| $L_{C307}$ | $R^{D11}$ | $R^{D64}$ | H |
| $L_{C308}$ | $R^{D11}$ | $R^{D66}$ | H |
| $L_{C309}$ | $R^{D11}$ | $R^{D68}$ | H |
| $L_{C310}$ | $R^{D11}$ | $R^{D76}$ | H |
| $L_{C311}$ | $R^{D13}$ | $R^{D5}$ | H |
| $L_{C312}$ | $R^{D13}$ | $R^{D6}$ | H |
| $L_{C313}$ | $R^{D13}$ | $R^{D9}$ | H |
| $L_{C314}$ | $R^{D13}$ | $R^{D10}$ | H |
| $L_{C315}$ | $R^{D13}$ | $R^{D12}$ | H |
| $L_{C316}$ | $R^{D13}$ | $R^{D14}$ | H |
| $L_{C317}$ | $R^{D13}$ | $R^{D15}$ | H |
| $L_{C318}$ | $R^{D13}$ | $R^{D16}$ | H |
| $L_{C319}$ | $R^{D13}$ | $R^{D17}$ | H |
| $L_{C320}$ | $R^{D13}$ | $R^{D18}$ | H |
| $L_{C321}$ | $R^{D13}$ | $R^{D19}$ | H |
| $L_{C322}$ | $R^{D13}$ | $R^{D20}$ | H |
| $L_{C323}$ | $R^{D13}$ | $R^{D21}$ | H |
| $L_{C324}$ | $R^{D13}$ | $R^{D22}$ | H |
| $L_{C325}$ | $R^{D13}$ | $R^{D23}$ | H |

-continued

| Ligand | $R^1$ | $R^2$ | $R^3$ |
|---|---|---|---|
| $L_{C326}$ | $R^{D13}$ | $R^{D24}$ | H |
| $L_{C327}$ | $R^{D13}$ | $R^{D25}$ | H |
| $L_{C328}$ | $R^{D13}$ | $R^{D26}$ | H |
| $L_{C329}$ | $R^{D13}$ | $R^{D27}$ | H |
| $L_{C330}$ | $R^{D13}$ | $R^{D28}$ | H |
| $L_{C331}$ | $R^{D13}$ | $R^{D29}$ | H |
| $L_{C332}$ | $R^{D13}$ | $R^{D30}$ | H |
| $L_{C333}$ | $R^{D13}$ | $R^{D31}$ | H |
| $L_{C334}$ | $R^{D13}$ | $R^{D32}$ | H |
| $L_{C335}$ | $R^{D13}$ | $R^{D33}$ | H |
| $L_{C336}$ | $R^{D13}$ | $R^{D34}$ | H |
| $L_{C337}$ | $R^{D13}$ | $R^{D35}$ | H |
| $L_{C338}$ | $R^{D13}$ | $R^{D40}$ | H |
| $L_{C339}$ | $R^{D13}$ | $R^{D41}$ | H |
| $L_{C340}$ | $R^{D13}$ | $R^{D42}$ | H |
| $L_{C341}$ | $R^{D13}$ | $R^{D64}$ | H |
| $L_{C342}$ | $R^{D13}$ | $R^{D66}$ | H |
| $L_{C343}$ | $R^{D13}$ | $R^{D68}$ | H |
| $L_{C344}$ | $R^{D13}$ | $R^{D76}$ | H |
| $L_{C345}$ | $R^{D14}$ | $R^{D5}$ | H |
| $L_{C346}$ | $R^{D14}$ | $R^{D6}$ | H |
| $L_{C347}$ | $R^{D14}$ | $R^{D9}$ | H |
| $L_{C348}$ | $R^{D14}$ | $R^{D10}$ | H |
| $L_{C349}$ | $R^{D14}$ | $R^{D12}$ | H |
| $L_{C350}$ | $R^{D14}$ | $R^{D15}$ | H |
| $L_{C351}$ | $R^{D14}$ | $R^{D16}$ | H |
| $L_{C352}$ | $R^{D14}$ | $R^{D17}$ | H |
| $L_{C353}$ | $R^{D14}$ | $R^{D18}$ | H |
| $L_{C354}$ | $R^{D14}$ | $R^{D19}$ | H |
| $L_{C355}$ | $R^{D14}$ | $R^{D20}$ | H |
| $L_{C356}$ | $R^{D14}$ | $R^{D21}$ | H |
| $L_{C357}$ | $R^{D14}$ | $R^{D22}$ | H |
| $L_{C358}$ | $R^{D14}$ | $R^{D23}$ | H |
| $L_{C359}$ | $R^{D14}$ | $R^{D24}$ | H |
| $L_{C360}$ | $R^{D14}$ | $R^{D25}$ | H |
| $L_{C361}$ | $R^{D14}$ | $R^{D26}$ | H |
| $L_{C362}$ | $R^{D14}$ | $R^{D27}$ | H |
| $L_{C363}$ | $R^{D14}$ | $R^{D28}$ | H |
| $L_{C364}$ | $R^{D14}$ | $R^{D29}$ | H |
| $L_{C365}$ | $R^{D14}$ | $R^{D30}$ | H |
| $L_{C366}$ | $R^{D14}$ | $R^{D31}$ | H |
| $L_{C367}$ | $R^{D14}$ | $R^{D32}$ | H |
| $L_{C368}$ | $R^{D14}$ | $R^{D33}$ | H |
| $L_{C369}$ | $R^{D14}$ | $R^{D34}$ | H |
| $L_{C370}$ | $R^{D14}$ | $R^{D35}$ | H |
| $L_{C371}$ | $R^{D14}$ | $R^{D40}$ | H |
| $L_{C372}$ | $R^{D14}$ | $R^{D41}$ | H |
| $L_{C373}$ | $R^{D14}$ | $R^{D42}$ | H |
| $L_{C374}$ | $R^{D14}$ | $R^{D64}$ | H |
| $L_{C375}$ | $R^{D14}$ | $R^{D66}$ | H |
| $L_{C376}$ | $R^{D14}$ | $R^{D68}$ | H |
| $L_{C377}$ | $R^{D14}$ | $R^{D76}$ | H |
| $L_{C378}$ | $R^{D22}$ | $R^{D5}$ | H |
| $L_{C379}$ | $R^{D22}$ | $R^{D6}$ | H |
| $L_{C380}$ | $R^{D22}$ | $R^{D9}$ | H |
| $L_{C381}$ | $R^{D22}$ | $R^{D10}$ | H |
| $L_{C382}$ | $R^{D22}$ | $R^{D12}$ | H |
| $L_{C383}$ | $R^{D22}$ | $R^{D15}$ | H |
| $L_{C384}$ | $R^{D22}$ | $R^{D16}$ | H |
| $L_{C385}$ | $R^{D22}$ | $R^{D17}$ | H |
| $L_{C386}$ | $R^{D22}$ | $R^{D18}$ | H |
| $L_{C387}$ | $R^{D22}$ | $R^{D19}$ | H |
| $L_{C388}$ | $R^{D22}$ | $R^{D20}$ | H |
| $L_{C389}$ | $R^{D22}$ | $R^{D21}$ | H |
| $L_{C390}$ | $R^{D22}$ | $R^{D23}$ | H |
| $L_{C391}$ | $R^{D22}$ | $R^{D24}$ | H |
| $L_{C392}$ | $R^{D22}$ | $R^{D25}$ | H |
| $L_{C393}$ | $R^{D22}$ | $R^{D26}$ | H |
| $L_{C394}$ | $R^{D22}$ | $R^{D27}$ | H |
| $L_{C395}$ | $R^{D22}$ | $R^{D28}$ | H |
| $L_{C396}$ | $R^{D22}$ | $R^{D29}$ | H |
| $L_{C397}$ | $R^{D22}$ | $R^{D30}$ | H |
| $L_{C398}$ | $R^{D22}$ | $R^{D31}$ | H |
| $L_{C399}$ | $R^{D22}$ | $R^{D32}$ | H |
| $L_{C400}$ | $R^{D22}$ | $R^{D33}$ | H |
| $L_{C401}$ | $R^{D22}$ | $R^{D34}$ | H |
| $L_{C402}$ | $R^{D22}$ | $R^{D35}$ | H |

-continued

| Ligand | $R^1$ | $R^2$ | $R^3$ |
|---|---|---|---|
| $L_{C403}$ | $R^{D22}$ | $R^{D40}$ | H |
| $L_{C404}$ | $R^{D22}$ | $R^{D41}$ | H |
| $L_{C405}$ | $R^{D22}$ | $R^{D42}$ | H |
| $L_{C406}$ | $R^{D22}$ | $R^{D64}$ | H |
| $L_{C407}$ | $R^{D22}$ | $R^{D66}$ | H |
| $L_{C408}$ | $R^{D22}$ | $R^{D68}$ | H |
| $L_{C409}$ | $R^{D22}$ | $R^{D76}$ | H |
| $L_{C410}$ | $R^{D26}$ | $R^{D5}$ | H |
| $L_{C411}$ | $R^{D26}$ | $R^{D6}$ | H |
| $L_{C412}$ | $R^{D26}$ | $R^{D9}$ | H |
| $L_{C413}$ | $R^{D26}$ | $R^{D10}$ | H |
| $L_{C414}$ | $R^{D26}$ | $R^{D12}$ | H |
| $L_{C415}$ | $R^{D26}$ | $R^{D15}$ | H |
| $L_{C416}$ | $R^{D26}$ | $R^{D16}$ | H |
| $L_{C417}$ | $R^{D26}$ | $R^{D17}$ | H |
| $L_{C418}$ | $R^{D26}$ | $R^{D18}$ | H |
| $L_{C419}$ | $R^{D26}$ | $R^{D19}$ | H |
| $L_{C420}$ | $R^{D26}$ | $R^{D20}$ | H |
| $L_{C421}$ | $R^{D26}$ | $R^{D21}$ | H |
| $L_{C422}$ | $R^{D26}$ | $R^{D23}$ | H |
| $L_{C423}$ | $R^{D26}$ | $R^{D24}$ | H |
| $L_{C424}$ | $R^{D26}$ | $R^{D25}$ | H |
| $L_{C425}$ | $R^{D26}$ | $R^{D27}$ | H |
| $L_{C426}$ | $R^{D26}$ | $R^{D28}$ | H |
| $L_{C427}$ | $R^{D26}$ | $R^{D29}$ | H |
| $L_{C428}$ | $R^{D26}$ | $R^{D30}$ | H |
| $L_{C429}$ | $R^{D26}$ | $R^{D31}$ | H |
| $L_{C430}$ | $R^{D26}$ | $R^{D32}$ | H |
| $L_{C431}$ | $R^{D26}$ | $R^{D33}$ | H |
| $L_{C432}$ | $R^{D26}$ | $R^{D34}$ | H |
| $L_{C433}$ | $R^{D26}$ | $R^{D35}$ | H |
| $L_{C434}$ | $R^{D26}$ | $R^{D40}$ | H |
| $L_{C435}$ | $R^{D26}$ | $R^{D41}$ | H |
| $L_{C436}$ | $R^{D26}$ | $R^{D42}$ | H |
| $L_{C437}$ | $R^{D26}$ | $R^{D64}$ | H |
| $L_{C438}$ | $R^{D26}$ | $R^{D66}$ | H |
| $L_{C439}$ | $R^{D26}$ | $R^{D68}$ | H |
| $L_{C440}$ | $R^{D26}$ | $R^{D76}$ | H |
| $L_{C441}$ | $R^{D35}$ | $R^{D5}$ | H |
| $L_{C442}$ | $R^{D35}$ | $R^{D6}$ | H |
| $L_{C443}$ | $R^{D35}$ | $R^{D9}$ | H |
| $L_{C444}$ | $R^{D35}$ | $R^{D10}$ | H |
| $L_{C445}$ | $R^{D35}$ | $R^{D12}$ | H |
| $L_{C446}$ | $R^{D35}$ | $R^{D15}$ | H |
| $L_{C447}$ | $R^{D35}$ | $R^{D16}$ | H |
| $L_{C448}$ | $R^{D35}$ | $R^{D17}$ | H |
| $L_{C449}$ | $R^{D35}$ | $R^{D18}$ | H |
| $L_{C450}$ | $R^{D35}$ | $R^{D19}$ | H |
| $L_{C451}$ | $R^{D35}$ | $R^{D20}$ | H |
| $L_{C452}$ | $R^{D35}$ | $R^{D21}$ | H |
| $L_{C453}$ | $R^{D35}$ | $R^{D23}$ | H |
| $L_{C454}$ | $R^{D35}$ | $R^{D24}$ | H |
| $L_{C455}$ | $R^{D35}$ | $R^{D25}$ | H |
| $L_{C456}$ | $R^{D35}$ | $R^{D27}$ | H |
| $L_{C457}$ | $R^{D35}$ | $R^{D28}$ | H |
| $L_{C458}$ | $R^{D35}$ | $R^{D29}$ | H |
| $L_{C459}$ | $R^{D35}$ | $R^{D30}$ | H |
| $L_{C460}$ | $R^{D35}$ | $R^{D31}$ | H |
| $L_{C461}$ | $R^{D35}$ | $R^{D32}$ | H |
| $L_{C462}$ | $R^{D35}$ | $R^{D33}$ | H |
| $L_{C463}$ | $R^{D35}$ | $R^{D34}$ | H |
| $L_{C464}$ | $R^{D35}$ | $R^{D40}$ | H |
| $L_{C465}$ | $R^{D35}$ | $R^{D41}$ | H |
| $L_{C466}$ | $R^{D35}$ | $R^{D42}$ | H |
| $L_{C467}$ | $R^{D35}$ | $R^{D64}$ | H |
| $L_{C468}$ | $R^{D35}$ | $R^{D66}$ | H |
| $L_{C469}$ | $R^{D35}$ | $R^{D68}$ | H |
| $L_{C470}$ | $R^{D35}$ | $R^{D76}$ | H |
| $L_{C471}$ | $R^{D40}$ | $R^{D5}$ | H |
| $L_{C472}$ | $R^{D40}$ | $R^{D6}$ | H |
| $L_{C473}$ | $R^{D40}$ | $R^{D9}$ | H |
| $L_{C474}$ | $R^{D40}$ | $R^{D10}$ | H |
| $L_{C475}$ | $R^{D40}$ | $R^{D12}$ | H |
| $L_{C476}$ | $R^{D40}$ | $R^{D15}$ | H |
| $L_{C477}$ | $R^{D40}$ | $R^{D16}$ | H |
| $L_{C478}$ | $R^{D40}$ | $R^{D17}$ | H |
| $L_{C479}$ | $R^{D40}$ | $R^{D18}$ | H |

-continued

| Ligand | $R^1$ | $R^2$ | $R^3$ |
|---|---|---|---|
| $L_{C480}$ | $R^{D40}$ | $R^{D19}$ | H |
| $L_{C481}$ | $R^{D40}$ | $R^{D20}$ | H |
| $L_{C482}$ | $R^{D40}$ | $R^{D21}$ | H |
| $L_{C483}$ | $R^{D40}$ | $R^{D23}$ | H |
| $L_{C484}$ | $R^{D40}$ | $R^{D24}$ | H |
| $L_{C485}$ | $R^{D40}$ | $R^{D25}$ | H |
| $L_{C486}$ | $R^{D40}$ | $R^{D27}$ | H |
| $L_{C487}$ | $R^{D40}$ | $R^{D28}$ | H |
| $L_{C488}$ | $R^{D40}$ | $R^{D29}$ | H |
| $L_{C489}$ | $R^{D40}$ | $R^{D30}$ | H |
| $L_{C490}$ | $R^{D40}$ | $R^{D31}$ | H |
| $L_{C491}$ | $R^{D40}$ | $R^{D32}$ | H |
| $L_{C492}$ | $R^{D40}$ | $R^{D33}$ | H |
| $L_{C493}$ | $R^{D40}$ | $R^{D34}$ | H |
| $L_{C494}$ | $R^{D40}$ | $R^{D41}$ | H |
| $L_{C495}$ | $R^{D40}$ | $R^{D42}$ | H |
| $L_{C496}$ | $R^{D40}$ | $R^{D64}$ | H |
| $L_{C497}$ | $R^{D40}$ | $R^{D66}$ | H |
| $L_{C498}$ | $R^{D40}$ | $R^{D68}$ | H |
| $L_{C499}$ | $R^{D40}$ | $R^{D76}$ | H |
| $L_{C500}$ | $R^{D41}$ | $R^{D5}$ | H |
| $L_{C501}$ | $R^{D41}$ | $R^{D6}$ | H |
| $L_{C502}$ | $R^{D41}$ | $R^{D9}$ | H |
| $L_{C503}$ | $R^{D41}$ | $R^{D10}$ | H |
| $L_{C504}$ | $R^{D41}$ | $R^{D12}$ | H |
| $L_{C505}$ | $R^{D41}$ | $R^{D15}$ | H |
| $L_{C506}$ | $R^{D41}$ | $R^{D16}$ | H |
| $L_{C507}$ | $R^{D41}$ | $R^{D17}$ | H |
| $L_{C508}$ | $R^{D41}$ | $R^{D18}$ | H |
| $L_{C509}$ | $R^{D41}$ | $R^{D19}$ | H |
| $L_{C510}$ | $R^{D41}$ | $R^{D20}$ | H |
| $L_{C511}$ | $R^{D41}$ | $R^{D21}$ | H |
| $L_{C512}$ | $R^{D41}$ | $R^{D23}$ | H |
| $L_{C513}$ | $R^{D41}$ | $R^{D24}$ | H |
| $L_{C514}$ | $R^{D41}$ | $R^{D25}$ | H |
| $L_{C515}$ | $R^{D41}$ | $R^{D27}$ | H |
| $L_{C516}$ | $R^{D41}$ | $R^{D28}$ | H |
| $L_{C517}$ | $R^{D41}$ | $R^{D29}$ | H |
| $L_{C518}$ | $R^{D41}$ | $R^{D30}$ | H |
| $L_{C519}$ | $R^{D41}$ | $R^{D31}$ | H |
| $L_{C520}$ | $R^{D41}$ | $R^{D32}$ | H |
| $L_{C521}$ | $R^{D41}$ | $R^{D33}$ | H |
| $L_{C522}$ | $R^{D41}$ | $R^{D34}$ | H |
| $L_{C523}$ | $R^{D41}$ | $R^{D42}$ | H |
| $L_{C524}$ | $R^{D41}$ | $R^{D64}$ | H |
| $L_{C525}$ | $R^{D41}$ | $R^{D66}$ | H |
| $L_{C526}$ | $R^{D41}$ | $R^{D68}$ | H |
| $L_{C527}$ | $R^{D41}$ | $R^{D76}$ | H |
| $L_{C528}$ | $R^{D64}$ | $R^{D5}$ | H |
| $L_{C529}$ | $R^{D64}$ | $R^{D6}$ | H |
| $L_{C530}$ | $R^{D64}$ | $R^{D9}$ | H |
| $L_{C531}$ | $R^{D64}$ | $R^{D10}$ | H |
| $L_{C532}$ | $R^{D64}$ | $R^{D12}$ | H |
| $L_{C533}$ | $R^{D64}$ | $R^{D15}$ | H |
| $L_{C534}$ | $R^{D64}$ | $R^{D16}$ | H |
| $L_{C535}$ | $R^{D64}$ | $R^{D17}$ | H |
| $L_{C536}$ | $R^{D64}$ | $R^{D18}$ | H |
| $L_{C537}$ | $R^{D64}$ | $R^{D19}$ | H |
| $L_{C538}$ | $R^{D64}$ | $R^{D20}$ | H |
| $L_{C539}$ | $R^{D64}$ | $R^{D21}$ | H |
| $L_{C540}$ | $R^{D64}$ | $R^{D23}$ | H |
| $L_{C541}$ | $R^{D64}$ | $R^{D24}$ | H |
| $L_{C542}$ | $R^{D64}$ | $R^{D25}$ | H |
| $L_{C543}$ | $R^{D64}$ | $R^{D27}$ | H |
| $L_{C544}$ | $R^{D64}$ | $R^{D28}$ | H |
| $L_{C545}$ | $R^{D64}$ | $R^{D29}$ | H |
| $L_{C546}$ | $R^{D64}$ | $R^{D30}$ | H |
| $L_{C547}$ | $R^{D64}$ | $R^{D31}$ | H |
| $L_{C548}$ | $R^{D64}$ | $R^{D32}$ | H |
| $L_{C549}$ | $R^{D64}$ | $R^{D33}$ | H |
| $L_{C550}$ | $R^{D64}$ | $R^{D34}$ | H |
| $L_{C551}$ | $R^{D64}$ | $R^{D42}$ | H |
| $L_{C552}$ | $R^{D64}$ | $R^{D64}$ | H |
| $L_{C553}$ | $R^{D64}$ | $R^{D66}$ | H |
| $L_{C554}$ | $R^{D64}$ | $R^{D68}$ | H |
| $L_{C555}$ | $R^{D64}$ | $R^{D76}$ | H |
| $L_{C556}$ | $R^{D66}$ | $R^{D5}$ | H |

-continued

| Ligand | $R^1$ | $R^2$ | $R^3$ |
|---|---|---|---|
| $L_{C557}$ | $R^{D66}$ | $R^{D6}$ | H |
| $L_{C558}$ | $R^{D66}$ | $R^{D9}$ | H |
| $L_{C559}$ | $R^{D66}$ | $R^{D10}$ | H |
| $L_{C560}$ | $R^{D66}$ | $R^{D12}$ | H |
| $L_{C561}$ | $R^{D66}$ | $R^{D15}$ | H |
| $L_{C562}$ | $R^{D66}$ | $R^{D16}$ | H |
| $L_{C563}$ | $R^{D66}$ | $R^{D17}$ | H |
| $L_{C564}$ | $R^{D66}$ | $R^{D18}$ | H |
| $L_{C565}$ | $R^{D66}$ | $R^{D19}$ | H |
| $L_{C566}$ | $R^{D66}$ | $R^{D20}$ | H |
| $L_{C567}$ | $R^{D66}$ | $R^{D21}$ | H |
| $L_{C568}$ | $R^{D66}$ | $R^{D23}$ | H |
| $L_{C569}$ | $R^{D66}$ | $R^{D24}$ | H |
| $L_{C570}$ | $R^{D66}$ | $R^{D25}$ | H |
| $L_{C571}$ | $R^{D66}$ | $R^{D27}$ | H |
| $L_{C572}$ | $R^{D66}$ | $R^{D28}$ | H |
| $L_{C573}$ | $R^{D66}$ | $R^{D29}$ | H |
| $L_{C574}$ | $R^{D66}$ | $R^{D30}$ | H |
| $L_{C575}$ | $R^{D66}$ | $R^{D31}$ | H |
| $L_{C576}$ | $R^{D66}$ | $R^{D32}$ | H |
| $L_{C577}$ | $R^{D66}$ | $R^{D33}$ | H |
| $L_{C578}$ | $R^{D66}$ | $R^{D34}$ | H |
| $L_{C579}$ | $R^{D66}$ | $R^{D42}$ | H |
| $L_{C580}$ | $R^{D66}$ | $R^{D68}$ | H |
| $L_{C581}$ | $R^{D66}$ | $R^{D76}$ | H |
| $L_{C582}$ | $R^{D68}$ | $R^{D5}$ | H |
| $L_{C583}$ | $R^{D68}$ | $R^{D6}$ | H |
| $L_{C584}$ | $R^{D68}$ | $R^{D9}$ | H |
| $L_{C585}$ | $R^{D68}$ | $R^{D10}$ | H |
| $L_{C586}$ | $R^{D68}$ | $R^{D12}$ | H |
| $L_{C587}$ | $R^{D68}$ | $R^{D15}$ | H |
| $L_{C588}$ | $R^{D68}$ | $R^{D16}$ | H |
| $L_{C589}$ | $R^{D68}$ | $R^{D17}$ | H |
| $L_{C590}$ | $R^{D68}$ | $R^{D18}$ | H |
| $L_{C591}$ | $R^{D68}$ | $R^{D19}$ | H |
| $L_{C592}$ | $R^{D68}$ | $R^{D20}$ | H |
| $L_{C593}$ | $R^{D68}$ | $R^{D21}$ | H |
| $L_{C594}$ | $R^{D68}$ | $R^{D23}$ | H |
| $L_{C595}$ | $R^{D68}$ | $R^{D24}$ | H |
| $L_{C596}$ | $R^{D68}$ | $R^{D25}$ | H |
| $L_{C597}$ | $R^{D68}$ | $R^{D27}$ | H |
| $L_{C598}$ | $R^{D68}$ | $R^{D28}$ | H |
| $L_{C599}$ | $R^{D68}$ | $R^{D29}$ | H |
| $L_{C600}$ | $R^{D68}$ | $R^{D30}$ | H |
| $L_{C601}$ | $R^{D68}$ | $R^{D31}$ | H |
| $L_{C602}$ | $R^{D68}$ | $R^{D32}$ | H |
| $L_{C603}$ | $R^{D68}$ | $R^{D33}$ | H |
| $L_{C604}$ | $R^{D68}$ | $R^{D34}$ | H |
| $L_{C605}$ | $R^{D68}$ | $R^{D42}$ | H |
| $L_{C606}$ | $R^{D68}$ | $R^{D76}$ | H |
| $L_{C607}$ | $R^{D76}$ | $R^{D5}$ | H |
| $L_{C608}$ | $R^{D76}$ | $R^{D6}$ | H |
| $L_{C609}$ | $R^{D76}$ | $R^{D9}$ | H |
| $L_{C610}$ | $R^{D76}$ | $R^{D10}$ | H |
| $L_{C611}$ | $R^{D76}$ | $R^{D12}$ | H |
| $L_{C612}$ | $R^{D76}$ | $R^{D15}$ | H |
| $L_{C613}$ | $R^{D76}$ | $R^{D16}$ | H |
| $L_{C614}$ | $R^{D76}$ | $R^{D17}$ | H |
| $L_{C615}$ | $R^{D76}$ | $R^{D18}$ | H |
| $L_{C616}$ | $R^{D76}$ | $R^{D19}$ | H |
| $L_{C617}$ | $R^{D76}$ | $R^{D20}$ | H |
| $L_{C618}$ | $R^{D76}$ | $R^{D21}$ | H |
| $L_{C619}$ | $R^{D76}$ | $R^{D23}$ | H |
| $L_{C620}$ | $R^{D76}$ | $R^{D24}$ | H |
| $L_{C621}$ | $R^{D76}$ | $R^{D25}$ | H |
| $L_{C622}$ | $R^{D76}$ | $R^{D27}$ | H |
| $L_{C623}$ | $R^{D76}$ | $R^{D28}$ | H |
| $L_{C624}$ | $R^{D76}$ | $R^{D29}$ | H |
| $L_{C625}$ | $R^{D76}$ | $R^{D30}$ | H |
| $L_{C626}$ | $R^{D76}$ | $R^{D31}$ | H |
| $L_{C627}$ | $R^{D76}$ | $R^{D32}$ | H |
| $L_{C628}$ | $R^{D76}$ | $R^{D33}$ | H |
| $L_{C629}$ | $R^{D76}$ | $R^{D34}$ | H |
| $L_{C630}$ | $R^{D76}$ | $R^{D42}$ | H |
| $L_{C631}$ | $R^{D1}$ | $R^{D1}$ | $R^{D1}$ |
| $L_{C632}$ | $R^{D2}$ | $R^{D2}$ | $R^{D1}$ |
| $L_{C633}$ | $R^{D3}$ | $R^{D3}$ | $R^{D1}$ |

-continued

| Ligand | $R^1$ | $R^2$ | $R^3$ |
|---|---|---|---|
| $L_{C634}$ | $R^{D4}$ | $R^{D4}$ | $R^{D1}$ |
| $L_{C635}$ | $R^{D5}$ | $R^{D5}$ | $R^{D1}$ |
| $L_{C636}$ | $R^{D6}$ | $R^{D6}$ | $R^{D1}$ |
| $L_{C637}$ | $R^{D7}$ | $R^{D7}$ | $R^{D1}$ |
| $L_{C638}$ | $R^{D8}$ | $R^{D8}$ | $R^{D1}$ |
| $L_{C639}$ | $R^{D9}$ | $R^{D9}$ | $R^{D1}$ |
| $L_{C640}$ | $R^{D10}$ | $R^{D10}$ | $R^{D1}$ |
| $L_{C641}$ | $R^{D11}$ | $R^{D11}$ | $R^{D1}$ |
| $L_{C642}$ | $R^{D12}$ | $R^{D12}$ | $R^{D1}$ |
| $L_{C643}$ | $R^{D13}$ | $R^{D13}$ | $R^{D1}$ |
| $L_{C644}$ | $R^{D14}$ | $R^{D14}$ | $R^{D1}$ |
| $L_{C645}$ | $R^{D15}$ | $R^{D15}$ | $R^{D1}$ |
| $L_{C646}$ | $R^{D16}$ | $R^{D16}$ | $R^{D1}$ |
| $L_{C647}$ | $R^{D17}$ | $R^{D17}$ | $R^{D1}$ |
| $L_{C648}$ | $R^{D18}$ | $R^{D18}$ | $R^{D1}$ |
| $L_{C649}$ | $R^{D19}$ | $R^{D19}$ | $R^{D1}$ |
| $L_{C650}$ | $R^{D20}$ | $R^{D20}$ | $R^{D1}$ |
| $L_{C651}$ | $R^{D21}$ | $R^{D21}$ | $R^{D1}$ |
| $L_{C652}$ | $R^{D22}$ | $R^{D22}$ | $R^{D1}$ |
| $L_{C653}$ | $R^{D23}$ | $R^{D23}$ | $R^{D1}$ |
| $L_{C654}$ | $R^{D24}$ | $R^{D24}$ | $R^{D1}$ |
| $L_{C655}$ | $R^{D25}$ | $R^{D25}$ | $R^{D1}$ |
| $L_{C656}$ | $R^{D26}$ | $R^{D26}$ | $R^{D1}$ |
| $L_{C657}$ | $R^{D27}$ | $R^{D27}$ | $R^{D1}$ |
| $L_{C658}$ | $R^{D28}$ | $R^{D28}$ | $R^{D1}$ |
| $L_{C659}$ | $R^{D29}$ | $R^{D29}$ | $R^{D1}$ |
| $L_{C660}$ | $R^{D30}$ | $R^{D30}$ | $R^{D1}$ |
| $L_{C661}$ | $R^{D31}$ | $R^{D31}$ | $R^{D1}$ |
| $L_{C662}$ | $R^{D32}$ | $R^{D32}$ | $R^{D1}$ |
| $L_{C663}$ | $R^{D33}$ | $R^{D33}$ | $R^{D1}$ |
| $L_{C664}$ | $R^{D34}$ | $R^{D34}$ | $R^{D1}$ |
| $L_{C665}$ | $R^{D35}$ | $R^{D35}$ | $R^{D1}$ |
| $L_{C666}$ | $R^{D40}$ | $R^{D40}$ | $R^{D1}$ |
| $L_{C667}$ | $R^{D41}$ | $R^{D41}$ | $R^{D1}$ |
| $L_{C668}$ | $R^{D42}$ | $R^{D42}$ | $R^{D1}$ |
| $L_{C669}$ | $R^{D64}$ | $R^{D64}$ | $R^{D1}$ |
| $L_{C670}$ | $R^{D66}$ | $R^{D66}$ | $R^{D1}$ |
| $L_{C671}$ | $R^{D68}$ | $R^{D68}$ | $R^{D1}$ |
| $L_{C672}$ | $R^{D76}$ | $R^{D76}$ | $R^{D1}$ |
| $L_{C673}$ | $R^{D1}$ | $R^{D2}$ | $R^{D1}$ |
| $L_{C674}$ | $R^{D1}$ | $R^{D3}$ | $R^{D1}$ |
| $L_{C675}$ | $R^{D1}$ | $R^{D4}$ | $R^{D1}$ |
| $L_{C676}$ | $R^{D1}$ | $R^{D5}$ | $R^{D1}$ |
| $L_{C677}$ | $R^{D1}$ | $R^{D6}$ | $R^{D1}$ |
| $L_{C678}$ | $R^{D1}$ | $R^{D7}$ | $R^{D1}$ |
| $L_{C679}$ | $R^{D1}$ | $R^{D8}$ | $R^{D1}$ |
| $L_{C680}$ | $R^{D1}$ | $R^{D9}$ | $R^{D1}$ |
| $L_{C681}$ | $R^{D1}$ | $R^{D10}$ | $R^{D1}$ |
| $L_{C682}$ | $R^{D1}$ | $R^{D11}$ | $R^{D1}$ |
| $L_{C683}$ | $R^{D1}$ | $R^{D12}$ | $R^{D1}$ |
| $L_{C684}$ | $R^{D1}$ | $R^{D13}$ | $R^{D1}$ |
| $L_{C685}$ | $R^{D1}$ | $R^{D14}$ | $R^{D1}$ |
| $L_{C686}$ | $R^{D1}$ | $R^{D15}$ | $R^{D1}$ |
| $L_{C687}$ | $R^{D1}$ | $R^{D16}$ | $R^{D1}$ |
| $L_{C688}$ | $R^{D1}$ | $R^{D17}$ | $R^{D1}$ |
| $L_{C689}$ | $R^{D1}$ | $R^{D18}$ | $R^{D1}$ |
| $L_{C690}$ | $R^{D1}$ | $R^{D19}$ | $R^{D1}$ |
| $L_{C691}$ | $R^{D1}$ | $R^{D20}$ | $R^{D1}$ |
| $L_{C692}$ | $R^{D1}$ | $R^{D21}$ | $R^{D1}$ |
| $L_{C693}$ | $R^{D1}$ | $R^{D22}$ | $R^{D1}$ |
| $L_{C694}$ | $R^{D1}$ | $R^{D23}$ | $R^{D1}$ |
| $L_{C695}$ | $R^{D1}$ | $R^{D24}$ | $R^{D1}$ |
| $L_{C696}$ | $R^{D1}$ | $R^{D25}$ | $R^{D1}$ |
| $L_{C697}$ | $R^{D1}$ | $R^{D26}$ | $R^{D1}$ |
| $L_{C698}$ | $R^{D1}$ | $R^{D27}$ | $R^{D1}$ |
| $L_{C699}$ | $R^{D1}$ | $R^{D28}$ | $R^{D1}$ |
| $L_{C700}$ | $R^{D1}$ | $R^{D29}$ | $R^{D1}$ |
| $L_{C701}$ | $R^{D1}$ | $R^{D30}$ | $R^{D1}$ |
| $L_{C702}$ | $R^{D1}$ | $R^{D31}$ | $R^{D1}$ |
| $L_{C703}$ | $R^{D1}$ | $R^{D32}$ | $R^{D1}$ |
| $L_{C704}$ | $R^{D1}$ | $R^{D33}$ | $R^{D1}$ |
| $L_{C705}$ | $R^{D1}$ | $R^{D34}$ | $R^{D1}$ |
| $L_{C706}$ | $R^{D1}$ | $R^{D35}$ | $R^{D1}$ |
| $L_{C707}$ | $R^{D1}$ | $R^{D40}$ | $R^{D1}$ |
| $L_{C708}$ | $R^{D1}$ | $R^{D41}$ | $R^{D1}$ |
| $L_{C709}$ | $R^{D1}$ | $R^{D42}$ | $R^{D1}$ |
| $L_{C710}$ | $R^{D1}$ | $R^{D64}$ | $R^{D1}$ |

-continued

| Ligand | $R^1$ | $R^2$ | $R^3$ |
|---|---|---|---|
| $L_{C711}$ | $R^{D1}$ | $R^{D66}$ | $R^{D1}$ |
| $L_{C712}$ | $R^{D1}$ | $R^{D68}$ | $R^{D1}$ |
| $L_{C713}$ | $R^{D1}$ | $R^{D76}$ | $R^{D1}$ |
| $L_{C714}$ | $R^{D2}$ | $R^{D1}$ | $R^{D1}$ |
| $L_{C715}$ | $R^{D2}$ | $R^{D3}$ | $R^{D1}$ |
| $L_{C716}$ | $R^{D2}$ | $R^{D4}$ | $R^{D1}$ |
| $L_{C717}$ | $R^{D2}$ | $R^{D5}$ | $R^{D1}$ |
| $L_{C718}$ | $R^{D2}$ | $R^{D6}$ | $R^{D1}$ |
| $L_{C719}$ | $R^{D2}$ | $R^{D7}$ | $R^{D1}$ |
| $L_{C720}$ | $R^{D2}$ | $R^{D8}$ | $R^{D1}$ |
| $L_{C721}$ | $R^{D2}$ | $R^{D9}$ | $R^{D1}$ |
| $L_{C722}$ | $R^{D2}$ | $R^{D10}$ | $R^{D1}$ |
| $L_{C723}$ | $R^{D2}$ | $R^{D11}$ | $R^{D1}$ |
| $L_{C724}$ | $R^{D2}$ | $R^{D12}$ | $R^{D1}$ |
| $L_{C725}$ | $R^{D2}$ | $R^{D13}$ | $R^{D1}$ |
| $L_{C726}$ | $R^{D2}$ | $R^{D14}$ | $R^{D1}$ |
| $L_{C727}$ | $R^{D2}$ | $R^{D15}$ | $R^{D1}$ |
| $L_{C728}$ | $R^{D2}$ | $R^{D16}$ | $R^{D1}$ |
| $L_{C729}$ | $R^{D2}$ | $R^{D17}$ | $R^{D1}$ |
| $L_{C730}$ | $R^{D2}$ | $R^{D18}$ | $R^{D1}$ |
| $L_{C731}$ | $R^{D2}$ | $R^{D19}$ | $R^{D1}$ |
| $L_{C732}$ | $R^{D2}$ | $R^{D20}$ | $R^{D1}$ |
| $L_{C733}$ | $R^{D2}$ | $R^{D21}$ | $R^{D1}$ |
| $L_{C734}$ | $R^{D2}$ | $R^{D22}$ | $R^{D1}$ |
| $L_{C735}$ | $R^{D2}$ | $R^{D23}$ | $R^{D1}$ |
| $L_{C736}$ | $R^{D2}$ | $R^{D24}$ | $R^{D1}$ |
| $L_{C737}$ | $R^{D2}$ | $R^{D25}$ | $R^{D1}$ |
| $L_{C738}$ | $R^{D2}$ | $R^{D26}$ | $R^{D1}$ |
| $L_{C739}$ | $R^{D2}$ | $R^{D27}$ | $R^{D1}$ |
| $L_{C740}$ | $R^{D2}$ | $R^{D28}$ | $R^{D1}$ |
| $L_{C741}$ | $R^{D2}$ | $R^{D29}$ | $R^{D1}$ |
| $L_{C742}$ | $R^{D2}$ | $R^{D30}$ | $R^{D1}$ |
| $L_{C743}$ | $R^{D2}$ | $R^{D31}$ | $R^{D1}$ |
| $L_{C744}$ | $R^{D2}$ | $R^{D32}$ | $R^{D1}$ |
| $L_{C745}$ | $R^{D2}$ | $R^{D33}$ | $R^{D1}$ |
| $L_{C746}$ | $R^{D2}$ | $R^{D34}$ | $R^{D1}$ |
| $L_{C747}$ | $R^{D2}$ | $R^{D35}$ | $R^{D1}$ |
| $L_{C748}$ | $R^{D2}$ | $R^{D40}$ | $R^{D1}$ |
| $L_{C749}$ | $R^{D2}$ | $R^{D41}$ | $R^{D1}$ |
| $L_{C750}$ | $R^{D2}$ | $R^{D42}$ | $R^{D1}$ |
| $L_{C751}$ | $R^{D2}$ | $R^{D64}$ | $R^{D1}$ |
| $L_{C752}$ | $R^{D2}$ | $R^{D66}$ | $R^{D1}$ |
| $L_{C753}$ | $R^{D2}$ | $R^{D68}$ | $R^{D1}$ |
| $L_{C754}$ | $R^{D2}$ | $R^{D76}$ | $R^{D1}$ |
| $L_{C755}$ | $R^{D3}$ | $R^{D4}$ | $R^{D1}$ |
| $L_{C756}$ | $R^{D3}$ | $R^{D5}$ | $R^{D1}$ |
| $L_{C757}$ | $R^{D3}$ | $R^{D6}$ | $R^{D1}$ |
| $L_{C758}$ | $R^{D3}$ | $R^{D7}$ | $R^{D1}$ |
| $L_{C759}$ | $R^{D3}$ | $R^{D8}$ | $R^{D1}$ |
| $L_{C760}$ | $R^{D3}$ | $R^{D9}$ | $R^{D1}$ |
| $L_{C761}$ | $R^{D3}$ | $R^{D10}$ | $R^{D1}$ |
| $L_{C762}$ | $R^{D3}$ | $R^{D11}$ | $R^{D1}$ |
| $L_{C763}$ | $R^{D3}$ | $R^{D12}$ | $R^{D1}$ |
| $L_{C764}$ | $R^{D3}$ | $R^{D13}$ | $R^{D1}$ |
| $L_{C765}$ | $R^{D3}$ | $R^{D14}$ | $R^{D1}$ |
| $L_{C766}$ | $R^{D3}$ | $R^{D15}$ | $R^{D1}$ |
| $L_{C767}$ | $R^{D3}$ | $R^{D16}$ | $R^{D1}$ |
| $L_{C768}$ | $R^{D3}$ | $R^{D17}$ | $R^{D1}$ |
| $L_{C769}$ | $R^{D3}$ | $R^{D18}$ | $R^{D1}$ |
| $L_{C770}$ | $R^{D3}$ | $R^{D19}$ | $R^{D1}$ |
| $L_{C771}$ | $R^{D3}$ | $R^{D20}$ | $R^{D1}$ |
| $L_{C772}$ | $R^{D3}$ | $R^{D21}$ | $R^{D1}$ |
| $L_{C773}$ | $R^{D3}$ | $R^{D22}$ | $R^{D1}$ |
| $L_{C774}$ | $R^{D3}$ | $R^{D23}$ | $R^{D1}$ |
| $L_{C775}$ | $R^{D3}$ | $R^{D24}$ | $R^{D1}$ |
| $L_{C776}$ | $R^{D3}$ | $R^{D25}$ | $R^{D1}$ |
| $L_{C777}$ | $R^{D3}$ | $R^{D26}$ | $R^{D1}$ |
| $L_{C778}$ | $R^{D3}$ | $R^{D27}$ | $R^{D1}$ |
| $L_{C779}$ | $R^{D3}$ | $R^{D28}$ | $R^{D1}$ |
| $L_{C780}$ | $R^{D3}$ | $R^{D29}$ | $R^{D1}$ |
| $L_{C781}$ | $R^{D3}$ | $R^{D30}$ | $R^{D1}$ |
| $L_{C782}$ | $R^{D3}$ | $R^{D31}$ | $R^{D1}$ |
| $L_{C783}$ | $R^{D3}$ | $R^{D32}$ | $R^{D1}$ |
| $L_{C784}$ | $R^{D3}$ | $R^{D33}$ | $R^{D1}$ |
| $L_{C785}$ | $R^{D3}$ | $R^{D34}$ | $R^{D1}$ |
| $L_{C786}$ | $R^{D3}$ | $R^{D35}$ | $R^{D1}$ |
| $L_{C787}$ | $R^{D3}$ | $R^{D40}$ | $R^{D1}$ |

-continued

| Ligand | $R^1$ | $R^2$ | $R^3$ |
|---|---|---|---|
| $L_{C788}$ | $R^{D3}$ | $R^{D41}$ | $R^{D1}$ |
| $L_{C789}$ | $R^{D3}$ | $R^{D42}$ | $R^{D1}$ |
| $L_{C790}$ | $R^{D3}$ | $R^{D64}$ | $R^{D1}$ |
| $L_{C791}$ | $R^{D3}$ | $R^{D66}$ | $R^{D1}$ |
| $L_{C792}$ | $R^{D3}$ | $R^{D68}$ | $R^{D1}$ |
| $L_{C793}$ | $R^{D3}$ | $R^{D76}$ | $R^{D1}$ |
| $L_{C794}$ | $R^{D4}$ | $R^{D5}$ | $R^{D1}$ |
| $L_{C795}$ | $R^{D4}$ | $R^{D6}$ | $R^{D1}$ |
| $L_{C796}$ | $R^{D4}$ | $R^{D7}$ | $R^{D1}$ |
| $L_{C797}$ | $R^{D4}$ | $R^{D8}$ | $R^{D1}$ |
| $L_{C798}$ | $R^{D4}$ | $R^{D9}$ | $R^{D1}$ |
| $L_{C799}$ | $R^{D4}$ | $R^{D10}$ | $R^{D1}$ |
| $L_{C800}$ | $R^{D4}$ | $R^{D11}$ | $R^{D1}$ |
| $L_{C801}$ | $R^{D4}$ | $R^{D12}$ | $R^{D1}$ |
| $L_{C802}$ | $R^{D4}$ | $R^{D13}$ | $R^{D1}$ |
| $L_{C803}$ | $R^{D4}$ | $R^{D14}$ | $R^{D1}$ |
| $L_{C804}$ | $R^{D4}$ | $R^{D15}$ | $R^{D1}$ |
| $L_{C805}$ | $R^{D4}$ | $R^{D16}$ | $R^{D1}$ |
| $L_{C806}$ | $R^{D4}$ | $R^{D17}$ | $R^{D1}$ |
| $L_{C807}$ | $R^{D4}$ | $R^{D18}$ | $R^{D1}$ |
| $L_{C808}$ | $R^{D4}$ | $R^{D19}$ | $R^{D1}$ |
| $L_{C809}$ | $R^{D4}$ | $R^{D20}$ | $R^{D1}$ |
| $L_{C810}$ | $R^{D4}$ | $R^{D21}$ | $R^{D1}$ |
| $L_{C811}$ | $R^{D4}$ | $R^{D22}$ | $R^{D1}$ |
| $L_{C812}$ | $R^{D4}$ | $R^{D23}$ | $R^{D1}$ |
| $L_{C813}$ | $R^{D4}$ | $R^{D24}$ | $R^{D1}$ |
| $L_{C814}$ | $R^{D4}$ | $R^{D25}$ | $R^{D1}$ |
| $L_{C815}$ | $R^{D4}$ | $R^{D26}$ | $R^{D1}$ |
| $L_{C816}$ | $R^{D4}$ | $R^{D27}$ | $R^{D1}$ |
| $L_{C817}$ | $R^{D4}$ | $R^{D28}$ | $R^{D1}$ |
| $L_{C818}$ | $R^{D4}$ | $R^{D29}$ | $R^{D1}$ |
| $L_{C819}$ | $R^{D4}$ | $R^{D30}$ | $R^{D1}$ |
| $L_{C820}$ | $R^{D4}$ | $R^{D31}$ | $R^{D1}$ |
| $L_{C821}$ | $R^{D4}$ | $R^{D32}$ | $R^{D1}$ |
| $L_{C822}$ | $R^{D4}$ | $R^{D33}$ | $R^{D1}$ |
| $L_{C823}$ | $R^{D4}$ | $R^{D34}$ | $R^{D1}$ |
| $L_{C824}$ | $R^{D4}$ | $R^{D35}$ | $R^{D1}$ |
| $L_{C825}$ | $R^{D4}$ | $R^{D40}$ | $R^{D1}$ |
| $L_{C826}$ | $R^{D4}$ | $R^{D41}$ | $R^{D1}$ |
| $L_{C827}$ | $R^{D4}$ | $R^{D42}$ | $R^{D1}$ |
| $L_{C828}$ | $R^{D4}$ | $R^{D64}$ | $R^{D1}$ |
| $L_{C829}$ | $R^{D4}$ | $R^{D66}$ | $R^{D1}$ |
| $L_{C830}$ | $R^{D4}$ | $R^{D68}$ | $R^{D1}$ |
| $L_{C831}$ | $R^{D4}$ | $R^{D76}$ | $R^{D1}$ |
| $L_{C832}$ | $R^{D4}$ | $R^{D1}$ | $R^{D1}$ |
| $L_{C833}$ | $R^{D7}$ | $R^{D5}$ | $R^{D1}$ |
| $L_{C834}$ | $R^{D7}$ | $R^{D6}$ | $R^{D1}$ |
| $L_{C835}$ | $R^{D7}$ | $R^{D8}$ | $R^{D1}$ |
| $L_{C836}$ | $R^{D7}$ | $R^{D9}$ | $R^{D1}$ |
| $L_{C837}$ | $R^{D7}$ | $R^{D10}$ | $R^{D1}$ |
| $L_{C838}$ | $R^{D7}$ | $R^{D11}$ | $R^{D1}$ |
| $L_{C839}$ | $R^{D7}$ | $R^{D12}$ | $R^{D1}$ |
| $L_{C840}$ | $R^{D7}$ | $R^{D13}$ | $R^{D1}$ |
| $L_{C841}$ | $R^{D7}$ | $R^{D14}$ | $R^{D1}$ |
| $L_{C842}$ | $R^{D7}$ | $R^{D15}$ | $R^{D1}$ |
| $L_{C843}$ | $R^{D7}$ | $R^{D16}$ | $R^{D1}$ |
| $L_{C844}$ | $R^{D7}$ | $R^{D17}$ | $R^{D1}$ |
| $L_{C845}$ | $R^{D7}$ | $R^{D18}$ | $R^{D1}$ |
| $L_{C846}$ | $R^{D7}$ | $R^{D19}$ | $R^{D1}$ |
| $L_{C847}$ | $R^{D7}$ | $R^{D20}$ | $R^{D1}$ |
| $L_{C848}$ | $R^{D7}$ | $R^{D21}$ | $R^{D1}$ |
| $L_{C849}$ | $R^{D7}$ | $R^{D22}$ | $R^{D1}$ |
| $L_{C850}$ | $R^{D7}$ | $R^{D23}$ | $R^{D1}$ |
| $L_{C851}$ | $R^{D7}$ | $R^{D24}$ | $R^{D1}$ |
| $L_{C852}$ | $R^{D7}$ | $R^{D25}$ | $R^{D1}$ |
| $L_{C853}$ | $R^{D7}$ | $R^{D26}$ | $R^{D1}$ |
| $L_{C854}$ | $R^{D7}$ | $R^{D27}$ | $R^{D1}$ |
| $L_{C855}$ | $R^{D7}$ | $R^{D28}$ | $R^{D1}$ |
| $L_{C856}$ | $R^{D7}$ | $R^{D29}$ | $R^{D1}$ |
| $L_{C857}$ | $R^{D7}$ | $R^{D30}$ | $R^{D1}$ |
| $L_{C858}$ | $R^{D7}$ | $R^{D31}$ | $R^{D1}$ |
| $L_{C859}$ | $R^{D7}$ | $R^{D32}$ | $R^{D1}$ |
| $L_{C860}$ | $R^{D7}$ | $R^{D33}$ | $R^{D1}$ |
| $L_{C861}$ | $R^{D7}$ | $R^{D34}$ | $R^{D1}$ |
| $L_{C862}$ | $R^{D7}$ | $R^{D35}$ | $R^{D1}$ |
| $L_{C863}$ | $R^{D7}$ | $R^{D40}$ | $R^{D1}$ |
| $L_{C864}$ | $R^{D7}$ | $R^{D41}$ | $R^{D1}$ |

-continued

| Ligand | $R^1$ | $R^2$ | $R^3$ |
|---|---|---|---|
| $L_{C865}$ | $R^{D7}$ | $R^{D42}$ | $R^{D1}$ |
| $L_{C866}$ | $R^{D7}$ | $R^{D64}$ | $R^{D1}$ |
| $L_{C867}$ | $R^{D7}$ | $R^{D66}$ | $R^{D1}$ |
| $L_{C868}$ | $R^{D7}$ | $R^{D68}$ | $R^{D1}$ |
| $L_{C869}$ | $R^{D7}$ | $R^{D76}$ | $R^{D1}$ |
| $L_{C870}$ | $R^{D8}$ | $R^{D5}$ | $R^{D1}$ |
| $L_{C871}$ | $R^{D8}$ | $R^{D6}$ | $R^{D1}$ |
| $L_{C872}$ | $R^{D8}$ | $R^{D9}$ | $R^{D1}$ |
| $L_{C873}$ | $R^{D8}$ | $R^{D10}$ | $R^{D1}$ |
| $L_{C874}$ | $R^{D8}$ | $R^{D11}$ | $R^{D1}$ |
| $L_{C875}$ | $R^{D8}$ | $R^{D12}$ | $R^{D1}$ |
| $L_{C876}$ | $R^{D8}$ | $R^{D13}$ | $R^{D1}$ |
| $L_{C877}$ | $R^{D8}$ | $R^{D14}$ | $R^{D1}$ |
| $L_{C878}$ | $R^{D8}$ | $R^{D15}$ | $R^{D1}$ |
| $L_{C879}$ | $R^{D8}$ | $R^{D16}$ | $R^{D1}$ |
| $L_{C880}$ | $R^{D8}$ | $R^{D17}$ | $R^{D1}$ |
| $L_{C881}$ | $R^{D8}$ | $R^{D18}$ | $R^{D1}$ |
| $L_{C882}$ | $R^{D8}$ | $R^{D19}$ | $R^{D1}$ |
| $L_{C883}$ | $R^{D8}$ | $R^{D20}$ | $R^{D1}$ |
| $L_{C884}$ | $R^{D8}$ | $R^{D21}$ | $R^{D1}$ |
| $L_{C885}$ | $R^{D8}$ | $R^{D22}$ | $R^{D1}$ |
| $L_{C886}$ | $R^{D8}$ | $R^{D23}$ | $R^{D1}$ |
| $L_{C887}$ | $R^{D8}$ | $R^{D24}$ | $R^{D1}$ |
| $L_{C888}$ | $R^{D8}$ | $R^{D25}$ | $R^{D1}$ |
| $L_{C889}$ | $R^{D8}$ | $R^{D26}$ | $R^{D1}$ |
| $L_{C890}$ | $R^{D8}$ | $R^{D27}$ | $R^{D1}$ |
| $L_{C891}$ | $R^{D8}$ | $R^{D28}$ | $R^{D1}$ |
| $L_{C892}$ | $R^{D8}$ | $R^{D29}$ | $R^{D1}$ |
| $L_{C893}$ | $R^{D8}$ | $R^{D30}$ | $R^{D1}$ |
| $L_{C894}$ | $R^{D8}$ | $R^{D31}$ | $R^{D1}$ |
| $L_{C895}$ | $R^{D8}$ | $R^{D32}$ | $R^{D1}$ |
| $L_{C896}$ | $R^{D8}$ | $R^{D33}$ | $R^{D1}$ |
| $L_{C897}$ | $R^{D8}$ | $R^{D34}$ | $R^{D1}$ |
| $L_{C898}$ | $R^{D8}$ | $R^{D35}$ | $R^{D1}$ |
| $L_{C899}$ | $R^{D8}$ | $R^{D40}$ | $R^{D1}$ |
| $L_{C900}$ | $R^{D8}$ | $R^{D41}$ | $R^{D1}$ |
| $L_{C901}$ | $R^{D8}$ | $R^{D42}$ | $R^{D1}$ |
| $L_{C902}$ | $R^{D8}$ | $R^{D64}$ | $R^{D1}$ |
| $L_{C903}$ | $R^{D8}$ | $R^{D66}$ | $R^{D1}$ |
| $L_{C904}$ | $R^{D8}$ | $R^{D68}$ | $R^{D1}$ |
| $L_{C905}$ | $R^{D8}$ | $R^{D76}$ | $R^{D1}$ |
| $L_{C906}$ | $R^{D11}$ | $R^{D5}$ | $R^{D1}$ |
| $L_{C907}$ | $R^{D11}$ | $R^{D6}$ | $R^{D1}$ |
| $L_{C908}$ | $R^{D11}$ | $R^{D9}$ | $R^{D1}$ |
| $L_{C909}$ | $R^{D11}$ | $R^{D10}$ | $R^{D1}$ |
| $L_{C910}$ | $R^{D11}$ | $R^{D12}$ | $R^{D1}$ |
| $L_{C911}$ | $R^{D11}$ | $R^{D13}$ | $R^{D1}$ |
| $L_{C912}$ | $R^{D11}$ | $R^{D14}$ | $R^{D1}$ |
| $L_{C913}$ | $R^{D11}$ | $R^{D15}$ | $R^{D1}$ |
| $L_{C914}$ | $R^{D11}$ | $R^{D16}$ | $R^{D1}$ |
| $L_{C915}$ | $R^{D11}$ | $R^{D17}$ | $R^{D1}$ |
| $L_{C916}$ | $R^{D11}$ | $R^{D18}$ | $R^{D1}$ |
| $L_{C917}$ | $R^{D11}$ | $R^{D19}$ | $R^{D1}$ |
| $L_{C918}$ | $R^{D11}$ | $R^{D20}$ | $R^{D1}$ |
| $L_{C919}$ | $R^{D11}$ | $R^{D21}$ | $R^{D1}$ |
| $L_{C920}$ | $R^{D11}$ | $R^{D22}$ | $R^{D1}$ |
| $L_{C921}$ | $R^{D11}$ | $R^{D23}$ | $R^{D1}$ |
| $L_{C922}$ | $R^{D11}$ | $R^{D24}$ | $R^{D1}$ |
| $L_{C923}$ | $R^{D11}$ | $R^{D25}$ | $R^{D1}$ |
| $L_{C924}$ | $R^{D11}$ | $R^{D26}$ | $R^{D1}$ |
| $L_{C925}$ | $R^{D11}$ | $R^{D27}$ | $R^{D1}$ |
| $L_{C926}$ | $R^{D11}$ | $R^{D28}$ | $R^{D1}$ |
| $L_{C927}$ | $R^{D11}$ | $R^{D29}$ | $R^{D1}$ |
| $L_{C928}$ | $R^{D11}$ | $R^{D30}$ | $R^{D1}$ |
| $L_{C929}$ | $R^{D11}$ | $R^{D31}$ | $R^{D1}$ |
| $L_{C930}$ | $R^{D11}$ | $R^{D32}$ | $R^{D1}$ |
| $L_{C931}$ | $R^{D11}$ | $R^{D33}$ | $R^{D1}$ |
| $L_{C932}$ | $R^{D11}$ | $R^{D34}$ | $R^{D1}$ |
| $L_{C933}$ | $R^{D11}$ | $R^{D35}$ | $R^{D1}$ |
| $L_{C934}$ | $R^{D11}$ | $R^{D40}$ | $R^{D1}$ |
| $L_{C935}$ | $R^{D11}$ | $R^{D41}$ | $R^{D1}$ |
| $L_{C936}$ | $R^{D11}$ | $R^{D42}$ | $R^{D1}$ |
| $L_{C937}$ | $R^{D11}$ | $R^{D64}$ | $R^{D1}$ |
| $L_{C938}$ | $R^{D11}$ | $R^{D66}$ | $R^{D1}$ |
| $L_{C939}$ | $R^{D11}$ | $R^{D68}$ | $R^{D1}$ |
| $L_{C940}$ | $R^{D11}$ | $R^{D76}$ | $R^{D1}$ |
| $L_{C941}$ | $R^{D13}$ | $R^{D5}$ | $R^{D1}$ |

-continued

| Ligand | $R^1$ | $R^2$ | $R^3$ |
|---|---|---|---|
| $L_{C942}$ | $R^{D13}$ | $R^{D6}$ | $R^{D1}$ |
| $L_{C943}$ | $R^{D13}$ | $R^{D9}$ | $R^{D1}$ |
| $L_{C944}$ | $R^{D13}$ | $R^{D10}$ | $R^{D1}$ |
| $L_{C945}$ | $R^{D13}$ | $R^{D12}$ | $R^{D1}$ |
| $L_{C946}$ | $R^{D13}$ | $R^{D14}$ | $R^{D1}$ |
| $L_{C947}$ | $R^{D13}$ | $R^{D15}$ | $R^{D1}$ |
| $L_{C948}$ | $R^{D13}$ | $R^{D16}$ | $R^{D1}$ |
| $L_{C949}$ | $R^{D13}$ | $R^{D17}$ | $R^{D1}$ |
| $L_{C950}$ | $R^{D13}$ | $R^{D18}$ | $R^{D1}$ |
| $L_{C951}$ | $R^{D13}$ | $R^{D19}$ | $R^{D1}$ |
| $L_{C952}$ | $R^{D13}$ | $R^{D20}$ | $R^{D1}$ |
| $L_{C953}$ | $R^{D13}$ | $R^{D21}$ | $R^{D1}$ |
| $L_{C954}$ | $R^{D13}$ | $R^{D22}$ | $R^{D1}$ |
| $L_{C955}$ | $R^{D13}$ | $R^{D23}$ | $R^{D1}$ |
| $L_{C956}$ | $R^{D13}$ | $R^{D24}$ | $R^{D1}$ |
| $L_{C957}$ | $R^{D13}$ | $R^{D25}$ | $R^{D1}$ |
| $L_{C958}$ | $R^{D13}$ | $R^{D26}$ | $R^{D1}$ |
| $L_{C959}$ | $R^{D13}$ | $R^{D27}$ | $R^{D1}$ |
| $L_{C960}$ | $R^{D13}$ | $R^{D28}$ | $R^{D1}$ |
| $L_{C961}$ | $R^{D13}$ | $R^{D29}$ | $R^{D1}$ |
| $L_{C962}$ | $R^{D13}$ | $R^{D30}$ | $R^{D1}$ |
| $L_{C963}$ | $R^{D13}$ | $R^{D31}$ | $R^{D1}$ |
| $L_{C964}$ | $R^{D13}$ | $R^{D32}$ | $R^{D1}$ |
| $L_{C965}$ | $R^{D13}$ | $R^{D33}$ | $R^{D1}$ |
| $L_{C966}$ | $R^{D13}$ | $R^{D34}$ | $R^{D1}$ |
| $L_{C967}$ | $R^{D13}$ | $R^{D35}$ | $R^{D1}$ |
| $L_{C968}$ | $R^{D13}$ | $R^{D40}$ | $R^{D1}$ |
| $L_{C969}$ | $R^{D13}$ | $R^{D41}$ | $R^{D1}$ |
| $L_{C970}$ | $R^{D13}$ | $R^{D42}$ | $R^{D1}$ |
| $L_{C971}$ | $R^{D13}$ | $R^{D64}$ | $R^{D1}$ |
| $L_{C972}$ | $R^{D13}$ | $R^{D66}$ | $R^{D1}$ |
| $L_{C973}$ | $R^{D13}$ | $R^{D68}$ | $R^{D1}$ |
| $L_{C974}$ | $R^{D13}$ | $R^{D76}$ | $R^{D1}$ |
| $L_{C975}$ | $R^{D14}$ | $R^{D5}$ | $R^{D1}$ |
| $L_{C976}$ | $R^{D14}$ | $R^{D6}$ | $R^{D1}$ |
| $L_{C977}$ | $R^{D14}$ | $R^{D9}$ | $R^{D1}$ |
| $L_{C978}$ | $R^{D14}$ | $R^{D10}$ | $R^{D1}$ |
| $L_{C979}$ | $R^{D14}$ | $R^{D12}$ | $R^{D1}$ |
| $L_{C980}$ | $R^{D14}$ | $R^{D15}$ | $R^{D1}$ |
| $L_{C981}$ | $R^{D14}$ | $R^{D16}$ | $R^{D1}$ |
| $L_{C982}$ | $R^{D14}$ | $R^{D17}$ | $R^{D1}$ |
| $L_{C983}$ | $R^{D14}$ | $R^{D18}$ | $R^{D1}$ |
| $L_{C984}$ | $R^{D14}$ | $R^{D19}$ | $R^{D1}$ |
| $L_{C985}$ | $R^{D14}$ | $R^{D20}$ | $R^{D1}$ |
| $L_{C986}$ | $R^{D14}$ | $R^{D21}$ | $R^{D1}$ |
| $L_{C987}$ | $R^{D14}$ | $R^{D22}$ | $R^{D1}$ |
| $L_{C988}$ | $R^{D14}$ | $R^{D23}$ | $R^{D1}$ |
| $L_{C989}$ | $R^{D14}$ | $R^{D24}$ | $R^{D1}$ |
| $L_{C990}$ | $R^{D14}$ | $R^{D25}$ | $R^{D1}$ |
| $L_{C991}$ | $R^{D14}$ | $R^{D26}$ | $R^{D1}$ |
| $L_{C992}$ | $R^{D14}$ | $R^{D27}$ | $R^{D1}$ |
| $L_{C993}$ | $R^{D14}$ | $R^{D28}$ | $R^{D1}$ |
| $L_{C994}$ | $R^{D14}$ | $R^{D29}$ | $R^{D1}$ |
| $L_{C995}$ | $R^{D14}$ | $R^{D30}$ | $R^{D1}$ |
| $L_{C996}$ | $R^{D14}$ | $R^{D31}$ | $R^{D1}$ |
| $L_{C997}$ | $R^{D14}$ | $R^{D32}$ | $R^{D1}$ |
| $L_{C998}$ | $R^{D14}$ | $R^{D33}$ | $R^{D1}$ |
| $L_{C999}$ | $R^{D14}$ | $R^{D34}$ | $R^{D1}$ |
| $L_{C1000}$ | $R^{D14}$ | $R^{D35}$ | $R^{D1}$ |
| $L_{C1001}$ | $R^{D14}$ | $R^{D40}$ | $R^{D1}$ |
| $L_{C1002}$ | $R^{D14}$ | $R^{D41}$ | $R^{D1}$ |
| $L_{C1003}$ | $R^{D14}$ | $R^{D42}$ | $R^{D1}$ |
| $L_{C1004}$ | $R^{D14}$ | $R^{D64}$ | $R^{D1}$ |
| $L_{C1005}$ | $R^{D14}$ | $R^{D66}$ | $R^{D1}$ |
| $L_{C1006}$ | $R^{D14}$ | $R^{D68}$ | $R^{D1}$ |
| $L_{C1007}$ | $R^{D14}$ | $R^{D76}$ | $R^{D1}$ |
| $L_{C1008}$ | $R^{D22}$ | $R^{D5}$ | $R^{D1}$ |
| $L_{C1009}$ | $R^{D22}$ | $R^{D6}$ | $R^{D1}$ |
| $L_{C1010}$ | $R^{D22}$ | $R^{D9}$ | $R^{D1}$ |
| $L_{C1011}$ | $R^{D22}$ | $R^{D10}$ | $R^{D1}$ |
| $L_{C1012}$ | $R^{D22}$ | $R^{D12}$ | $R^{D1}$ |
| $L_{C1013}$ | $R^{D22}$ | $R^{D15}$ | $R^{D1}$ |
| $L_{C1014}$ | $R^{D22}$ | $R^{D16}$ | $R^{D1}$ |
| $L_{C1015}$ | $R^{D22}$ | $R^{D17}$ | $R^{D1}$ |
| $L_{C1016}$ | $R^{D22}$ | $R^{D18}$ | $R^{D1}$ |
| $L_{C1017}$ | $R^{D22}$ | $R^{D19}$ | $R^{D1}$ |
| $L_{C1018}$ | $R^{D22}$ | $R^{D20}$ | $R^{D1}$ |

-continued

| Ligand | $R^1$ | $R^2$ | $R^3$ |
|---|---|---|---|
| $L_{C1019}$ | $R^{D22}$ | $R^{D21}$ | $R^{D1}$ |
| $L_{C1020}$ | $R^{D22}$ | $R^{D23}$ | $R^{D1}$ |
| $L_{C1021}$ | $R^{D22}$ | $R^{D24}$ | $R^{D1}$ |
| $L_{C1022}$ | $R^{D22}$ | $R^{D25}$ | $R^{D1}$ |
| $L_{C1023}$ | $R^{D22}$ | $R^{D26}$ | $R^{D1}$ |
| $L_{C1024}$ | $R^{D22}$ | $R^{D27}$ | $R^{D1}$ |
| $L_{C1025}$ | $R^{D22}$ | $R^{D28}$ | $R^{D1}$ |
| $L_{C1026}$ | $R^{D22}$ | $R^{D29}$ | $R^{D1}$ |
| $L_{C1027}$ | $R^{D22}$ | $R^{D30}$ | $R^{D1}$ |
| $L_{C1028}$ | $R^{D22}$ | $R^{D31}$ | $R^{D1}$ |
| $L_{C1029}$ | $R^{D22}$ | $R^{D32}$ | $R^{D1}$ |
| $L_{C1030}$ | $R^{D22}$ | $R^{D33}$ | $R^{D1}$ |
| $L_{C1031}$ | $R^{D22}$ | $R^{D34}$ | $R^{D1}$ |
| $L_{C1032}$ | $R^{D22}$ | $R^{D35}$ | $R^{D1}$ |
| $L_{C1033}$ | $R^{D22}$ | $R^{D40}$ | $R^{D1}$ |
| $L_{C1034}$ | $R^{D22}$ | $R^{D41}$ | $R^{D1}$ |
| $L_{C1035}$ | $R^{D22}$ | $R^{D42}$ | $R^{D1}$ |
| $L_{C1036}$ | $R^{D22}$ | $R^{D64}$ | $R^{D1}$ |
| $L_{C1037}$ | $R^{D22}$ | $R^{D66}$ | $R^{D1}$ |
| $L_{C1038}$ | $R^{D22}$ | $R^{D68}$ | $R^{D1}$ |
| $L_{C1039}$ | $R^{D22}$ | $R^{D76}$ | $R^{D1}$ |
| $L_{C1040}$ | $R^{D26}$ | $R^{D5}$ | $R^{D1}$ |
| $L_{C1041}$ | $R^{D26}$ | $R^{D6}$ | $R^{D1}$ |
| $L_{C1042}$ | $R^{D26}$ | $R^{D9}$ | $R^{D1}$ |
| $L_{C1043}$ | $R^{D26}$ | $R^{D10}$ | $R^{D1}$ |
| $L_{C1044}$ | $R^{D26}$ | $R^{D12}$ | $R^{D1}$ |
| $L_{C1045}$ | $R^{D26}$ | $R^{D15}$ | $R^{D1}$ |
| $L_{C1046}$ | $R^{D26}$ | $R^{D16}$ | $R^{D1}$ |
| $L_{C1047}$ | $R^{D26}$ | $R^{D17}$ | $R^{D1}$ |
| $L_{C1048}$ | $R^{D26}$ | $R^{D18}$ | $R^{D1}$ |
| $L_{C1049}$ | $R^{D26}$ | $R^{D19}$ | $R^{D1}$ |
| $L_{C1050}$ | $R^{D26}$ | $R^{D20}$ | $R^{D1}$ |
| $L_{C1051}$ | $R^{D26}$ | $R^{D21}$ | $R^{D1}$ |
| $L_{C1052}$ | $R^{D26}$ | $R^{D23}$ | $R^{D1}$ |
| $L_{C1053}$ | $R^{D26}$ | $R^{D24}$ | $R^{D1}$ |
| $L_{C1054}$ | $R^{D26}$ | $R^{D25}$ | $R^{D1}$ |
| $L_{C1055}$ | $R^{D26}$ | $R^{D27}$ | $R^{D1}$ |
| $L_{C1056}$ | $R^{D26}$ | $R^{D28}$ | $R^{D1}$ |
| $L_{C1057}$ | $R^{D26}$ | $R^{D29}$ | $R^{D1}$ |
| $L_{C1058}$ | $R^{D26}$ | $R^{D30}$ | $R^{D1}$ |
| $L_{C1059}$ | $R^{D26}$ | $R^{D31}$ | $R^{D1}$ |
| $L_{C1060}$ | $R^{D26}$ | $R^{D32}$ | $R^{D1}$ |
| $L_{C1061}$ | $R^{D26}$ | $R^{D33}$ | $R^{D1}$ |
| $L_{C1062}$ | $R^{D26}$ | $R^{D34}$ | $R^{D1}$ |
| $L_{C1063}$ | $R^{D26}$ | $R^{D35}$ | $R^{D1}$ |
| $L_{C1064}$ | $R^{D26}$ | $R^{D40}$ | $R^{D1}$ |
| $L_{C1065}$ | $R^{D26}$ | $R^{D41}$ | $R^{D1}$ |
| $L_{C1066}$ | $R^{D26}$ | $R^{D42}$ | $R^{D1}$ |
| $L_{C1067}$ | $R^{D26}$ | $R^{D64}$ | $R^{D1}$ |
| $L_{C1068}$ | $R^{D26}$ | $R^{D66}$ | $R^{D1}$ |
| $L_{C1069}$ | $R^{D26}$ | $R^{D68}$ | $R^{D1}$ |
| $L_{C1070}$ | $R^{D26}$ | $R^{D76}$ | $R^{D1}$ |
| $L_{C1071}$ | $R^{D35}$ | $R^{D5}$ | $R^{D1}$ |
| $L_{C1072}$ | $R^{D35}$ | $R^{D6}$ | $R^{D1}$ |
| $L_{C1073}$ | $R^{D35}$ | $R^{D9}$ | $R^{D1}$ |
| $L_{C1074}$ | $R^{D35}$ | $R^{D10}$ | $R^{D1}$ |
| $L_{C1075}$ | $R^{D35}$ | $R^{D12}$ | $R^{D1}$ |
| $L_{C1076}$ | $R^{D35}$ | $R^{D15}$ | $R^{D1}$ |
| $L_{C1077}$ | $R^{D35}$ | $R^{D16}$ | $R^{D1}$ |
| $L_{C1078}$ | $R^{D35}$ | $R^{D17}$ | $R^{D1}$ |
| $L_{C1079}$ | $R^{D35}$ | $R^{D18}$ | $R^{D1}$ |
| $L_{C1080}$ | $R^{D35}$ | $R^{D19}$ | $R^{D1}$ |
| $L_{C1081}$ | $R^{D35}$ | $R^{D20}$ | $R^{D1}$ |
| $L_{C1082}$ | $R^{D35}$ | $R^{D21}$ | $R^{D1}$ |
| $L_{C1083}$ | $R^{D35}$ | $R^{D23}$ | $R^{D1}$ |
| $L_{C1084}$ | $R^{D35}$ | $R^{D24}$ | $R^{D1}$ |
| $L_{C1085}$ | $R^{D35}$ | $R^{D25}$ | $R^{D1}$ |
| $L_{C1086}$ | $R^{D35}$ | $R^{D27}$ | $R^{D1}$ |
| $L_{C1087}$ | $R^{D35}$ | $R^{D28}$ | $R^{D1}$ |
| $L_{C1088}$ | $R^{D35}$ | $R^{D29}$ | $R^{D1}$ |
| $L_{C1089}$ | $R^{D35}$ | $R^{D30}$ | $R^{D1}$ |
| $L_{C1090}$ | $R^{D35}$ | $R^{D31}$ | $R^{D1}$ |
| $L_{C1091}$ | $R^{D35}$ | $R^{D32}$ | $R^{D1}$ |
| $L_{C1092}$ | $R^{D35}$ | $R^{D33}$ | $R^{D1}$ |
| $L_{C1093}$ | $R^{D35}$ | $R^{D34}$ | $R^{D1}$ |
| $L_{C1094}$ | $R^{D35}$ | $R^{D40}$ | $R^{D1}$ |
| $L_{C1095}$ | $R^{D35}$ | $R^{D41}$ | $R^{D1}$ |

-continued

| Ligand | $R^1$ | $R^2$ | $R^3$ |
|---|---|---|---|
| $L_{C1096}$ | $R^{D35}$ | $R^{D42}$ | $R^{D1}$ |
| $L_{C1097}$ | $R^{D35}$ | $R^{D64}$ | $R^{D1}$ |
| $L_{C1098}$ | $R^{D35}$ | $R^{D66}$ | $R^{D1}$ |
| $L_{C1099}$ | $R^{D35}$ | $R^{D68}$ | $R^{D1}$ |
| $L_{C1100}$ | $R^{D35}$ | $R^{D76}$ | $R^{D1}$ |
| $L_{C1101}$ | $R^{D40}$ | $R^{D5}$ | $R^{D1}$ |
| $L_{C1102}$ | $R^{D40}$ | $R^{D6}$ | $R^{D1}$ |
| $L_{C1103}$ | $R^{D40}$ | $R^{D9}$ | $R^{D1}$ |
| $L_{C1104}$ | $R^{D40}$ | $R^{D10}$ | $R^{D1}$ |
| $L_{C1105}$ | $R^{D40}$ | $R^{D12}$ | $R^{D1}$ |
| $L_{C1106}$ | $R^{D40}$ | $R^{D15}$ | $R^{D1}$ |
| $L_{C1107}$ | $R^{D40}$ | $R^{D16}$ | $R^{D1}$ |
| $L_{C1108}$ | $R^{D40}$ | $R^{017}$ | $R^{D1}$ |
| $L_{C1109}$ | $R^{D40}$ | $R^{D18}$ | $R^{D1}$ |
| $L_{C1110}$ | $R^{D40}$ | $R^{D19}$ | $R^{D1}$ |
| $L_{C1111}$ | $R^{D40}$ | $R^{D20}$ | $R^{D1}$ |
| $L_{C1112}$ | $R^{D40}$ | $R^{D21}$ | $R^{D1}$ |
| $L_{C1113}$ | $R^{D40}$ | $R^{D23}$ | $R^{D1}$ |
| $L_{C1114}$ | $R^{D40}$ | $R^{D24}$ | $R^{D1}$ |
| $L_{C1115}$ | $R^{D40}$ | $R^{D25}$ | $R^{D1}$ |
| $L_{C1116}$ | $R^{D40}$ | $R^{D27}$ | $R^{D1}$ |
| $L_{C1117}$ | $R^{D40}$ | $R^{D28}$ | $R^{D1}$ |
| $L_{C1118}$ | $R^{D40}$ | $R^{D29}$ | $R^{D1}$ |
| $L_{C1119}$ | $R^{D40}$ | $R^{D30}$ | $R^{D1}$ |
| $L_{C1120}$ | $R^{D40}$ | $R^{D31}$ | $R^{D1}$ |
| $L_{C1121}$ | $R^{D40}$ | $R^{D32}$ | $R^{D1}$ |
| $L_{C1122}$ | $R^{D40}$ | $R^{D33}$ | $R^{D1}$ |
| $L_{C1123}$ | $R^{D40}$ | $R^{D34}$ | $R^{D1}$ |
| $L_{C1124}$ | $R^{D40}$ | $R^{D41}$ | $R^{D1}$ |
| $L_{C1125}$ | $R^{D40}$ | $R^{D42}$ | $R^{D1}$ |
| $L_{C1126}$ | $R^{D40}$ | $R^{D64}$ | $R^{D1}$ |
| $L_{C1127}$ | $R^{D40}$ | $R^{D66}$ | $R^{D1}$ |
| $L_{C1128}$ | $R^{D40}$ | $R^{D68}$ | $R^{D1}$ |
| $L_{C1129}$ | $R^{D40}$ | $R^{D76}$ | $R^{D1}$ |
| $L_{C1130}$ | $R^{D41}$ | $R^{D5}$ | $R^{D1}$ |
| $L_{C1131}$ | $R^{D41}$ | $R^{D6}$ | $R^{D1}$ |
| $L_{C1132}$ | $R^{D41}$ | $R^{D9}$ | $R^{D1}$ |
| $L_{C1133}$ | $R^{D41}$ | $R^{D10}$ | $R^{D1}$ |
| $L_{C1134}$ | $R^{D41}$ | $R^{D12}$ | $R^{D1}$ |
| $L_{C1135}$ | $R^{D41}$ | $R^{D15}$ | $R^{D1}$ |
| $L_{C1136}$ | $R^{D41}$ | $R^{D16}$ | $R^{D1}$ |
| $L_{C1137}$ | $R^{D41}$ | $R^{D17}$ | $R^{D1}$ |
| $L_{C1138}$ | $R^{D41}$ | $R^{D18}$ | $R^{D1}$ |
| $L_{C1139}$ | $R^{D41}$ | $R^{D19}$ | $R^{D1}$ |
| $L_{C1140}$ | $R^{D41}$ | $R^{D20}$ | $R^{D1}$ |
| $L_{C1141}$ | $R^{D41}$ | $R^{D21}$ | $R^{D1}$ |
| $L_{C1142}$ | $R^{D41}$ | $R^{D23}$ | $R^{D1}$ |
| $L_{C1143}$ | $R^{D41}$ | $R^{D24}$ | $R^{D1}$ |
| $L_{C1144}$ | $R^{D41}$ | $R^{D25}$ | $R^{D1}$ |
| $L_{C1145}$ | $R^{D41}$ | $R^{D27}$ | $R^{D1}$ |
| $L_{C1146}$ | $R^{D41}$ | $R^{D28}$ | $R^{D1}$ |
| $L_{C1147}$ | $R^{D41}$ | $R^{D29}$ | $R^{D1}$ |
| $L_{C1148}$ | $R^{D41}$ | $R^{D30}$ | $R^{D1}$ |
| $L_{C1149}$ | $R^{D41}$ | $R^{D31}$ | $R^{D1}$ |
| $L_{C1150}$ | $R^{D41}$ | $R^{D32}$ | $R^{D1}$ |
| $L_{C1151}$ | $R^{D41}$ | $R^{D33}$ | $R^{D1}$ |
| $L_{C1152}$ | $R^{D41}$ | $R^{D34}$ | $R^{D1}$ |
| $L_{C1153}$ | $R^{D41}$ | $R^{D42}$ | $R^{D1}$ |
| $L_{C1154}$ | $R^{D41}$ | $R^{D64}$ | $R^{D1}$ |
| $L_{C1155}$ | $R^{D41}$ | $R^{D66}$ | $R^{D1}$ |
| $L_{C1156}$ | $R^{D41}$ | $R^{D68}$ | $R^{D1}$ |
| $L_{C1157}$ | $R^{D41}$ | $R^{D76}$ | $R^{D1}$ |
| $L_{C1158}$ | $R^{D64}$ | $R^{D5}$ | $R^{D1}$ |
| $L_{C1159}$ | $R^{D64}$ | $R^{D6}$ | $R^{D1}$ |
| $L_{C1160}$ | $R^{D64}$ | $R^{D9}$ | $R^{D1}$ |
| $L_{C1161}$ | $R^{D64}$ | $R^{D10}$ | $R^{D1}$ |
| $L_{C1162}$ | $R^{D64}$ | $R^{D12}$ | $R^{D1}$ |
| $L_{C1163}$ | $R^{D64}$ | $R^{D15}$ | $R^{D1}$ |
| $L_{C1164}$ | $R^{D64}$ | $R^{D16}$ | $R^{D1}$ |
| $L_{C1165}$ | $R^{D64}$ | $R^{D17}$ | $R^{D1}$ |
| $L_{C1166}$ | $R^{D64}$ | $R^{D18}$ | $R^{D1}$ |
| $L_{C1167}$ | $R^{D64}$ | $R^{D19}$ | $R^{D1}$ |
| $L_{C1168}$ | $R^{D64}$ | $R^{D20}$ | $R^{D1}$ |
| $L_{C1169}$ | $R^{D64}$ | $R^{D21}$ | $R^{D1}$ |
| $L_{C1170}$ | $R^{D64}$ | $R^{D23}$ | $R^{D1}$ |
| $L_{C1171}$ | $R^{D64}$ | $R^{D24}$ | $R^{D1}$ |
| $L_{C1172}$ | $R^{D64}$ | $R^{D25}$ | $R^{D1}$ |

-continued

| Ligand | $R^1$ | $R^2$ | $R^3$ |
|---|---|---|---|
| $L_{C1173}$ | $R^{D64}$ | $R^{D27}$ | $R^{D1}$ |
| $L_{C1174}$ | $R^{D64}$ | $R^{D28}$ | $R^{D1}$ |
| $L_{C1175}$ | $R^{D64}$ | $R^{D29}$ | $R^{D1}$ |
| $L_{C1176}$ | $R^{D64}$ | $R^{D30}$ | $R^{D1}$ |
| $L_{C1177}$ | $R^{D64}$ | $R^{D31}$ | $R^{D1}$ |
| $L_{C1178}$ | $R^{D64}$ | $R^{D32}$ | $R^{D1}$ |
| $L_{C1179}$ | $R^{D64}$ | $R^{D33}$ | $R^{D1}$ |
| $L_{C1180}$ | $R^{D64}$ | $R^{D34}$ | $R^{D1}$ |
| $L_{C1181}$ | $R^{D64}$ | $R^{D42}$ | $R^{D1}$ |
| $L_{C1182}$ | $R^{D64}$ | $R^{D64}$ | $R^{D1}$ |
| $L_{C1183}$ | $R^{D64}$ | $R^{D66}$ | $R^{D1}$ |
| $L_{C1184}$ | $R^{D64}$ | $R^{D68}$ | $R^{D1}$ |
| $L_{C1185}$ | $R^{D64}$ | $R^{D76}$ | $R^{D1}$ |
| $L_{C1186}$ | $R^{D66}$ | $R^{D5}$ | $R^{D1}$ |
| $L_{C1187}$ | $R^{D66}$ | $R^{D6}$ | $R^{D1}$ |
| $L_{C1188}$ | $R^{D66}$ | $R^{D9}$ | $R^{D1}$ |
| $L_{C1189}$ | $R^{D66}$ | $R^{D10}$ | $R^{D1}$ |
| $L_{C1190}$ | $R^{D66}$ | $R^{D12}$ | $R^{D1}$ |
| $L_{C1191}$ | $R^{D66}$ | $R^{D15}$ | $R^{D1}$ |
| $L_{C1192}$ | $R^{D66}$ | $R^{D16}$ | $R^{D1}$ |
| $L_{C1193}$ | $R^{D66}$ | $R^{D17}$ | $R^{D1}$ |
| $L_{C1194}$ | $R^{D66}$ | $R^{D18}$ | $R^{D1}$ |
| $L_{C1195}$ | $R^{D66}$ | $R^{D19}$ | $R^{D1}$ |
| $L_{C1196}$ | $R^{D66}$ | $R^{D20}$ | $R^{D1}$ |
| $L_{C1197}$ | $R^{D66}$ | $R^{D21}$ | $R^{D1}$ |
| $L_{C1198}$ | $R^{D66}$ | $R^{D23}$ | $R^{D1}$ |
| $L_{C1199}$ | $R^{D66}$ | $R^{D24}$ | $R^{D1}$ |
| $L_{C1200}$ | $R^{D66}$ | $R^{D25}$ | $R^{D1}$ |
| $L_{C1201}$ | $R^{D66}$ | $R^{D27}$ | $R^{D1}$ |
| $L_{C1202}$ | $R^{D66}$ | $R^{D28}$ | $R^{D1}$ |
| $L_{C1203}$ | $R^{D66}$ | $R^{D29}$ | $R^{D1}$ |
| $L_{C1204}$ | $R^{D66}$ | $R^{D30}$ | $R^{D1}$ |
| $L_{C1205}$ | $R^{D66}$ | $R^{D31}$ | $R^{D1}$ |
| $L_{C1206}$ | $R^{D66}$ | $R^{D32}$ | $R^{D1}$ |
| $L_{C1207}$ | $R^{D66}$ | $R^{D33}$ | $R^{D1}$ |
| $L_{C1208}$ | $R^{D66}$ | $R^{D34}$ | $R^{D1}$ |
| $L_{C1209}$ | $R^{D66}$ | $R^{D42}$ | $R^{D1}$ |
| $L_{C1210}$ | $R^{D66}$ | $R^{D68}$ | $R^{D1}$ |
| $L_{C1211}$ | $R^{D66}$ | $R^{D76}$ | $R^{D1}$ |
| $L_{C1212}$ | $R^{D68}$ | $R^{D5}$ | $R^{D1}$ |
| $L_{C1213}$ | $R^{D68}$ | $R^{D6}$ | $R^{D1}$ |
| $L_{C1214}$ | $R^{D68}$ | $R^{D9}$ | $R^{D1}$ |
| $L_{C1215}$ | $R^{D68}$ | $R^{D10}$ | $R^{D1}$ |
| $L_{C1216}$ | $R^{D68}$ | $R^{D12}$ | $R^{D1}$ |
| $L_{C1217}$ | $R^{D68}$ | $R^{D15}$ | $R^{D1}$ |
| $L_{C1218}$ | $R^{D68}$ | $R^{D16}$ | $R^{D1}$ |
| $L_{C1219}$ | $R^{D68}$ | $R^{D17}$ | $R^{D1}$ |
| $L_{C1220}$ | $R^{D68}$ | $R^{D18}$ | $R^{D1}$ |
| $L_{C1221}$ | $R^{D68}$ | $R^{D19}$ | $R^{D1}$ |
| $L_{C1222}$ | $R^{D68}$ | $R^{D20}$ | $R^{D1}$ |
| $L_{C1223}$ | $R^{D68}$ | $R^{D21}$ | $R^{D1}$ |
| $L_{C1224}$ | $R^{D68}$ | $R^{D23}$ | $R^{D1}$ |
| $L_{C1225}$ | $R^{D68}$ | $R^{D24}$ | $R^{D1}$ |
| $L_{C1226}$ | $R^{D68}$ | $R^{D25}$ | $R^{D1}$ |
| $L_{C1227}$ | $R^{D68}$ | $R^{D27}$ | $R^{D1}$ |
| $L_{C1228}$ | $R^{D68}$ | $R^{D28}$ | $R^{D1}$ |
| $L_{C1229}$ | $R^{D68}$ | $R^{D29}$ | $R^{D1}$ |
| $L_{C1230}$ | $R^{D68}$ | $R^{D30}$ | $R^{D1}$ |
| $L_{C1231}$ | $R^{D68}$ | $R^{D31}$ | $R^{D1}$ |
| $L_{C1232}$ | $R^{D68}$ | $R^{D32}$ | $R^{D1}$ |
| $L_{C1233}$ | $R^{D68}$ | $R^{D33}$ | $R^{D1}$ |
| $L_{C1234}$ | $R^{D68}$ | $R^{D34}$ | $R^{D1}$ |
| $L_{C1235}$ | $R^{D68}$ | $R^{D42}$ | $R^{D1}$ |
| $L_{C1236}$ | $R^{D68}$ | $R^{D76}$ | $R^{D1}$ |
| $L_{C1237}$ | $R^{D76}$ | $R^{D5}$ | $R^{D1}$ |
| $L_{C1238}$ | $R^{D76}$ | $R^{D6}$ | $R^{D1}$ |
| $L_{C1239}$ | $R^{D76}$ | $R^{D9}$ | $R^{D1}$ |
| $L_{C1240}$ | $R^{D76}$ | $R^{D10}$ | $R^{D1}$ |
| $L_{C1241}$ | $R^{D76}$ | $R^{D12}$ | $R^{D1}$ |
| $L_{C1242}$ | $R^{D76}$ | $R^{D15}$ | $R^{D1}$ |
| $L_{C1243}$ | $R^{D76}$ | $R^{D16}$ | $R^{D1}$ |
| $L_{C1244}$ | $R^{D76}$ | $R^{D17}$ | $R^{D1}$ |
| $L_{C1245}$ | $R^{D76}$ | $R^{D18}$ | $R^{D1}$ |
| $L_{C1246}$ | $R^{D76}$ | $R^{D19}$ | $R^{D1}$ |
| $L_{C1247}$ | $R^{D76}$ | $R^{D20}$ | $R^{D1}$ |
| $L_{C1248}$ | $R^{D76}$ | $R^{D21}$ | $R^{D1}$ |
| $L_{C1249}$ | $R^{D76}$ | $R^{D23}$ | $R^{D1}$ |

-continued

| Ligand | $R^1$ | $R^2$ | $R^3$ |
|---|---|---|---|
| $L_{C1250}$ | $R^{D76}$ | $R^{D24}$ | $R^{D1}$ |
| $L_{C1251}$ | $R^{D76}$ | $R^{D25}$ | $R^{D1}$ |
| $L_{C1252}$ | $R^{D76}$ | $R^{D27}$ | $R^{D1}$ |
| $L_{C1253}$ | $R^{D76}$ | $R^{D28}$ | $R^{D1}$ |
| $L_{C1254}$ | $R^{D76}$ | $R^{D29}$ | $R^{D1}$ |
| $L_{C1255}$ | $R^{D76}$ | $R^{D30}$ | $R^{D1}$ |
| $L_{C1256}$ | $R^{D76}$ | $R^{D31}$ | $R^{D1}$ |
| $L_{C1257}$ | $R^{D76}$ | $R^{D32}$ | $R^{D1}$ |
| $L_{C1258}$ | $R^{D76}$ | $R^{D33}$ | $R^{D1}$ |
| $L_{C1259}$ | $R^{D76}$ | $R^{D34}$ | $R^{D1}$ |
| $L_{C1260}$ | $R^{D76}$ | $R^{D42}$ | $R^{D1}$ |

where $R^{D1}$ to $R^{D21}$ has the following structures:

$R^{D1}$

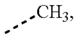

$R^{D2}$

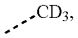

$R^{D3}$

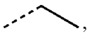

$R^{D4}$

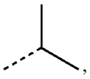

$R^{D5}$

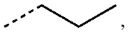

$R^{D6}$

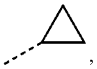

$R^{D7}$

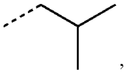

$R^{D8}$

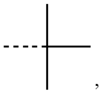

$R^{D9}$

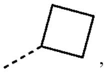

$R^{D10}$

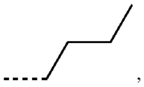

$R^{D11}$

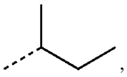

$R^{D12}$

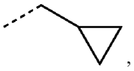

$R^{D13}$

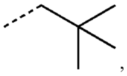

-continued $R^{D14}$

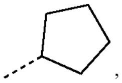

$R^{D15}$

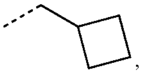

$R^{D16}$

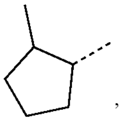

$R^{D17}$

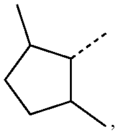

$R^{D18}$

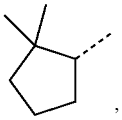

$R^{D19}$

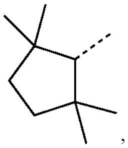

$R^{D20}$

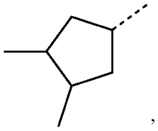

$R^{D21}$

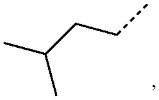

$R^{D22}$

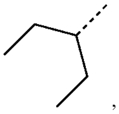

$R^{D23}$

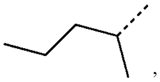

$R^{D24}$

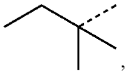

$R^{D25}$

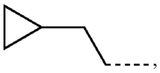

$R^{D26}$

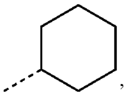

-continued
$R^{D27}$
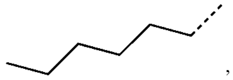,
$R^{D28}$
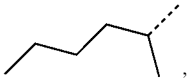,
$R^{D29}$
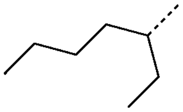,
$R^{D30}$
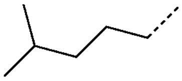,
$R^{D31}$
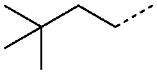,
$R^{D32}$
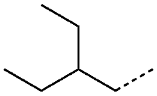,
$R^{D33}$
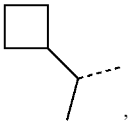,
$R^{D34}$
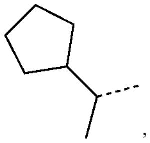,
$R^{D35}$
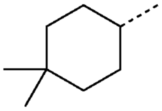,
$R^{D36}$
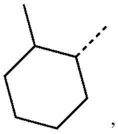,
$R^{D37}$
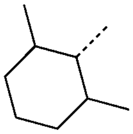,
$R^{D38}$
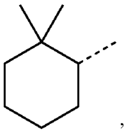,
-continued
$R^{D39}$
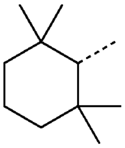,
$R^{D40}$
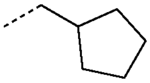,
$R^{D41}$
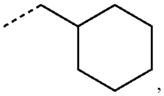,
$R^{D42}$
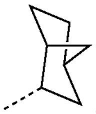,
$R^{D43}$
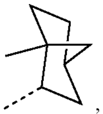,
$R^{D44}$
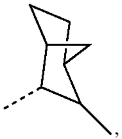,
$R^{D45}$
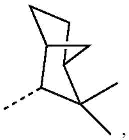,
$R^{D46}$
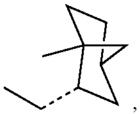,
$R^{D47}$
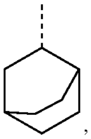,
$R^{D48}$
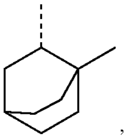,
$R^{D49}$
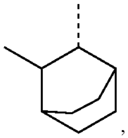, -continued
$R^{D50}$
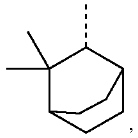
$R^{D51}$
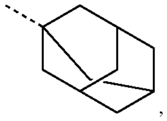
$R^{D52}$
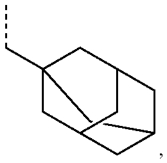
$R^{D53}$
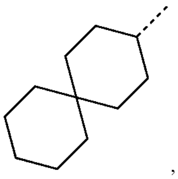
$R^{D54}$
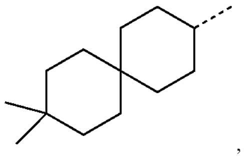
$R^{D55}$
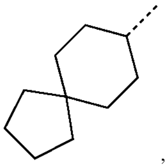
$R^{D56}$
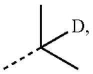
$R^{D57}$
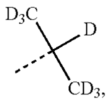
$R^{D58}$
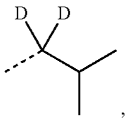
$R^{D59}$
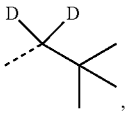
$R^{D60}$
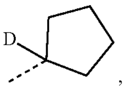
-continued
$R^{D61}$
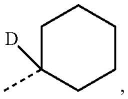
$R^{D62}$
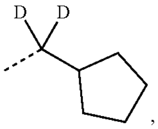
$R^{D63}$
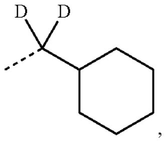
$R^{D64}$
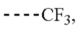
$R^{D65}$
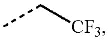
$R^{D66}$
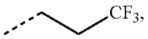
$R^{D67}$
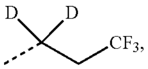
$R^{D68}$
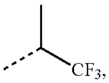
$R^{D69}$
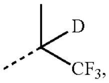
$R^{D70}$
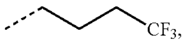
$R^{D71}$
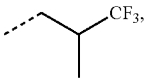
$R^{D72}$
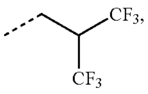
$R^{D73}$
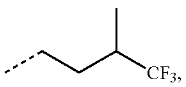
$R^{D74}$
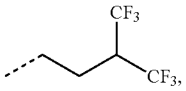
$R^{D75}$
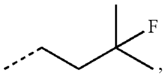
$R^{D76}$
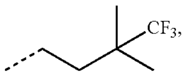

-continued $R^{D77}$

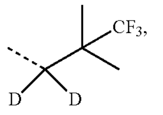

$R^{D78}$

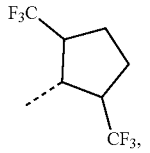

$R^{D79}$

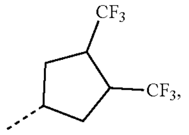

$R^{D80}$

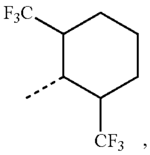

, and $R^{D81}$

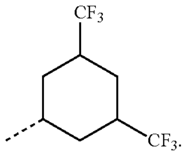

According to another aspect of the present disclosure, a compound comprising a first ligand $L_X$ of Formula II,

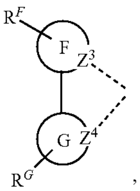

, is disclosed. In the compound of Formula II,

F is a 5-membered or 6-membered carbocyclic or heterocyclic ring;

$R^F$ and $R^G$ independently represent mono to the maximum possible number of substitutions, or no substitution;

$Z^3$ and $Z^4$ are each independently C or N and coordinated to a metal M to form a 5-membered chelate ring;

G is a fused ring structure comprising five or more fused heterocyclic or carbocyclic rings, of which at least one ring is of Formula III,

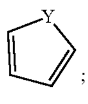

;

the fused heterocyclic or carbocyclic rings comprised by Ring G are 5-membered or 6-membered; of which if two or more 5-membered rings are present, at least two of the 5-membered rings are fused to one another;

Y is selected from the group consisting of BR', NR', PR', O, S, Se, C=O, S=O, $SO_2$, CR'R", SiR'R", and GeR'R";

each R', R", $R^F$, and $R^G$ is independently hydrogen or one of the general substituents defined above;

metal M is optionally coordinated to other ligands; and the ligand $L_X$ is optionally linked with other ligands to comprise a tridentate, tetradentate, pentadentate, or hexadentate ligand.

In some embodiments, rings F and G are independently aryl or heteroaryl.

In some embodiments, $L_X$ has a structure of Formula IV,

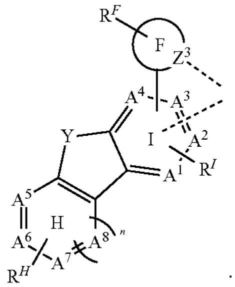

.

In Formula IV:

$A^1$ to $A^4$ are each independently C or N;

one of $A^1$ to $A^4$ is $Z^4$ in Formula II;

$R^H$ and $R^I$ represents mono to the maximum possibly number of substitutions, or no substitution;

ring H is a 5-membered or 6-membered aromatic ring;

n is 0 or 1;

when n is 0, $A^8$ is not present, two adjacent atoms of $A^5$ to $A^7$ are C, and the remaining atom of $A^5$ to $A^7$ is selected from the group consisting of NR', O, S, and Se;

when n is 1, two adjacent of $A^5$ to $A^8$ are C, and the remaining atoms of $A^5$ to $A^8$ are selected from the group consisting of C and N, and adjacent substituents of $R^H$ and $R^I$ join or fuse together to form at least two fused heterocyclic or carbocyclic rings;

R' and each $R^H$ and $R^I$ is independently hydrogen or one of the general substituents defined above; and any two substituents may be joined or fused together to form a ring.

In some embodiments, adjacent substituents of $R^H$ and $R^I$ join or fuse together to form at least two fused aryl or heteroaryl rings. In some embodiments, at least two sets of adjacent substituents of $R^H$ and $R^I$ join or fuse together to form fused rings. In some embodiments, one set of adjacent substituents includes two fused rings (i.e., a fused ring with another ring fused to it). In some such embodiments, each $R^F$, $R^H$, and $R^I$ is independently hydrogen or one of the preferred general substituents defined above.

In some embodiments, M is selected from the group consisting of Ir, Rh, Re, Ru, Os, Pt, Au, and Cu. In some embodiments, M is Ir or Pt.

In some embodiments, the compound is homoleptic. In some embodiments, the compound is heteroleptic.

In some embodiments, Y is O. In some embodiments, Y is CR'R". In some embodiments, n is 0. In some embodiments, n is 1.

In some embodiments, n is 0 and $R^H$ includes two 6-membered rings fused to one another and to ring H. In some embodiments, n is 1, $A^5$ to $A^8$ are each C, a 6-membered ring is fused to $A^5$ and $A^6$, and another 6-membered ring is fused to $A^7$ and $A^8$. In some embodiments, ring F is selected from the group consisting of pyridine, pyrimidine, pyrazine, imidazole, pyrazole, and N-heterocyclic carbene.
In some embodiments, the first ligand $L_x$ is selected from the group consisting of
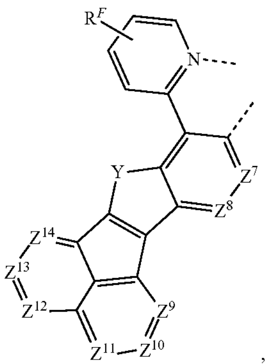
,
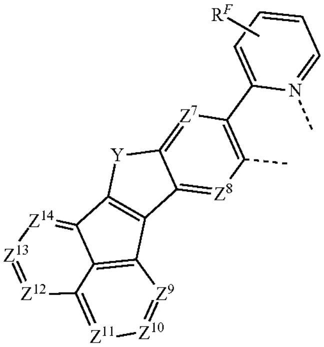
,
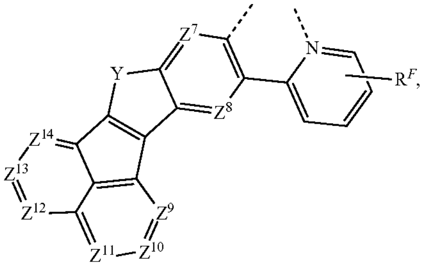
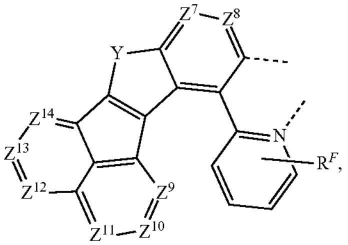
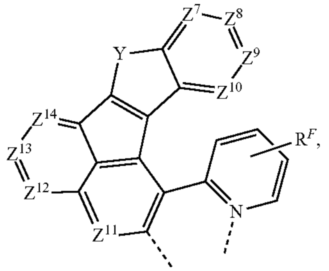
-continued
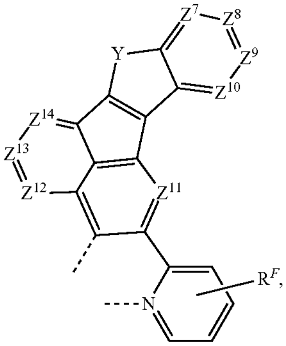
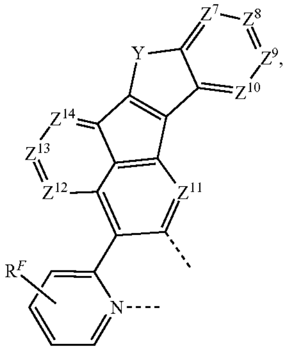
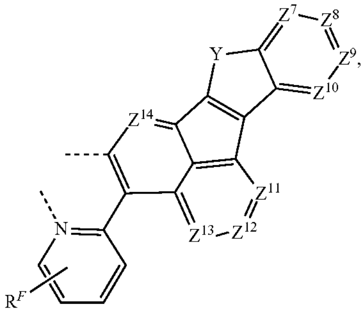
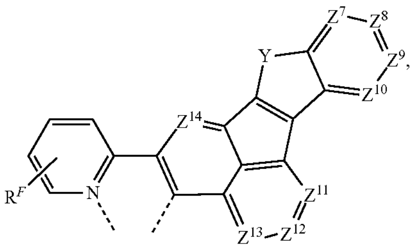
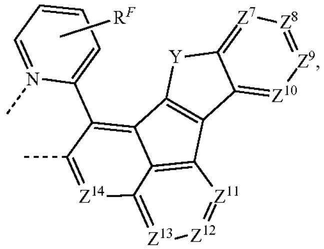

-continued
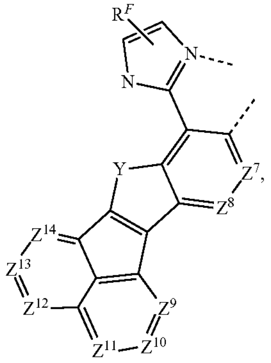
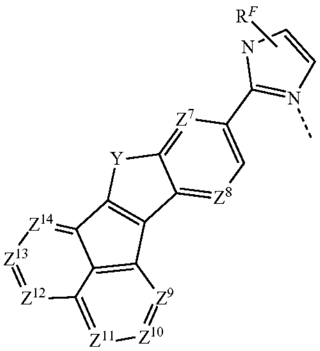
,
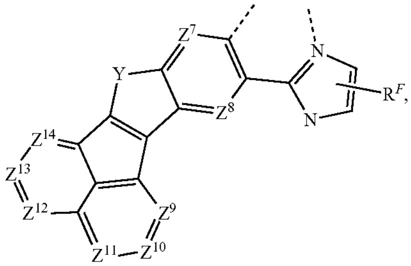
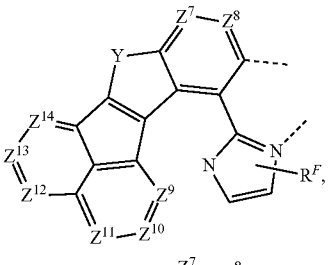
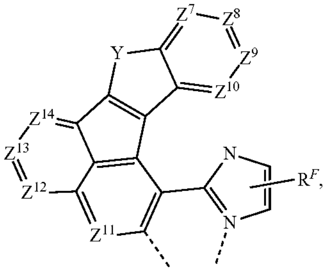
-continued
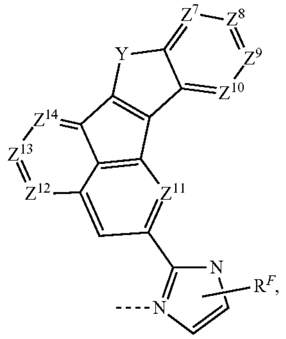
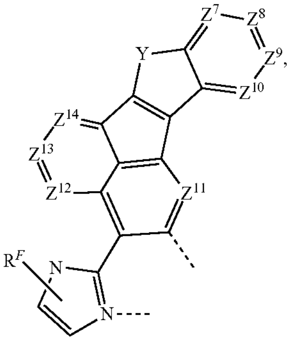
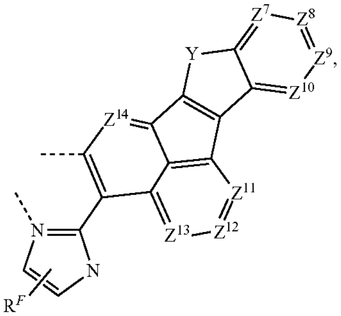
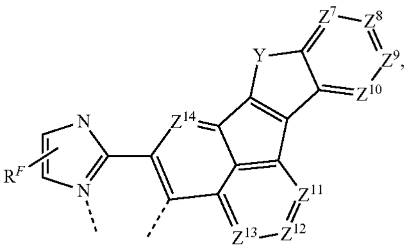
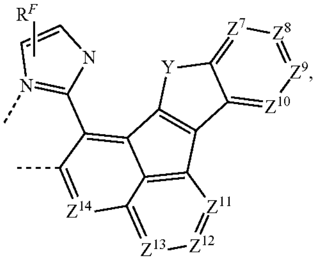

-continued
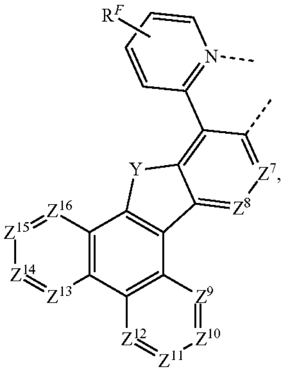
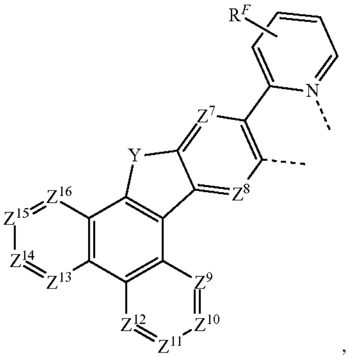
,
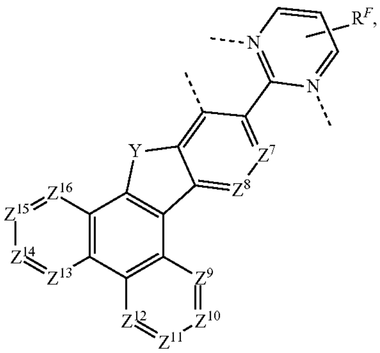
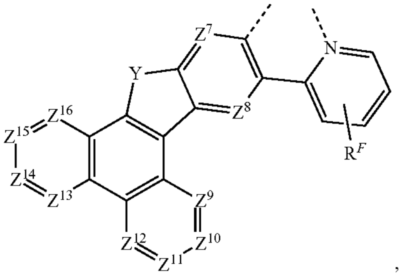
,
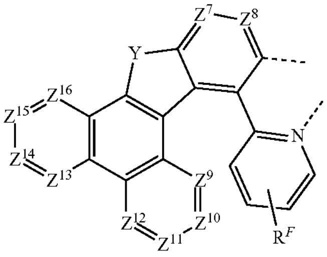
,
-continued
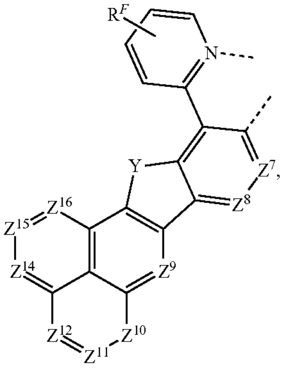
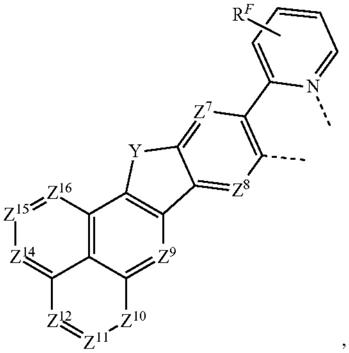
,
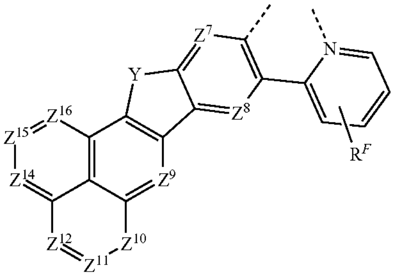
,
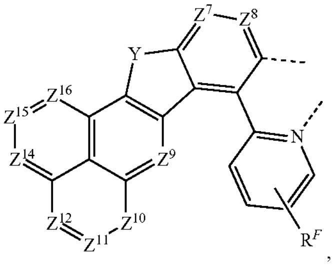
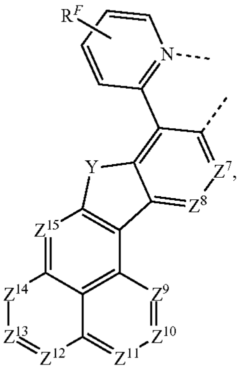

-continued
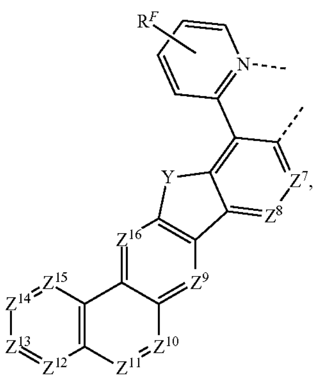
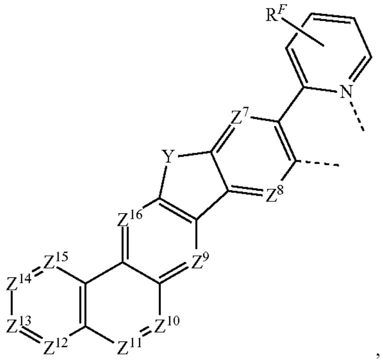
,
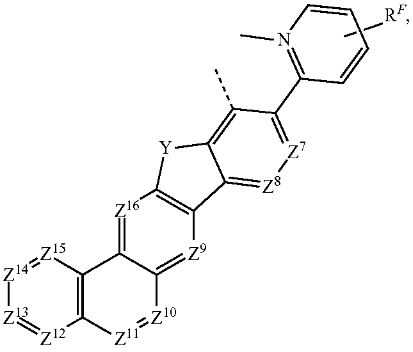
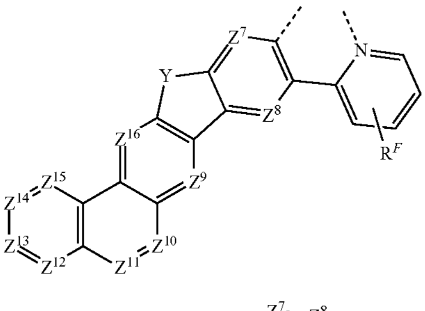
,
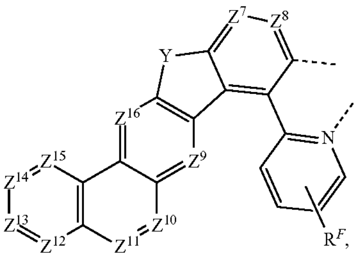
-continued
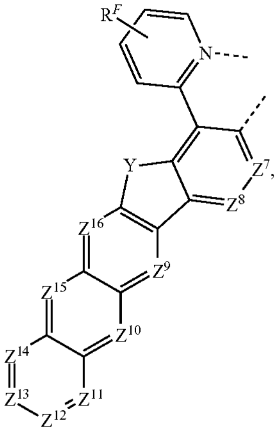
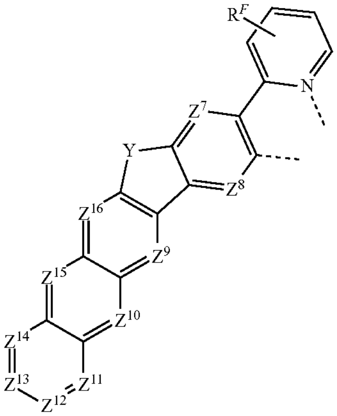
,
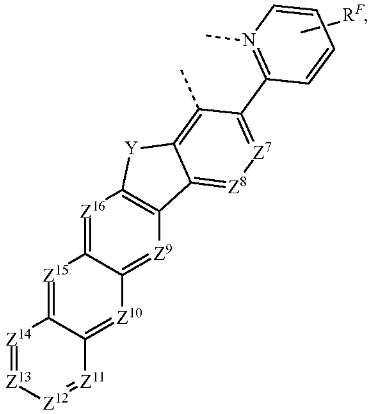
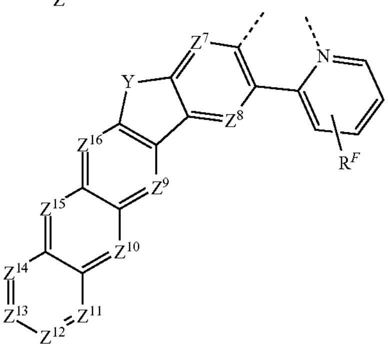
, -continued
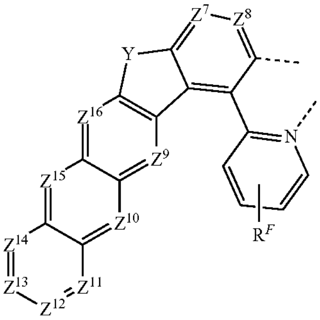
,
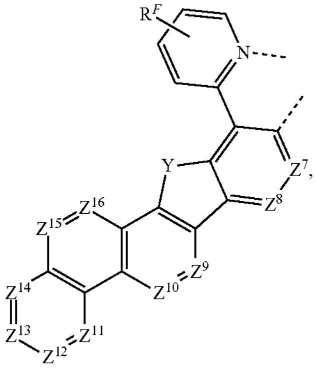
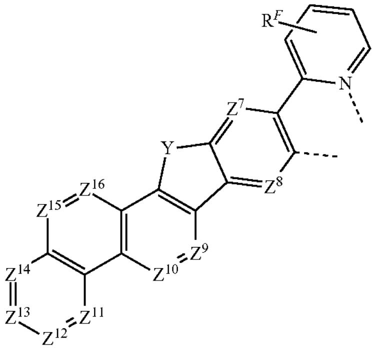
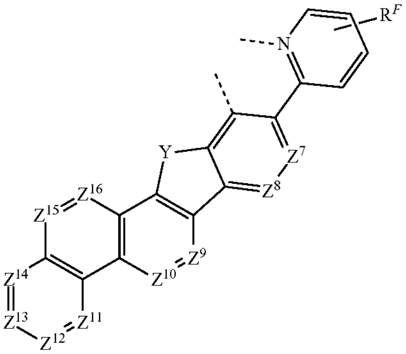
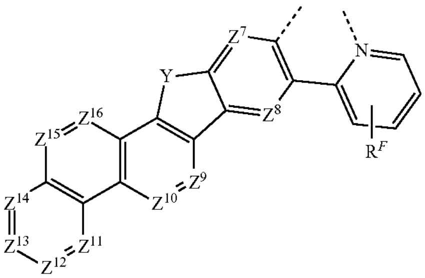
,
-continued
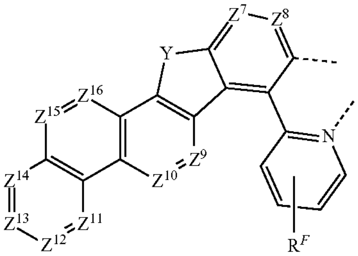
,
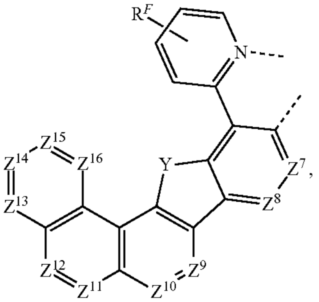
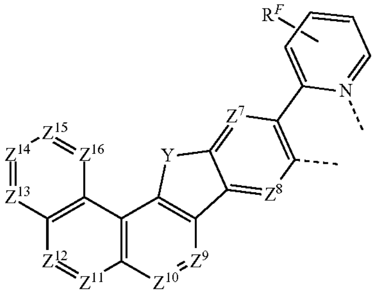
,
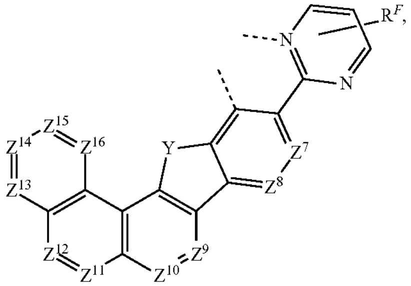
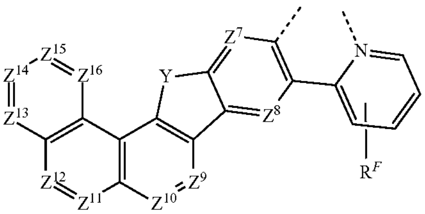
,
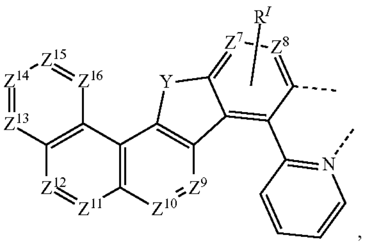
, -continued
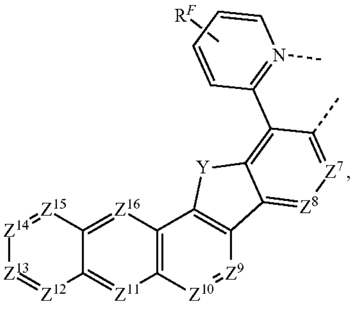
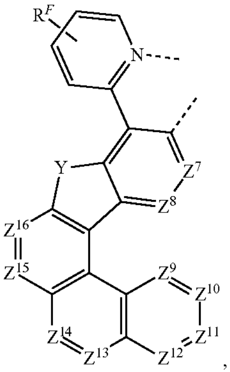
,
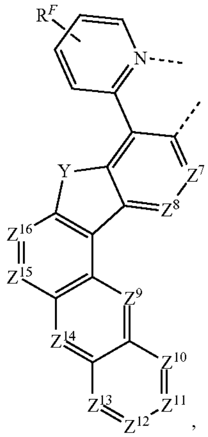
,
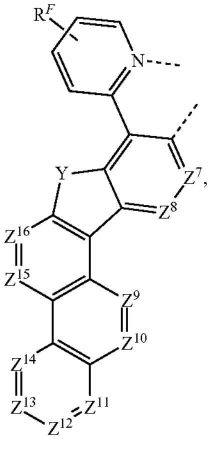
-continued
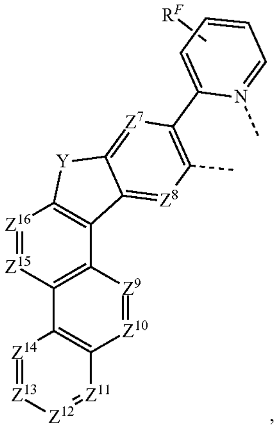
,
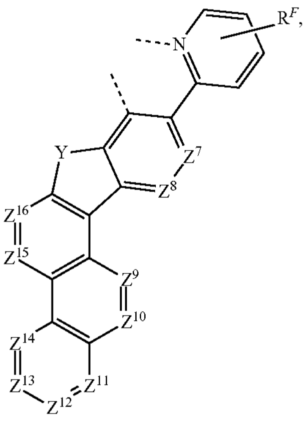
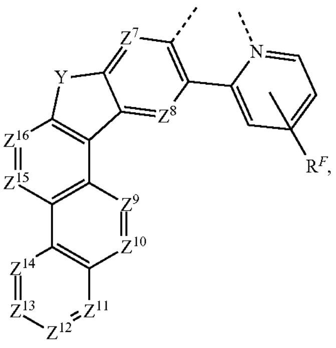
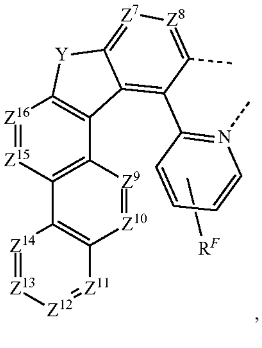
, -continued
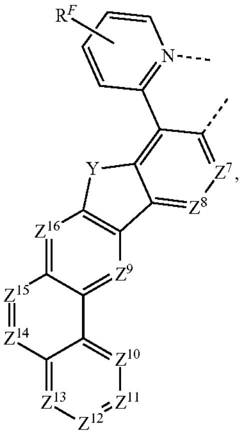
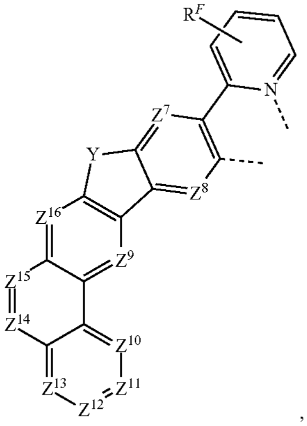
,
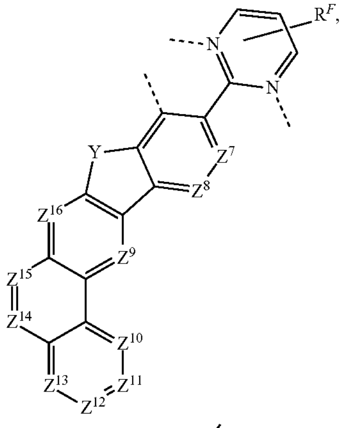
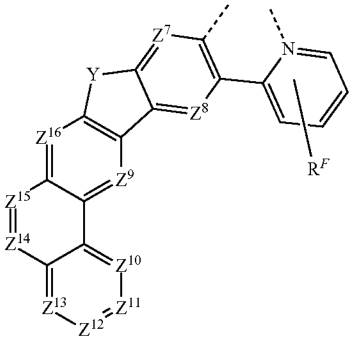
,
-continued
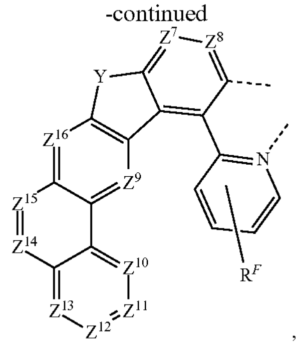
,
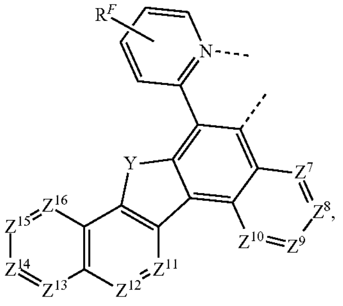
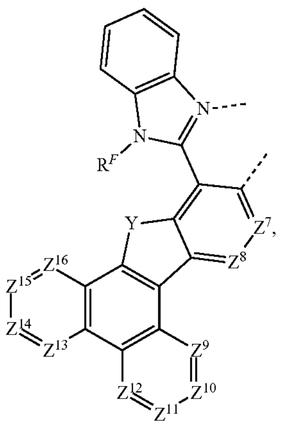
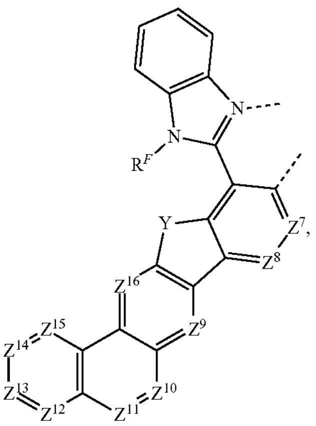

-continued
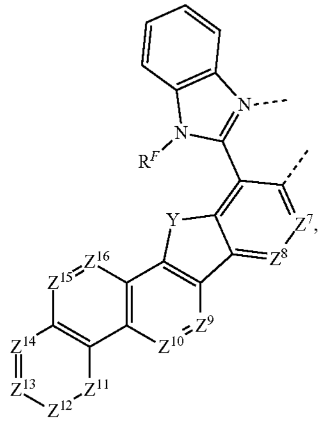
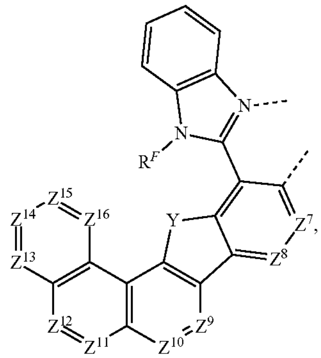
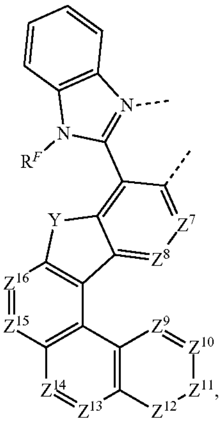
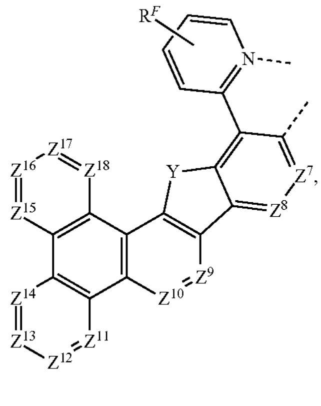
-continued
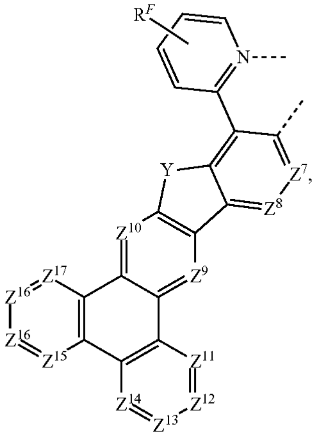
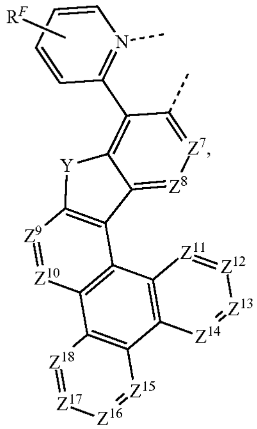
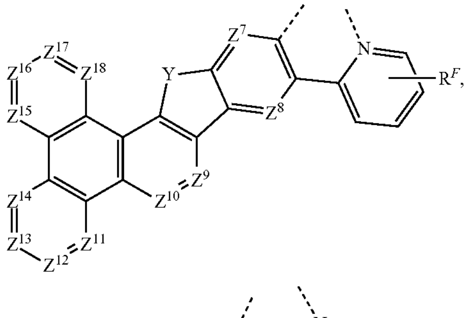
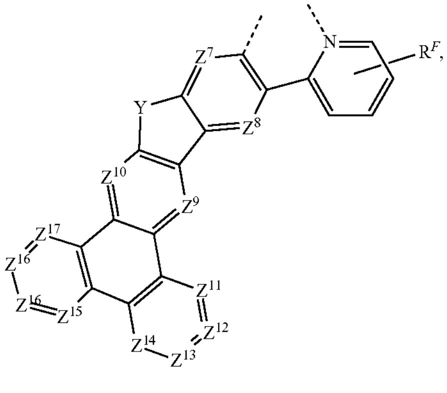
and -continued

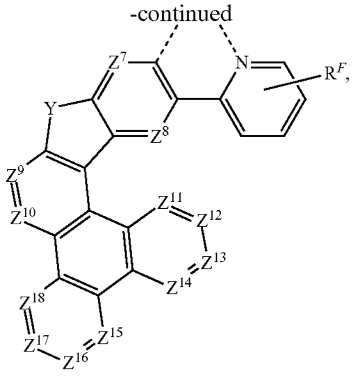

where $Z^7$ to $Z^{14}$ and, when present, $Z^{15}$ to $Z^{18}$ are each independently N or $CR^Q$; where each $R^Q$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof; and where any two substituents may be joined or fused together to form a ring.

In some embodiments, the first ligand $L_X$ is selected from the group consisting of $L_{X1}$ to $L_{X222}$, based on the following substructures:

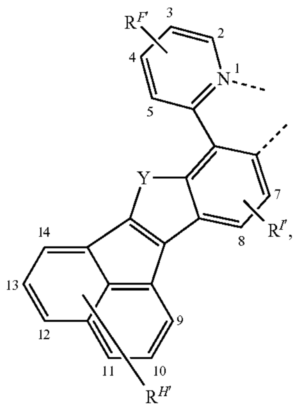

$L_{X1-1}$, where Y = O,
$L_{X1-2}$, where Y = S,
$L_{X1-3}$, where Y = $CR^K_2$,

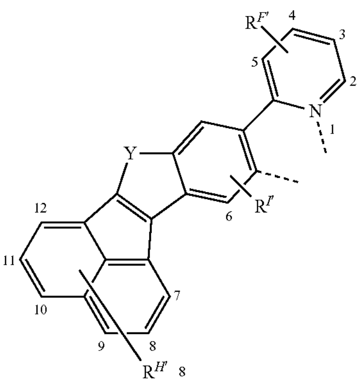

, $L_{X2-1}$, where Y = O
$L_{X2-2}$, where Y = S
$L_{X2-3}$, where Y = $CR^K_2$ -continued

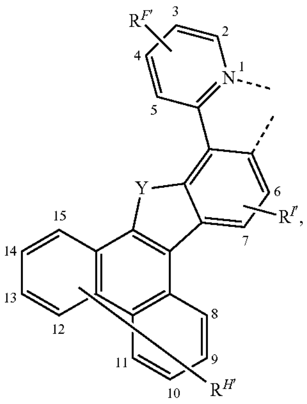

$L_{X3-1}$, where Y = O
$L_{X3-2}$, where Y = S
$L_{X3-3}$, where Y = $CRK_2$

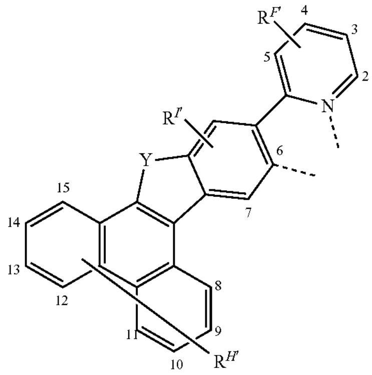

, $L_{X4-1}$, where Y = O
$L_{X4-2}$, where Y = S
$L_{X4-3}$, where Y = $CRK_2$

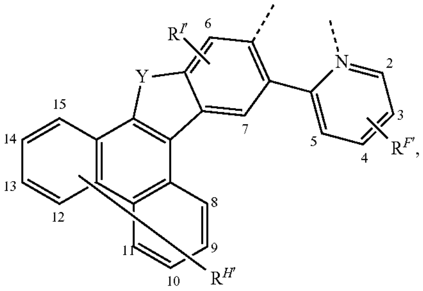

$L_{X5-1}$, where Y = O
$L_{X5-2}$, where Y = S
$L_{X5-3}$, where Y = $CRK_2$

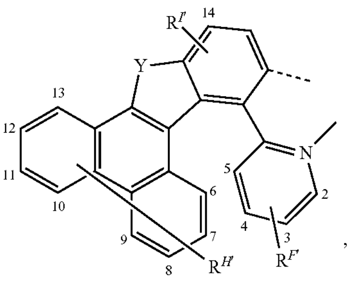

, $L_{X6-1}$, where Y = O
$L_{X6-2}$, where Y = S
$L_{X6-3}$, where Y = $CR_2$

-continued
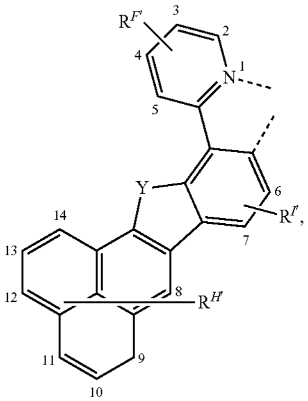
$L_{X7-1}$, where Y = O
$L_{X7-2}$, where Y = S
$L_{X7-3}$, where Y = $CRK_2$
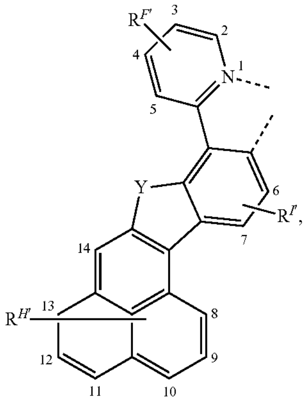
$L_{X8-1}$, where Y = O
$L_{X8-2}$, where Y = S
$L_{X8-3}$, where Y = $CRK_2$
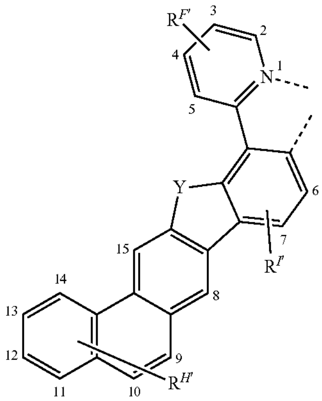
,
$L_{X9-1}$, where Y = O
$L_{X9-2}$, where Y = S
$L_{X9-3}$, where Y = $CRK_2$
-continued
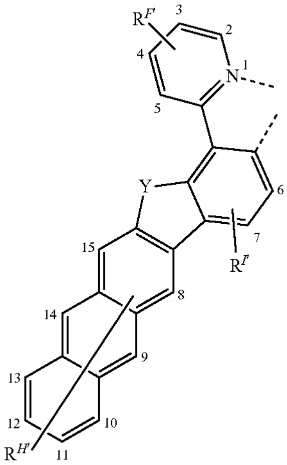
,
$L_{X10-1}$, where Y = O
$L_{X10-2}$, where Y = S
$L_{X10-3}$, where Y = $CRK_2$
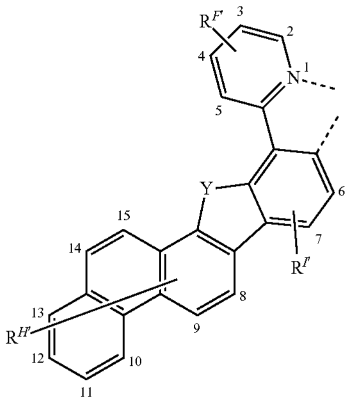
,
$L_{X11-1}$, where Y = O
$L_{X11-2}$, where Y = S
$L_{X11-3}$, where Y = $CRK_2$
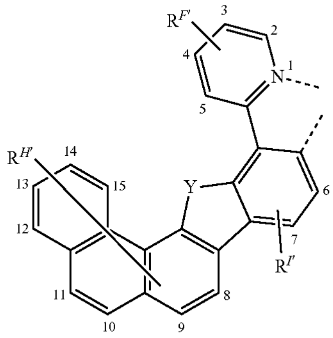
,
$L_{X12-1}$, where Y = O
$L_{X12-2}$, where Y = S
$L_{X12-3}$, where Y = $CRK_2$ -continued

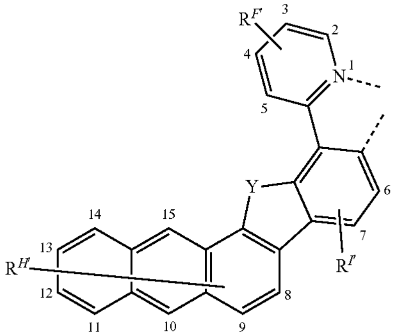

, $L_{X\,13\text{-}1}$, where Y = O
$L_{X\,13\text{-}2}$, where Y = S
$L_{X\,13\text{-}3}$, where Y = $CRK_2$

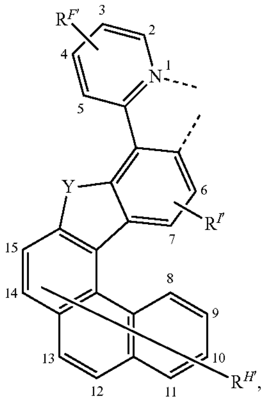

$L_{X\,14\text{-}1}$, where Y = O
$L_{X\,114\text{-}2}$, where Y = S
$L_{X\,14\text{-}3}$, where Y = $CRK_2$

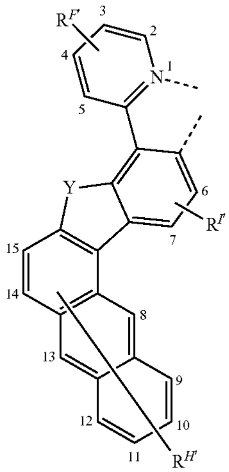

, $L_{X\,15\text{-}1}$, where Y = O
$L_{X\,15\text{-}2}$, where Y = S
$L_{X\,15\text{-}3}$, where Y = $CRK_2$

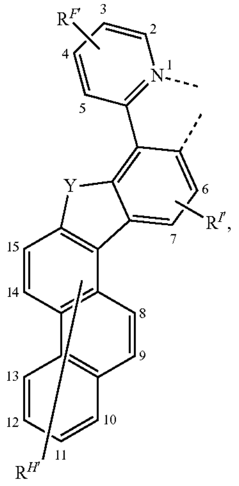

$L_{X\,16\text{-}1}$, where Y = O
$L_{X\,16\text{-}2}$, where Y = S
$L_{X\,16\text{-}3}$, where Y = $CRK_2$

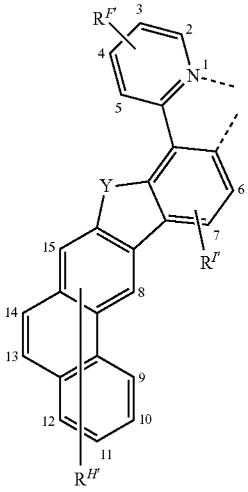

, $L_{X\,17\text{-}1}$, where Y = O
$L_{X\,17\text{-}2}$, where Y = S
$L_{X\,17\text{-}3}$, where Y = $CRK_2$ -continued

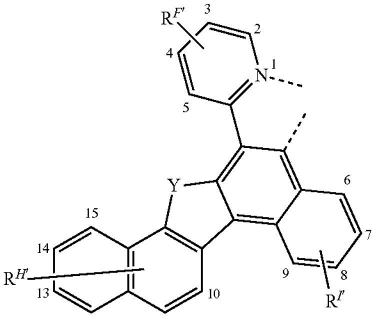

, $L_{X\,18\text{-}1}$, where Y = O
$L_{X\,18\text{-}2}$, where Y = S
$L_{X\,18\text{-}3}$, where Y = $CRK_2$

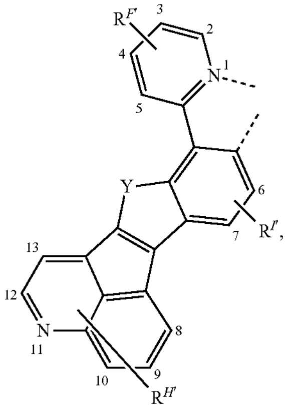

$L_{X\,19\text{-}1}$, where Y = O
$L_{X\,19\text{-}2}$, where Y = S
$L_{X\,19\text{-}3}$, where Y = $CRK_2$

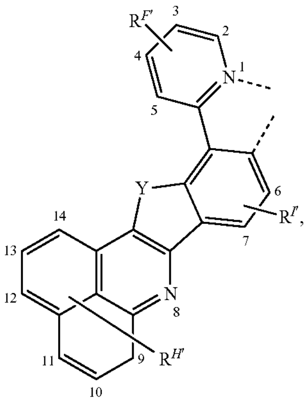

$L_{X\,20\text{-}1}$, where Y = O
$L_{X\,20\text{-}2}$, where Y = S
$L_{X\,20\text{-}3}$, where Y = $CRK_2$ -continued
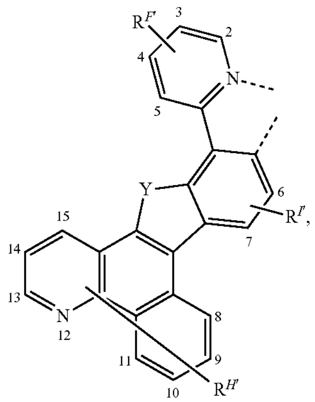
$L_{X21-1}$, where Y = O
$L_{X21-2}$, where Y = S
$L_{X21-3}$, where Y = $CRK_2$
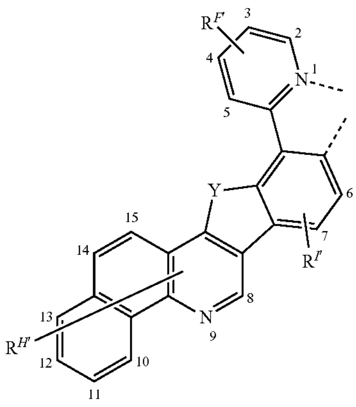
,
$L_{X22-1}$, where Y = O
$L_{X22-2}$, where Y = S
$L_{X22-3}$, where Y = $CRK_2$
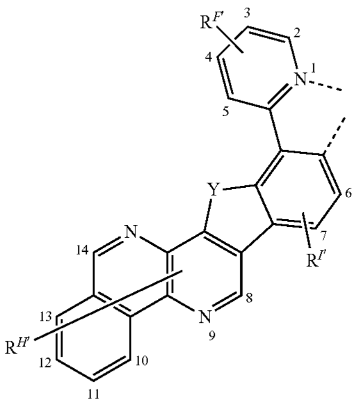
,
$L_{X23-1}$, where Y = O
$L_{X23-2}$, where Y = S
$L_{X23-3}$, where Y = $CRK_2$
-continued
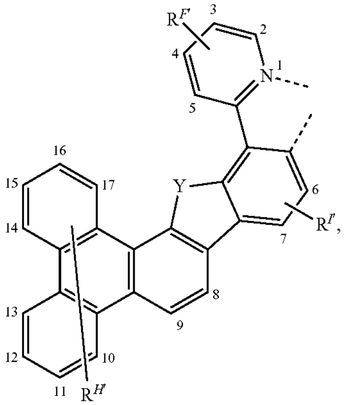
$L_{X24-1}$, where Y = O
$L_{X24-2}$, where Y = S
$L_{X24-3}$, where Y = $CRK_2$
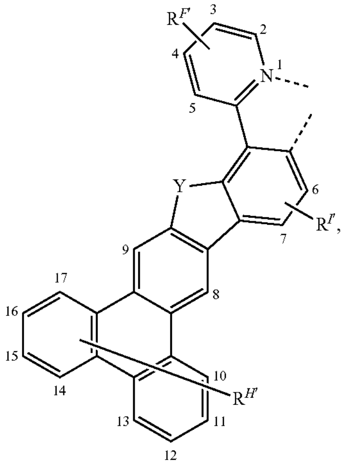
$L_{X25-1}$, where Y = O
$L_{X25-2}$, where Y = S
$L_{X25-3}$, where Y = $CRK_2$
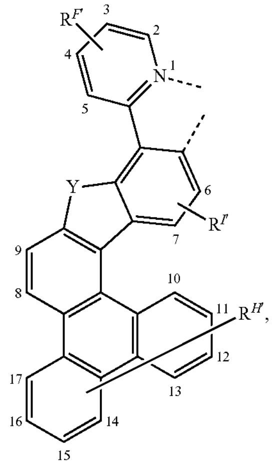
$L_{X26-1}$, where Y = O
$L_{X26-2}$, where Y = S
$L_{X26-3}$, where Y = $CRK_2$ where ligands $L_{X1}$ to $L_{X166}$ have the following definitions:

| $L_{Xi}$ | Ligand subtype | $R^{F'}$ | $R^{I'}$ | $R^{H'}$ | $R^{K}$ |
|---|---|---|---|---|---|
| 1. | $L_{X1-1}$ | 3-Me | H | H | — |
| 2. | $L_{X1-1}$ | 4-Me | H | H | — |
| 3. | $L_{X1-1}$ | 3,4-Me | H | H | — |
| 4. | $L_{X1-1}$ | 4-$CH_2CMe_3$ | H | H | — |
| 5. | $L_{X1-1}$ | 3-Me, 4-$CH_2CMe_3$ | H | H | — |
| 6. | $L_{X1-1}$ | 4-Me | 8-Me | 14-Me | — |
| 7. | $L_{X1-2}$ | 3-Me | H | H | — |
| 8. | $L_{X1-2}$ | 4-Me | H | H | — |
| 9. | $L_{X1-2}$ | 3,4-Me | H | H | — |
| 10. | $L_{X1-2}$ | 4-$CH_2CMe_3$ | H | H | — |
| 11. | $L_{X1-2}$ | 3-Me, 4-$CH_2CMe_3$ | H | H | — |
| 12. | $L_{X1-2}$ | 4-Me | 8-Me | 14-Me | — |
| 13. | $L_{X1-3}$ | 3-Me | H | H | Me |
| 14. | $L_{X2-1}$ | 3-Me | H | H | — |
| 15. | $L_{X2-1}$ | 4-Me | H | H | — |
| 16. | $L_{X2-1}$ | 3,4-Me | H | H | — |
| 17. | $L_{X2-1}$ | 4-$CH_2CMe_3$ | H | H | — |
| 18. | $L_{X2-1}$ | 3-Me, 4-$CH_2CMe_3$ | H | H | — |
| 19. | $L_{X2-2}$ | 3-Me | H | H | — |
| 20. | $L_{X2-2}$ | 3-Me | H | H | — |
| 21. | $L_{X2-2}$ | 4-Me | H | H | — |
| 22. | $L_{X2-2}$ | 3,4-Me | H | H | — |
| 23. | $L_{X2-2}$ | 4-$CH_2CMe_3$ | H | H | — |
| 24. | $L_{X2-3}$ | 3-Me | H | H | Me |
| 25. | $L_{X2-3}$ | 4-Me | H | H | Me |
| 26. | $L_{X2-3}$ | 3,4-Me | H | H | Me |
| 27. | $L_{X3-1}$ | 3-Me | H | H | — |
| 28. | $L_{X3-1}$ | 4-Me | H | H | — |
| 29. | $L_{X3-1}$ | 3,4-Me | H | H | — |
| 30. | $L_{X3-1}$ | 4-$CH_2CMe_3$ | H | H | — |
| 31. | $L_{X3-1}$ | 3-Me, 4-$CH_2CMe_3$ | H | H | — |
| 32. | $L_{X3-1}$ | 4-Me, 3-$CH_2CMe_3$ | 7-Me | 15-Me | — |
| 33. | $L_{X3-1}$ | 4-Ph | H | H | — |
| 34. | $L_{X3-1}$ | 3-$CD_3$ | H | H | — |
| 35. | $L_{X3-1}$ | 4-$CD_3$ | H | H | — |
| 36. | $L_{X3-1}$ | 3,4-$CD_3$ | H | H | — |
| 37. | $L_{X3-1}$ | 4-$CD_2CMe_3$ | H | H | — |
| 38. | $L_{X3-1}$ | 3-$CD_3$, 4-$CD_2CMe_3$ | H | H | — |
| 39. | $L_{X3-2}$ | 3-Me | H | H | — |
| 40. | $L_{X3-2}$ | 4-Me | H | H | — |
| 41. | $L_{X3-3}$ | 4-Me | H | H | Me |
| 42. | $L_{X4-1}$ | 3,4-Me | H | H | — |
| 43. | $L_{X4-2}$ | 3,4-Me | H | H | — |
| 44. | $L_{X4-3}$ | 3,4-Me | H | H | Me |
| 45. | $L_{X5-1}$ | 3,4-Me | H | H | — |
| 46. | $L_{X5-2}$ | 3,4-Me | H | H | — |
| 47. | $L_{X5-3}$ | 3,4-Me | H | H | Me |
| 48. | $L_{X6-1}$ | 3,4-Me | H | H | — |
| 49. | $L_{X6-1}$ | 4-Me | H | H | — |
| 50. | $L_{X6-1}$ | 3-Me | H | H | — |
| 51. | $L_{X6-2}$ | 3,4-Me | H | H | — |
| 52. | $L_{X6-2}$ | 4-Me | H | H | — |
| 53. | $L_{X6-3}$ | 3-Me | H | H | Me |
| 54. | $L_{X7-1}$ | 3,4-Me | H | H | — |
| 55. | $L_{X7-1}$ | 4-Me | H | H | — |
| 56. | $L_{X7-1}$ | 3-Me | H | H | — |
| 57. | $L_{X7-2}$ | 3,4-Me | H | H | — |
| 58. | $L_{X7-2}$ | 4-Me | H | H | — |
| 59. | $L_{X7-3}$ | 3-Me | H | H | Me |
| 60. | $L_{X8-1}$ | 3,4-Me | H | H | — |
| 61. | $L_{X8-1}$ | 4-Me | H | H | — |
| 62. | $L_{X8-1}$ | 3-Me | H | H | — |
| 63. | $L_{X8-2}$ | 3,4-Me | H | H | — |
| 64. | $L_{X8-2}$ | 4-Me | H | H | — |
| 65. | $L_{X8-3}$ | 3-Me | H | H | Me |
| 66. | $L_{X9-1}$ | 3-Me | H | H | — |
| 67. | $L_{X9-1}$ | 4-Me | H | H | — |
| 68. | $L_{X9-1}$ | 3,4-Me | H | H | — |
| 69. | $L_{X9-1}$ | 4-$CH_2CMe_3$ | H | H | — |
| 70. | $L_{X9-1}$ | 3-Me, 4-$CH_2CMe_3$ | H | H | — |
| 71. | $L_{X9-1}$ | 3-Me | H | H | — |
| 72. | $L_{X9-1}$ | 3-Me | 7-Ph | H | — |
| 73. | $L_{X9-1}$ | 3-Me | 7-Me | H | — |
| 74. | $L_{X9-1}$ | 3-Me | H | 11-Me | — |
| 75. | $L_{X9-1}$ | 3-$CD_3$, 4-$CD_2CMe_3$ | H | 9,10-$(CH)_4$ | — |
| 76. | $L_{X9-1}$ | 3-$CD_3$ | H | H | — |

-continued

| $L_{Xi}$ | Ligand subtype | $R^{F'}$ | $R^{I'}$ | $R^{H'}$ | $R^{K}$ |
|---|---|---|---|---|---|
| 77. | $L_{X9-1}$ | 4-$CD_3$ | H | H | — |
| 78. | $L_{X9-1}$ | 3,4-$CD_3$ | H | H | — |
| 79. | $L_{X9-1}$ | 4-$CD_2CMe_3$ | H | H | — |
| 80. | $L_{X9-1}$ | 3-$CD_3$, 4-$CD_2CMe_3$ | H | H | — |
| 81. | $L_{X9-2}$ | 3-Me | H | H | — |
| 82. | $L_{X9-2}$ | 4-Me | H | H | — |
| 83. | $L_{X9-2}$ | 3,4-Me | H | H | — |
| 84. | $L_{X9-3}$ | 3-Me | H | H | Me |
| 85. | $L_{X10-1}$ | 4-Me | H | H | — |
| 86. | $L_{X10-2}$ | 4-Me | H | H | — |
| 87. | $L_{X10-3}$ | 4-Me | H | H | Me |
| 88. | $L_{X11-1}$ | 3-Me | H | H | — |
| 89. | $L_{X11-1}$ | 4-Me | H | H | — |
| 90. | $L_{X11-1}$ | 3,4-Me | H | H | — |
| 91. | $L_{X11-1}$ | 4-$CH_2CMe_3$ | H | H | — |
| 92. | $L_{X11-1}$ | 3-$CH_2CMe_3$ | H | H | — |
| 93. | $L_{X11-1}$ | 3-Me, 4-$CH_2CMe_3$ | H | H | — |
| 94. | $L_{X11-1}$ | 4-Ph | H | H | — |
| 95. | $L_{X11-1}$ | 3,4-Me | 7-Me | H | — |
| 96. | $L_{X11-1}$ | 3,4-Me | H | 15-Me | — |
| 97. | $L_{X11-1}$ | 3-$CD_3$ | H | H | — |
| 98. | $L_{X11-1}$ | 4-$CD_3$ | H | H | — |
| 99. | $L_{X11-1}$ | 3,4-$CD_3$ | H | H | — |
| 100. | $L_{X11-1}$ | 4-$CD_2CMe_3$ | H | H | — |
| 101. | $L_{X11-1}$ | 3-$CD_3$, 4-$CD_2CMe_3$ | H | H | — |
| 102. | $L_{X11-2}$ | 3-Me | H | H | — |
| 103. | $L_{X11-2}$ | 4-Me | H | H | — |
| 104. | $L_{X11-2}$ | 3,4-Me | H | H | — |
| 105. | $L_{X11-3}$ | 3-Me | H | H | Me |
| 106. | $L_{X11-3}$ | 4-Me | H | H | Me |
| 107. | $L_{X12-1}$ | 3-Me | H | H | — |
| 108. | $L_{X12-1}$ | 4-Me | H | H | — |
| 109. | $L_{X12-1}$ | 3,4-Me | H | H | — |
| 110. | $L_{X12-1}$ | 3-Me | 7-Me | H | — |
| 111. | $L_{X12-1}$ | 4-Me | 7-Me | H | — |
| 112. | $L_{X12-1}$ | 3-Me | H | 11-Me | — |
| 113. | $L_{X12-1}$ | 4-Me | H | 14-Me | — |
| 114. | $L_{X12-1}$ | 3-$CD_3$, 4-$CD_2CMe_3$ | H | 10,11-$(CH)_4$ | — |
| 115. | $L_{X12-1}$ | 3-$CD_3$ | H | H | — |
| 116. | $L_{X12-1}$ | 4-$CD_3$ | H | H | — |
| 117. | $L_{X12-1}$ | 3,4-$CD_3$ | H | H | — |
| 118. | $L_{X12-1}$ | 4-$CD_2CMe_3$ | H | H | — |
| 119. | $L_{X12-1}$ | 3-$CD_3$, 4-$CD_2CMe_3$ | H | H | — |
| 120. | $L_{X12-2}$ | 3-Me | H | H | — |
| 121. | $L_{X12-2}$ | 4-Me | H | H | — |
| 122. | $L_{X12-2}$ | 3,4-Me | H | H | — |
| 123. | $L_{X12-3}$ | 3,4-Me | H | H | Me |
| 124. | $L_{X13-1}$ | 3,4-Me | H | H | — |
| 125. | $L_{X13-2}$ | 3,4-Me | H | H | — |
| 126. | $L_{X13-3}$ | 3,4-Me | H | H | Me |
| 127. | $L_{X14-1}$ | 3,4-Me | H | H | — |
| 128. | $L_{X14-1}$ | 3-$CD_3$, 4-$CD_2CMe_3$ | H | 12,13-$(CH)_4$ | — |
| 129. | $L_{X14-1}$ | 3-$CD_3$ | H | H | — |
| 130. | $L_{X14-1}$ | 4-$CD_3$ | H | H | — |
| 131. | $L_{X14-1}$ | 3,4-$CD_3$ | H | H | — |
| 132. | $L_{X14-1}$ | 4-$CD_2CMe_3$ | H | H | — |
| 133. | $L_{X14-1}$ | 3-$CD_3$, 4-$CD_2CMe_3$ | H | H | — |
| 134. | $L_{X14-2}$ | 3,4-Me | H | H | — |
| 135. | $L_{X14-3}$ | 3,4-Me | H | H | Me |
| 136. | $L_{X15-1}$ | 3,4-Me | H | H | — |
| 137. | $L_{X15-2}$ | 3,4-Me | H | H | — |
| 138. | $L_{X15-3}$ | 3,4-Me | H | H | Me |
| 139. | $L_{X16-1}$ | 3-Me | H | H | — |
| 140. | $L_{X16-1}$ | 4-Me | H | H | — |
| 141. | $L_{X16-1}$ | 3,4-Me | H | H | — |
| 142. | $L_{X16-1}$ | 4-$CH_2CMe_3$ | H | H | — |
| 143. | $L_{X16-1}$ | 3-$CH_2CMe_3$ | H | H | — |
| 144. | $L_{X16-1}$ | 3-Me, 4-$CH_2CMe_3$ | H | H | — |
| 145. | $L_{X16-1}$ | 3,4-Me | 7-Me | H | — |
| 146. | $L_{X16-1}$ | 3,4-Me | H | 8-Me | — |
| 147. | $L_{X16-1}$ | 3,4-Me | H | 15-Me | — |
| 148. | $L_{X16-1}$ | 3-$CD_3$ | H | H | — |
| 149. | $L_{X16-1}$ | 4-$CD_3$ | H | H | — |
| 150. | $L_{X16-1}$ | 3,4-$CD_3$ | H | H | — |
| 151. | $L_{X16-1}$ | 4-$CD_2CMe_3$ | H | H | — |
| 152. | $L_{X16-1}$ | 3-$CD_3$, 4-$CD_2CMe_3$ | H | H | — |
| 153. | $L_{X16-2}$ | 3,4-Me | H | H | — |

-continued

| $L_{Xi}$ | Ligand subtype | $R^F$ | $R^I$ | $R^H$ | $R^K$ |
|---|---|---|---|---|---|
| 154. | $L_{X16-3}$ | 3,4-Me | H | H | Me |
| 155. | $L_{X17-1}$ | 3-Me | H | H | — |
| 156. | $L_{X17-1}$ | 4-Me | H | H | — |
| 157. | $L_{X17-1}$ | 3,4-Me | H | H | — |
| 158. | $L_{X17-1}$ | 4-$CH_2CMe_3$ | H | H | — |
| 159. | $L_{X17-1}$ | 3-Me, 4-$CH_2CMe_3$ | H | H | — |
| 160. | $L_{X17-1}$ | 3-Me | 7-Me | H | — |
| 161. | $L_{X17-1}$ | 4-Me | 7-Ph | H | — |
| 162. | $L_{X17-1}$ | 3,4-Me | H | 13-Me | — |
| 163. | $L_{X17-1}$ | 3,4-Me | H | 14-Me | — |
| 164. | $L_{X17-1}$ | 3,4-Me | H | 15-Me | — |
| 165. | $L_{X17-1}$ | 3-$CD_3$ | H | H | — |
| 166. | $L_{X17-1}$ | 4-$CD_3$ | H | H | — |
| 167. | $L_{X17-1}$ | 3,4-$CD_3$ | H | H | — |
| 168. | $L_{X17-1}$ | 4-$CD_2CMe_3$ | H | H | — |
| 169. | $L_{X17-1}$ | 3-$CD_3$, 4-$CD_2CMe_3$ | H | H | — |
| 170. | $L_{X17-2}$ | 3-Me | H | H | — |
| 171. | $L_{X17-2}$ | 4-Me | H | H | — |
| 172. | $L_{X17-2}$ | 3,4-Me | H | H | — |
| 173. | $L_{X17-3}$ | 3,4-Me | H | H | Me |
| 174. | $L_{X18-1}$ | 3,4-Me | H | H | — |
| 175. | $L_{X18-2}$ | 3,4-Me | H | H | — |
| 176. | $L_{X18-3}$ | 3,4-Me | H | H | Me |
| 177. | $L_{X19-1}$ | 3,4-Me | H | H | — |
| 178. | $L_{X19-1}$ | 3,4-Me | 7-Me | H | — |
| 179. | $L_{X19-1}$ | 3,4-Me | H | 12-Me | — |
| 180. | $L_{X19-2}$ | 3,4-Me | H | H | — |
| 181. | $L_{X19-3}$ | 3,4-Me | H | H | Me |
| 182. | $L_{X20-1}$ | 3,4-Me | H | H | — |
| 183. | $L_{X20-2}$ | 3,4-Me | H | H | — |
| 184. | $L_{X20-3}$ | 3,4-Me | H | H | Me |
| 185. | $L_{X21-1}$ | 3-Me | H | H | — |
| 186. | $L_{X21-1}$ | 4-Me | H | H | — |
| 187. | $L_{X21-1}$ | 3,4-Me | H | H | — |
| 188. | $L_{X21-1}$ | 4-$CH_2CMe_3$ | H | H | — |
| 189. | $L_{X21-1}$ | 3-Me, 4-$CH_2CMe_3$ | H | H | — |
| 190. | $L_{X21-1}$ | 3,4-Me | 7-Me | H | — |
| 191. | $L_{X21-1}$ | 3,4-Me | H | 13-Me | — |
| 192. | $L_{X21-2}$ | 3-Me | H | H | — |
| 193. | $L_{X21-2}$ | 4-Me | H | H | — |
| 194. | $L_{X21-2}$ | 3,4-Me | H | H | — |
| 195. | $L_{X21-3}$ | 3,4-Me | H | H | Me |
| 196. | $L_{X22-1}$ | 3,4-Me | H | H | — |
| 197. | $L_{X22-2}$ | 3,4-Me | H | H | — |
| 198. | $L_{X22-3}$ | 3,4-Me | H | H | Me |
| 199. | $L_{X23-1}$ | 3,4-Me | H | H | — |
| 200. | $L_{X23-2}$ | 3,4-Me | H | H | — |
| 201. | $L_{X23-3}$ | 3,4-Me | H | H | Me |
| 202. | $L_{X24-1}$ | 3-$CD_3$ | H | H | — |
| 203. | $L_{X24-1}$ | 4-$CD_3$ | H | H | — |
| 204. | $L_{X24-1}$ | 3,4-$CD_3$ | H | H | — |
| 205. | $L_{X24-1}$ | 4-$CD_2CMe_3$ | H | H | — |
| 206. | $L_{X24-1}$ | 3-$CD_3$, 4-$CD_2CMe_3$ | H | H | — |
| 207. | $L_{X24-2}$ | 3-$CD_3$, 4-$CD_2CMe_3$ | H | H | — |
| 208. | $L_{X24-3}$ | 3-$CD_3$, 4-$CD_2CMe_3$ | H | H | Me |
| 209. | $L_{X25-1}$ | 3-$CD_3$ | H | H | — |
| 210. | $L_{X25-1}$ | 4-$CD_3$ | H | H | — |
| 211. | $L_{X25-1}$ | 3,4-$CD_3$ | H | H | — |
| 212. | $L_{X25-1}$ | 4-$CD_2CMe_3$ | H | H | — |
| 213. | $L_{X25-1}$ | 3-$CD_3$, 4-$CD_2CMe_3$ | H | H | — |
| 214. | $L_{X25-2}$ | 3-$CD_3$, 4-$CD_2CMe_3$ | H | H | — |
| 215. | $L_{X25-3}$ | 3-$CD_3$, 4-$CD_2CMe_3$ | H | H | Me |
| 216. | $L_{X26-1}$ | 3-$CD_3$ | H | H | — |
| 217. | $L_{X26-1}$ | 4-$CD_3$ | H | H | — |
| 218. | $L_{X26-1}$ | 3,4-$CD_3$ | H | H | — |
| 219. | $L_{X26-1}$ | 4-$CD_2CMe_3$ | H | H | — |
| 220. | $L_{X26-1}$ | 3-$CD_3$, 4-$CD_2CMe_3$ | H | H | — |
| 221. | $L_{X26-2}$ | 3-$CD_3$, 4-$CD_2CMe_3$ | H | H | — |
| 222. | $L_{X26-3}$ | 3-$CD_3$, 4-$CD_2CMe_3$ | H | H | Me |

In some embodiments, the compound has a formula of $M(L_A)_x(L_B)_y(L_C)_z$ where each one of $L_B$ and $L_C$ is a bidentate ligand; where x is 1, 2, or 3; y is 0, 1, or 2; z is 0, 1, or 2; and x+y+z is the oxidation state of the metal M.

In some embodiments of formula $M(L_A)_x(L_B)_y(L_C)_z$ the compound has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; and where $L_A$, $L_B$, and $L_C$ are different from each other.

In some embodiments of formula $M(L_A)_x(L_B)_y(L_C)_z$, the compound has a formula of $Pt(L_A)(L_B)$; and where $L_A$ and $L_B$ can be same or different. In some such embodiments, ligands $L_A$ and $L_B$ are connected to form a tetradentate ligand. In some such embodiments, ligands $L_A$ and $L_B$ are connected at two places to form a macrocyclic tetradentate ligand.

In some embodiments of formula $M(L_A)_x(L_B)_y(L_C)_z$, ligands $L_B$ and $L_C$ are each independently selected from the group consisting of

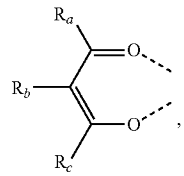
,
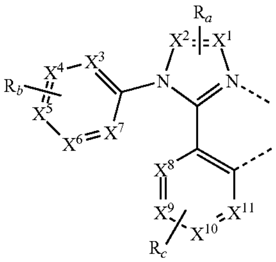
,
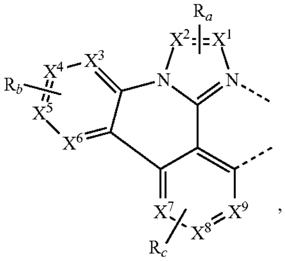
,
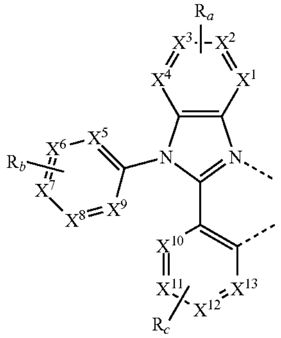
,
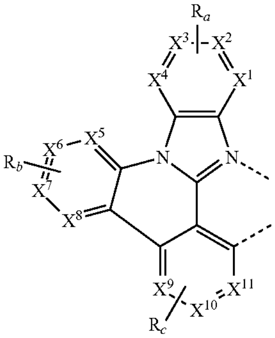
,
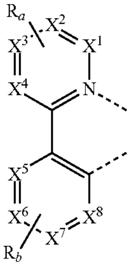
,
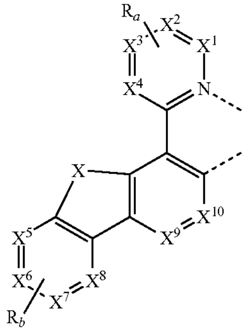
,
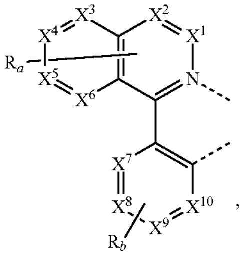
, -continued

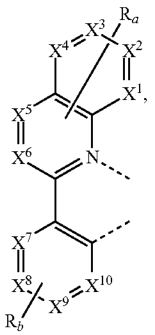

,

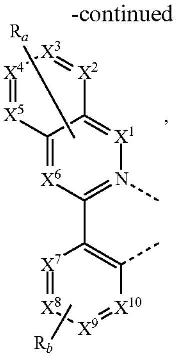

,

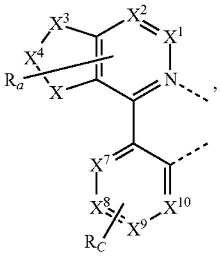

,

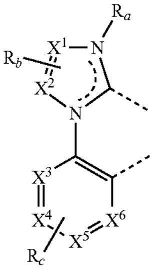

,

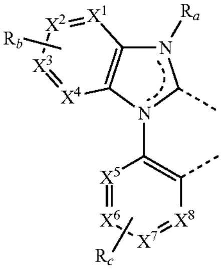

,

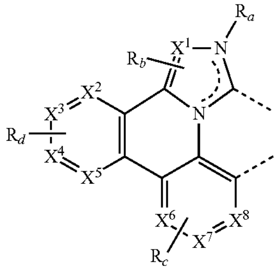

,

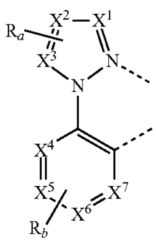

,

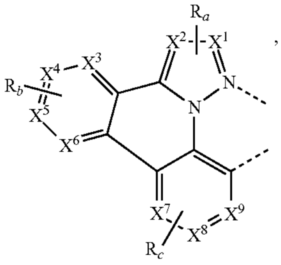

,

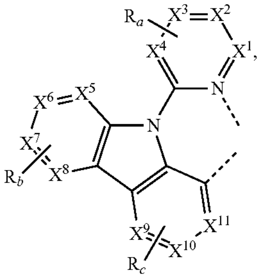

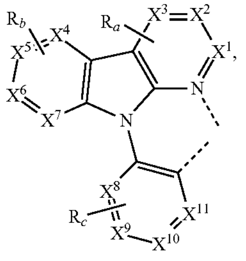

and

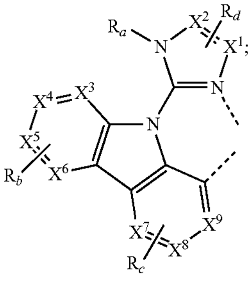

where each $X^1$ to $X^{13}$ are independently selected from the group consisting of carbon and nitrogen;

where X is selected from the group consisting of BR', NR', PR', O, S, Se, C═O, S═O, $SO_2$, CR'R", SiR'R", and GeR'R";

where R' and R" are optionally fused or joined to form a ring; where each $R_a$, $R_b$, $R_c$, and $R_d$ may represent from mono substitution to the possible maximum number of substitution, or no substitution;

where R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and where any two adjacent substitutents of $R_a$, $R_b$, R, and $R_d$ are optionally fused or joined to form a ring or form a multidentate ligand.

In some such embodiments, ligands $L_B$ and $L_C$ are each independently selected from the group consisting of

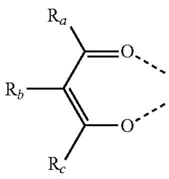

,

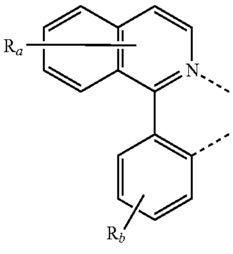

,

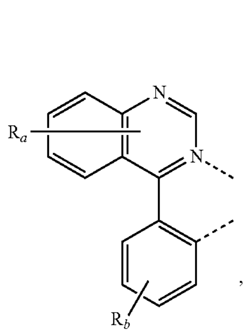

,

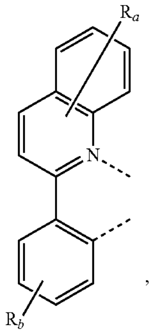

,

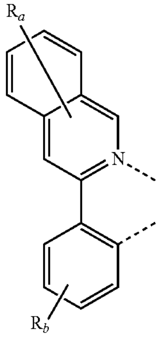

,

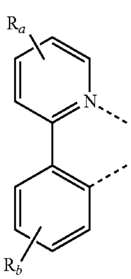

,

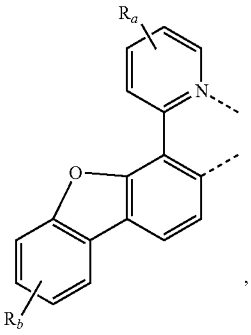

,

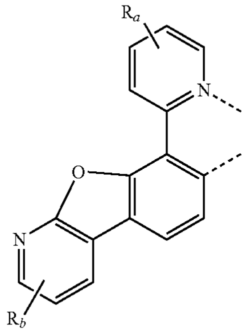

,

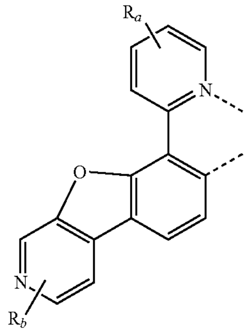

,

-continued

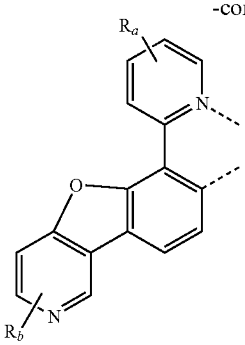,

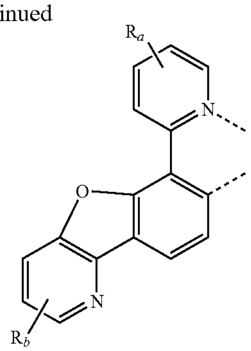,

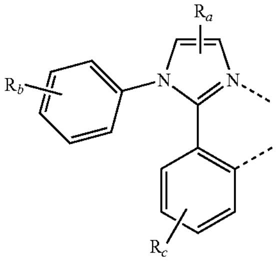,

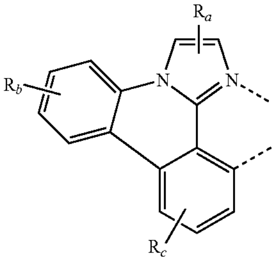,

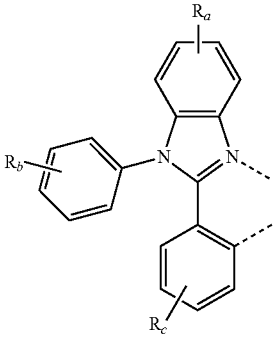,

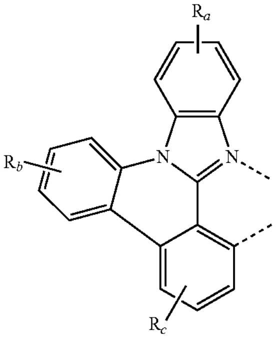,

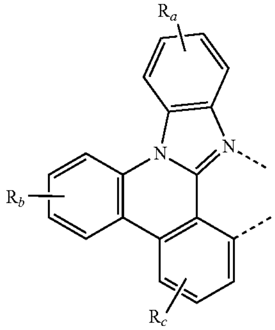,

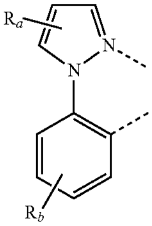,

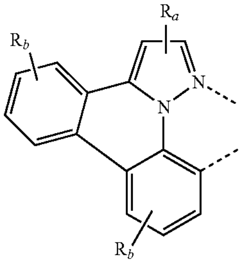,

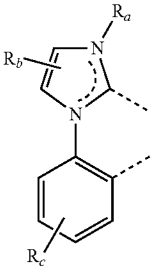,

-continued

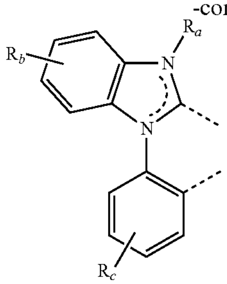,

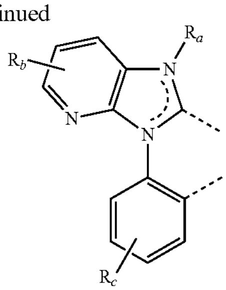,

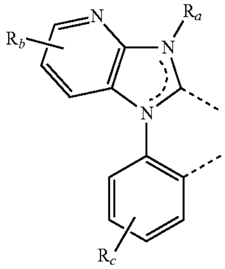,

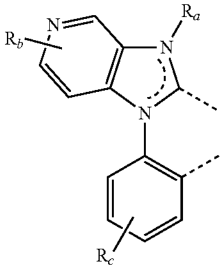,

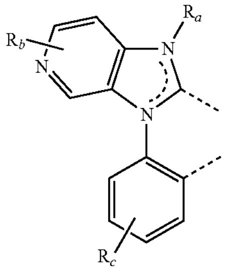,

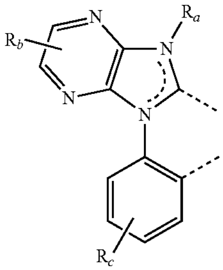,

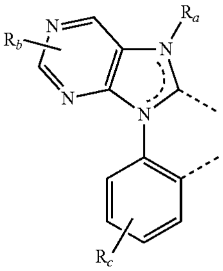,

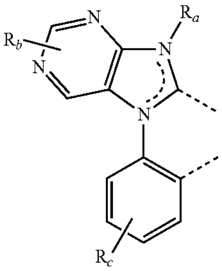, and

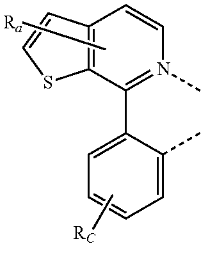.

In some embodiments, the compound is the Compound Ax having the formula $Ir(L_{Ai})_3$, the Compound By having the formula $Ir(L_{Ai})(L_{Bk})_2$, or the Compound Cz having the formula $Ir(L_{Ai})_2(L_{Cj})$. In the formulas of Compounds Ax, By, and Cz, x=i, y=468i+k−468, and z=1260+j−1260, where i is an integer from 1 to 166, k is an integer from 1 to 468, and j is an integer from 1 to 1260. In the formulas of Compounds Ax, By, and Cz, ligand $L_{Bk}$ is selected from $L_{B1}$ to $L_{B468}$; and ligand $L_{Cj}$ is selected from $L_{C1}$ to $L_{C1260}$.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

According to another aspect, an emissive region in an OLED (e.g., the organic layer described herein) is disclosed. The emissive region comprises a compound comprising a first ligand $L_A$ of Formula I as described herein or a first ligand $L_X$ of Formula II. In some embodiments, the first compound in the emissive region is an emissive dopant or a non-emissive dopant.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer.

In some embodiments, the compound can be used as a phosphorescent sensitizer in an OLED where one or multiple layers in the OLED contains a fluorescent emitter. The compound must be capable of energy transfer to the fluorescent material and emission can occur from the fluorescent emitter. The fluorescent emitter could be doped in a matrix or as a neat layer. The fluorescent emitter could be in either the same layer as the phosphorescent sensitizer or a different layer. In some embodiments, the fluorescent emitter is a TADF emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH{=}CH{-}C_nH_{2n+1}$, $C{\equiv}C{-}C_nH_{2n+1}$, $Ar_1$, $Ar_1{-}Ar_2$, and $C_nH_{2n}{-}Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

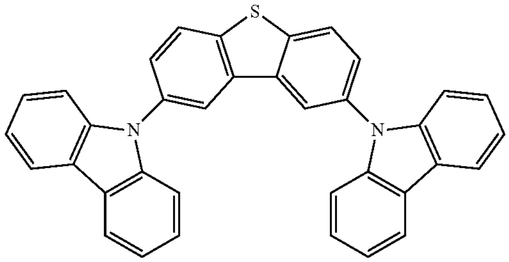
,
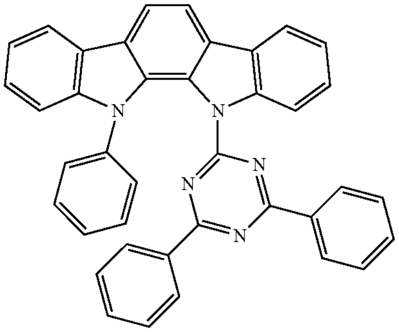
,
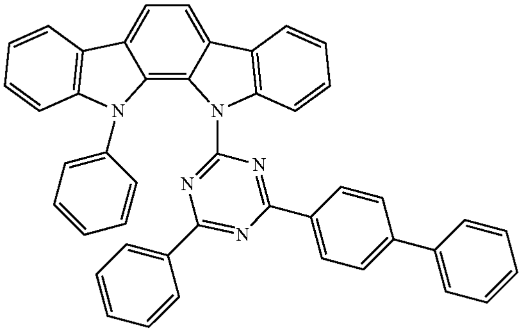
,
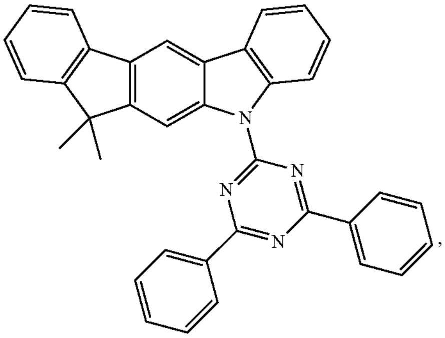
,
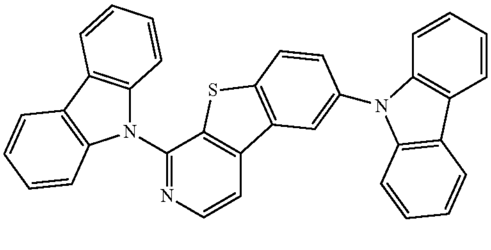
,

-continued
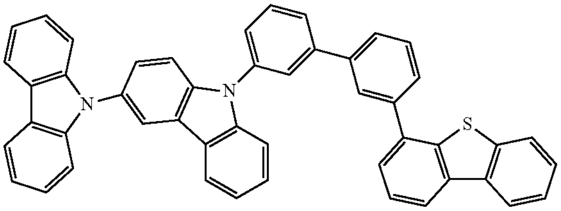
,
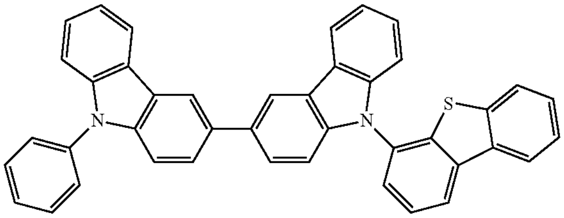
,
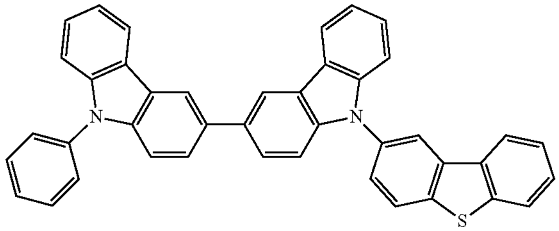
,
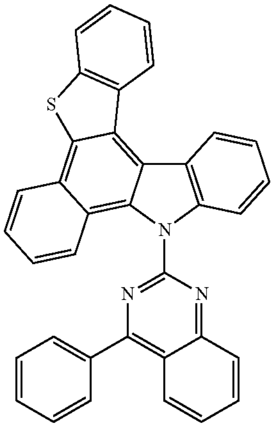
,
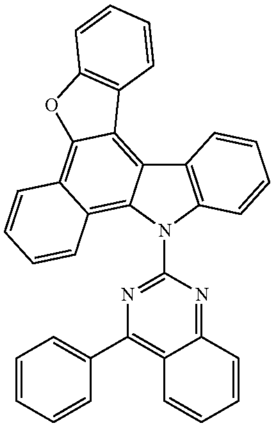
,
-continued
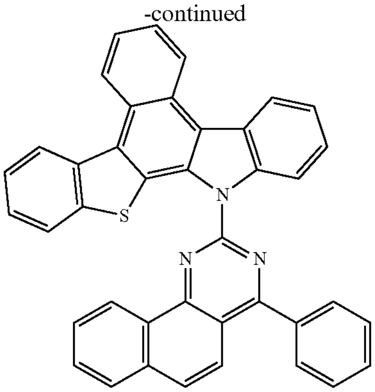
,
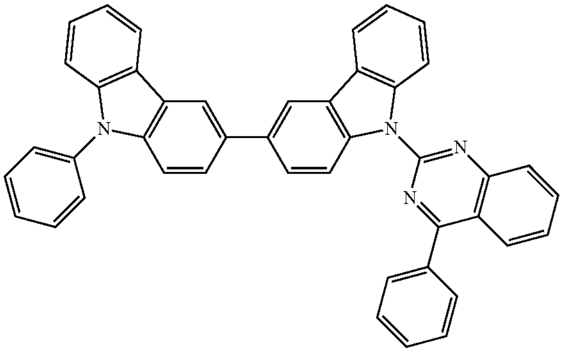
,
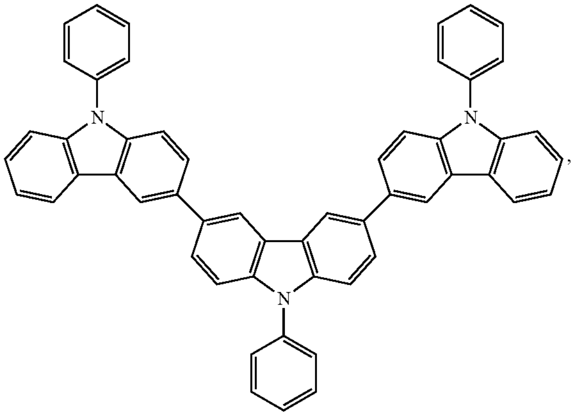
,
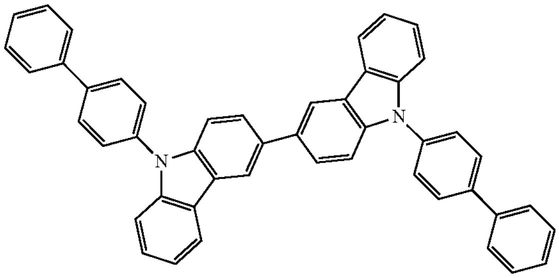
,
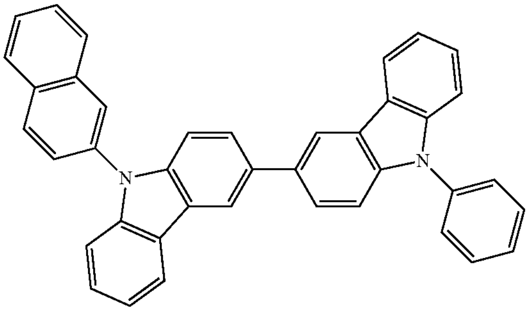
, -continued

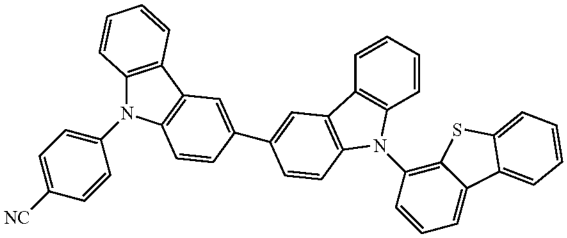

,

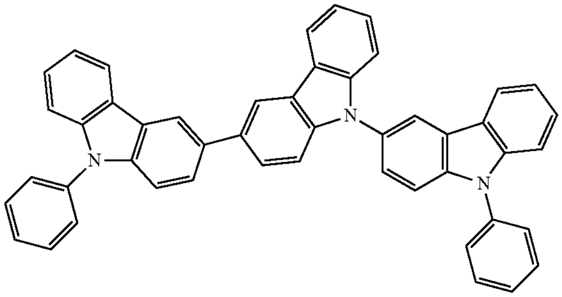

,

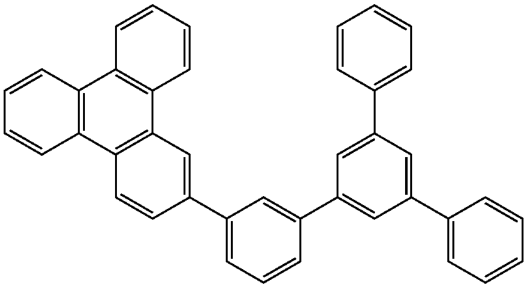

,

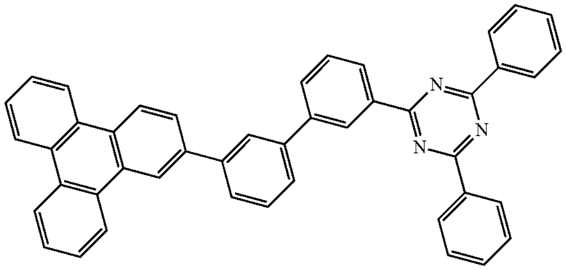

,

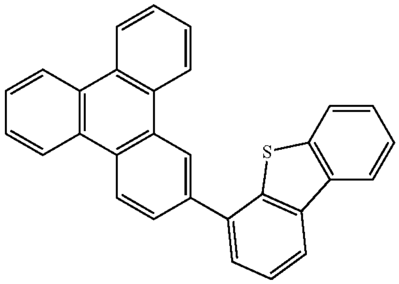

,

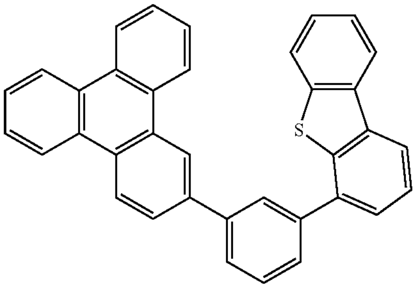

,

-continued

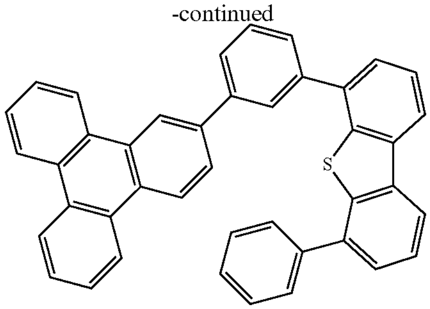

,

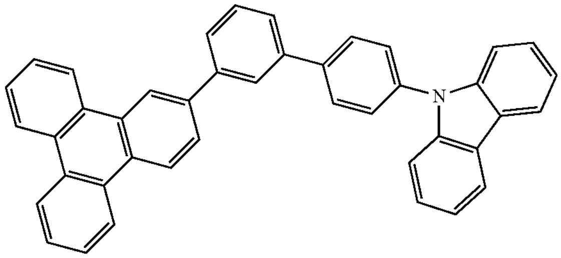

,

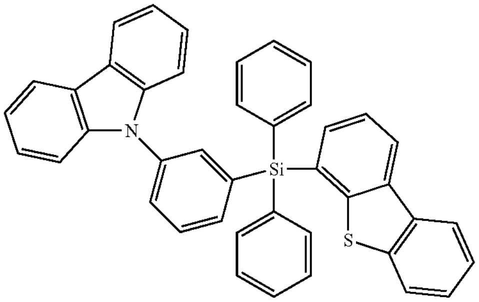

,

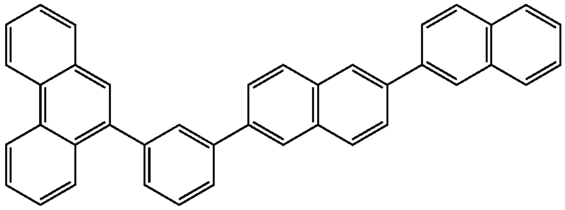

, and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

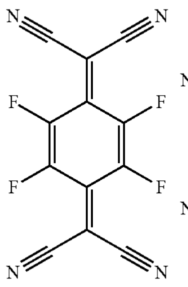

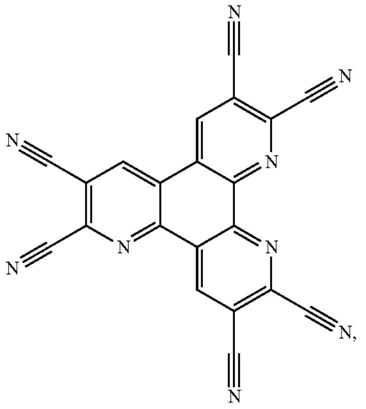

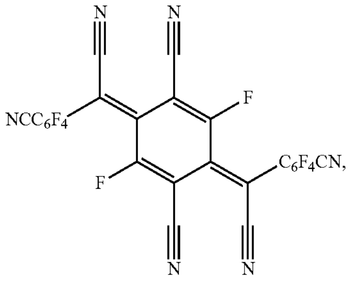

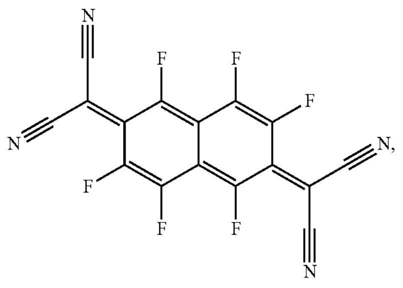

-continued

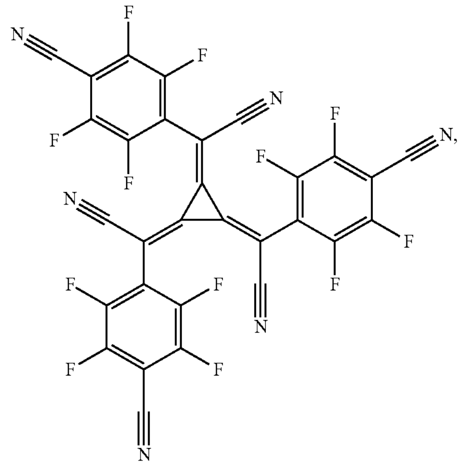

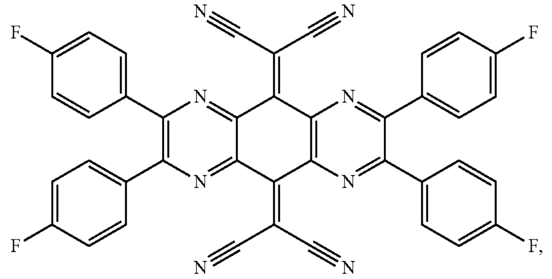

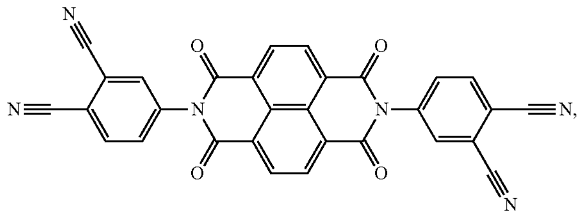

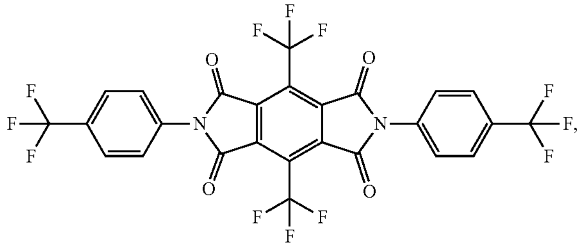

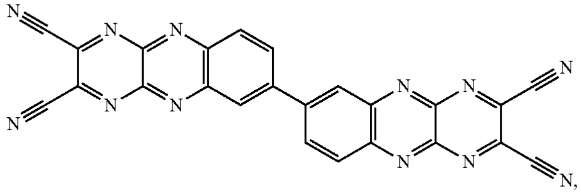

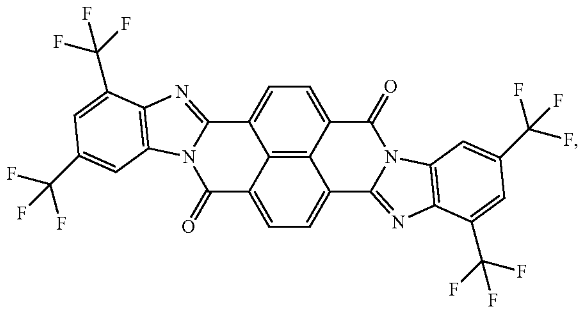

-continued

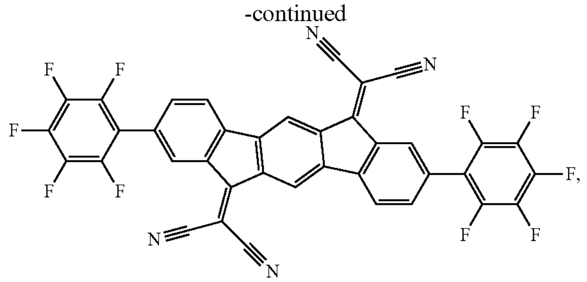

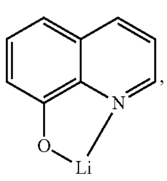

, and

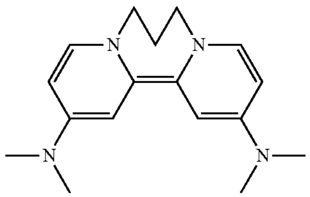

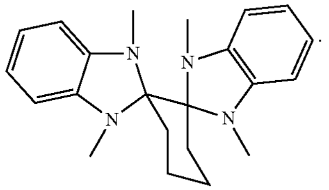

.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

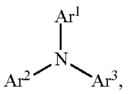

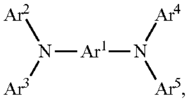

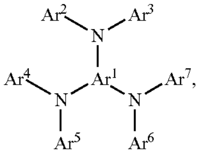

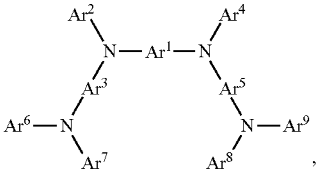

, and

-continued

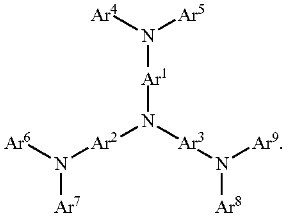

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

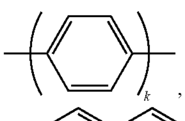

,

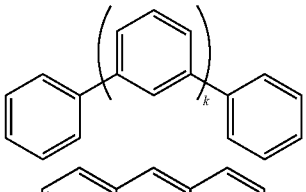

,

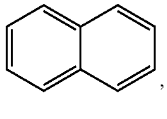

,

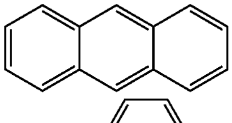

,

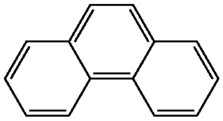

,

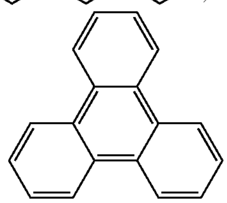

,

-continued

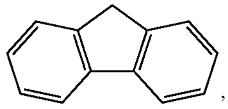
,
and
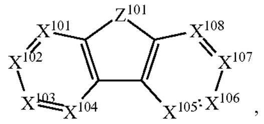
, wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

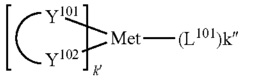

wherein Met is a metal, which can have an atomic weight greater than 40; ($Y^{101}$—$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$—$Y^{102}$) is a 2-phenylpyridine derivative. In another aspect, ($Y^{101}$—$Y^{102}$) is a carbene ligand. In another aspect, Met is selected from Ir, Pt, Os, and Zn. In a further aspect, the metal complex has a smallest oxidation potential in solution vs. Fe/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, US06517957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

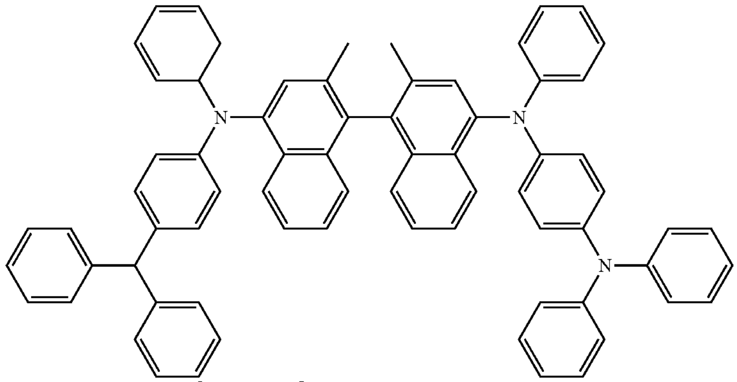
,

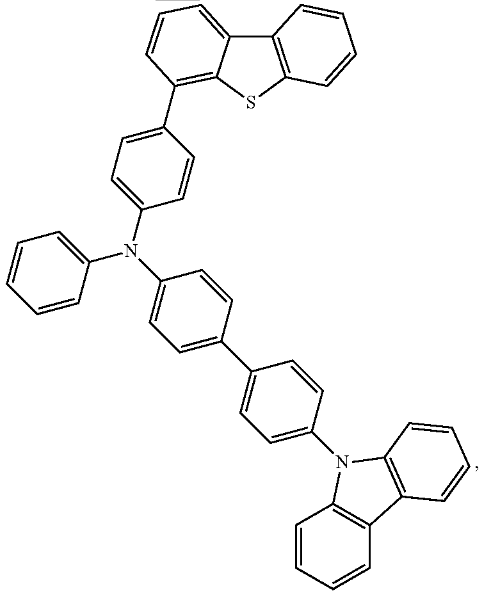
,

-continued
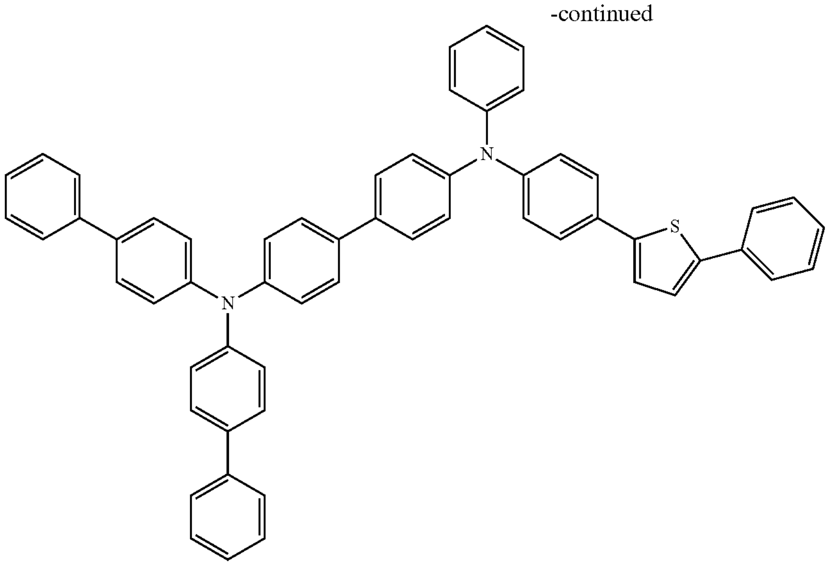
,
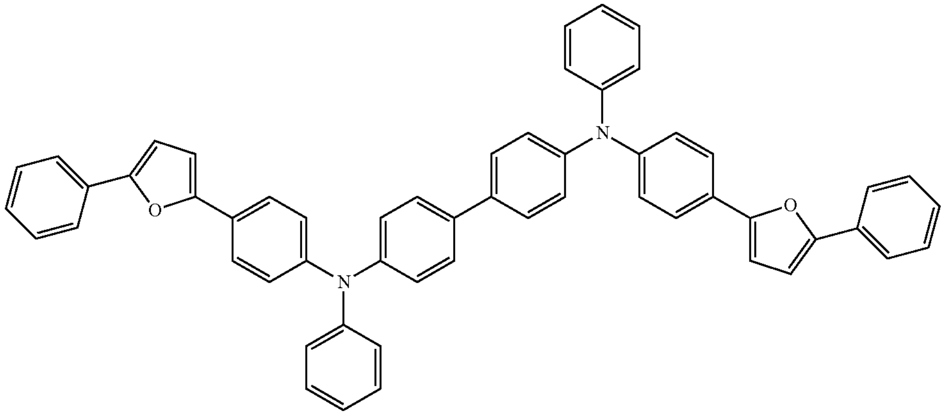
,
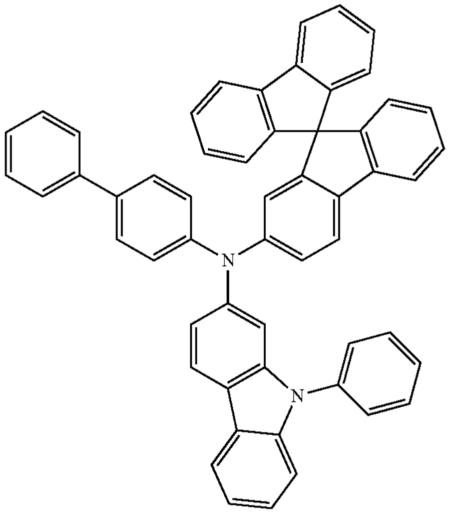
,
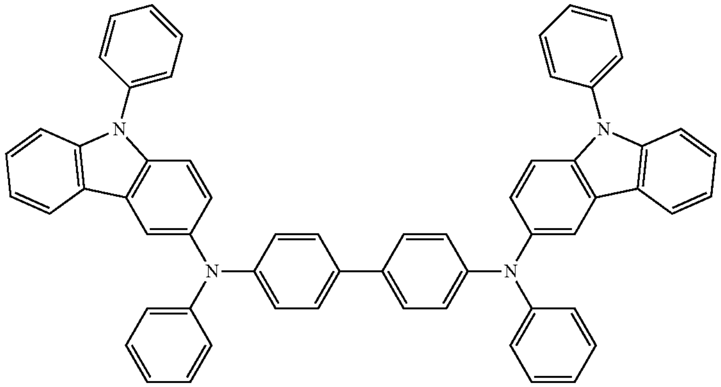

-continued
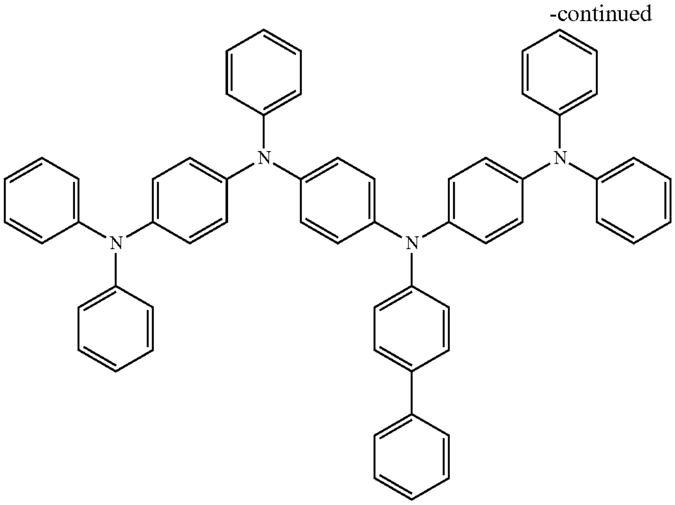
,
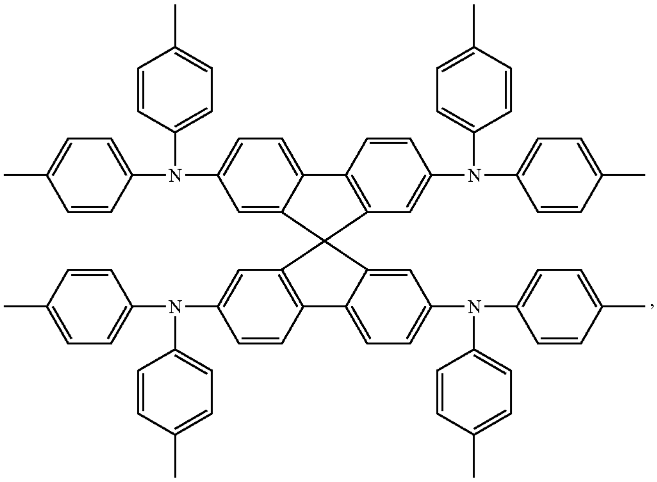
,
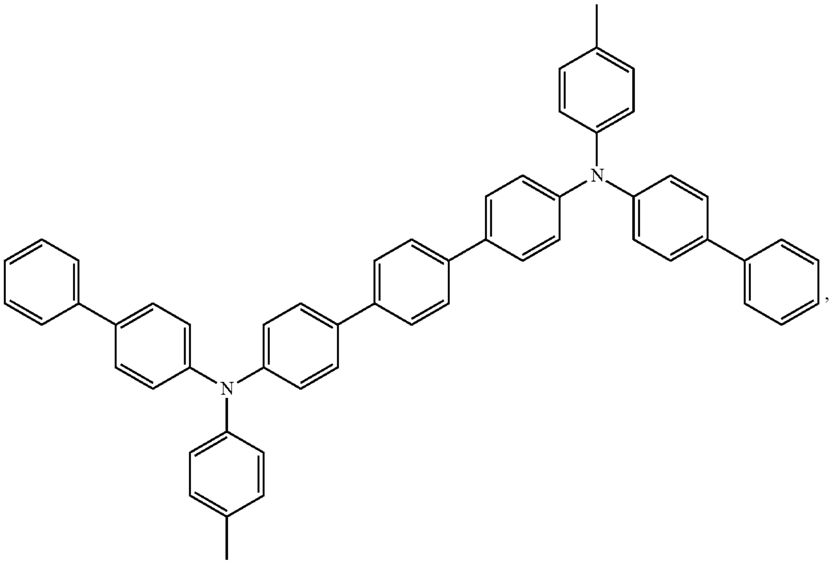
,

-continued
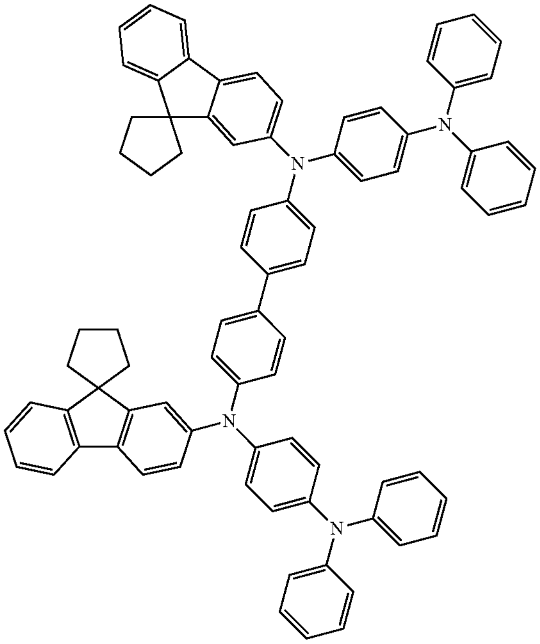
,
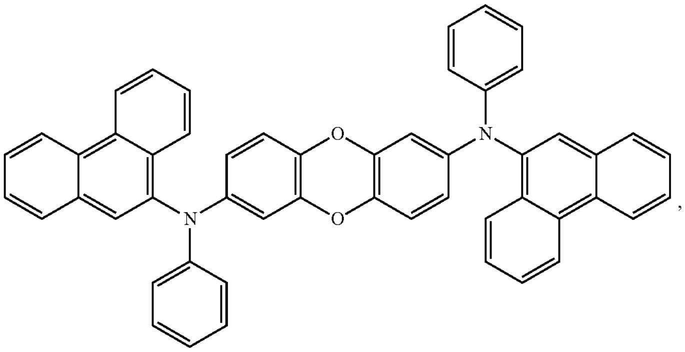
,
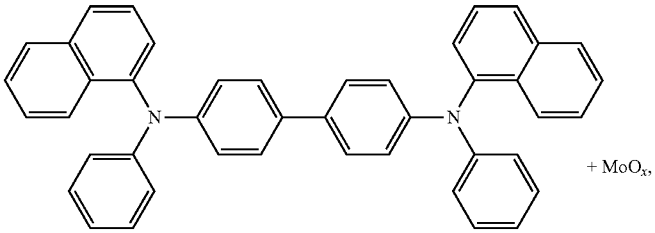
+ $MoO_x$,
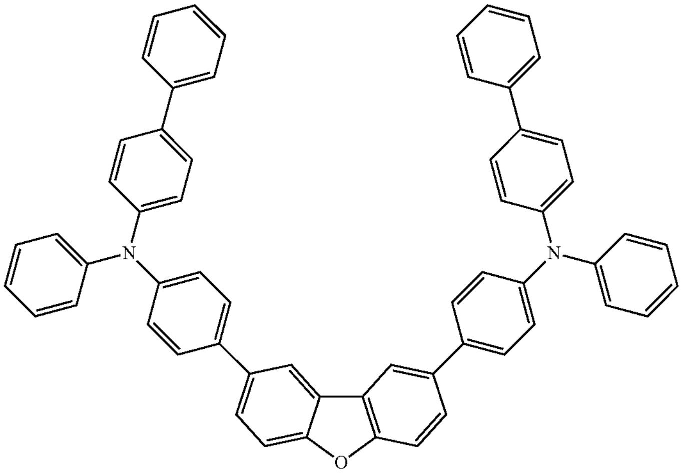
,
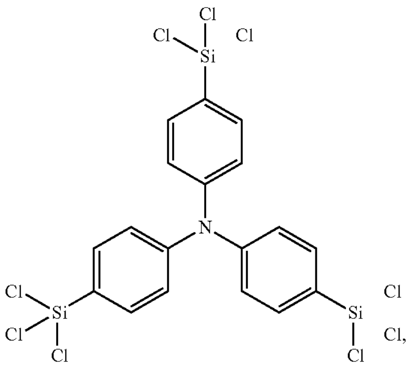
, -continued
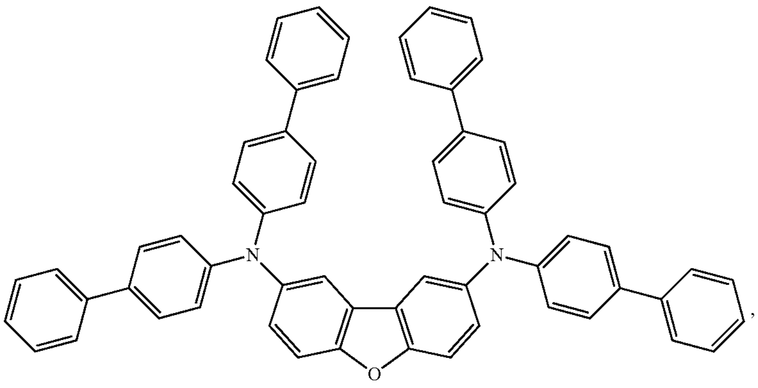
,
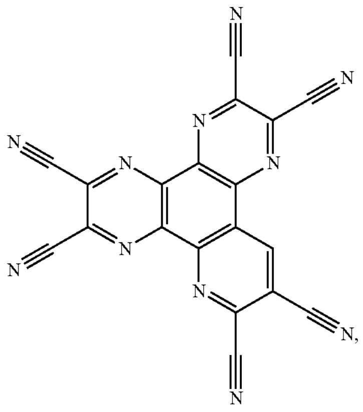
,
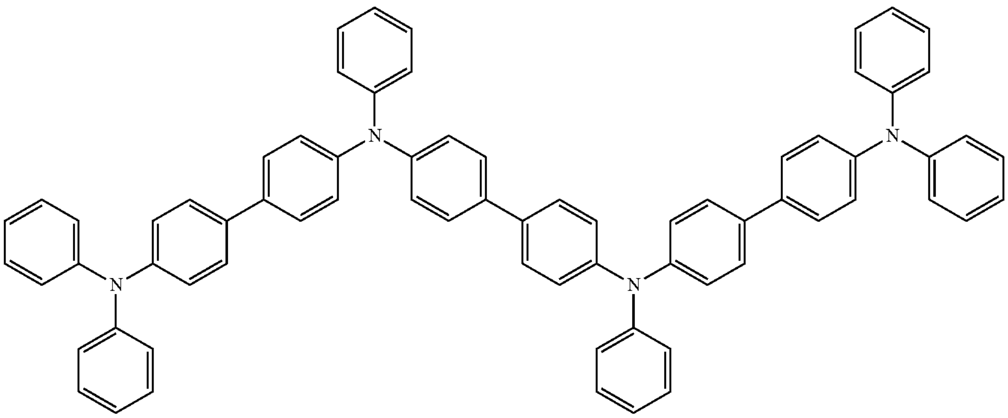
,
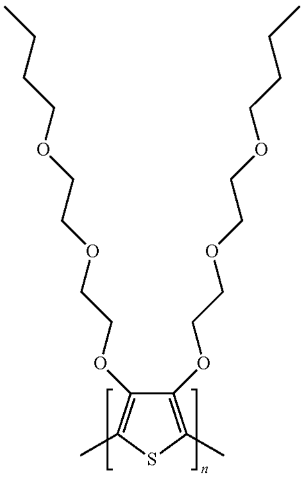
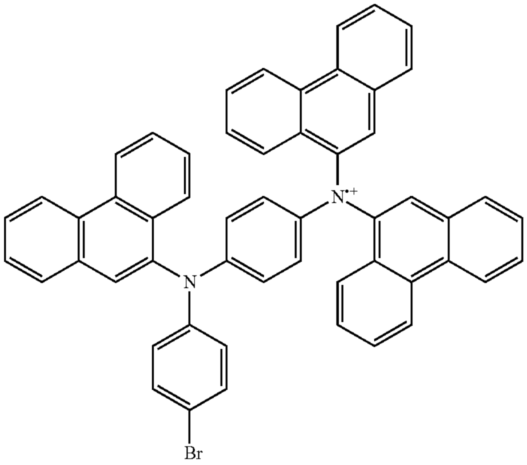

-continued
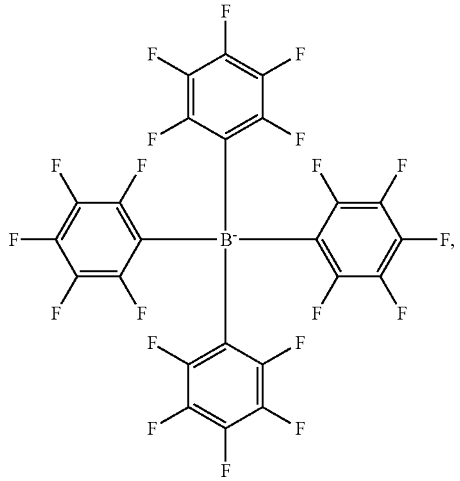
,
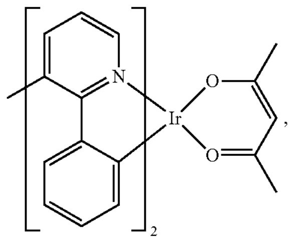
,
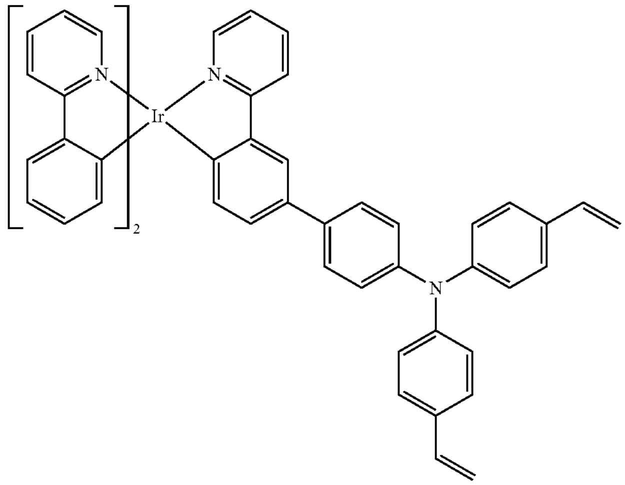
,
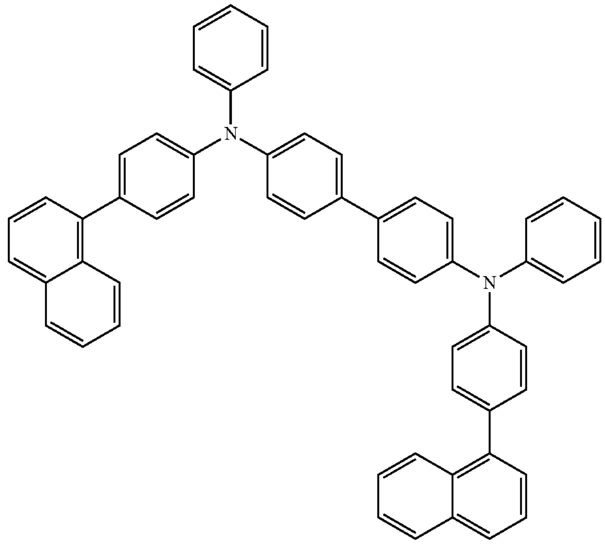
,

-continued
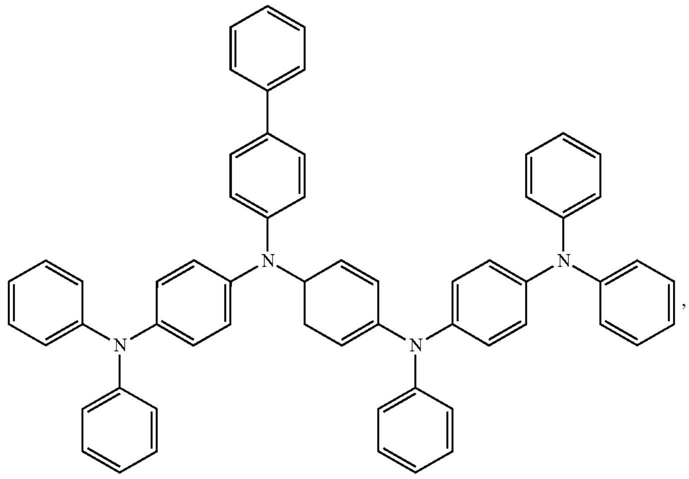
,
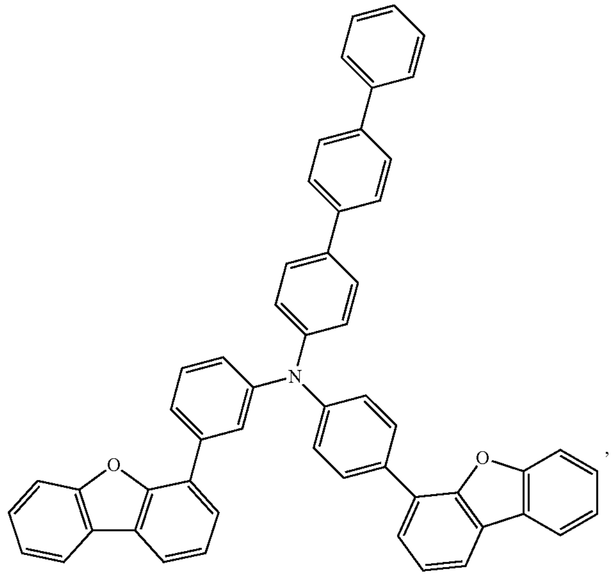
,
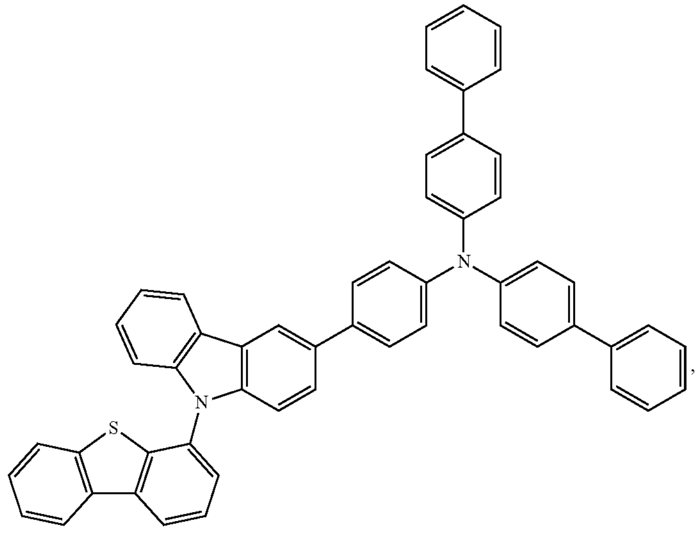
,

-continued
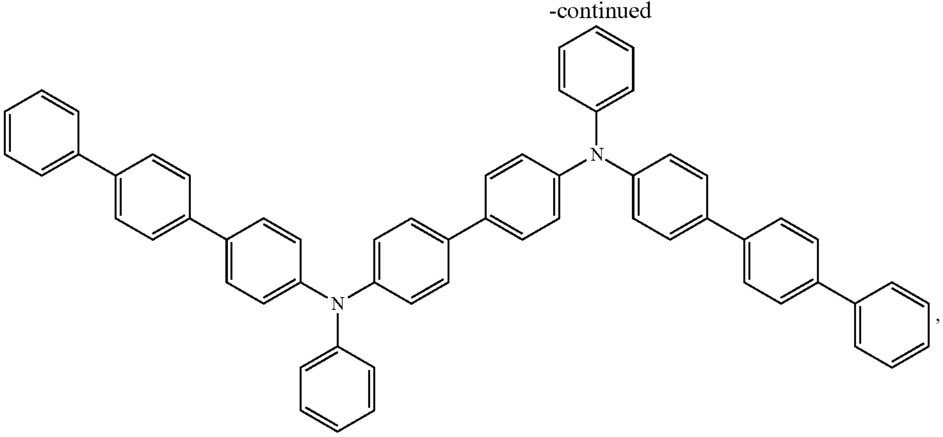
,
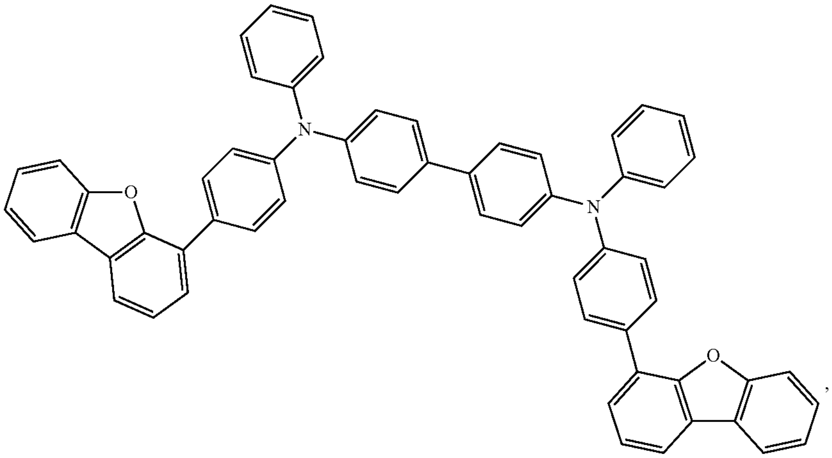
,
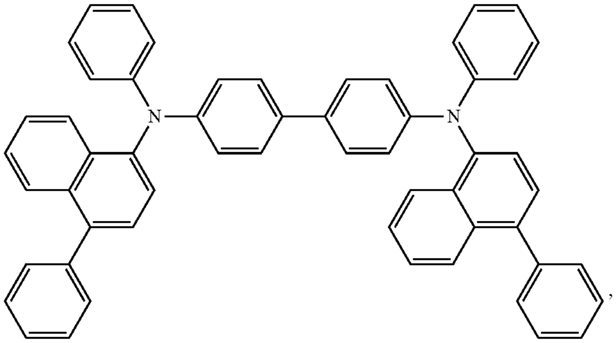
,

-continued
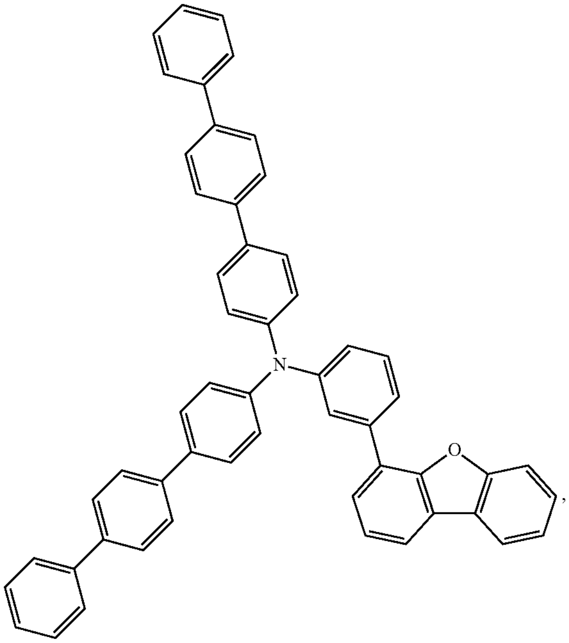
,
,
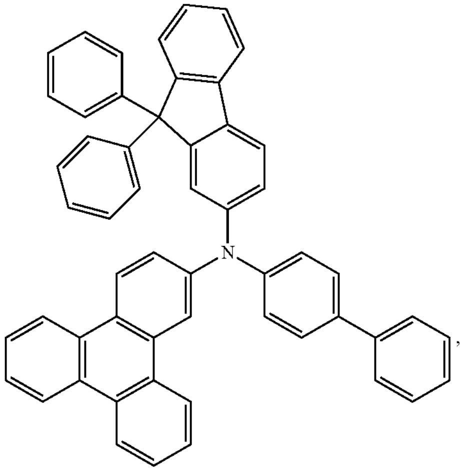
,
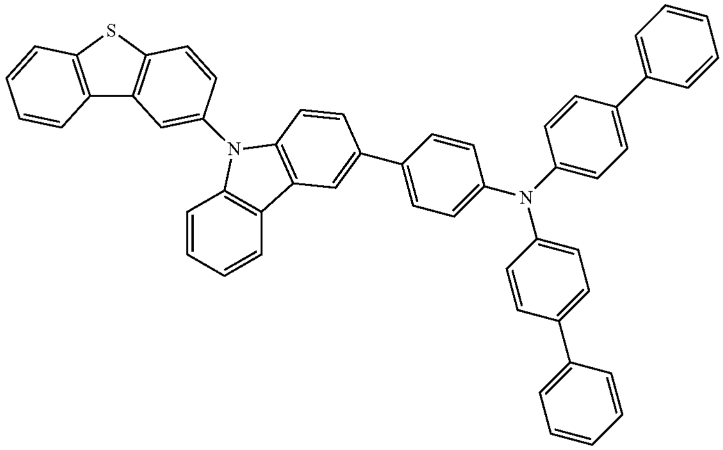
,
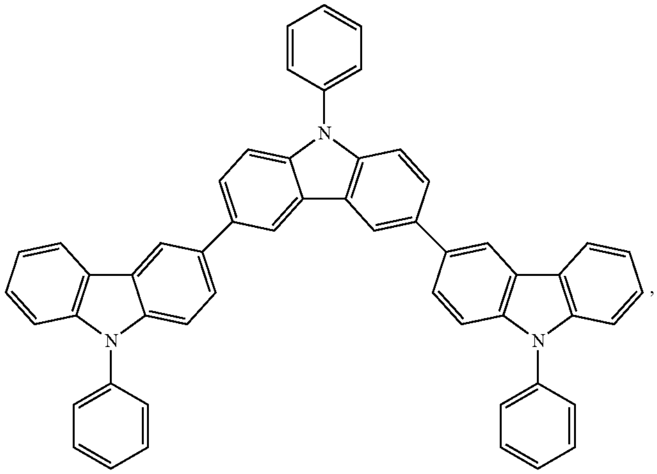
,
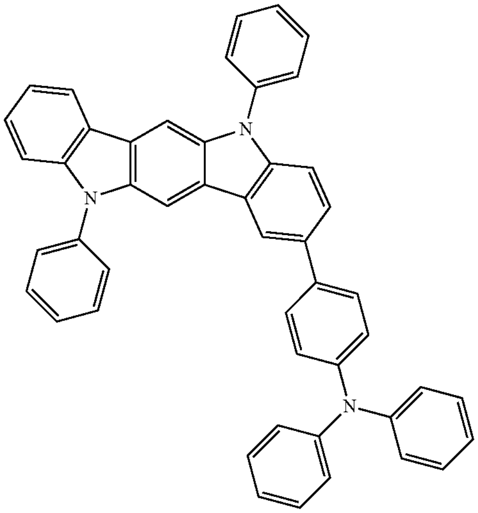
, -continued
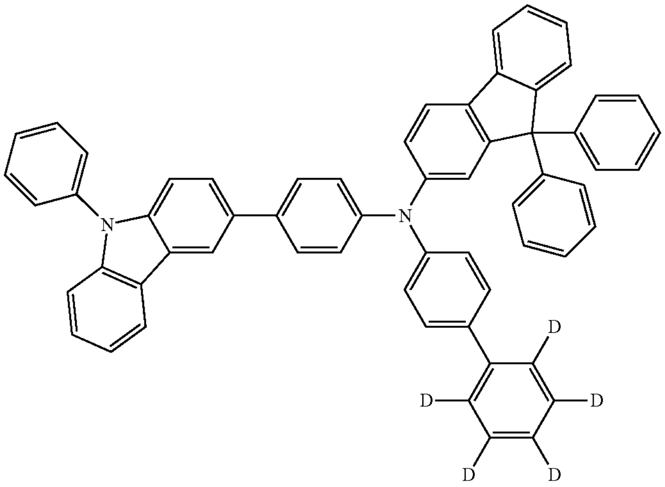
,
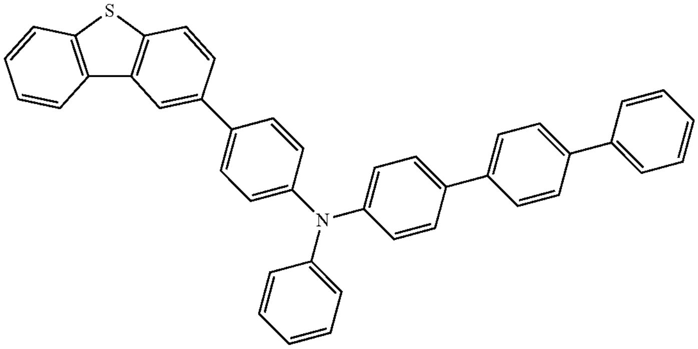
,
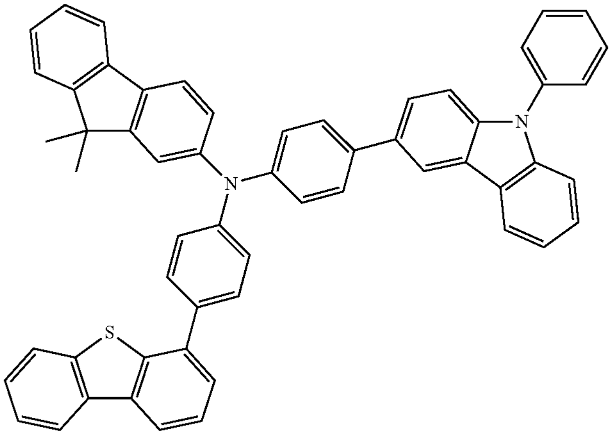
,
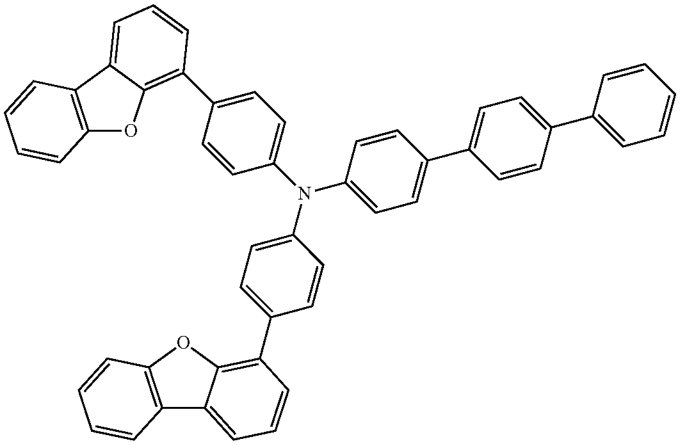
, -continued
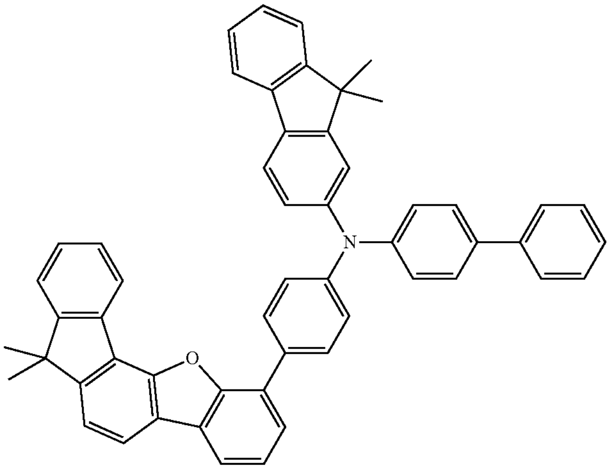
,
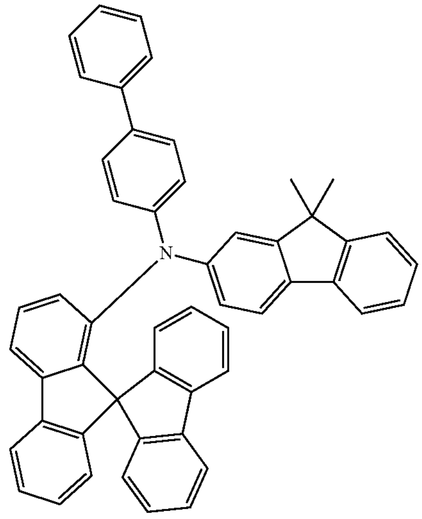
,
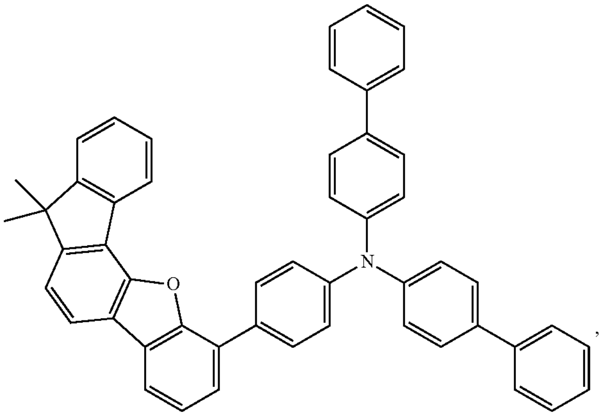
,
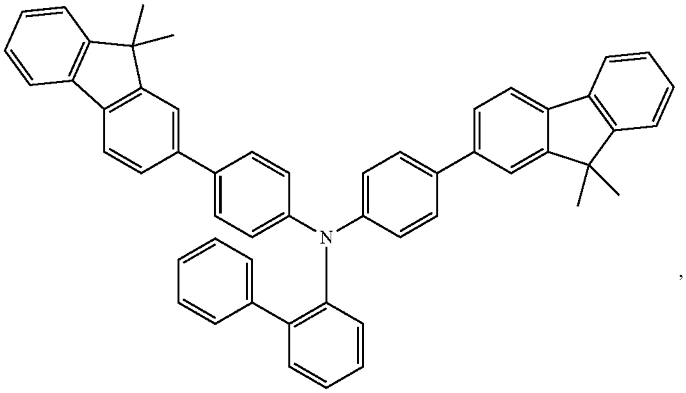
, -continued
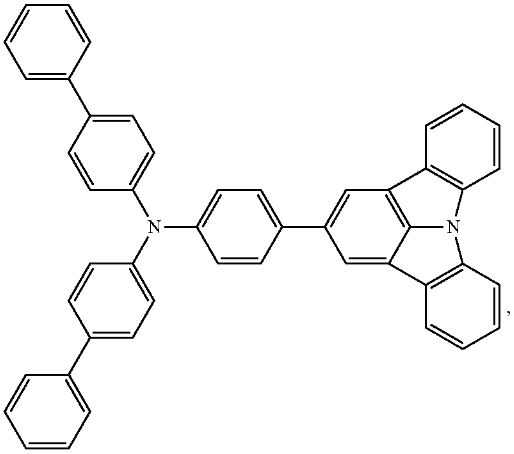,
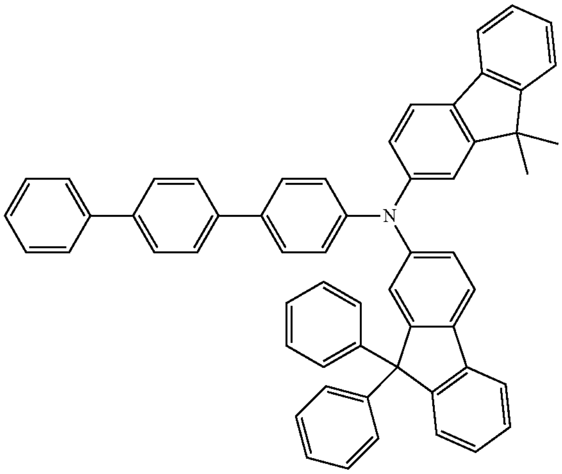,
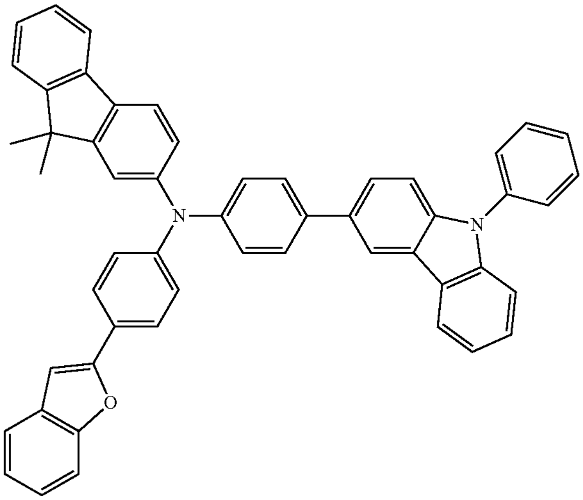,
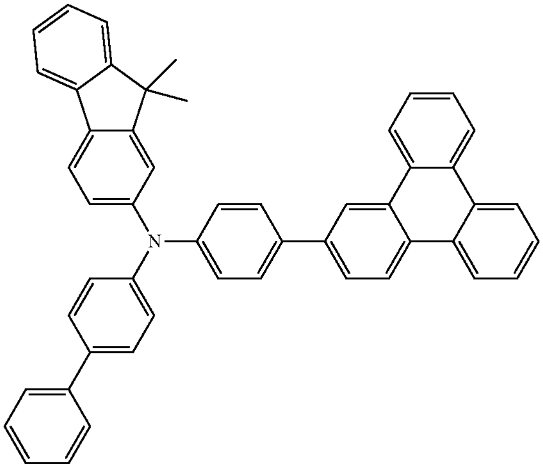,
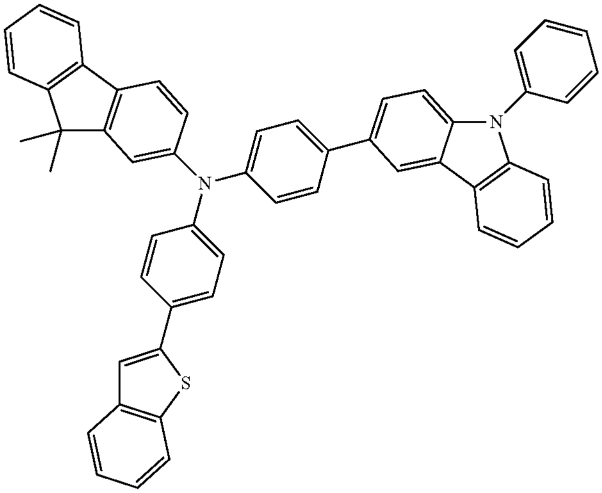, -continued
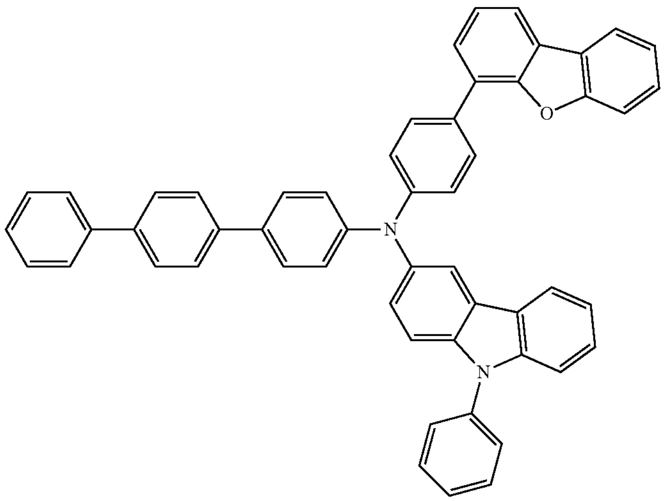
,
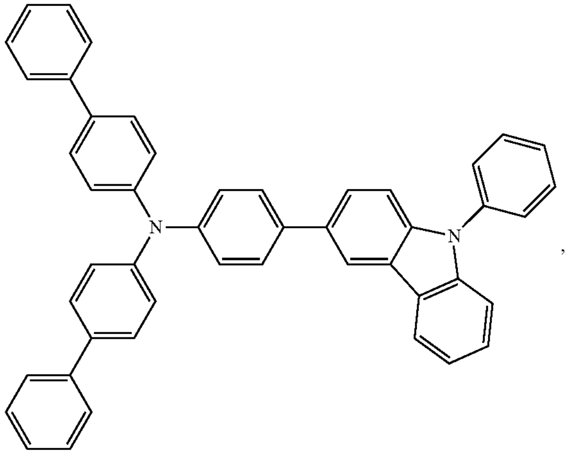
,
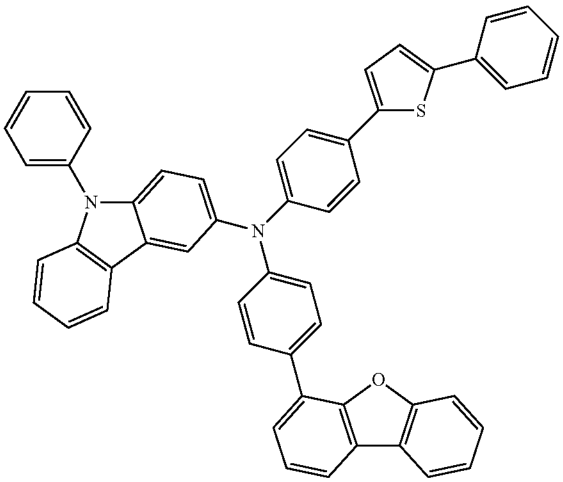
,
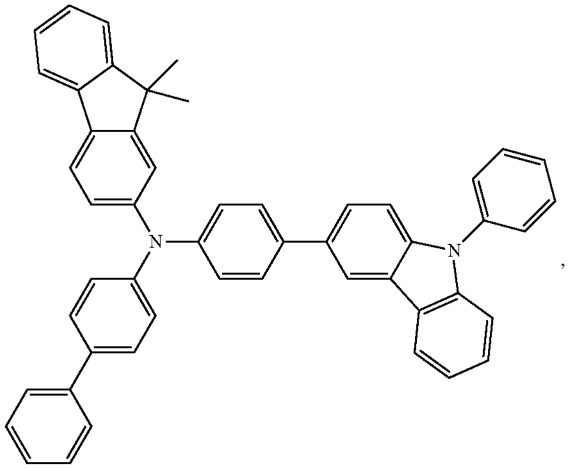
,
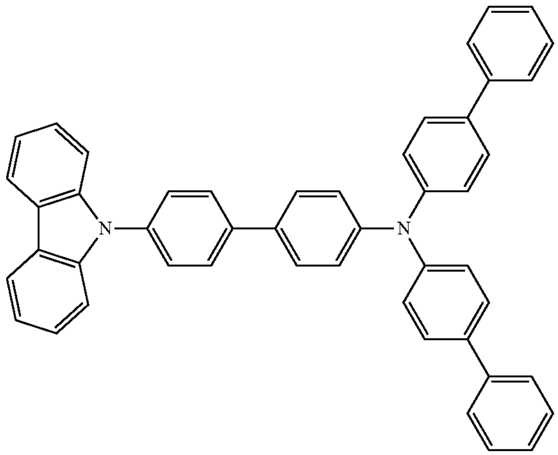
, -continued
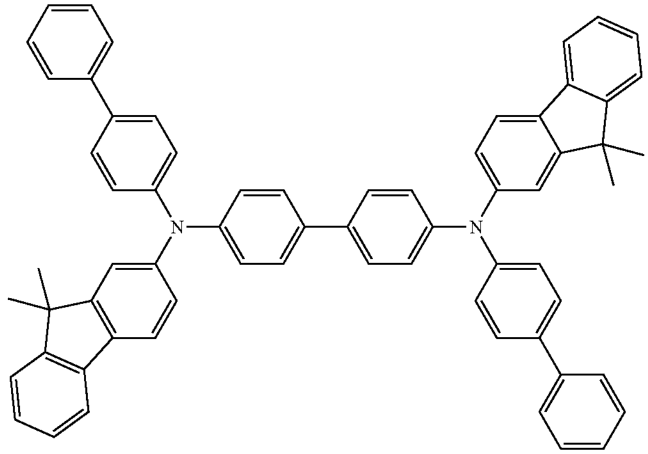
,
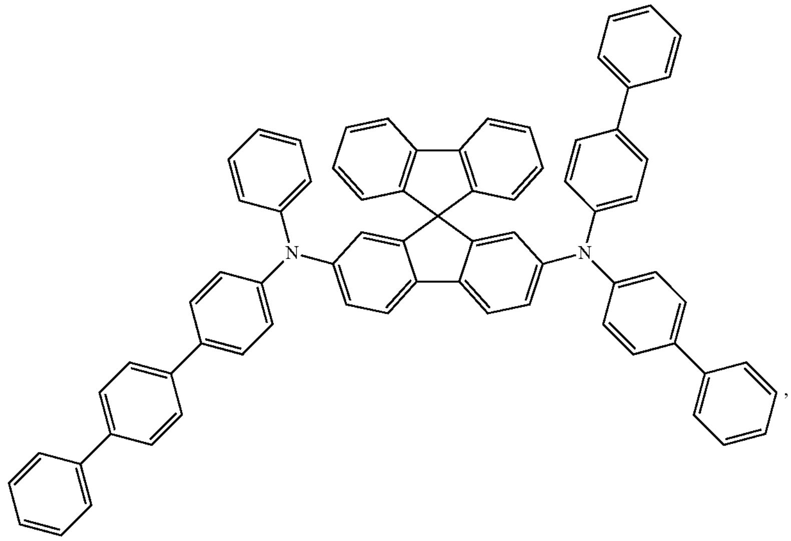
,
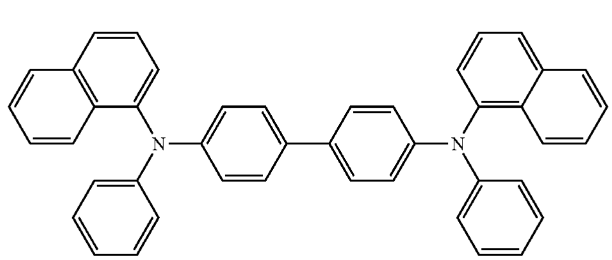
,
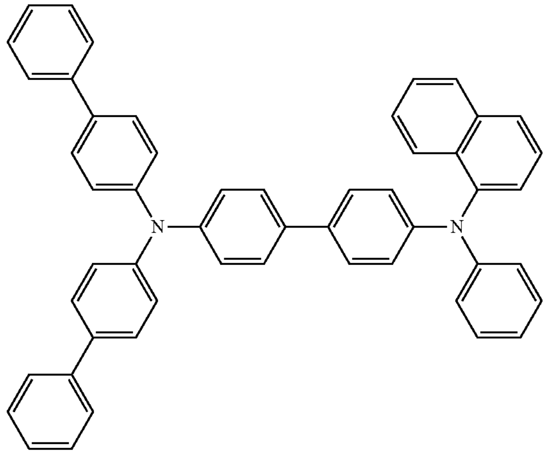
, -continued
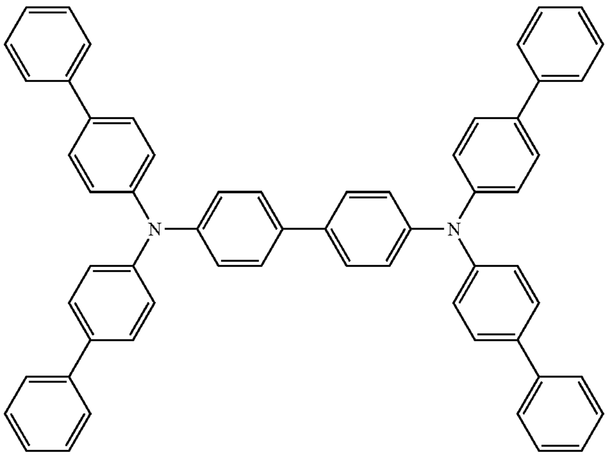
,
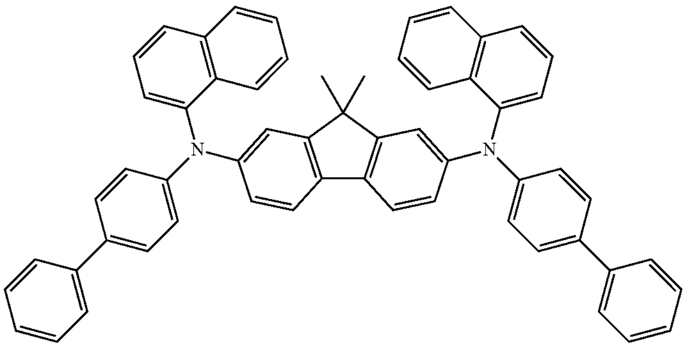
,
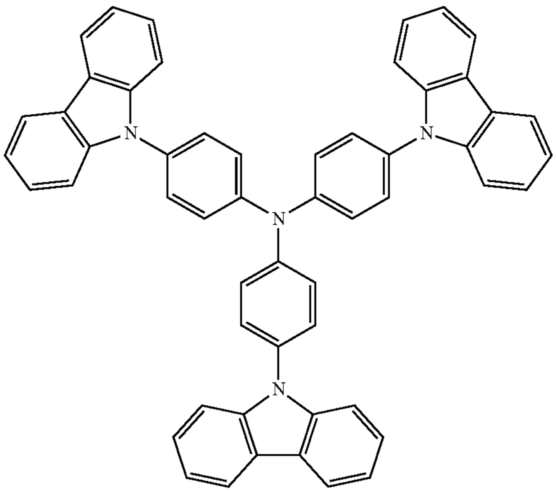
,
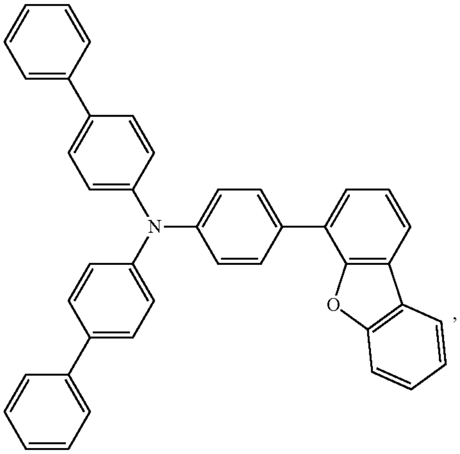
,
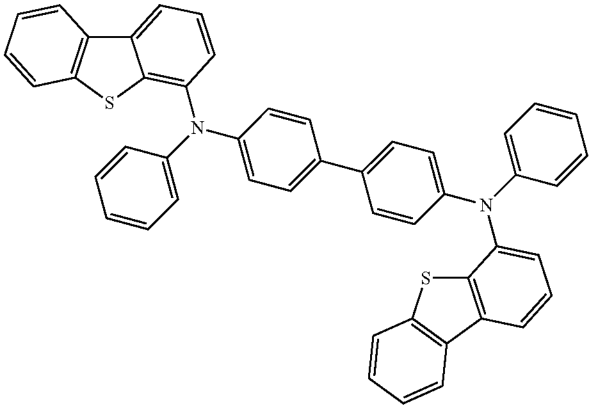
, -continued

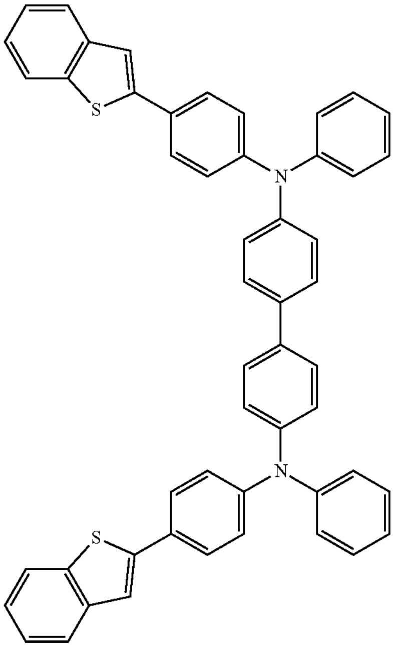

, and

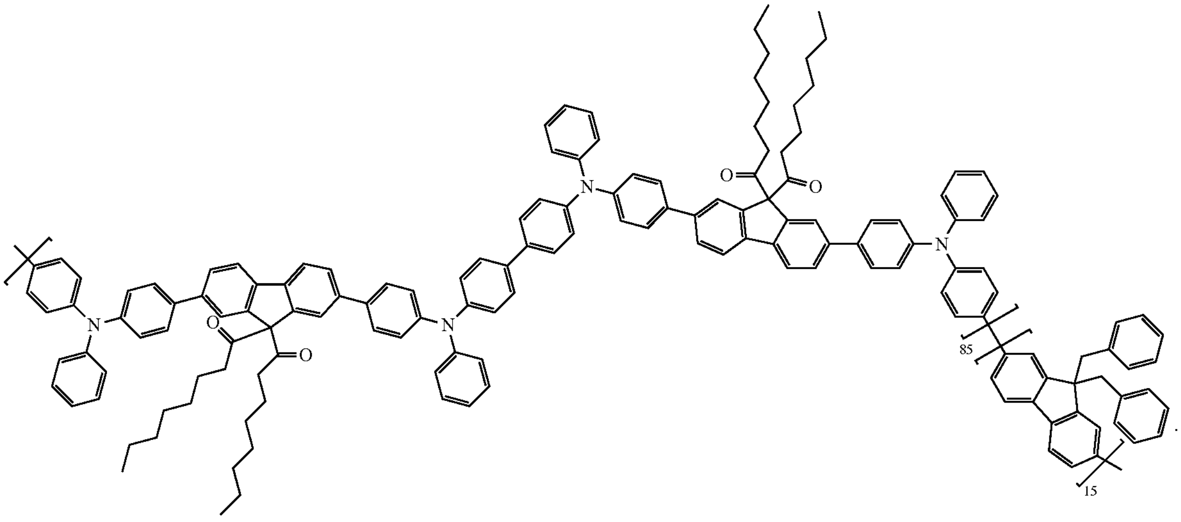

.

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

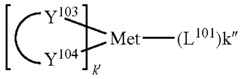

wherein Met is a metal; ($Y^{103}$—$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

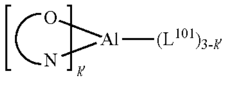
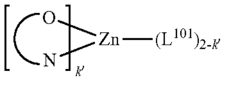

wherein (O—N) is a bidentate ligand, having metal coordinated to atoms O and N.

In another aspect, Met is selected from Ir and Pt. In a further aspect, ($Y^{103}$—$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

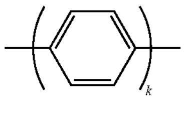,
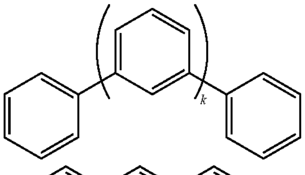,
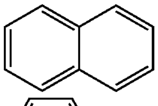,
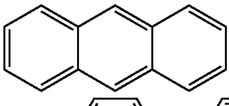,
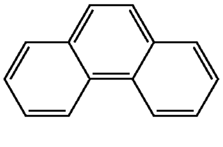,
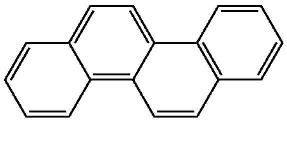,

-continued

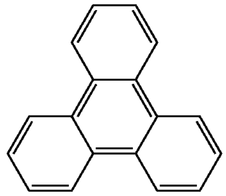,
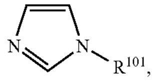
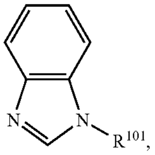
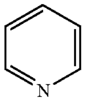,
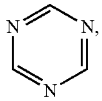
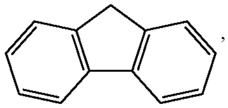,
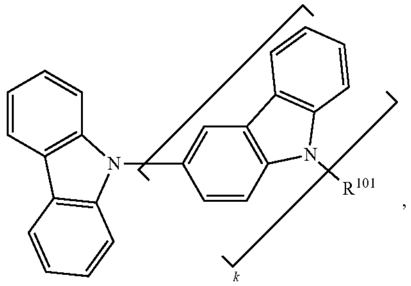,
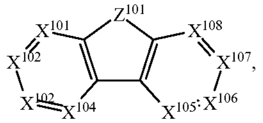
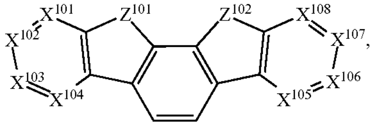
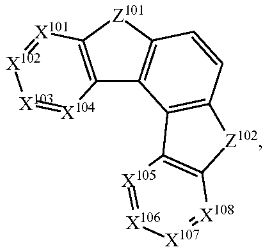
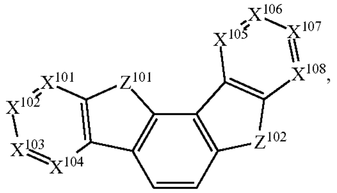
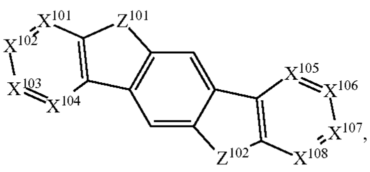
and
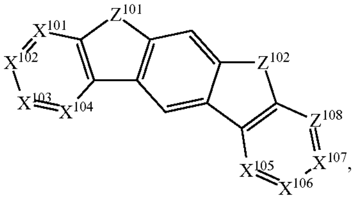

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, US7154114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

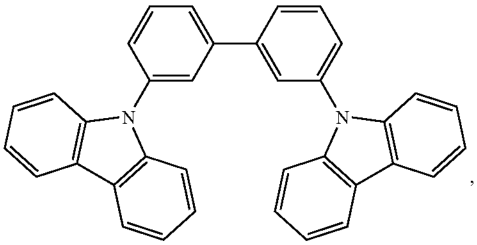
,
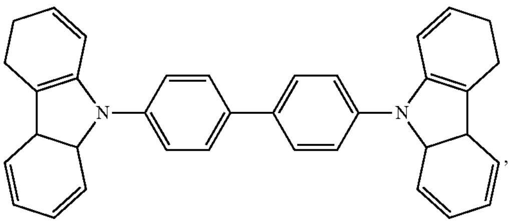
,
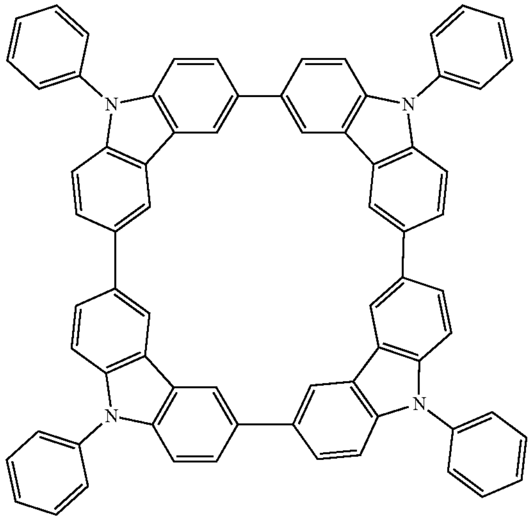
,
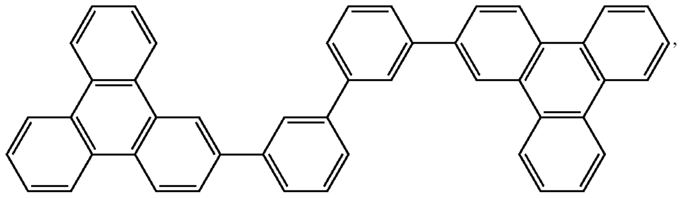
,
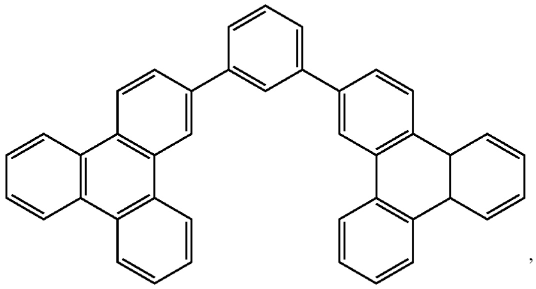
,
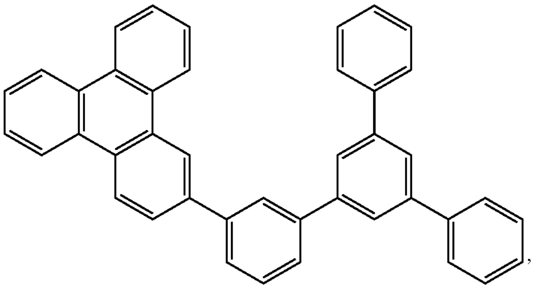
, -continued
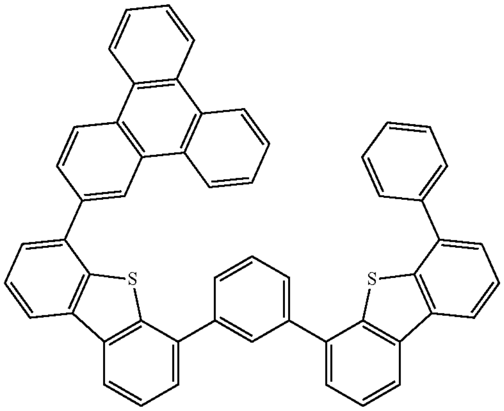,
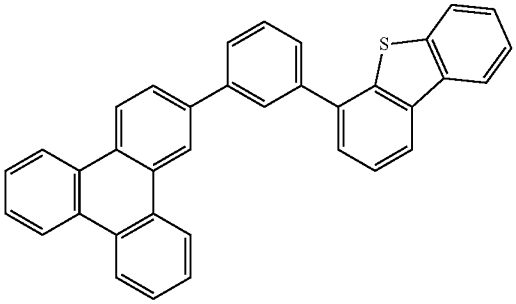,
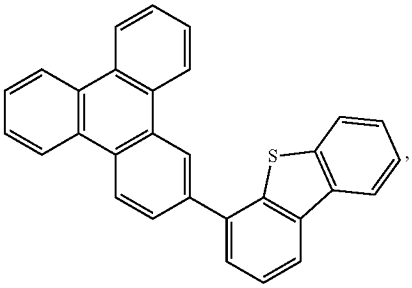,
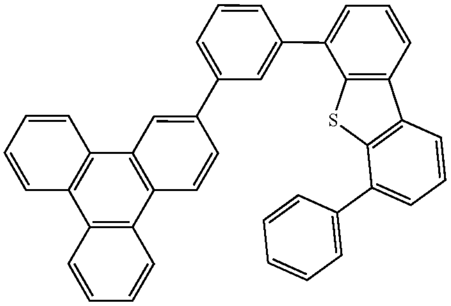,
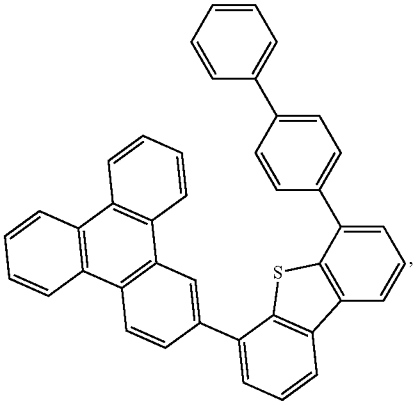,
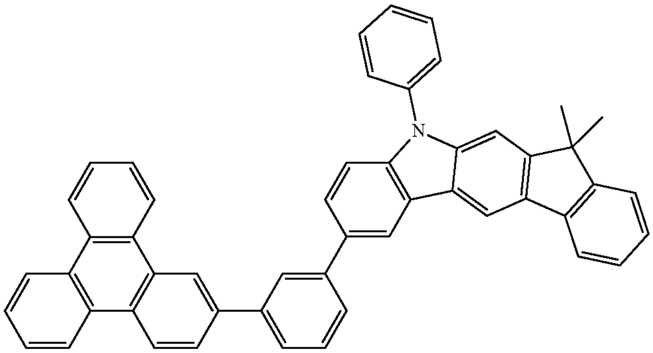,
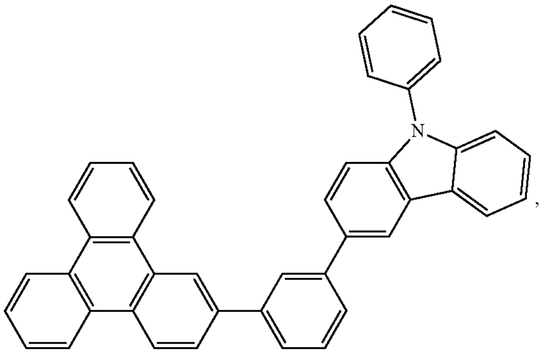,
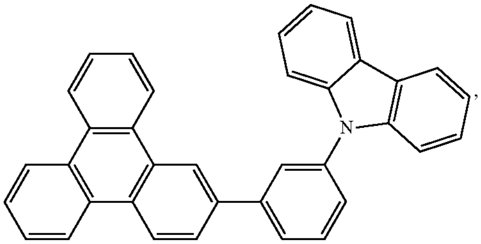, -continued
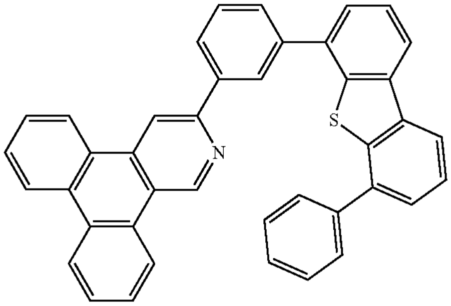
,
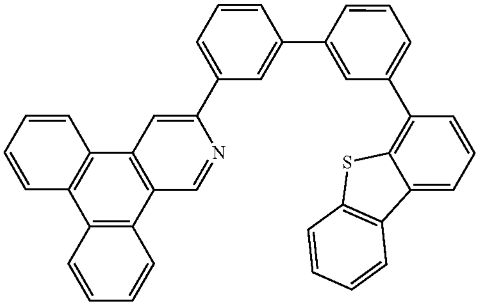
,
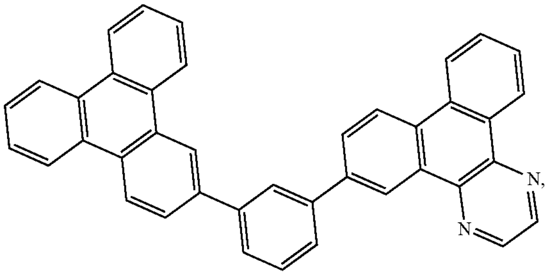
,
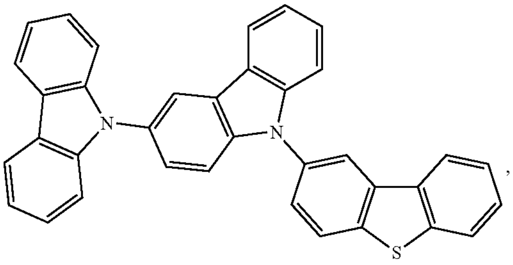
,
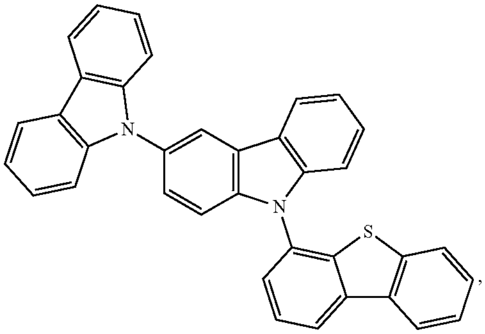
,
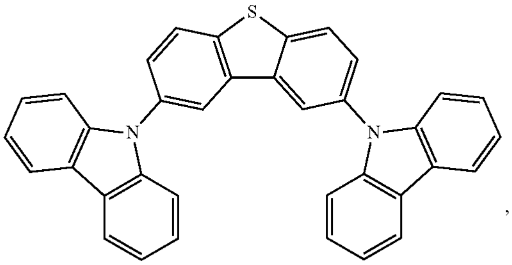
,
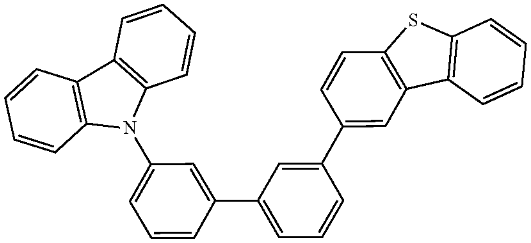
,
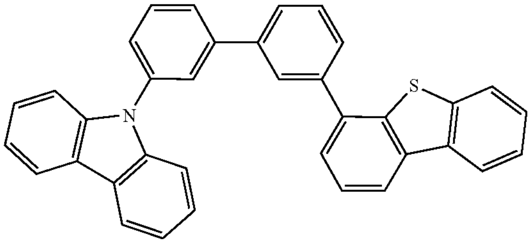
,
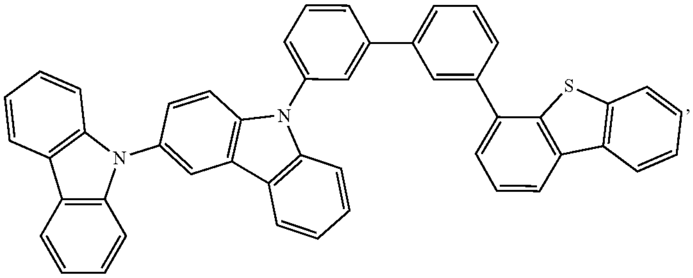
,
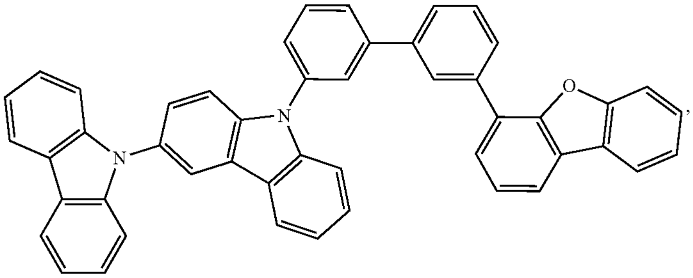
, -continued
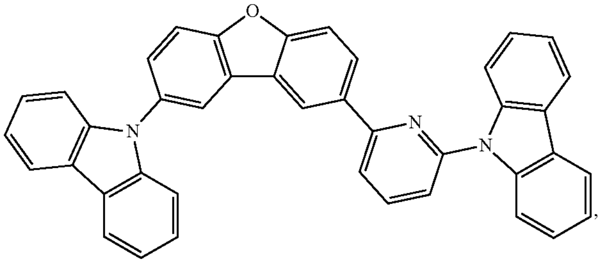
,
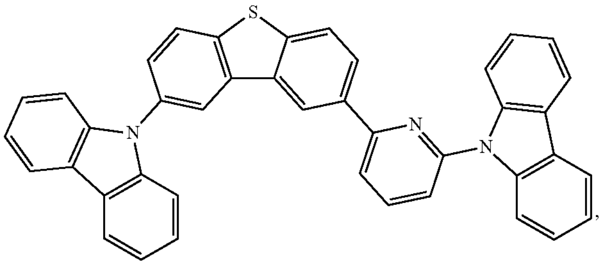
,
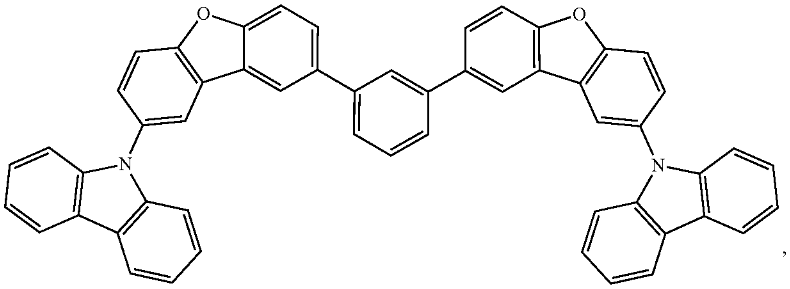
,
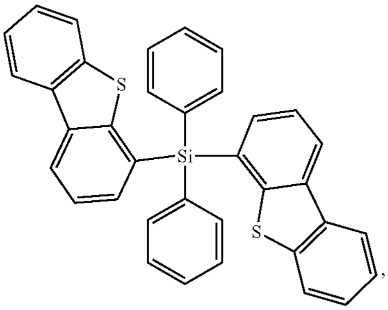
,
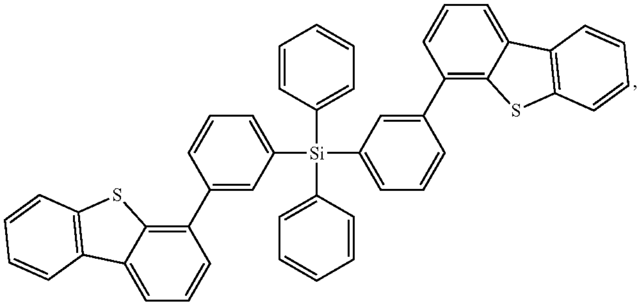
,
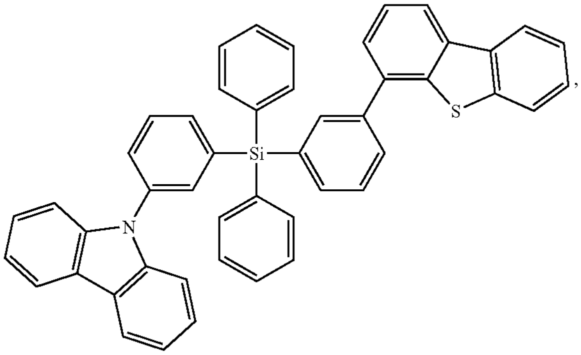
, -continued
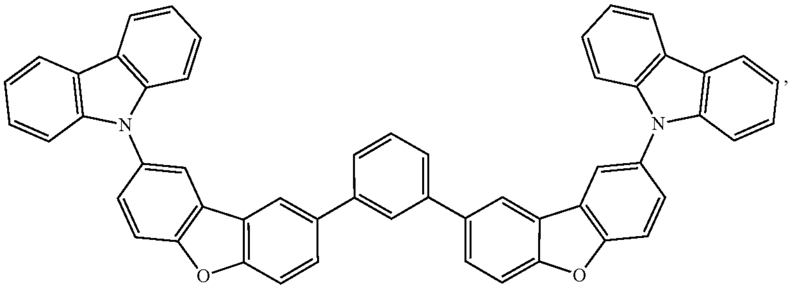
,
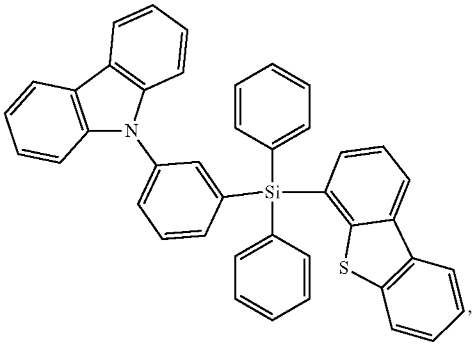
,
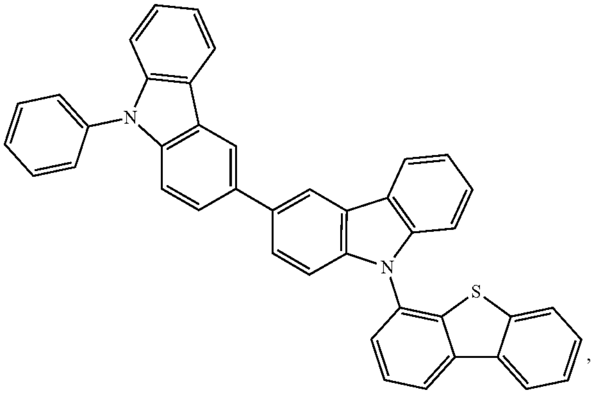
,
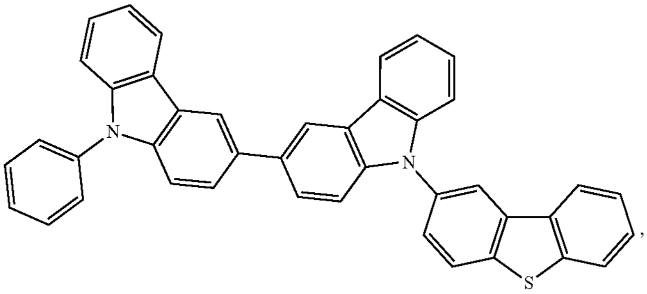
,
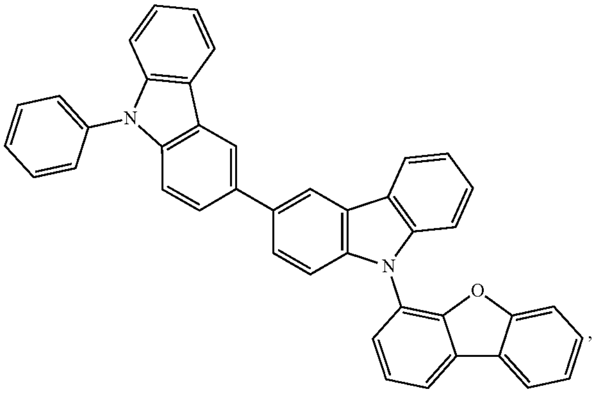
, -continued
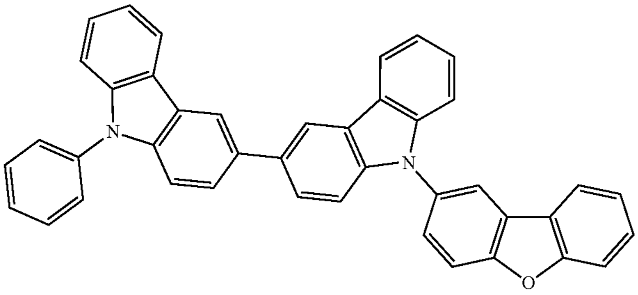
,
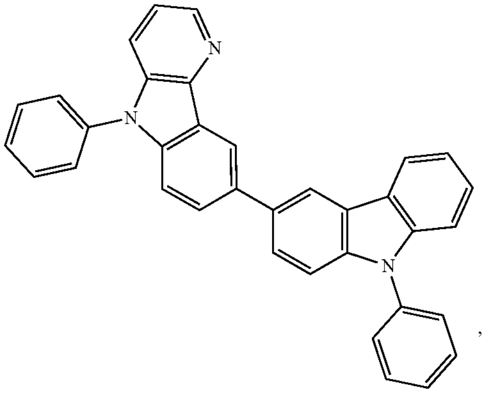
,
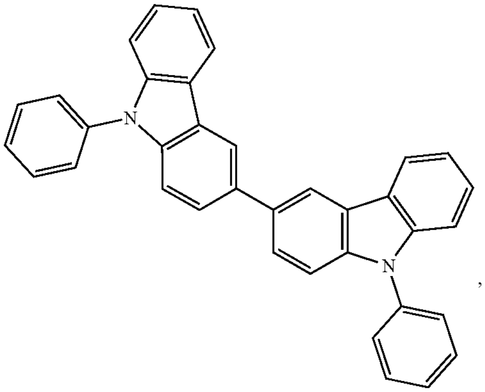
,
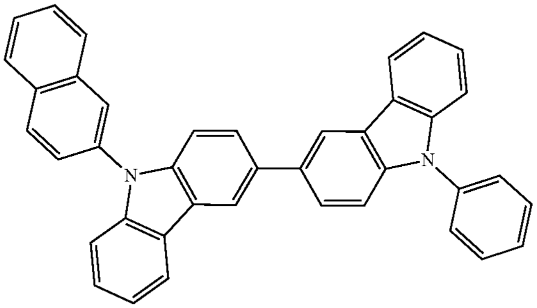
,
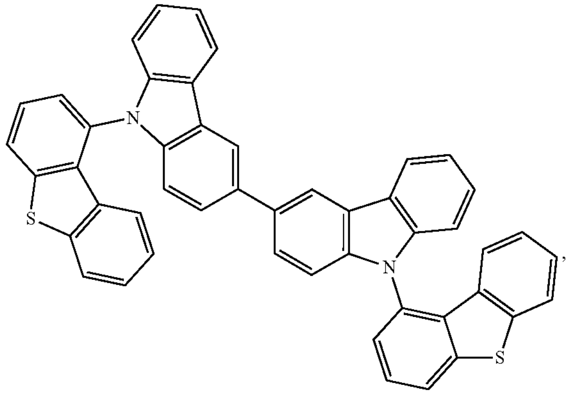
,
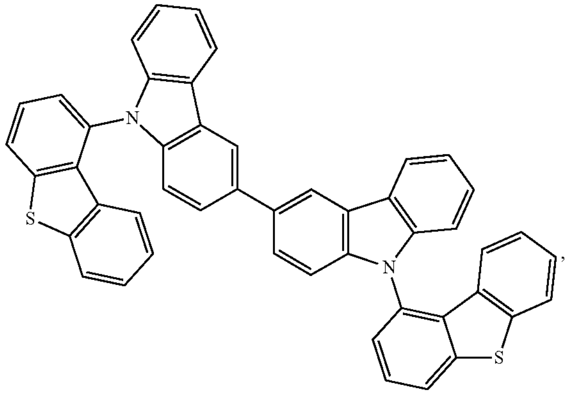
,
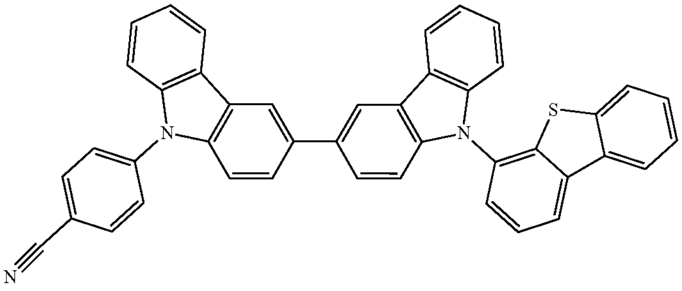
, -continued
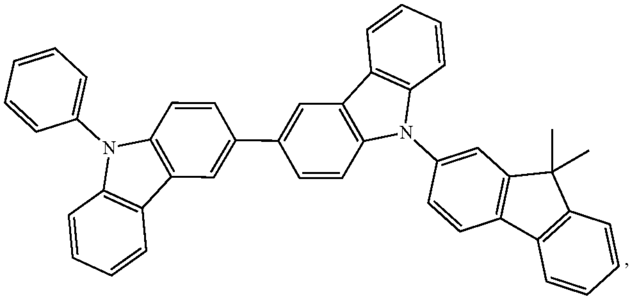
,
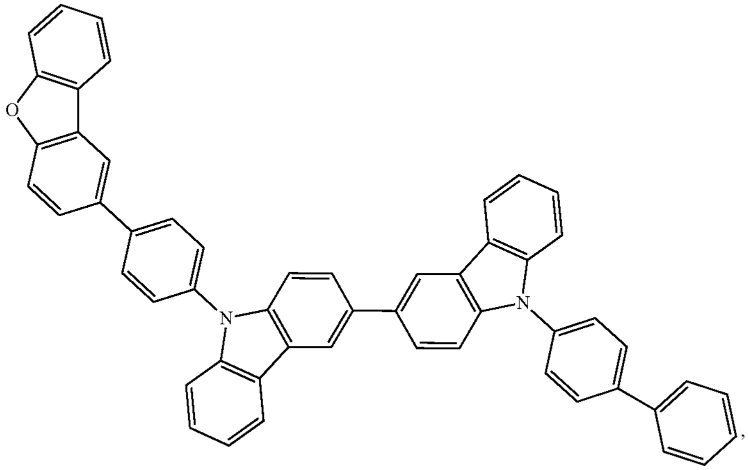
,
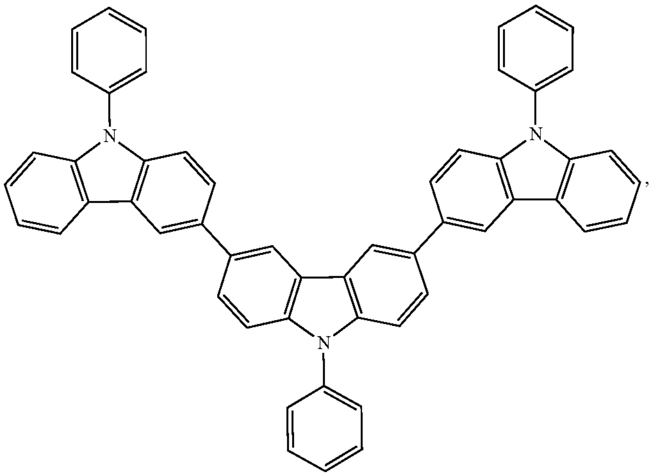
,
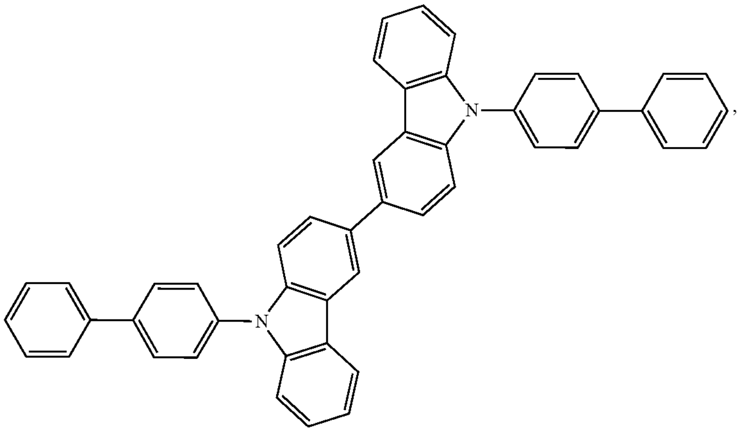
, -continued
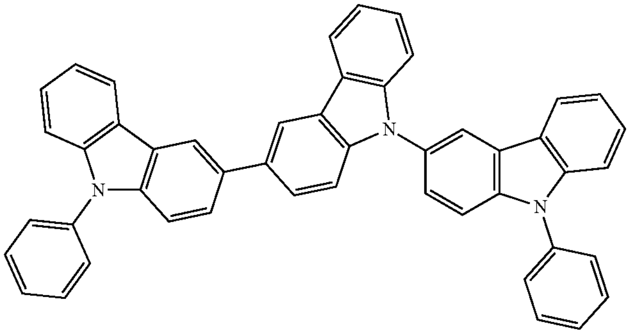
,
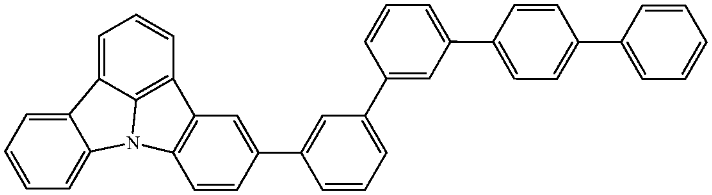
,
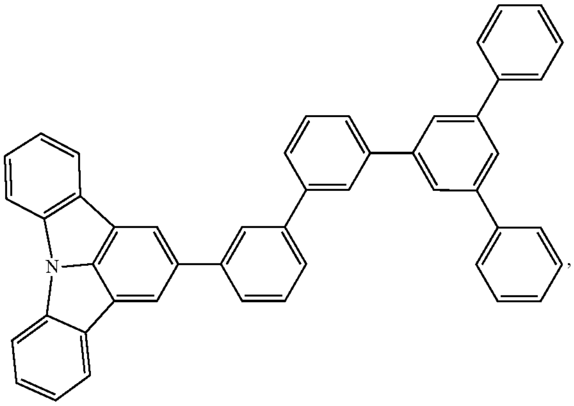
,
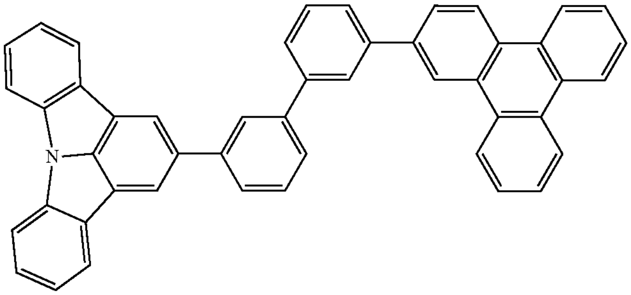
,
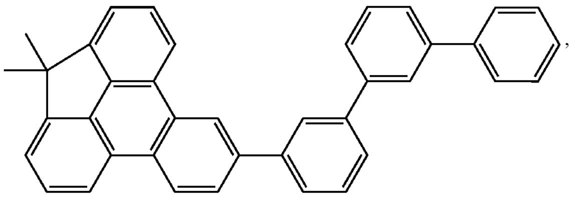
,
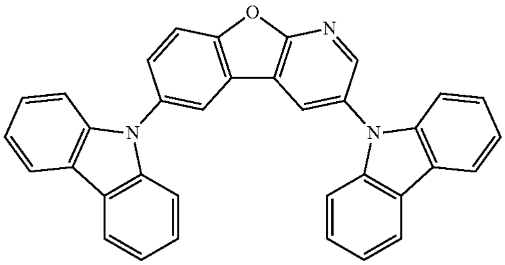
, -continued
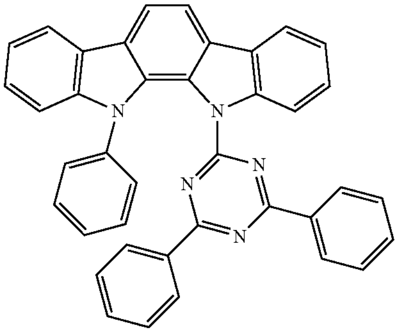
,
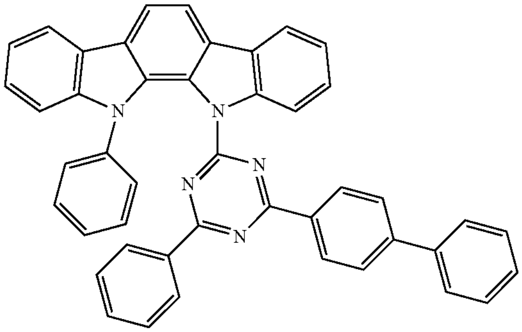
,
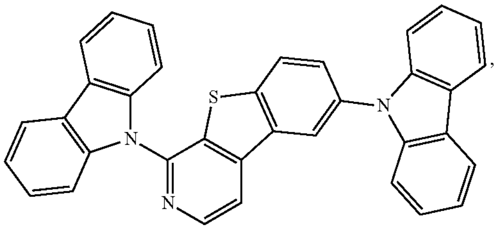
,
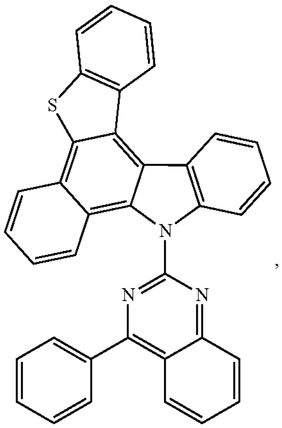
,
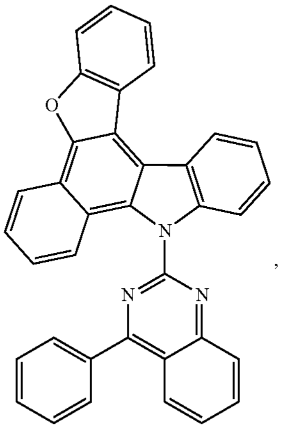
,
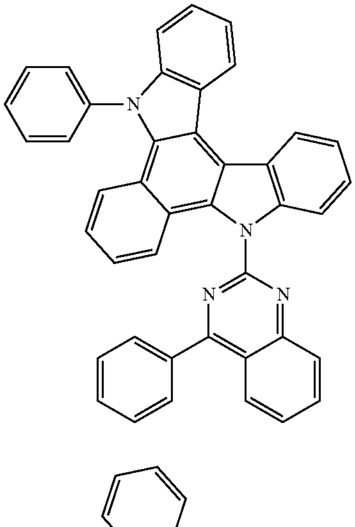
,
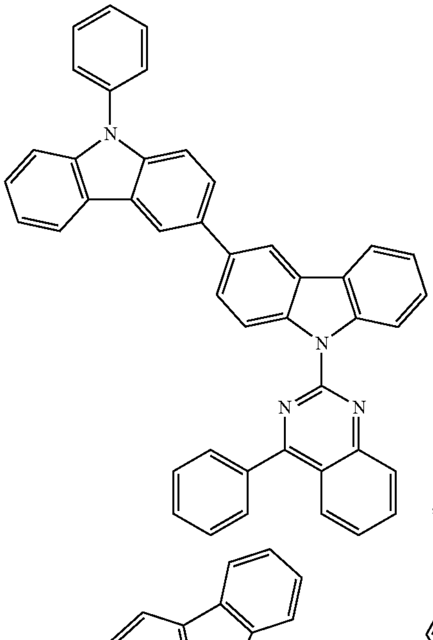
,
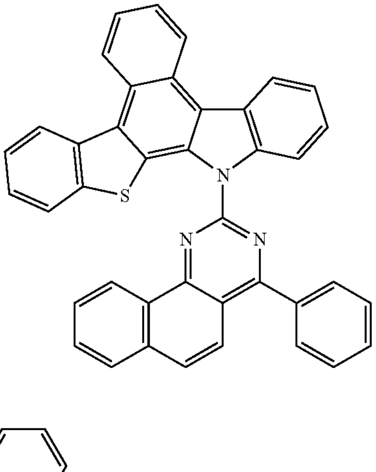
,
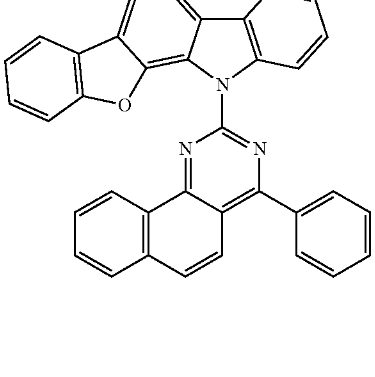
,
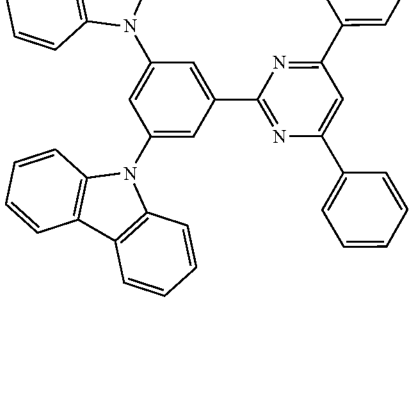
, -continued
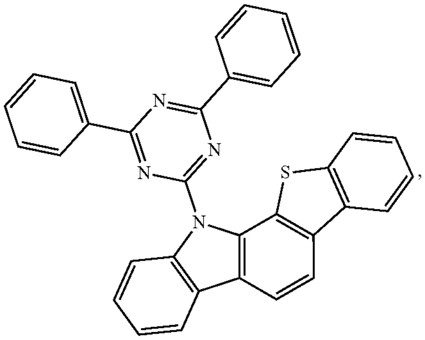,
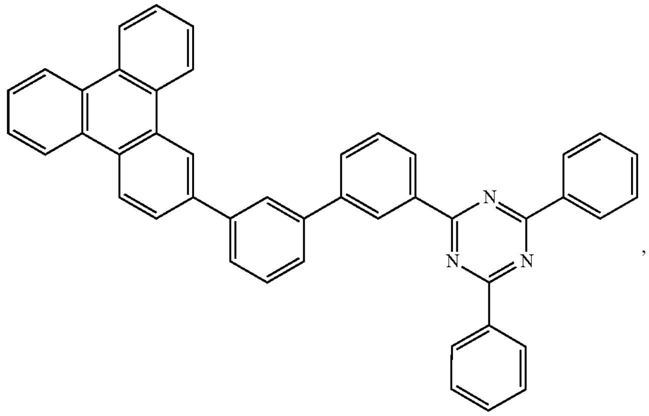,
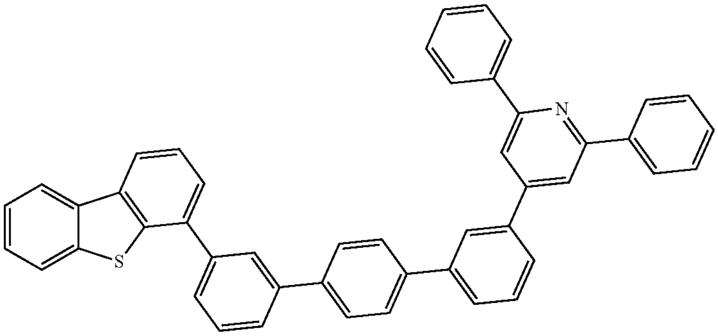,
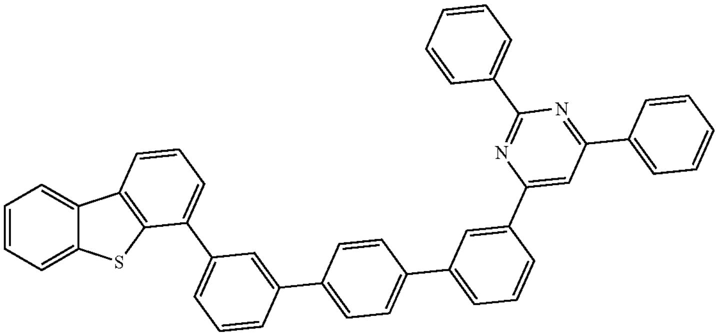,
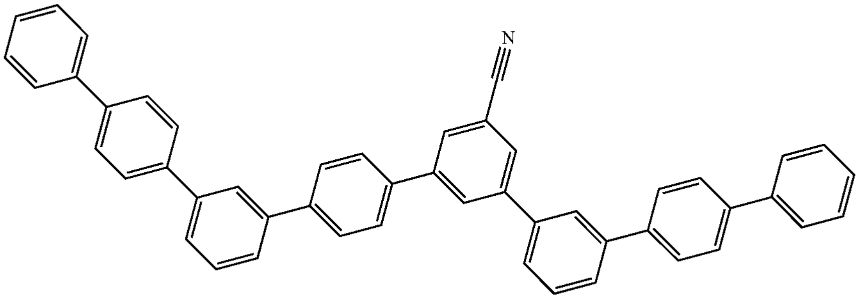,
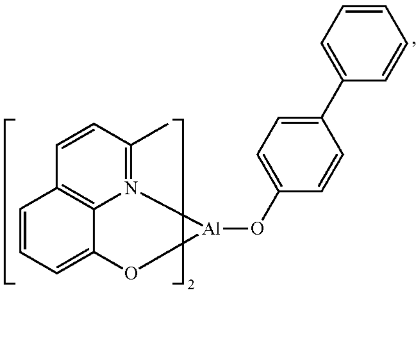,
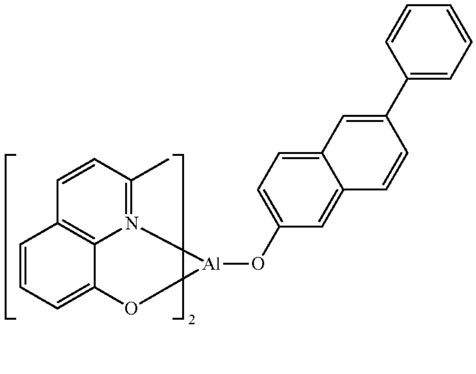, -continued

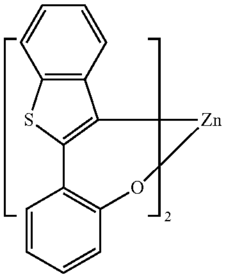

,

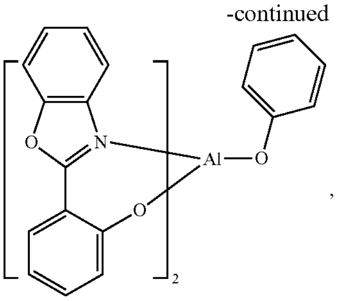

,

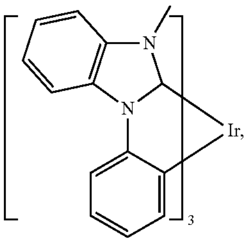

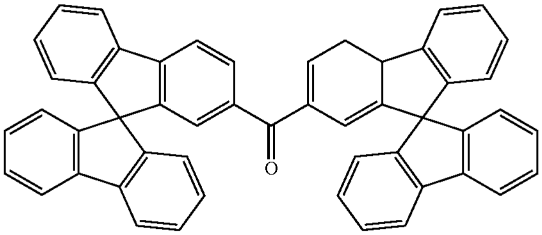

,

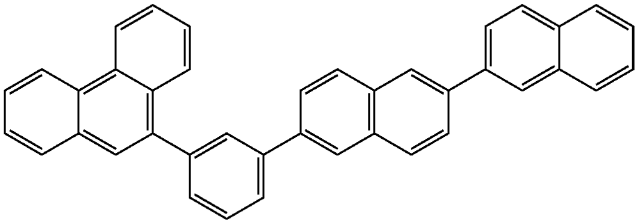

,

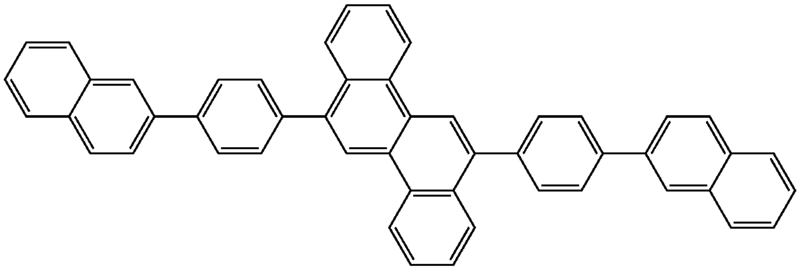

, and

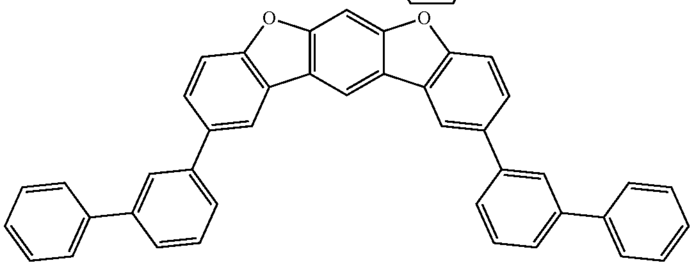

.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014223377, WO2014024131, WO2014031977, WO2014038456, WO2014112450.
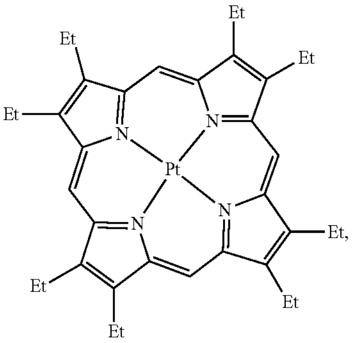
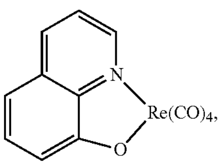
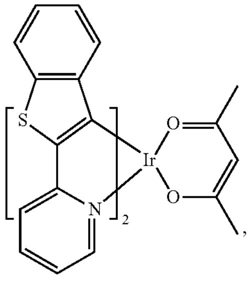
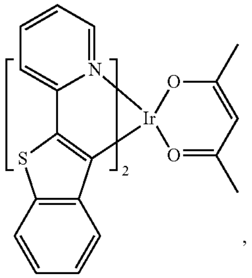
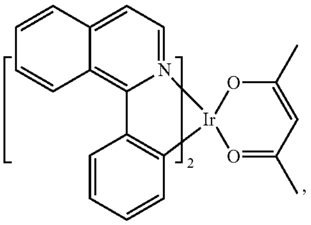
-continued
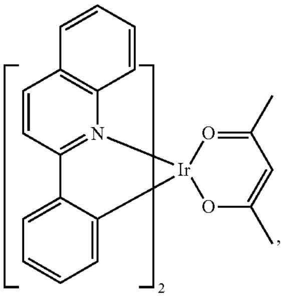
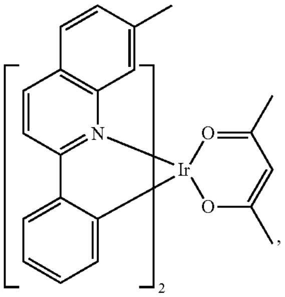
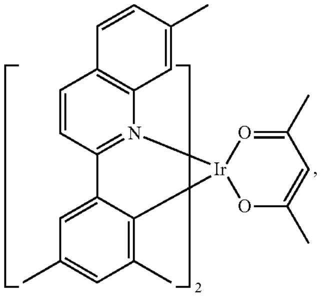
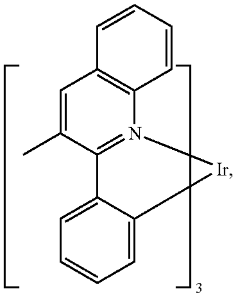
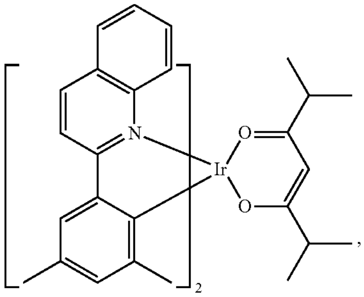
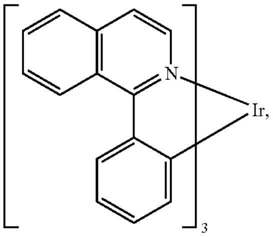
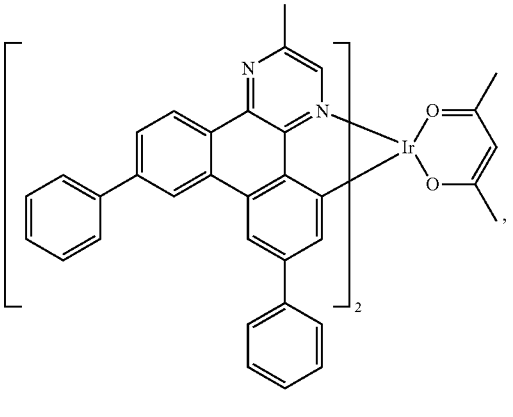

-continued
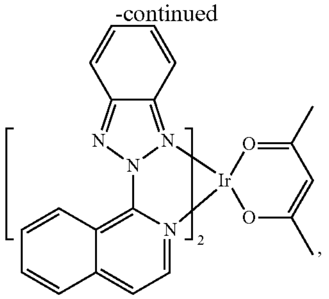
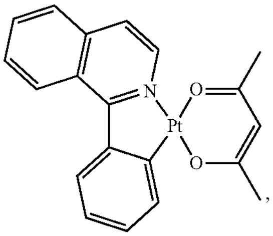
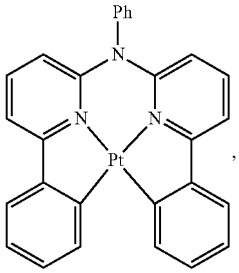
,
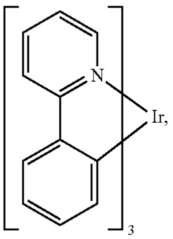
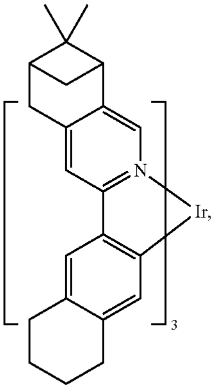
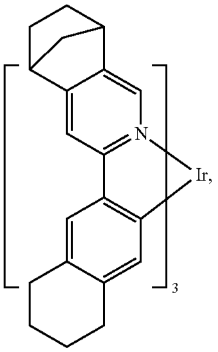
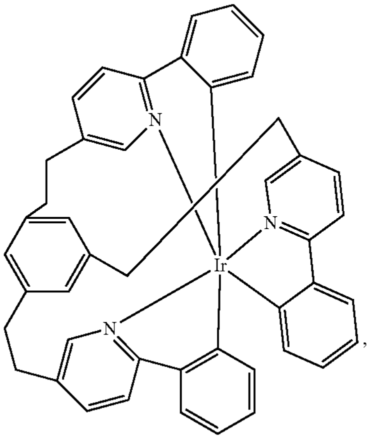
-continued
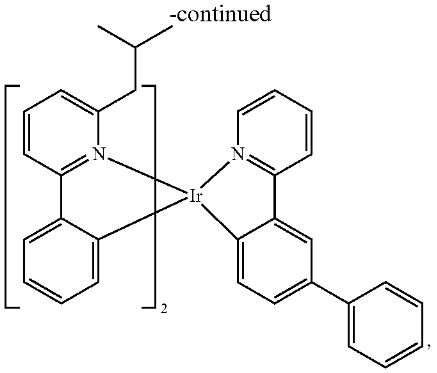
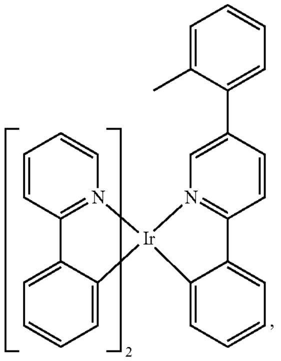
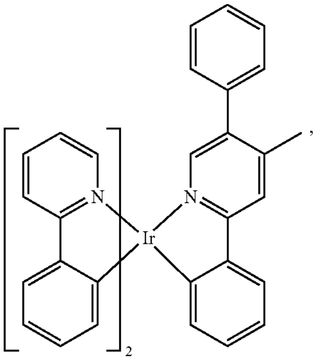
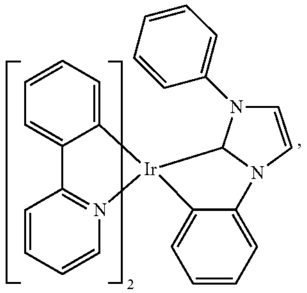
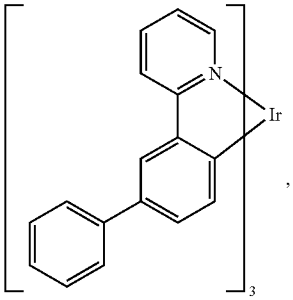
,
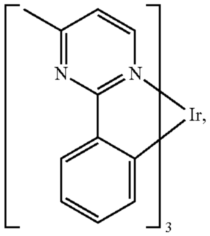

-continued
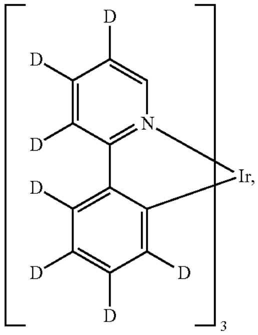
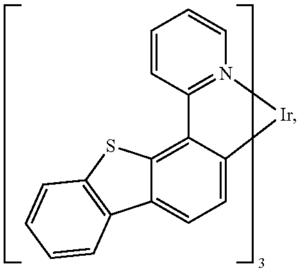
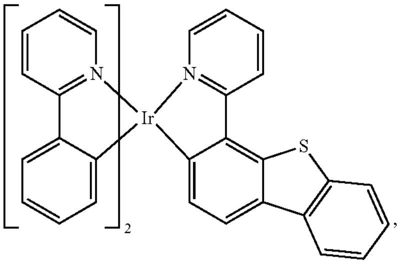
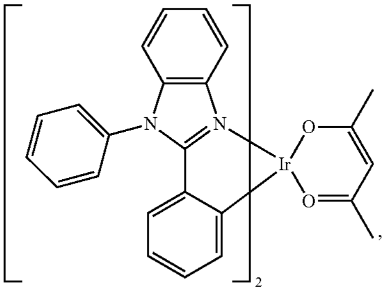
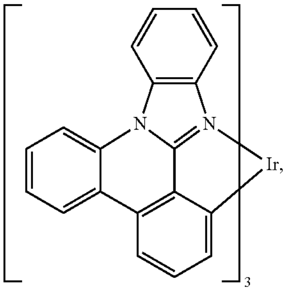
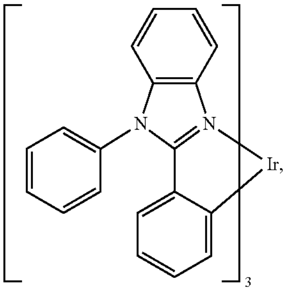
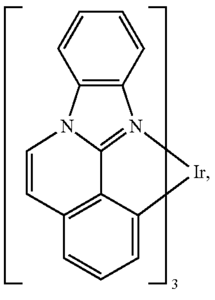
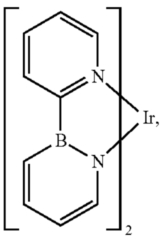
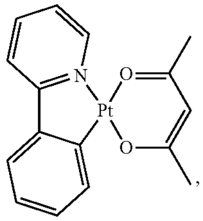
-continued
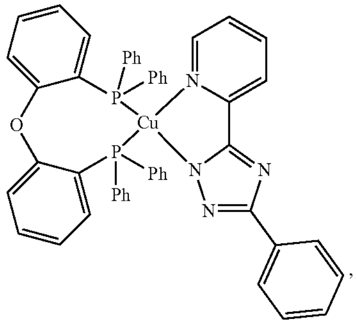
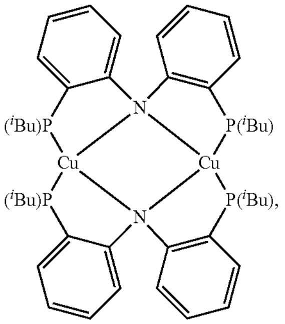
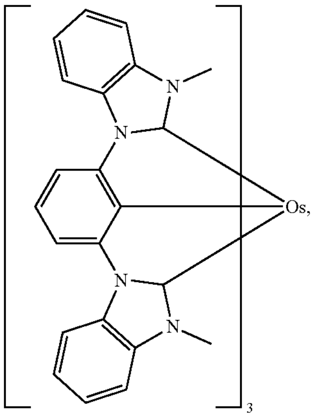
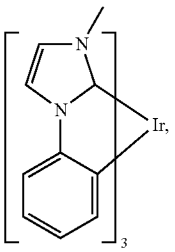
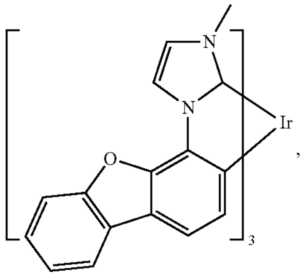
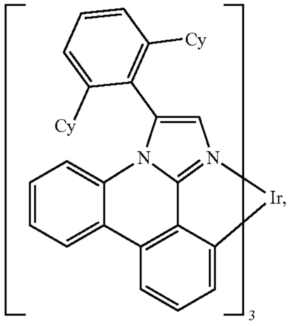

-continued
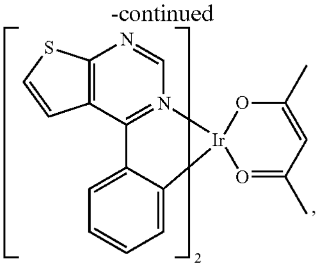
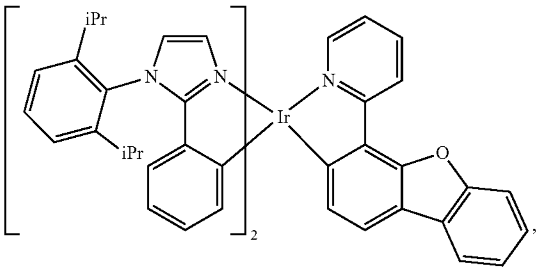
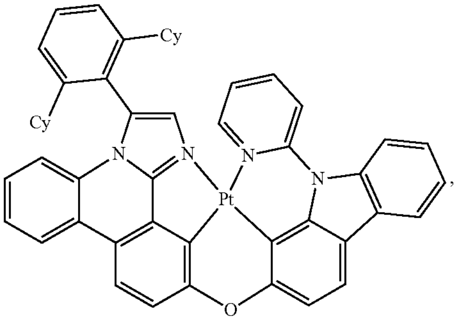
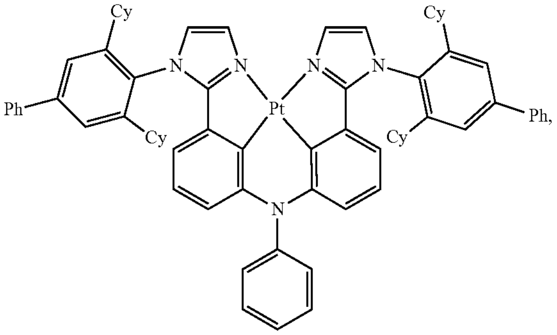
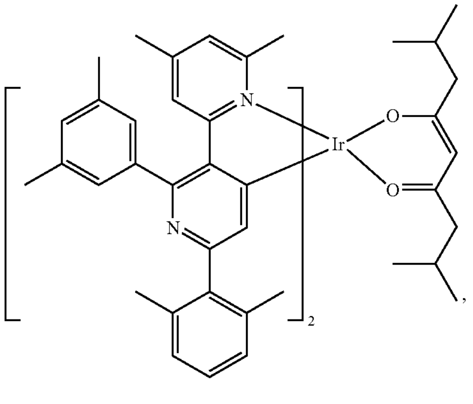
-continued
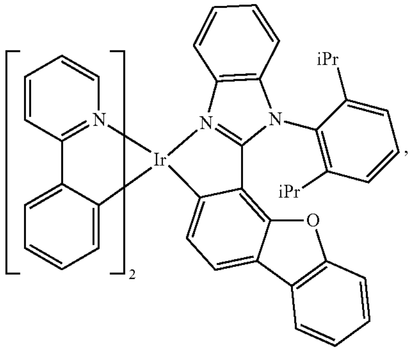
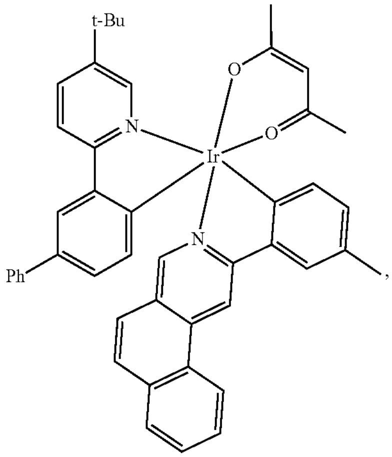
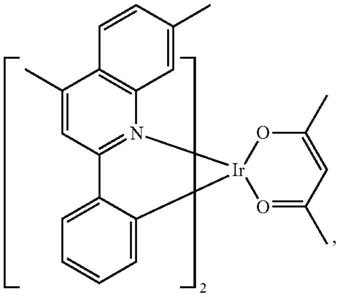
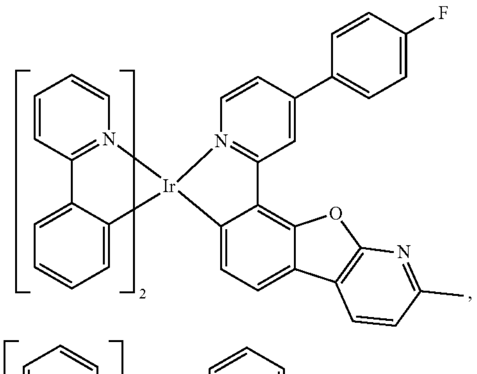
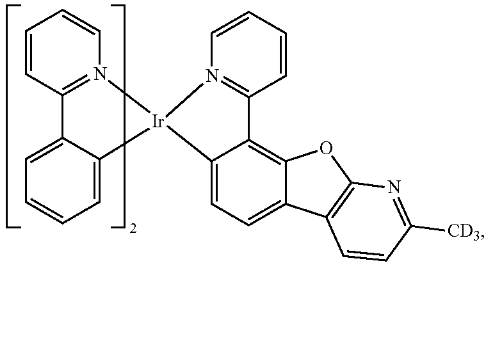

-continued
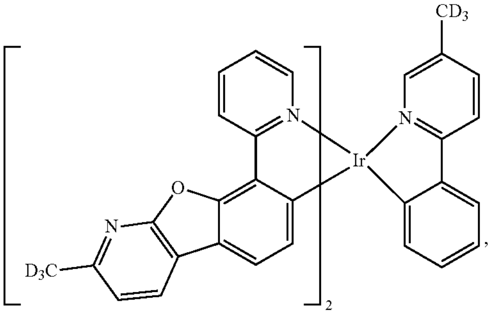
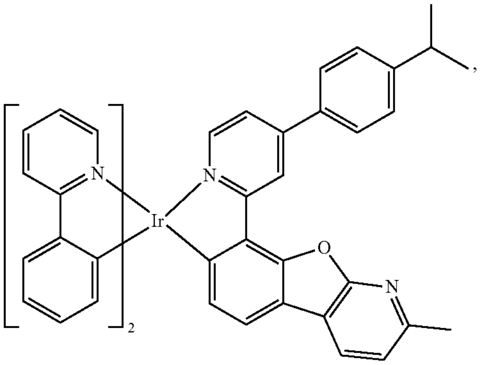
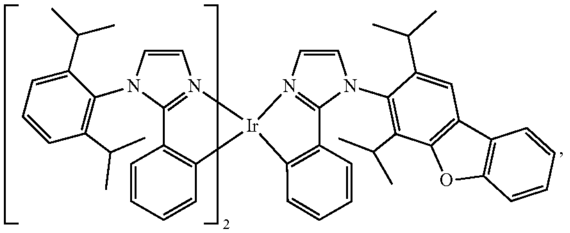
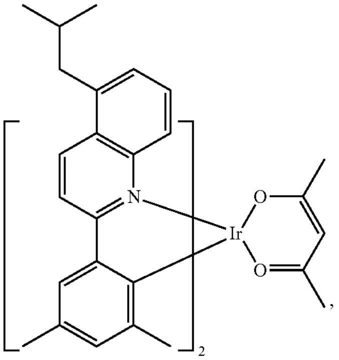
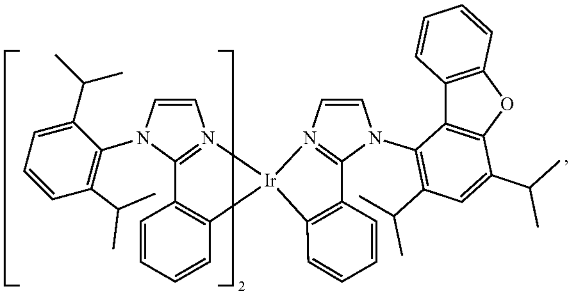
-continued
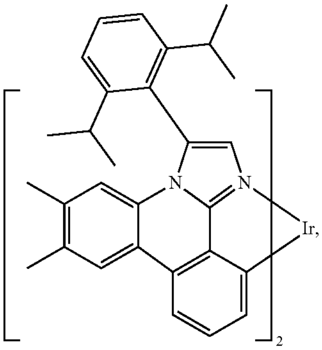
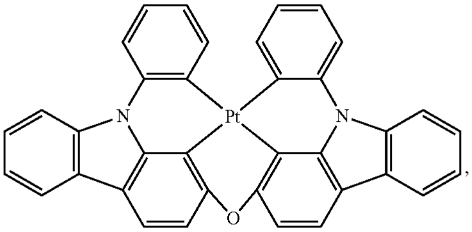
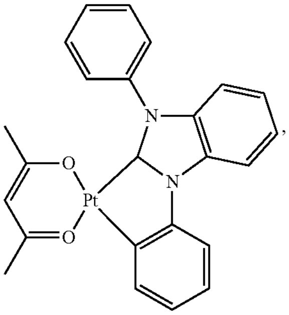
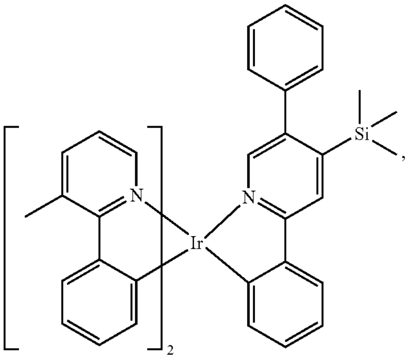
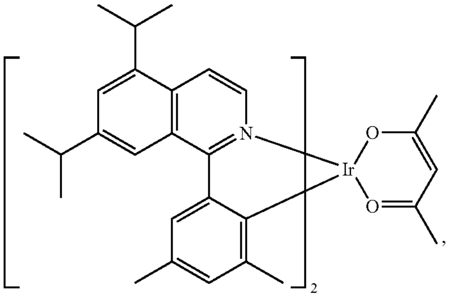

-continued
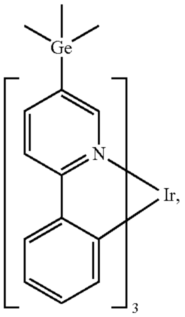
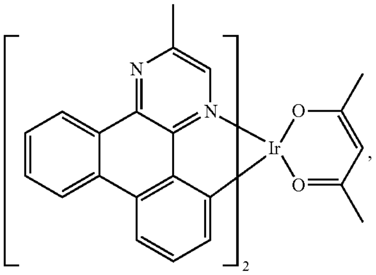
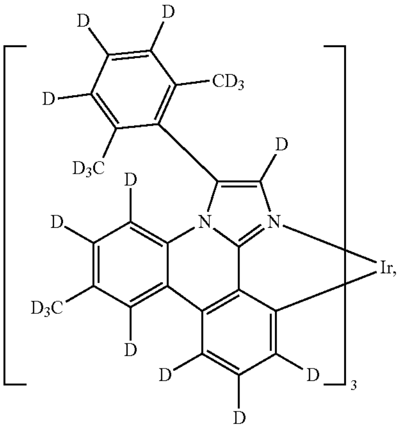
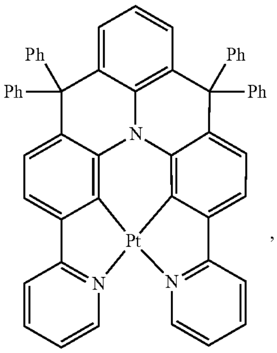
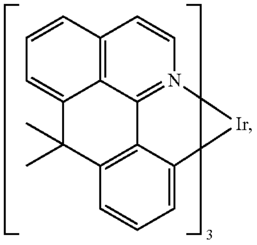
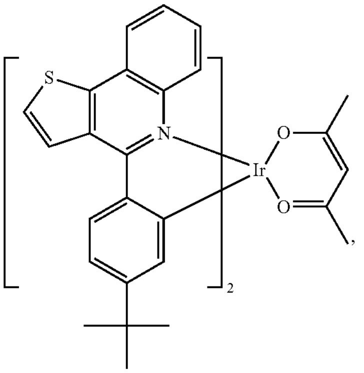
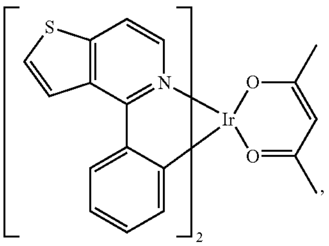
-continued
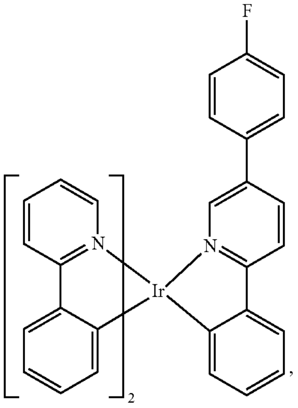
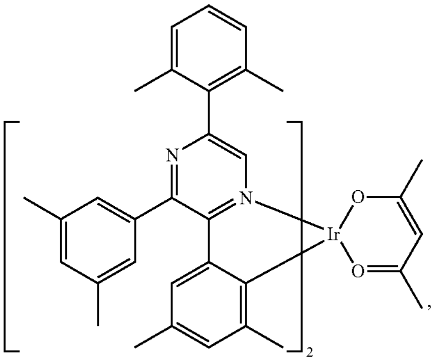
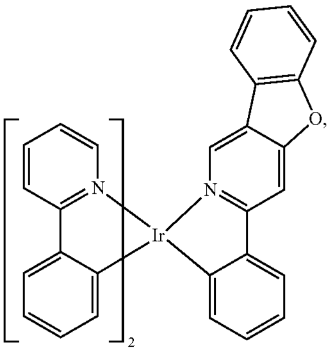
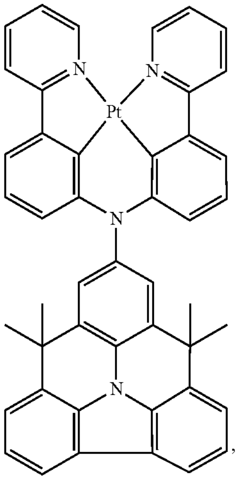

-continued
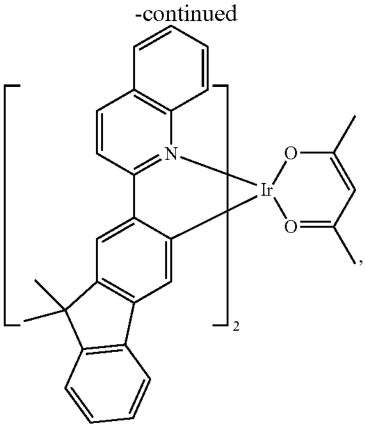
,
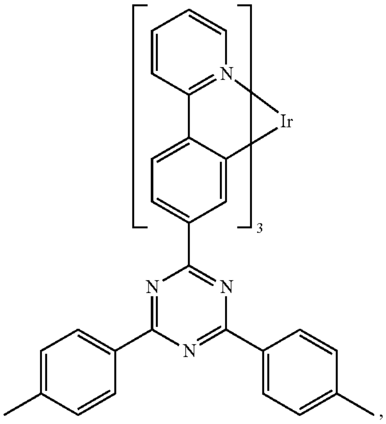
,
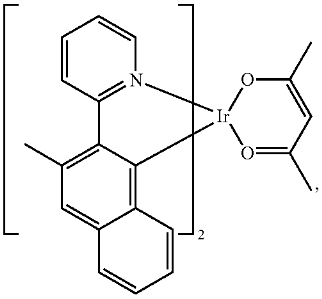
,
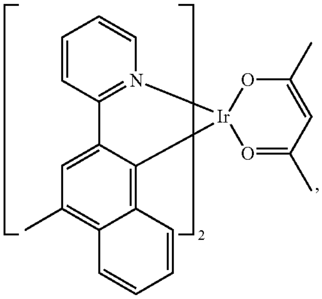
,
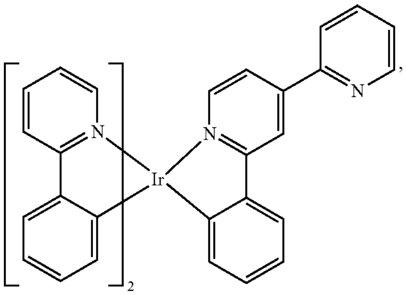
,
-continued
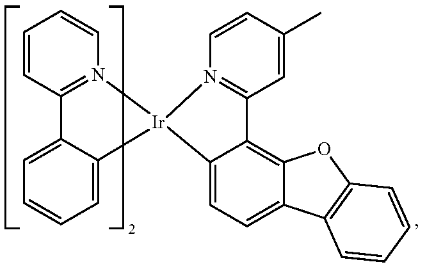
,
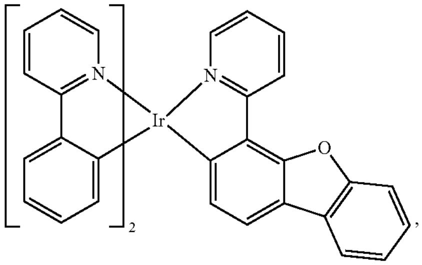
,
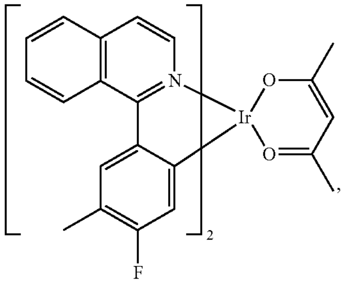
,
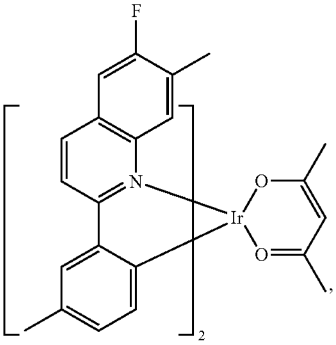
,
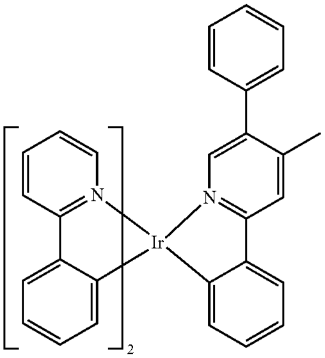
, -continued
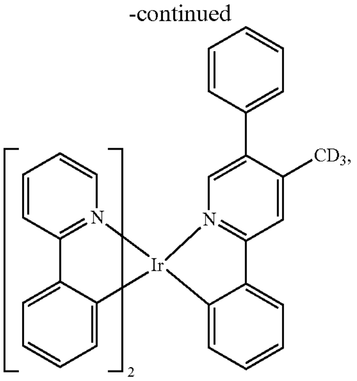
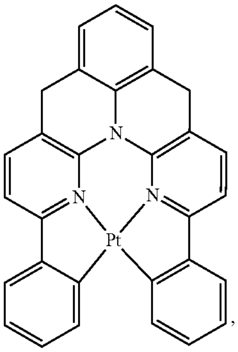
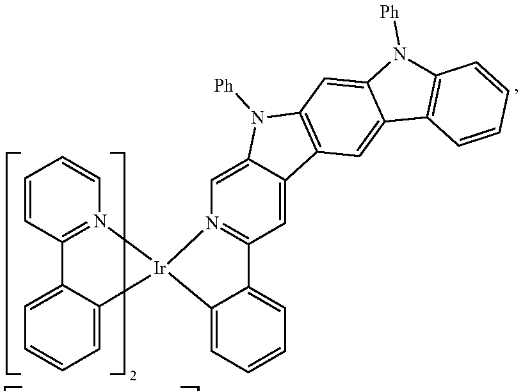
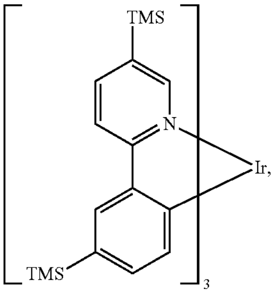
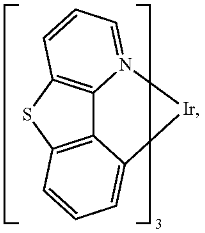
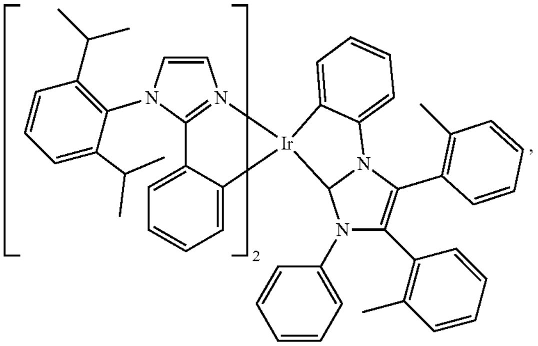
-continued
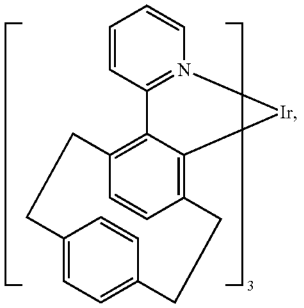
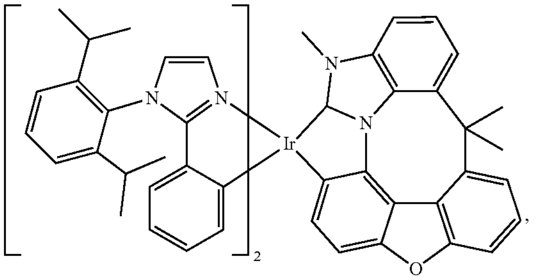
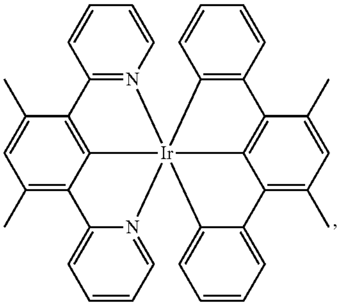
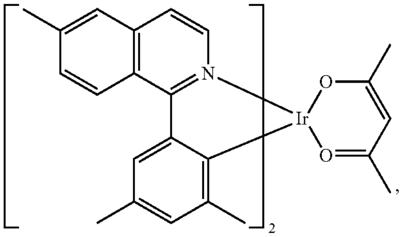
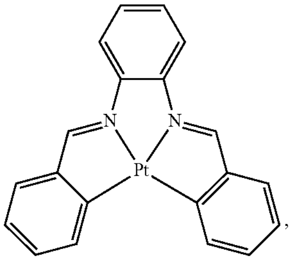
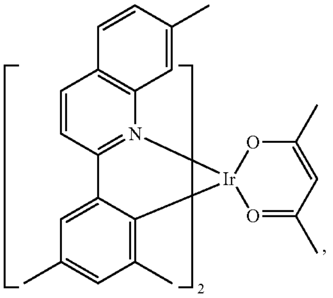

-continued
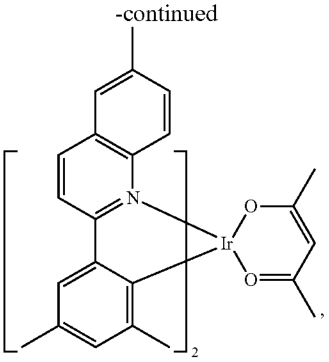
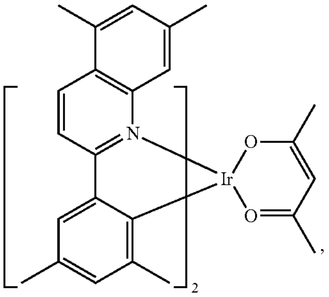
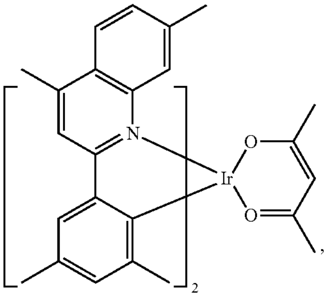
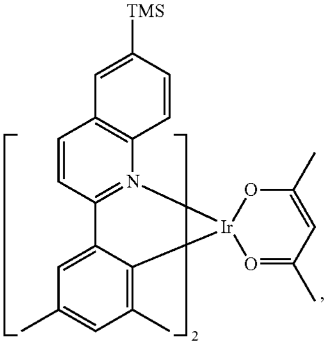
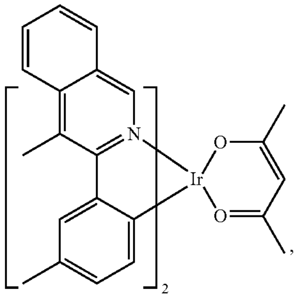
-continued
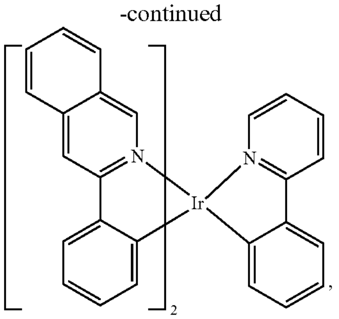
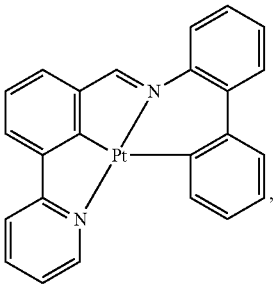
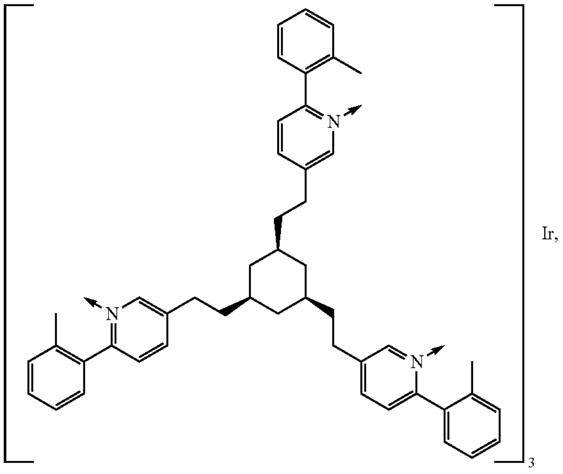
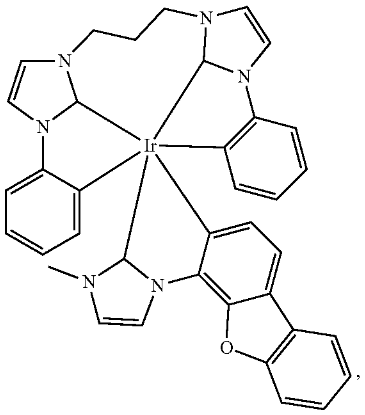

-continued
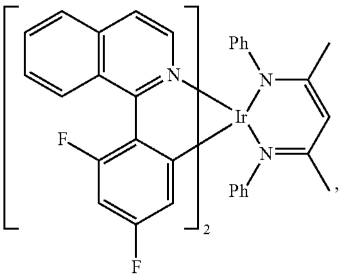
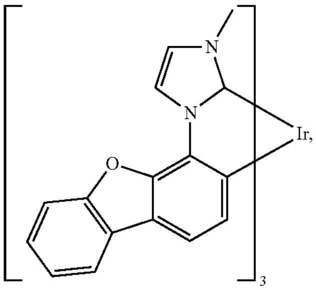
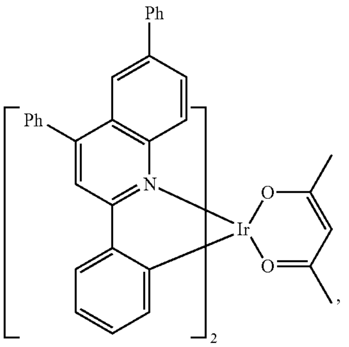
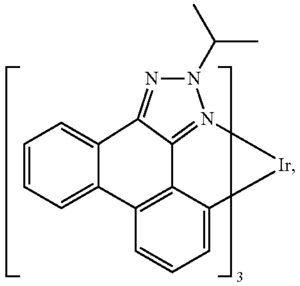
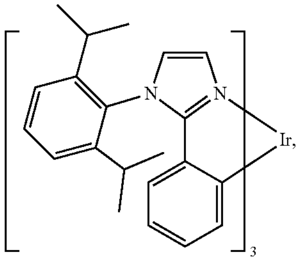
-continued
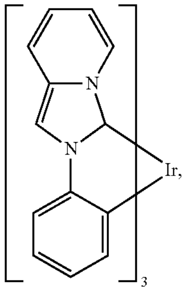
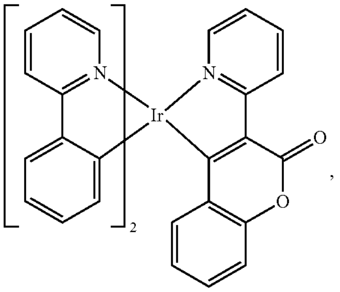
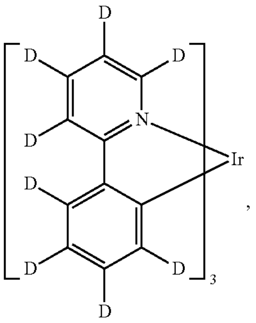
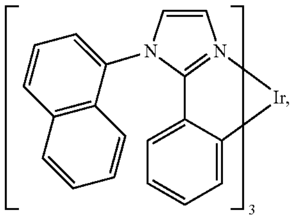
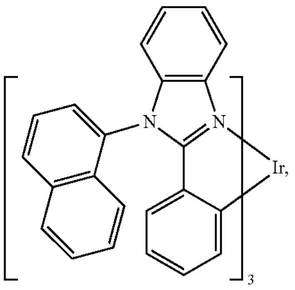
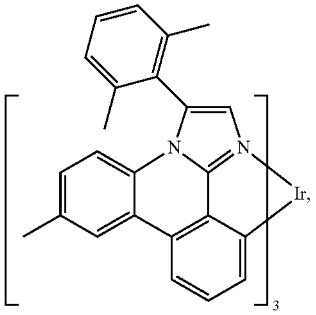
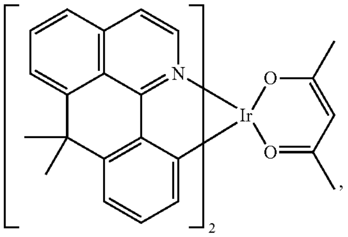
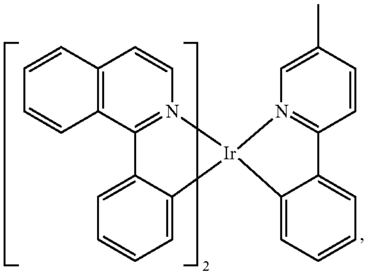

-continued

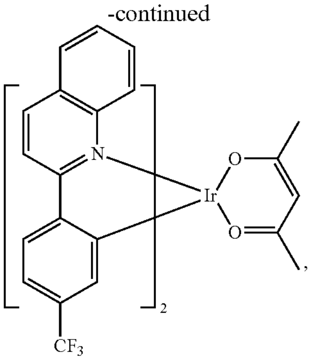

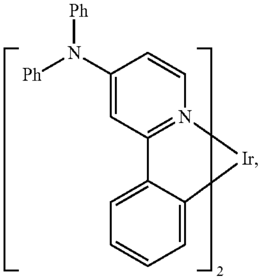

and

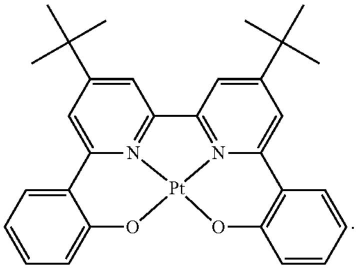

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

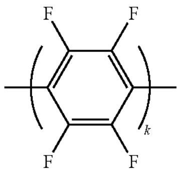

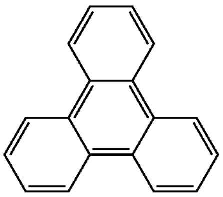

-continued

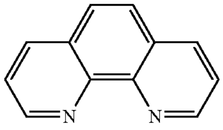

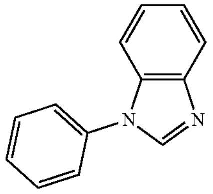

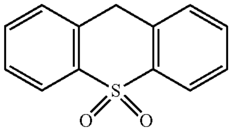

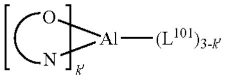

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

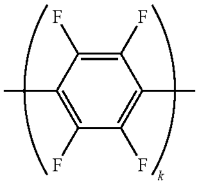

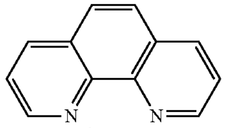

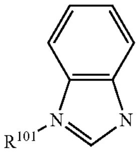

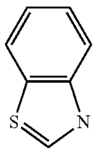

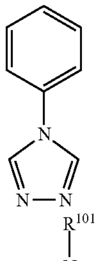

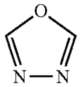

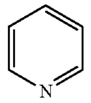

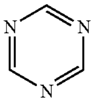

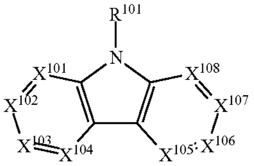

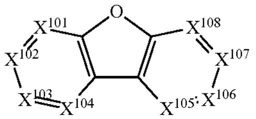

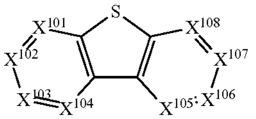

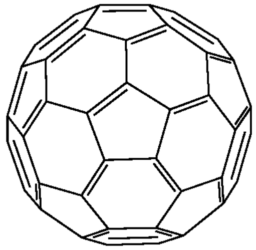

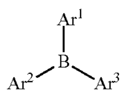

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

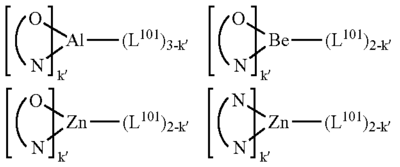

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, US6656612, US8415031, WO2003060956, WO2007111263, WO2009148269, WO2010067894, WO2010072300, WO2011074770, WO2011105373, WO2013079217, WO2013145667, WO2013180376, WO2014104499, WO2014104535,

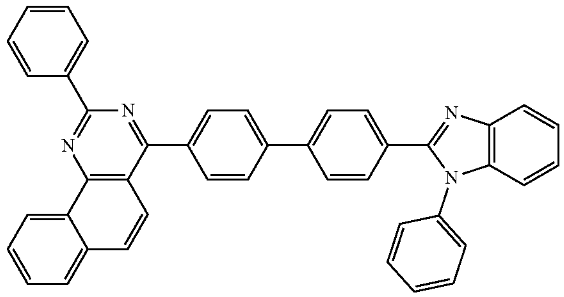

,

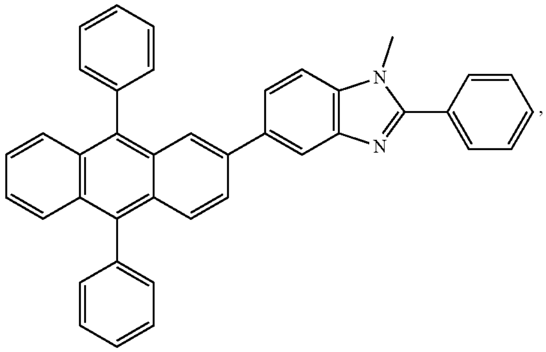

,

-continued

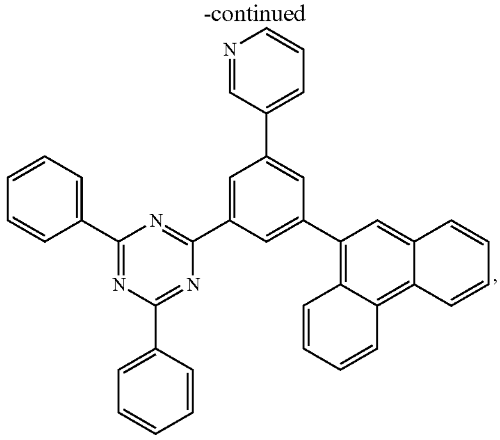

,

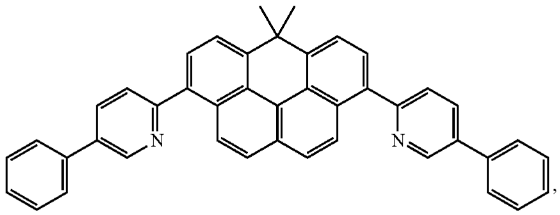

,

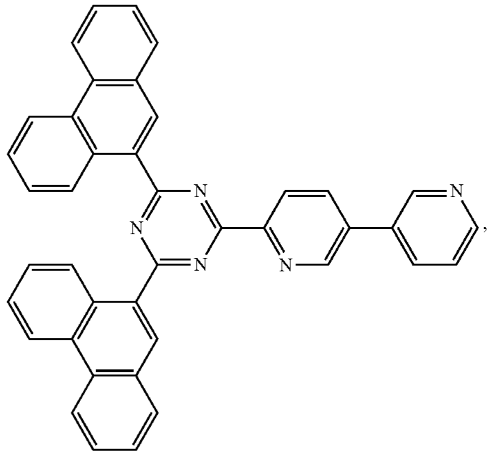

,

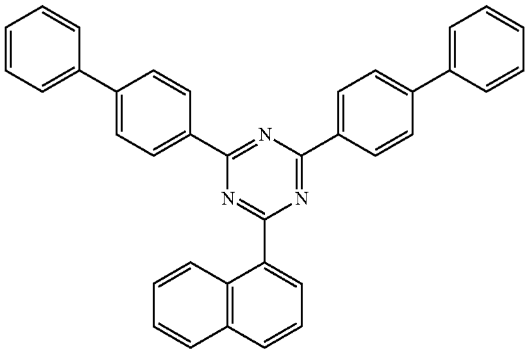

,

-continued
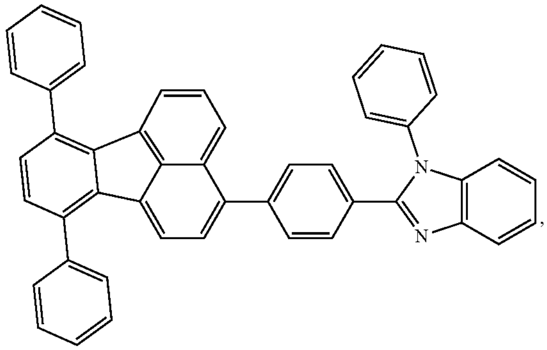
,
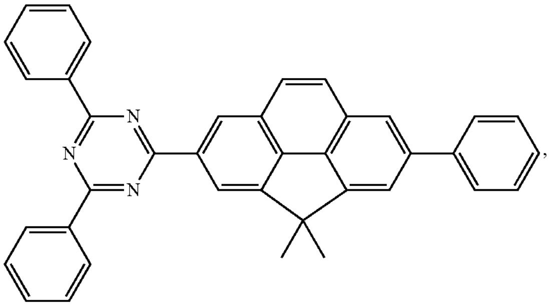
,
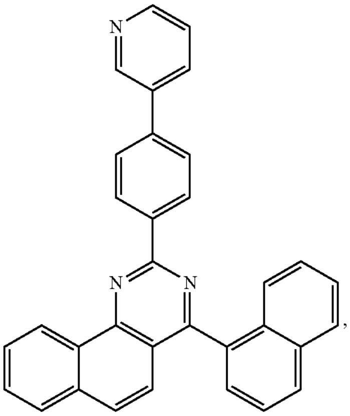
,
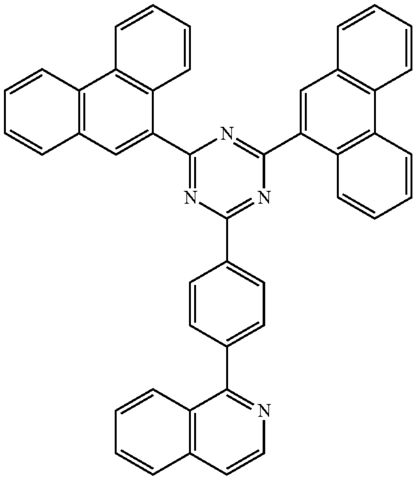
,
-continued
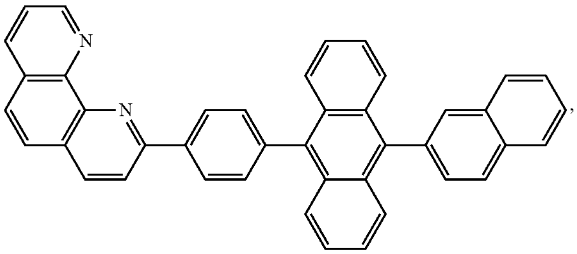
,
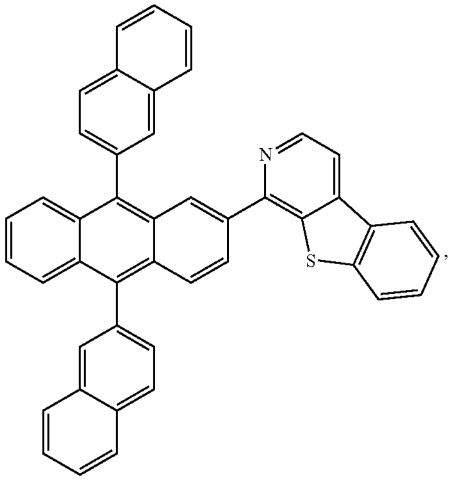
,
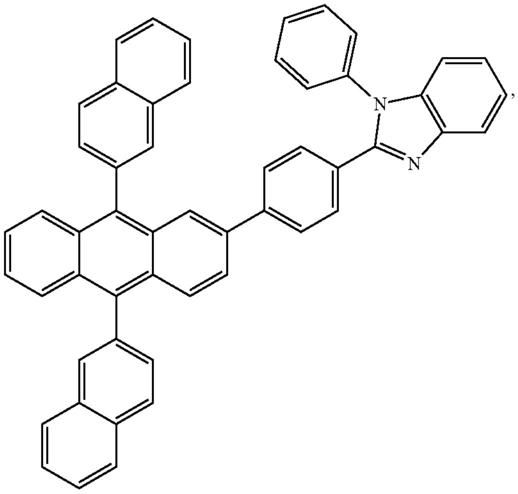
,
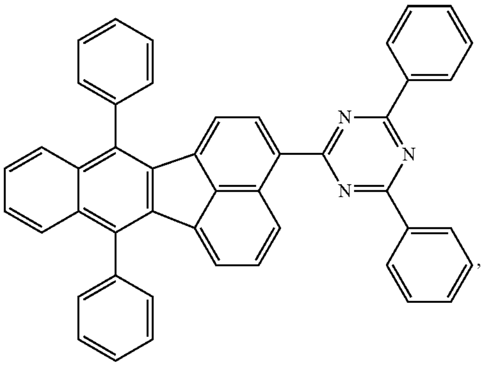
, -continued
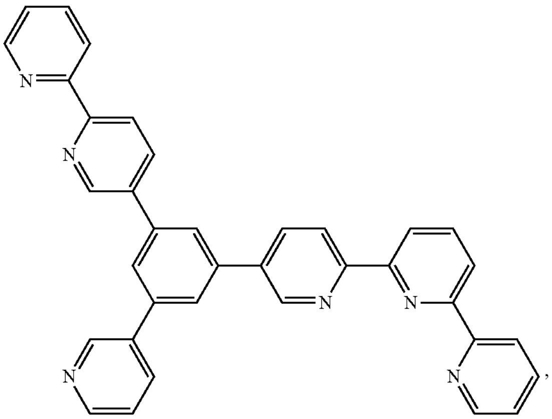
,
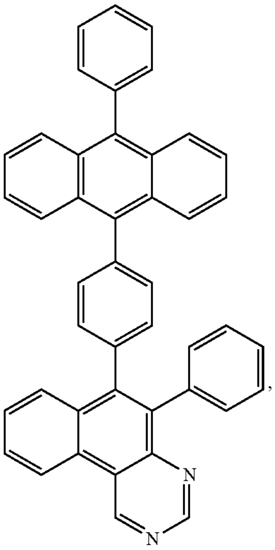
,
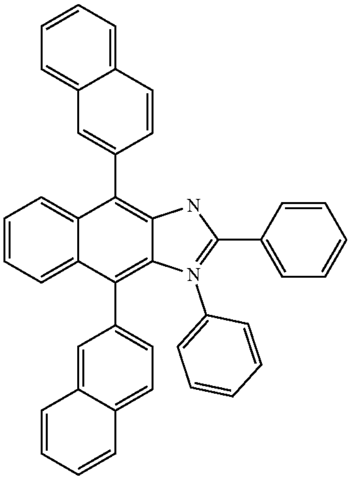
,
-continued
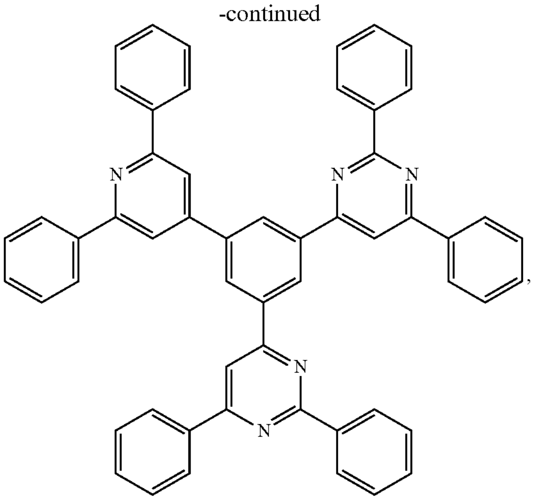
,
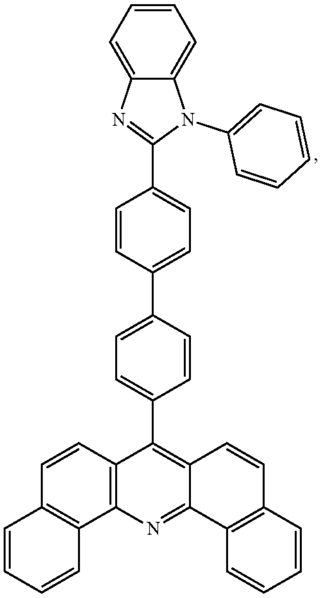
,
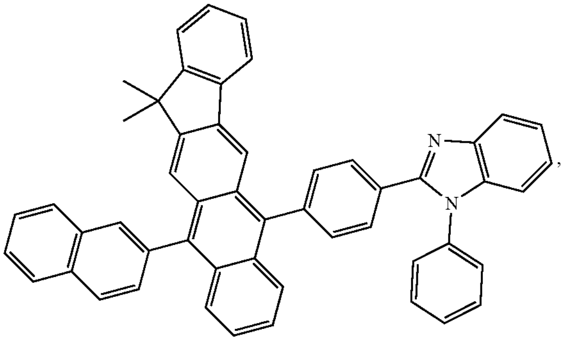
, -continued
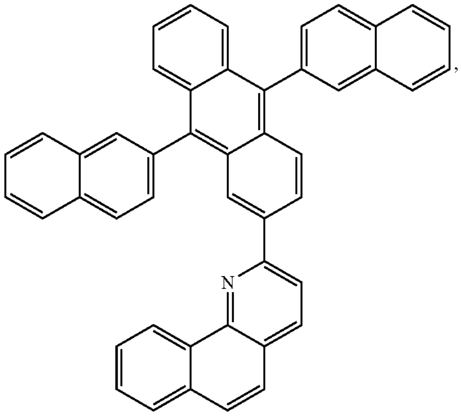
,
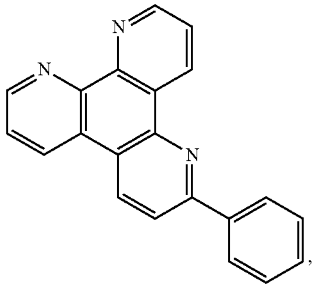
,
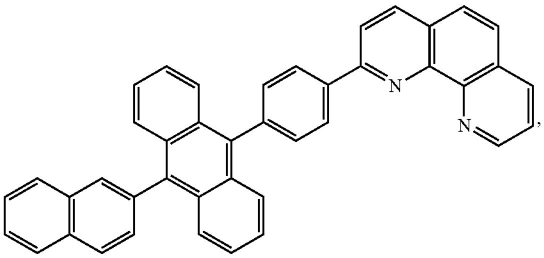
,
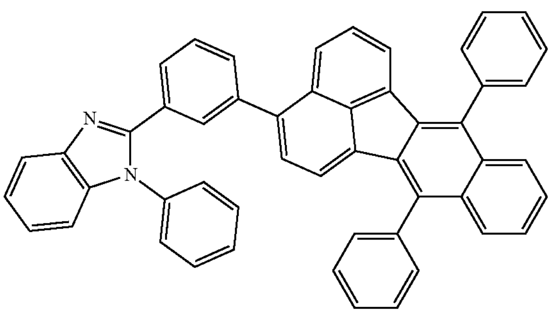
,
-continued
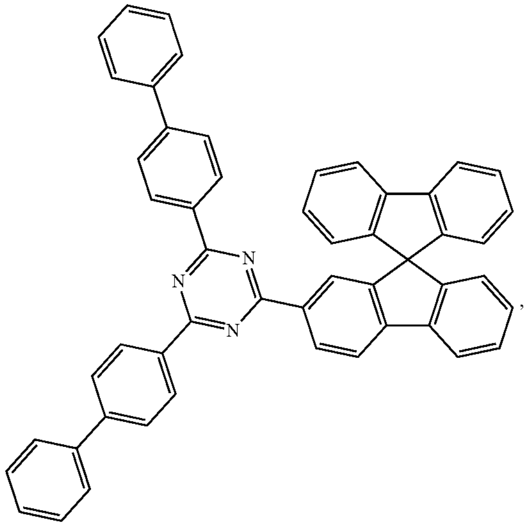
,
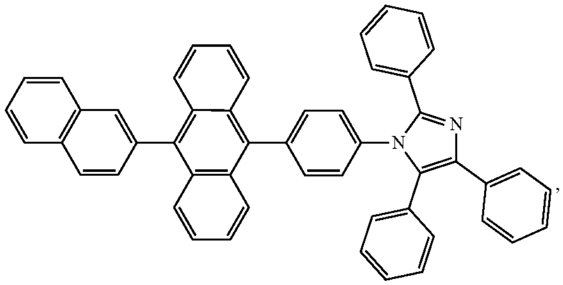
,
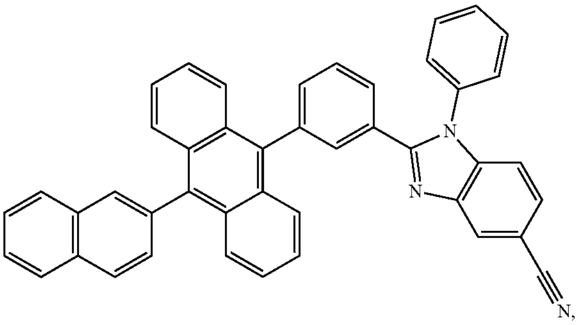
,
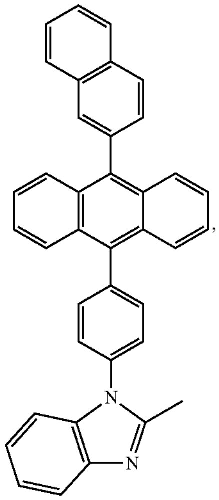
, -continued

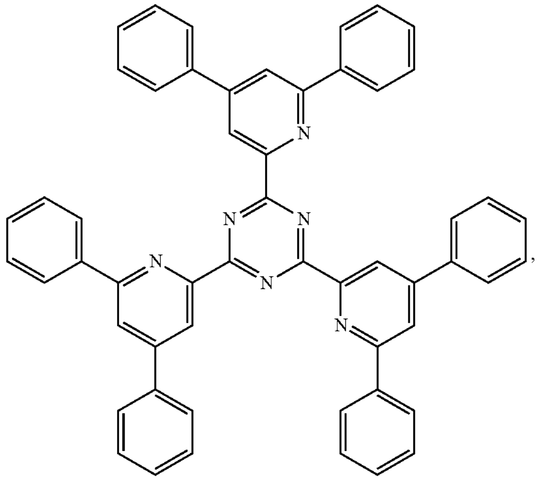

,

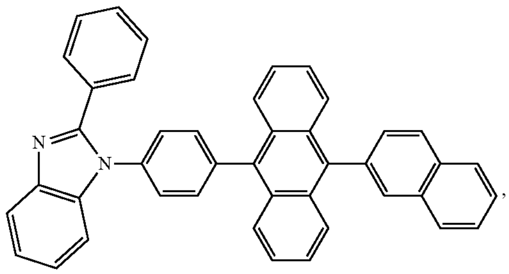

,

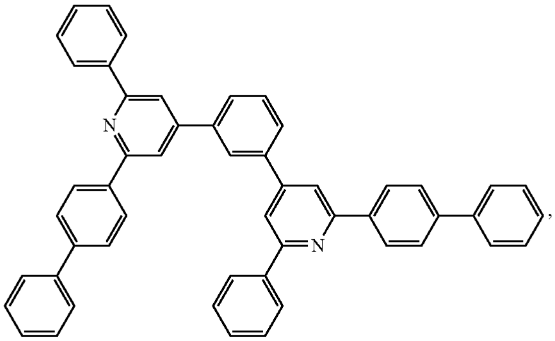

,

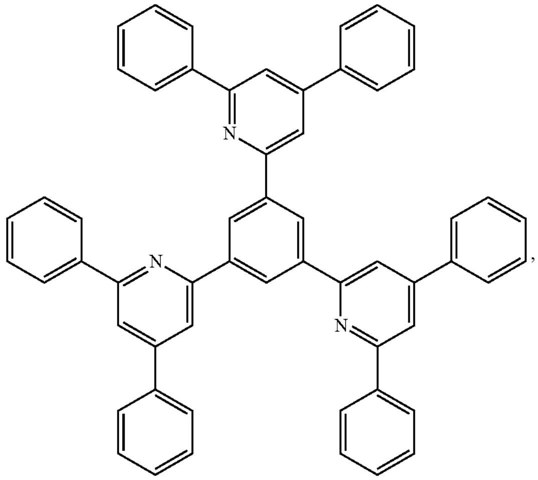

,

-continued

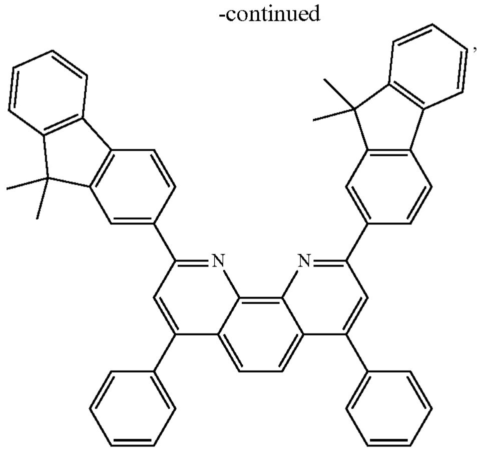

, and

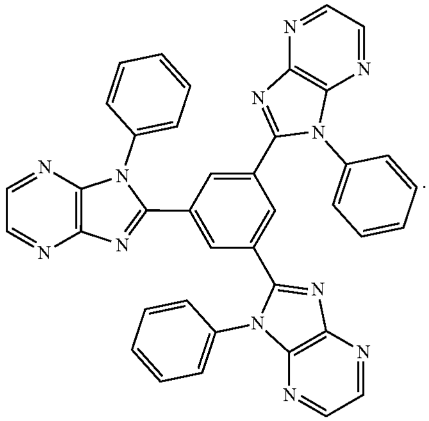

.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

Synthesis of $IrL_{X36}(L_{B461})_2$

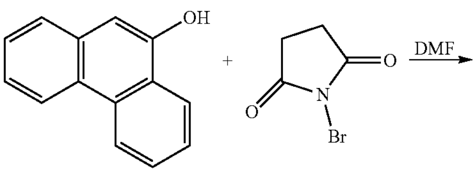

-continued

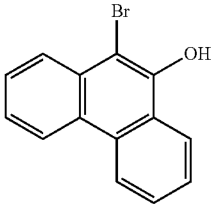

Phenanthren-9-ol (16 g, 82 mmol) was dissolved in 100 mL of dimethylformamide (DMF) and was cooled in an ice bath. 1-Bromopyrrolidine-2,5-dione (NBS, 14.95 g, 84 mmol) was dissolved in 50 mL of DMF and was added dropwise to the cooled reaction mixture over a 15-minute period. Stirring was continued for 30 minutes, then reaction was quenched with 300 mL of water. This mixture was extracted by dichloromethane (DCM). The DCM extracts were washed with aqueous LiCl then were dried over magnesium sulfate. These extracts were then filtered and concentrated under vacuum. The crude residue was passed through silica gel column eluting with 20-23% DCM in heptanes. Pure product fractions were combined and concentrated in vacuo to afford 10-bromophenanthren-9-ol (12.07 g, 44.2 mmol, 53.6% yield).

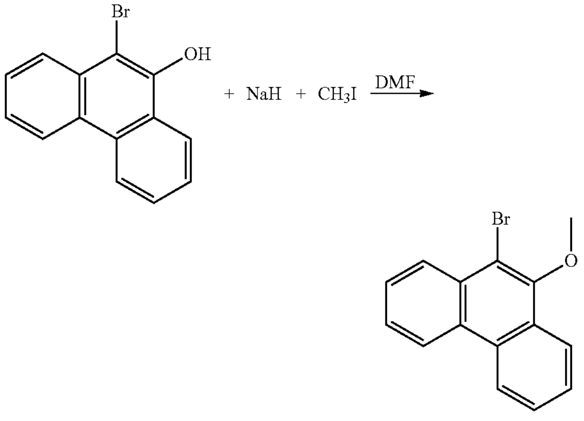

10-bromophenanthren-9-ol (13.97 g, 51.1 mmol) was charged into the reaction flask with 100 mL of dry DMF. This solution was cooled in a wet ice bath followed by the portion wise addition of sodium hydride (2.97 g, 74.2 mmol) over a 15 minute period. This mixture was then stirred for 1 hour and cooled using a wet ice bath. Iodomethane (18.15 g, 128 mmol) was dissolved in 70 mL of DMF, then was added dropwise to the cooled reaction mixture. This mixture developed a thick tan precipitate. Stirring was continued as the mixture gradually warmed up to room temperature (~22° C.). The reaction mixture was quenched with 300 mL of water then extracted with DCM. The organic extracts were combined, washed with aqueous LiCl then dried over magnesium sulfate. These extracts were filtered and concentrated in vacuo. The crude residue was passed through silica gel column eluting with 15-22% DCM in heptanes. Pure product fractions yielded 9-bromo-10-methoxyphenanthrene (5.72 g, 19.92 mmol, 38.9% yield) as a light yellow solid.

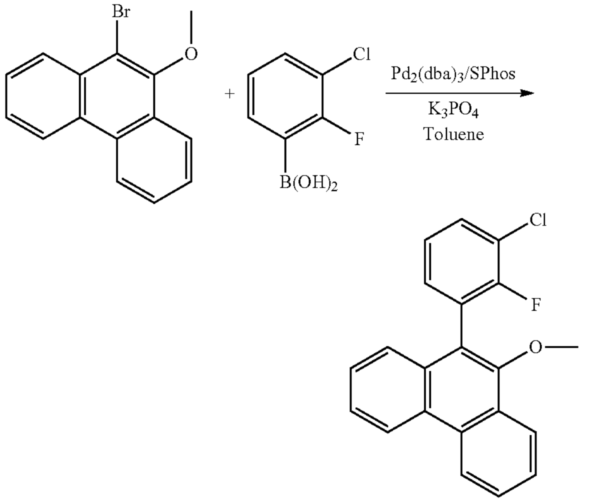

9-bromo-10-methoxyphenanthrene (8.75 g, 30.5 mmol), (3-chloro-2-fluorophenyl)boronic acid (6.11 g, 35.0 mmol), potassium phosphate tribasic monohydrate (21.03 g, 91 mmol), tris(dibenzylideneacetone)palladium(0) ($Pd_2(dba)_3$) (0.558 g, 0.609 mmol) and 2-dicyclohexylphosphino-2',6'-dimethoxybiphenyl (Sphos) (1.4 g, 3.41 mmol) were suspended in 300 mL of toluene. This mixture was degassed with nitrogen then heated to reflux for 18 hours. Heating was discontinued and the reaction mixture was diluted with 300 mL of water. The toluene layer was separated and was dried over magnesium sulfate. The organic solution was filtered and concentrated in vacuo. The crude residue was passed through silica gel columns eluting the columns with 25-30% DCM in heptanes. Pure product fractions were combined and concentrated yielding 9-(3-chloro-2-fluorophenyl)-10-methoxyphenanthrene (8.75 g, 26.0 mmol, 85% yield) as a white solid.

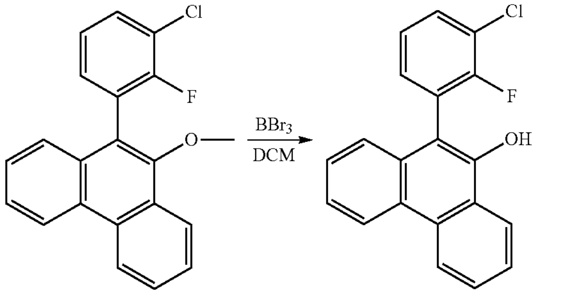

9-(3-chloro-2-fluorophenyl)-10-methoxyphenanthrene (1.5 g, 4.45 mmol) was dissolved in 40 mL of DCM. This homogeneous mixture was cooled to 0° C. A 1M boron tribromide ($BBr_3$) solution in DCM (11.13 ml, 11.13 mmol) was added dropwise to the reaction mixture over a 5-minute period. Stirring was continued at 0° C. for 3.5 hours. The reaction mixture was poured into a beaker of wet ice. The organic layer was separated. The aqueous phase was extracted with DCM. The DCM extracts were combined with organic phase and washed with aqueous LiCl then dried over magnesium sulfate. This solution was filtered and concentrated in vacuo yielding 10-(3-chloro-2-fluorophenyl)phenanthren-9-ol (1.4 g, 4.34 mmol, 97% yield) as an off-white solid.

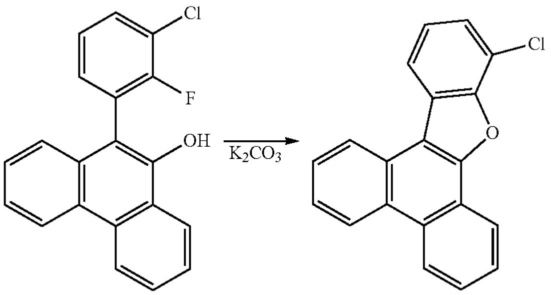

3-Chloro-10-(2-fluorophenyl)phenanthren-9-ol (1.4 g, 4.34 mmol) and potassium carbonate (1.796 g, 13.01 mmol) were suspended in 1-methylpyrrolidin-2-one (15 ml, 156 mmol). This mixture was degassed with nitrogen then was heated in an oil bath set at 150° C. for 18 h. The reaction mixture was cooled down to room temperature, diluted with 200 mL of water, and grey precipitate was filtered under reduced pressure. This solid was dissolved in hot DCM, washed with aqueous LiCl, then dried over magnesium sulfate. The solution was filtered and concentrated in vacuo yielding 10-chlorophenanthro[9,10-b]benzofuran (1.23 g, 4.06 mmol, 94% yield).

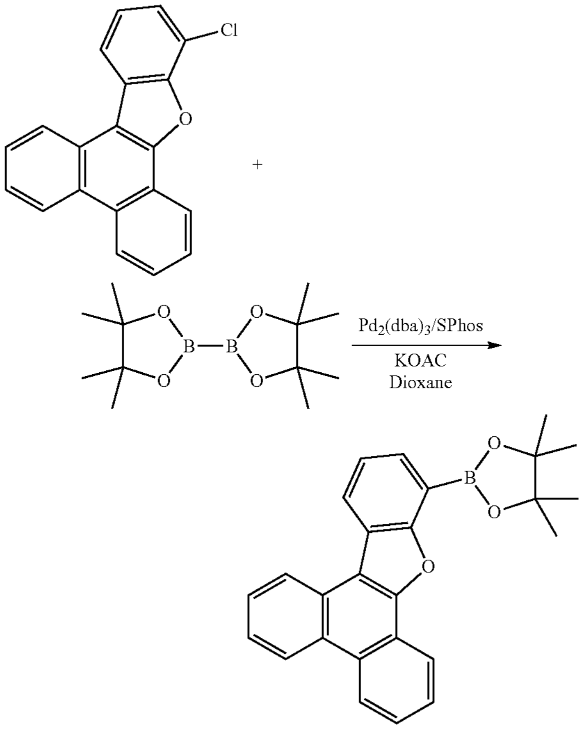

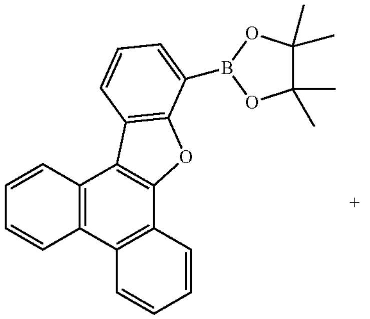

-continued

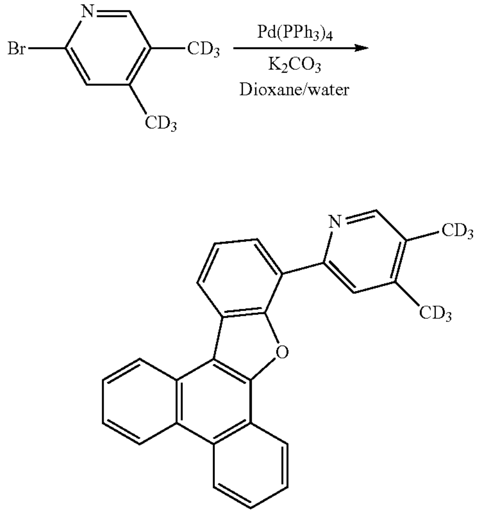

10-Chlorophenanthro[9,10-b]benzofuran (1.23 g, 4.06 mmol), 4,4,4',4',5,5,5',5'-octamethyl-2,2'-bi(1,3,2-dioxaborolane) (1.341 g, 5.28 mmol), tris(dibenzylideneacetone) palladium(0) (0.093 g, 0.102 mmol) and SPhos (0.250 g, 0.609 mmol) were suspended in 80 mL of dioxane. Potassium acetate (0.995 g, 10.16 mmol) was then added to the reaction flask as one portion. This mixture was degassed with nitrogen then heated to reflux for 18 hours. Heating was discontinued. 2-Bromo-4,5-bis(methyl-d3)pyridine (1.052 g, 5.48 mmol), tetrakis(triphenylphosphine)palladium(0) ($Pd(PPh_3)_4$) (0.140 g, 0.122 mmol) and potassium phosphate tribasic monohydrate (2.80 g, 12.17 mmol) were added followed by 10 mL of water. This mixture was degassed with nitrogen then was heated to reflux for 18 hours. The reaction mixture was cooled to room temperature 22° C.) then was diluted with 200 mL of water. This mixture was extracted with DCM, extracts were combined, washed with aqueous LiCl, then dried over magnesium sulfate. These extracts were filtered and concentrated in vacuo. The crude residue was passed through a silica gel column eluting with 0.5-4% ethyl acetate in DCM. Pure fractions were combined together and concentrated under vacuum yielding 4,5-bis(methyl-d3)-2-(phenanthro[9,10-b]benzofuran-10-yl)pyridine (1.13 g, 2.98 mmol, 73.4% yield).

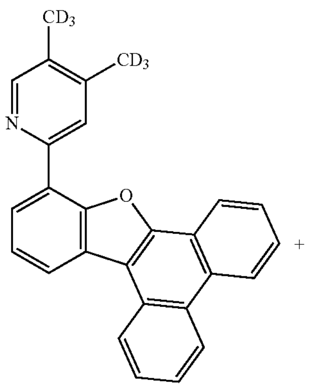

-continued

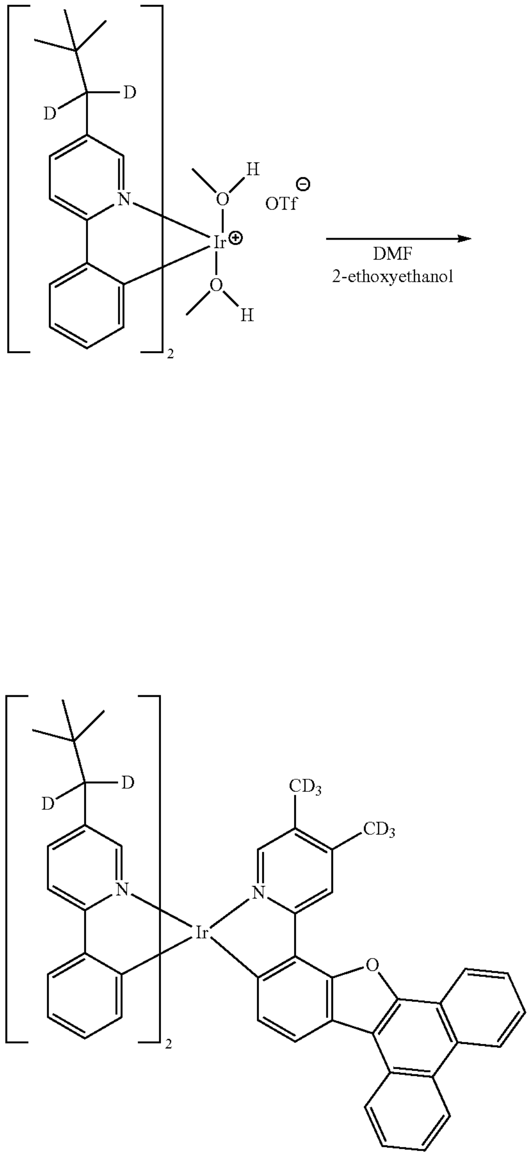

4,5-bis(Methyl-d3)-2-(phenanthro[9,10-b]benzofuran-10-yl)pyridine (2 g, 5.27 mmol) and the iridium complex triflic salt shown above (2.445 g, 2.85 mmol) were suspended in the mixture of 25 mL of 2-ethoxyethanol and 25 mL of DMF. This mixture was degassed with nitrogen, then heated at 95° C. for 21 days. The reaction mixture was cooled down and diluted with 150 mL of methanol. A yellow precipitate was collected and dried in vacuo. This solid was then dissolved in 500 mL of DCM and was passed through a plug of basic alumina. The DCM filtrate was concentrated and dried in vacuo leaving an orange colored solid. This solid was passed through a silica gel column eluting with 10% DCM/45% toluene/heptanes and then 65% toluene in heptanes.

Pure fractions after evaporation yielded the desired iridium complex, $IrL_{X36}(L_{B461})_2$ (1.07 g, 1.046 mmol, 36.7% yield).

Synthesis of $IrL_{X169}(L_{B461})_2$

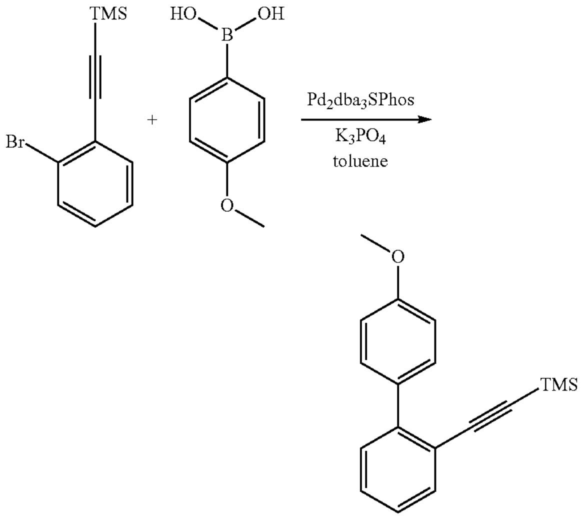

(4-Methoxyphenyl)boronic acid (22.50 g, 148 mmol) and potassium phosphate tribasic monohydrate (68.2 g, 296 mmol) were suspended in 500 mL of toluene and 10 mL of water. The reaction mixture was purged with nitrogen for 15 min then tris(dibenzylideneacetone)dipalladium(0) (2.71 g, 2.96 mmol), dicyclohexyl(2',6'-dimethoxy-[1,1'-biphenyl1]-2-yl)phosphane (Sphos, 4.86 g, 11.85 mmol) and ((2-bromophenyl)ethynyl)trimethylsilane (35.3 ml, 99 mmol) were added. The reaction mixture was heated in an oil bath set at 100° C. for 13 hours under nitrogen. The reaction mixture was filtered through silica gel and the filtrate was concentrated down to a brown oil. The brown oil was purified on a silica gel column eluting with heptane/DCM 75/25 (v/v) mixture to get ((4'-methoxy-[1,1'-biphenyl]-2-yl)ethynyl) trimethylsilane (25.25 g, 91% yield).

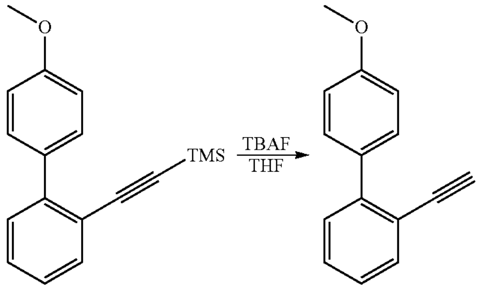

((4'-Methoxy-[1,1'-biphenyl]-2-yl)ethynyptrimethylsilane (25.2 g, 90 mmol) was dissolved in 300 mL of tetrahydrofuran (THF). The reaction was cooled in an ice bath then a 1 M solution of tetra-n-butylammonium fluoride in THF (108 mL, 108 mmol) was added dropwise. The reaction mixture was allowed to warm up to room temperature. After two hours the reaction mixture was concentrated down, washed with ammonium chloride solution and brine, dried over sodium sulfate, filtered and concentrated down to a brown oil. The brown oil was purified on a silica gel column eluting with heptane/DCM 75/25 (v/v) to produce 2-ethynyl-4'-methoxy-1,1'-biphenyl as an orange oil (17.1 g, 91% yield).

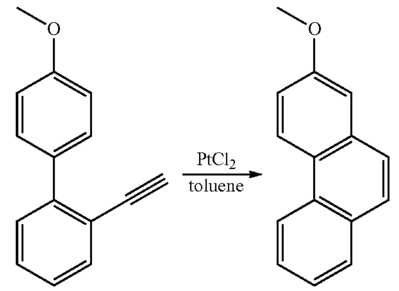

2-Ethynyl-4'-methoxy-1,1'-biphenyl (19.5 g, 94 mmol) was dissolved in 600 ml of toluene and platinum(II) chloride (2.490 g, 9.36 mmol) was added as a slurry mixture in 200 ml of toluene. The reaction was heated to 80° C. for 14 hours. The reaction was then cooled down and filtered through a silica gel plug. The filtrate was concentrated down to a brown solid. The solid was purified on a silica gel column eluting with heptane/DCM 75/25 (v/v) to afford 2-methoxyphenanthrene as off-white solid (14.0 g, 71.8% yield).

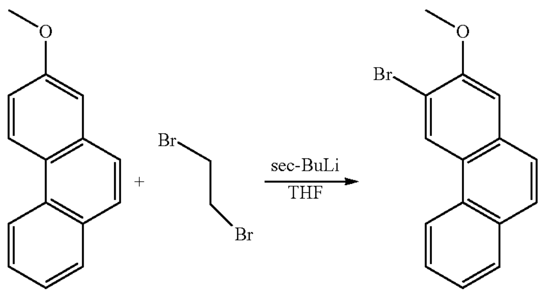

2-Methoxyphenanthrene (11.7 g, 56.2 mmol) was dissolved in dry THF (300 ml) under nitrogen. The solution was cooled in a brine/dry ice bath to maintain a temperature below −10° C., then a sec-butyllithium THF solution (40.4 ml, 101 mmol) was added in portions keeping the temperature of the mixture below −10° C. The reaction mixture immediately turned dark. The reaction mixture was continuously stirred in the cooling bath for 1 hour. Then the reaction mixture was removed from the bath and stirred at room temperature for three hours.

The reaction was placed back in the cooling bath for 30 min, then 1,2-dibromoethane (11.14 ml, 129 mmol) was added in portions keeping the temperature below −10° C. The reaction was allowed to warm up room temperature over 16 hours. The reaction mixture was then diluted with water and extracted with ethyl acetate. The combined organic extracts were washed with saturated brine once, then dried over sodium sulfate, filtered, and concentrated down to a brown solid. The solid was purified on a silica gel column, eluted with heptane/DCM 75/25 (v/v) to provide 3-bromo-2-methoxyphenanthrene as a white solid (13.0 g, 80% yield).

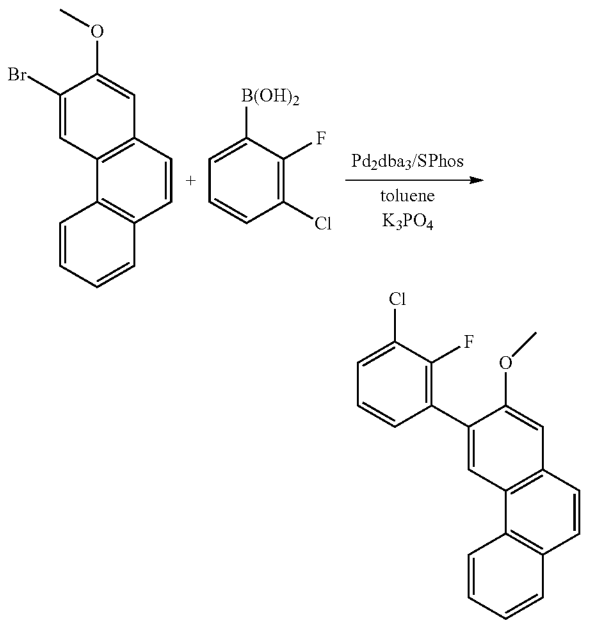

3-Bromo-2-methoxyphenanthrene (13.0 g, 45.3 mmol), (3-chloro-2-fluorophenyl)boronic acid (7.89 g, 45.3 mmol), potassium phosphate tribasic monohydrate (31.3 g, 136 mmol) and toluene (400 ml) were combined in a flask. The solution was purged with nitrogen for 15 min, then tris (dibenzylideneacetone)dipalladium(0) (1.244 g, 1.358 mmol) and dicyclohexyl(2',6'-dimethoxy-[1,1'-biphenyl]-2-yl)phosphane (SPhos, 2.230 g, 5.43 mmol) were added. The reaction mixture was heated to reflux under nitrogen for 13 hours. Another 0.5 g of (3-chloro-2-fluorophenyl)boronic acid, 0.2 g of $Pd_2dba_3$ and 0.4 g of dicyclohexyl(2',6'-dimethoxy-[1,1'-biphenyl]1-2-yl)phosphane were added and the reaction mixture was maintained at reflux for another day to complete the reaction.

The resulting reaction solution was decanted off and the flask was rinsed twice with ethyl acetate. The resulting black residue was dissolved with water, extracted twice with ethyl acetate, and then filtered through filter paper to remove the black precipitate. The combined organic solution was washed once with brine, dried over sodium sulfate, filtered and concentrated down to a brown solid. The brown solid was purified on a silica gel column, eluting with heptanes/DCM 75/25 (v/v) mixture to isolate 3-(3-chloro-2-fluorophenyl)-2-methoxyphenanthrene (6.95 g, 45.6% yield).

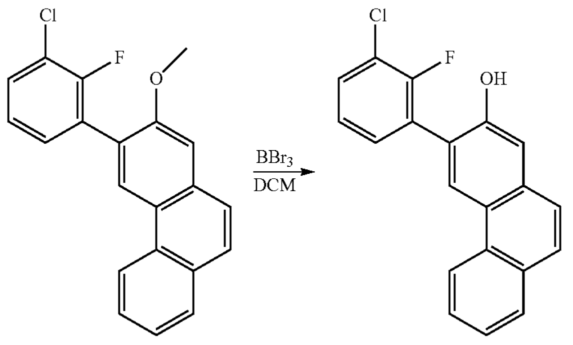

3-(3-Chloro-2-fluorophenyl)-2-methoxyphenanthrene (6.9 g, 20.49 mmol) was dissolved in DCM (100 mL) and was cooled in a brine/ice bath. Boron tribromide 1 M solution in DCM (41.0 mL, 41.0 mmol) was added rapidly dropwise, then the reaction was allowed to warm up to room temperature 22° C.) and stirred for 4 hours. The reaction was cooled in an ice bath, then carefully quenched with cold water. The reaction was stirred for 30 minutes, then more water was added and reaction was extracted with DCM. The combined DCM solution was washed once with water, dried over sodium sulfate, filtered and concentrated down to isolate 3-(3-chloro-2-fluorophenyl)phenanthren-2-ol as a beige solid (6.55 g, 99% yield).

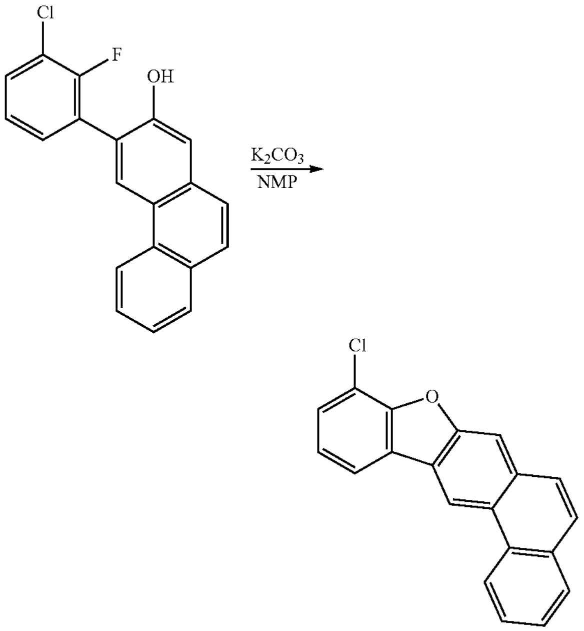

3-(3-Chloro-2-fluorophenyl)phenanthren-2-ol (6.5 g, 20.14 mmol) was dissolved in 1-methylpyrrolidin-2-one (NMP) (97 ml, 1007 mmol). The reaction was purged with nitrogen for 15 min, then potassium carbonate (8.35 g, 60.4 mmol) was added. The reaction was heated under nitrogen in an oil bath set at 150° C. for 8 hours. The reaction was diluted with water and extracted with ethyl acetate. The combined organic extracts were washed with brine, dried over sodium sulfate, filtered and concentrated down to a beige solid. The beige solid was purified on a silica gel column eluted with heptanes/DCM 85/15 (v/v) to obtain 9-chlorophenanthro[2,3-b]benzofuran as a white solid (5.5 g, 91% yield).

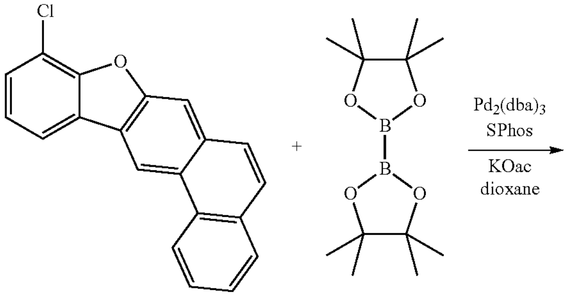

-continued

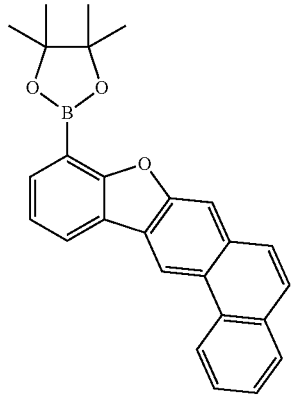

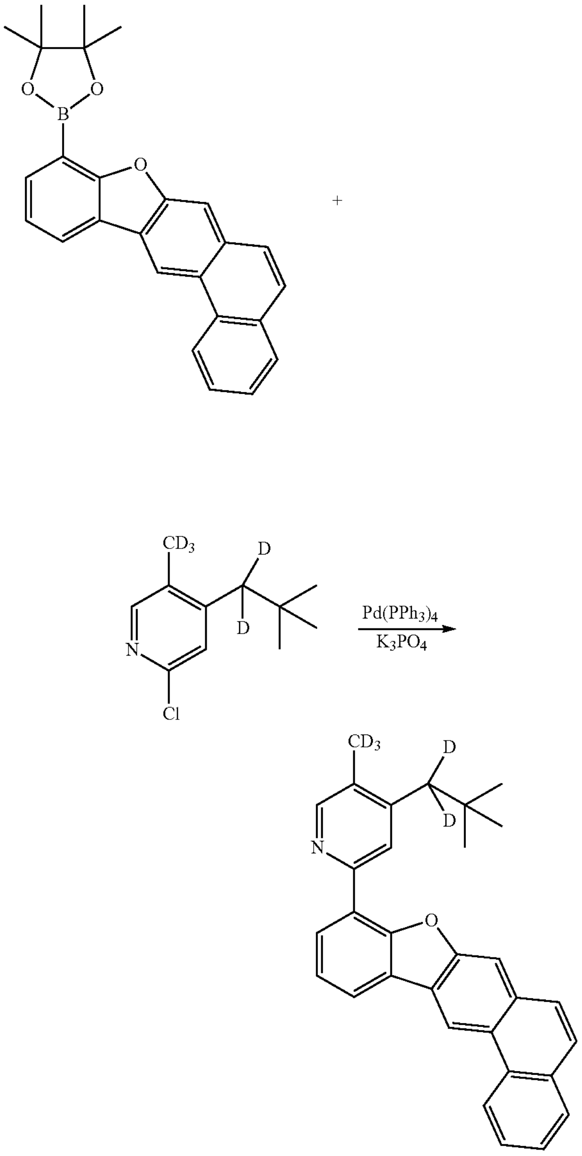

9-Chlorophenanthro[2,3-b]benzofuran (5.2 g, 17.18 mmol), 4,4,4',4',5,5,5',5'-octamethyl-2,2'-bi(1,3,2-dioxaborolane) (8.72 g, 34.4 mmol), and potassium acetate (5.06 g, 51.5 mmol) were suspended in 1,4-dioxane (150 ml). The reaction mixture was purged with nitrogen for 15 min, then tris(dibenzylideneacetone)dipalladium(0) (0.315 g, 0.344 mmol) and dicyclohexyl(2',6'-dimethoxy-[1,1'-biphenyl]-2-yl)phosphane (SPhos, 0.564 g, 1.374 mmol) were added. The reaction was heated in an oil bath set at 110° C. for 14 hours. The reaction was cooled to room temperature, then 2-chloro-4-(2,2-dimethylpropyl-1,1-d2)-5-(methyl-d3)pyridine (3.48 g, 17.18 mmol), potassium phosphate tribasic hydrate (10.94 g, 51.5 mmol) and 40 ml water were added. The reaction was purged with nitrogen for 15 min then tetrakis(triphenylphosphine)palladium(0) (0.595 g, 0.515 mmol) was added. The reaction was heated in an oil bath set at 100° C. for 14 hours.

The reaction mixture was diluted with ethyl acetate, washed once with water then brine once, then dried over sodium sulfate, filtered, then concentrated down to a beige solid. The beige solid was purified on a silica gel column eluting with heptanes/ethyl acetate/DCM 80/10/10 to 75/10/15 (v/v/v) gradient mixture to get 4-(2,2-dimethylpropyl-1,1-d2)-5-(methyl-d3)-2-(phenanthro[2,3-b]benzofuran-9-yl)pyridine (5.9 g, light yellow solid). The sample was additionally purified on a silica gel column eluting with toluene/ethyl acetate/DCM 85/5/10 to 75/10/15 (v/v/v) gradient mixture, providing 4-(2,2-dimethylpropyl-1,1-d2)-5-(methyl-d3)-2-(phenanthro[2,3-b]benzofuran-9-yl)pyridine as a white solid (3.75 g, 50.2% yield).

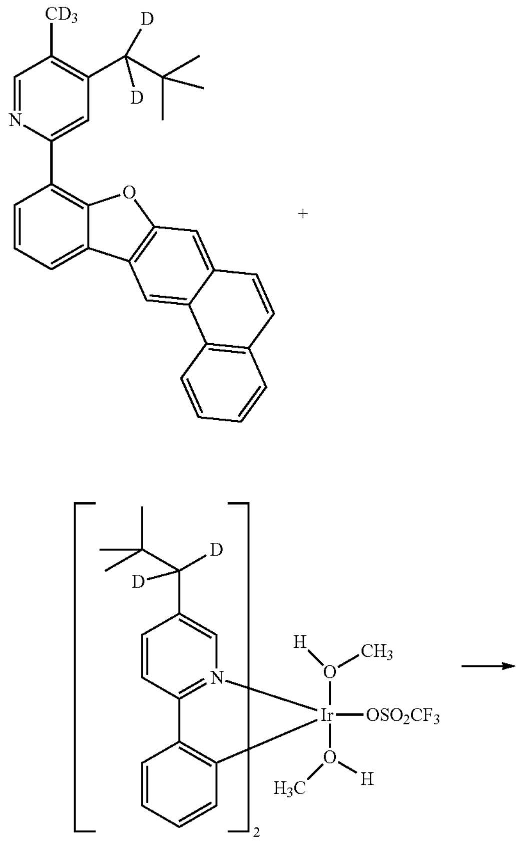

-continued

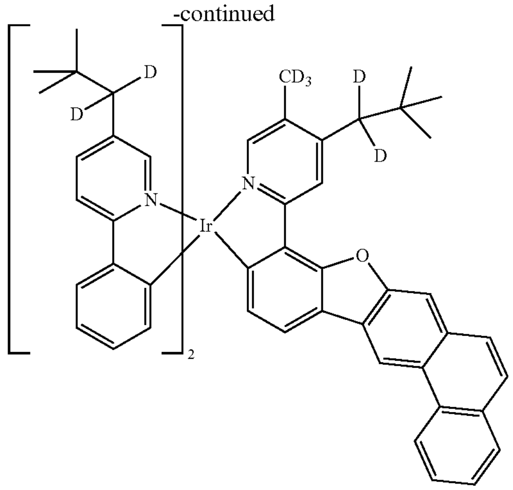

The triflic salt complex of iridium shown above (2.1 g, 2.61 mmol) and 442,2-dimethylpropyl-1,1-d2)-5-(methyl-d3)-2-(phenanthro[2,3-b]benzofuran-9-yl)pyridine (2.043 g, 4.70 mmol) were suspended in DMF (30 ml) and 2-ethoxyethanol (30.0 ml) mixture. The reaction mixture was purged with nitrogen for 15 min then heated to 80° C. for 10 days. The solvents were evaporated in vacuo, and the residue then was diluted with methanol (MeOH). A brown-yellow precipitate was filtered off and washed with MeOH. The precipitate was purified on a silica gel column eluting with heptanes/toluene 25/75 to 10/90 (v/v) gradient mixture to get a yellow solid. The solid was dissolved in DCM, the ethyl acetate was added and the resulting mixture concentrated down on the rotovap. The precipitate was filtered off and dried for 4 hours in vacuo to obtain the target compound, $IrL_{X169}(L_{B461})_2$, as a bright yellow solid (1.77 g, 62.8% yield).

Synthesis of $IrL_{X99}(L_{B461})_2$

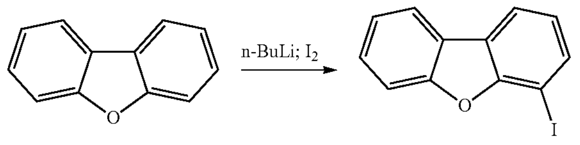 [SMILES: c1ccc2c(c1)oc1ccccc12 ; Ic1cccc2c1oc1ccccc12]

Dibenzo[b,d]furan (38.2 g, 227 mmol) was dissolved in dry THF (450 ml) under a nitrogen atmosphere. The solution was cooled in a dry ice-acetone bath, then a 2.5 M n-butyllithium solution in hexanes (100 ml, 250 mmol) was added dropwise. The reaction mixture was stirred at room temperature (~22° C.) for 5 hours, then cooled in a dry ice-acetone bath. Iodine (57.6 g, 227 mmol) in 110 mL of THF was added dropwise, then the resulting mixture was allowed to warm to room temperature over 16 hours. Saturated sodium bicarbonate solution and ethyl acetate were added and the resulting reaction mixture was stirred, the layers separated, and the aqueous phase was extracted with ethyl acetate while the combined organic extracts were washed with sodium bisulfite solution, dried over magnesium sulfate, filtered and evaporated. The resulting composition was purified on a silica gel column eluting with heptane, the recrystallized from 250 mL heptanes. The solid material was filtered off, washed with heptane and dried, to yield 4-iododibenzo[b,d]furan (43.90 g, 64% yield).

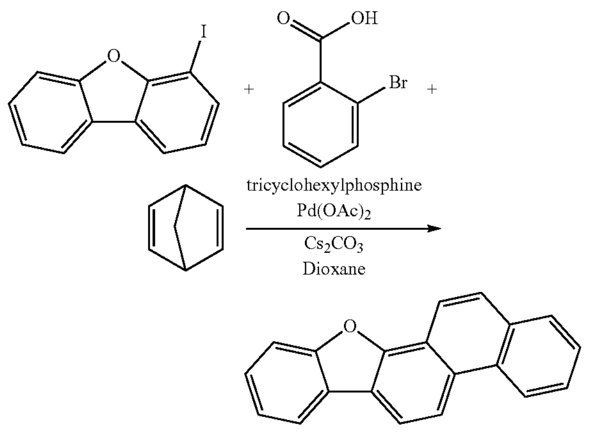

4-Iododibenzo[b,d]furan (10.52 g, 35.8 mmol), 2-bromobenzoic acid (14.38 g, 71.5 mmol), tricyclohexylphosphine tetraflouroborate (1.970 g, 5.37 mmol), and cesium carbonate (46.6 g, 143 mmol) were suspended in dioxane (300 ml). The reaction mixture was degassed and bicyclo [2.2.1]hepta-2,5-diene (14.49 ml, 143 mmol) was added followed by palladium acetate (0.402 g, 1.789 mmol). The reaction mixture was then heated to 130° C. After 2 hours, bicyclo[2.2.1]hepta-2,5-diene (14.49 ml, 143 mmol) at 130° C. for 16 hours under nitrogen. Water was added and the resulting composition was extracted twice with ethyl acetate. The organic solution was dried over magnesium sulfate, filtered, evaporated, and the residue dissolved in DCM. The target compound was purified using a silica gel column eluting with 0-40% DCM in heptanes. The resulting product was then triturated with heptanes, filtered, and washed with heptanes to yield phenanthro[1,2-b]benzofuran (5.0 g, 52% yield).

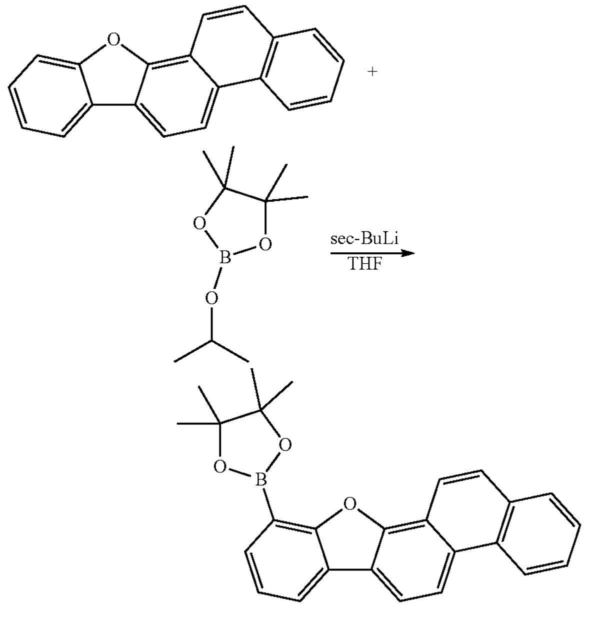

Phenanthro[1,2-b]benzofuran (4 g, 14.91 mmol) was dissolved in dry THF (80 mL). The solution was cooled in a dry ice-acetone bath, and sec-butyllithium hexanes solution (15.97 ml, 22.36 mmol) was added. The reaction was stirred in a cooling bath for 3 hours, and 2-isopropoxy-4,4,5,5-tetramethyl-1,3,2-dioxaborolane (6.08 ml, 29.8 mmol) in 10 mL THF was added and the resulting reaction mixture was stirred for 16 hours at room temperature under nitrogen. The resulting mixture was quenched with water, extracted twice with ethyl acetate, then the organics were washed with brine, dried organics over magnesium sulfate, filtered, evaporated to yield 4,4,5,5-Tetramethyl-2-(phenanthro[1,2-b]benzofuran-12-yl)-1,3,2-dioxaborolane (5.88 g) as a solid.

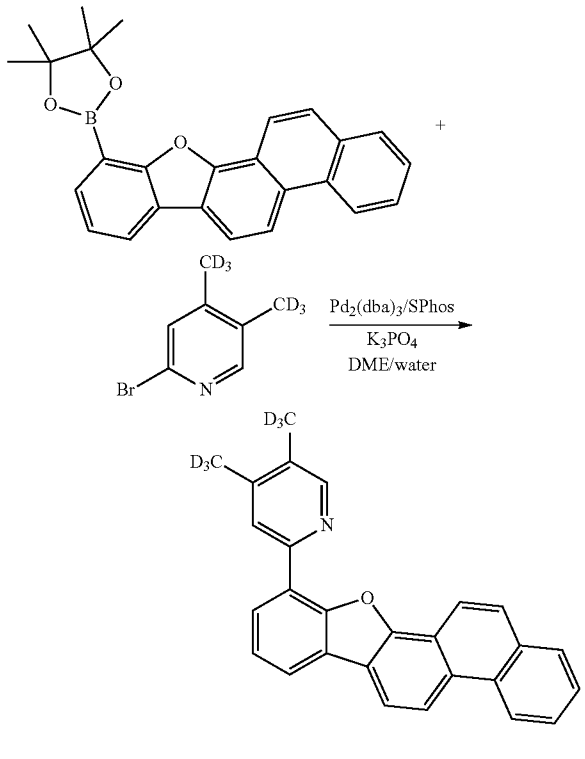

4,4,5,5-Tetramethyl-2-(phenanthro[1,2-b]benzofuran-12-yl)-1,3,2-dioxaborolane (7.3 g, 17.59 mmol), 2-bromo-4,5-bis(methyl-d3)pyridine (3.72 g, 19.35 mmol), dicyclohexyl (2',6'1-dimethoxy-[1,1'-biphenyl]-2-yl)phosphane (SPhos, 0.433 g, 1.055 mmol), and potassium phosphate tribasic monohydrate (8.10 g, 35.2 mmol) were suspended in a dimethyl ether (DME)(120 mL) and water (20.00 mL) mixture. The reaction mixture was degassed, tris(dibenzylideneacetone)dipalladium(0) (0.483 g, 0.528 mmol) was added, and the resulting mixture heated to 100° C. under nitrogen for 13 hours. The mixture was then diluted with water and ethyl acetate, and an insoluble solid was filtered off, the layers separated with the aqueous layer being extracted with ethyl acetate and the organics being dried over magnesium sulfate. They were then filtered and evaporated to a brown oil. Very little product in the brown oil. The insoluble material is the product. Most of the insoluble material was dissolved in 350 mL of hot DCM, filtered through a silica plug to remove a black impurity and a small amount of insoluble white solid. A white solid precipitated out of the yellow filtrate. The solid was filtered off to obtain 4,5-bis(methyl-d3)-2-(phenanthro[1,2-b]benzofuran-12-yl) pyridine as white solid (2.27 g, 34% yield).

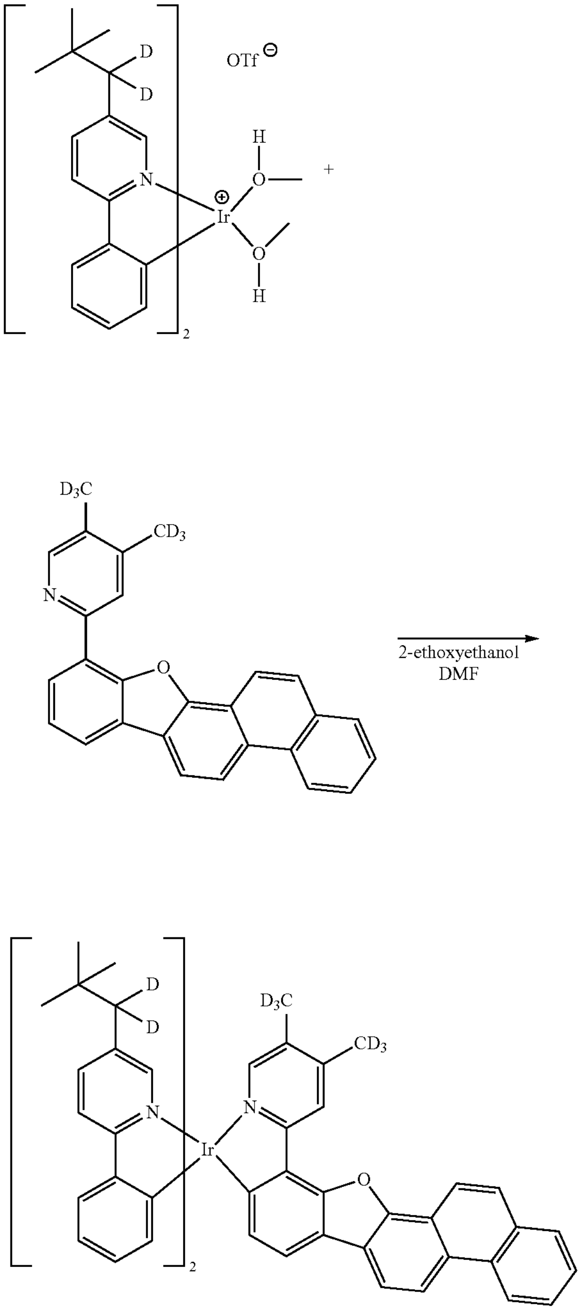

4,5-Bis(methyl-d3)-2-(phenanthro[1,2-b]benzofuran-12-yl)pyridine (2.70 g, 7.13 mmol) was suspended in DMF (120 ml), heated to 100° C. in an oil bath to dissolve solid materials. 2-ethoxyethanol (40 ml) was added, then the resulting mixture was cooled until a solid precipitated and the iridium complex triflic salt (3.38 g, 4.07 mmol) shown above degassed and heated to 100° C. under nitrogen until the solids dissolved. The resulting mixture was heated at 100° C. under nitrogen for 2 weeks before being cooled down to room temperature. The solvent was then evaporated in vacuo. The solid residue was purified by column chromatography on a silica gel column, eluting with 70 to 90% toluene in heptanes. The target material, $IrL_{X99}(L_{B461})_2$, was isolated as a bright yellow solid (1.53 g, 37% yield).

Synthesis of Compound $IrL_{X101}(L_{B463})_2$

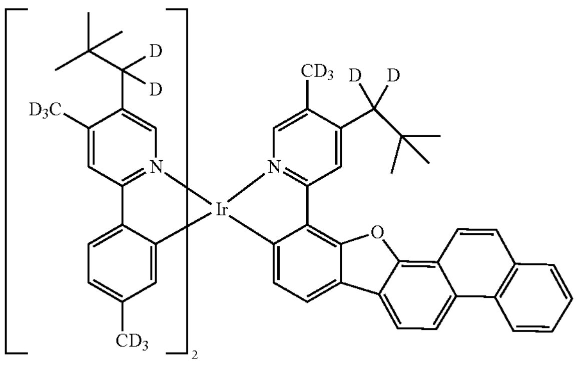

Compound $IrL_{X101}(L_{B463})_2$ was synthesized using the same techniques as $IrL_{X99}(L_{B461})_2$.

Synthesis of $IrL_{X152}(L_{B461})_2$

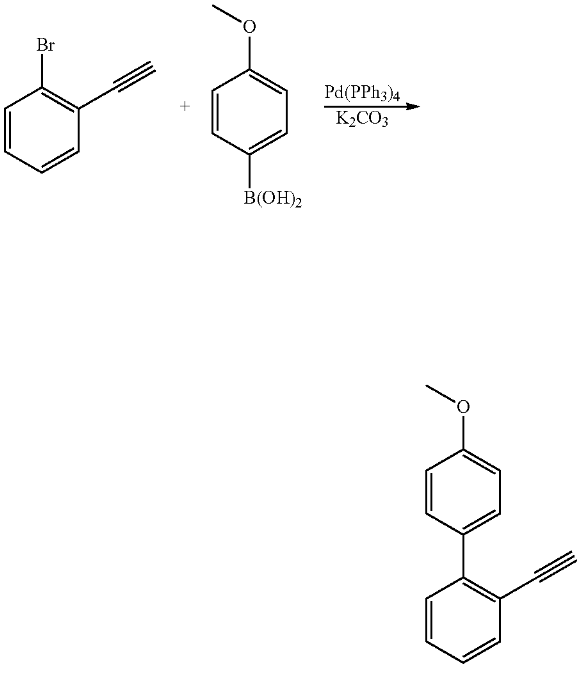

(4-Methoxyphenyl)boronic acid (26.2 g, 173 mmol) and potassium carbonate (47.7 g, 345 mmol) were suspended in DME (500 ml) and water (125 ml). The solution was purged with nitrogen for 15 min then 1-bromo-2-ethynylbenzene (25 g, 138 mmol) and tetrakis(triphenylphosphine) palladium(0) (4.79 g, 4.14 mmol) were added. The reaction mixture was heated to reflux under nitrogen for 14 hours. The heating was stopped, and the organic phase was separated and concentrated down to a dark oil. It was purified by column chromatography on silica gel, eluted with heptanes/DCM 3/1 (v/v), providing 2-ethynyl-4'-methoxy-1,1'-biphenyl as an orange oil (20.0 g, 69% yield).

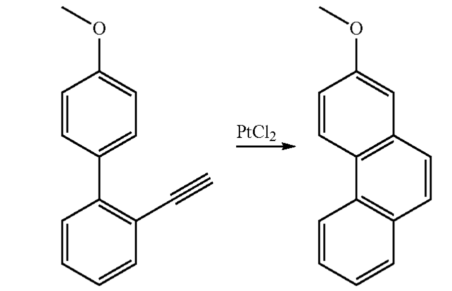

2-Ethynyl-4'-methoxy-1,1'-biphenyl (20 g, 96 mmol) and platinum(II) chloride (2.55 g, 9.60 mmol) were suspended in 600 ml of toluene. The reaction was heated to 80° C. for 14 hours. Toluene was evaporated, and the residue was subjected to column chromatography on a silica gel eluted with heptanes/DCM 85/15 (v/v) to isolate 2-methoxyphenanthrene (13.8 g, 69% yield).

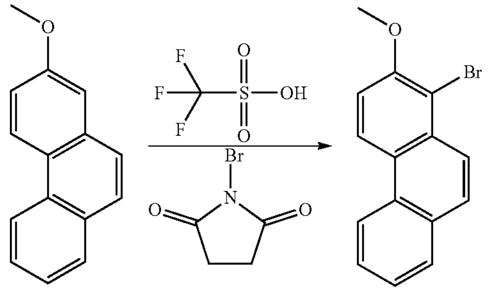

2-Methoxyphenanthrene (13.86 g, 66.6 mmol) was dissolved in acetonitrile (500 ml) and the mixture was cooled to −20° C. Trifluoromethanesulfonic acid (6.46 ml, 73.2 mmol) was slowly added, followed by 1-bromopyrrolidine-2,5-dione (13.03 g, 73.2 mmol). The mixture was allowed to warm up to room temperature and stirred for 5 hours. The reaction was quenched with water and extracted with ethyl acetate (EtOAc). The organic extracts were combined, dried over sodium sulfate, filtered and evaporated. The residue was purified on silica gel column eluted with 20% DCM in heptane to isolate 1-bromo-2-methoxyphenanthrene (21 g, 99% yield).

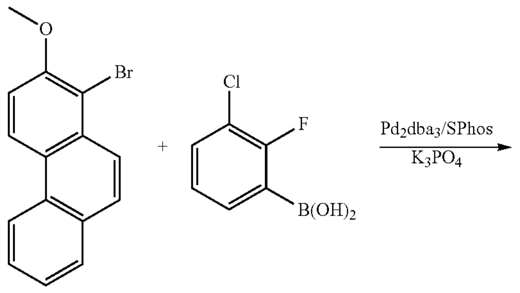

-continued

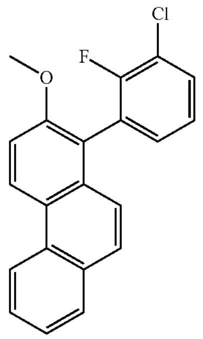

1-Bromo-2-methoxyphenanthrene (19 g, 66.2 mmol), tris(dibenzylideneacetone)dipalladium(0) (1.212 g, 1.323 mmol), (3-chloro-2-fluorophenyl)boronic acid (13.84 g, 79 mmol), SPhos (2.173 g, 5.29 mmol) and potassium phosphate tribasic monohydrate (3 eq.) were suspended in DME (250 ml)/water (50.0 ml). The mixture was degassed and heated to 90° C. for 14 hours. After the reaction mixture was cooled down to room temperature, the mixture was diluted with water and extracted with ethyl acetate (EtOAc). The organic phase was separated, dried over sodium sulfate, filtered and evaporated. The resulting residue was purified on a silica gel column eluted with a mixture of heptane and DCM (8/2, v/v) to give yield 1-(3-chloro-2-fluorophenyl)-2-methoxyphenanthrene (19 g, 56.4 mmol, 85% yield).

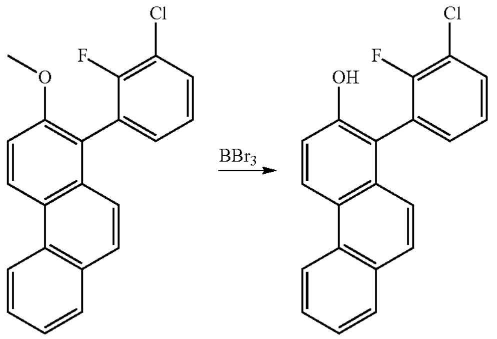

1-(3-Chloro-2-fluorophenyl)-2-methoxyphenanthrene (19 g, 56.4 mmol) was dissolved in DCM (200 ml) and cooled in the ice bath. A 1 M boron tribromide solution in DCM (113 ml, 113 mmol) was added dropwise. The mixture was stirred at room temperature for 16 hours and quenched with water at 0° C. The mixture was extracted with DCM, and the organic phases were combined. The solvent was evaporated, and the residue was purified on a silica gel column eluted with 7/3 DCM/heptane (v/v) to yield 1-(3-chloro-2-fluorophenyl)phenanthren-2-ol (16.5 g, 51.1 mmol, 91% yield).

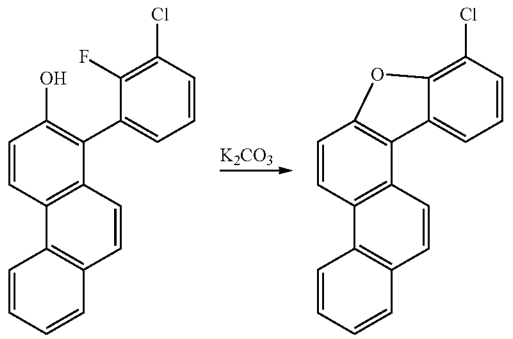

A mixture of 1-(3-chloro-2-fluorophenyl)phenanthren-2-ol (16.5 g, 51.1 mmol) and $K_2CO_3$ (21.20 g, 153 mmol) in 1-methylpyrrolidin-2-one (271 ml, 2812 mmol) was vacuumed and filled with argon gas. The mixture was heated at 150° C. for 16 hours. After cooling to room temperature, the solution was extracted with EtOAc, and the organic extract was washed with brine. The solvent was evaporated, and the residue was purified on a silica gel column eluted with a heptane/DCM gradient mixture followed by crystallization from DCM/heptanes to give 8-chlorophenanthro[2,1-b]benzofuran (10 g, 33.0 mmol, 64.6% yield).

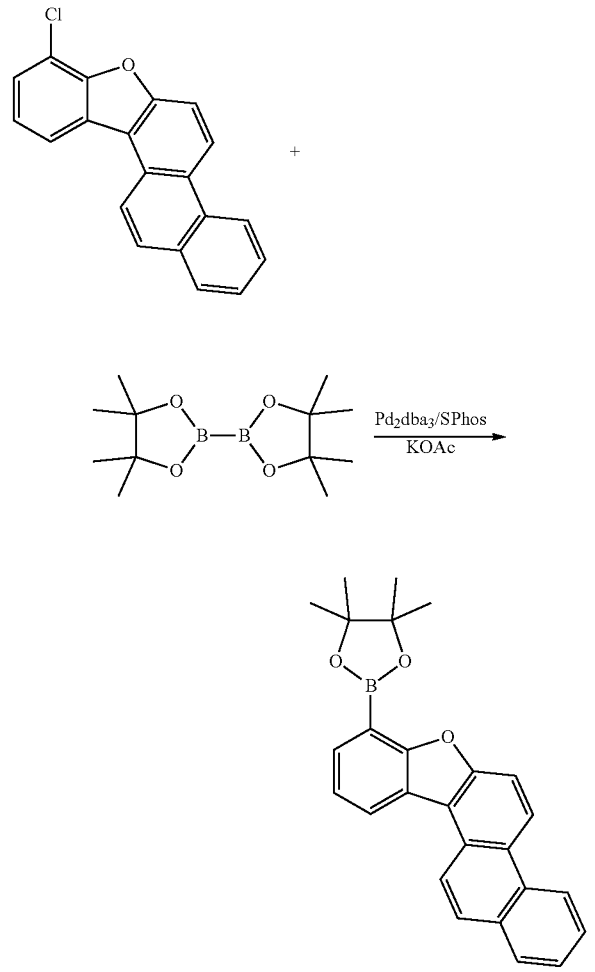

-continued

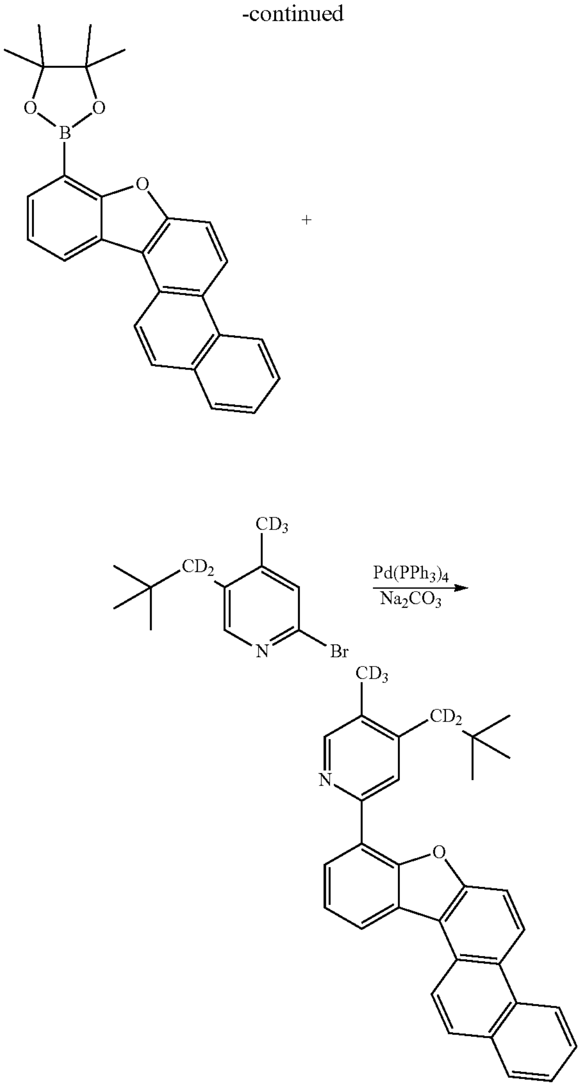

8-Chlorophenanthro[2,1-b]benzofuran (3.0 g, 9.91 mmol), 4,4,4',4',5,5,5',5'-octamethyl-2,2'-bi(1,3,2-dioxaborolane) (5.03 g, 19.8 mmol) and potassium acetate (2.92 g, 30 mmol) were suspended in 100 mL of dry 1,4-dioxane. Tris(dibenzylideneacetone)dipalladium(0) (181 mg, 2 mol. %) and dicyclohexyl(2',6'-dimethoxy-[1,1'-biphenyl]-2-yl)phosphane (Sphos, 325 mg, 8 mol. %) were added as one portion. The reaction mixture was degassed and heated to reflux under nitrogen for 14 hours. It was then cooled down to room temperature, and sodium carbonate (3.15 g, 30 mmol), 10 mL of water, tetrakis(triphenylphosphine)palladium(0) (344 mg, 3 mol. %) and 2-chloro-4-(2,2-dimethylpropyl-1,1-d2)-5-(methyl-d3)pyridine (2.03 g, 9.9 mmol) were added. The reaction mixture was degassed and heated to reflux under nitrogen for 12 hours. The organic phase was separated, while the aqueous phase was extracted with ethyl acetate. The combined organic solutions were dried over sodium sulfate, filtered and evaporated. The residue was subjected to column chromatography on silica gel eluted with heptanes/ethyl acetate 5-10% gradient mixture to yield 4-(2,2-dimethylpropyl-1,1-d2)-5-(methyl-d3)-2-(phenanthro[2,1-b]benzofuran-8-yl)pyridine as white solid (2.37 g, 63% yield).

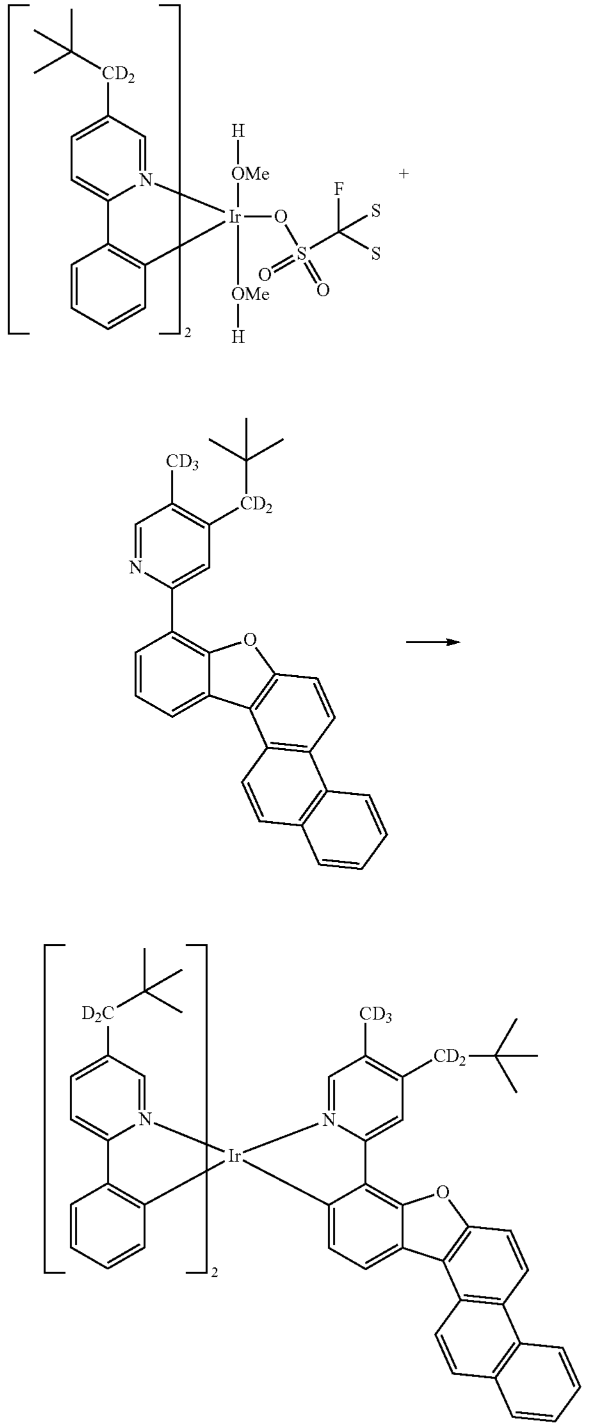

The iridium complex triflic salt shown above (2.0 g, 2.33 mmol) and 442,2-dimethylpropyl-1,1-d2)-5-(methyl-d3)-2-(phenanthro[2,1-b]benzofuran-8-yl)pyridine (2.127 g, 4.89 mmol) were suspended in a DMF (30 mL)/2-ethoxyethanol (30 mL) mixture. The reaction mixture was degassed and heated to 100° C. for 10 days. Solvents were evaporated in vacuum, and the residue was subjected to column chromatography on silica gel column eluted with toluene/DCM/heptanes 4/3/3 (v/v/v) to produce the target material, $IrL_{X152}(L_{B461})_2$, as bright yellow solid (1.25 g, 50% yield).

Synthesis of $IrL_{X79}(L_{B463})_2$

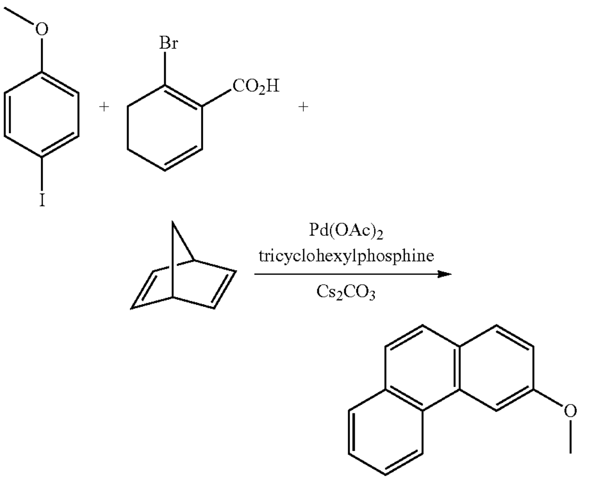

In a nitrogen flushed 500 mL two-necked round-bottomed flask, 1-iodo-4-methoxybenzene (12 g, 51.3 mmol), 2-bromobenzoic acid (20.61 g, 103 mmol), cesium carbonate (75 g, 231 mmol), diacetoxypalladium ($Pd(OAc)_2$) (0.576 g, 2.56 mmol) and tricyclohexylphosphine, $BF_4$-salt (2.82 g, 7.69 mmol) were dissolved in 200 ml of 1,4-dioxane under nitrogen to give a red suspension. The reaction mixture was heated to reflux under nitrogen for 14 hours. It was then cooled down to room temperature, diluted with water and extracted with EtOAc. Organic solution was dried over $Na_2SO_4$ and evaporated. The crude product was added to a silica gel column and was eluted with DCM/heptanes gradient mixture to give 3-methoxyphenanthrene (3.5 g, 16.81 mmol, 32.8% yield) as a yellow solid.

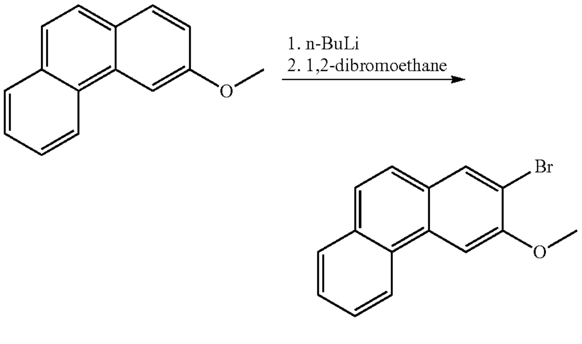

3-Methoxyphenanthrene (2.73 g, 13.11 mmol) was dissolved in dry THF under a nitrogen atmosphere and cooled in an IPA/dry ice bath. A solution of n-butyllithium in THF (8.39 ml, 20.97 mmol) was added to the reaction via syringe. The reaction mixture was warmed up to room temperature and stirred for 4 hours. Then, it was cooled down to −75°, and 1,2-dibromoethane was added via syringe. The reaction mixture was then warmed to room temperature and stirred for 16 hours. The resulting reaction mixture was evaporated and purified by column chromatography on a silica gel eluted with heptanes/DCM 3/1 (v/v) to yield 2-bromo-3-methoxyphenanthrene (2.65 g, 70% yield).

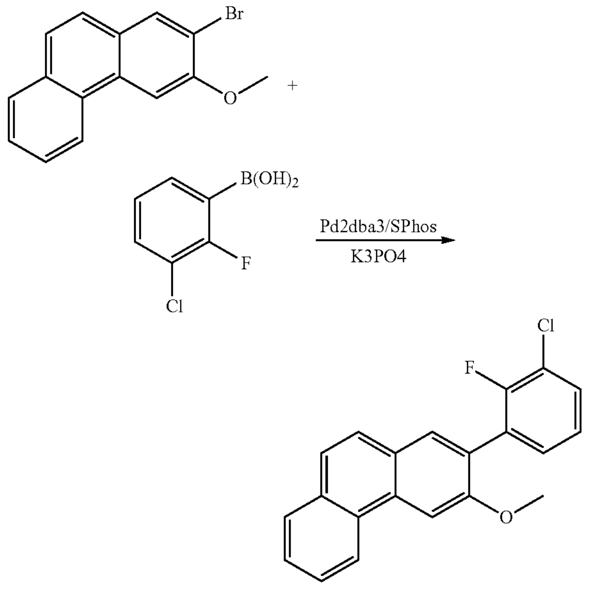

In a nitrogen flushed 500 mL two-necked round-bottomed flask, 2-bromo-3-methoxyphenanthrene (8.9 g, 31.0 mmol), (3-chloro-2-fluorophenyl)boronic acid (9.73 g, 55.8 mmol), and potassium phosphate tribasic hydrate (21.41 g, 93 mmol) were dissolved in a DME (80 ml)/toluene (80 ml) mixture under nitrogen to give a colorless suspension. Tris(dibenzylideneacetone)dipalladium(0) (0.568 g, 0.620 mmol) and dicyclohexyl(2',6'-dimethoxy-[1,1'-biphenyl]-2-yl)phosphane (SPhos, 1.018 g, 2.479 mmol) were added to the reaction mixture in one portion. The reaction mixture was degassed and heated to reflux under nitrogen for 16 hours. The reaction mixture was then cooled down, filtered through a silica gel and evaporated. The crude product was added to a silica gel column eluted with heptanes/DCM 3/1 (v/v) to yield 2-(3-chloro-2-fluorophenyl)-3-methoxyphenanthrene (8.5 g, 25.2 mmol, 81% yield) as a white solid.

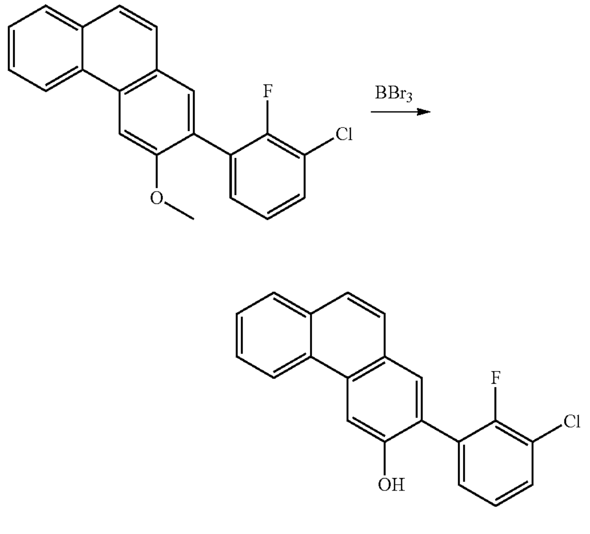

In a nitrogen flushed 500 mL round-bottomed flask, 2-(3-chloro-2-fluorophenyl)-3-methoxyphenanthrene (7.85 g, 23.31 mmol) was dissolved in DCM (100 ml) under nitrogen to give a colorless solution. The reaction mixture was cooled to −20° C. with a dry ice/acetonitrile bath. A 1 M solution of tribromoborane in DCM (46.6 ml, 46.6 mmol) was added to the reaction mixture over 30 min. The reaction mixture was allowed to warm to room temperature and was stirred for 14 hours. The reaction mixture was carefully quenched with cold water, diluted with DCM, and washed with water. The organic solution was dried over sodium sulfate, filtered and concentrated. The crude product was added to a silica gel column and eluted with heptanes/ethyl acetate 1/1 (v/v) to give 2-(3-chloro-2-fluorophenyl)phenanthren-3-ol (6.2 g, 19.21 mmol, 82% yield) as a yellow solid.

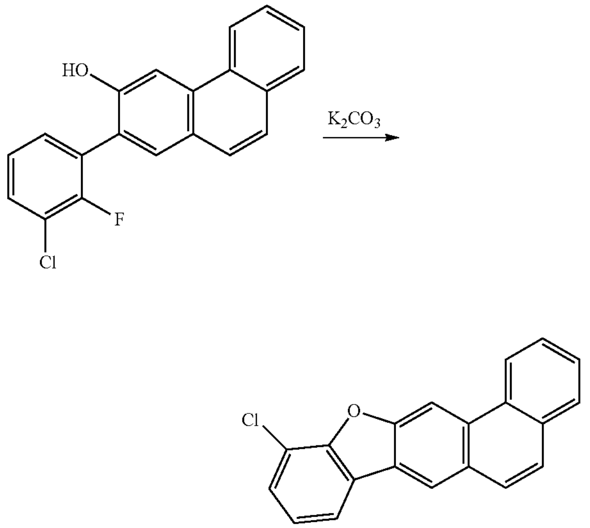

2-(3-Chloro-2-fluorophenyl)phenanthren-3-ol (12 g, 37 mmol) and potassium carbonate (10.3 g, 2 eq.) were suspended in 100 mL of N-methylpyrrolidone (NMP), degassed and heated to 120° C. for 14 hours. About half of the NMP solvent was then evaporated and the reaction mixture was diluted with 10% aq. solution of LiCl. The product was precipitated from the reaction mixture and was then filtered off. It was purified by column chromatography on silica gel column and eluted with heptanes/DCM 7/3 (v/v) to obtain 1-chlorophenanthro[3,2-b]benzofuran (9.1 g, 81% yield).

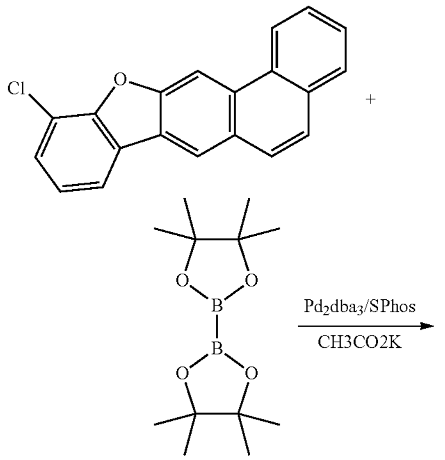

-continued

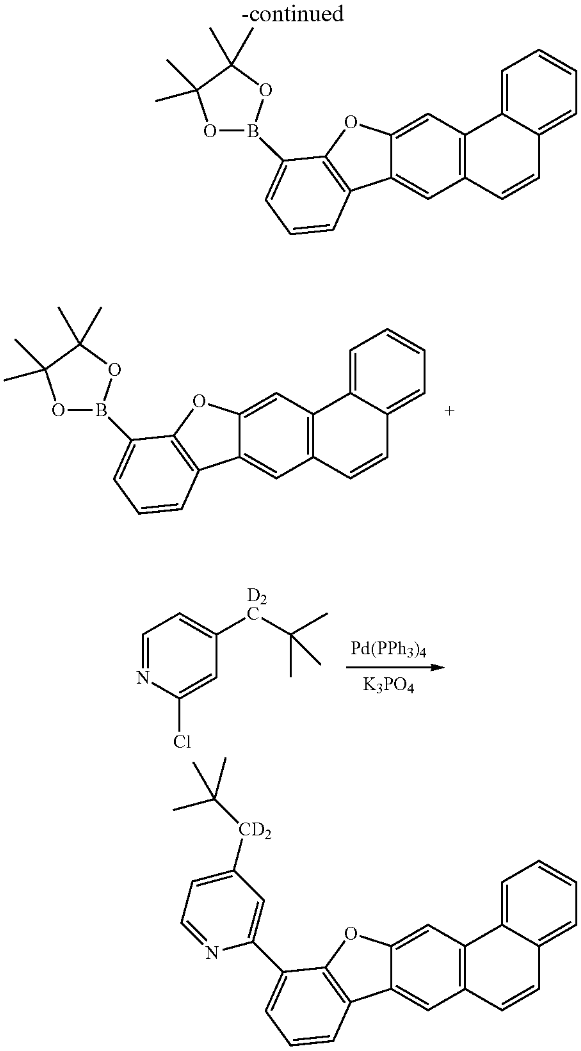

1-Chlorophenanthro[3,2-b]benzofuran (3.0 g, 9.9 mmol), 4,4,4',4',5,5,5',5'-octamethyl-2,2'-bi(1,3,2-dioxaborolane) (4.03 g, 16 mmol) and potassium acetate (1.94 g, 20 mmol) were suspended in 100 mL of dry dioxane. Tris(dibenzylideneacetone)dipalladium(0) (181 mg, 2 mol. %) and dicyclohexyl(2',6'-dimethoxy-[1,1'-biphenyl]-2-yl)phosphane (SPhos, 325 mg, 4 mol. %) were added as one portion. The reaction mixture was degassed and heated to reflux under nitrogen for 16 hours. The reaction mixture was cooled to room temperature, and potassium phosphate tribasic hydrate (4.56 g, 19.8 mmol), 2-chloro-4-(2,2-dimethylpropyl-1,1-d2)pyridine (1.84 g, 9.9 mmol), 10 mL of water, tetrakis (triphenylphosphine)palladium(0) (229 mg, 2 mol. %) and 75 mL of DMF were added.

The reaction mixture was degassed and immersed in an oil bath at 90° C. for 16 hours. The reaction mixture was then cooled to room temperature, diluted with water, and extracted with ethyl acetate. The organic extracts were combined, dried over anhydrous sodium sulfate, filtered and evaporated. The resulting material was purified on a silica gel column eluted with heptanes/ethyl acetate 3-20% gradient mixture to obtain pure 4-(2,2-dimethylpropyl-1,1-d2)-2-(phenanthro[3,2-b]benzofuran-11-yl)pyridine (1.9 g, 47% yield).

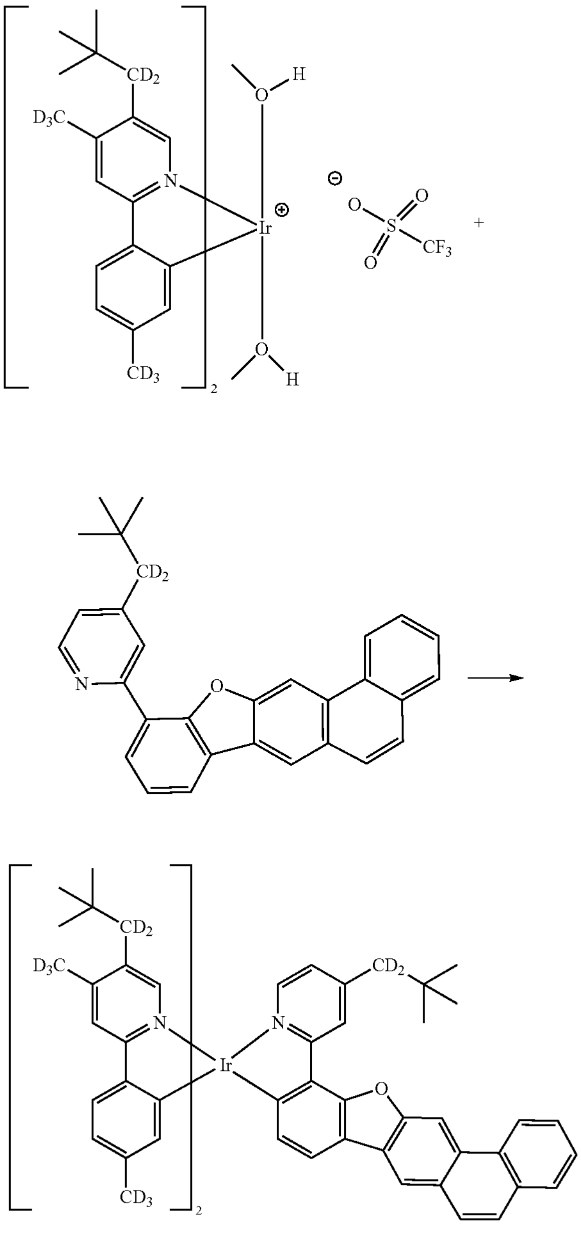

4-(2,2-Dimethylpropyl-1,1-d2)-2-(phenanthro[3,2-b]benzofuran-11-yl)pyridine (1.62 g, 1.8 eq.) was dissolved in 75 mL of 2-ethoxyethanol/DMF mixture (1/1, v/v) at room temperature and the iridium complex triflic salt (1.44 g, 1.0 eq.) shown above was added as one portion. The reaction mixture was degassed and immersed in the oil bath at 100° C. for 7 days. The reaction mixture was cooled down, diluted with water and a yellow precipitate was filtered off. The precipitate was washed with water, methanol and heptanes and dried in vacuo. The residue was subjected to column chromatography on a silica gel column eluted with heptanes/toluene/DCM mixture (70/15/15, v/v/v) to yield the target complex as bright yellow solid. Additional crystallization from toluene/heptanes provided 1.2 g (49% yield) of pure target material, $IrL_{X79}(L_{B463})_2$.

Compound $IrL_{X75}(L_{B284})_2$, below, was prepared by the same method with 45% yield at the last step:

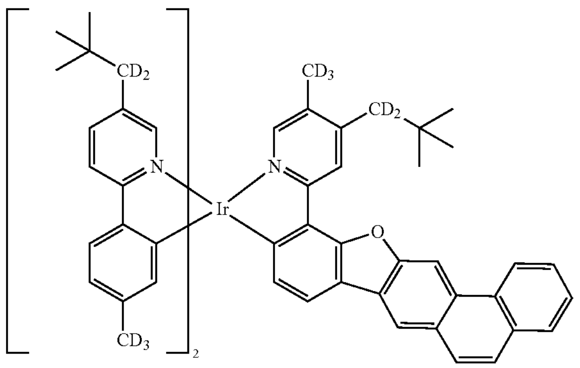

Synthesis of $IrL_{X114}(L_{B461})_2$

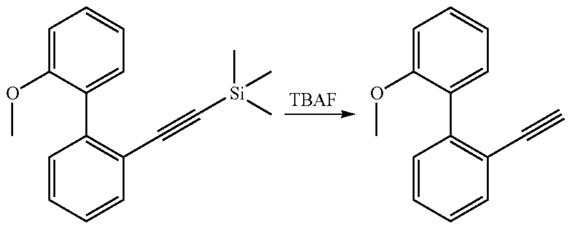

((2'-Methoxy-[1,1'-biphenyl]-2-yl)ethynyl)trimethylsilane (18 g, 64 mmol) was dissolved in 120 ml of THF and 1 N solution of tetra-n-butylammonium fluoride (TBAF) in THF (2 equivalents) was added dropwise. The reaction mixture was stirred for 12 hours at room temperature, diluted with water and extracted with ethyl acetate. The organic phase was dried over sodium sulfate, filtered and evaporated, providing 2-ethynyl-2'-methoxy-1,1'-biphenyl (13 g, 97% yield).

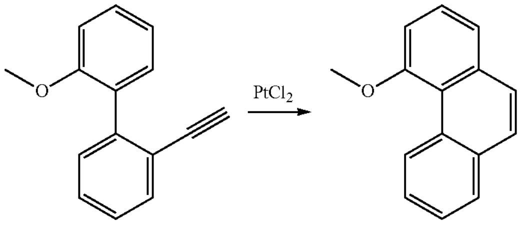

2-Ethynyl-2'-methoxy-1,1'-biphenyl (11.7 g, 56 mmol) and platinum (II) chloride (1.5 g, 0.1 eq.) were suspended in 250 mL of toluene and heated to reflux for 14 hours. The toluene was evaporated and the crude material was purified by column chromatography on a silica gel column, eluted with heptanes/DCM 9/1 (v/v), providing 4-methoxyphenanthrene (8.7 g, 74% yield).

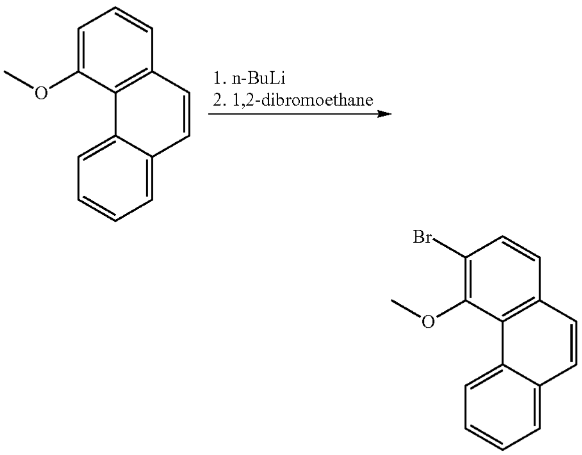

4-Methoxyphenanthrene (8.7 g, 42 mmol) was dissolved in 130 mL of dry THF under nitrogen atmosphere, added 0.5 mL of tetramethylethylenediamine (TMEDA) and solution was cooled in the isopropanol (IPA)/dry ice cooling bath. N-Butyl lithium (1.6 M solution in THF, 2 eq.) was added dropwise, and the reaction mixture was stirred for 2 hours at −78° C. 1,2-Dibromoethane (19.6 g, 2.5 eq.) in 20 mL of dry THF was added dropwise and the reaction mixture was allowed to warm up to room temperature. It was concentrated on the rotovap, diluted with water and extracted with DCM. The organic phase was evaporated, and the residue was purified by column chromatography on a silica gel column, eluted with heptanes/DCM gradient mixture. 3-Bromo-4-methoxyphenanthrene (9.2 g, 77% yield) was obtained as white solid.

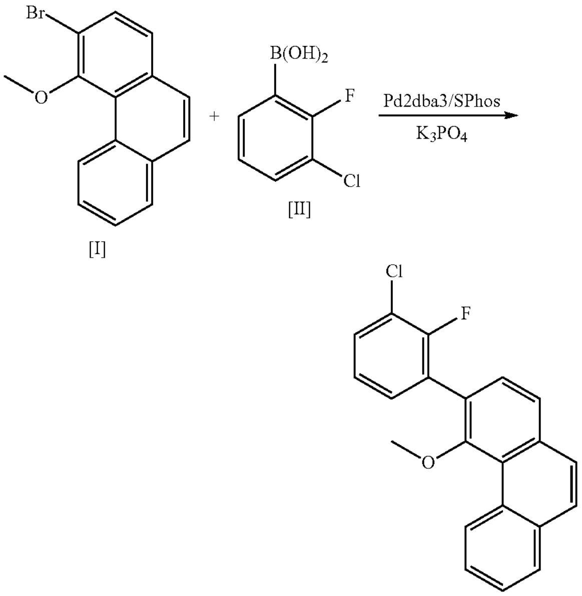

[I] [II]

3-Bromo-4-methoxyphenanthrene (15.0 g, 52 mmol), (3-chloro-2-fluorophenyl)boronic acid (9.11 g, 52 mmol), tris(dibenzylideneacetone)dipalladium(0) ($Pd_2(dba)_3$) (957 mg, 2 mol. %), dicyclohexyl(2',6'-dimethoxy-[1,1'-biphenyl]-2-yl)phosphane (SPhos, 1716 mg, 8 mol. %) and potassium phosphate tribasic hydrate (24.06 g, 104 mmol) were suspended in the 250 mL of dimethoxyethane (DME) and 50 mL of water mixture. The reaction mixture was degassed and heated to reflux under nitrogen for 14 hours. It was then cooled down to room temperature, diluted with ethyl acetate and washed with water. The organic solution was dried over anhydrous sodium sulfate, filtered and evaporated. The residue was subjected to column chromatography on a silica gel column, eluted with heptanes/ethyl acetate 5-10% gradient mixture, to yield 3-(3-chloro-2-fluorophenyl)-4-methoxyphenanthrene as white solid (14.8 g, 84% yield).

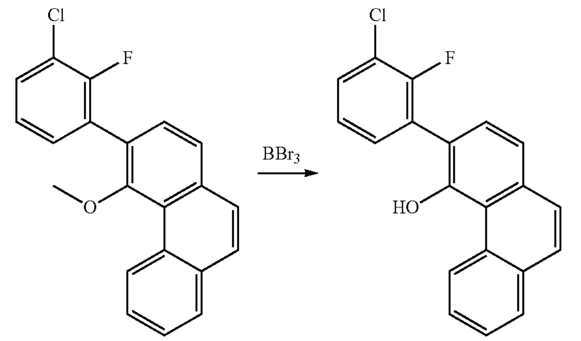

3-(3-Chloro-2-fluorophenyl)-4-methoxyphenanthrene (20 g, 59.4 mmol) was dissolved in 300 mL of DCM at room temperature. A 1M solution of boron tribromide in DCM (2 equivalents) was added dropwise and the reaction mixture was stirred at room temperature for 14 hours. The reaction mixture was quenched with water, then washed with water and sodium bicarbonate solution. The organic solution was dried and evaporated, and the residue was purified by column chromatography on a silica gel column, eluted with heptanes/ethyl acetate 1/1 (v/v), to yield pure 3-(3-chloro-2-fluorophenyl)phenanthren-4-ol (12.0 g, 59% yield).

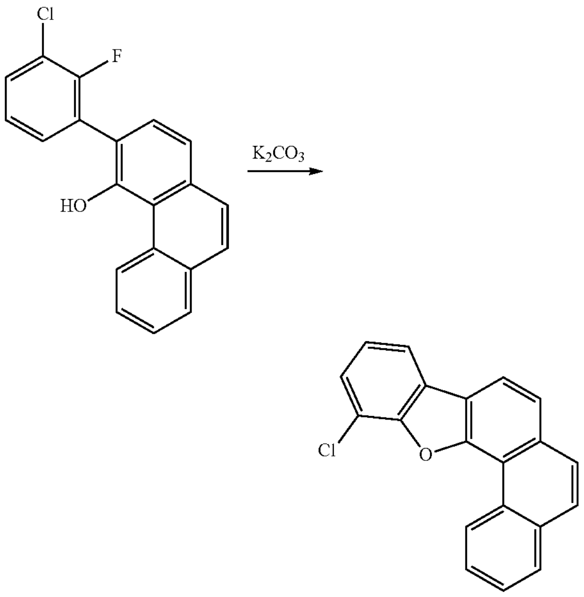

In an oven-dried 250 mL round-bottomed flask, 3-(3-chloro-2-fluorophenyl)phenanthren-4-ol (5.5 g, 17.04 mmol) and potassium carbonate (4.71 g, 34.1 mmol) were dissolved in N-methylpyrrolidone (NMP) (75 ml) under nitrogen to give a reddish suspension. The reaction mixture was degassed and heated to 120° C. for 10 hours. The reaction mixture was then cooled to room temperature, diluted with water, stirred and filtered. The precipitate was washed with water, ethanol, and heptanes. Crystallization of the precipitate from DCM/heptanes provided 12-chlorophenanthro[4,3-b]benzofuran (4.0 g, 78% yield).

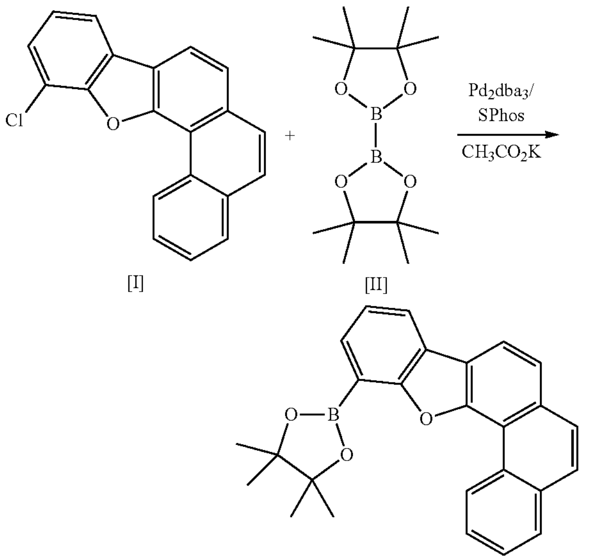

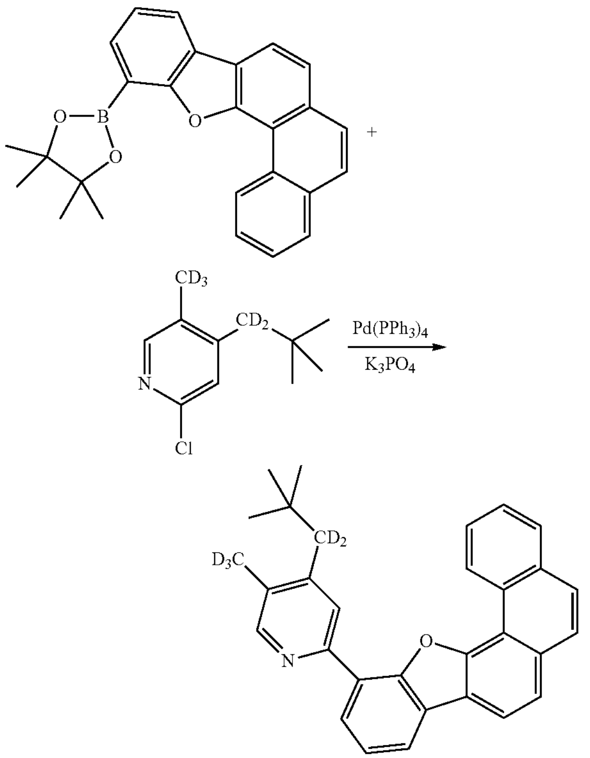

12-Chlorophenanthro[4,3-b]benzofuran (5 g, 16.5 mmol), 4,4,4',4',5,5,5',5'-octamethyl-2,2'-bi(1,3,2-dioxaborolane) (8.4 g, 33 mmol) and potassium acetate (3.24 g, 33 mmol) were suspended in 120 mL of dry dioxane. Tris(dibenzylideneacetone)dipalladium(0) (151 mg, 1 mol. %) and dicyclohexyl(2',6'-dimethoxy-[1,1'-biphenyl]-2-yl)phosphane (Sphos, 271 mg, 4 mol. %) were added as one portion. The reaction mixture was degassed and heated to reflux under nitrogen for 16 hours.

The reaction mixture was cooled down, added potassium phosphate tribasic hydrate (11.4 g, 3 equivalents), 10 mL of water, tetrakis(triphenylphosphine)palladium(0) (382 mg, 2 mol. %), 2-chloro-4-(2,2-dimethylpropyl-1,1-d2)-5-(methyl-d3)pyridine (3.68 g, 18.2 mmol) and 75 mL of dimethylformamide (DMF). The reaction mixture was degassed and immersed in the oil bath at 90° C. for 16 hours. The reaction mixture was then cooled down, diluted with water and extracted multiple times with ethyl acetate. The organic extracts were combined, dried over sodium sulfate anhydrous, filtered and evaporated. The resultant product was purified on a silica gel column, eluted with heptanes/ethyl acetate gradient mixture to yield pure 4-(2,2-dimethylpropyl-1,1-d2)-5-(methyl-d3)-2-(phenanthro[4,3-b]benzofuran-12-yl)pyridine (2.8 g, 39% yield).

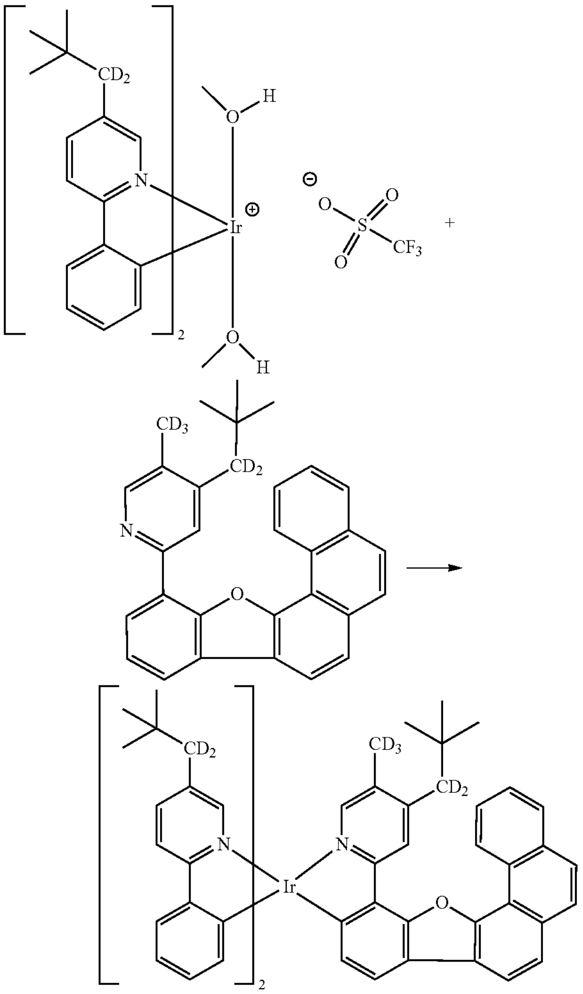

The iridium complex triflic salt shown above (2.1 g, 2.447 mmol) and 4-(2,2-dimethylpropyl-1,1-d2)-5-(methyl-d3)-2-(phenanthro[4,3-b]benzofuran-12-yl)pyridine (1.915 g, 4.41 mmol) were suspended together in a DMF (25 mL)/ethoxyethanol (25 mL) mixture, which was then degassed and heated in an oil bath at 100° C. for 10 days. The reaction mixture was cooled down, diluted with EtOAc (200 mL), washed with water and evaporated to obtain a crude product.

The crude product was added to a silica gel column and was eluted with heptanes/DCM/toluene 70/15/15 to 60/20/20 (v/v/v) gradient mixture to yield the target compound, $IrL_{X114}(L_{B461})_2$ (1.1 g, 1.020 mmol, 41.7% yield) as a yellow solid.

Synthesis of $IrL_{X206}(L_{B467})_2$

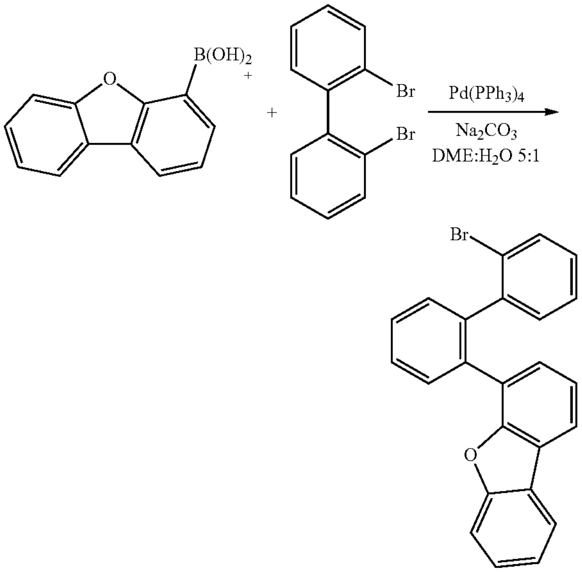

Dibenzo[b,d]furan-4-ylboronic acid (10 g, 47.2 mmol), 2,2'-dibromo-1,1'-biphenyl (22.07 g, 70.8 mmol), sodium carbonate (12.50 g, 118 mmol), dimethoxyethane (DME) (200 ml), and water (40 ml) were combined in a flask. The reaction mixture was purged with nitrogen for 15 minutes, then tetrakis(triphenylphosphine)palladium(0) (1.635 g, 1.415 mmol) was added. The reaction mixture was heated in an oil bath set at 90° C. or 16 hours. The reaction mixture was then transferred to a separatory funnel and was extracted twice with ethyl acetate. The combined organics were washed with brine once, dried with sodium sulfate, filtered, and concentrated down to a brown oil. The brown oil was purified on a silica gel column, using 95/5 to 90/10 heptanes/DCM (v/v) to get a clear solidified oil of 4-(2'-bromo-[1,1'-biphenyl]-2-yl)dibenzo[b,d]furan (11.25 g, 59.7% yield).

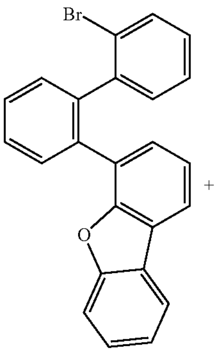

-continued

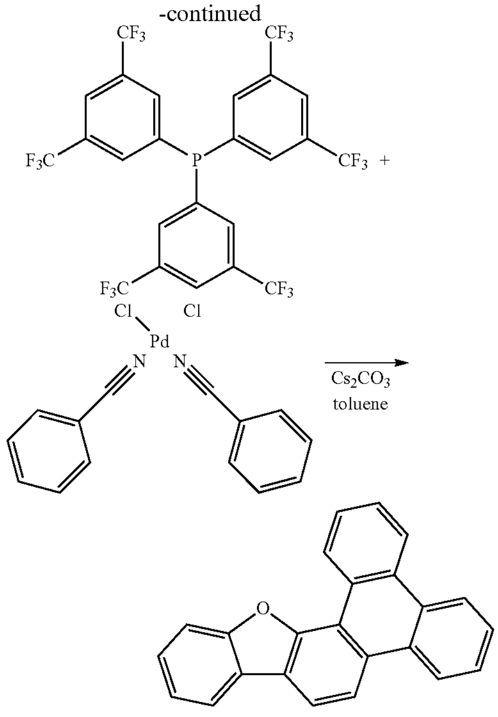

4-(2'-Bromo-[1,1'-biphenyl]-2-yl)dibenzo[b,d]furan (11.25 g, 28.2 mmol) was dissolved in 240 mL of toluene and purged with nitrogen for 15 min. Cesium carbonate (22.03 g, 67.6 mmol), tris(3,5-bis(trifluoromethyl)phenyl) phosphane (1.889 g, 2.82 mmol) and bis-(benzonitrile) dichloloropalladium (II) (0.540 g, 1.409 mmol) were added, and the resulting reaction mixture was heated under nitrogen in an oil bath set at 115° C. for 16 hours. The reaction was filtered through silica gel, which was washed with ethyl acetate, then the combined organic solution was concentrated down to a brown solid.

The brown solid was purified on a silica gel column, eluted with 85/15 to 75/25 heptanes/DCM (v/v) to get triphenyleno[1,2-b]benzofuran as an off-white solid. The solid was dissolved in DCM, the heptane was added and the solution was partially concentrated down using a Rotovap at 30° C. The solids were then filtered off as a fluffy white solid. The solid was dried in the vacuum for 16 hours to get triphenyleno[1,2-b]benzofuran (3.9 g, 43.5% yield).

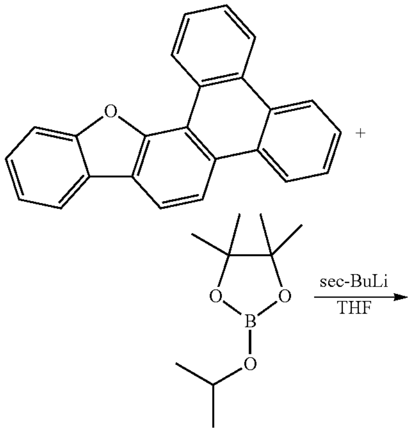

-continued

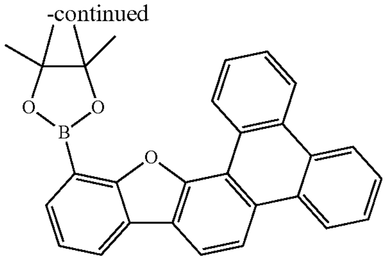

Triphenyleno[1,2-b]benzofuran (3.37 g, 10.59 mmol) was placed in a flask and the system was purged with nitrogen for 30 min. Tetrahydrofuran (THF) (150 ml) was added, then the solution was cooled in a dry ice/acetone bath for 30 min. The reaction changed to a white suspension and sec-butyllithium (13.23 ml, 18.52 mmol) 1.4 M solution in THF was added with the temperature below −60° C. The reaction turned black. After 2.5 hours, 2-isopropoxy-4,4,5,5-tetramethyl-1,3,2-dioxaborolane (4.32 ml, 21.17 mmol) was added all at once. The reaction mixture was allowed to warm up in an ice bath for 2 hours. Then, the reaction was quenched with water, brine was added, and the aqueous phase was extracted twice with EtOAc. The combined organics were washed with brine, then dried over sodium sulfate, filtered and concentrated down to obtain 4,4,5,5-tetramethyl-2-(triphenyleno[1,2-b]benzofuran-14-yl)-1,3,2-dioxaborolane as white solid (4.5 g, 96% yield).

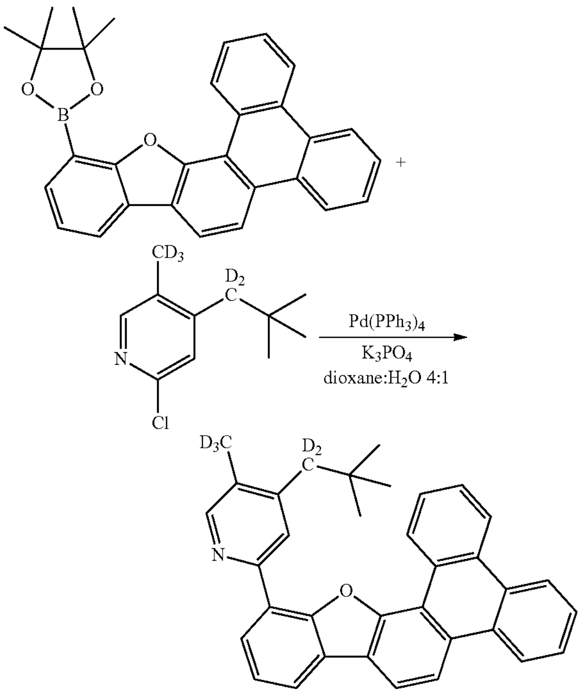

4,4,5,5-Tetramethyl-2-(triphenyleno[1,2-b]benzofuran-14-yl)-1,3,2-dioxaborolane (4.5 g, 10.13 mmol), 2-chloro-4-(2,2-dimethylpropyl-1,1-d2)-5-(methyl-d3)pyridine (2.156 g, 10.63 mmol), and potassium phosphate monohydrate (6.45 g, 30.4 mmol) were suspended in 1,4-dioxane (120 ml) and water (30.0 ml). The reaction mixture was purged with nitrogen for 15 minutes then tetrakis(triphenylphosphine)palladium(0) (0.351 g, 0.304 mmol) was added. The reaction was heated in an oil bath set at 100° C.

for 16 hours. The resulting reaction mixture was partially concentrated down on the rotovap, then diluted with water and extracted with DCM. The combined organics were washed with water once, dried over sodium sulfate, filtered and concentrated down to a light brown solid. The light brown solid was purified on a silica gel column eluting with 98.5/1.5 to 98/2 DCM/EtOAc gradient mixture providing 5.1 g of a white solid. The 5.1 g sample was dissolved in 400 ml of hot DCM, then EtOAc was added and the resulting mixture was partially concentrated down on the rotovap with a bath set at 30° C. The precipitate was filtered off and dried in the vacuum oven for 16 hours to obtain 4-(2,2-dimethylpropyl-1,1-d2)-5-(methyl-d3)-2-(triphenyleno[1,2-b]benzofuran-14-yl)pyridine as white solid (3.1 g, 63.2% yield).

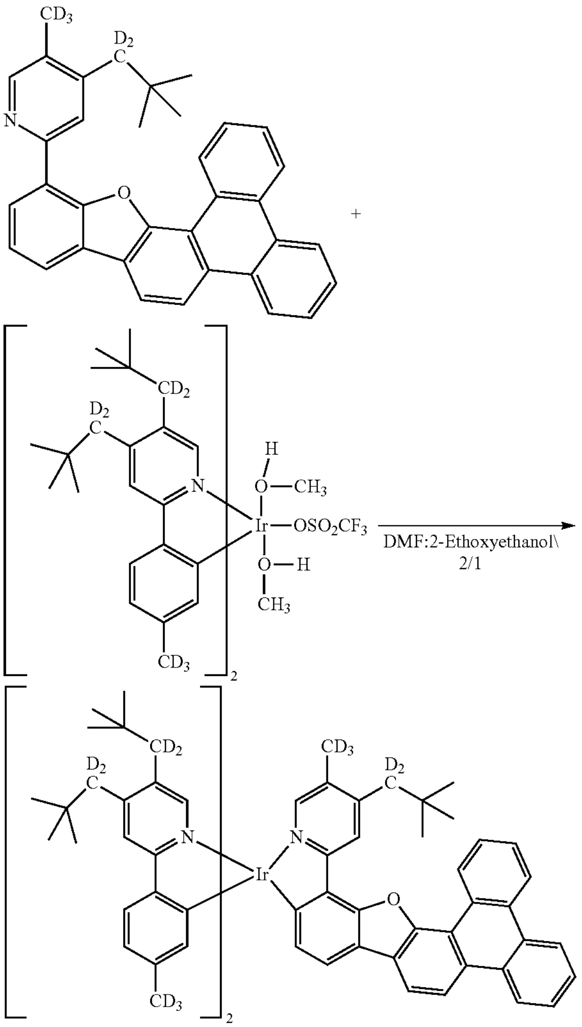

The iridium complex triflic salt shown above (2.2 g, 2.123 mmol) and 442,2-dimethylpropyl-1,1-d2)-5-(methyl-d3)-2-(triphenyleno[1,2-b]benzofuran-14-yl)pyridine (1.852 g, 3.82 mmol) were suspended in the mixture of DMF (25 ml) and 2-ethoxyethanol (25.00 ml). The reaction mixture was purged with nitrogen for 15 minutes then heated to 80° C. under nitrogen for 3.5 days. The resulting mixture was concentrated on the rotovap, cooled down, then diluted with methanol. A brown-yellow precipitate was filtered off, washed with methanol then recovered the solid using DCM. The solid was purified on a silica gel column eluting with 50/50 to 25/75 heptanes/toluene gradient mixture to get 2.2 g of a yellow solid. The yellow solid was further purified on a basic alumina column using 70/30 to 40/60 heptanes/DCM (v/v) to get 1.8 g of a yellow solid. The solid was dissolved in DCM, mixed with 50 ml of toluene and 300 ml of isopropyl alcohol, then partially concentrated down on the rotovap. The precipitate was filtered off and dried for 3 hours in the vacuum oven to get target complex as bright yellow solid $IrL_{X206}(L_{B467})_2$ (1.23 g, 44.3% yield).

Synthesis of $IrL_{X133}(L_{B461})_2$

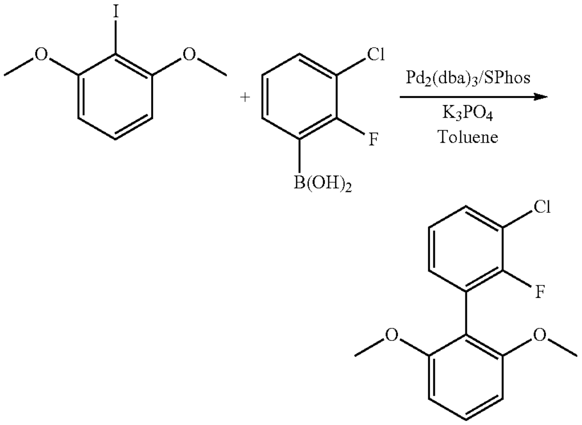

2-iodo-1,3-dimethoxybenzene (16 g, 60.6 mmol), (3-chloro-2-fluorophenyl)boronic acid (12.15 g, 69.7 mmol), tris(dibenzylideneacetone)palladium(0) (1.109 g, 1.212 mmol) and SPhos (2.73 g, 6.67 mmol) were charged into a reaction flask with 300 mL of toluene. Potassium phosphate tribasic monohydrate (41.8 g, 182 mmol) was then added to the reaction mixture. This mixture was degassed with nitrogen then was stirred and heated in an oil bath set at 115° C. for 47 hours. The reaction mixture was cooled down to room temperature, then washed with water. The organic phase was dried over magnesium sulfate then filtered and concentrated in vacuo. The crude residue was passed through a silica gel column eluting with 15-25% DCM in heptanes. After evaporation, pure product fractions yielded 3-chloro-2-fluoro-2',6'-dimethoxy-1,1'-biphenyl (8.5 g, 31.9 mmol, 52.6% yield) as a white solid.

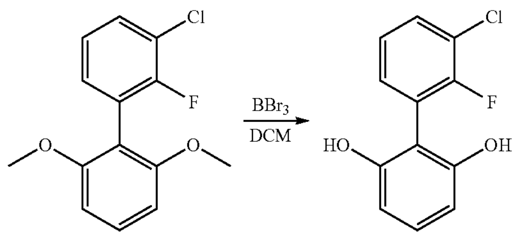

3-Chloro-2-fluoro-2',6'-dimethoxy-1,1'-biphenyl (8.5 g, 31.9 mmol) was dissolved in 75 mL of DCM. This solution was cooled in a wet ice bath, and a 1 M solution of boron tribromide in DCM (130 ml, 130 mmol) was added dropwise. Stirring was continued as the reaction mixture was allowed to gradually warm up to room temperature over 16 hours. The reaction mixture was poured into a beaker of wet ice. A solid was collected via filtration. The filtrate was separated, dissolved in DCM and the solution was dried over magnesium sulfate. This solution was then filtered and concentrated in vacuo yielding 3'-chloro-2'-fluoro-[1,1'-biphenyl]-2,6-diol (7.45 g, 31.2 mmol, 98% yield) as a white solid.

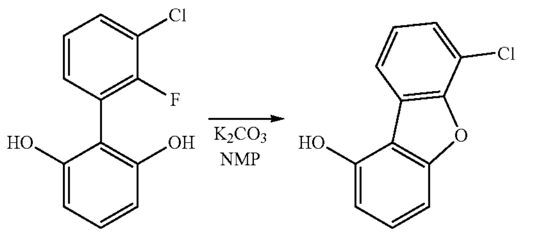 [SMILES: Oc1cccc(O)c1-c1cccc(Cl)c1F ; Oc1cccc2oc3c(Cl)cccc3c12]

3'-Chloro-2'-fluoro-[1,1'-biphenyl]-2,6-diol (7.45 g, 31.2 mmol) and potassium carbonate (9.49 g, 68.7 mmol) were charged into the reaction flask with 70 mL of NMP. This reaction mixture was heated at 130° C. for 18 hours. Heating was discontinued. The reaction mixture was diluted with 200 mL of water, then extracted with DCM. The extracts were combined, washed with aqueous LiCl, dried over magnesium sulfate, filtered and the solvent was evaporated in vacuo. This crude residue was subjected to a bulb-bulb distillation to remove NMP. The remaining residue was passed through a silica gel column eluted with 70-80% DCM in heptanes. Pure fractions were combined and concentrated in vacuo. The solid was then triturated with heptanes. A tan solid was collected via filtration and then was dried yielding 6-chlorodibenzo[b,d]furan-1-ol (5.6 g, 25.6 mmol, 82% yield).

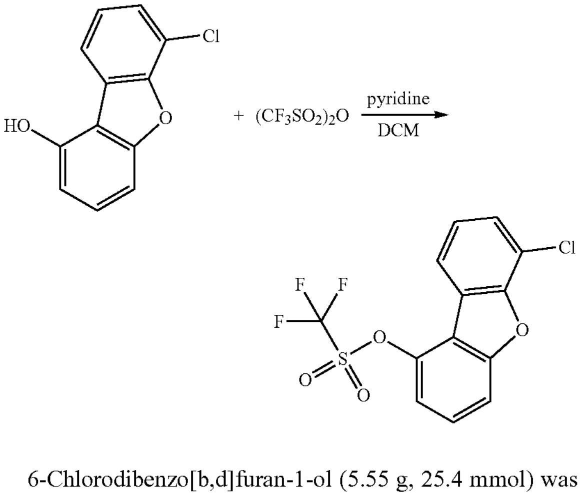

6-Chlorodibenzo[b,d]furan-1-ol (5.55 g, 25.4 mmol) was dissolved in DCM. Pyridine (5.74 ml, 71.1 mmol) was added to this reaction mixture as one portion. The homogeneous solution was cooled to 0° C. using a wet ice bath. Trifluoromethanesulfonic anhydride (10.03 g, 35.5 mmol) was dissolved in 20 mL of DCM and was added dropwise to the cooled reaction mixture. Stirring was continued as the reaction mixture was allowed to gradually warm up to room temperature over 16 hours. The reaction mixture was washed with aqueous LiCl, dried over magnesium sulfate, filtered and concentrated in vacuo. The crude product was passed through silica gel column eluting with 5-30% DCM in heptanes. The Pure product fractions were combined and concentrated yielding 6-chlorodibenzo[b,d]furan-1-yl trifluoromethanesulfonate (8.9 g, 25.4 mmol, 100% yield) as a white solid.

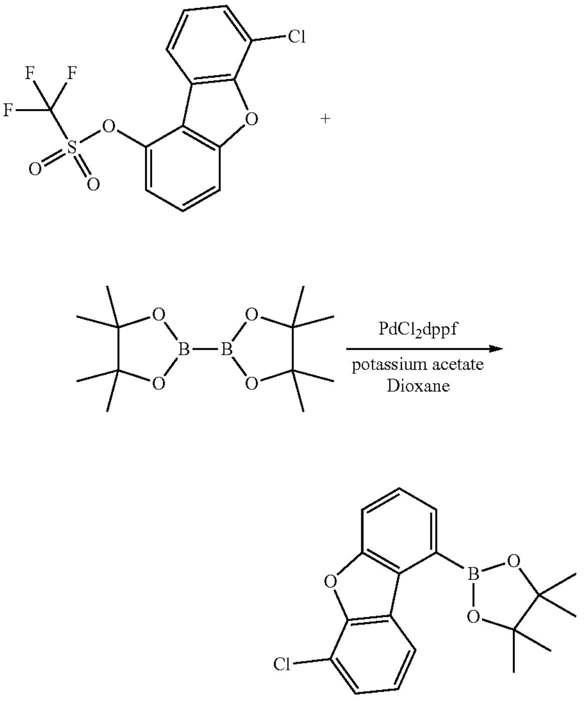

6-Chlorodibenzo[b,d]furan-1-yl trifluoromethanesulfonate (10 g, 28.5 mmol), 4,4,4',4',5,5,5',5'-octamethyl-2,2'-bi(1,3,2-dioxaborolane) (9.41 g, 37.1 mmol), potassium acetate (6.43 g, 65.6 mmol) and [1,1'-bis(diphenylphosphino)ferrocene]palladium(II) dichloride (0.93 g, 1.14 mmol) were charged into the reaction flask with 250 mL of dioxane. This mixture was degassed with nitrogen then heated to reflux for 14 hours. Heating was discontinued. The solvent was evaporated, then the crude product was partitioned with 500 mL water and 200 mL DCM. The organic solution was dried over magnesium sulfate then filtered and concentrated in vacuo. The crude product was passed through a silica gel column eluting with 20-35% DCM in heptanes. Pure product fractions were combined and concentrated in vacuo yielding 2-(6-chlorodibenzo[b,d]furan-1-yl)-4,4,5,5-tetramethyl-1,3,2-dioxaborolane (6.9 g, 21.00 mmol, 73.6% yield) as a solid.

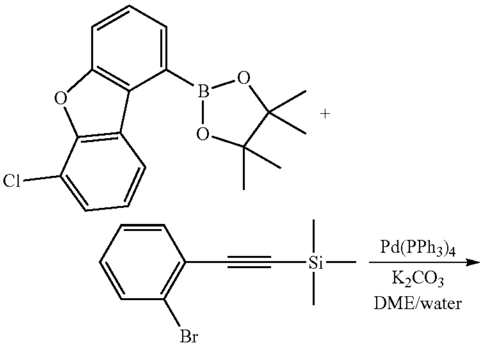

-continued

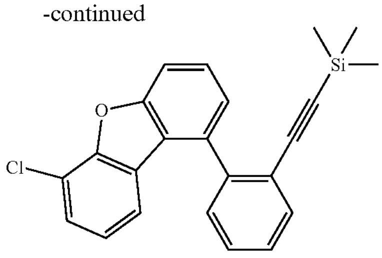

2-(6-Chlorodibenzo[b,d]furan-1-yl)-4,4,5,5-tetramethyl-1,3,2-dioxaborolane (7.5 g, 22.82 mmol), ((2-bromophenyl) ethynyl)trimethylsilane (7.34 g, 29.0 mmol) and tetrakis (triphenylphosphine)palladium(0) (1.07 g, 0.927 mmol) were charged into a reaction flask with 150 mL of DME. Potassium carbonate (9.5 g, 68.8 mmol) was dissolved in 15 mL of water then was added all at once to the reaction mixture. This reaction mixture was degassed with nitrogen, then heated to reflux for 18 hours. The reaction mixture was cooled to room temperature, then the solvent was removed in vacuo. The crude product was partitioned between 200 mL of DCM and 100 mL of water. The aqueous phase was extracted with DCM. The DCM extracts were combined, dried over magnesium sulfate, then filtered and concentrated in vacuo. The crude product was passed through a silica gel column with 7-12% DCM in heptanes. Pure product fractions were combined and concentrated in vacuo yielding ((2-(6-chlorodibenzo[b,d]furan-1-yl)phenypethynyptrimethylsilane (7.35 g, 19.60 mmol, 86% yield) as a viscous yellow oil that solidified upon standing overnight.

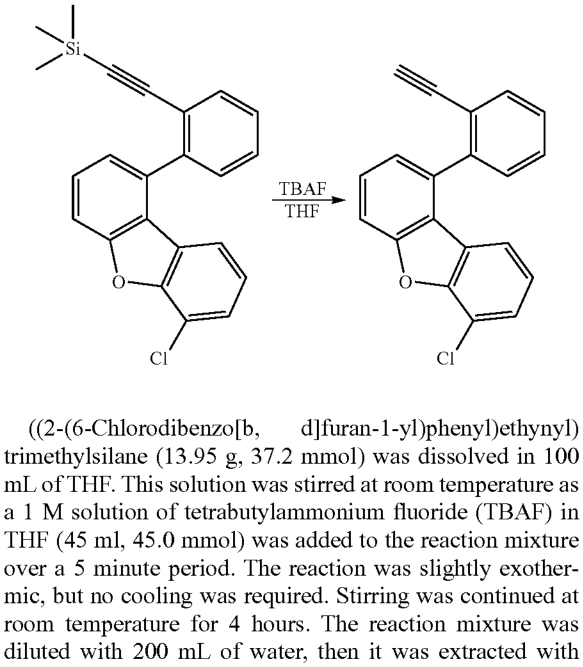

((2-(6-Chlorodibenzo[b, d]furan-1-yl)phenyl)ethynyl) trimethylsilane (13.95 g, 37.2 mmol) was dissolved in 100 mL of THF. This solution was stirred at room temperature as a 1 M solution of tetrabutylammonium fluoride (TBAF) in THF (45 ml, 45.0 mmol) was added to the reaction mixture over a 5 minute period. The reaction was slightly exothermic, but no cooling was required. Stirring was continued at room temperature for 4 hours. The reaction mixture was diluted with 200 mL of water, then it was extracted with DCM. The extracts were combined, dried over magnesium sulfate, filtered and concentrated in vacuo. The crude residue was passed through silica gel column eluting with 10-15% DCM in heptanes to yield ethynylphenyl)dibenzo[b,d]furan (9.6 g, 31.7 mmol, 85% yield) as a white solid.

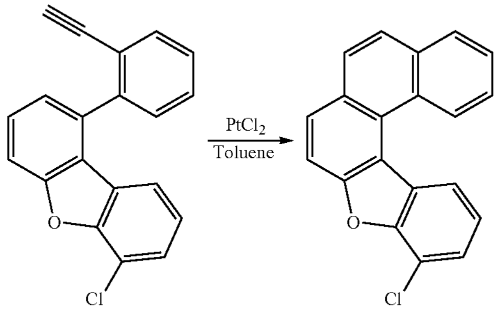

Platinum(II) chloride (0.527 g, 1.982 mmol) was charged into a reaction flask with 50 mL of toluene. 6-Chloro-1-(2-ethynylphenyl)dibenzo[b,d]furan (5 g, 16.51 mmol) was then added to the reaction flask followed by 100 mL of toluene. This mixture was degassed with nitrogen then heated in an oil bath set at 93° C. for 24 hours. Heating was discontinued. The reaction mixture was passed through a pad of silica gel. The toluene filtrate was concentrated under vacuum. This crude residue was passed through silica gel column eluting with 10-15% DCM in heptanes. Pure product fractions were combined and concentrated in vacuo yielding 10-chlorophenanthro[3,4-b]benzofuran (3.2 g, 10.57 mmol, 64.0% yield) as a white solid.

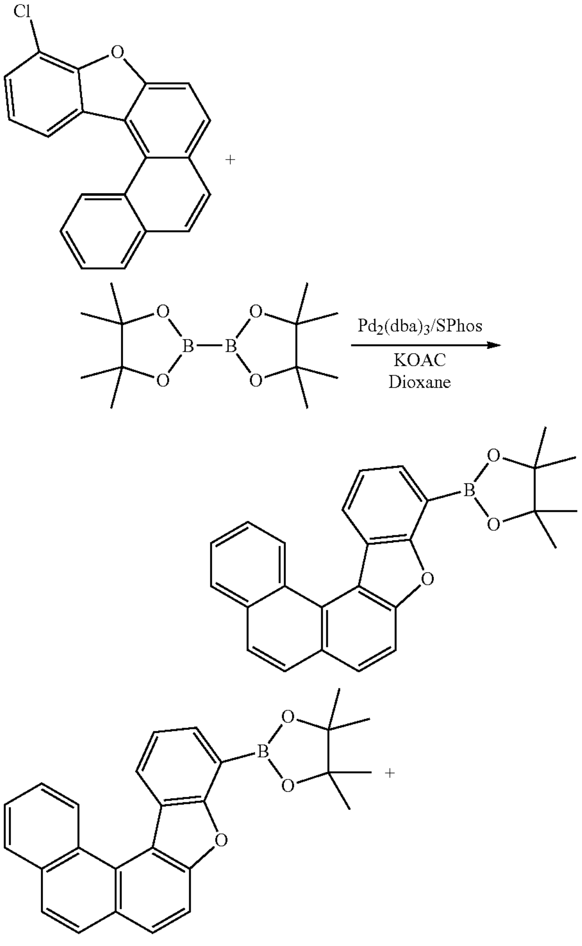

-continued

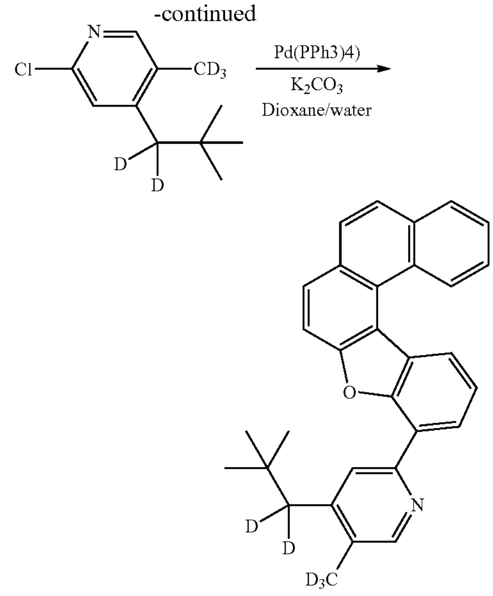

10-Chlorophenanthro[3,4-b]benzofuran (3.25 g, 10.73 mmol), 4,4,4',4',5,5,5',5'-octamethyl-2,2'-bi(1,3,2-dioxaborolane) (3.54 g, 13.96 mmol), potassium acetate (2.63 g, 26.8 mmol), tris(dibenzylideneacetone) palladium(0) (0.246 g, 0.268 mmol), and SPhos (0.682 g, 1.664 mmol) were charged into a reaction flask with 140 mL of dioxane. This mixture was degassed with nitrogen then heated to reflux for 18 hours. The heating was discontinued. The reaction mixture was used for the next step without purification.

2-Chloro-4-(2,2-dimethylpropyl-1,1-d2)-5-(methyl-d3) pyridine (2.98 g, 14.70 mmol), tetrakis(triphenylphosphine) palladium(0) (0.743 g, 0.644 mmol), potassium phosphate tribasic monohydrate (7.40 g, 32.2 mmol), and 20 mL of water were added to the reaction mixture from previous step. This mixture was degassed with nitrogen then heated to reflux for 18 hours. The reaction mixture was cooled down to room temperature. The dioxane was removed under vacuum. The crude residue was diluted with 100 mL of water then was extracted with DCM. The extracts were dried over magnesium sulfate, filtered, and concentrated. The crude residue was passed through a silica gel column eluting with 0.5-2% ethyl acetate in DCM to yield 4-(2,2-dimethylpropyl-1,1-d2)-5-(methyl-d3)-2-(phenanthro[3,4-b]benzofuran-10-yl)pyridine (3.2 g, 7.36 mmol, 68.6% yield) as a white solid.

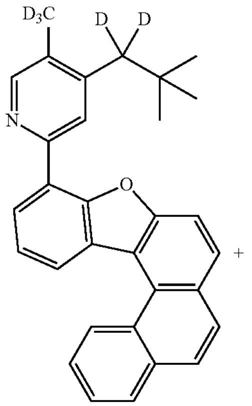

-continued

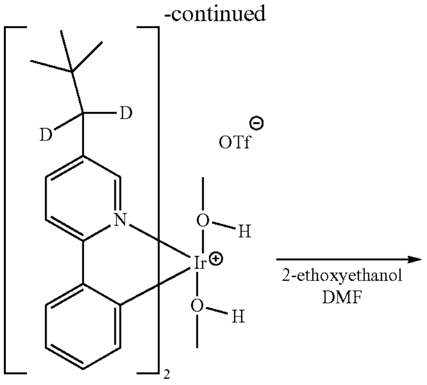

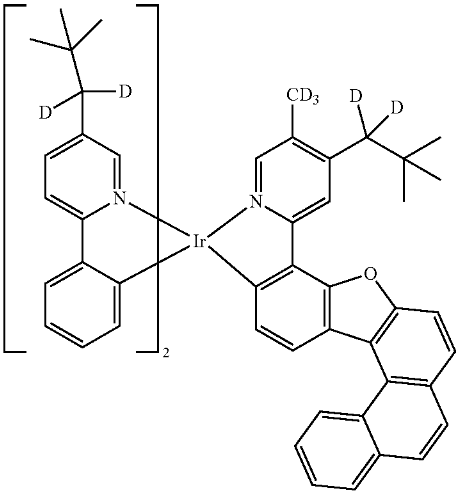

4-(2,2-Dimethylpropyl-1,1-d2)-5-(methyl-d3)-2-(phenanthro[3,4-b]benzofuran-10-yl)pyridine (1.773 g, 4.08 mmol) and the iridium complex triflic salt shown above (2 g, 2.331 mmol) were charged into a reaction flask with 40 mL of 2-ethoxyethanol and 40 mL of DMF. This mixture was degassed with nitrogen then heated in an oil bath set at 100° C. for 10 days. Heating was discontinued and the solvent was removed in vacuo. The crude residue was then triturated with 150 mL of methanol. A solid was isolated via filtration. This material was dried under vacuum then was dissolved in 80% DCM in heptanes and was passed through 10 inches of activated basic alumina. The alumina column was eluted with 80% DCM in heptanes. The pure product fractions were combined and concentrated in vacuo yielding 2.6 g of a yellow solid. This solid was then passed through a silica gel column eluting with 35-60% toluene in heptanes. The material was subjected to a second chromatographic purification on the silica gel column eluted with 35% toluene in heptanes. The pure fractions were combined, concentrated in vacuo, then triturated with methanol. A bright yellow solid was collected via filtration yielding the desired iridium complex, $IrL_{X133}(L_{B461})_2$ (1.45 g, 1.344 mmol, 57.7% yield)

Synthesis of $IrL_{X220}(L_{B467})_2$

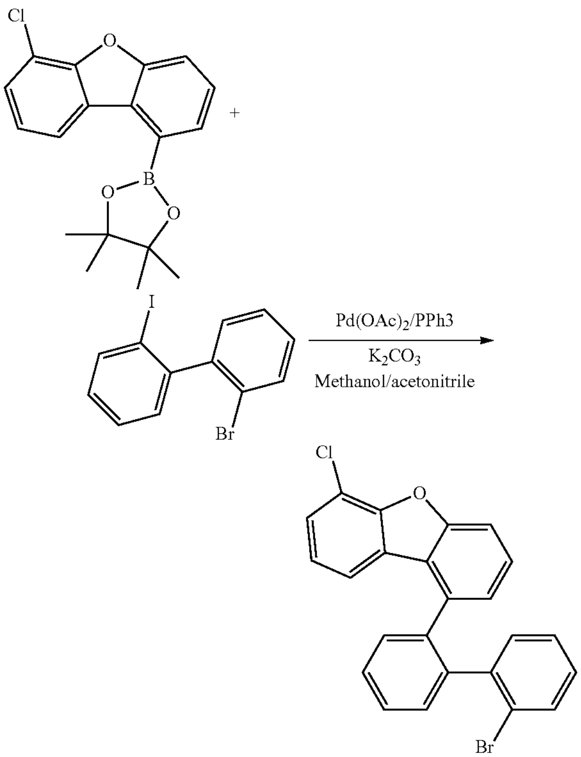

Triphenylphosphine (0.974 g, 3.71 mmol), diacetoxypalladium (0.417 g, 1.856 mmol), potassium carbonate (10.26 g, 74.3 mmol), 2-bromo-2'-iodo-1,1'-biphenyl (13.33 g, 37.1 mmol) and 2-(6-chlorodibenzo[b,d]furan-1-yl)-4,4,5,5-tetramethyl-1,3,2-dioxaborolane (12.2 g, 37.1 mmol) were suspended in a ethanol (65 ml)/etonitrile (130 ml) mixture. The reaction mixture was degassed and heated at 35° C. under nitrogen atmosphere for 16 hours. The reaction mixture was cooled down to room temperature, then filtered through a silica gel plug that was washed with EtOAc. The filtrate was evaporated. Dichloromethane was added and the resulting mixture was washed with water, dried and evaporated leaving a dark brown semi-solid that was absorbed onto a silica gel and chromatographed on silica gel eluting with 98% heptane/2% THF. The impurities were eluted with this eluant. The eluant was changed to 100% DCM and pure product was eluted from the silica gel yielding 1-(2'-bromo-[1,1'-biphenyl]-2-yl)-6-chlorodibenzo[b,d]furan (8.8 g, 20.3 mmol, 54.66% yield).

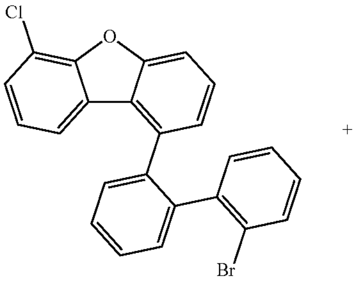

-continued

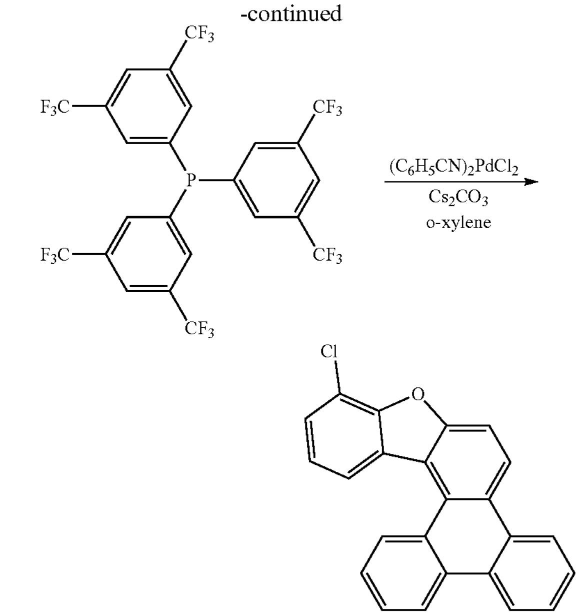

1-(2'-bromo-[1,1'-biphenyl]-2-yl)-6-chlorodibenzo[b,d]furan (3 g, 6.92 mmol), tris(3,5-bis(trifluoromethyl)phenyl)phosphane (0.695 g, 1.038 mmol), cesium carbonate (5.40 g, 16.60 mmol) and bis(benzonitrile)palladium(II) chloride (0.199 g, 0.519 mmol) were charged into a reaction flask with 125 mL of o-xylene. This mixture was degassed with nitrogen then heated in an oil bath at 148° C. for 18 hours. The reaction mixture was cooled down to room temperature. Gas chromatography/mass spectroscopy (GC/MS) analysis showed about 15% of the product formed. Palladium catalyst (0.4 g) and 1.5 g of triarylphosphine were added to the reaction mixture. This mixture was degassed with nitrogen, then heated in a bath at 148° C. for 2½ days. The reaction mixture was cooled to room temperature. GC/MS analysis showed no starting material. This mixture was filtered through a thin pad of silica gel. The pad was rinsed with toluene. The toluene/xylene filtrate was concentrated in vacuo. This crude product was absorbed onto a silica gel then passed through a silica gel column eluted with 15-18% DCM/heptanes. The product fractions were combined and concentrated in vacuo to near dryness. This material was then triturated with heptanes. A white solid was collected via filtration yielding 8-chlorotriphenyleno[2,1-b]benzofuran (1.48 g, 4.19 mmol, 60.6% yield) as a white solid.

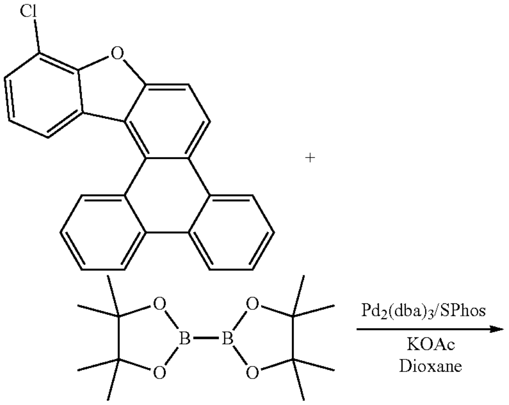

-continued

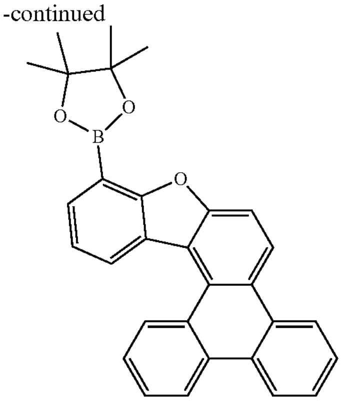

8-Chlorotriphenyleno[2,1-b]benzofuran (3.05 g, 8.64 mmol), 4,4,4',4',5,5,5',5'-octamethyl-2,2'-bi(1,3,2-dioxaborolane) (2.96 g, 11.67 mmol), tris(dibenzylideneacetone) palladium(0) (0.21 g, 0.230 mmol) and SPhos (0.65 g, 1.585 mmol) were charged into a reaction flask with 100 ml of dioxane. Potassium acetate (2.25 g, 22.96 mmol) was then added to the reaction mixture. This mixture was degassed with nitrogen then heated to reflux for 20 hours. The reaction mixture was cooled down to room temperature and reaction mixture was used "as is" as a dioxane solution.

4,4,5,5-Tetramethyl-2-(triphenyleno[2,1-b]benzofuran-8-yl)-1,3,2-dioxaborolane (3.84 g, 8.64 mmol), 2-chloro-4-(2,2-dimethylpropyl-1,1-d2)-5-(methyl-d3)pyridine (2.452 g, 12.10 mmol) and tetrakis(triphenylphosphine)palladium(0) (0.42 g, 0.364 mmol) were charged into a r mixture. Potassium phosphate tribasic monohydrate (5.96 g, 25.9 mmol) was then dissolved in 20 mL of water and added to the mixture. This reaction mixture was degassed with nitrogen then heated to reflux for 24 hours. The reaction mixture was cooled to room temperature and white precipitate formed. This mixture was diluted with 150 mL of water and the precipitate was collected via filtration then dissolved in 400 mL of DCM. This solution was dried over magnesium sulfate then filtered and evaporated. The crude residue was passed through silica gel column eluting with 100% DCM then 1-4% ethyl acetate/DCM. Pure product fractions were combined and concentrated in vacuo. This material was triturated with warm heptane. A white solid was collected via filtration then was dried in vacuo yielding 4-(2,2-dimethylpropyl-1,1-d2)-5-(methyl-d3)-2-(triphenyleno[2,1-b]benzofuran-8-yl)pyridine (2.85 g, 5.88 mmol, 68.1% yield).

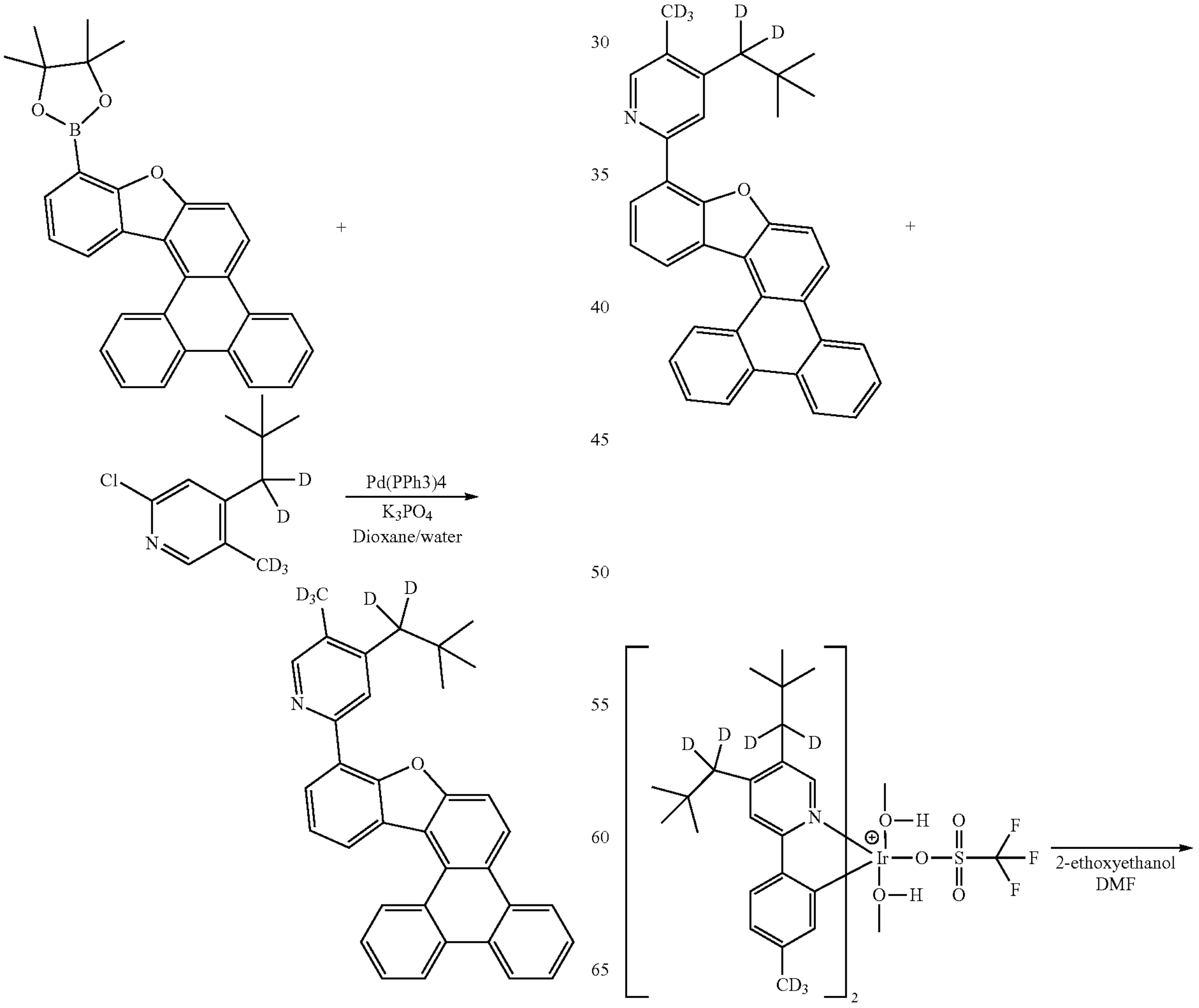

-continued

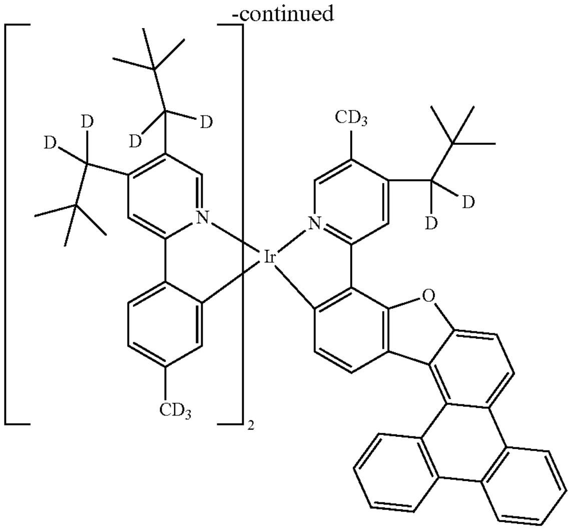

4-(2,2-dimethylpropyl-1,1-d2)-5-(methyl-d3)-2-(triphenyleno[2, 1-b]benzofuran-8-yl)pyridine (2.1 g, 4.33 mmol) and the iridium complex triflic salt show above (2.5 g, 2.412 mmol) were charged into the reaction flask with 60 mL of 2-ethoxyethanol and 60 mL of DMF. This reaction mixture was degassed with nitrogen then heated in an oil bath set at 100° C. for 8 days. Heating was discontinued and the solvents were evaporated in vacuo. The crude product was then triturated with methanol. A yellow solid was collected via filtration. This material was dissolved in a small amount of DCM and passed through an activated basic alumina column eluted with 30-40% DCM/heptanes. Column fractions were combined and concentrated in vacuo yielding 2.25 g of product. This material was passed through silica gel column eluted with 35-50% toluene in heptanes. The pure product fractions were combined and concentrated, then were triturated with methanol. A yellow solid was collected via filtration yielding $IrL_{X220}(L_{B467})_2$ (2.15 g, 1.643 mmol, 68.1% yield) as a yellow solid.

Synthesis of $IrL_{X211}(L_{B466})_2$

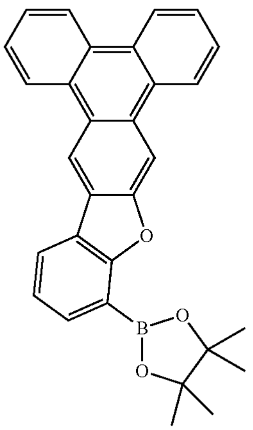

+

-continued

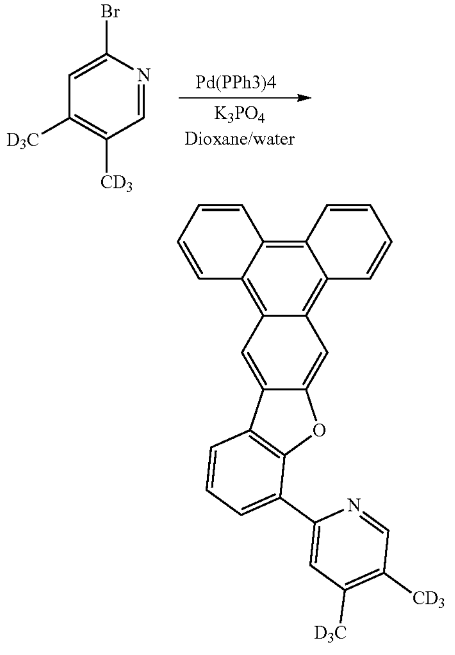

4,4,5,5-Tetramethyl-2-(triphenyleno[2,3-b]benzofuran-11-yl)-1,3,2-dioxaborolane (4.5 g, 10.13 mmol), 2-bromo-4,5-bis(methyl-d3)pyridine (3.12 g, 16.24 mmol), and tetrakis(triphenylphosphine)palladium(0) (0.584 g, 0.506 mmol) were charged into a reaction flask with 130 mL of 1,4-dioxane. Potassium phosphate tribasic monohydrate (6.99 g, 30.4 mmol) was then dissolved in 20 mL of water and added to the reaction mixture. This mixture was degassed with nitrogen, then heated at reflux for 26 hours. A white precipitate was formed in the reaction mixture. Heating was discontinued and the reaction mixture was concentrated to near dryness, then diluted with 300 mL of water. A precipitate was collected via filtration then rinsed with water. This solid was then suspended in 350 mL of DCM and was heated to reflux. This heterogeneous mixture was then cooled back to room temperature. A white solid was collected via filtration yielding 4,5-bis(methyl-d3)-2-(triphenyleno[2,3-b]benzofuran-11-yl)pyridine (2.7 g, 6.29 mmol, 62.1% yield)

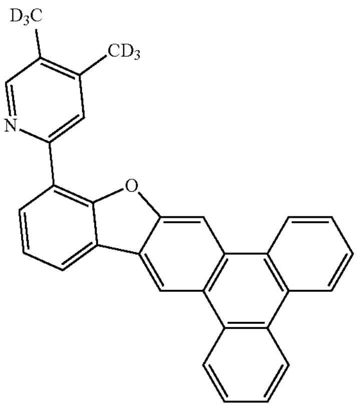

+

-continued

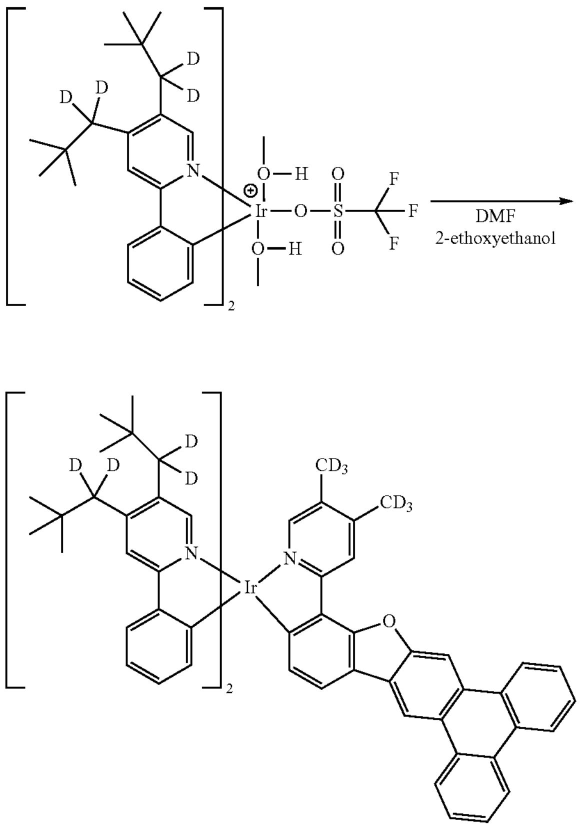

4,5-Bis(methyl-d3)-2-(triphenyleno[2,3-b]benzofuran-11-yl)pyridine (2 g, 4.66 mmol) was dissolved in a mixture of 80 mL of 2-ethoxyethanol and 80 mL of DMF. The iridium complex triflic salt shown above (2.56 g, 2.55 mmol) was then added and the reaction mixture was degassed using nitrogen then was stirred and heated in an oil bath set at 103° C. for 12 days. The reaction mixture was cooled down to room temperature and a yellow solid was collected via filtration. This solid was dried in vacuo then was dissolved in 40% DCM in heptanes and was passed through a basic alumina column eluting the column with 40-50% DCM in heptanes. Product fractions were combined and concentrated. This material was then passed through a silica gel column eluting with 40-70% toluene in heptanes. Pure product fractions were combined and concentrated in vacuo. This material was triturated with methanol then filtered and dried in vacuo yielding the desired iridium complex, $IrL_{X211}(L_{B466})_2$ (1.25 g, 1.026 mmol, 40.2% yield) as a yellow solid.

Synthesis of Comparative Compound 1

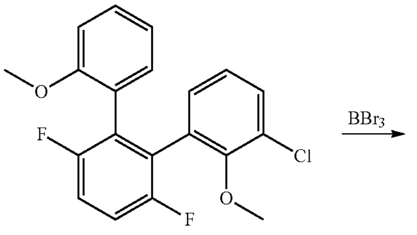

-continued

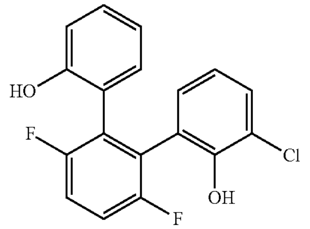

3-Chloro-3',6'-difluoro-2,2"-dimethoxy-1,1':2',1"-terphenyl (10.8 g, 29.9 mmol) was dissolved in DCM (400 ml) and then cooled to 0° C. A 1N tribromoborane ($BBr_3$) solution in DCM (90 ml, 90 mmol) was added dropwise. The reaction mixture was stirred at 20° C. for 16 hours, then quenched with water and extracted with DCM. The combined organic phase was washed with brine. After the solvent was removed, the residue was subjected to column chromatography on a silica gel column eluted with DCM/heptanes gradient mixture to yield 3-chloro-3',6'-difluoro-[1,1':2',1"-terphenyl]-2,2"-diol as white solid (4.9 g, 53% yield).

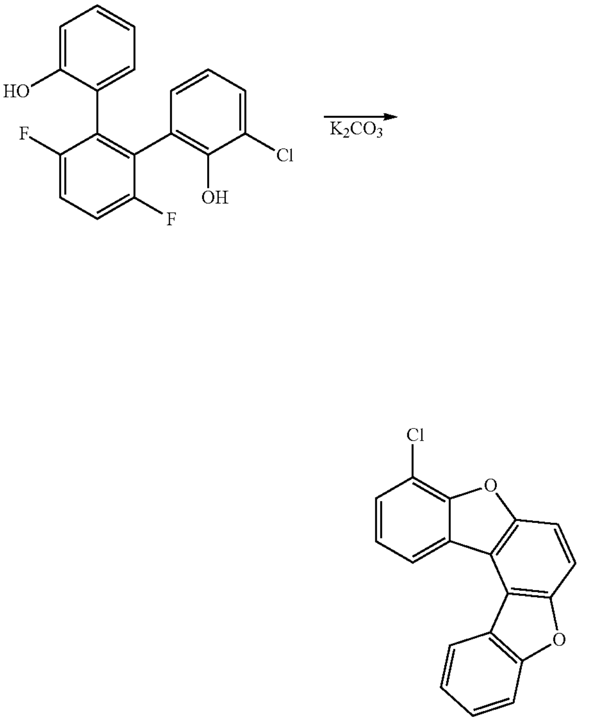

A mixture of 3-chloro-3',6'-difluoro-[1,1':2',1"-terphenyl]-2,2"-diol (5 g, 15.03 mmol) and $K_2CO_3$ (6.23 g, 45.08 mmol) in 1-methylpyrrolidin-2-one (75 mL) was vacuumed and stored under nitrogen. The mixture was heated at 150° C. for 16 hours. After the reaction was cooled to 20° C., it was diluted with water and extracted with EtOAc. The combined organic phase was washed with brine. After the solvent was removed, the residue was subjected to column chromatography on a silica gel column eluted with 20% DCM in heptane to yield the target chloride as white solid (3.0 g, 68% yield).

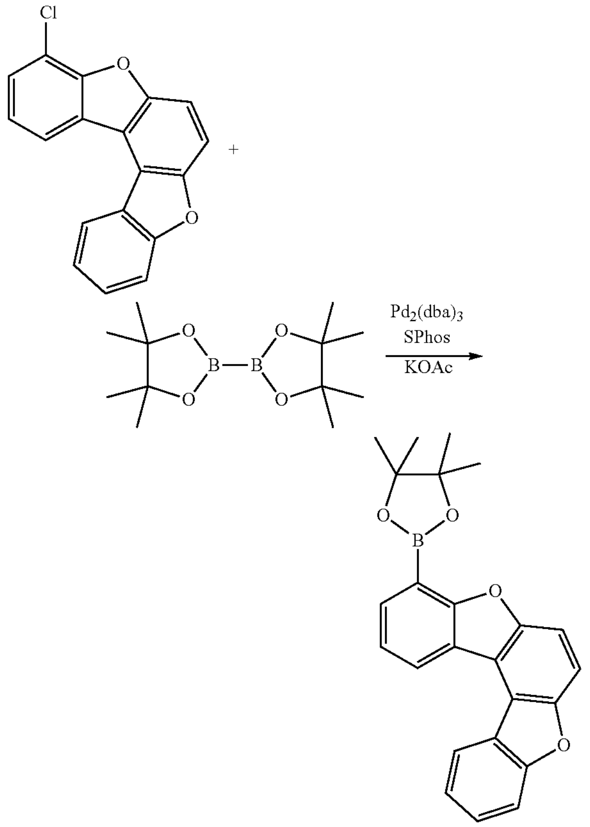

The chloride molecule above (3 g, 10.25 mmol) was mixed with 4,4,4',4',5,5,5',5'-octamethyl-2,2'-bi(1,3,2-dioxaborolane) (5.21 g, 20.50 mmol), tris(dibenzylideneacetone)dipalladium(0) (0.188 g, 0.205 mmol), dicyclohexyl (2',6'-dimethoxy-[1,1'-biphenyl]-2-yl)phosphane (SPhos, 0.337 g, 0.820 mmol), and potassium acetate ("KOAc") (2.012 g, 20.50 mmol) and suspended in 1,4-dioxane (80 ml). The mixture was degassed and heated at 100° C. for 16 hours. The reaction mixture was cooled to 20° C. before being diluted with 200 mL of water and extracted with EtOAc (3 times by 50 mL). The combined organic phase was washed with brine. After the solvent was evaporated, the residue was purified on a silica gel column eluted with 2% EtOAc in DCM to yield the target boronic ester as white solid (3.94 g, 99% yield).

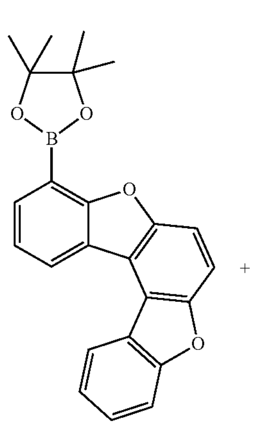

-continued

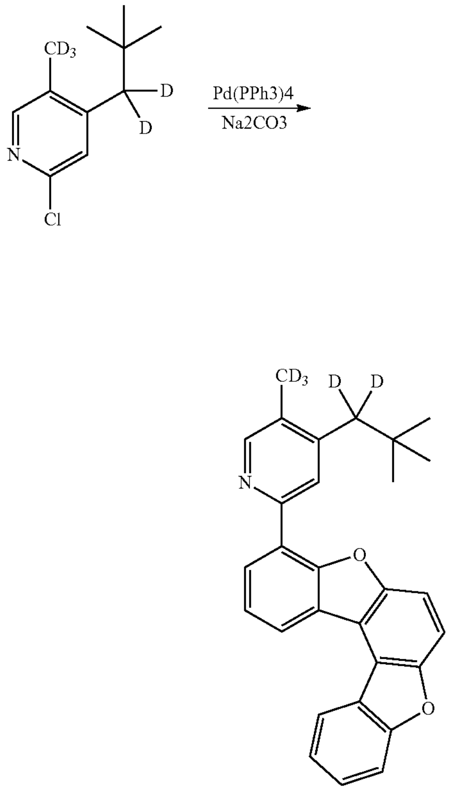

The boronic ester from above (3.94 g, 10.25 mmol), 2-chloro-4-(2,2-dimethylpropyl-1,1-d2)-5-(methyl-d3)pyridine (3.12 g, 15.38 mmol) and sodium carbonate (2.72 g, 25.6 mmol) were suspended in the mixture of DME (80 ml) and water (20 ml). The reaction mixture was degassed and tetrakis(triphenylphosphine)palladium(0) (0.722 g, 0.625 mmol) was added as one portion. The mixture was heated at 100° C. for 14 hours. After the reaction was cooled to 20° C., it was diluted with water and extracted with EtOAc. The combined organic phase was washed with brine. After the solvent was evaporated, the residue was subjected to column chromatography on a silica gel column eluted with 2% EtOAc in DCM to yield the target ligand as a white solid (1.6 g, 37% yield)

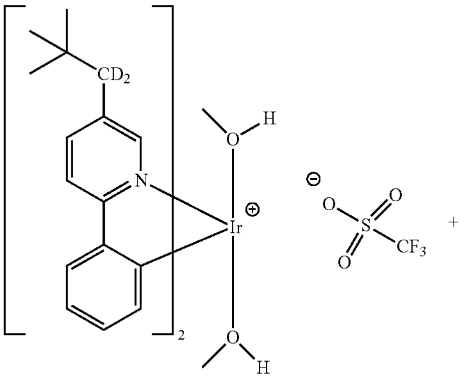

-continued

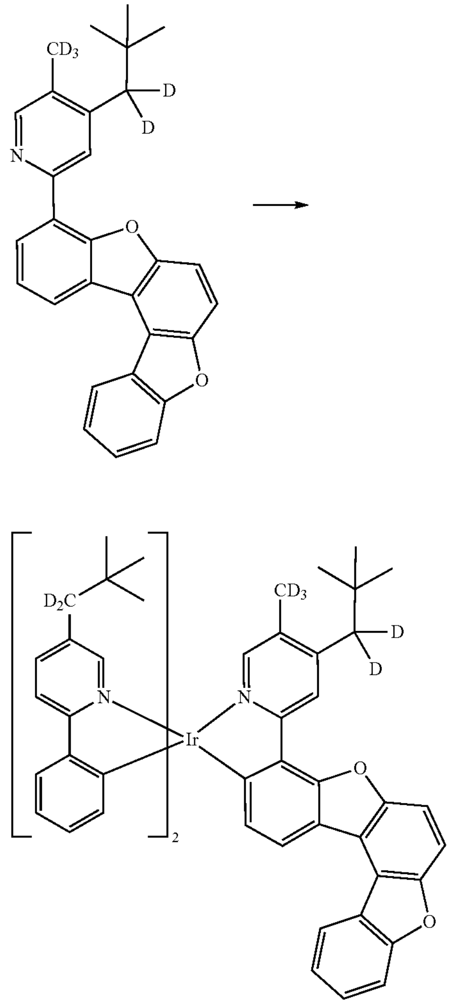

The iridium complex triflic salt shown above (1.7 g) and the target ligand from the previous step (1.5 g, 3.57 mmol) were suspended in the mixture of 2-ethoxy ethanol (35 ml) and DMF (35 ml). The mixture was degassed for 20 minutes and was heated to reflux (90° C.) under nitrogen for 18 hours. After the reaction was cooled to 20° C., the solvent was evaporated. The residue was dissolved in DCM and the filtered through a short silica gel plug. The solvent was evaporated, and the residue was subjected to column chromatography on a silica gel then eluted with a mixture of DCM and heptane (7/3, v/v) to yield the comparative compound 1 as yellow crystals (0.8 g, 38% yield).

Synthesis of Comparative Compound 2

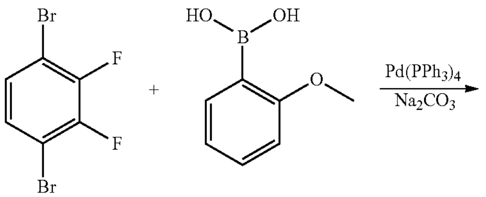

-continued

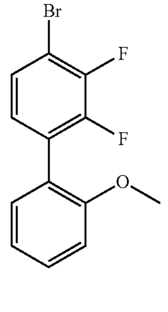

Sodium carbonate (11.69 g, 110 mmol), 1,4-dibromo-2,3-difluorobenzene (15 g, 55.2 mmol), (2-methoxyphenyl) boronic acid (8.80 g, 57.9 mmol) and tetrakis(triphenylphosphine)palladium(0) (3.19 g, 2.76 mmol) were suspended in a water (140 mL)/dioxane (140 mL) mixture. The reaction mixture was degassed, heated in a 80° C. oil bath for 20 hours and allowed to cool. The resulting mixture was mixed with brine and extracted with EtOAc. The extracts were washed with water and brine, then dried and evaporated leaving a solid/liquid mixture that was absorbed onto a silica gel and chromatographed on silica gel column eluted with heptane followed by heptanes/DCM 4/1 (v/v), providing 12.5 g of the target structure as a colorless liquid (76% yield).

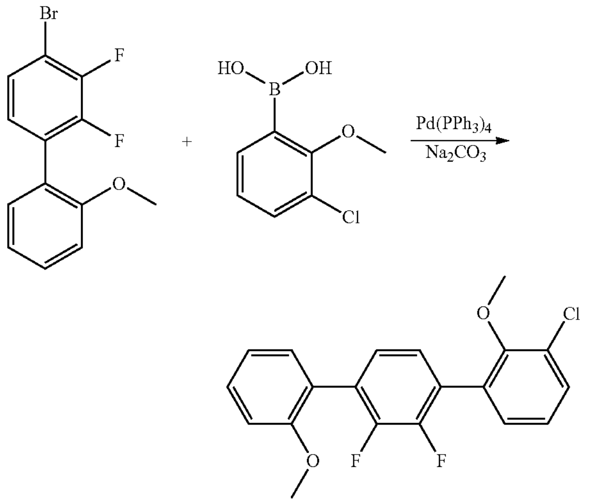

Sodium carbonate (8.77 g, 83 mmol), tetrakis(triphenylphosphine)palladium(0) (1.435 g, 1.242 mmol), 4-bromo-2,3-difluoro-2'-methoxy-1,1'-biphenyl (12.38 g, 41.4 mmol) and (3-chloro-2-methoxyphenyl)boronic acid (8.10 g, 43.5 mmol) were suspended in a water (125 mL)/dioxane (125 mL) mixture. The reaction mixture was degassed and heated in a 80° C. oil bath for 20 hours. Then additional catalyst (1.435 g, 1.242 mmol) and boronic acid (2.4 g, 0.3 equivalents) were added and the reaction mixture was degassed again and heated in a 80° C. oil bath under nitrogen for 12 hours. The reaction mixture was allowed to cool before being diluted with brine and extracted with DCM. The extracts were washed with water and brine, then dried and evaporated leaving 23.7 g of white solid that was purified by column chromatography on silica gel, eluted with heptane/DCM gradient mixture, providing 9.95 g of the target material as a white solid (67% yield).

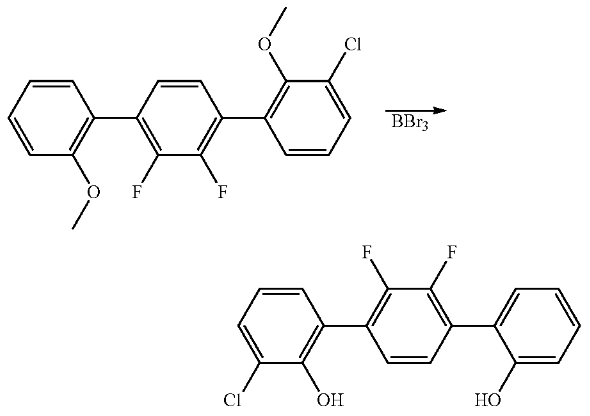

A solution of 3-chloro-2',3'-difluoro-2,2"-dimethoxy-1,1':4',1"-terphenyl (9.95 g, 27.6 mmol) in DCM (150 mL) was cooled in an ice/salt bath and a 1M solution of boron tribromide in DCM (110 mL, 110 mmol) was added dropwise. The reaction mixture was stirred for 14 hours and allowed to slowly warm up to room temperature. The reaction mixture was then cooled in an ice bath and 125 mL of water was added dropwise. The resulting mixture was stirred for 30 minutes, then extracted with DCM and then EtOAc. The extracts were washed with water, dried and evaporated providing 8.35 g of white solid (91% yield).

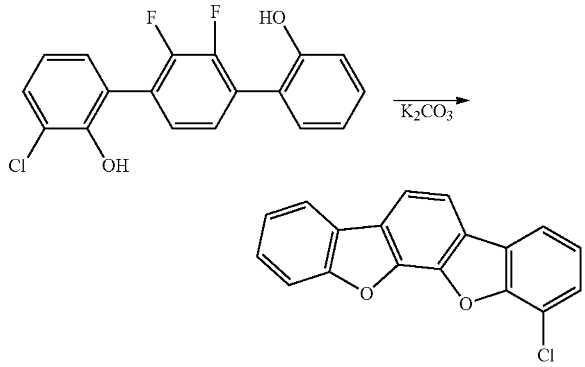

3-Chloro-2',3'-difluoro-[1,1':4',1"-terphenyl]-2,2"-diol (8.35 g, 25.10 mmol) and potassium carbonate (7.63 g, 55.2 mmol) were suspended under nitrogen in N-Methyl-2-pyrrolidinone (100 mL) and heated to 130° C. in an oil bath for 16 hours. The reaction mixture was allowed to cool and the solvent was distilled off. The residue was chromatographed on silica gel column and eluted with heptanes/ethyl acetate 9/1 (v/v), providing the target chloride as a white solid (6.5 g, 88% yield).

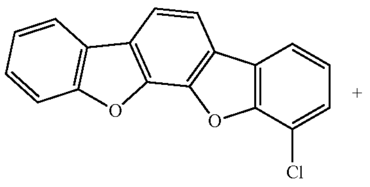

-continued

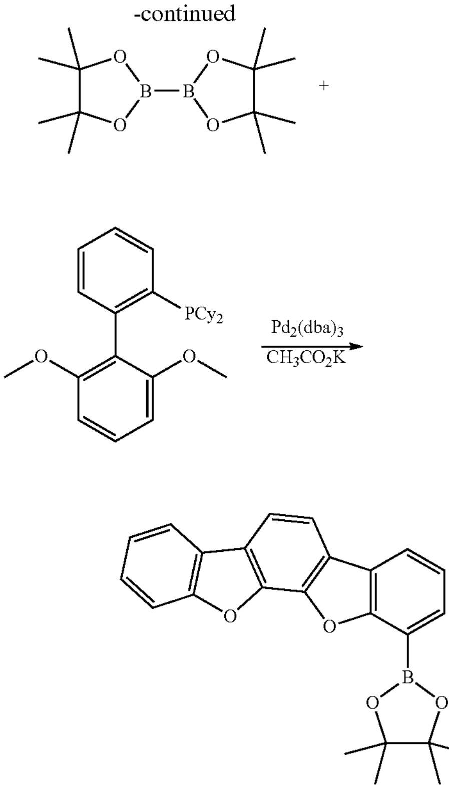

The chloride from the previous step (6.5 g, 22.21 mmol), 4,4,4',4',5,5,5',5'-octamethyl-2,2'-bi(1,3,2-dioxaborolane) (11.28 g, 44.4 mmol), and ethoxy-[1,1'-biphenyl]-2-yl)phosphane (SPhos, 0.547 g, 1.332 mmol) and tris(dibenzylideneacetone)dipalladium(0) (0.305 g, 1.5 mol. %) were dissolved in dioxane (250 mL)he reaction mixture was degassed and heated to reflux under nitrogen for 18 hours. The reaction mixture was allowed to cool before it was diluted with water and extracted with EtOAc. The extracts were combined, washed with water, dried and evaporated leaving an orange semi-solid. The orange semi-solid was tritiarated with heptane and the solid was filtered off to yield 7.3 g of the target boronic ester (85% yield).

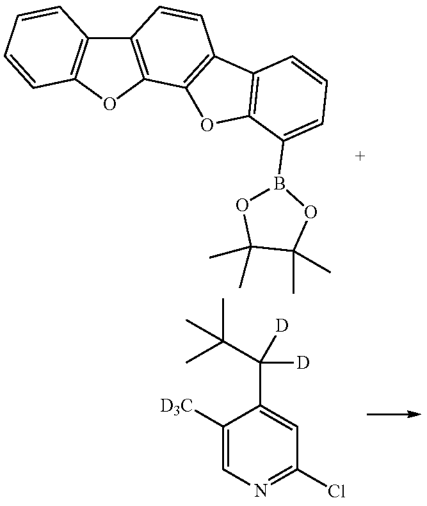

-continued

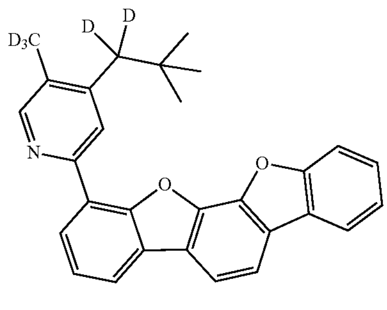

The boronic ester from the previous step (3.6 g, 9.37 mmol), 2-chloro-4-(2,2-dimethylpropyl-1,1-d2)-5-(methyl-d3)pyridine (1.899 g, 9.37 mmol), and tetrakis(triphenyl) phosphine)palladium(0) (0.541 g, 0.468 mmol) were suspended in dioxane (110 ml). Potassium phosphate tribasic monohydrate (6.46 g, 28.1 mmol) in water (20 mL) was added as one portion. The reaction mixture was degassed and heated to reflux under nitrogen for 24 hours. The reaction mixture was allowed to cool, before it was diluted with brine and extracted with ethyl acetate. The extracts were washed with brine, dried and evaporated leaving a solid that was absorbed onto a plug of silica gel and chromatographed on a silica gel column, eluted with heptanes/DCM 1/1 (v/v) then 5% methanol in DCM, to isolate the desired ligand as a white solid (3.17 g, 80% yield).

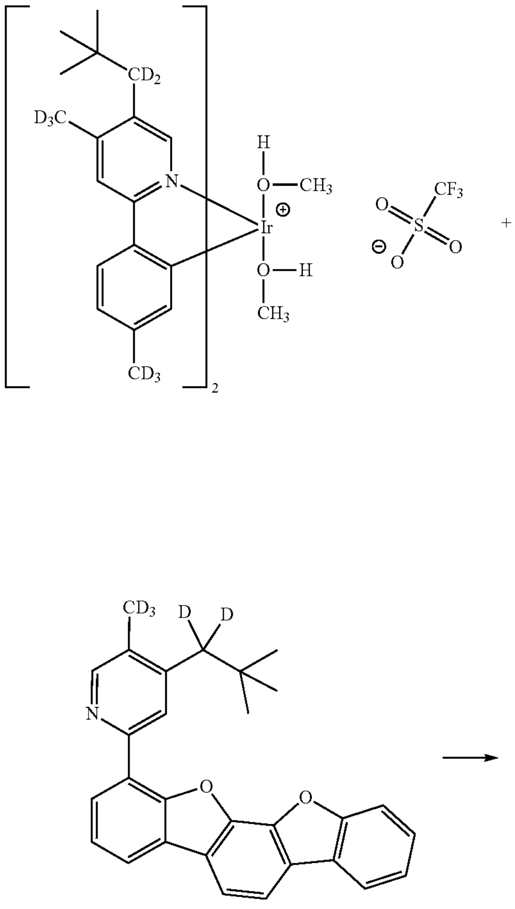

-continued

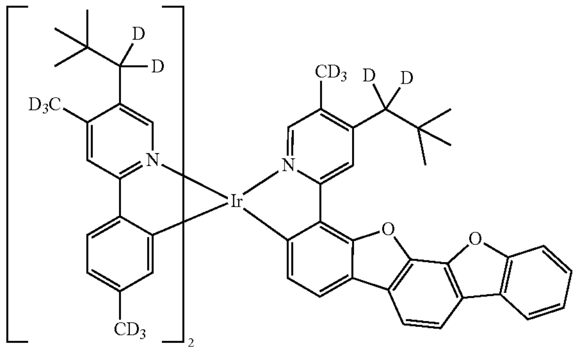

The ligand from the previous step (1.95 g, 4.59 mmol) was suspended in a 2-ethoxy ethanol (25 mL)/DMF (25 mL) mixture. The iridium complex triflic salt shown above (2.362 g, 2.55 mmol) was added as one portion. The reaction mixture was degassed and heated in a 100° C. oil bath under nitrogen for 9 days. The reaction mixture was allowed to cool, and the solvents were evaporated. The residue was tritiarated with methanol to recover 3.4 g of yellow solid, which was absorbed onto a silica gel plug and chromatographed on silica gel column, eluted with heptanes/toluene/DCM 6/3/1 (v/v/v) mixture. Additional purification on a silica gel column, eluted with heptanes/toluene 1/1 (v/v) solvents provided a bright yellow solid material, which was tritiarated with methanol, filtered and dried to yield 0.93 g of the pure iridium target material (comparative compound 2) shown above (19% yield).

Device Examples

All example devices were fabricated by high vacuum (<$10^{-7}$ Torr) thermal evaporation. The anode electrode was 800 Å of indium tin oxide (ITO). The cathode consisted of 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package. The organic stack of the device examples consisted of sequentially, from the ITO surface, 100 Å of HATCN as the hole injection layer (HIL); 400 Å of HTL-1 as the hole transporting layer (HTL); 50 Å of EBL-1 as the electron blocking layer; 400 Å of an emissive layer (EML) comprising 12% of the dopant in a host comprising a 60/40 mixture of Host-1 and Host-2; 350 Å of Liq doped with 35% of ETM-1 as the ETL; and 10 Å of Liq as the electron injection layer (EIL).

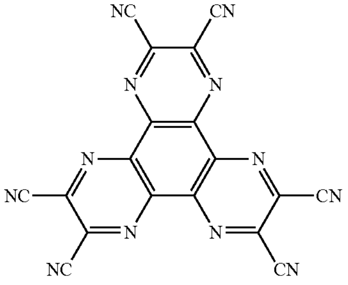

HATCN

-continued
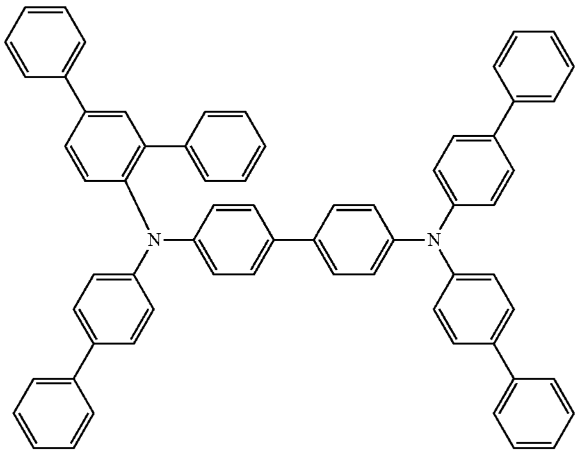
HTL-1
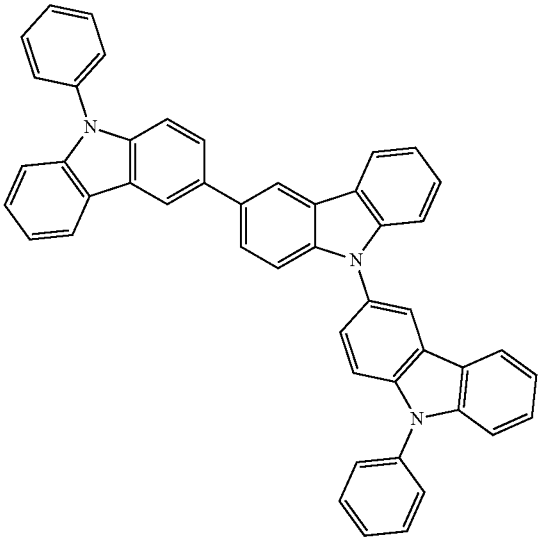
EBL-1
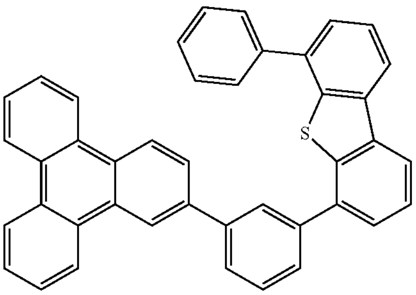
Host-1
-continued
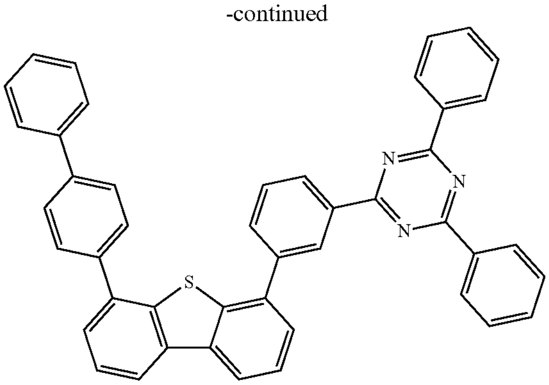
Host-2
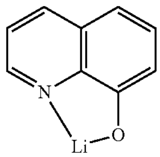
Liq
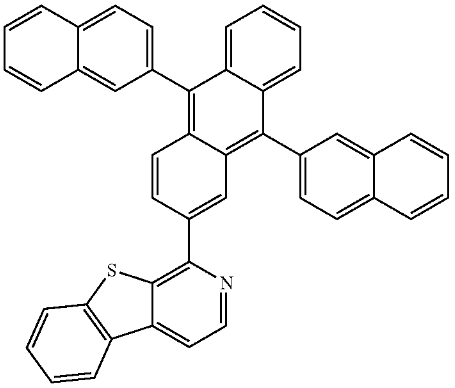
ETM-1
Comparative example 1
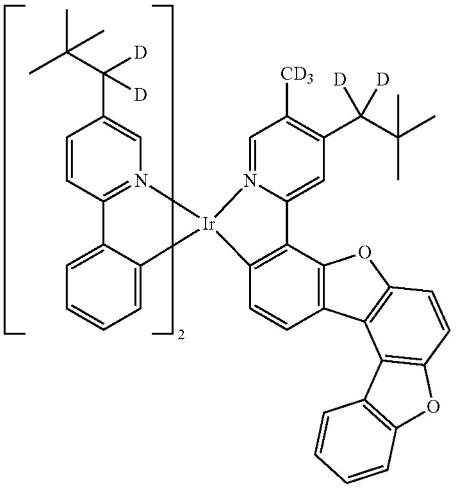

-continued
Comparative example 2
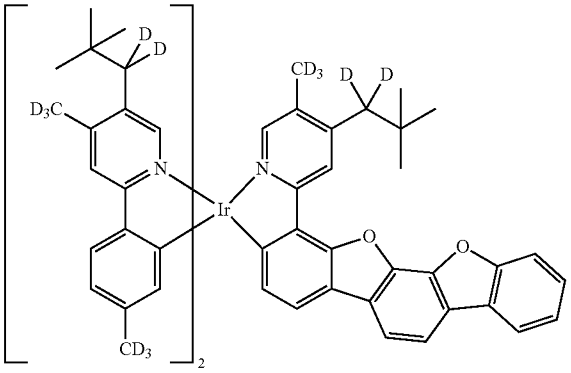
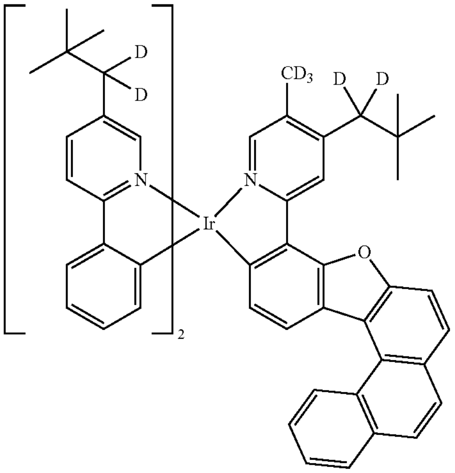
Inventive example for device 1
$IrL_{X133}(L_{B461})_2$
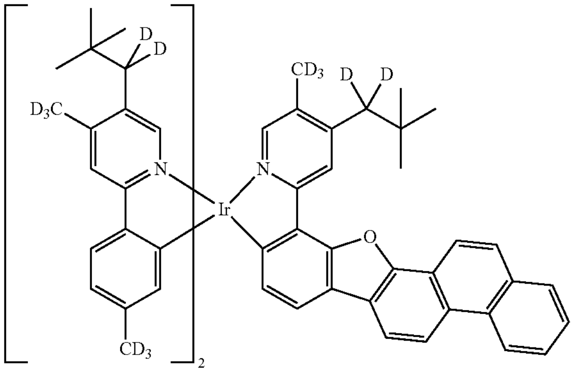
Inventive example for device 2
$IrL_{X101}(L_{B463})_2$
-continued
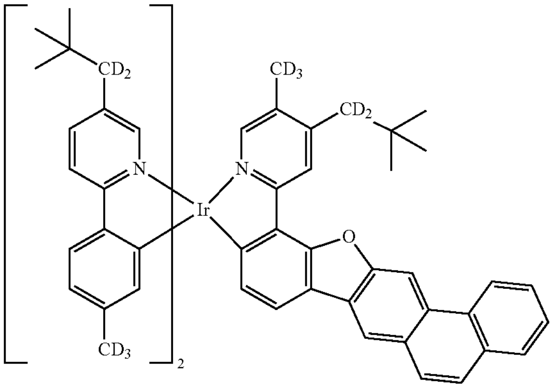
Inventive example for device 3
$IrL_{X75}(L_{B284})_2$
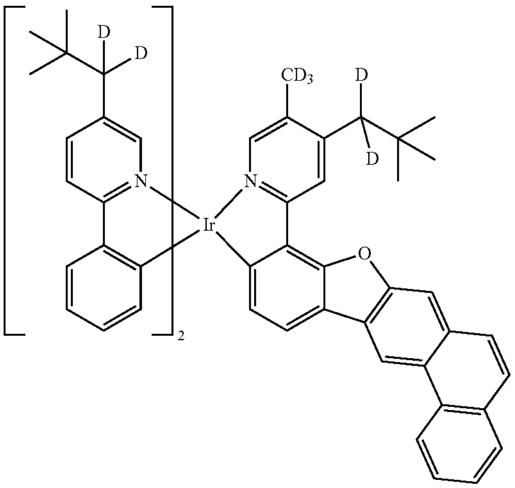
Inventive example for device 4
$IrL_{X169}(L_{B461})_2$
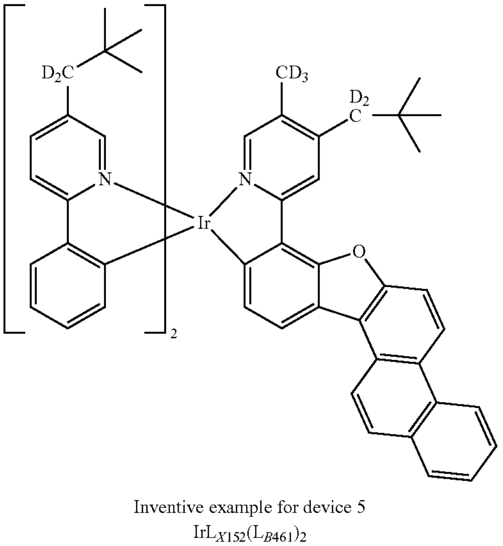
Inventive example for device 5
$IrL_{X152}(L_{B461})_2$ -continued

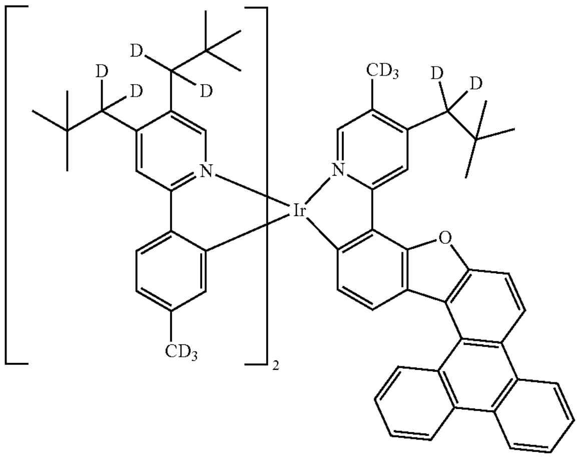

Inventive example for device 6
$IrL_{X220}(L_{B467})_2$

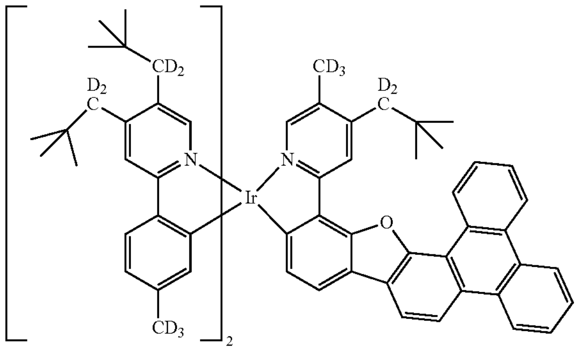

Inventive example for device 7
$IrL_{X206}(L_{B467})_2$

-continued

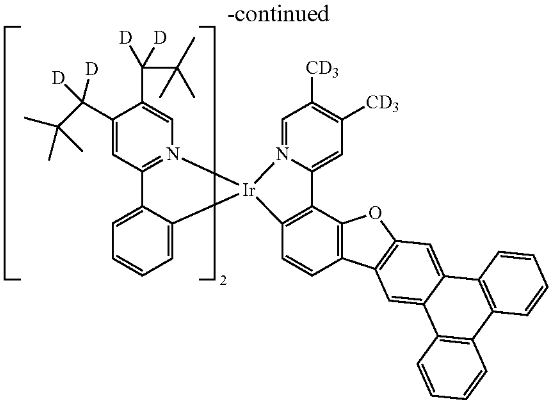

Inventive example for device 8
$IrL_{X211}(L_{B466})_2$

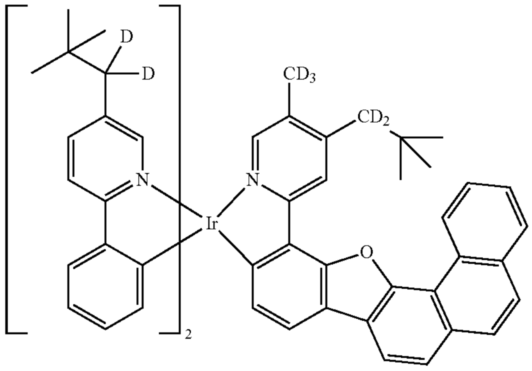

Inventive example for device 9
$IrL_{X114}(L_{B461})_2$

Upon fabrication, the electroluminescence (EL) and current density-voltage-luminance (JVL) performance of the devices was measured. The device lifetimes were evaluated at a current density of 80 mA/cm$^2$. The device data are normalized to Comparative Example 1 and is summarized in Table 1. The device data demonstrates that the dopants of the present invention afford green emitting devices with better device lifetime than the comparative example. For example, comparing device example 1 vs 1' and 2 vs 2' it can be observed that replacing the dibenzofuran moiety with a phenanthrene moiety (see the following scheme) substantially increases the device lifetime (9 fold improvement for 1 vs 1' and 6.2 fold improvement for 2 vs 2'). Furthermore, the narrowness of the emission spectrum substantially improves for the dopants of the present invention. For example, comparing device example 1 vs 1', it can be observed that replacing the dibenzofuran moiety with phenanthrene moiety (see the following scheme) results in a decrease of the FWHM (Full width at half maximum) from 53 nm to 38 nm (1' vs 1). In general, the dopants of the present invention have the FWHM less than 50 nm (see device example 1,3,4,5,8 and 9). As known to the person skilled in the art, the device lifetime and the narrowness of the emission spectrum are two parameters that are very important to producing a commercially useful OLED device and are also some of the most difficult parameters to improve. In general, a few percent improvement is consider a significant improvement to those skilled in the OLED arts. In this invention, these two parameters unexpectedly have a huge improvement with one design change to the molecule.

-continued

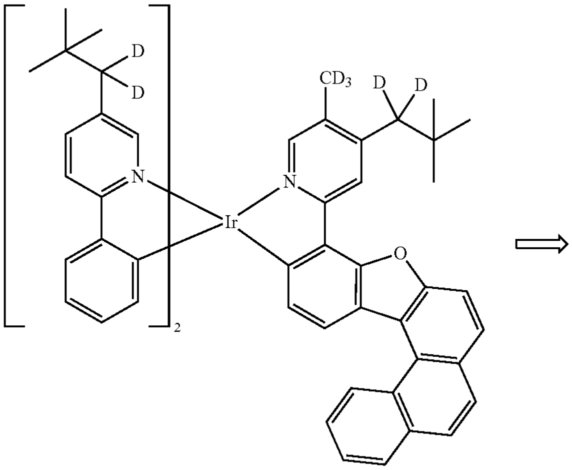

Inventive example 1 $IrL_{X133}(L_{B461})_2$

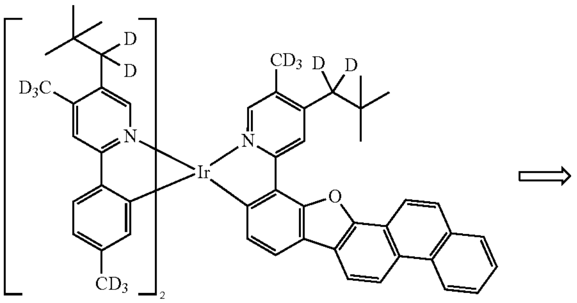

Invenative example 2
$IrL_{X101}(L_{B463})_2$

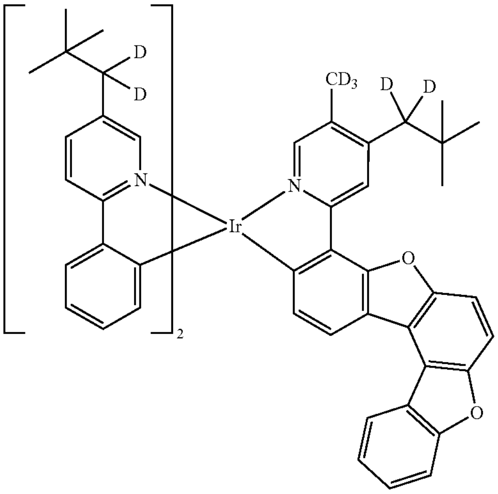

Comparative example 1

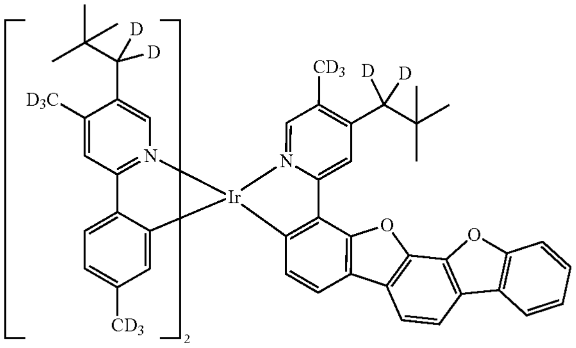

Comparative example 2

TABLE 1

| Device Example | Dopant | 1931 CIE x | 1931 CIE y | λ max [nm] | FWHM [nm] | At 10 mA/cm$^2$ Voltage [a.u.]* | At 10 mA/cm$^2$ EQE [a.u.]* | At 80 mA/cm2 $LT_{95\%}$ [a.u.]* |
|---|---|---|---|---|---|---|---|---|
| 1 | $IrL_{X133}(L_{B461})_2$ | 0.334 | 0.637 | 530 | 38 | 1.032 | 0.90 | 9 |
| 2 | $IrL_{X101}$ $(L_{B463})_2$ | 0.340 | 0.631 | 526 | 57 | 0.982 | 1.06 | 11.2 |
| 3 | $IrL_{X75}(L_{B284})_2$ | 0.319 | 0.645 | 524 | 49 | 1.026 | 0.985 | 5.4 |
| 4 | $IrL_{X169}(L_{B461})_2$ | 0.325 | 0.645 | 530 | 24 | 0.978 | 0.757 | 13.5 |
| 5 | $IrL_{X152}(L_{B461})_2$ | 0.342 | 0.633 | 530 | 28 | 0.978 | 0.85 | 14.6 |
| 6 | $IrL_{X220}(L_{B467})_2$ | 0.355 | 0.624 | 532 | 52 | 1.036 | 1.06 | 12.9 |
| 7 | $IrL_{X206}(L_{B467})_2$ | 0.345 | 0.630 | 529 | 52 | 1.03 | 1.04 | 8.6 |
| 8 | $IrL_{X211}(L_{B466})_2$ | 0.322 | 0.645 | 526 | 31 | 1.03 | 0.929 | 16.9 |
| 9 | $IrL_{X114}(L_{B461})_2$ | 0.366 | 0.636 | 528 | 29 | 1.06 | 0.962 | 19.6 |
| 1' | Comparative example 1 | 0.306 | 0.647 | 520 | 53 | 1 | 1 | 1 |
| 2' | Comparative example 2 | 0.332 | 0.634 | 524 | 57 | 0.97 | 1.084 | 1.8 |

*Value is normalized to comparative example 1'

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound comprising a first ligand $L_A$ wherein $L_A$ is a bidentate ligand comprising comprises the following formula:

Formula I

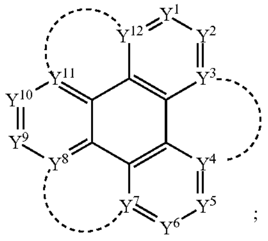

;

wherein each of $Y^1$ to $Y^{12}$ are independently CR or N;

wherein each R can be same or different, and any two adjacent Rs are optionally joined or fused into a ring;

wherein at least one pair selected from the group consisting of $Y^3$ and $Y^4$, $Y^7$ and $Y^8$, and $Y^{11}$ and $Y^{12}$ are CR where the Rs are joined or fused into a 5-membered or 6-membered carbocyclic or heterocyclic ring;

wherein each R is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

wherein $L_A$ is complexed to a metal M selected from the group consisting of Os, Ir, Pd, Pt, Cu, and Au;

wherein M is optionally coordinated to other ligands; and wherein the ligand $L_A$ is optionally linked with other ligands to comprise a tridentate, tetradentate, pentadentate, or hexadentate ligand.

2. A compound comprising a first ligand $L_x$ of Formula II

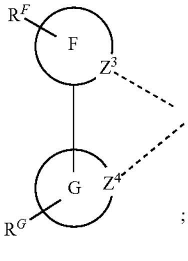

;

wherein F is a 5-membered or 6-membered carbocyclic or heterocyclic ring;

wherein each of $R^F$, $R^G$, $R^H$, and $R^I$ independently represent mono to the maximum possible number of substitutions, or no substitution;

wherein $Z^3$ and $Z^4$ are each independently C or N and coordinated to a metal M to form a 5-membered chelate ring;

wherein moiety G is a fused ring structure comprising five or more fused heterocyclic or carbocyclic rings, of which at least one ring is of Formula III

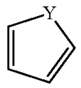

;

wherein the fused heterocyclic or carbocyclic rings comprised by moiety G are 5-membered or 6-membered if moiety G comprises two or more 5-membered rings, at least two of the 5-membered rings are fused to one another;

wherein at least one of $Z^3$ or $Z^4$ is part of a 6-membered ring;

wherein Y is selected from the group consisting of BR', NR', PR', O, S, Se, C═O, S═O, $SO_2$, CR'R", SiR'R", and GeR'R";

wherein each R', R", $R^F$, $R^G$, $R^H$, and $R^I$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

wherein metal M is optionally coordinated to other ligands;

wherein the ligand $L_x$ is optionally linked with other ligands to comprise a tridentate, tetradentate, pentadentate, or hexadentate ligand; and wherein at least one of the following conditions is true (1) Y is selected from the group consisting of BR', NR', PR', O, S, Se, C═O, S═O, $SO_2$, SiR'R", and GeR'R";

(2) Formula III is fused directly to moiety G and a 5-membered ring is fused directly to Formula III, (3) moiety G comprises exactly five fused heterocyclic or carbocyclic rings;

(4) moiety G includes at least one 6-membered, heteroaryl ring; or (5) the compound has a structure of Formula IV,

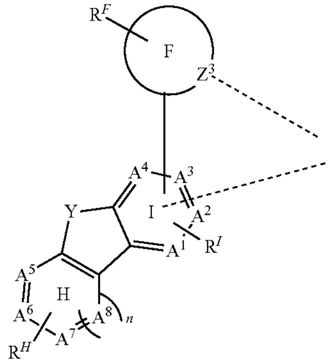

and at least one of the following is true:

(i) at least one additional ring is fused to ring I, (ii) two additional rings are directly fused to H, or (iii) exactly one additional ring, $H^1$, is fused directly to H and exactly one additional ring, $H^2$, is fused to $H^1$, wherein each of H1 and H2 is a 5- or 6-membered heterocyclic or carbocyclic ring;

wherein:

$A^1$ to $A^4$ are each independently C or N;

one of $A^1$ to $A^4$ is $Z^4$ in Formula II;

each of ring F and ring H is a 5-membered or 6-membered aryl or heteroaryl ring;

wherein n is 0 or 1;

wherein when n is 0, $A^8$ is not present, two adjacent atoms of $A^5$ to $A^7$ are C, and the remaining atom of $A^5$ to $A^7$ is selected from the group consisting of NR', O, S, and Se; and wherein any two substituents can be joined or fused together to form a ring;

wherein when n is 1, two adjacent of $A^5$ to $A^8$ are C, and the remaining atoms of $A^5$ to $A^8$ are selected from the group consisting of C and N.

3. The compound of claim 2, wherein Lx has Formula IV

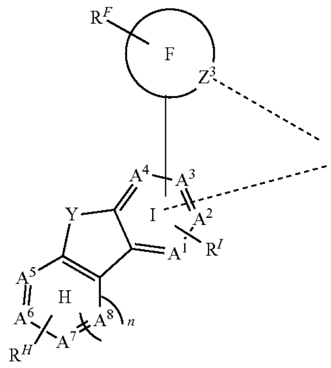

;

4. The compound of claim 3, wherein each $R^F$, $R^H$, and $R^I$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

5. The compound of claim 3, wherein M is selected from the group consisting of Ir, Rh, Re, Ru, Os, Pt, Au, and Cu.

6. The compound of claim 3, wherein Y is O.

7. The compound of claim 3, wherein n is 0, and $R^H$ includes two 6-membered rings fused to one another and to ring H.

8. The compound of claim 3, wherein n is 1, $A^5$ to $A^8$ are each C, a 6-membered ring is fused to $A^5$ and $A^6$, and another 6-membered ring is fused to $A^7$ and $A^8$.

9. The compound of claim 3, wherein ring F is selected from the group consisting of pyridine, pyrimidine, pyrazine, imidazole, pyrazole, and N-heterocyclic carbene.

10. The compound of claim 3, wherein the first ligand $L_x$ is selected from the group consisting of:

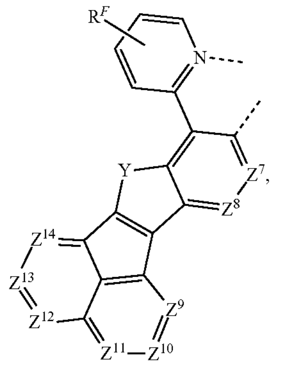

,

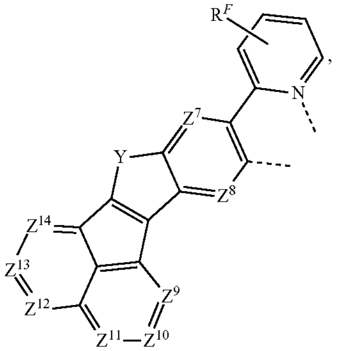

,

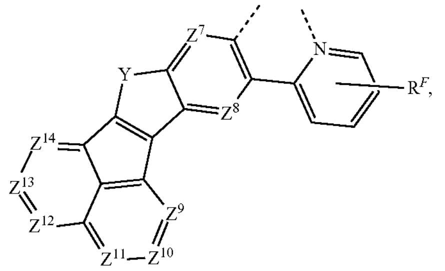

,

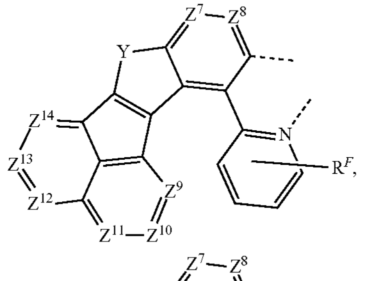

,

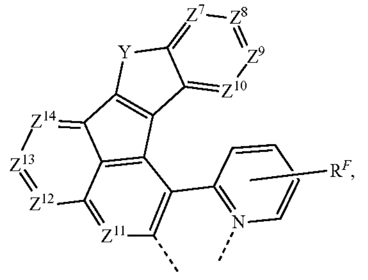

,

-continued
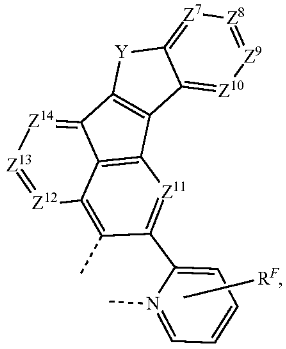
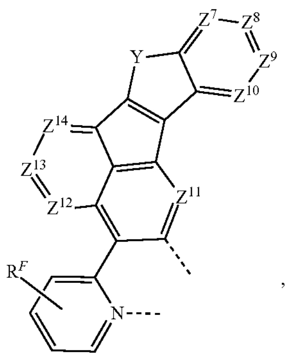
,
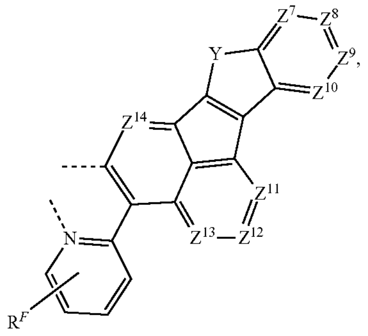
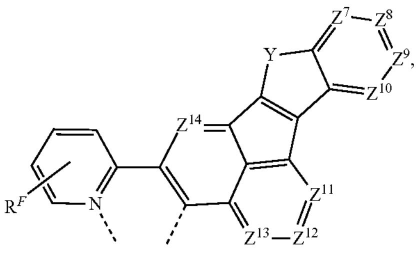
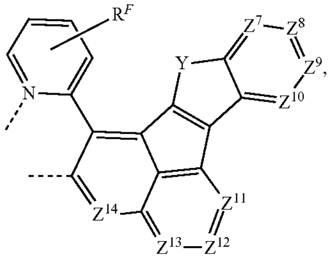
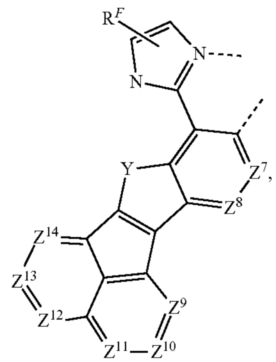
-continued
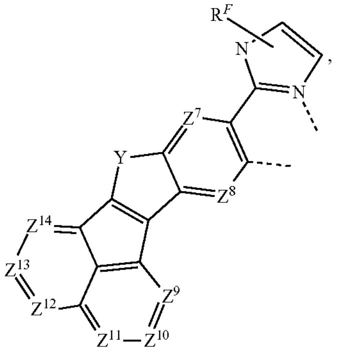
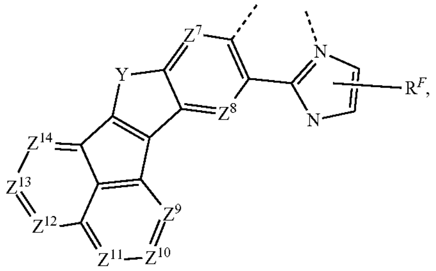
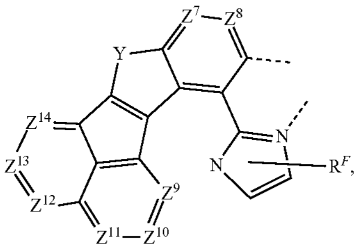
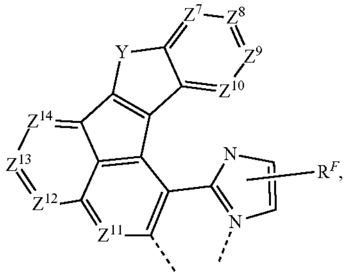
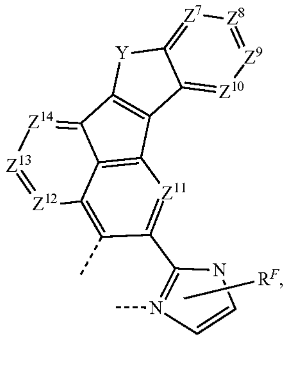
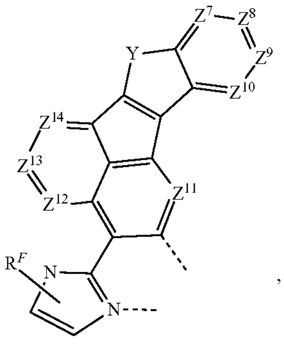
, -continued
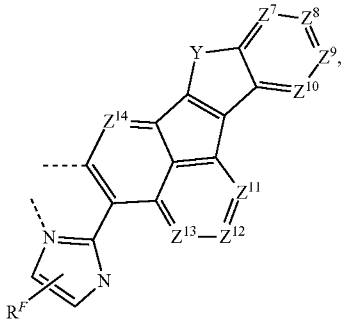
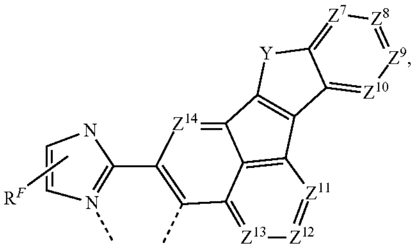
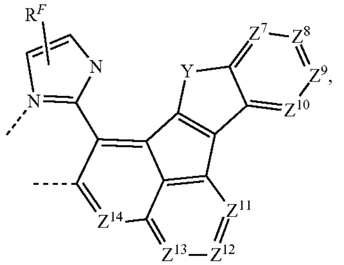
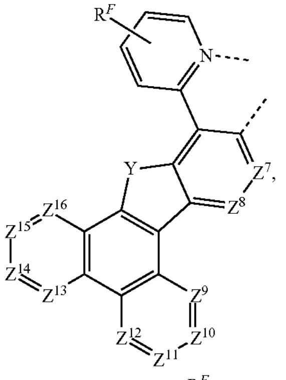
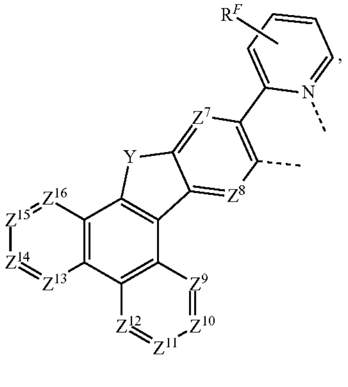
-continued
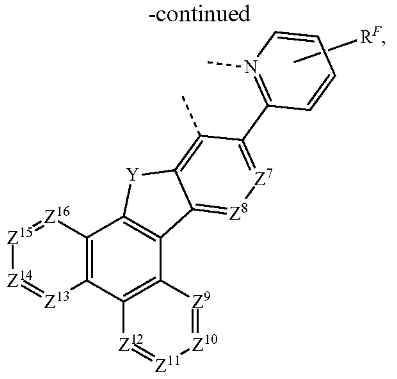
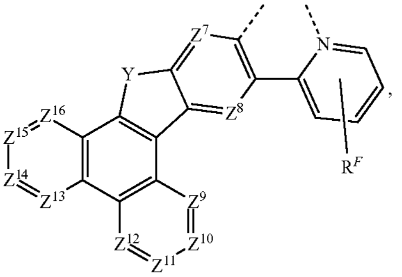
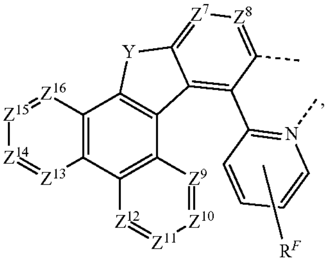
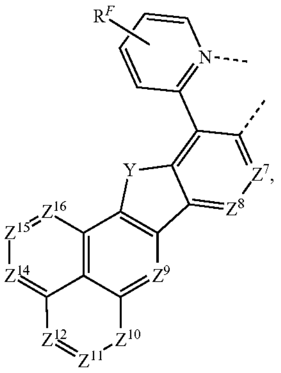
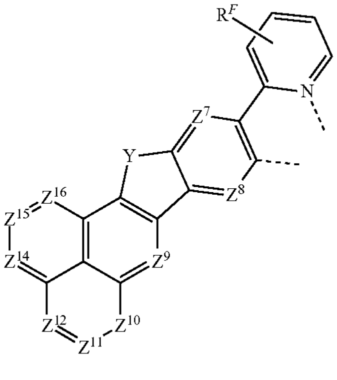

-continued
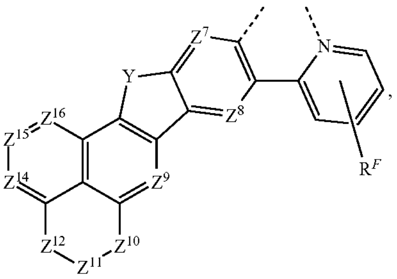
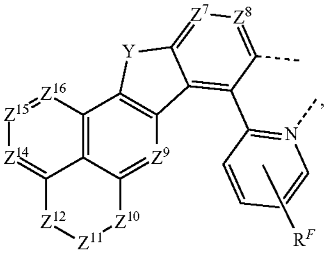
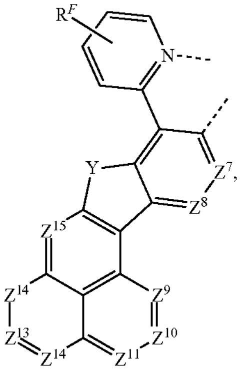
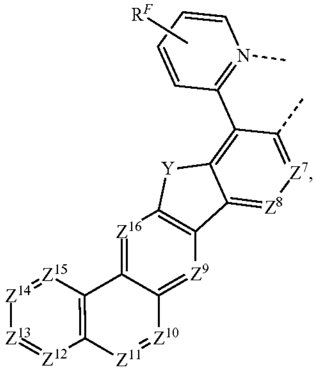
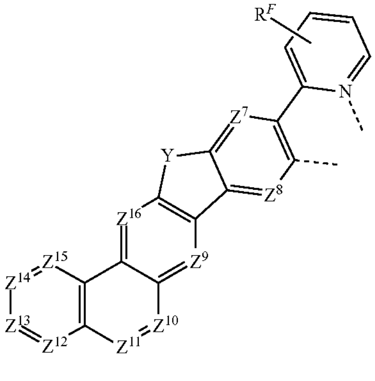
-continued
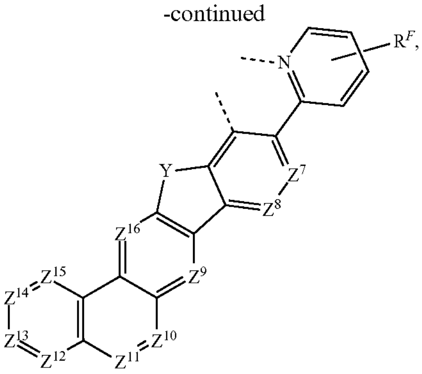
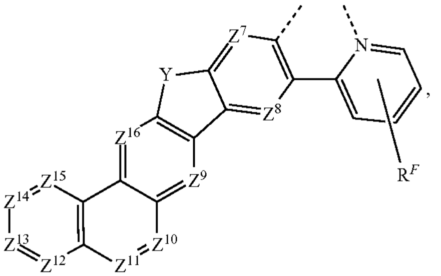
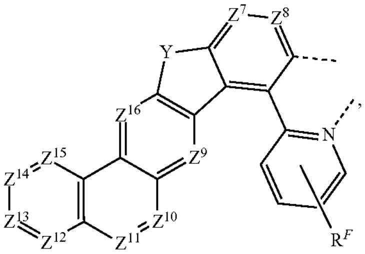
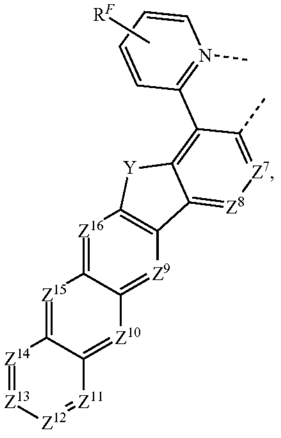
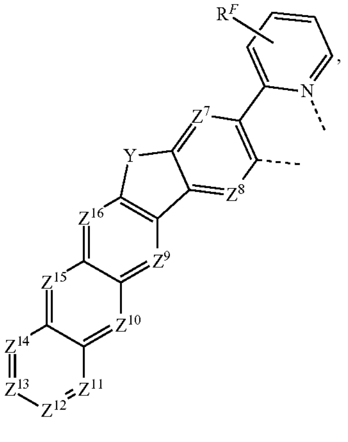

-continued
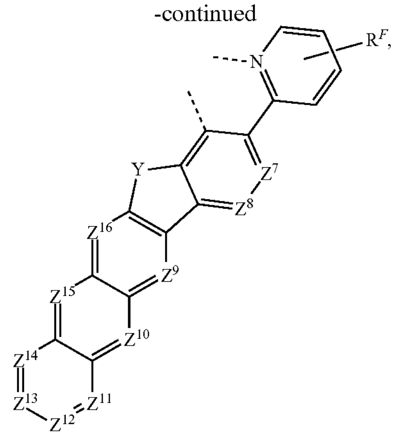
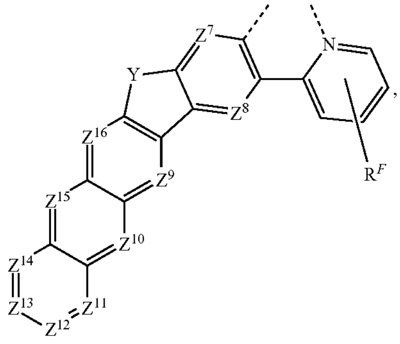
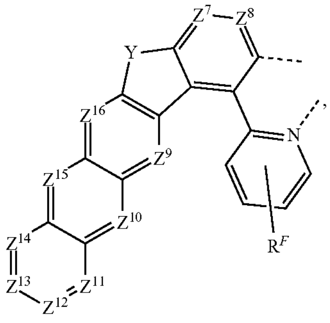
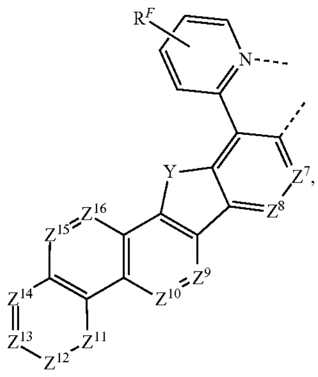
-continued
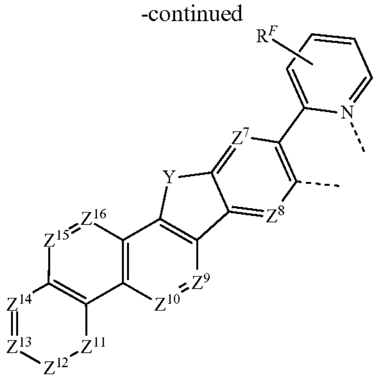
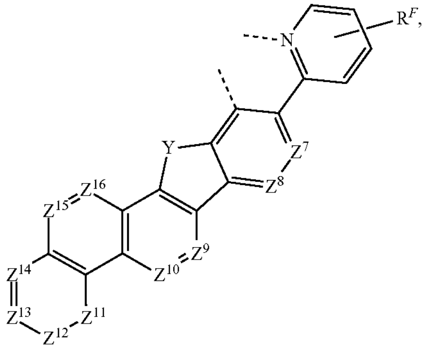
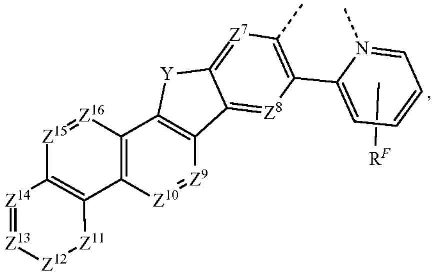
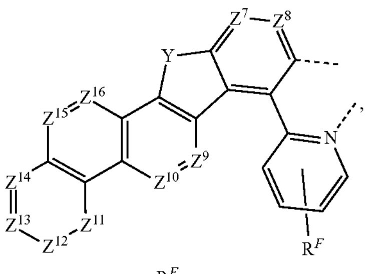
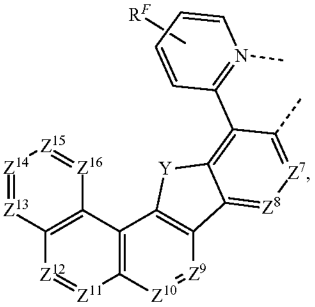

-continued
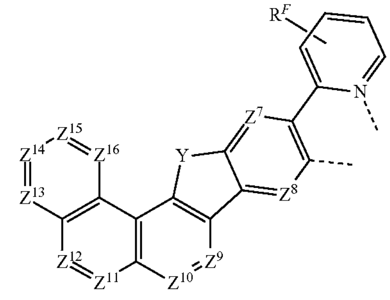
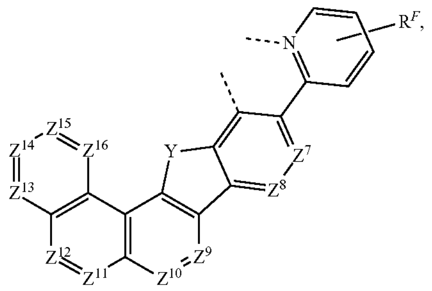
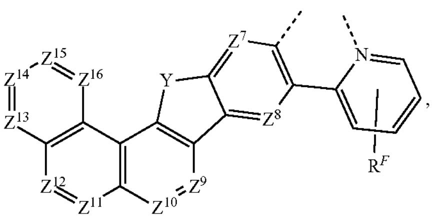
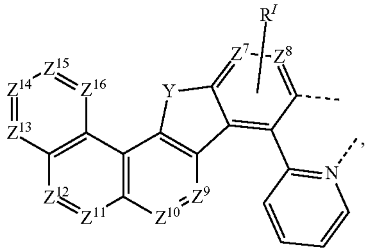
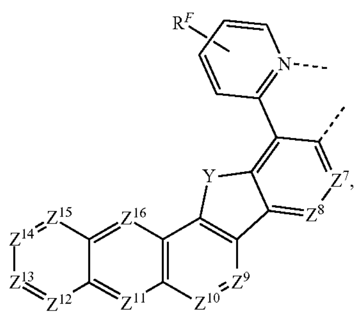
-continued
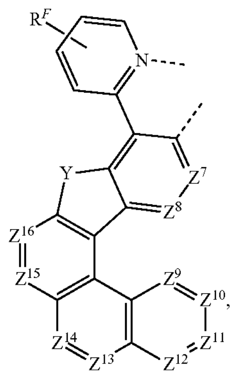
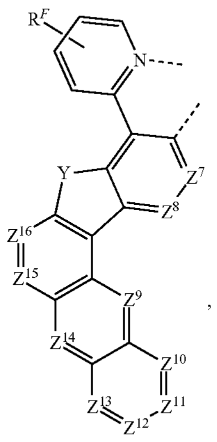
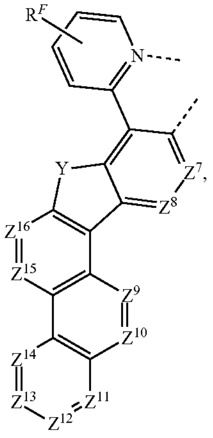
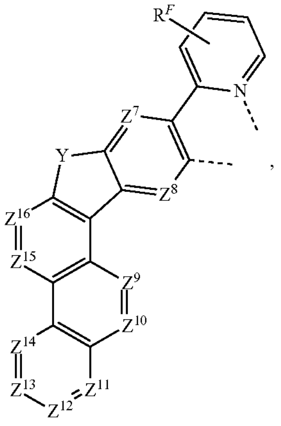
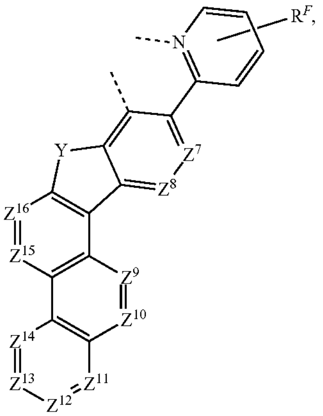
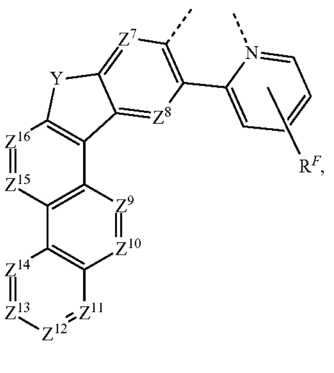

-continued
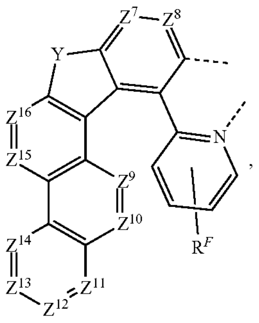
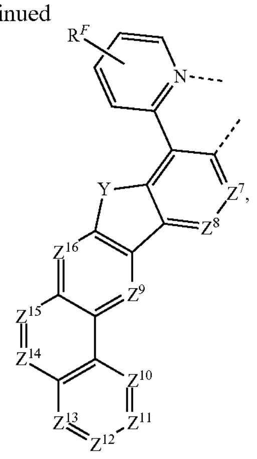
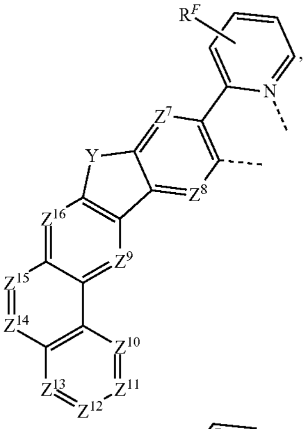
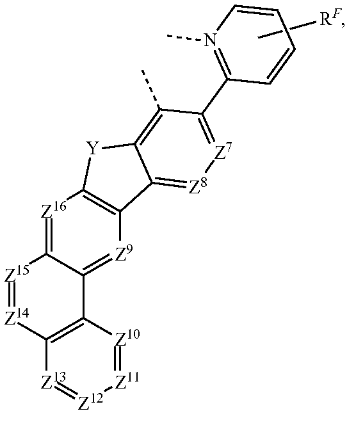
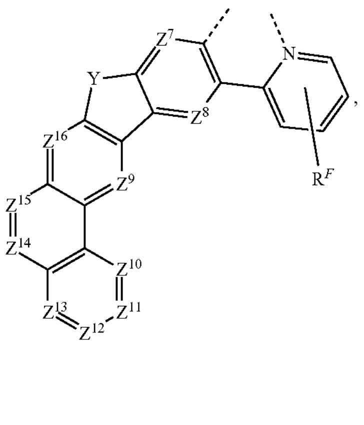
-continued
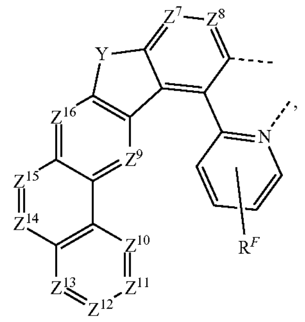
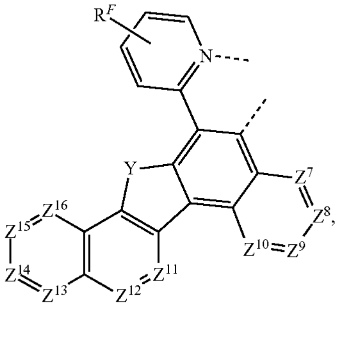
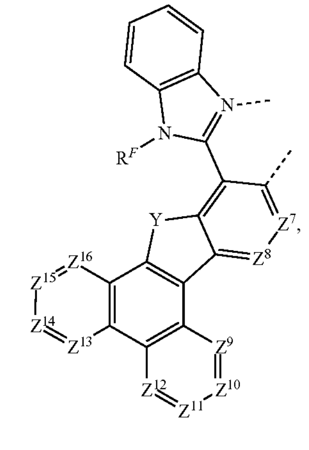
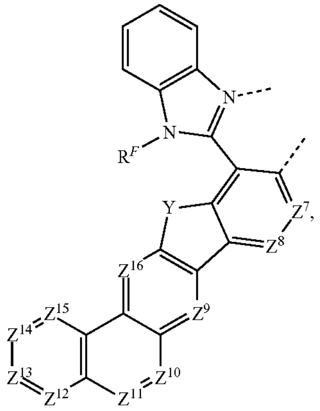

-continued

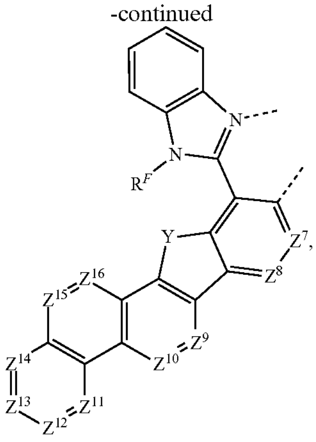

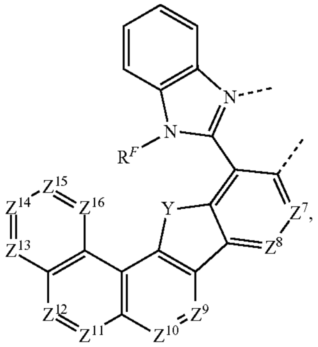

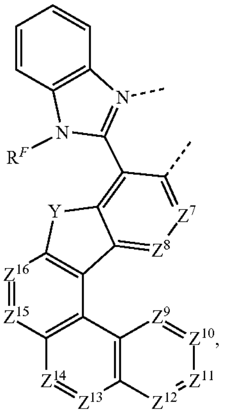

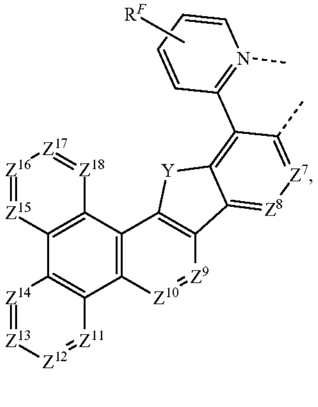

-continued

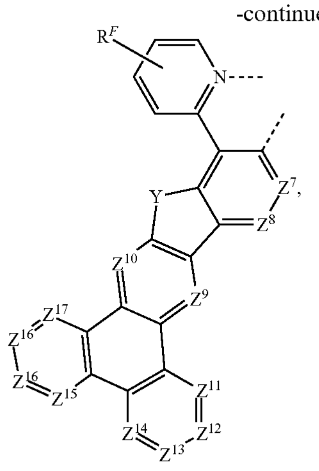

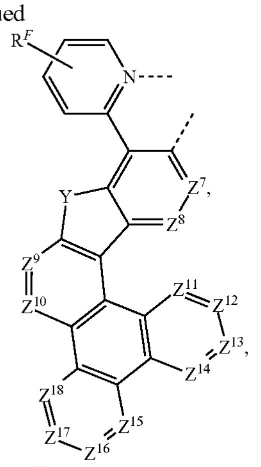

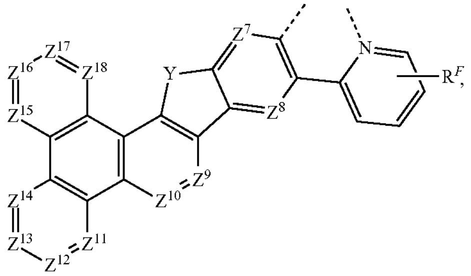

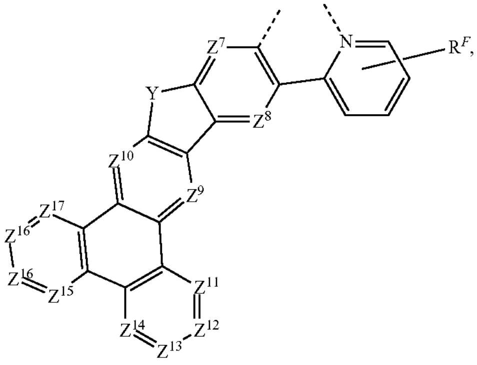

and

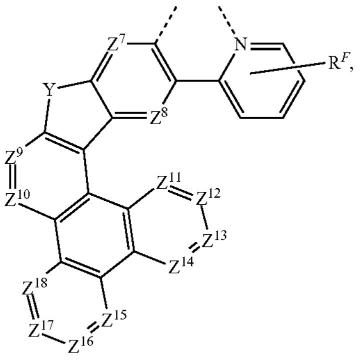

wherein $Z^7$ to $Z^{14}$ and, when present, $Z^{15}$ to $Z^{18}$ are each independently N or $CR^Q$;

wherein each $R^Q$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, and combinations thereof and wherein any two substituents may be joined or fused together to form a ring.

11. The compound of claim 3, wherein the compound has a formula of $M(L_x)_x(L_B)_y(L_C)_z$ wherein each one of $L_B$ and $L_C$ is a bidentate ligand; and wherein x is 1, 2, or 3; y is 0, 1, or 2; z is 0, 1, or 2; and x+y+z is the oxidation state of the metal M.

12. The compound of claim 11, wherein $L_B$ and $L_C$ are each independently selected from the group consisting of:

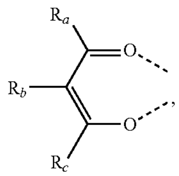
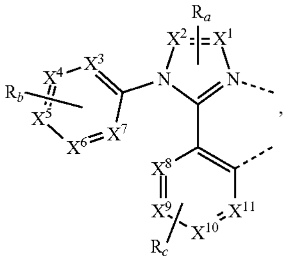
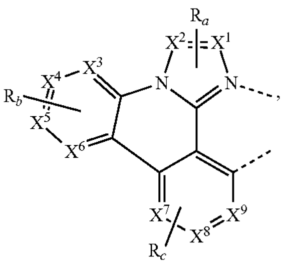
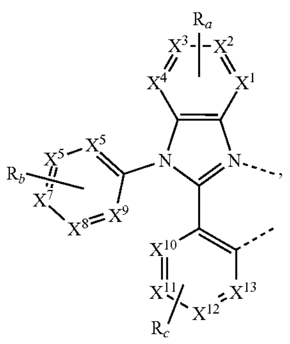
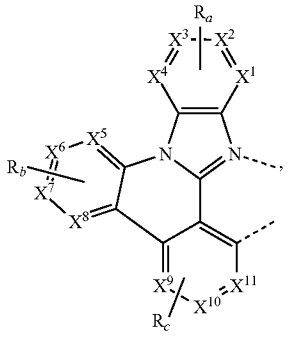
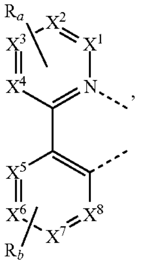
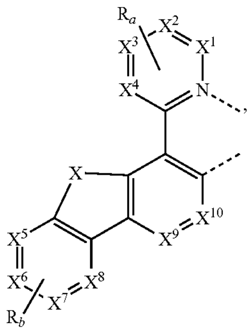
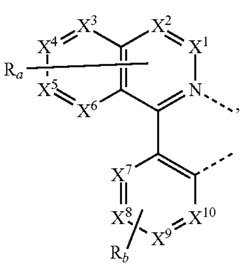

-continued

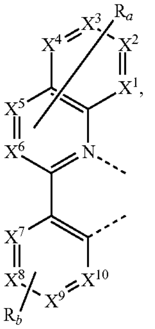
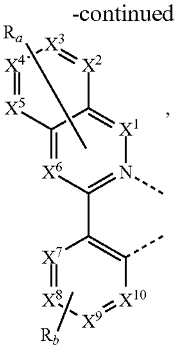
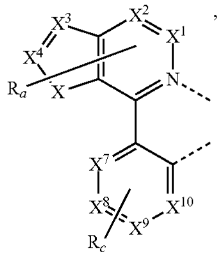
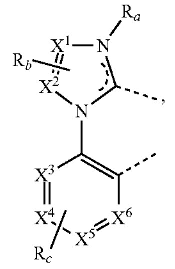
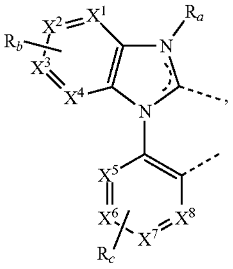
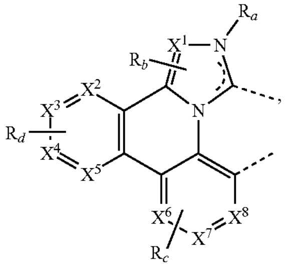
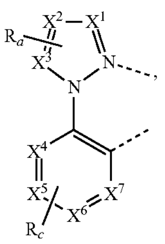
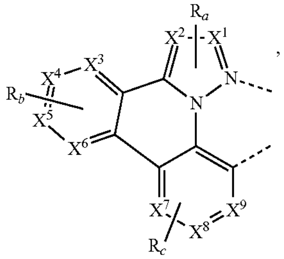
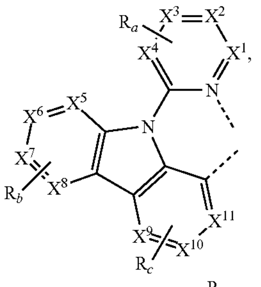
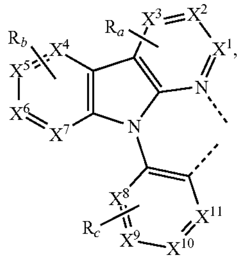

and

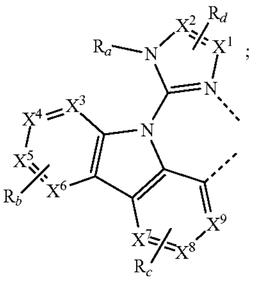

wherein each $X^1$ to $X^{13}$ are independently selected from the group consisting of carbon and nitrogen;

wherein X is selected from the group consisting of BR', NR', PR', O, S, Se, C═O, S═O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

13. The compound of claim 3, wherein the first ligand $L_A$ is selected from the group consisting of $L_{x1}$ to $L_{X207}$, $L_{X209}$ to $L_{X214}$, and $L_{x216}$ to $L_{x221}$, wherein i is an integer from 1 to 207, 209 to 214, and 216 to 222, wherein for each i from 1 to 207, 209 to 214, and 216 to 222, $L_{xi}$, is defined as follows:

| i | $L_{Xj-k}$ | $R^{F'}$ | $R^{I'}$ | $R^{H'}$ | RK |
|---|---|---|---|---|---|
| 1 | $L_{X1-1}$ | 3-Me | H | H | — |
| 2 | $L_{X1-1}$ | 4-Me | H | H | — |
| 3 | $L_{X1-1}$ | 3,4-Me | H | H | — |
| 4 | $L_{X1-1}$ | 4-$CH_2CMe_3$ | H | H | — |
| 5 | $L_{X1-1}$ | 3-Me, 4-$CH_2CMe_3$ | H | H | — |
| 6 | $L_{X1-1}$ | 4-Me | 8-Me | 14-Me | — |
| 7 | $L_{X1-2}$ | 3-Me | H | H | — |
| 8 | $L_{X1-2}$ | 4-Me | H | H | — |
| 9 | $L_{X1-2}$ | 3,4-Me | H | H | — |
| 10 | $L_{X1-2}$ | 4-$CH_2CMe_3$ | H | H | — |
| 11 | $L_{X1-2}$ | 3-Me, 4-$CH_2CMe_3$ | H | H | — |
| 12 | $L_{X1-2}$ | 4-Me | 8-Me | 14-Me | — |
| 13 | $L_{X1-3}$ | 3-Me | H | H | Me |
| 14 | $L_{X2-1}$ | 3-Me | H | H | — |
| 15 | $L_{X2-1}$ | 4-Me | H | H | — |
| 16 | $L_{X2-1}$ | 3,4-Me | H | H | — |
| 17 | $L_{X2-1}$ | 4-$CH_2CMe_3$ | H | H | — |
| 18 | $L_{X2-1}$ | 3-Me, 4-$CH_2CMe_3$ | H | H | — |
| 19 | $L_{X2-2}$ | 3-Me | H | H | — |
| 20 | $L_{X2-2}$ | 3-Me | H | H | — |
| 21 | $L_{X2-2}$ | 4-Me | H | H | — |
| 22 | $L_{X2-2}$ | 3,4-Me | H | H | — |
| 23 | $L_{X2-2}$ | 4-$CH_2CMe_3$ | H | H | — |
| 24 | $L_{X2-3}$ | 3-Me | H | H | Me |
| 25 | $L_{X2-3}$ | 4-Me | H | H | Me |
| 26 | $L_{X2-3}$ | 3,4-Me | H | H | Me |
| 27 | $L_{X3-1}$ | 3-Me | H | H | — |
| 28 | $L_{X3-1}$ | 4-Me | H | H | — |
| 29 | $L_{X3-1}$ | 3,4-Me | H | H | — |
| 30 | $L_{X3-1}$ | 4-$CH_2CMe_3$ | H | H | — |
| 31 | $L_{X3-1}$ | 3-Me, 4-$CH_2CMe_3$ | H | H | — |
| 32 | $L_{X3-1}$ | 4-Me, 3-$CH_2CMe_3$ | 7-Me | 15-Me | — |
| 33 | $L_{X3-1}$ | 4-Ph | H | H | — |
| 34 | $L_{X3-1}$ | 3-$CD_3$ | H | H | — |
| 35 | $L_{X3-1}$ | 4-$CD_3$ | H | H | — |
| 36 | $L_{X3-1}$ | 3,4-$CD_3$ | H | H | — |
| 37 | $L_{X3-1}$ | 4-$CD_2CMe_3$ | H | H | — |
| 38 | $L_{X3-1}$ | 3-$CD_3$, 4-$CD_2CMe_3$ | H | H | — |
| 39 | $L_{X3-2}$ | 3-Me | H | H | — |
| 40 | $L_{X3-2}$ | 4-Me | H | H | — |
| 41 | $L_{X3-3}$ | 4-Me | H | H | Me |
| 42 | $L_{X4-1}$ | 3,4-Me | H | H | — |
| 43 | $L_{X4-2}$ | 3,4-Me | H | H | — |
| 44 | $L_{X4-3}$ | 3,4-Me | H | H | Me |
| 45 | $L_{X5-1}$ | 3,4-Me | H | H | — |
| 46 | $L_{X5-2}$ | 3,4-Me | H | H | — |
| 47 | $L_{X5-3}$ | 3,4-Me | H | H | Me |
| 48 | $L_{X6-1}$ | 3,4-Me | H | H | — |
| 49 | $L_{X6-1}$ | 4-Me | H | H | — |
| 50 | $L_{X6-1}$ | 3-Me | H | H | — |
| 51 | $L_{X6-2}$ | 3,4-Me | H | H | — |
| 52 | $L_{X6-2}$ | 4-Me | H | H | — |
| 53 | $L_{X6-3}$ | 3-Me | H | H | Me |
| 54 | $L_{X7-1}$ | 3,4-Me | H | H | — |
| 55 | $L_{X7-1}$ | 4-Me | H | H | — |
| 56 | $L_{X7-1}$ | 3-Me | H | H | — |

-continued

| i | $L_{Xj-k}$ | $R^{F'}$ | $R^{I'}$ | $R^{H'}$ | RK |
|---|---|---|---|---|---|
| 57 | $L_{X7-2}$ | 3,4-Me | H | H | — |
| 58 | $L_{X7-2}$ | 4-Me | H | H | — |
| 59 | $L_{X7-3}$ | 3-Me | H | H | Me |
| 60 | $L_{X8-1}$ | 3,4-Me | H | H | — |
| 61 | $L_{X8-1}$ | 4-Me | H | H | — |
| 62 | $L_{X8-1}$ | 3-Me | H | H | — |
| 63 | $L_{X8-2}$ | 3,4-Me | H | H | — |
| 64 | $L_{X8-2}$ | 4-Me | H | H | — |
| 65 | $L_{X8-3}$ | 3-Me | H | H | Me |
| 66 | $L_{X9-1}$ | 3-Me | H | H | — |
| 67 | $L_{X9-1}$ | 4-Me | H | H | — |
| 68 | $L_{X9-1}$ | 3,4-Me | H | H | — |
| 69 | $L_{X9-1}$ | 4-$CH_2CMe_3$ | H | H | — |
| 70 | $L_{X9-1}$ | 3-Me, 4-$CH_2CMe_3$ | H | H | — |
| 71 | $L_{X9-1}$ | 3-Me | H | H | — |
| 72 | $L_{X9-1}$ | 3-Me | 7-Ph | H | — |
| 73 | $L_{X9-1}$ | 3-Me | 7-Me | H | — |
| 74 | $L_{X9-1}$ | 3-Me | H | 11-Me | — |
| 75 | $L_{X9-1}$ | 3-$CD_3$, 4-$CD_2CMe_3$ | H | 9,10-$(CH)_4$ | — |
| 76 | $L_{X9-1}$ | 3-$CD_3$ | H | H | — |
| 77 | $L_{X9-1}$ | 4-$CD_3$ | H | H | — |
| 78 | $L_{X9-1}$ | 3,4-$CD_3$ | H | H | — |
| 79 | $L_{X9-1}$ | 4-$CD_2CMe_3$ | H | H | — |
| 80 | $L_{X9-1}$ | 3-$CD_3$, 4-$CD_2CMe_3$ | H | H | — |
| 81 | $L_{X9-2}$ | 3-Me | H | H | — |
| 82 | $L_{X9-2}$ | 4-Me | H | H | — |
| 83 | $L_{X9-2}$ | 3,4-Me | H | H | — |
| 84 | $L_{X9-3}$ | 3-Me | H | H | Me |
| 85 | $L_{X10-1}$ | 4-Me | H | H | — |
| 86 | $L_{X10-2}$ | 4-Me | H | H | — |
| 87 | $L_{X10-3}$ | 4-Me | H | H | Me |
| 88 | $L_{X11-1}$ | 3-Me | H | H | — |
| 89 | $L_{X11-1}$ | 4-Me | H | H | — |
| 90 | $L_{X11-1}$ | 3,4-Me | H | H | — |
| 91 | $L_{X11-1}$ | 4-$CH_2CMe_3$ | H | H | — |
| 92 | $L_{X11-1}$ | 3-$CH_2CMe_3$ | H | H | — |
| 93 | $L_{X11-1}$ | 3-Me, 4-$CH_2CMe_3$ | H | H | — |
| 94 | $L_{X11-1}$ | 4-Ph | H | H | — |
| 95 | $L_{X11-1}$ | 3,4-Me | 7-Me | H | — |
| 96 | $L_{X11-1}$ | 3,4-Me | H | 15-Me | — |
| 97 | $L_{X11-1}$ | 3-$CD_3$ | H | H | — |
| 98 | $L_{X11-1}$ | 4-$CD_3$ | H | H | — |
| 99 | $L_{X11-1}$ | 3,4-$CD_3$ | H | H | — |
| 100 | $L_{X11-1}$ | 4-$CD_2CMe_3$ | H | H | — |
| 101 | $L_{X11-1}$ | 3-$CD_3$, 4-$CD_2CMe_3$ | H | H | — |
| 102 | $L_{X11-2}$ | 3-Me | H | H | — |
| 103 | $L_{X11-2}$ | 4-Me | H | H | — |
| 104 | $L_{X11-2}$ | 3,4-Me | H | H | — |
| 105 | $L_{X11-3}$ | 3-Me | H | H | Me |
| 106 | $L_{X11-3}$ | 4-Me | H | H | Me |
| 107 | $L_{X12-1}$ | 3-Me | H | H | — |
| 108 | $L_{X12-1}$ | 4-Me | H | H | — |
| 109 | $L_{X12-1}$ | 3,4-Me | H | H | — |
| 110 | $L_{X12-1}$ | 3-Me | 7-Me | H | — |
| 111 | $L_{X12-1}$ | 4-Me | 7-Me | H | — |
| 112 | $L_{X12-1}$ | 3-Me | H | 11-Me | — |
| 113 | $L_{X12-1}$ | 4-Me | H | 14-Me | — |
| 114 | $L_{X12-1}$ | 3-$CD_3$, 4-$CD_2CMe_3$ | H | 10,11-$(CH)_4$ | — |
| 115 | $L_{X12-1}$ | 3-$CD_3$ | H | H | — |
| 116 | $L_{X12-1}$ | 4-$CD_3$ | H | H | — |
| 117 | $L_{X12-1}$ | 3,4-$CD_3$ | H | H | — |
| 118 | $L_{X12-1}$ | 4-$CD_2CMe_3$ | H | H | — |
| 119 | $L_{X12-1}$ | 3-$CD_3$, 4-$CD_2CMe_3$ | H | H | — |
| 120 | $L_{X12-2}$ | 3-Me | H | H | — |
| 121 | $L_{X12-2}$ | 4-Me | H | H | — |
| 122 | $L_{X12-2}$ | 3,4-Me | H | H | — |
| 123 | $L_{X12-3}$ | 3,4-Me | H | H | Me |
| 124 | $L_{X13-1}$ | 3,4-Me | H | H | — |
| 125 | $L_{X13-2}$ | 3,4-Me | H | H | — |
| 126 | $L_{X13-3}$ | 3,4-Me | H | H | Me |
| 127 | $L_{X14-1}$ | 3,4-Me | H | H | — |
| 128 | $L_{X14-1}$ | 3-$CD_3$, 4-$CD_2CMe_3$ | H | 12,13-$(CH)_4$ | — |
| 129 | $L_{X14-1}$ | 3-$CD_3$ | H | H | — |
| 130 | $L_{X14-1}$ | 4-$CD_3$ | H | H | — |
| 131 | $L_{X14-1}$ | 3,4-$CD_3$ | H | H | — |
| 132 | $L_{X14-1}$ | 4-$CD_2CMe_3$ | H | H | — |
| 133 | $L_{X14-1}$ | 3-$CD_3$, 4-$CD_2CMe_3$ | H | H | — |

-continued

| i | $L_{Xj\text{-}k}$ | $R^{F'}$ | $R^{I'}$ | $R^{H'}$ | RK |
|---|---|---|---|---|---|
| 134 | $L_{X14\text{-}2}$ | 3,4-Me | H | H | — |
| 135 | $L_{X14\text{-}3}$ | 3,4-Me | H | H | Me |
| 136 | $L_{X15\text{-}1}$ | 3,4-Me | H | H | — |
| 137 | $L_{X15\text{-}2}$ | 3,4-Me | H | H | — |
| 138 | $L_{X15\text{-}3}$ | 3,4-Me | H | H | Me |
| 139 | $L_{X16\text{-}1}$ | 3-Me | H | H | — |
| 140 | $L_{X16\text{-}1}$ | 4-Me | H | H | — |
| 141 | $L_{X16\text{-}1}$ | 3,4-Me | H | H | — |
| 142 | $L_{X16\text{-}1}$ | 4-$CH_2CMe_3$ | H | H | — |
| 143 | $L_{X16\text{-}1}$ | 3-$CH_2CMe_3$ | H | H | — |
| 144 | $L_{X16\text{-}1}$ | 3-Me, 4-$CH_2CMe_3$ | H | H | — |
| 145 | $L_{X16\text{-}1}$ | 3,4-Me | 7-Me | H | — |
| 146 | $L_{X16\text{-}1}$ | 3,4-Me | H | 8-Me | — |
| 147 | $L_{X16\text{-}1}$ | 3,4-Me | H | 15-Me | — |
| 148 | $L_{X16\text{-}1}$ | 3-$CD_3$ | H | H | — |
| 149 | $L_{X16\text{-}1}$ | 4-$CD_3$ | H | H | — |
| 150 | $L_{X16\text{-}1}$ | 3,4-$CD_3$ | H | H | — |
| 151 | $L_{X16\text{-}1}$ | 4-$CD_2CMe_3$ | H | H | — |
| 152 | $L_{X16\text{-}1}$ | 3-$CD_3$, 4-$CD_2CMe_3$ | H | H | — |
| 153 | $L_{X16\text{-}2}$ | 3,4-Me | H | H | — |
| 154 | $L_{X16\text{-}3}$ | 3,4-Me | H | H | Me |
| 155 | $L_{X17\text{-}1}$ | 3-Me | H | H | — |
| 156 | $L_{X17\text{-}1}$ | 4-Me | H | H | — |
| 157 | $L_{X17\text{-}1}$ | 3,4-Me | H | H | — |
| 158 | $L_{X17\text{-}1}$ | 4-$CH_2CMe_3$ | H | H | — |
| 159 | $L_{X17\text{-}1}$ | 3-Me, 4-$CH_2CMe_3$ | H | H | — |
| 160 | $L_{X17\text{-}1}$ | 3-Me | 7-Me | H | — |
| 161 | $L_{X17\text{-}1}$ | 4-Me | 7-Ph | H | — |
| 162 | $L_{X17\text{-}1}$ | 3,4-Me | H | 13-Me | — |
| 163 | $L_{X17\text{-}1}$ | 3,4-Me | H | 14-Me | — |
| 164 | $L_{X17\text{-}1}$ | 3,4-Me | H | 15-Me | — |
| 165 | $L_{X17\text{-}1}$ | 3-$CD_3$ | H | H | — |
| 166 | $L_{X17\text{-}1}$ | 4-$CD_3$ | H | H | — |
| 167 | $L_{X17\text{-}1}$ | 3,4-$CD_3$ | H | H | — |
| 168 | $L_{X17\text{-}1}$ | 4-$CD_2CMe_3$ | H | H | — |
| 169 | $L_{X17\text{-}1}$ | 3-$CD_3$, 4-$CD_2CMe_3$ | H | H | — |
| 170 | $L_{X17\text{-}2}$ | 3-Me | H | H | — |
| 171 | $L_{X17\text{-}2}$ | 4-Me | H | H | — |
| 172 | $L_{X17\text{-}2}$ | 3,4-Me | H | H | — |
| 173 | $L_{X17\text{-}3}$ | 3,4-Me | H | H | Me |
| 174 | $L_{X18\text{-}1}$ | 3,4-Me | H | H | — |
| 175 | $L_{X18\text{-}2}$ | 3,4-Me | H | H | — |
| 176 | $L_{X18\text{-}3}$ | 3,4-Me | H | H | Me |
| 177 | $L_{X19\text{-}1}$ | 3,4-Me | H | H | — |
| 178 | $L_{X19\text{-}1}$ | 3,4-Me | 7-Me | H | — |
| 179 | $L_{X19\text{-}1}$ | 3,4-Me | H | 12-Me | — |
| 180 | $L_{X19\text{-}2}$ | 3,4-Me | H | H | — |
| 181 | $L_{X19\text{-}3}$ | 3,4-Me | H | H | Me |
| 182 | $L_{X20\text{-}1}$ | 3,4-Me | H | H | — |
| 183 | $L_{X20\text{-}2}$ | 3,4-Me | H | H | — |
| 184 | $L_{X20\text{-}3}$ | 3,4-Me | H | H | Me |
| 185 | $L_{X21\text{-}1}$ | 3-Me | H | H | — |
| 186 | $L_{X21\text{-}1}$ | 4-Me | H | H | — |
| 187 | $L_{X21\text{-}1}$ | 3,4-Me | H | H | — |
| 188 | $L_{X21\text{-}1}$ | 4-$CH_2CMe_3$ | H | H | — |
| 189 | $L_{X21\text{-}1}$ | 3-Me, 4-$CH_2CMe_3$ | H | H | — |
| 190 | $L_{X21\text{-}1}$ | 3,4-Me | 7-Me | H | — |
| 191 | $L_{X21\text{-}1}$ | 3,4-Me | H | 13-Me | — |
| 192 | $L_{X21\text{-}2}$ | 3-Me | H | H | — |
| 193 | $L_{X21\text{-}2}$ | 4-Me | H | H | — |
| 194 | $L_{X21\text{-}2}$ | 3,4-Me | H | H | — |
| 195 | $L_{X21\text{-}3}$ | 3,4-Me | H | H | Me |
| 196 | $L_{X22\text{-}1}$ | 3,4-Me | H | H | — |
| 197 | $L_{X22\text{-}2}$ | 3,4-Me | H | H | — |
| 198 | $L_{X22\text{-}3}$ | 3,4-Me | H | H | Me |
| 199 | $L_{X23\text{-}1}$ | 3,4-Me | H | H | — |
| 200 | $L_{X23\text{-}2}$ | 3,4-Me | H | H | — |
| 201 | $L_{X23\text{-}3}$ | 3,4-Me | H | H | Me |
| 202 | $L_{X24\text{-}1}$ | 3-$CD_3$ | H | H | — |
| 203 | $L_{X24\text{-}1}$ | 4-$CD_3$ | H | H | — |
| 204 | $L_{X24\text{-}1}$ | 3,4-$CD_3$ | H | H | — |
| 205 | $L_{X24\text{-}1}$ | 4-$CD_2CMe_3$ | H | H | — |
| 206 | $L_{X24\text{-}1}$ | 3-$CD_3$, 4-$CD_2CMe_3$ | H | H | — |
| 207 | $L_{X24\text{-}2}$ | 3-$CD_3$, 4-$CD_2CMe_3$ | H | H | — |
| 209 | $L_{X25\text{-}1}$ | 3-$CD_3$ | H | H | — |
| 210 | $L_{X25\text{-}1}$ | 4-$CD_3$ | H | H | — |
| 211 | $L_{X25\text{-}1}$ | 3,4-$CD_3$ | H | H | — |

-continued

| i | $L_{Xj\text{-}k}$ | $R^{F'}$ | $R^{I'}$ | $R^{H'}$ | RK |
|---|---|---|---|---|---|
| 212 | $L_{X25\text{-}1}$ | 4-$CD_2CMe_3$ | H | H | — |
| 213 | $L_{X25\text{-}1}$ | 3-$CD_3$, 4-$CD_2CMe_3$ | H | H | — |
| 214 | $L_{X25\text{-}2}$ | 3-$CD_3$, 4-$CD_2CMe_3$ | H | H | — |
| 216 | $L_{X26\text{-}1}$ | 3-$CD_3$ | H | H | — |
| 217 | $L_{X26\text{-}1}$ | 4-$CD_3$ | H | H | — |
| 218 | $L_{X26\text{-}1}$ | 3,4-$CD_3$ | H | H | — |
| 219 | $L_{X26\text{-}1}$ | 4-$CD_2CMe_3$ | H | H | — |
| 220 | $L_{X26\text{-}1}$ | 3-$CD_3$, 4-$CD_2CMe_3$ | H | H | — |
| 221 | $L_{X26\text{-}2}$ | 3-$CD_3$, 4-$CD_2CMe_3$ | H | H | —, |

wherein each $L_{X\,j\text{-}k}$ from $L_{X\,1\text{-}1}$ to $L_{X\,26\text{-}2}$ is defined as follows:

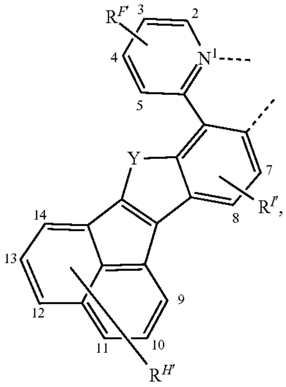

$L_{x\,1\text{-}1}$, where Y = O,
$L_{x\,1\text{-}2}$, where Y = S,
$L_{x1\text{-}3}$, where Y = $CRK_2$,

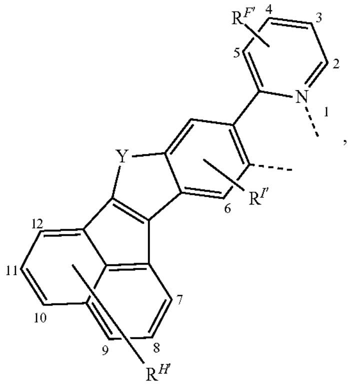

$L_{x\,2\text{-}1}$, where Y = O
$L_{x\,2\text{-}2}$, where Y = S
$L_{x\,2\text{-}3}$, where Y = $CRK_2$ -continued

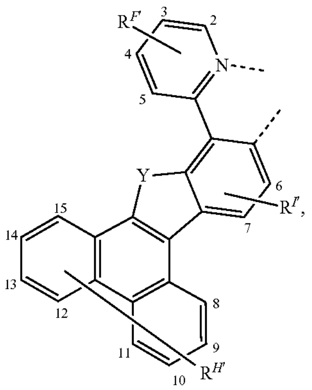

$L_{x\ 3-1}$, where Y = O
$L_{x\ 3-2}$, where Y = S
$L_{x\ 3-3}$, where Y = $CRK_2$

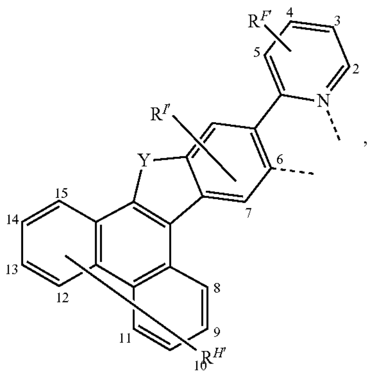

$L_{x\ 4-1}$, where Y = O
$L_{x\ 4-2}$, where Y = S
$L_{x\ 4-3}$, where Y = $CRK_2$

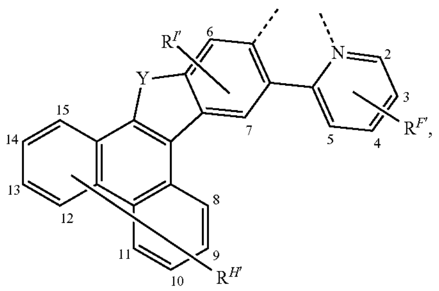

$L_{x\ 5-1}$, where Y = O
$L_{x\ 5-2}$, where Y = S
$L_{x\ 5-3}$, where Y = $CRK_2$

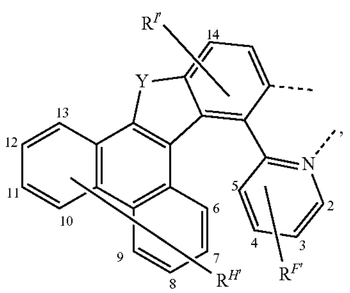

$L_{x\ 6-1}$, where Y = O
$L_{x\ 6-2}$, where Y = S
$L_{x\ 6-3}$, where Y = $CR_2$ -continued

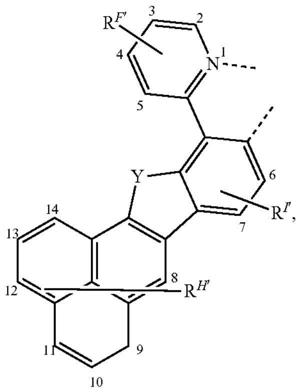

$L_{x\ 7-1}$, where Y = O
$L_{x\ 7-2}$, where Y = S
$L_{x\ 7-3}$, where Y = $CRK_2$

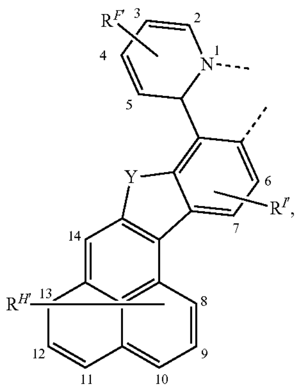

$L_{x\ 8-1}$, where Y = O
$L_{x\ 8-2}$, where Y = S
$L_{x\ 8-3}$, where Y = $CRK_2$

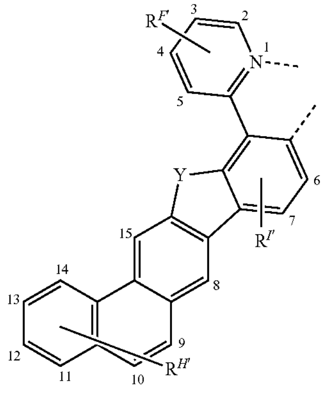

$L_{x\ 9-1}$, where Y = O
$L_{x\ 9-2}$, where Y = S
$L_{x\ 9-3}$, where Y = $CRK_2$

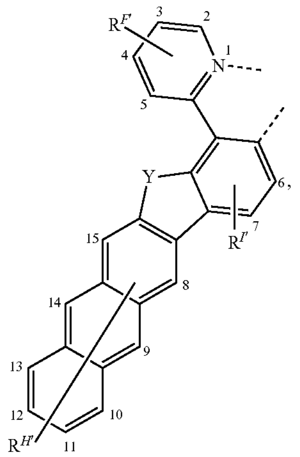

$L_{x\ 10\text{-}1}$, where Y = O
$L_{x\ 10\text{-}2}$, where Y = S
$L_{x\ 10\text{-}3}$, where Y = $CRK_2$

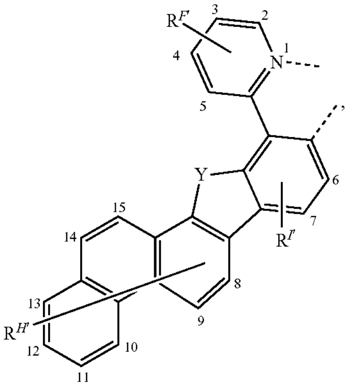

$L_{x\ 11\text{-}1}$, where Y = O
$L_{x\ 11\text{-}2}$, where Y = S
$L_{x\ 11\text{-}3}$, where Y = $CRK_2$

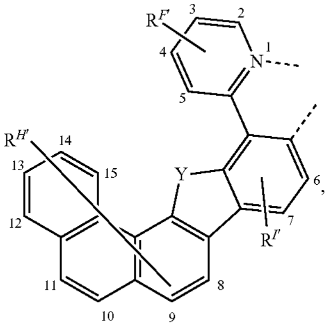

$L_{x\ 12\text{-}1}$, where Y = O
$L_{x\ 12\text{-}2}$, where Y = S
$L_{x\ 12\text{-}3}$, where Y = $CRK_2$

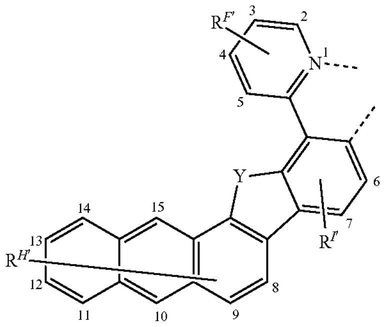

$L_{x\ 13\text{-}1}$, where Y = O
$L_{x\ 13\text{-}2}$, where Y = S
$L_{x\ 13\text{-}3}$, where Y = $CRK_2$

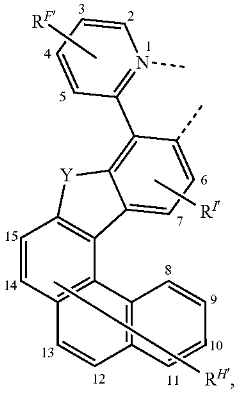

$L_{x\ 14\text{-}1}$, where Y = O
$L_{x\ 114\text{-}2}$, where Y = S
$L_{x\ 14\text{-}3}$, where Y = $CRK_2$

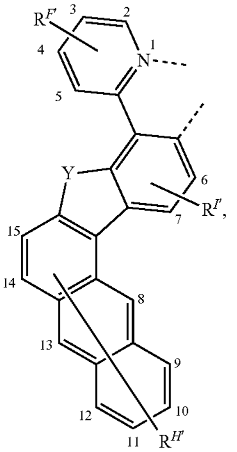

$L_{x\ 15\text{-}1}$, where Y = O
$L_{x\ 15\text{-}2}$, where Y = S
$L_{x\ 15\text{-}3}$, where Y = $CRK_2$

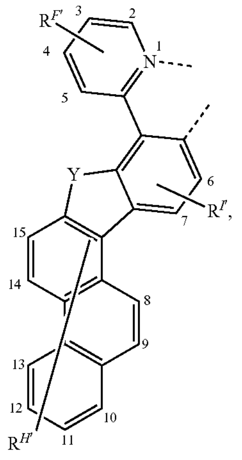
$L_{x\ 16-1}$, where Y = O
$L_{x\ 16-2}$, where Y = S
$L_{x\ 16-3}$, where Y = $CRK_2$
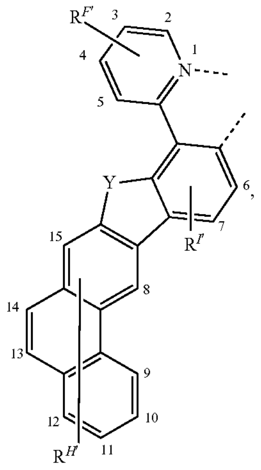
$L_{x\ 17-1}$, where Y = O
$L_{x\ 17-2}$, where Y = S
$L_{x\ 17-3}$, where Y = $CRK_2$
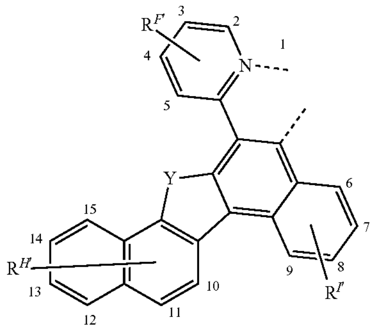
$L_{x\ 18-1}$, where Y = O
$L_{x\ 18-2}$, where Y = S
$L_{x\ 18-3}$, where Y = $CRK_2$
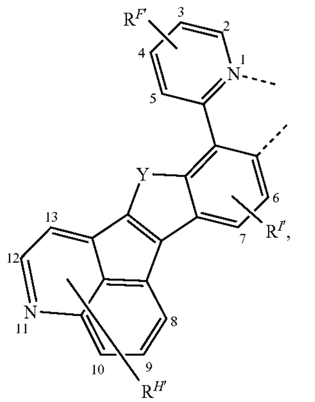
$L_{x\ 19-1}$, where Y = O
$L_{x\ 19-2}$, where Y = S
$L_{x\ 19-3}$, where Y = $CRK_2$
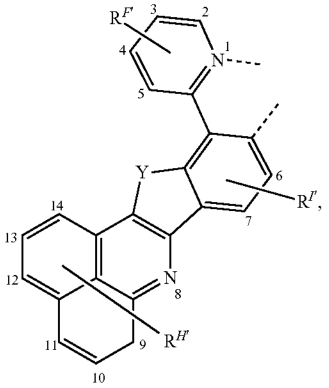
$L_{x\ 20-1}$, where Y = O
$L_{x\ 20-2}$, where Y = S
$L_{x\ 20-3}$, where Y = $CRK_2$
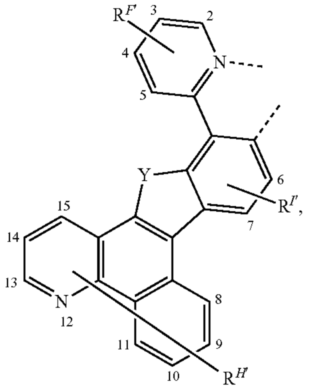
$L_{x\ 21-1}$, where Y = O
$L_{x\ 21-2}$, where Y = S
$L_{x\ 21-3}$, where Y = $CRK_2$ -continued

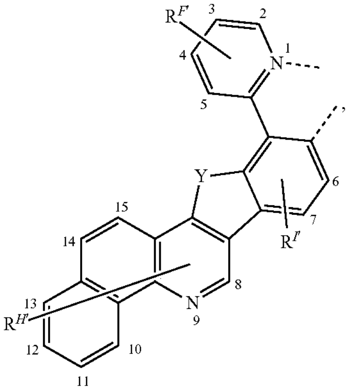

$L_{x\,22\text{-}1}$, where Y = O
$L_{x\,22\text{-}2}$, where Y = S
$L_{x\,22\text{-}3}$, where Y = $CRK_2$

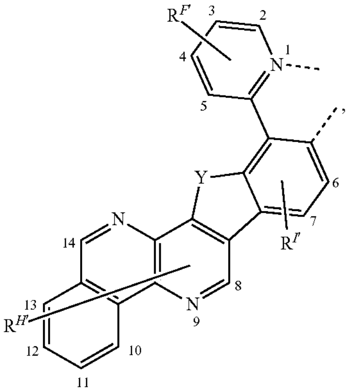

$L_{x\,23\text{-}1}$, where Y = O
$L_{x\,23\text{-}2}$, where Y = S
$L_{x\,23}$, where Y = $CRK_2$

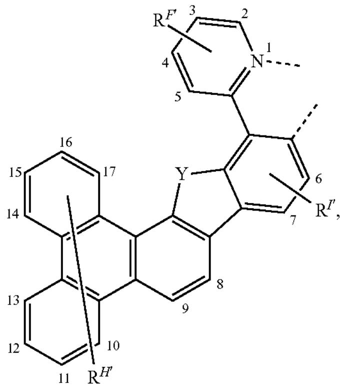

$L_{x\,24\text{-}1}$, where Y = O
$L_{x\,24\text{-}2}$, where Y = S

-continued

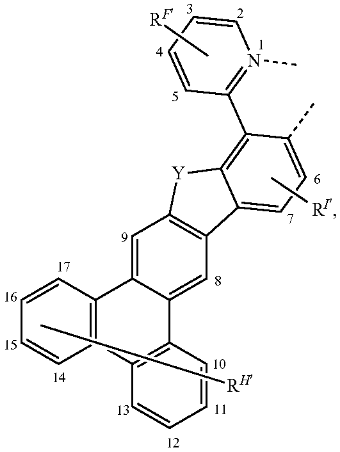

and $L_{x\,25\text{-}1}$, where Y = O
$L_{x\,25\text{-}2}$, where Y = S

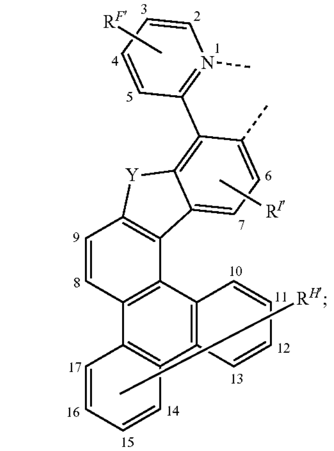

$L_{x\,26\text{-}1}$, where Y = O
$L_{x\,26\text{-}2}$, where Y = S and wherein Me is methyl and Ph is phenyl.

14. The compound of claim 13, wherein the compound is the Compound Ax having the formula $Ir(L_{xi})_3$, or the Compound By having the formula $Ir(L_{xi})(L_{Bk})_2$;

wherein x=i, and y=468i+k−468;

wherein i is an integer from 1 to 222, and k is an integer from 1 to 468;

wherein $L_{Bk}$ is selected from the group consisting of $L_{B1}$ to $L_{B468}$ having the following structures:

$L_{B1}$

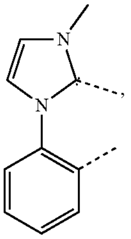

-continued
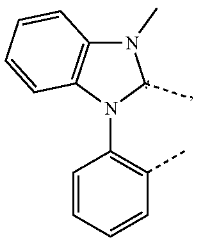
$L_{B2}$
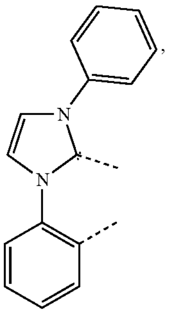
$L_{B3}$
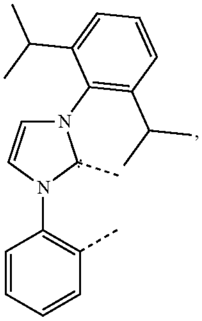
$L_{B4}$
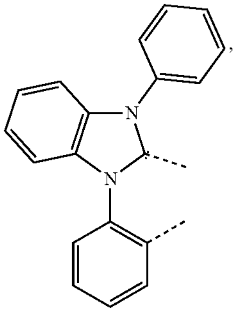
$L_{B5}$
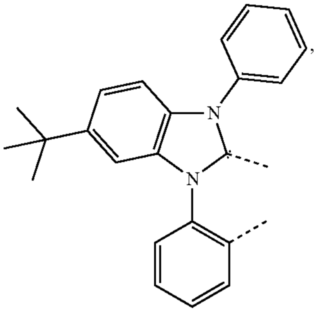
$L_{B6}$
-continued
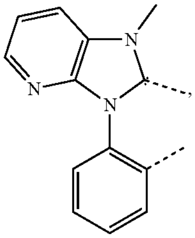
$L_{B7}$
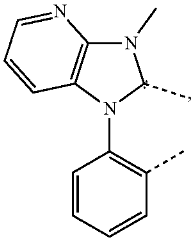
$L_{B8}$
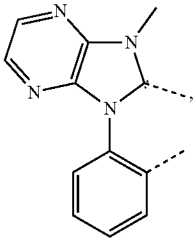
$L_{B9}$
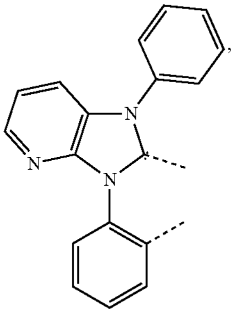
$L_{B10}$
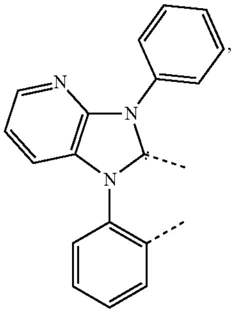
$L_{B11}$ -continued
$L_{B12}$
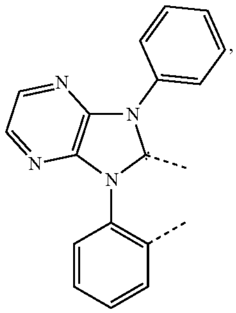
$L_{B13}$
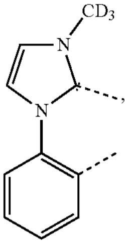
$L_{B14}$
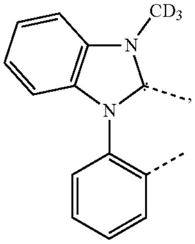
$L_{B15}$
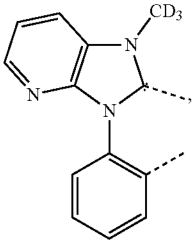
$L_{B16}$
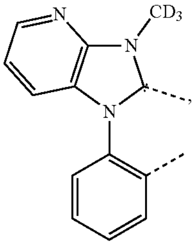
$L_{B17}$
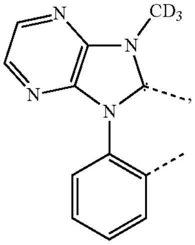
-continued
$L_{B18}$
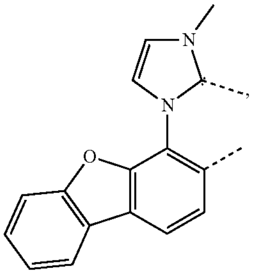
$L_{B19}$
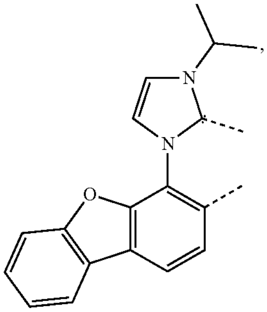
$L_{B20}$
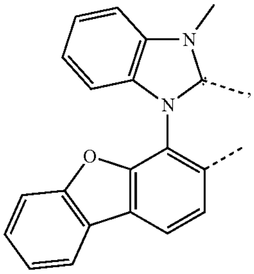
$L_{B21}$
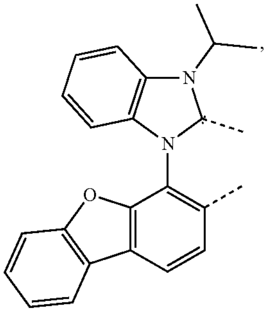
$L_{B22}$
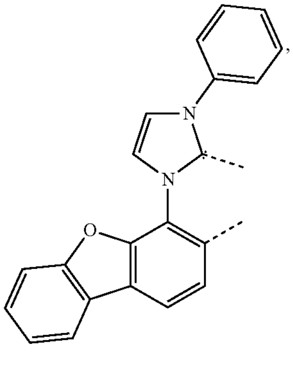

-continued
$L_{B23}$
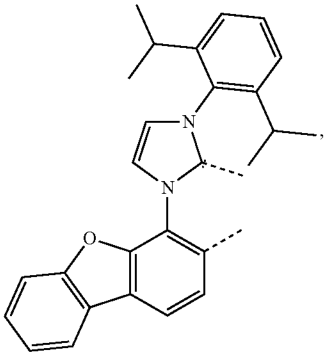
$L_{B24}$
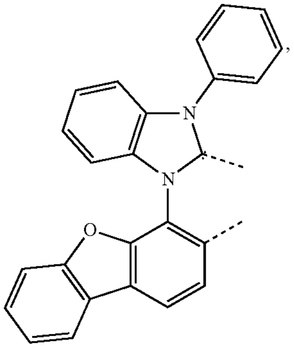
$L_{B25}$
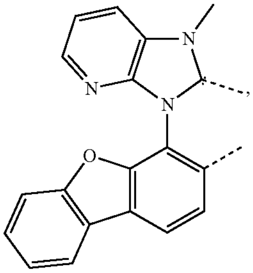
$L_{B26}$
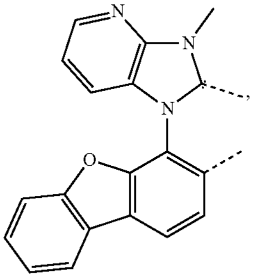
$L_{B27}$
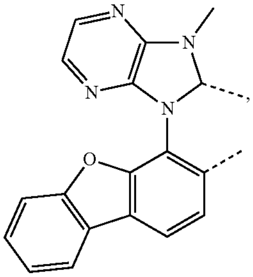
-continued
$L_{B28}$
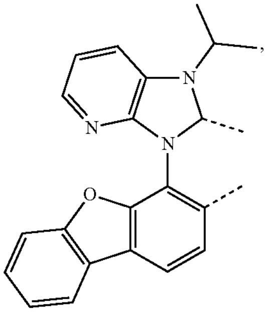
$L_{B29}$
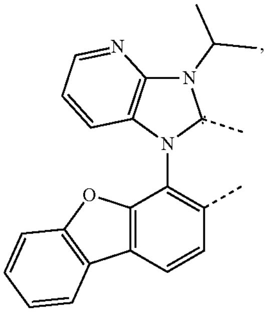
$L_{B30}$
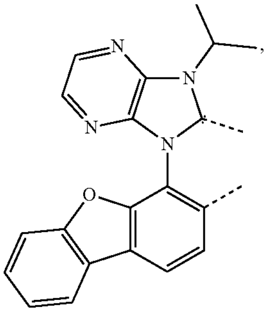
$L_{B31}$
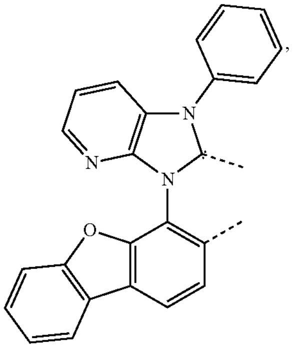

-continued
L$_{B32}$
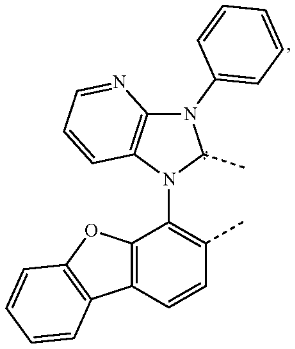
L$_{B33}$
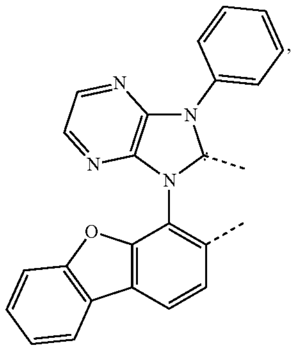
L$_{B34}$
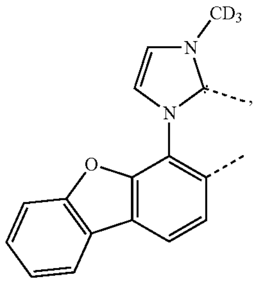
L$_{B35}$
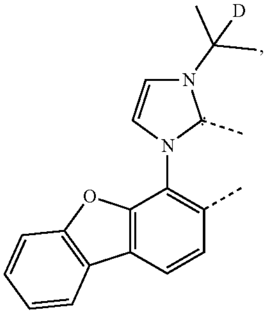
L$_{B36}$
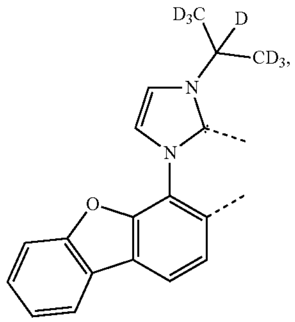
-continued
L$_{B37}$
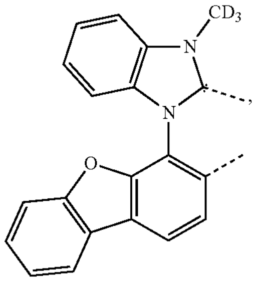
L$_{B38}$
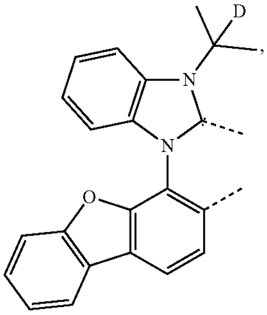
L$_{B39}$
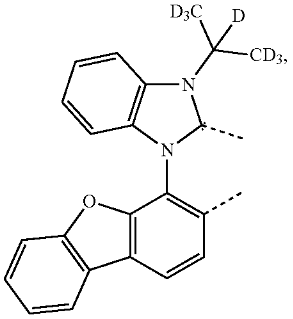
L$_{B40}$
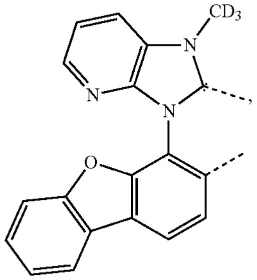
L$_{B41}$
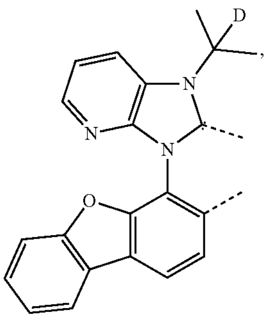

-continued
$L_{B42}$
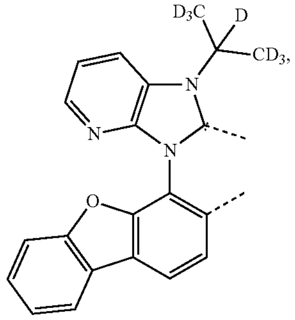
$L_{B43}$
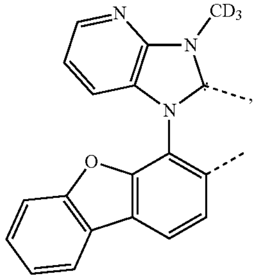
$L_{B44}$
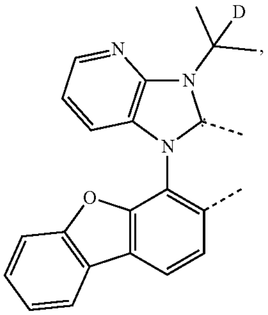
$L_{B45}$
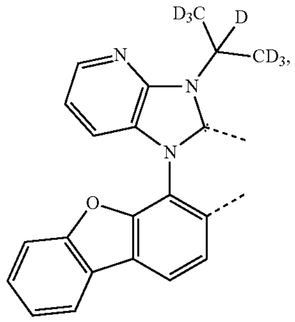
$L_{B46}$
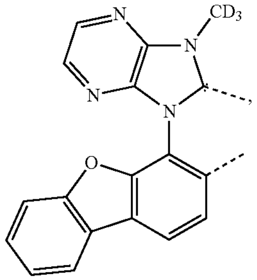
-continued
$L_{B47}$
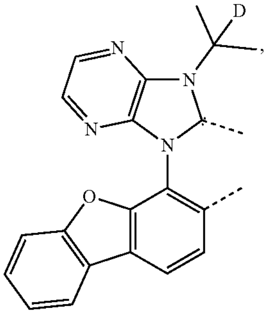
$L_{B48}$
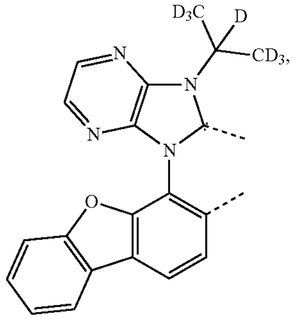
$L_{B49}$
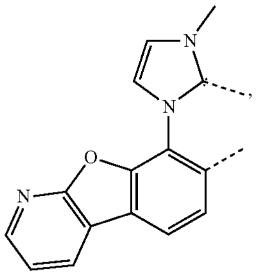
$L_{B50}$
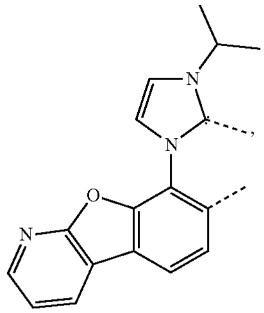
$L_{B51}$
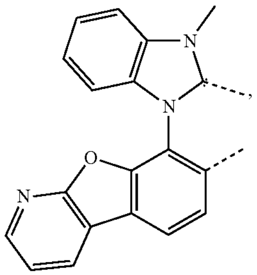

-continued
$L_{B52}$
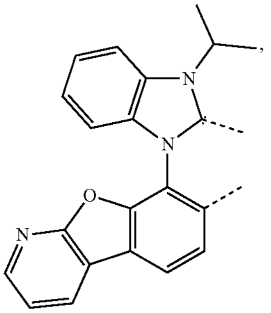
$L_{B53}$
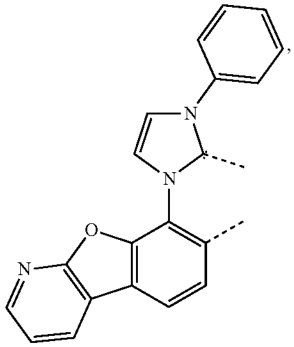
$L_{B54}$
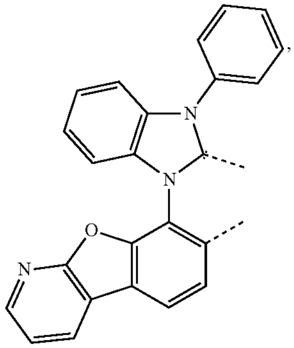
$L_{B55}$
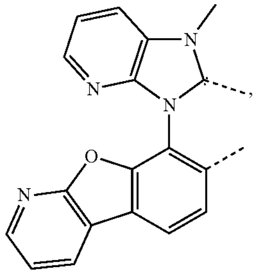
$L_{B56}$
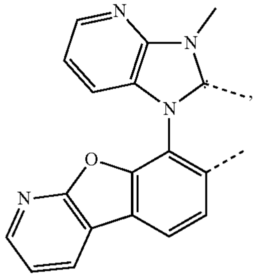
-continued
$L_{B57}$
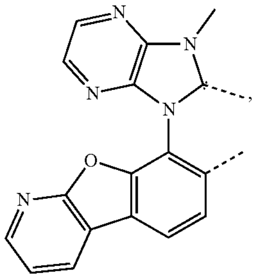
$L_{B58}$
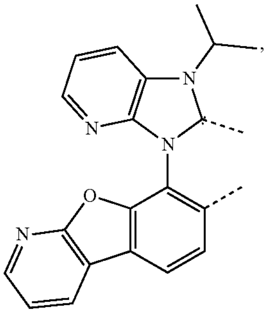
$L_{B59}$
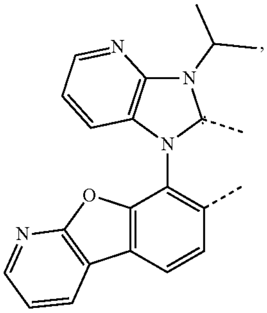
$L_{B60}$
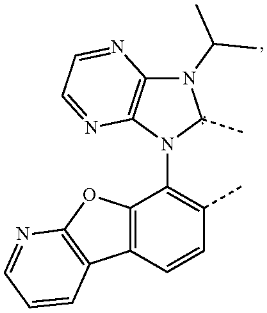
$L_{B61}$
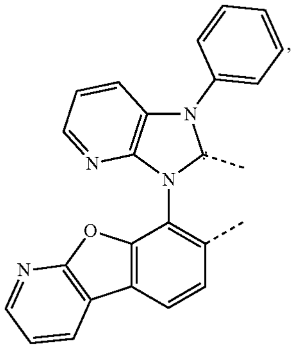

-continued
$L_{B62}$
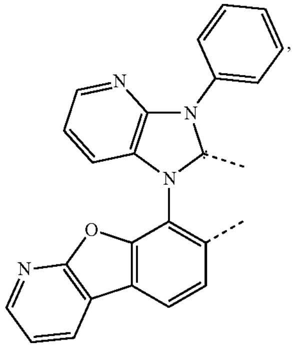
$L_{B63}$
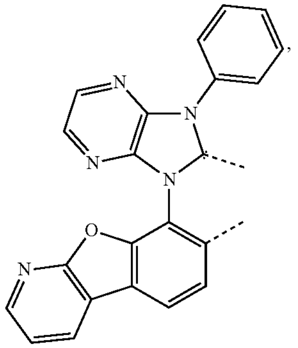
$L_{B64}$
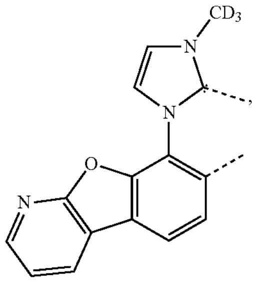
$L_{B65}$
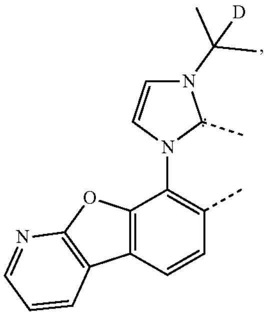
$L_{B66}$
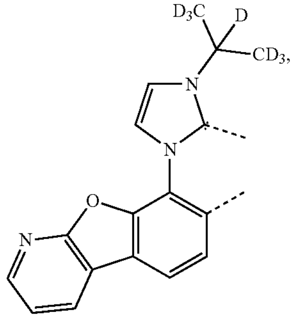
-continued
$L_{B67}$
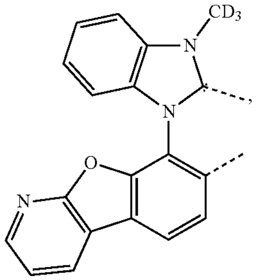
$L_{B68}$
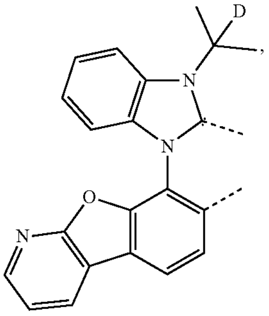
$L_{B69}$
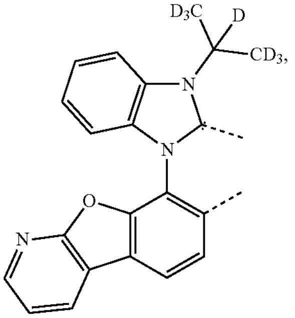
$L_{B70}$
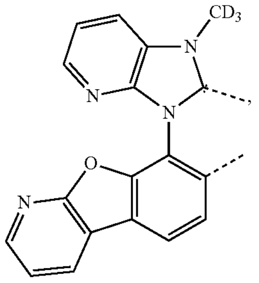
$L_{B71}$
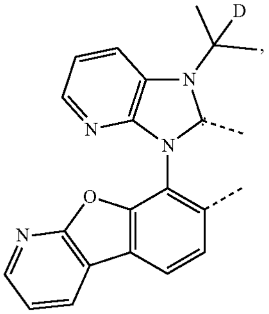

$L_{B72}$
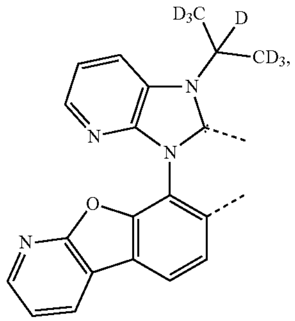
$L_{B73}$
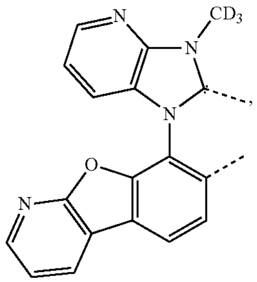
$L_{B74}$
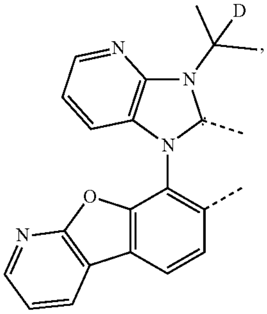
$L_{B75}$
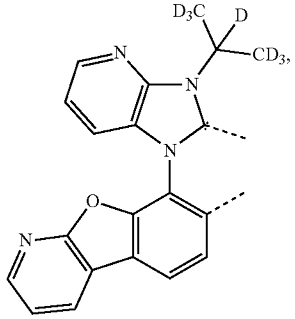
$L_{B76}$
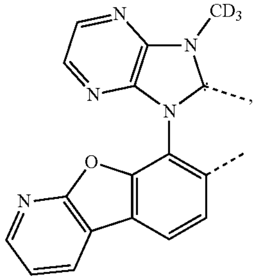
$L_{B77}$
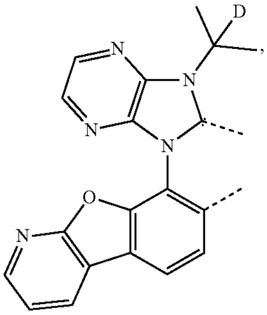
$L_{B78}$
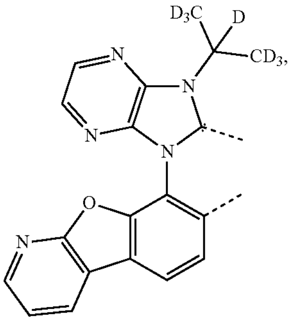
$L_{B79}$
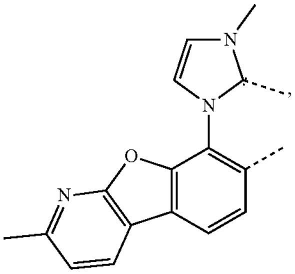
$L_{B80}$
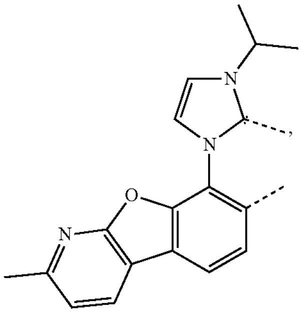
$L_{B81}$
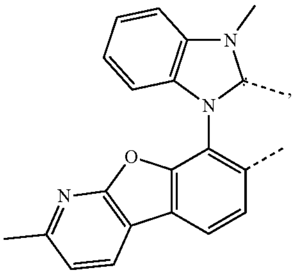

-continued
L$_{B82}$
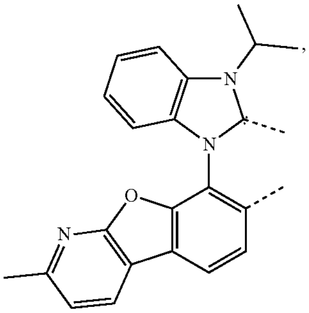
L$_{B83}$
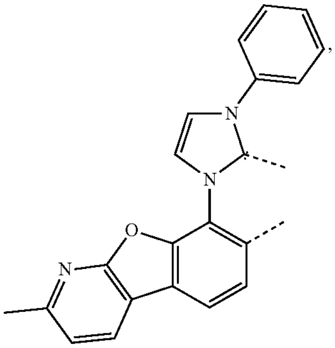
L$_{B84}$
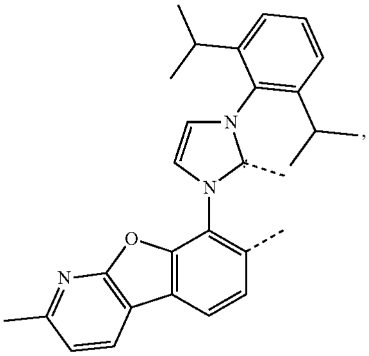
L$_{B85}$
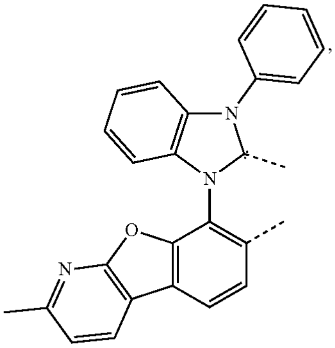
-continued
L$_{B86}$
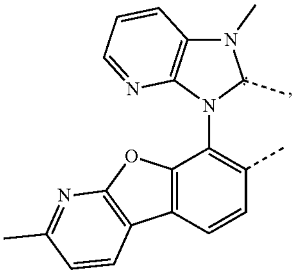
L$_{B87}$
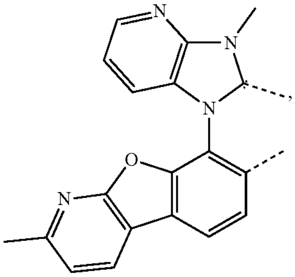
L$_{B88}$
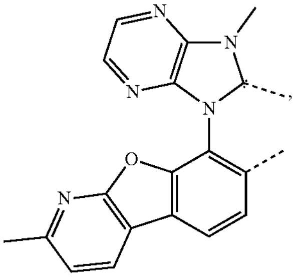
L$_{B89}$
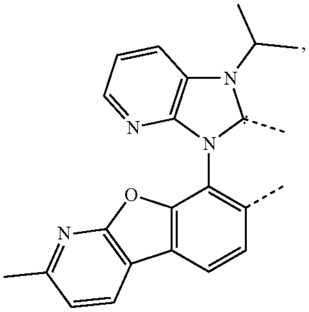
L$_{B90}$
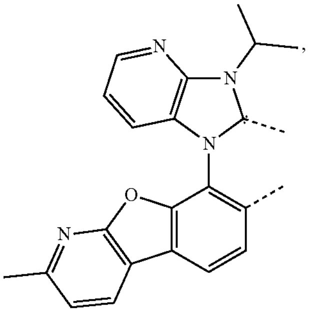

-continued
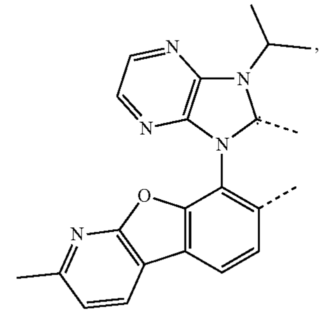
$L_{B91}$
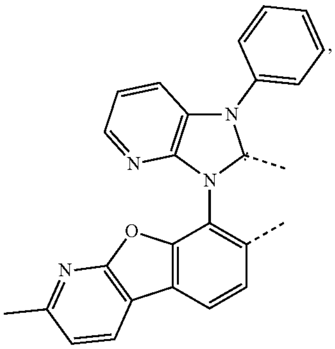
$L_{B92}$
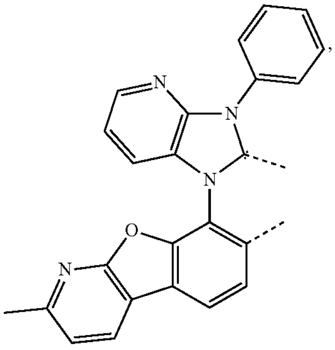
$L_{B93}$
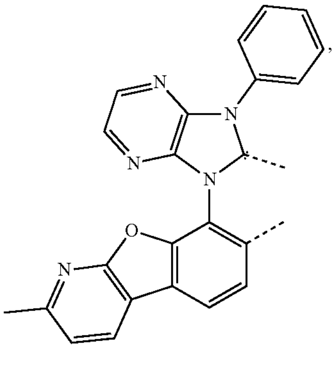
$L_{B94}$
-continued
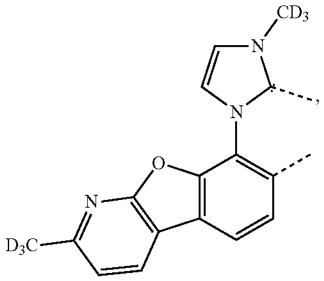
$L_{B95}$
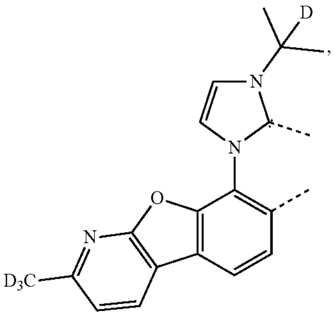
$L_{B96}$
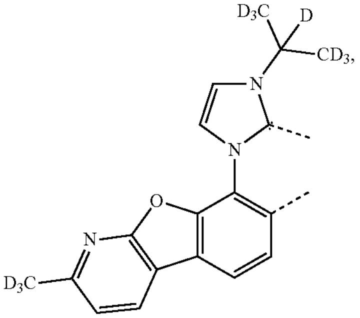
$L_{B97}$
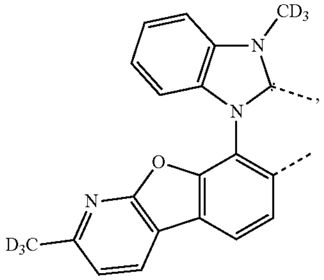
$L_{B98}$
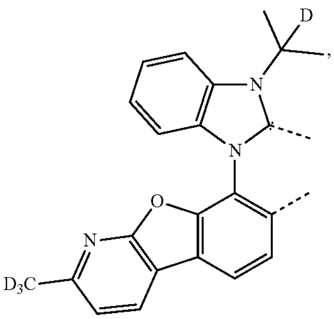
$L_{B99}$ -continued
$L_{B100}$
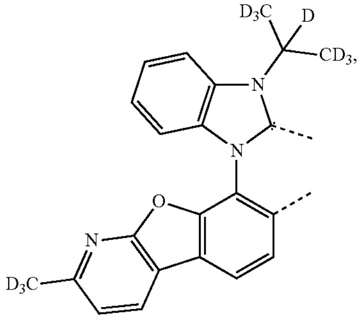
$L_{B101}$
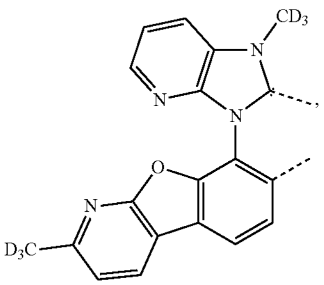
$L_{B102}$
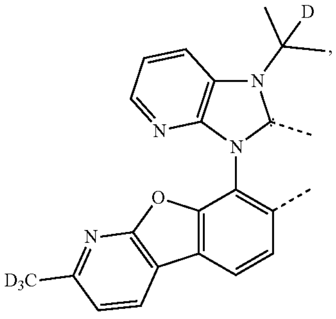
$L_{B103}$
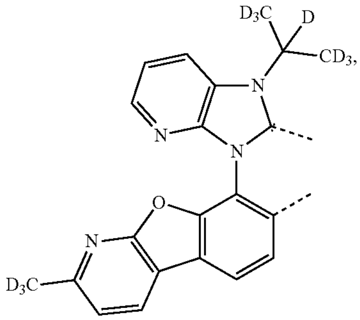
$L_{B104}$
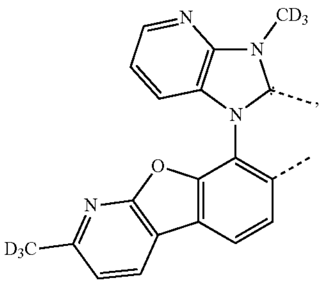
-continued
$L_{B105}$
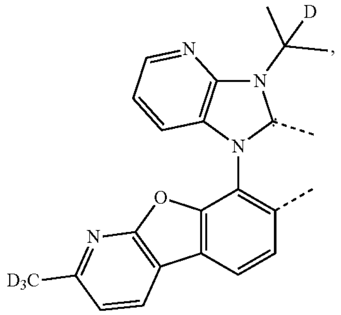
$L_{B106}$
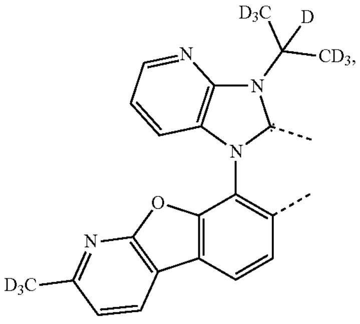
$L_{B107}$
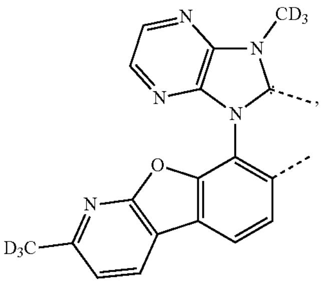
$L_{B108}$
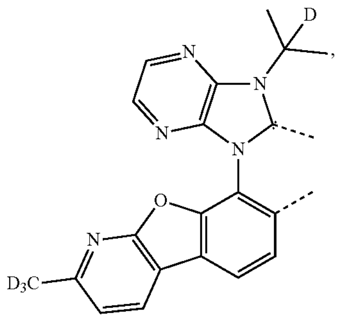
$L_{B109}$
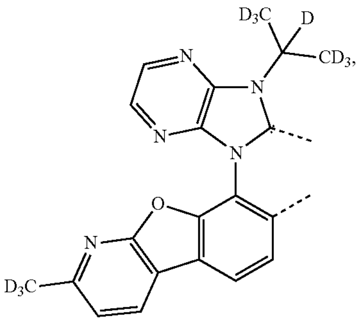

-continued
$L_{B110}$
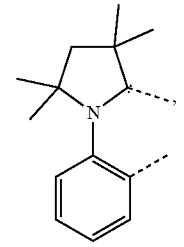
$L_{B111}$
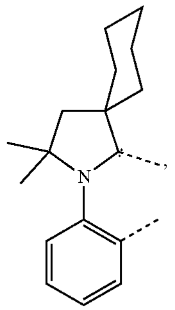
$L_{B112}$
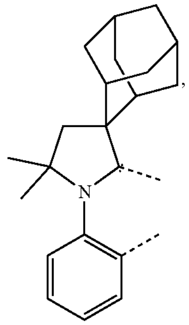
$L_{B113}$
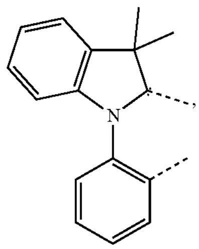
$L_{B114}$
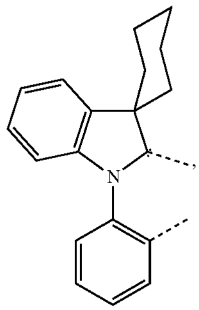
-continued
$L_{B115}$
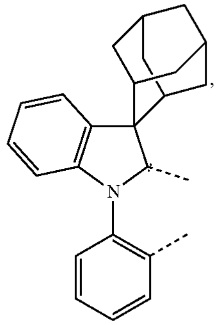
$L_{B116}$
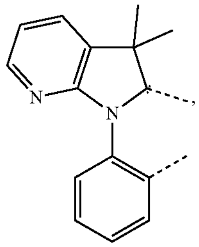
$L_{B120}$
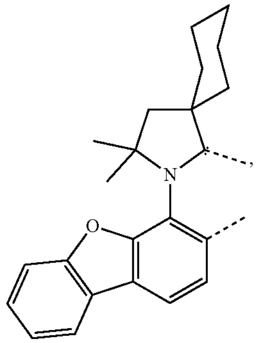
$L_{B121}$
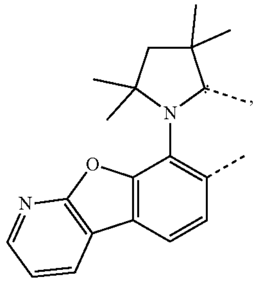
$L_{B122}$
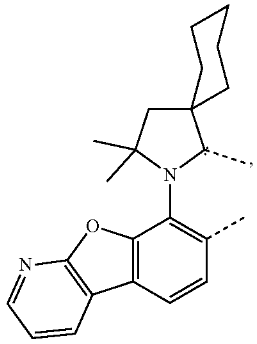

-continued
$L_{B123}$
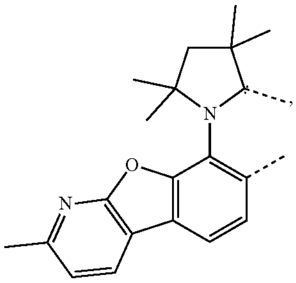
$L_{B124}$
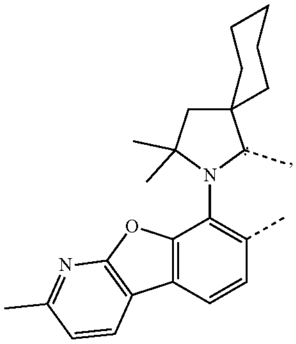
$L_{B125}$
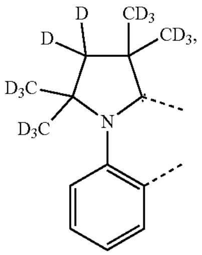
$L_{B126}$
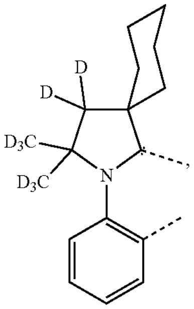
$L_{B127}$
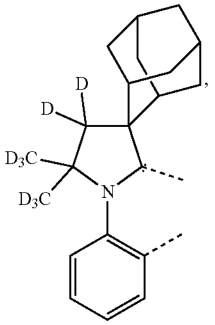
-continued
$L_{B128}$
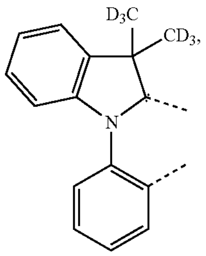
$L_{B129}$
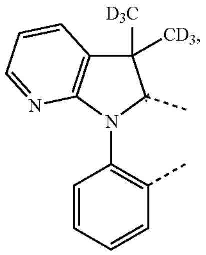
$L_{B130}$
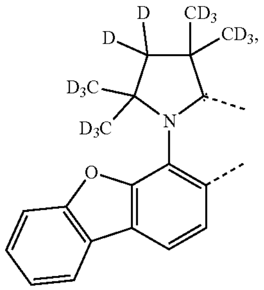
$L_{B131}$
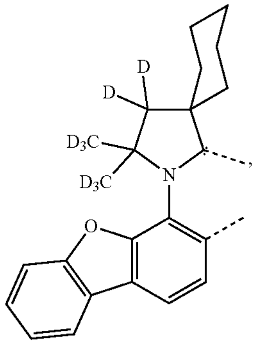
$L_{B132}$
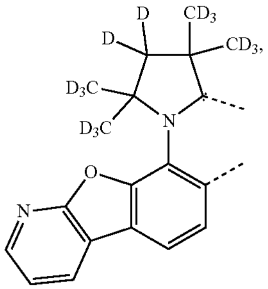

$L_{B133}$
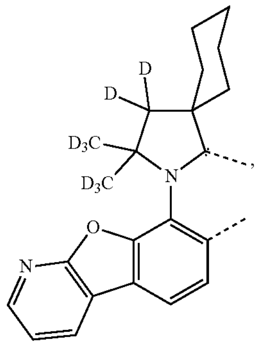
$L_{B134}$
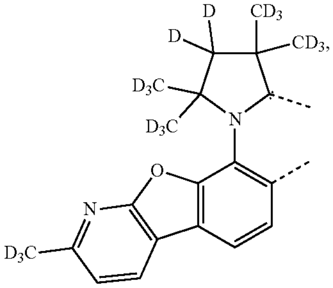
$L_{B135}$
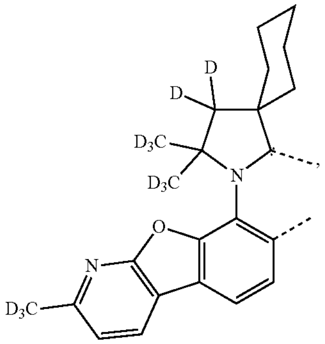
$L_{B136}$
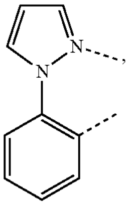
$L_{B137}$
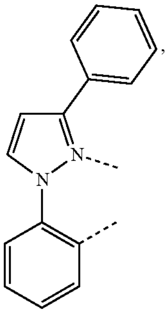
$L_{B138}$
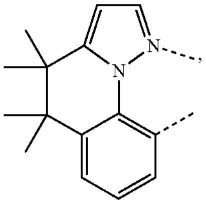
$L_{B139}$
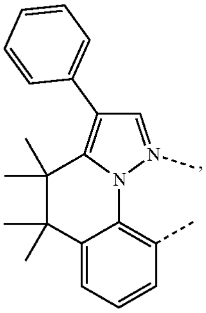
$L_{B140}$
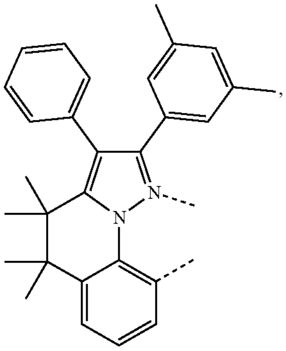
$L_{B141}$
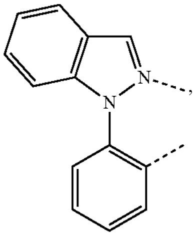
$L_{B142}$
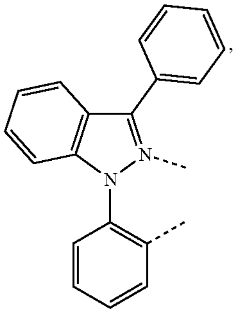

-continued
$L_{B143}$
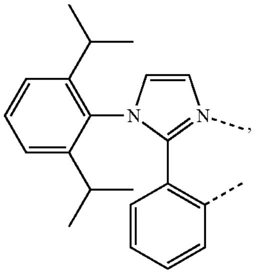
$L_{B144}$
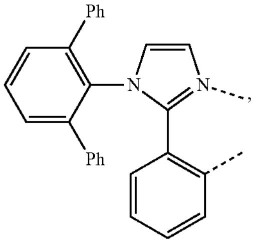
$L_{B145}$
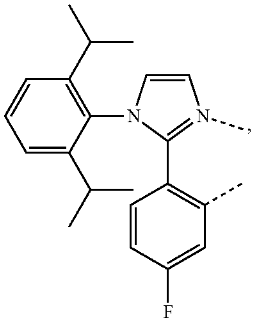
$L_{B146}$
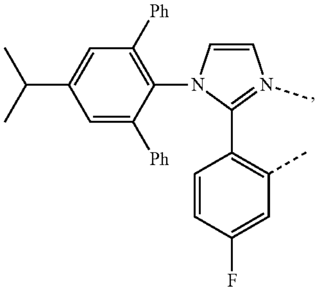
$L_{B147}$
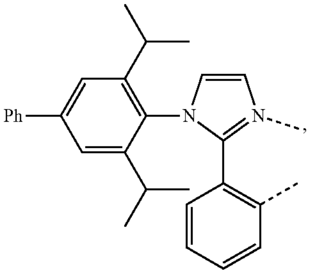
-continued
$L_{B148}$
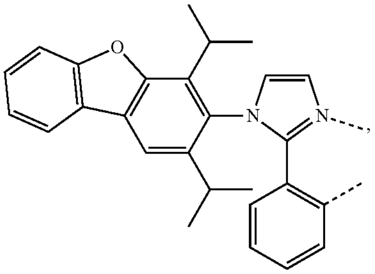
$L_{B149}$
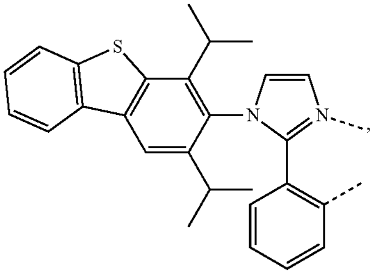
$L_{B150}$
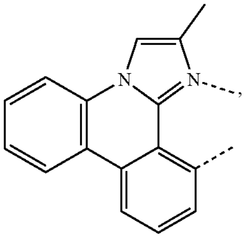
$L_{B151}$
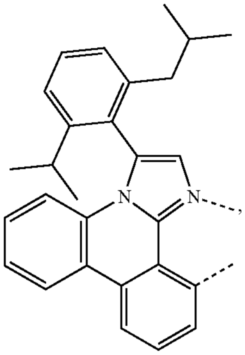
$L_{B152}$
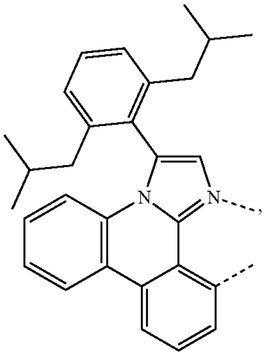

L$_{B153}$
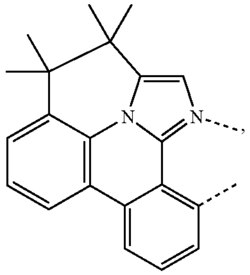
L$_{B154}$
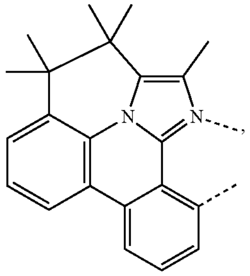
L$_{B155}$
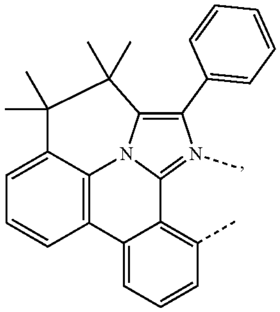
L$_{B156}$
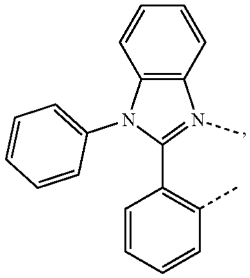
L$_{B157}$
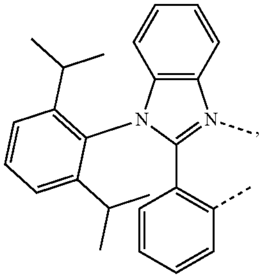
L$_{B158}$
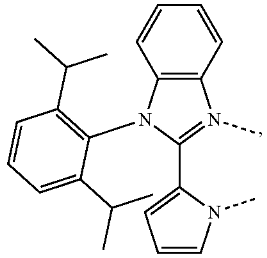
L$_{B159}$
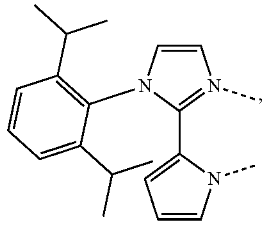
L$_{B160}$
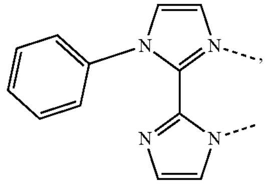
L$_{B161}$
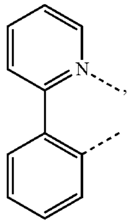
L$_{B162}$
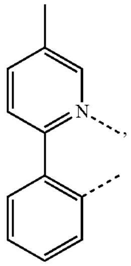
L$_{B163}$
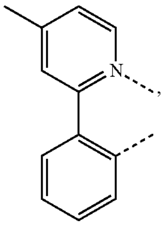

-continued
$L_{B164}$
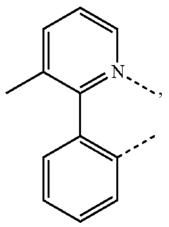
$L_{B165}$
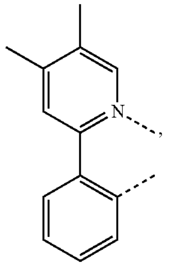
$L_{B166}$
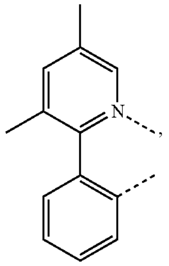
$L_{B167}$
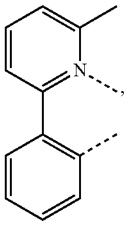
$L_{B168}$
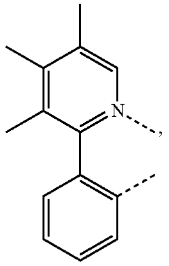
$L_{B169}$
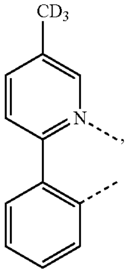
-continued
$L_{B170}$
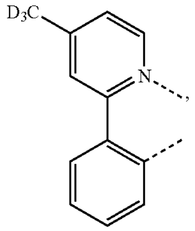
$L_{B171}$
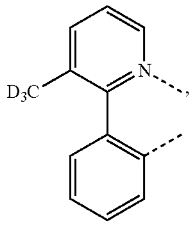
$L_{B172}$
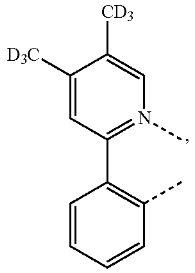
$L_{B173}$
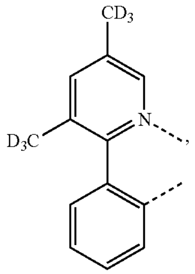
$L_{B174}$
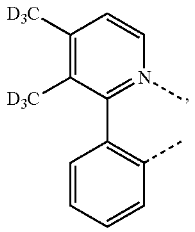
$L_{B175}$
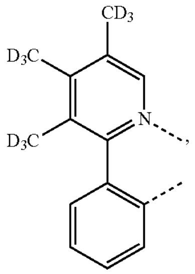

-continued
L$_{B176}$
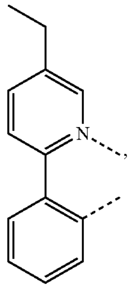
L$_{B177}$
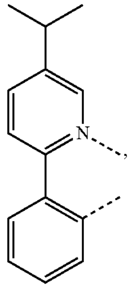
L$_{B178}$
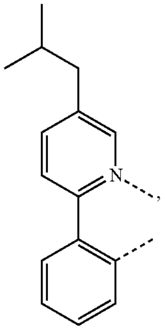
L$_{B179}$
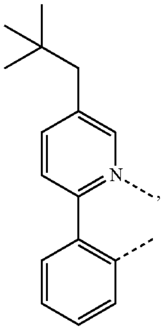
L$_{B180}$
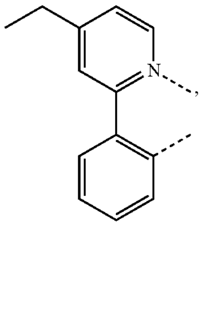
-continued
L$_{B181}$
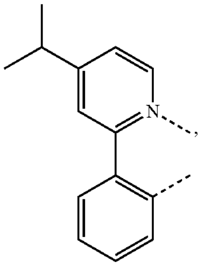
L$_{B182}$
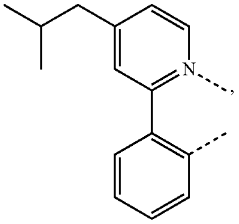
L$_{B183}$
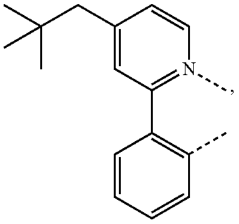
L$_{B184}$
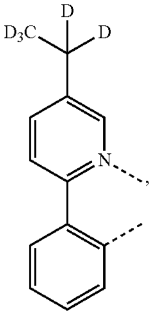
L$_{B185}$
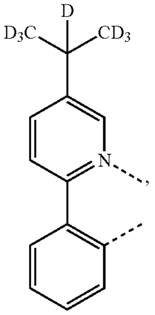

-continued
$L_{B186}$
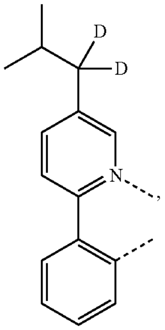
$L_{B187}$
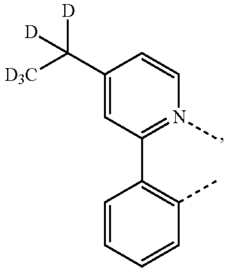
$L_{B188}$
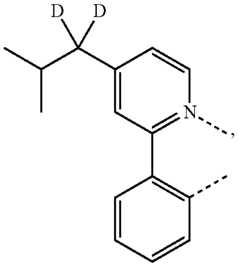
$L_{B189}$
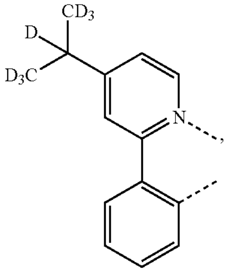
$L_{B190}$
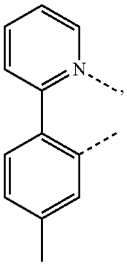
-continued
$L_{B191}$
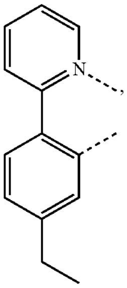
$L_{B192}$
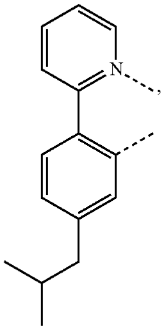
$L_{B193}$
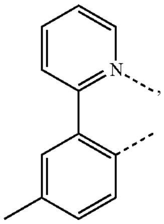
$L_{B194}$
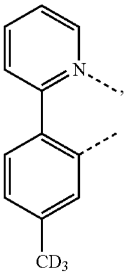
$L_{B195}$
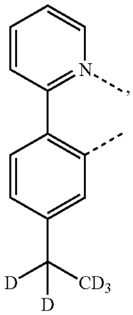

-continued
$L_{B196}$
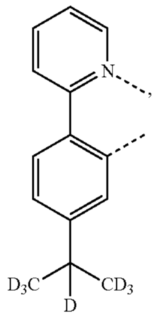
$L_{B197}$
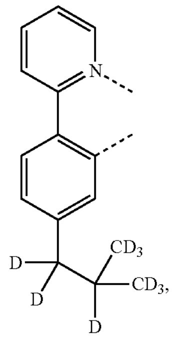
$L_{B198}$
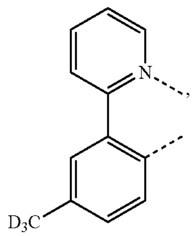
$L_{B199}$
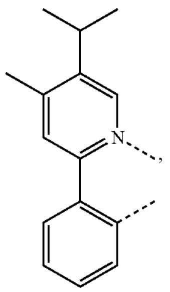
$L_{B200}$
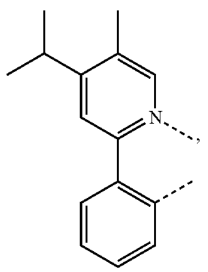
-continued
$L_{B201}$
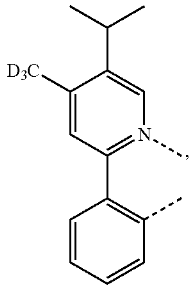
$L_{B202}$
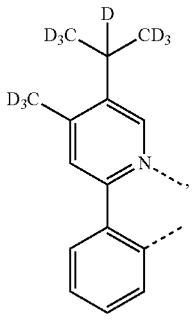
$L_{B203}$
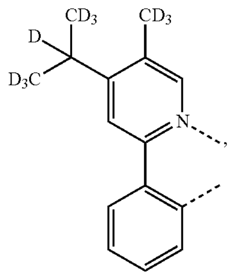
$L_{B204}$
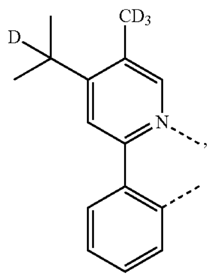
$L_{B205}$
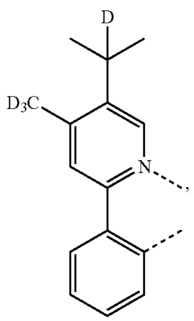

-continued
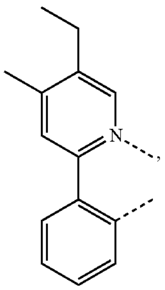
$L_{B206}$
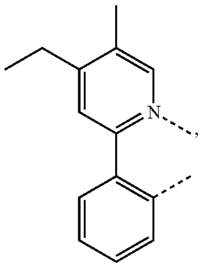
$L_{B207}$
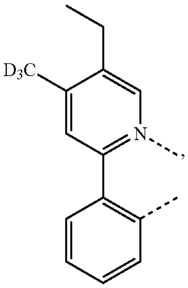
$L_{B208}$
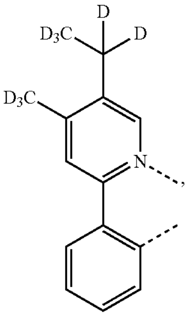
$L_{B209}$
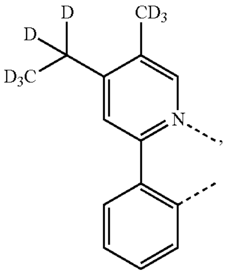
$L_{B210}$
-continued
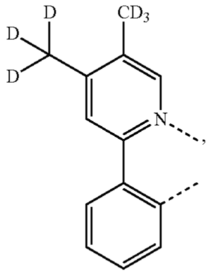
$L_{B211}$
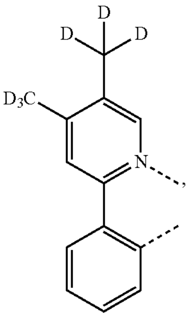
$L_{B212}$
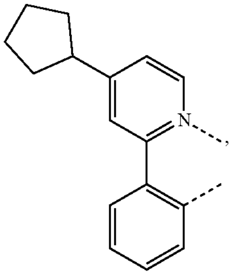
$L_{B213}$
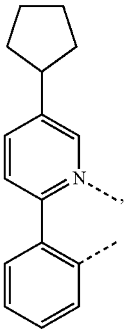
$L_{B214}$
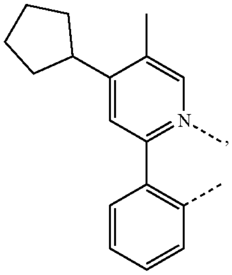
$L_{B215}$ -continued
$L_{B216}$
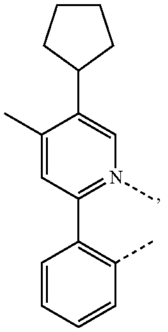
$L_{B217}$
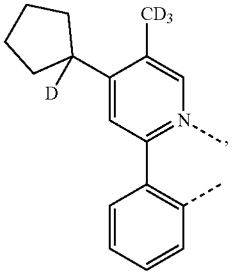
$L_{B218}$
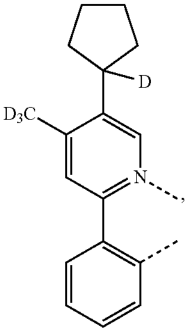
$L_{B219}$
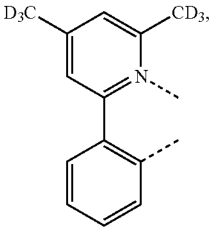
$L_{B220}$
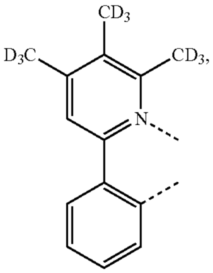
-continued
$L_{B221}$
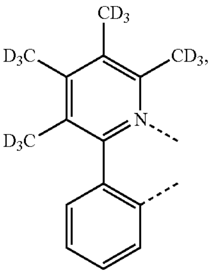
$L_{B222}$
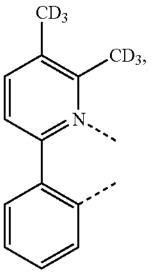
$L_{B223}$
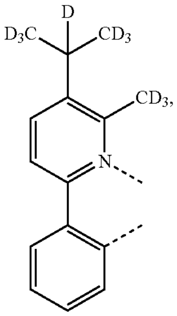
$L_{B224}$
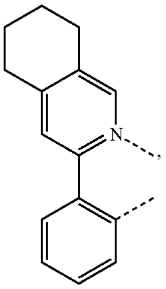
$L_{B225}$
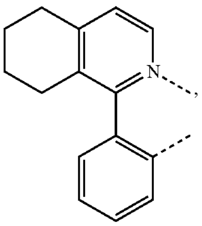

-continued
L$_{B226}$
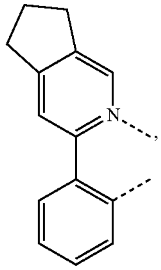
L$_{B227}$
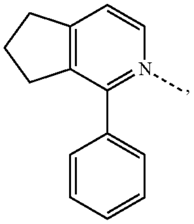
L$_{B228}$
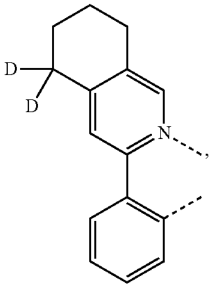
L$_{B229}$
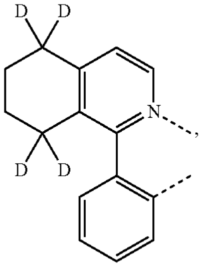
L$_{B230}$
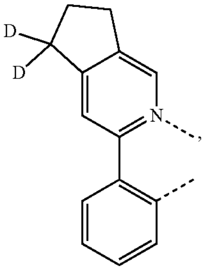
L$_{B231}$
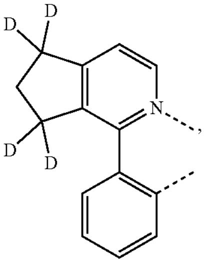
-continued
L$_{B232}$
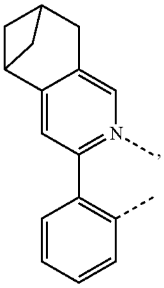
L$_{B233}$
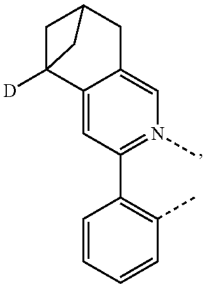
L$_{B234}$
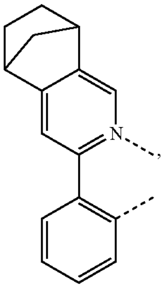
L$_{B235}$
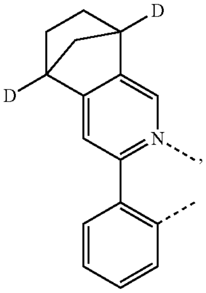
L$_{B236}$
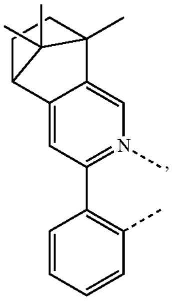

-continued
$L_{B237}$
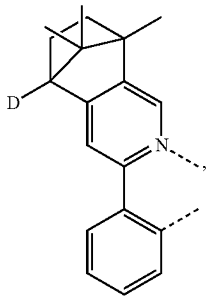
$L_{B238}$
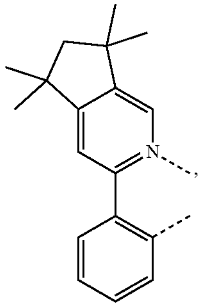
$L_{B239}$
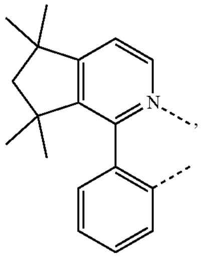
$L_{B240}$
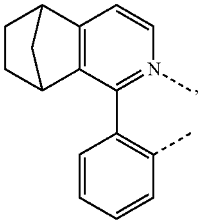
$L_{B241}$
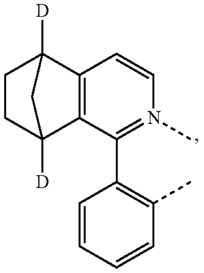
-continued
$L_{B242}$
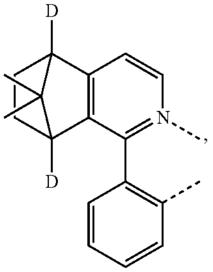
$L_{B243}$
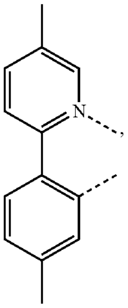
$L_{B244}$
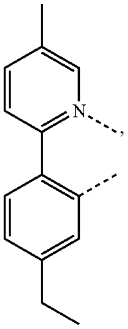
$L_{B245}$
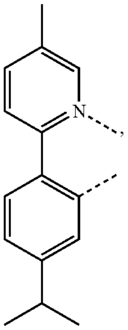
$L_{B246}$
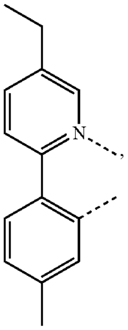

-continued
L$_{B247}$
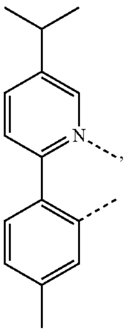
L$_{B248}$
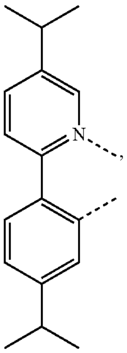
L$_{B249}$
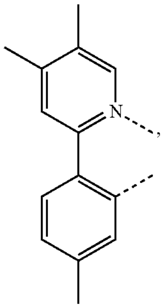
L$_{B250}$
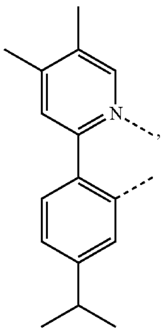
-continued
L$_{B251}$
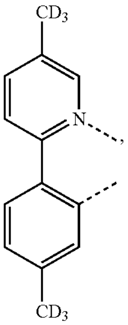
L$_{B252}$
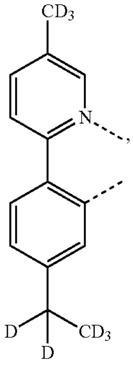
L$_{B253}$
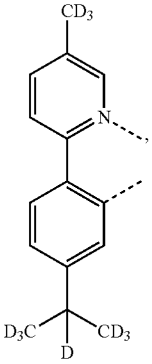
L$_{B254}$
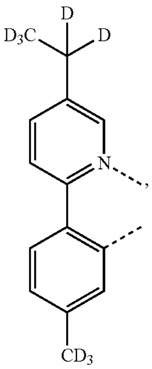

-continued
$L_{B255}$
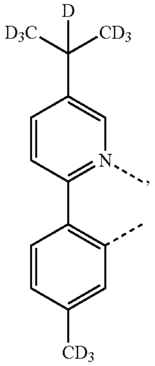
$L_{B256}$
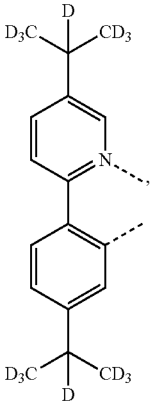
$L_{B257}$
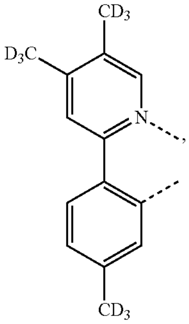
$L_{B258}$
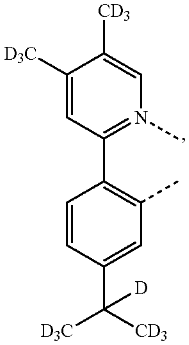
-continued
$L_{B259}$
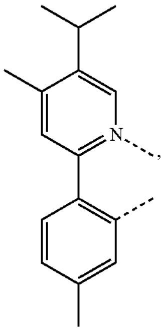
$L_{B260}$
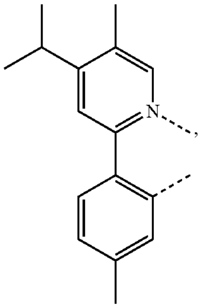
$L_{B261}$
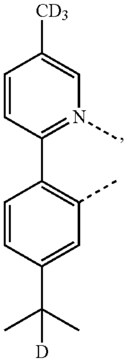
$L_{B262}$
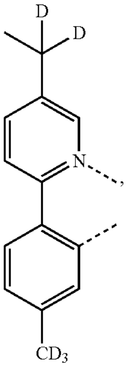

-continued
LB263
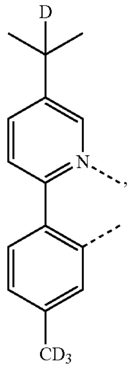
LB264
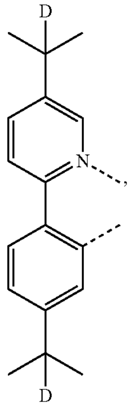
LB265
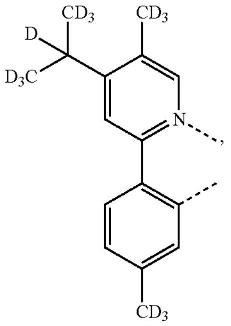
LB266
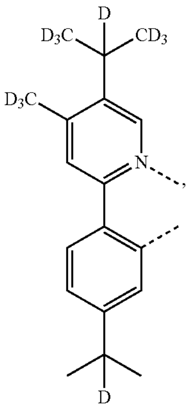
-continued
LB267
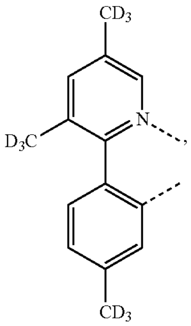
LB268
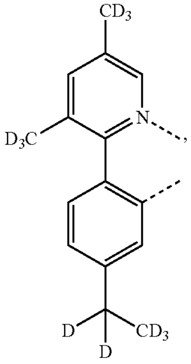
LB269
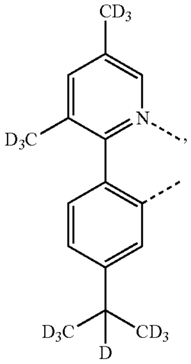
LB270
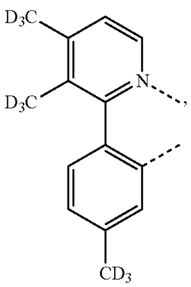

-continued
$L_{B271}$
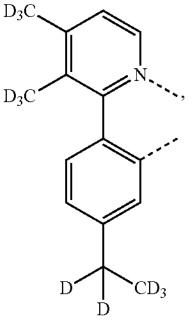
$L_{B272}$
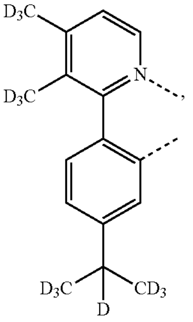
$L_{B273}$
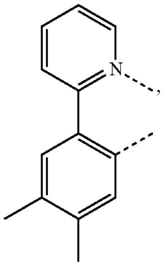
$L_{B274}$
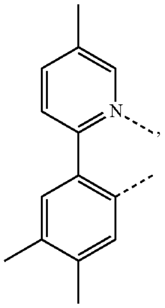
$L_{B275}$
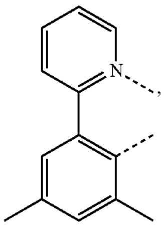
-continued
$L_{B276}$
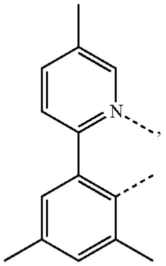
$L_{B277}$
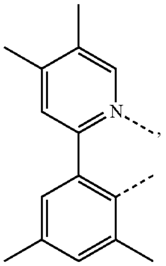
$L_{B278}$
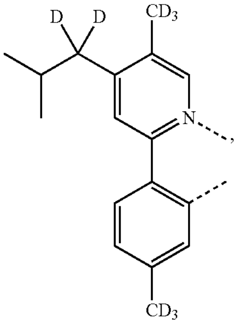
$L_{B279}$
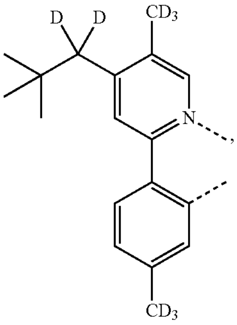
$L_{B280}$
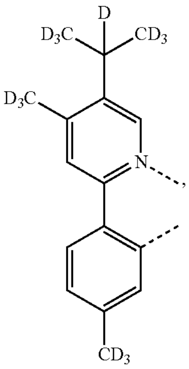

-continued
$L_{B281}$
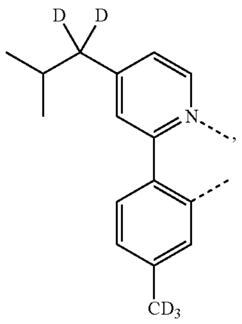
$L_{B282}$
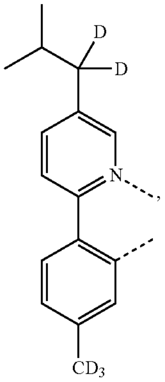
$L_{B283}$
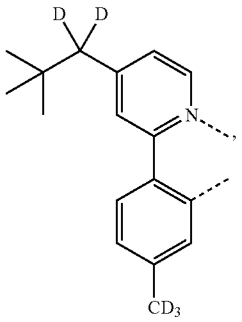
$L_{B284}$
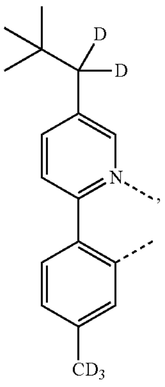
-continued
$L_{B285}$
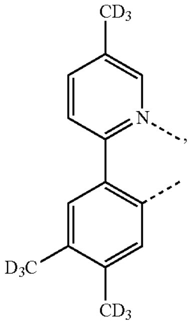
$L_{B286}$
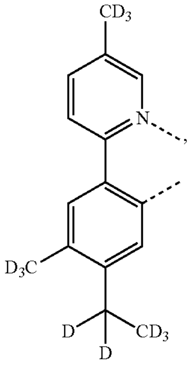
$L_{B287}$
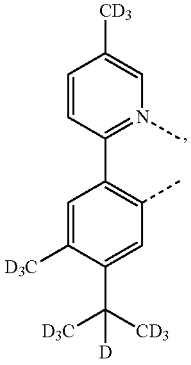
$L_{B288}$
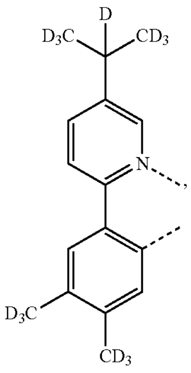

-continued
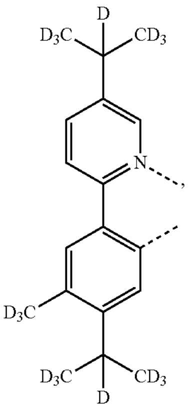
$L_{B289}$
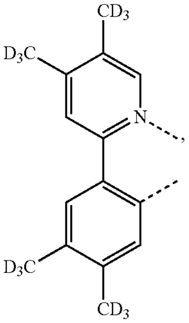
$L_{B290}$
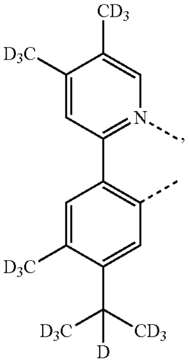
$L_{B291}$
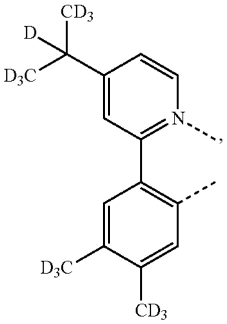
$L_{B292}$
-continued
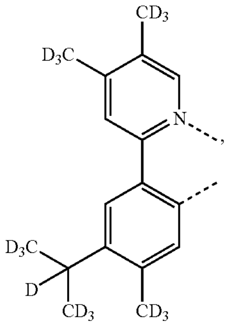
$L_{B293}$
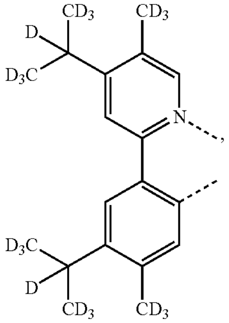
$L_{B294}$
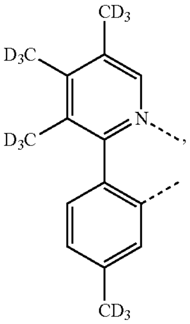
$L_{B295}$
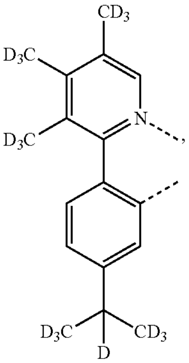
$L_{B296}$ -continued
$L_{B297}$
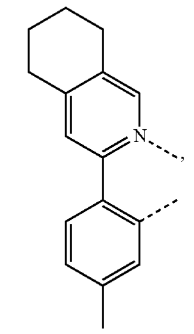
$L_{B298}$
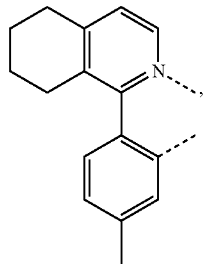
$L_{B299}$
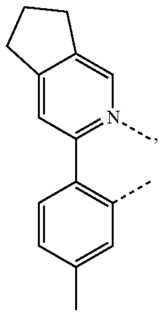
$L_{B300}$
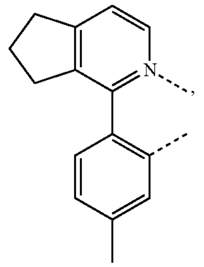
$L_{B301}$
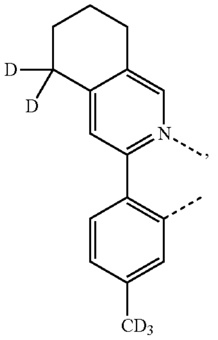
-continued
$L_{B302}$
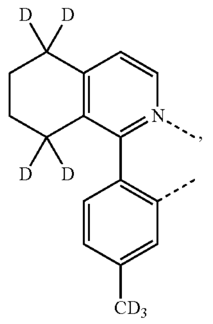
$L_{B303}$
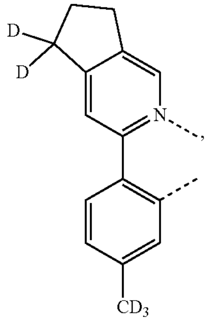
$L_{B304}$
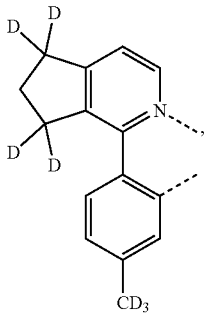
$L_{B305}$
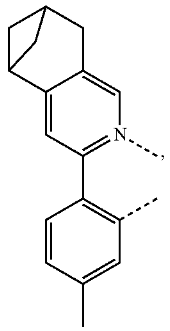

$L_{B306}$
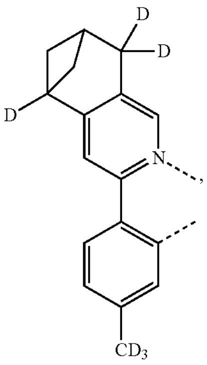
$L_{B307}$
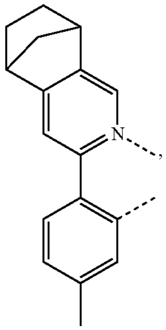
$L_{B308}$
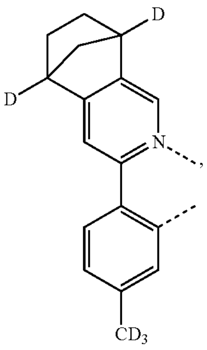
$L_{B309}$
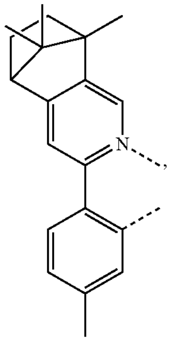
$L_{B310}$
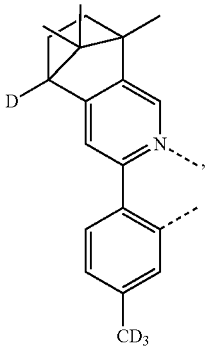
$L_{B311}$
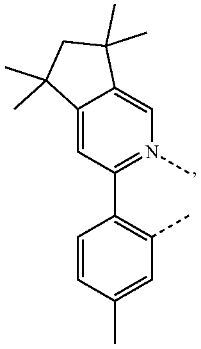
$L_{B312}$
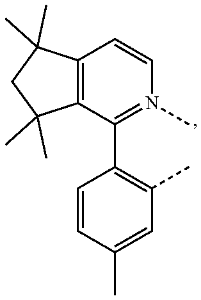
$L_{B312}$
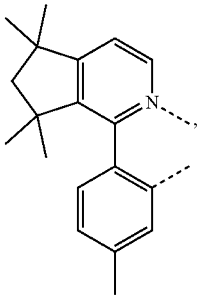
$L_{B313}$
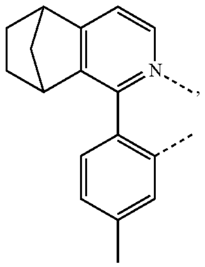

-continued
L$_{B314}$
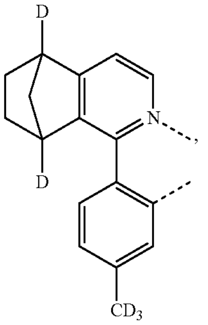
L$_{B315}$
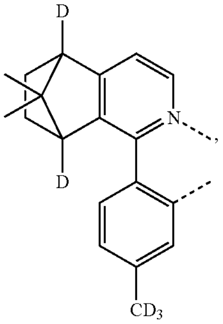
L$_{B316}$
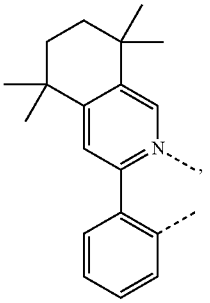
L$_{B317}$
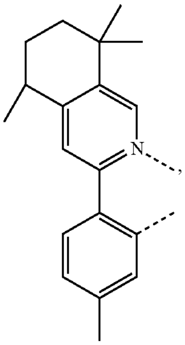
-continued
L$_{B318}$
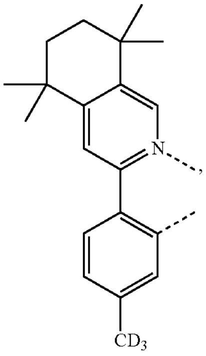
L$_{B319}$
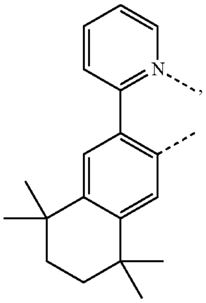
L$_{B320}$
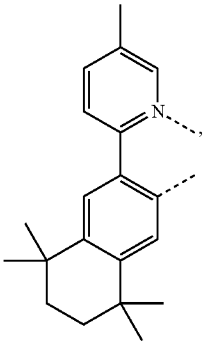
L$_{B321}$
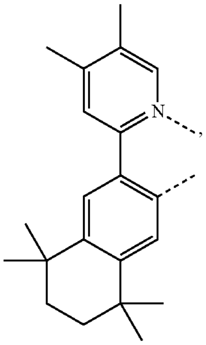

-continued
$L_{B322}$
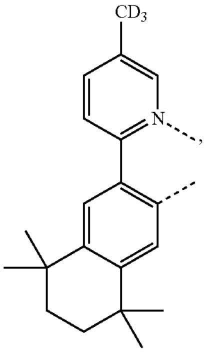
$L_{B323}$
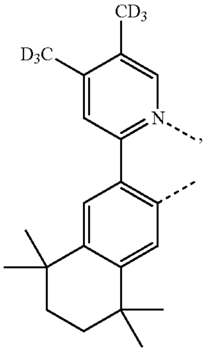
$L_{B324}$
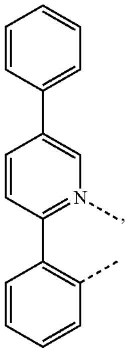
$L_{B325}$
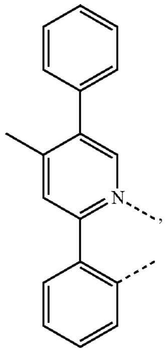
-continued
$L_{B326}$
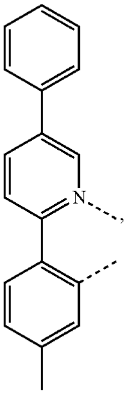
$L_{B327}$
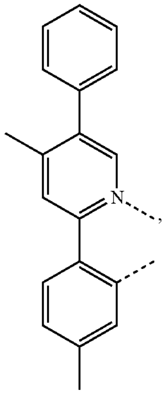
$L_{B328}$
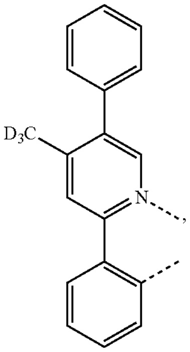
$L_{B329}$
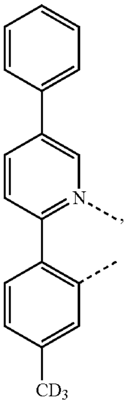

-continued
$L_{B330}$
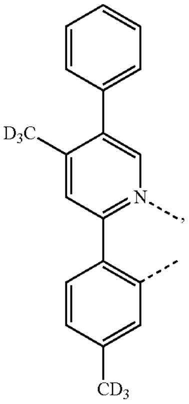
$L_{B331}$
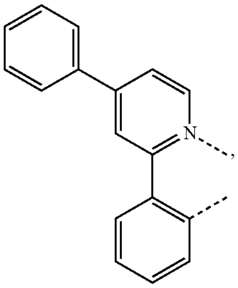
$L_{B332}$
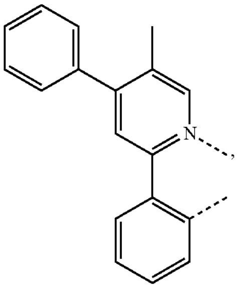
$L_{B333}$
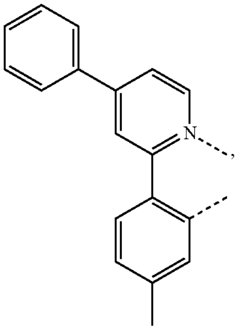
-continued
$L_{B334}$
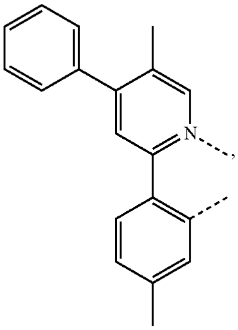
$L_{B335}$
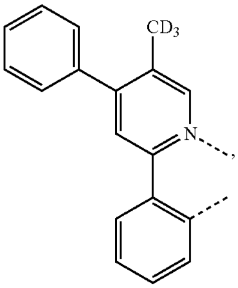
$L_{B336}$
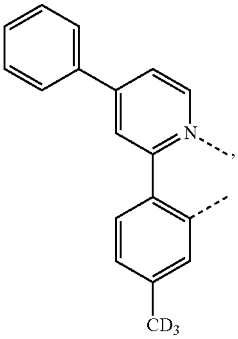
$L_{B337}$
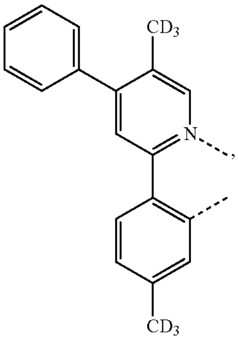

-continued
L_{B338}
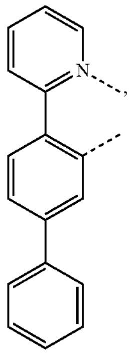
L_{B339}
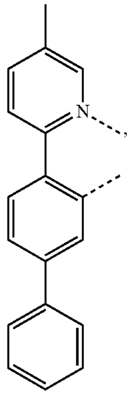
L_{B340}
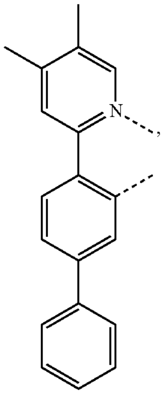
L_{B341}
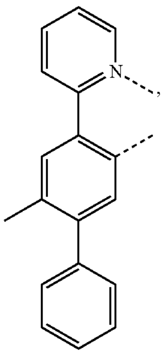
-continued
L_{B342}
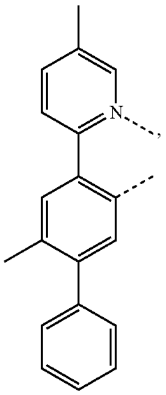
L_{B343}
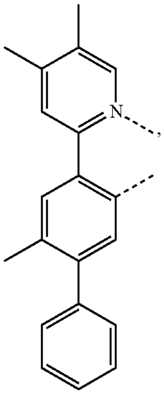
L_{B344}
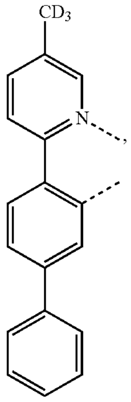
L_{B345}
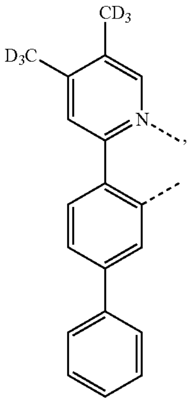

$L_{B346}$
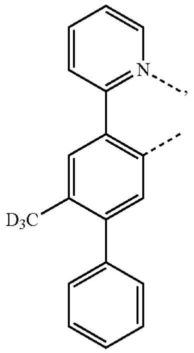
$L_{B347}$
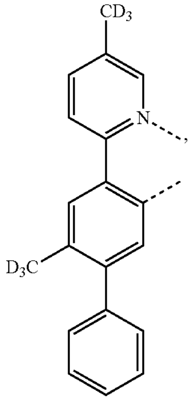
$L_{B348}$
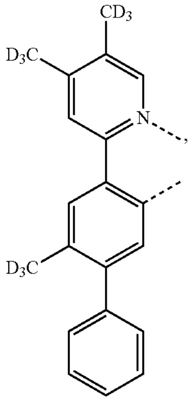
$L_{B349}$
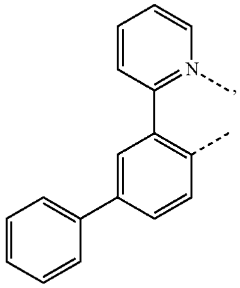
$L_{B350}$
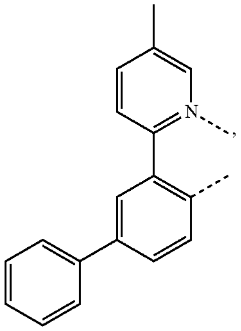
$L_{B351}$
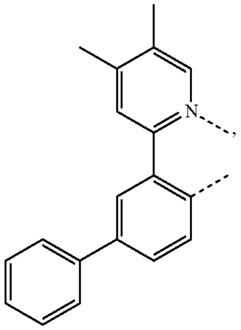
$L_{B352}$
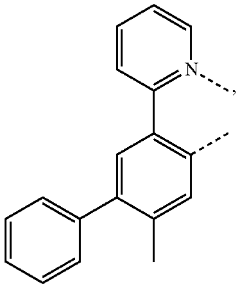
$L_{B353}$
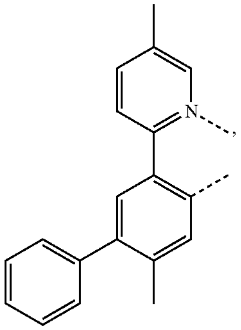
$L_{B354}$
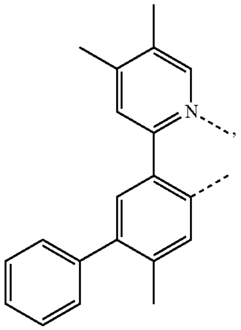

-continued
L$_{B355}$
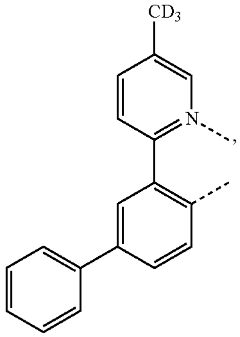
L$_{B356}$
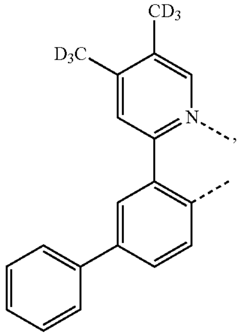
L$_{B357}$
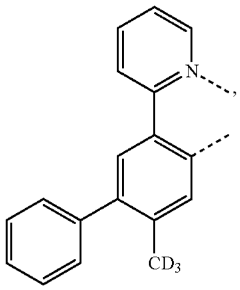
L$_{B358}$
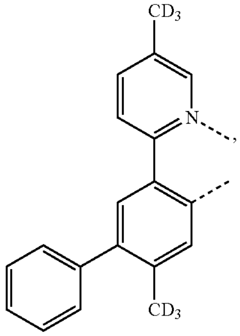
-continued
L$_{B359}$
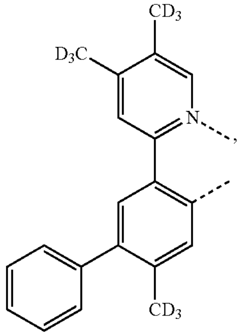
L$_{B360}$
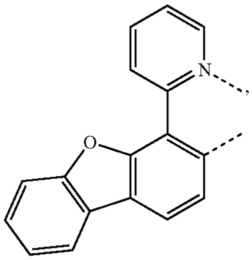
L$_{B361}$
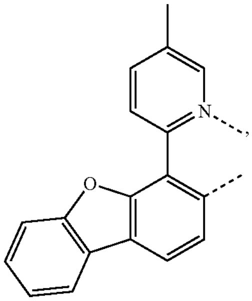
L$_{B362}$
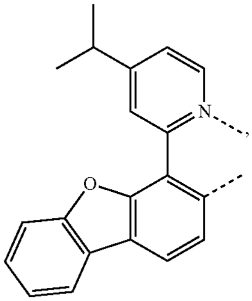
L$_{B363}$
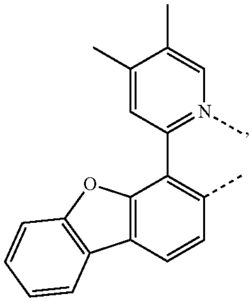

$L_{B364}$
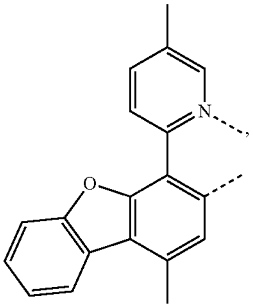
$L_{B365}$
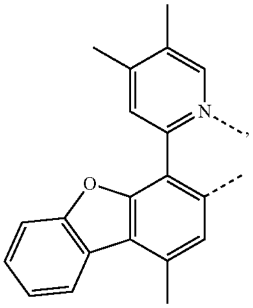
$L_{B366}$
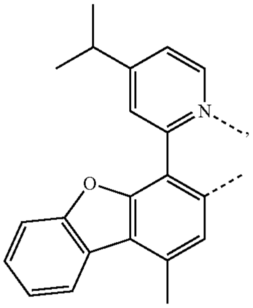
$L_{B367}$
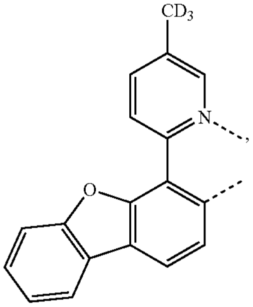
$L_{B368}$
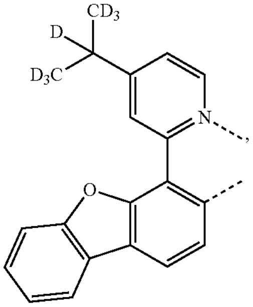
$L_{B369}$
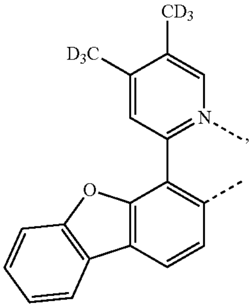
$L_{B370}$
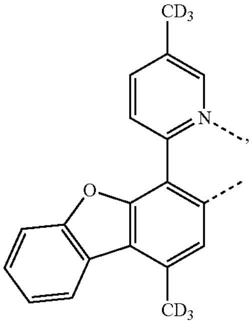
$L_{B371}$
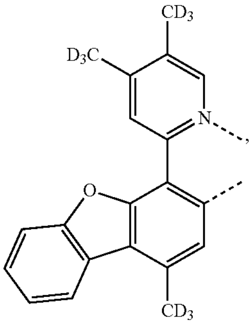
$L_{B372}$
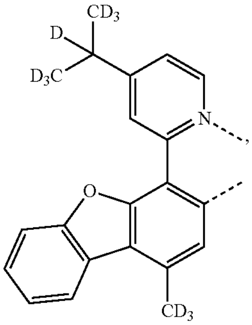
$L_{B373}$
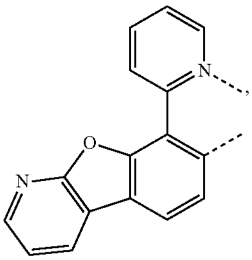

-continued
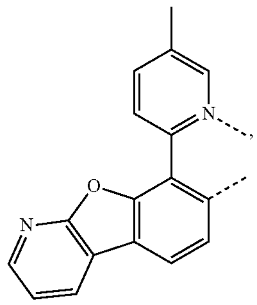
$L_{B374}$
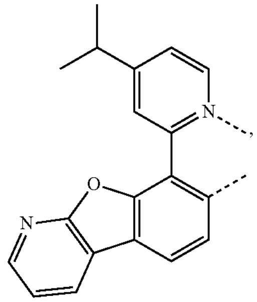
$L_{B375}$
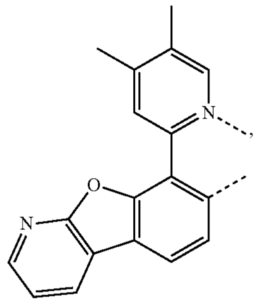
$L_{B376}$
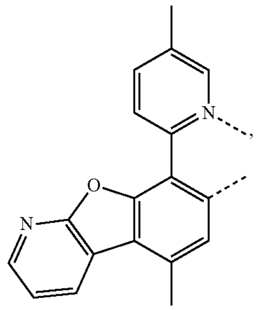
$L_{B377}$
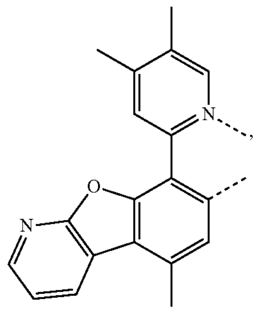
$L_{B378}$
-continued
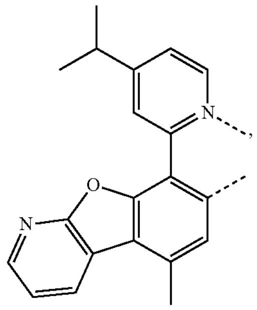
$L_{B379}$
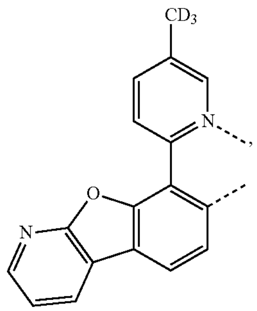
$L_{B380}$
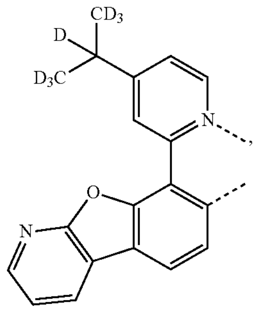
$L_{B381}$
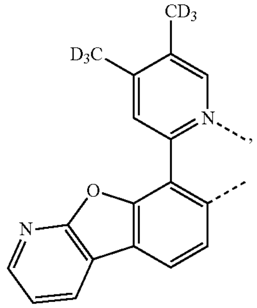
$L_{B382}$
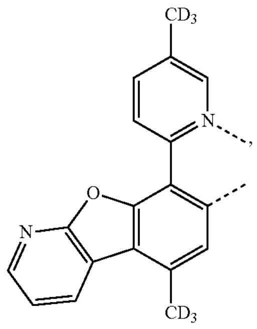
$L_{B383}$ -continued
$L_{B384}$
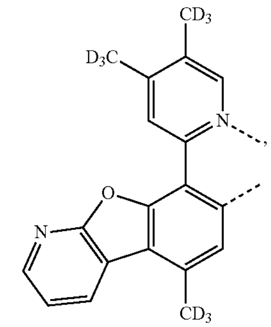
$L_{B385}$
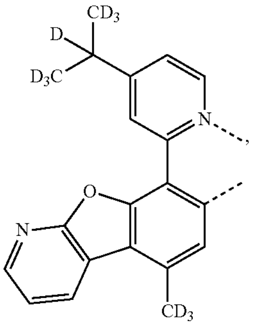
$L_{B386}$
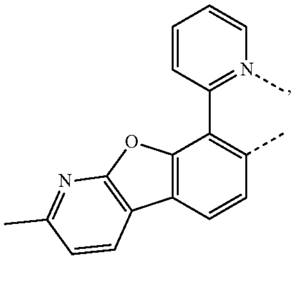
$L_{B387}$
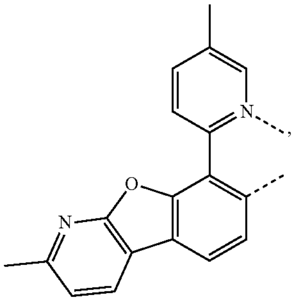
$L_{B388}$
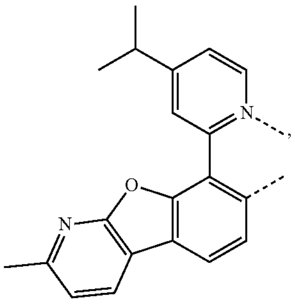
-continued
$L_{B389}$
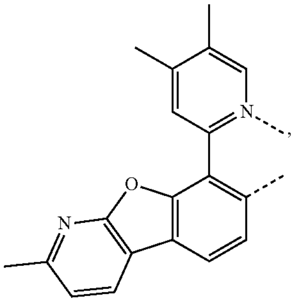
$L_{B390}$
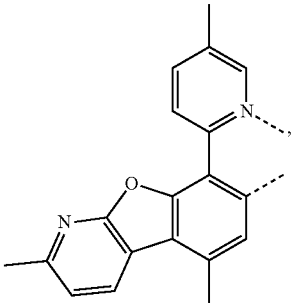
$L_{B391}$
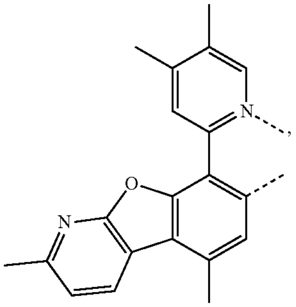
$L_{B392}$
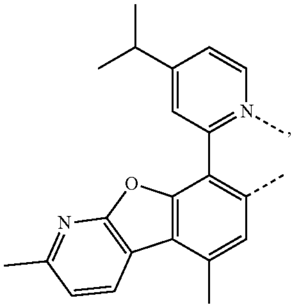
$L_{B393}$
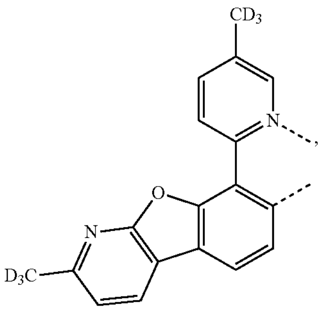

-continued
L$_{B394}$
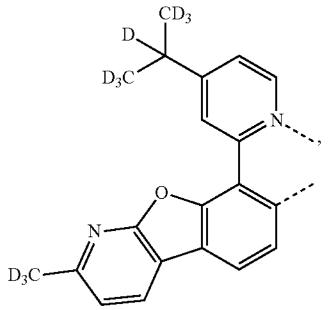
L$_{B395}$
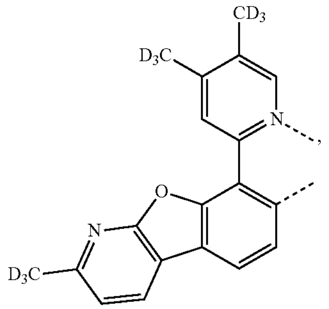
L$_{B396}$
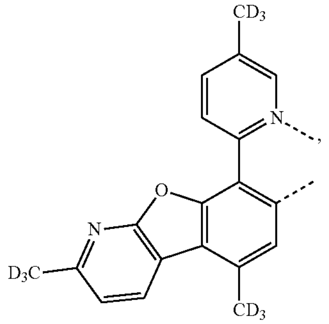
L$_{B397}$
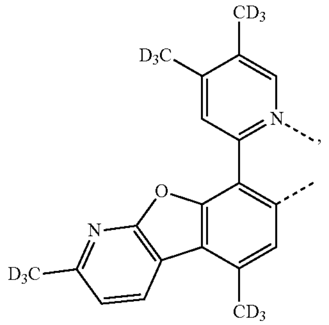
L$_{B398}$
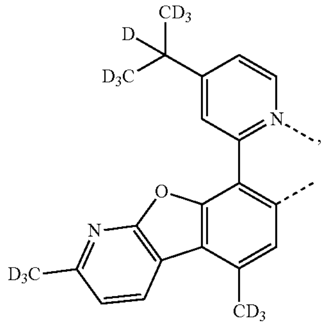
-continued
L$_{B399}$
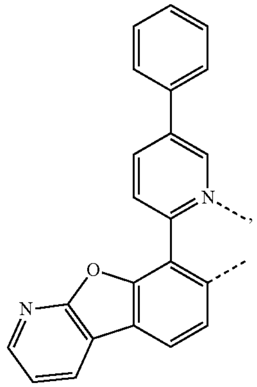
L$_{B400}$
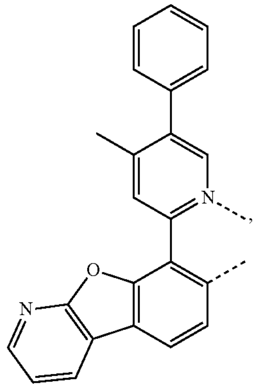
L$_{B401}$
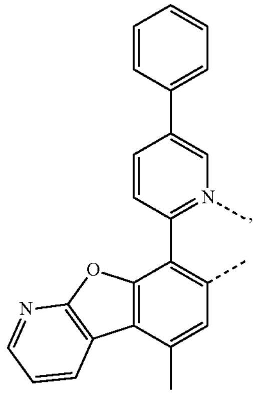
L$_{B402}$
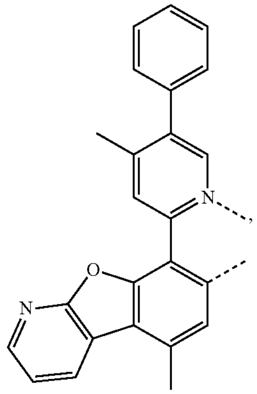

-continued
$L_{B403}$
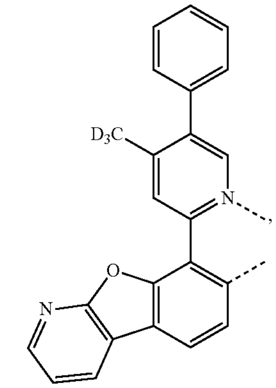
$L_{B404}$
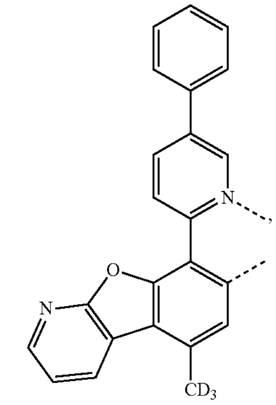
$L_{B405}$
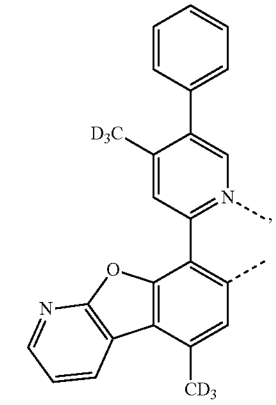
$L_{B406}$
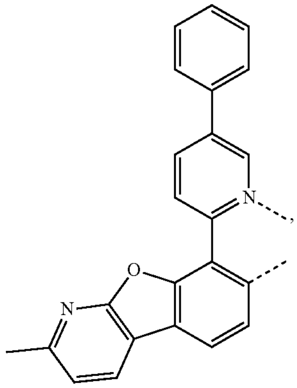
-continued
$L_{B407}$
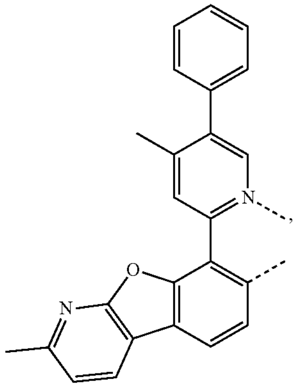
$L_{B408}$
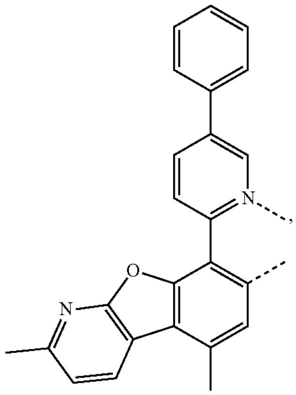
$L_{B409}$
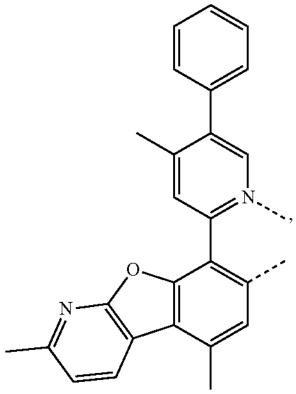
$L_{B410}$
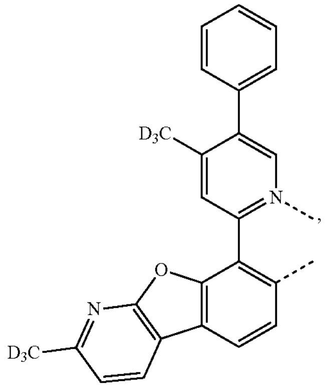

-continued
$L_{B411}$
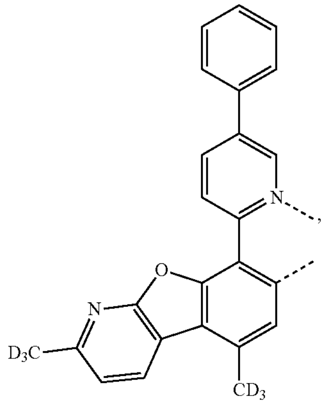
$L_{B412}$
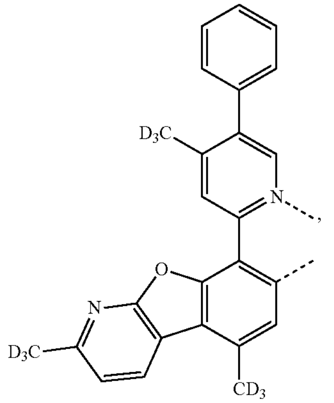
$L_{B413}$
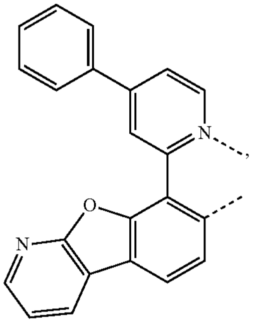
$L_{B414}$
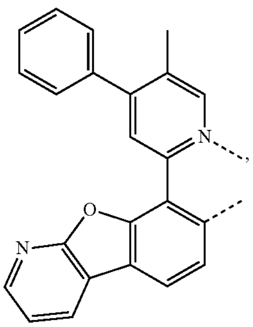
-continued
$L_{B415}$
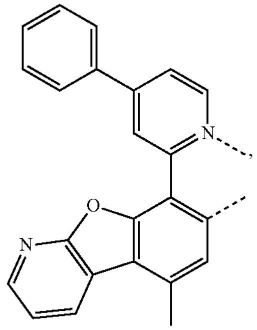
$L_{B416}$
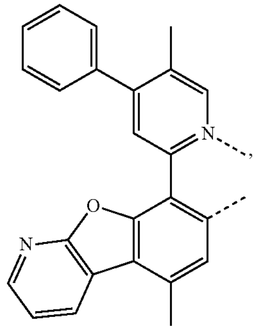
$L_{B417}$
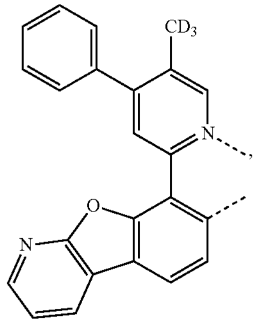
$L_{B418}$
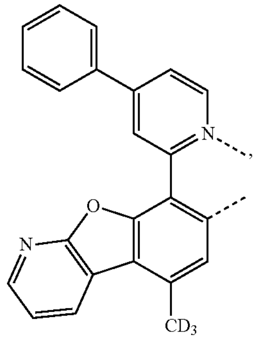

-continued
$L_{B419}$
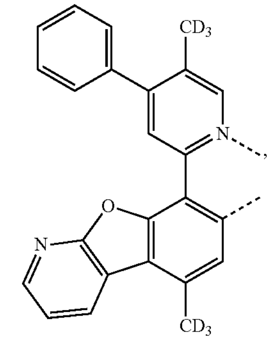
$L_{B420}$
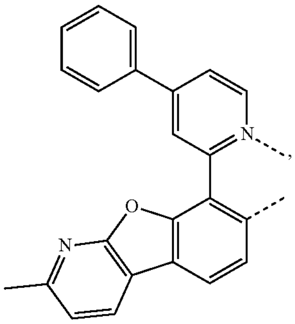
$L_{B421}$
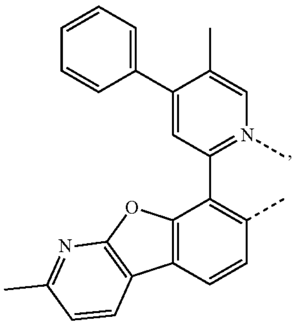
$L_{B422}$
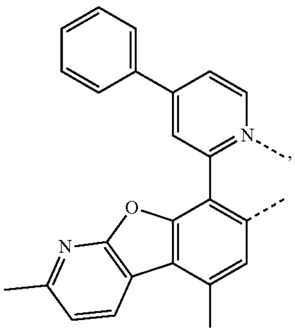
-continued
$L_{B423}$
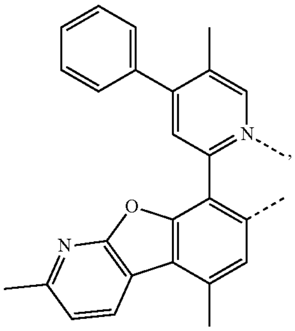
$L_{B424}$
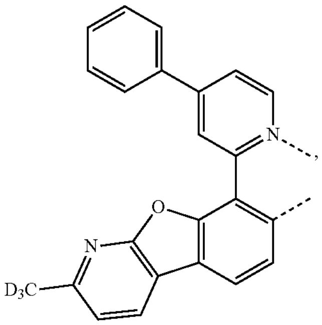
$L_{B425}$
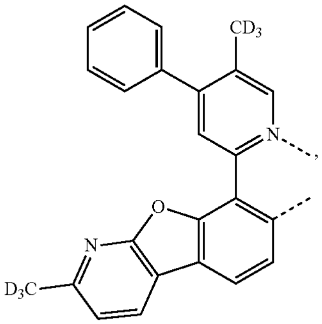
$L_{B426}$
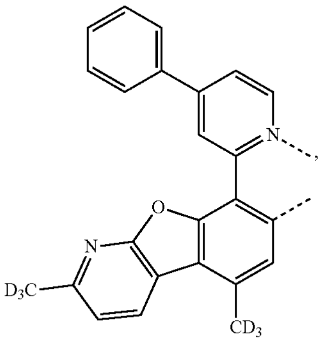

-continued
$L_{B427}$
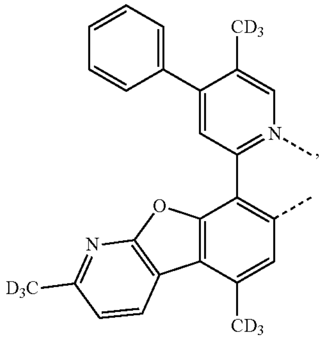
$L_{B428}$
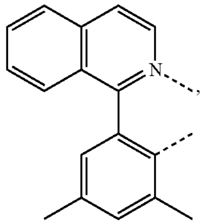
$L_{B429}$
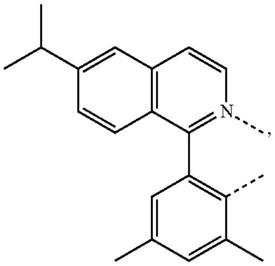
$L_{B430}$
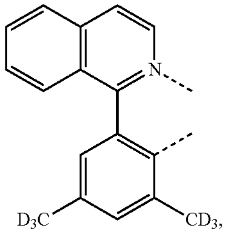
$L_{B431}$
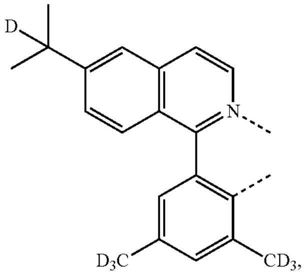
-continued
$L_{B432}$
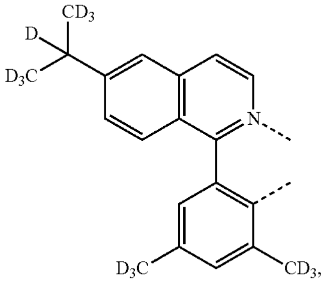
$L_{B433}$
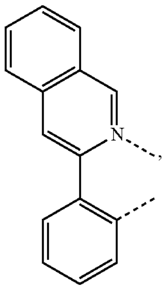
$L_{B434}$
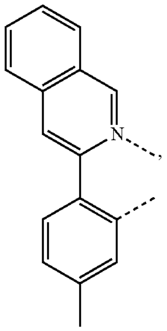
$L_{B435}$
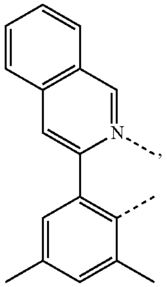
$L_{B436}$
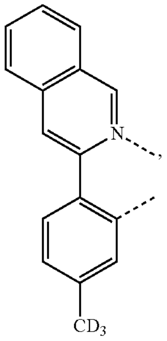

-continued
$L_{B437}$
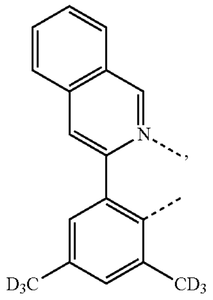
$L_{B438}$
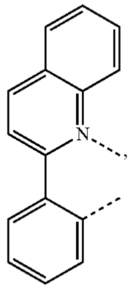
$L_{B439}$
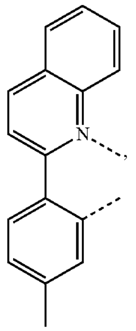
$L_{B440}$
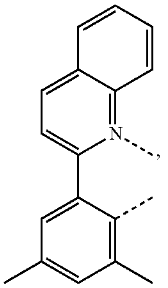
$L_{B441}$
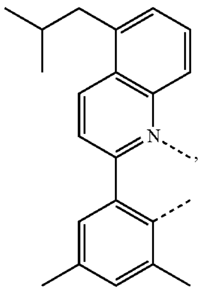
-continued
$L_{B442}$
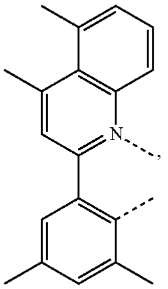
$L_{B443}$
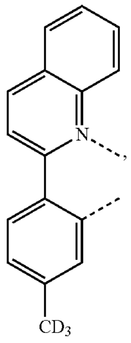
$L_{B444}$
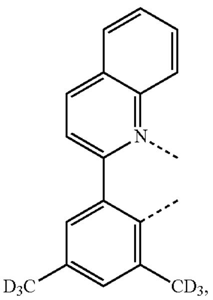
$L_{B445}$
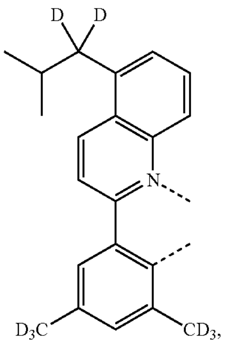
$L_{B446}$
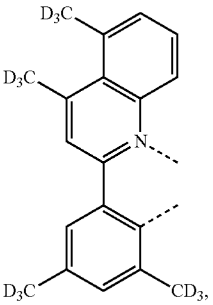

-continued
L$_{B447}$
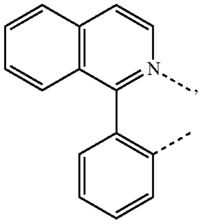
L$_{B448}$
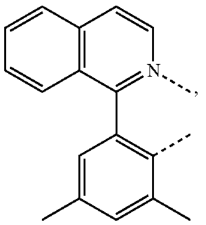
L$_{B449}$
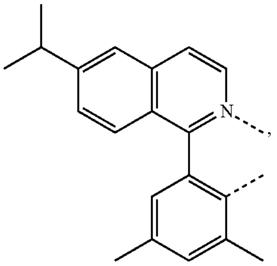
L$_{B450}$
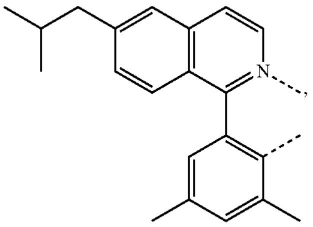
L$_{B451}$
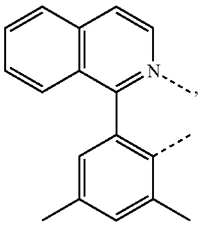
L$_{B452}$
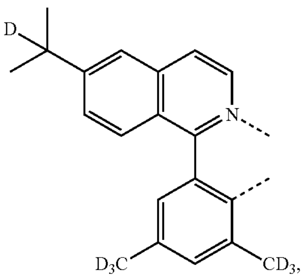
-continued
L$_{B453}$
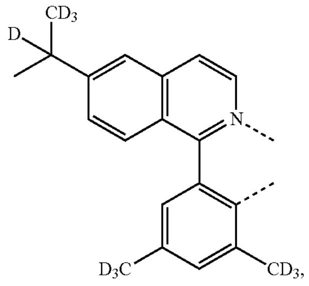
L$_{B454}$
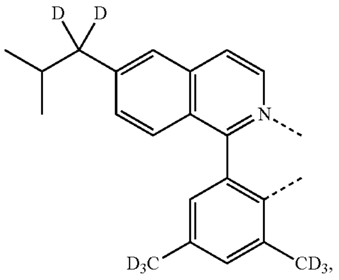
L$_{B455}$
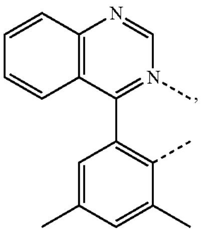
L$_{B456}$
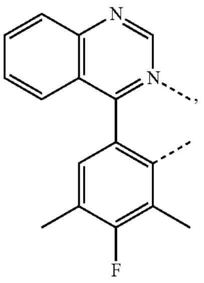
L$_{B457}$
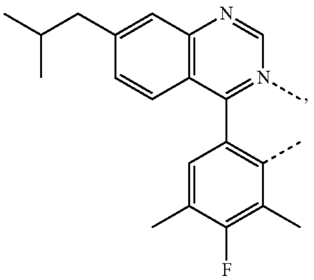

-continued
$L_{B458}$
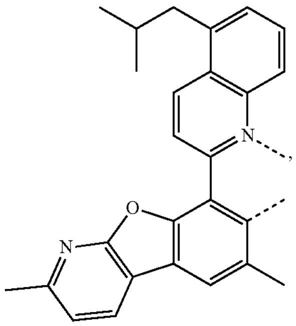
$L_{B459}$
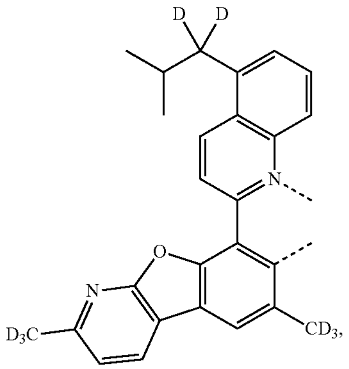
$L_{B460}$
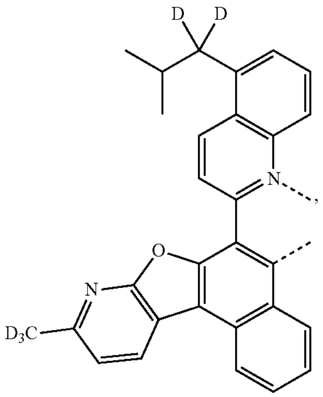
$L_{B461}$
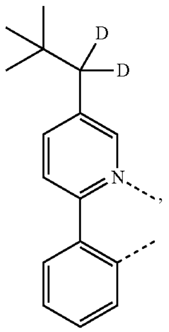
-continued
$L_{B462}$
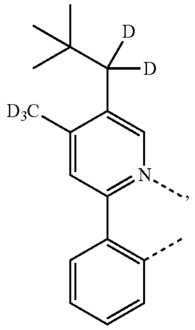
$L_{B463}$
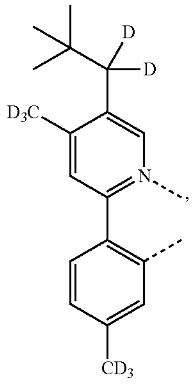
$L_{B464}$
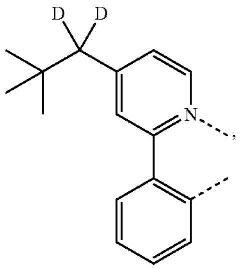
$L_{B465}$
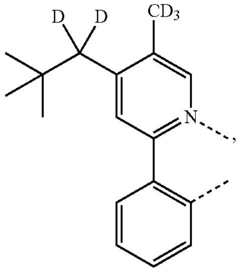
$L_{B466}$
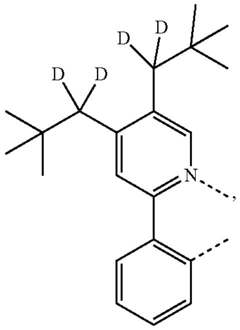

-continued $L_{B467}$

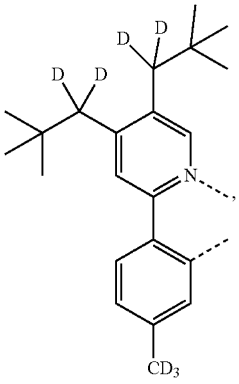

, and $L_{B468}$

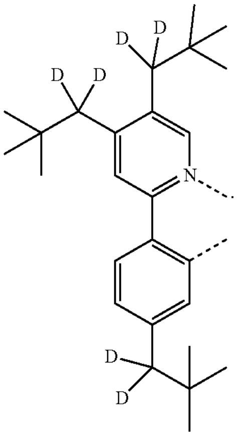

15. A consumer product comprising an organic light-emitting device (OLED) comprising:

an anode;

a cathode; and an organic layer, disposed between the anode and the cathode, comprising a compound according to claim 2.

16. A formulation comprising the compound of claim 2.

17. An organic light emitting device (OLED) comprising:

an anode;

a cathode; and an organic layer, disposed between the anode and the cathode, comprising a compound comprising a first ligand $L_x$ of Formula II

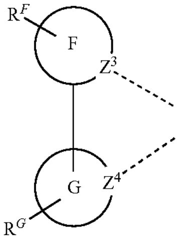

;

wherein F is a 5-membered or 6-membered carbocyclic or heterocyclic ring;

wherein each of $R^F$, $R^G$, $R^H$, and $R^I$ independently represent mono to the maximum possible number of substitutions, or no substitution;

wherein $Z^3$ and $Z^4$ are each independently C or N and coordinated to a metal M to form a 5-membered chelate ring;

wherein moiety G is a fused ring structure comprising five or more fused heterocyclic or carbocyclic rings, of which at least one ring is of Formula III

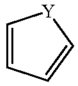

;

wherein the fused heterocyclic or carbocyclic rings comprised by moiety G are 5-membered or 6-membered if moiety G comprises two or more 5-membered rings, at least two of the 5-membered rings are fused to one another;

wherein at least one of $Z^3$ or $Z^4$ is part of a 6-membered ring;

wherein Y is selected from the group consisting of BR', NR', PR', O, S, Se, C═O, S═O, $SO_2$, CR'R", SiR'R", and GeR'R";

wherein each R', R", $R^G$, $R^H$, and $R^I$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

wherein metal M is optionally coordinated to other ligands;

wherein the ligand $L_x$ is optionally linked with other ligands to comprise a tridentate, tetradentate, pentadentate, or hexadentate ligand; and wherein at least one of the following conditions is true:

(1) Y is selected from the group consisting of BR', NR', PR', O, S, Se, C═O, S═O, $SO_2$, SiR'R", and GeR'R";

(2) Formula III is fused directly to moiety G and a 5-membered ring is fused directly to Formula III, (3) moiety G comprises exactly five fused heterocyclic or carbocyclic rings;

(4) moiety G includes at least one 6-membered, heteroaryl ring; or (5) the compound has a structure of Formula IV,

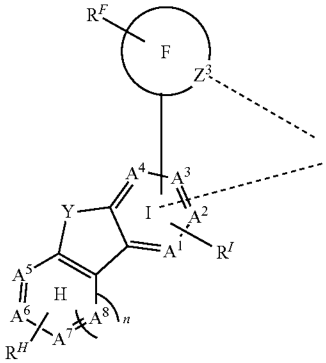

and at least one of the following is true:

(i) at least one additional ring is fused to ring I, (ii) two additional rings are directly fused to H, or (iii) exactly one additional ring, $H^1$, is fused directly to H and exactly one additional ring, $H^2$, is fused to $H^1$, wherein each of H1 and H2 is a 5- or 6-membered heterocyclic or carbocyclic ring;

wherein:

$A^1$ to $A^4$ are each independently C or N;

one of $A^1$ to $A^4$ is $Z^4$ in Formula II;

each of ring F and ring H is a 5-membered or 6-membered aryl or heteroaryl ring;

wherein n is 0 or 1;

wherein when n is 0, $A^8$ is not present, two adjacent atoms of $A^5$ to $A^7$ are C, and the remaining atom of $A^5$ to $A^7$ is selected from the group consisting of NR', O, S, and Se; and wherein any two substituents can be joined or fused together to form a ring;

wherein when n is 1, two adjacent of $A^5$ to $A^8$ are C, and the remaining atoms of $A^5$ to $A^8$ are selected from the group consisting of C and N.

18. The OLED of claim 17, wherein the organic layer is an emissive layer and the compound is an emissive dopant or a non-emissive dopant.

19. The OLED of claim 17, wherein the organic layer further comprises a host, wherein host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

20. The OLED of claim 19, wherein the host is selected from the group consisting of:

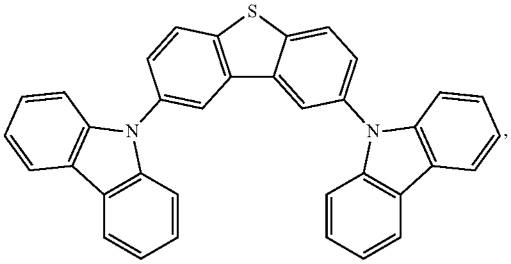
,
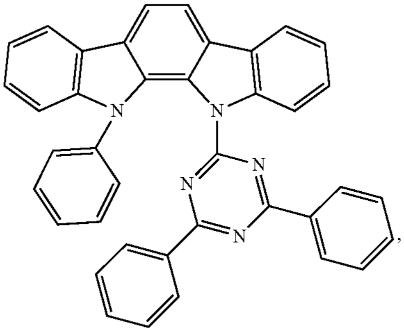
,
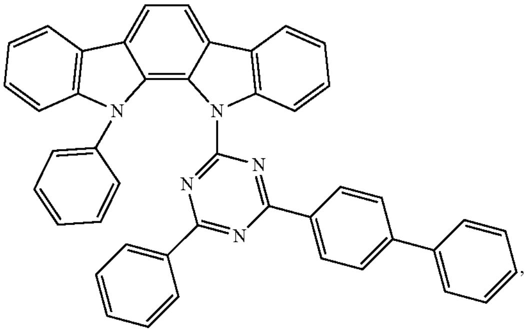
,

-continued

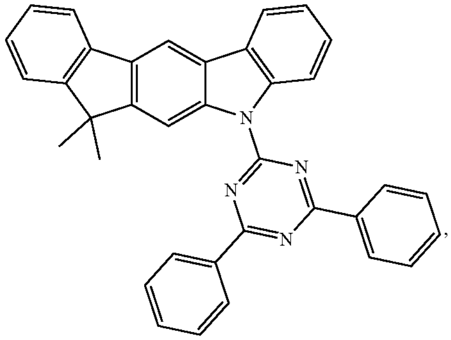
,
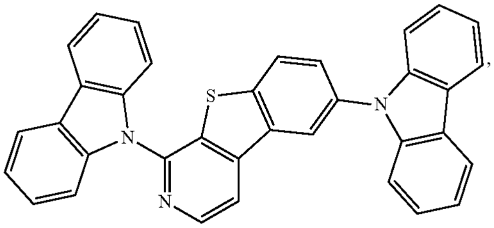
,
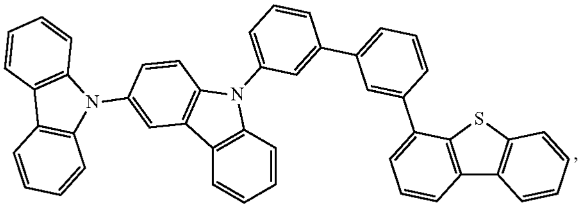
,
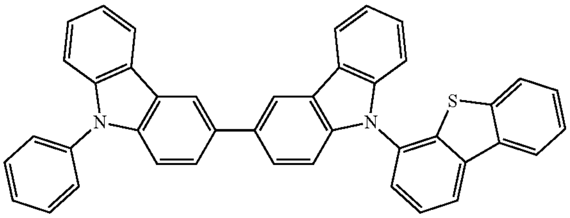
,
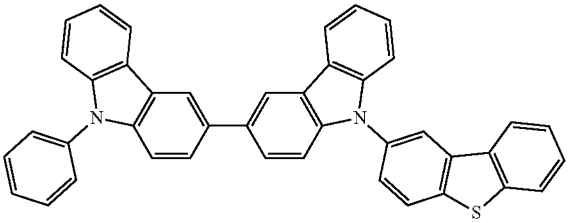
,
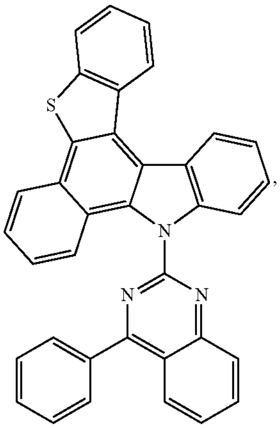
,
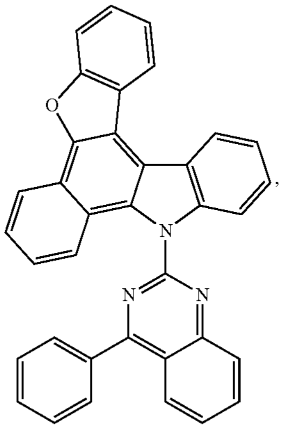
, -continued
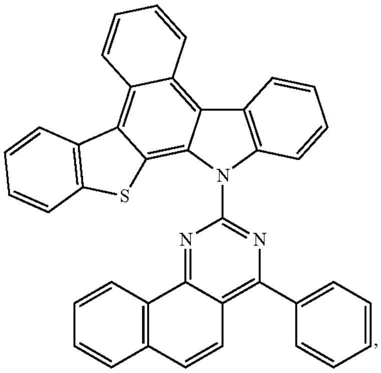
,
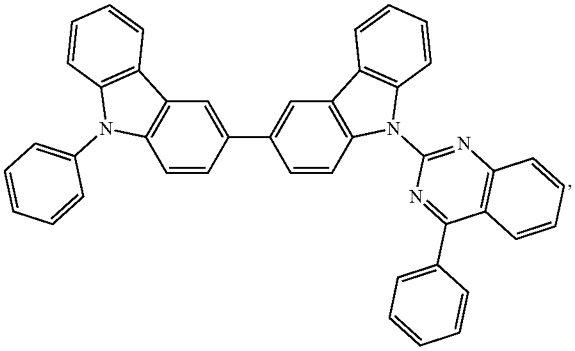
,
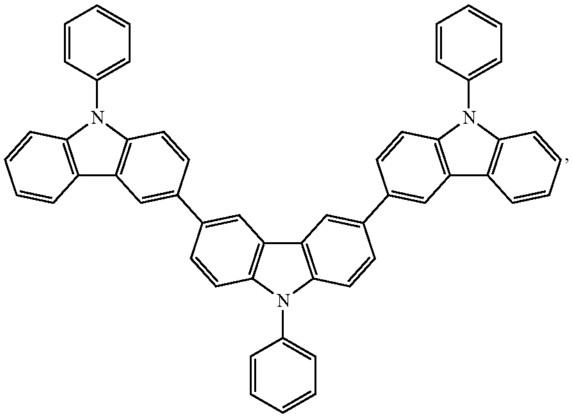
,
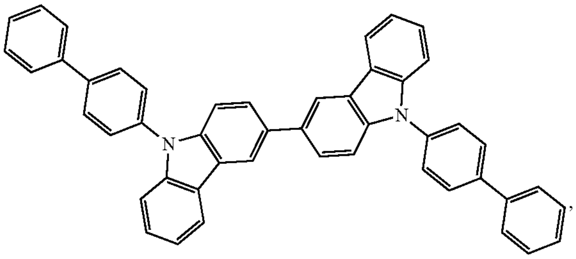
,
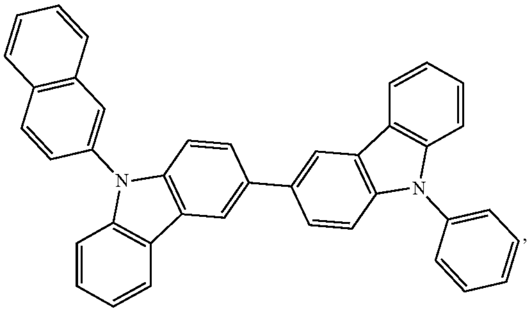
,
-continued
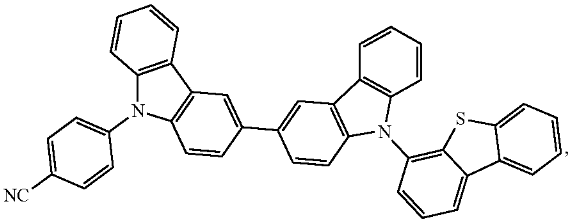
,
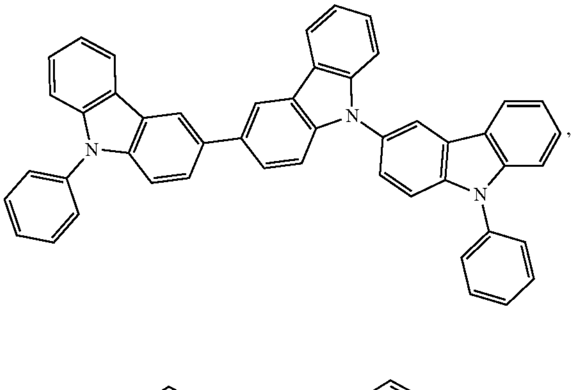
,
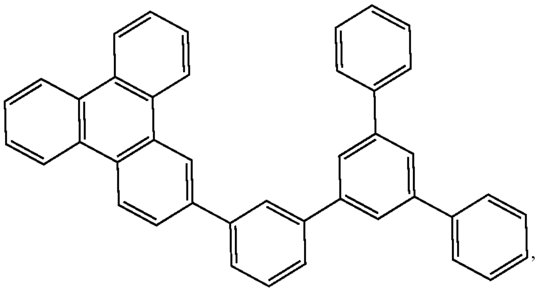
,
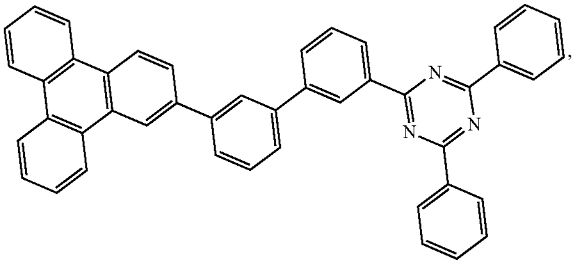
,
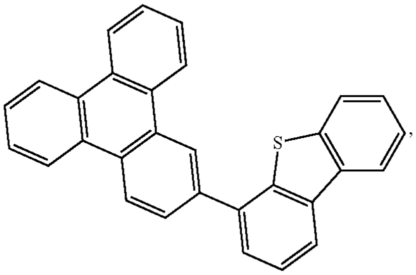
,
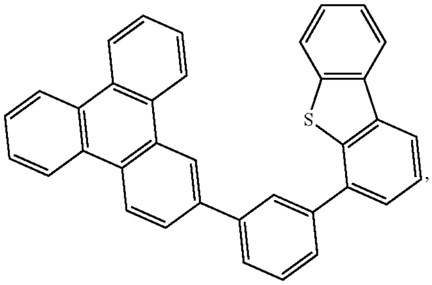
, -continued
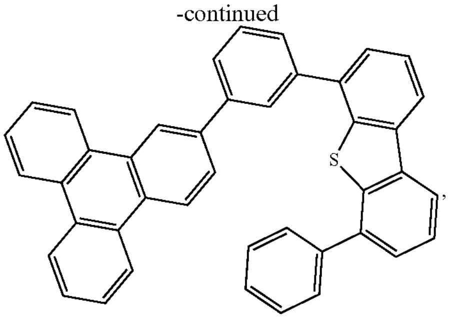
,
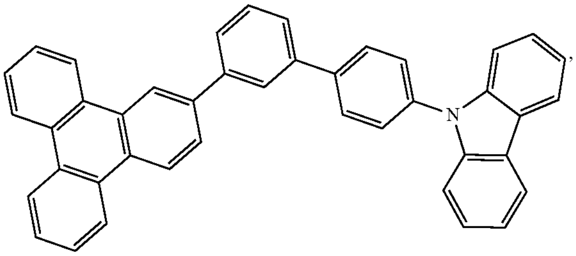
,
-continued
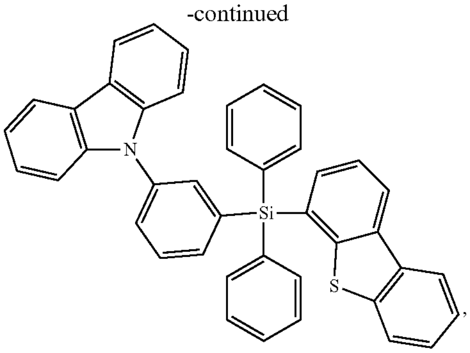
,
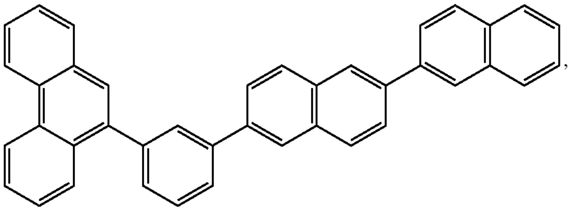
,
and combinations thereof.
* * * * *

UNITED STATES PATENT AND TRADEMARK OFFICE

CERTIFICATE OF CORRECTION

PATENT NO. : 11,165,028 B2
APPLICATION NO. : 16/283219
DATED : November 2, 2021
INVENTOR(S) : Jui-Yi Tsai et al.

It is certified that error appears in the above-identified patent and that said Letters Patent is hereby corrected as shown below:

In the Claims

In Claim 13, Column 386, Line 19, please delete "$L_{X26-2}$" and insert --$L_{X26-3}$--.

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*